US012616682B2

(12) United States Patent
Atkinson et al.

(10) Patent No.: US 12,616,682 B2
(45) Date of Patent: *May 5, 2026

(54) 1-H-PYRROLO[2,3-C]PYRIDINE COMPOUNDS

(71) Applicant: Acerta Pharma B.V., Oss (NL)

(72) Inventors: Stephen Atkinson, Saffron Walden (GB); Gerjan De Bruin, Oss (NL); Flavia Izzo, Oss (NL); Chimed Jansen, Oss (NL); Olaf Kinzel, Oss (NL); Martin Packer, Macclesfield (GB); Saskia Verkaik, Oss (NL); Robin Voets, Oss (NL)

(73) Assignee: ACERTA PHARMA B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 19/038,137

(22) Filed: Jan. 27, 2025

(65) Prior Publication Data

US 2025/0360112 A1 Nov. 27, 2025

Related U.S. Application Data

(63) Continuation of application No. 18/613,180, filed on Mar. 22, 2024.

(60) Provisional application No. 63/491,978, filed on Mar. 24, 2023.

(51) Int. Cl.

| | |
|---|---|
| ***A61K 31/437*** | (2006.01) |
| ***A61K 31/439*** | (2006.01) |
| ***A61K 31/4545*** | (2006.01) |
| ***A61K 31/506*** | (2006.01) |
| ***A61K 31/5377*** | (2006.01) |
| ***A61K 31/55*** | (2006.01) |
| ***C07D 471/04*** | (2006.01) |

(52) U.S. Cl.

CPC .......... *A61K 31/437* (2013.01); *A61K 31/439* (2013.01); *A61K 31/4545* (2013.01); *A61K 31/506* (2013.01); *A61K 31/5377* (2013.01); *A61K 31/55* (2013.01); *C07D 471/04* (2013.01)

(58) Field of Classification Search

None

See application file for complete search history.

(56) References Cited

U.S. PATENT DOCUMENTS

| | | | |
|---|---|---|---|
| 10,683,302 | B2 | 6/2020 | Cacatian et al. |
| 11,479,557 | B2 | 10/2022 | Cacatian et al. |
| 2023/0026872 | A1 | 1/2023 | Burrows et al. |
| 2023/0095934 | A1 | 3/2023 | Burrows |
| 2023/0165858 | A1 | 6/2023 | McGeehan et al. |

FOREIGN PATENT DOCUMENTS

| | | | |
|---|---|---|---|
| EP | 4232020 | A1 | 8/2023 |
| WO | 2011029054 | A1 | 3/2011 |
| WO | 2014164543 | A1 | 10/2014 |
| WO | 2016040330 | A1 | 3/2016 |
| WO | 2016195776 | A1 | 12/2016 |
| WO | 2016197027 | A1 | 12/2016 |
| WO | 2017112768 | A1 | 6/2017 |
| WO | 2017161002 | A1 | 9/2017 |
| WO | 2017161028 | A1 | 9/2017 |
| WO | 2017192543 | A1 | 11/2017 |
| WO | 2017207387 | A1 | 12/2017 |
| WO | 2017214367 | A1 | 12/2017 |
| WO | 2018024602 | A1 | 2/2018 |
| WO | 2018050684 | A1 | 3/2018 |
| WO | 2018050686 | A1 | 3/2018 |
| WO | 2018053267 | A1 | 3/2018 |
| WO | 2018109088 | A1 | 6/2018 |
| WO | 2019120209 | A1 | 6/2019 |
| WO | 2020032105 | A1 | 2/2020 |
| WO | 2020045334 | A1 | 3/2020 |
| WO | 2020116662 | A1 | 6/2020 |

(Continued)

OTHER PUBLICATIONS

Borkin D., et al., "Property Focused Structure-Based Optimization of Small Molecule Inhibitors of the Protein-Protein Interaction between Menin and Mixed Lineage Leukemia (MLL)", Journal of Medicinal Chemistry, vol. 59, No. 3, Feb. 11, 2016, pp. 892-913.

Cierpicki T., et al., "Challenges and Opportunities in Targeting the Menin-MLL Interaction", Future Medicinal Chemistry, vol. 6, No. 4, Mar. 2014, pp. 1-25.

Grembecka J., et al., "Menin-MLL Inhibitors Reverse Oncogenic Activity of MLL Fusion Proteins in Leukemia", Nature Chemical Biology, vol. 8, Mar. 2012, pp. 277-284.

He S., et al., "High-Affinity Small-Molecule Inhibitors of the Menin-Mixed Lineage Leukemia (MLL) Interaction Closely Mimic a Natural Protein-Protein Interaction", Journal of Medicinal Chemistry, vol. 57, Jan. 28, 2014, pp. 1543-1556.

(Continued)

*Primary Examiner* — James H Alstrum-Acevedo
*Assistant Examiner* — Lauren Wells

(57) ABSTRACT

Compounds having the structure of Formula (I):

(I)

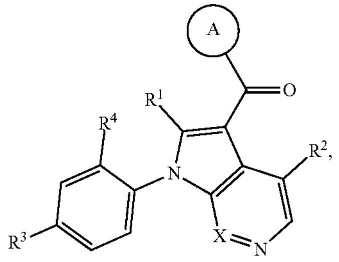

and pharmaceutically acceptable salts thereof, wherein $R^1$, $R^2$, $R^3$, $R^4$, and A are as defined in the specification; pharmaceutical compositions comprising such compounds and salts; use of such compounds and salts to treat or prevent Menin-mediated conditions; kits comprising such compounds and salts; and methods for manufacturing such compounds and salts.

19 Claims, 12 Drawing Sheets

(56) References Cited

FOREIGN PATENT DOCUMENTS

| | | | |
|---|---|---|---|
| WO | 2020142559 | A1 | 7/2020 |
| WO | 2021060453 | A1 | 4/2021 |
| WO | 2021067215 | A1 | 4/2021 |
| WO | 2021204159 | A1 | 10/2021 |
| WO | 2022086986 | A1 | 4/2022 |
| WO | 2022133064 | A1 | 6/2022 |
| WO | 2022241122 | A1 | 11/2022 |
| WO | 2022241265 | A1 | 11/2022 |
| WO | 2022253167 | A1 | 12/2022 |
| WO | 2022253167 | A8 | 3/2023 |
| WO | 2023114867 | A2 | 6/2023 |
| WO | 2023172925 | A1 | 9/2023 |
| WO | 2024109942 | A1 | 5/2024 |
| WO | 2024112853 | A1 | 5/2024 |

OTHER PUBLICATIONS

International Search Report and Written Opinion for International Application No. PCT/IB2024/052766, mailed Jun. 10, 2024, 13 Pages.

Ren J., et al., “Design and Synthesis of Benzylpiperidine Inhibitors Targeting the Menin-MLL1 Interface”, Bioorganic & Medicinal Chemistry Letters, vol. 26, No. 18, Sep. 15, 2016, pp. 4472-4476.

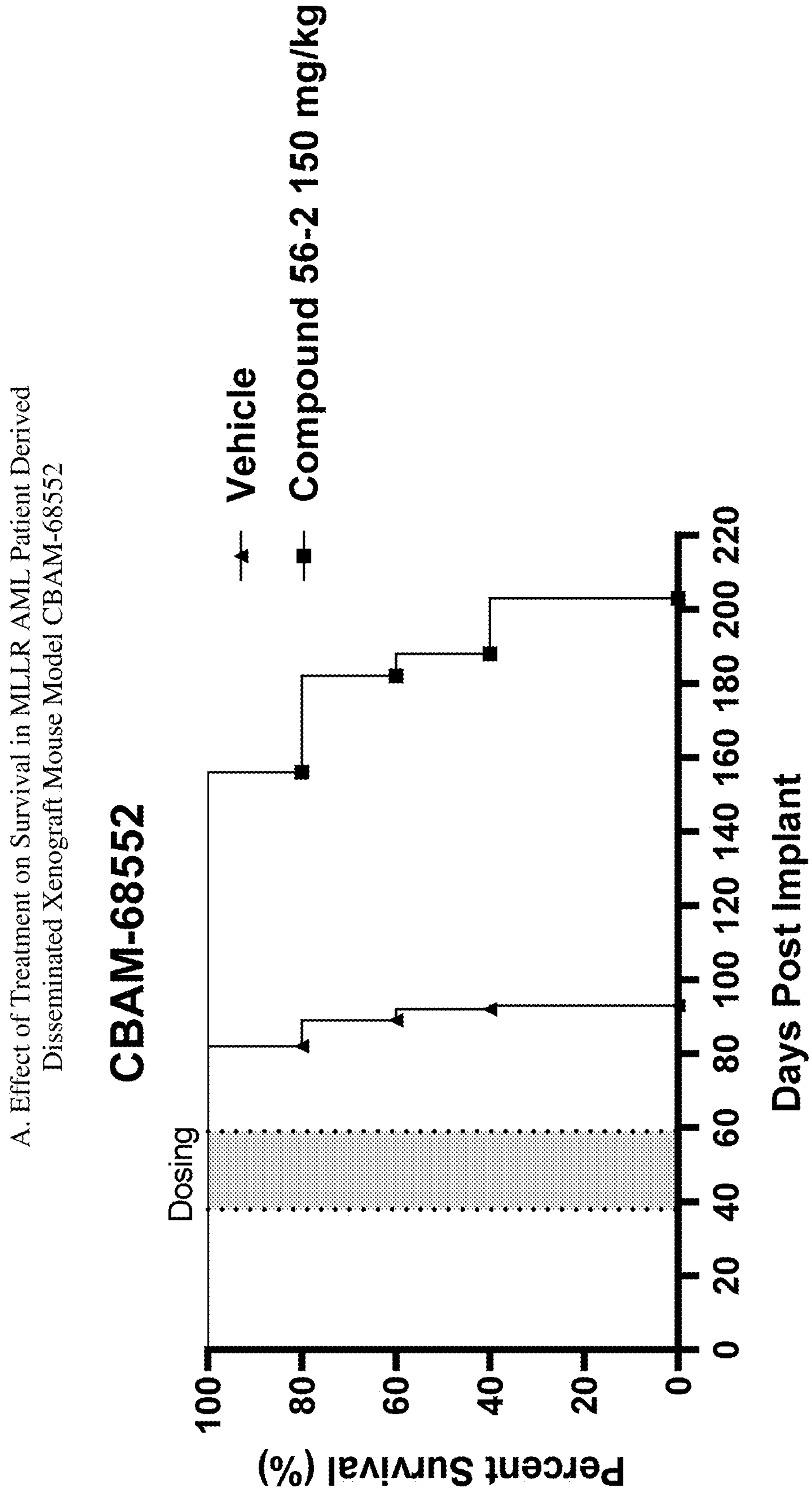
FIG. 3-A

B. Effect of Treatment on Survival in MLLR AML Patient Derived Disseminated Xenograft Mouse Model CBAM-44728
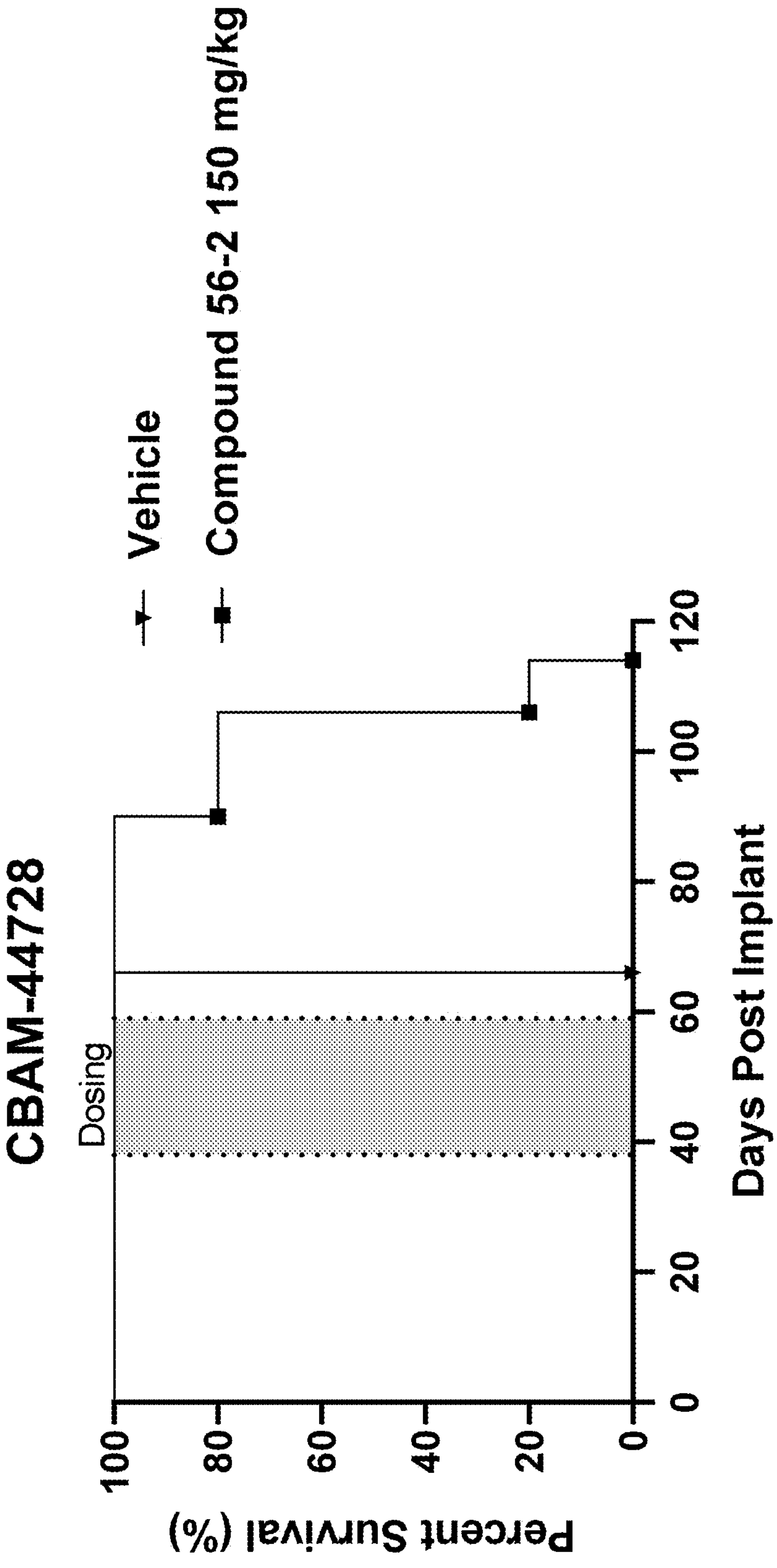
FIG. 3-B C. Effect of Treatment on Survival in MLLR AML Patient Derived Disseminated Xenograft Mouse Model DFAL-49600
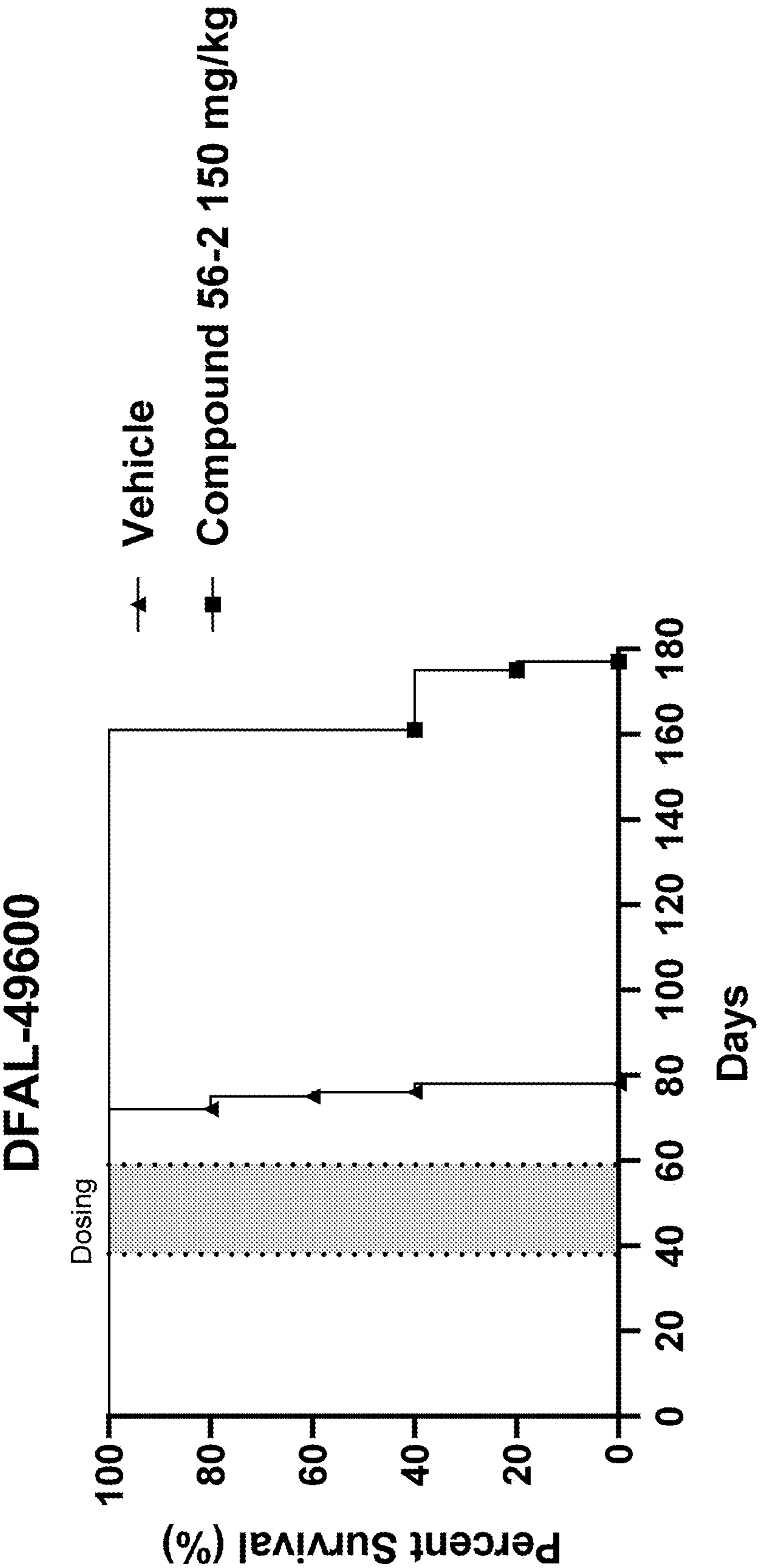
FIG. 3-C Anti-Tumor Effect in NPM1 mutant AML Patient Derived Disseminated Xenograft Model DFAM-16835

Combination Signal Heatmap (% Cell Viability) in MOLM-13 Cell Line (Compound 56-2/Venetoclax)

Anti-Tumor Effect in NPM1 mutant AML Patient Derived Disseminated Xenograft Model DFAM-16835
(Compound 56-2 in Combination with Venetoclax)

A. Effect of Treatment on Menin Protein Levels in MV-4-11 Cell Line (DMSO/Control)
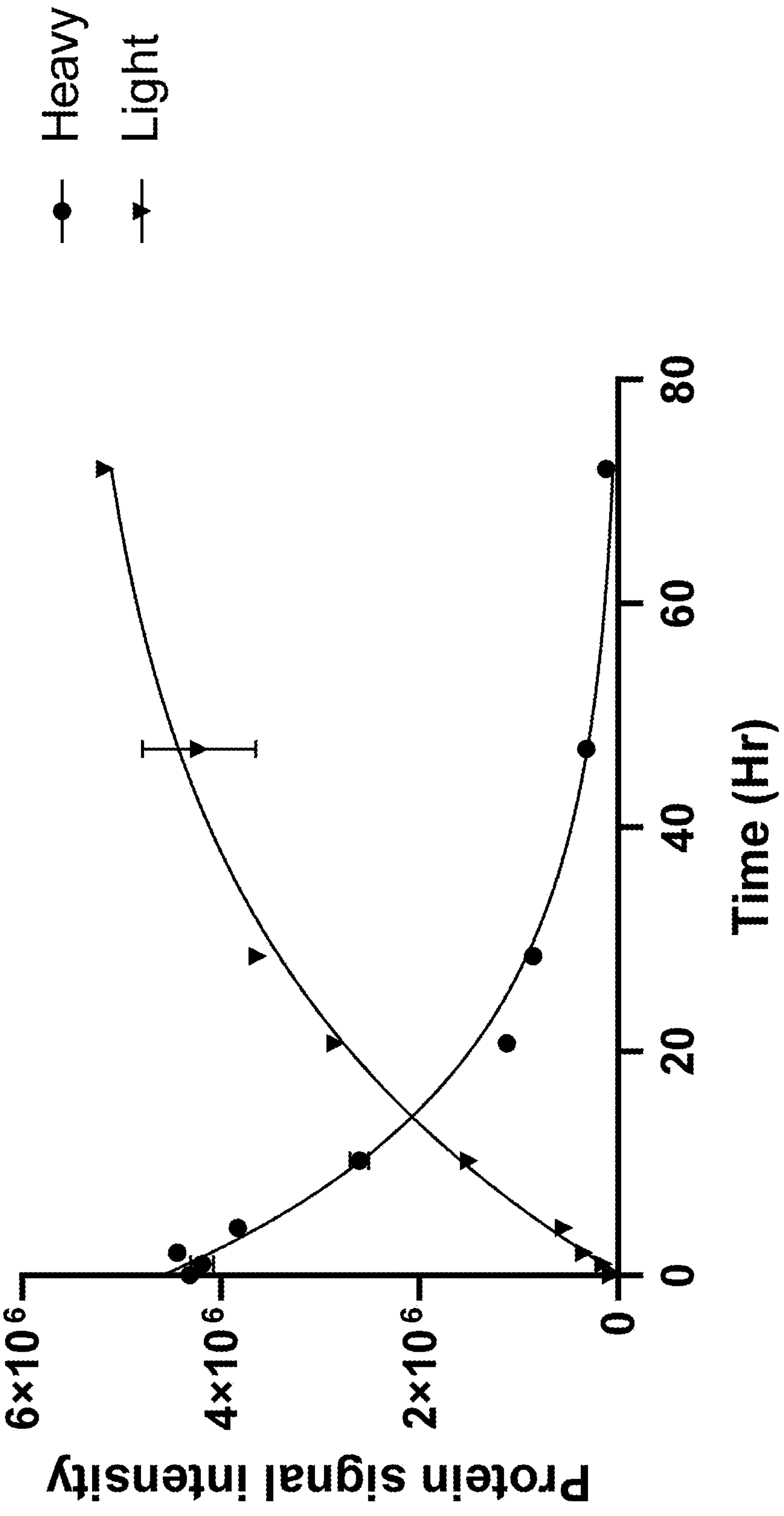
FIG. 7-A B. Effect of Treatment on Menin Protein Levels in MV-4-11 Cell Line (Compound 56-2)
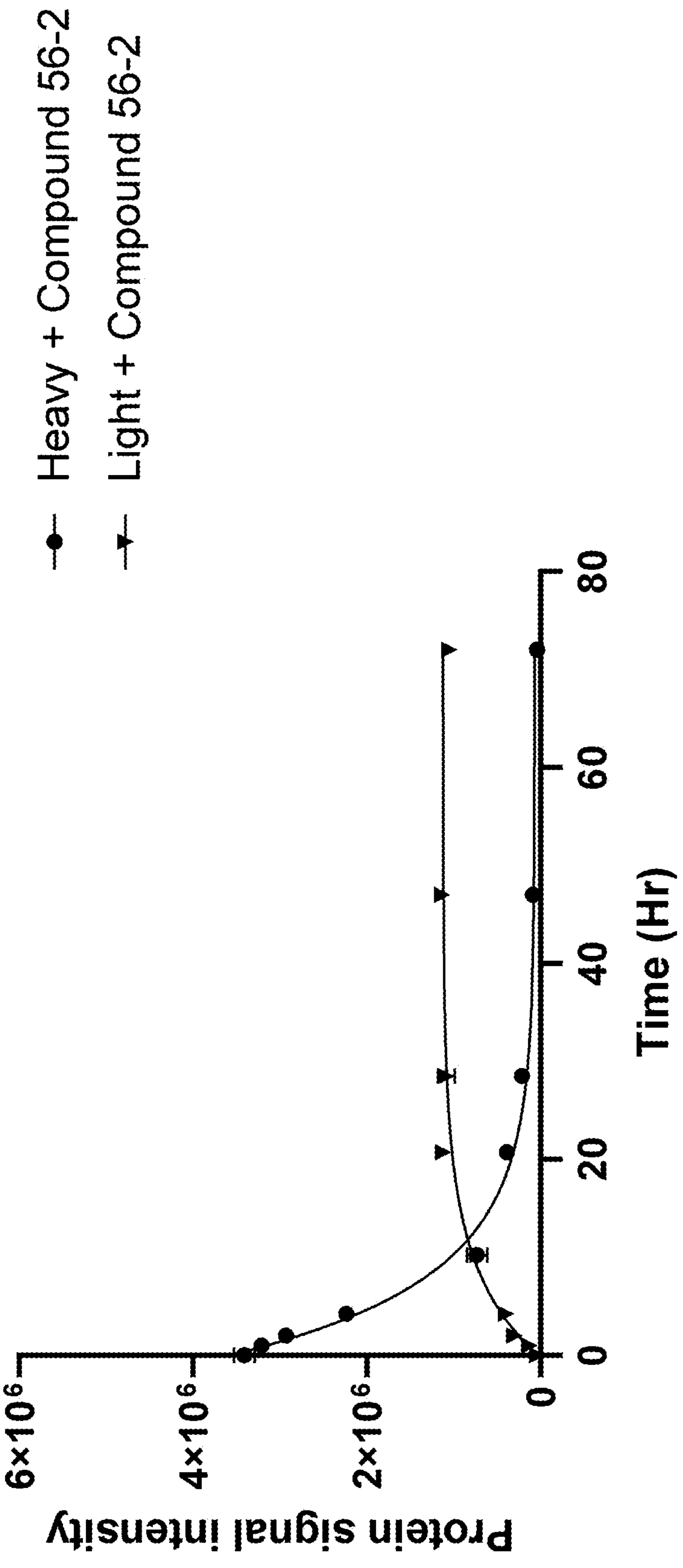
FIG. 7-B C. Effect of Treatment on Total Menin Protein Levels in MV-4-11 Cell Line (DMSO/Compound 56-2)
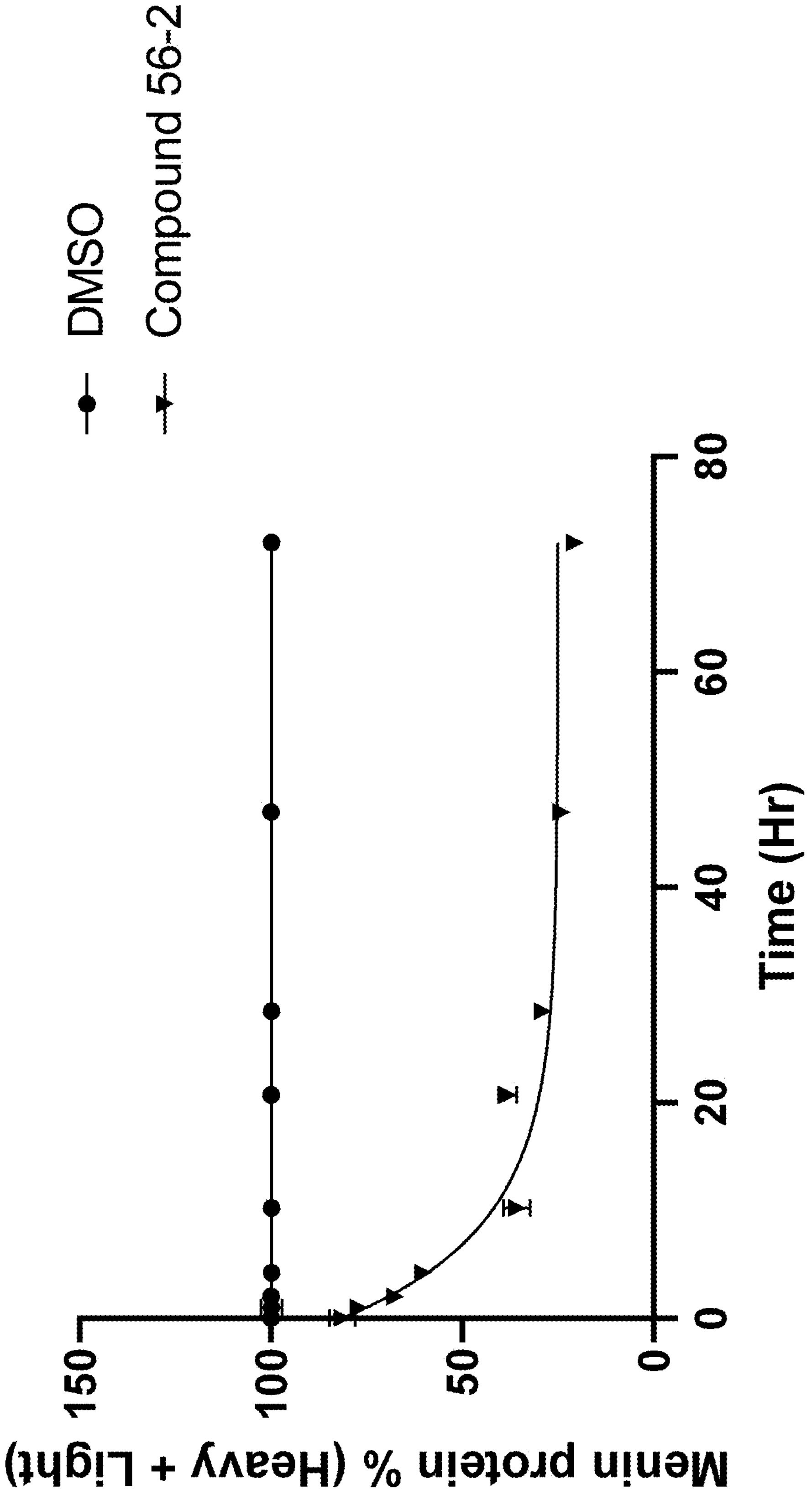
FIG. 7-C

1-H-PYRROLO[2,3-C]PYRIDINE COMPOUNDS

CROSS-REFERENCE TO RELATED APPLICATIONS

This application is a continuation of U.S. application Ser. No. 18/613,180 filed on Mar. 22, 2024, which claims the benefit under 35 U.S.C. § 119(e) of U.S. Provisional Application No. 63/491,978, filed on Mar. 24, 2023. The above-listed applications are incorporated by reference in their entirety for all purposes.

FIELD

The present disclosure relates generally to 1-H-pyrrolo[2,3-c]pyridines and pharmaceutically acceptable salts thereof. The specification further relates to pharmaceutical compositions comprising such compounds and salts; use of such compounds and salts to treat or prevent Menin-mediated conditions; kits comprising such compounds and salts; and methods for manufacturing such compounds and salts.

BACKGROUND

MLL1 is a histone methyltransferase encoded by the mixed-lineage leukemia 1 (MLL1) gene (also known as the KMT2A gene) on chromosome 11q23. MLL1 is a transcriptional coactivator that plays an essential role in regulating gene expression during early development and hematopoiesis. Multiple chromosomal translocations involving the MLL1 gene are the cause of certain acute myeloid leukemias (AML) and acute lymphoid leukemias (ALL). These chromosomal translocations have the downstream effect of upregulating HOXA9 and MEIS1 gene expression critical to leukemogenesis. HOXA9 and MEIS1 then contribute to enhanced proliferation and blockage of hematopoietic differentiation ultimately leading to acute leukemias. MLL1-rearranged (MLL1-r) leukemias are associated with resistance to standard therapies and higher rates of relapse. Patients with MLL1-r leukemias generally have an unfavorable prognosis and respond poorly to available treatments relative to patients with non-MLL1-r leukemias.

MLL1 normally associates with a cohort of highly conserved cofactors to form a macromolecular complex. One of these cofactors is Menin, a product of the MEN1 tumor suppressor gene. Menin is an essential cofactor necessary for binding of the MLL1 complex to promoters of target genes. The Menin binding site on MLL1 is located on the N-terminus and preserved throughout MLL1 fusion proteins resulting from the chromosomal rearrangements.

Current treatments for MLL1-r leukemias are conventional chemotherapeutics that non-selectively kill all rapidly proliferating cells including normal stem/progenitor cells in the bone marrow and other organs including the intestines. Such treatments can cause severe toxicities, side effects, and even secondary cancers. Targeted pharmacologic inhibition of Menin-MLL1 binding is a presently unexploited therapeutic approach for treating leukemias and other diseases associated with Menin activity. No approved pharmacological agents that inhibit Menin activity generally, or that inhibit Menin activity specifically, are currently available. Accordingly, there is a need for Menin inhibitors, particularly Menin inhibitors having pharmacologically appropriate properties including selectivity and bioavailability, that are suitable for administration to a subject in need of such treatment. The present disclosure addresses this large unmet need by providing such compounds together with corresponding pharmaceutical compositions and methods for the treatment or prevention of cancers, particularly MLL1-r leukemias, and other Menin-mediated conditions.

SUMMARY

In one aspect, the present disclosure provides compounds having the structure of Formula (I):

(I)

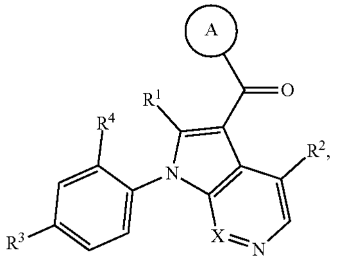

and pharmaceutically acceptable salts thereof, wherein:

$R^1$ is selected from the group consisting of hydrogen and methyl;

$R^2$ is hydrogen or fluoro;

$R^3$ is hydrogen or fluoro;

$R^4$ is selected from the group consisting of:

(a) —C(O)NR$^5$R$^6$;

(b) phenyl optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and (c) 5- or 6-membered ring heteroaryl having one, two, or three ring atoms independently selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

$R^5$ and $R^6$ are independently selected from $C_{1-4}$-alkyl and halo-$C_{1-4}$-alkyl; or $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl;

X is —C(R$^9$)— or —N—;

$R^9$ is selected from the group consisting of hydrogen, fluorine, and methyl;

A is selected from the group consisting of:

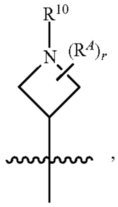
,
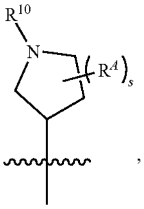
,
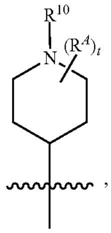
, and

-continued

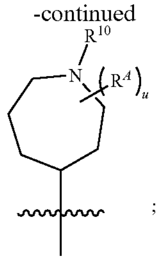

;

each $R^A$ substituent is optionally and independently selected from the group consisting of fluoro and $C_{1-4}$-alkyl;

r is 0, 1, or 2;

s is 0, 1, 2, or 3;

t is 0, 1, 2, 3, or 4;

u is 0, 1, 2, 3, 4, or 5;

$R^{10}$ is selected from the group consisting of $C_{1-10}$-alkyl, —$CH_2R^{11}$, or —$C(O)R^{12}$; wherein the $C_{1-10}$-alkyl is substituted with one or more —$NR^{13}R^{14}$.

$R^{11}$ is cyclohexyl optionally substituted with one or more substituents independently selected from the group consisting of $C_{1-4}$-alkyl, —$NR^{15}R^{16}$, and —$N(R^{17})S(O)_2R^{18}$;

$R^{12}$ is 5- to 10-membered ring heterocyclyl, wherein the heterocyclyl: (i) is a saturated or partially saturated monocyclic ring, bicyclic ring, or spirocyclic ring system, (ii) has one or two nitrogen ring atoms with the remaining ring atoms being carbon, and (iii) is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$;

$R^{13}$ and $R^{14}$ are independently selected from the group consisting of $C_{1-6}$-alkyl and $C_{1-6}$-alkoxy-$C_{1-6}$-alkyl; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

In another aspect, the present disclosure provides compounds of Formula (I) having a structure selected from Formulae (I-1) through (I-69) as further defined in this specification, and pharmaceutically acceptable salts thereof.

In another aspect, the present disclosure provides pharmaceutical compositions comprising a therapeutically-effective amount of a compound having the structure of Formula (I), or a pharmaceutically acceptable salt thereof, and a pharmaceutically acceptable carrier.

In another aspect, the present disclosure provides pharmaceutical compositions comprising therapeutically-effective amounts of a compound having the structure of Formula (I), or a pharmaceutically acceptable salt thereof; a second pharmacological agent; and a pharmaceutically acceptable carrier.

In another aspect, the present disclosure provides methods for treating or preventing a Menin-mediated condition by administering a therapeutically effective amount of a compound having the structure of Formula (I), or pharmaceutically acceptable salt thereof, to a subject in need thereof. In a further aspect, the Menin-mediated condition cancer. In a still further aspect, the Menin-mediated condition is a hematological malignancy. In a still further aspect, the Menin-mediated condition is a solid tumor cancer.

In another aspect, the present disclosure provides compounds having the structure of Formula (I), or pharmaceutically acceptable salts thereof, for use as a medicament for treating or preventing a Menin-mediated condition.

In another aspect, the present disclosure provides use of compounds having the structure of Formula (I), or pharmaceutically acceptable salts thereof, to prepare a medicament for treating or preventing a Menin-mediated condition.

In another aspect, the present disclosure provides kits comprising a compound having the structure of Formula (I), or pharmaceutically acceptable salt thereof.

In another aspect, the present disclosure provides methods for preparing compounds having the structure of Formula (I), or pharmaceutically acceptable salts thereof.

BRIEF DESCRIPTION OF THE DRAWINGS

FIGS. 3-A, 3-B, and 3-C illustrate the effect of treatment with a Menin inhibitor (the compound of Example 56-2) on survival in MLLr AML Patient Derived Disseminated Xenograft Mouse Models CBAM-68552 (FIG. 3-A), CBAM-44728 (3-B), and DFAL-49600 (3-C).

FIGS. 7-A, 7-B, and 7-C illustrate the effect of treatment with a Menin inhibitor (the compound of Example 56-2) on Menin protein levels in an MV-4-11 cell line. FIG. 7-A shows treatment with a DMSO control. FIG. 7-B shows treatment with a Menin inhibitor (the compound of Example 56-2). FIG. 7-C shows total Menin protein ("heavy" and "light") signal normalized to DMSO.

DETAILED DESCRIPTION

Figure 1:
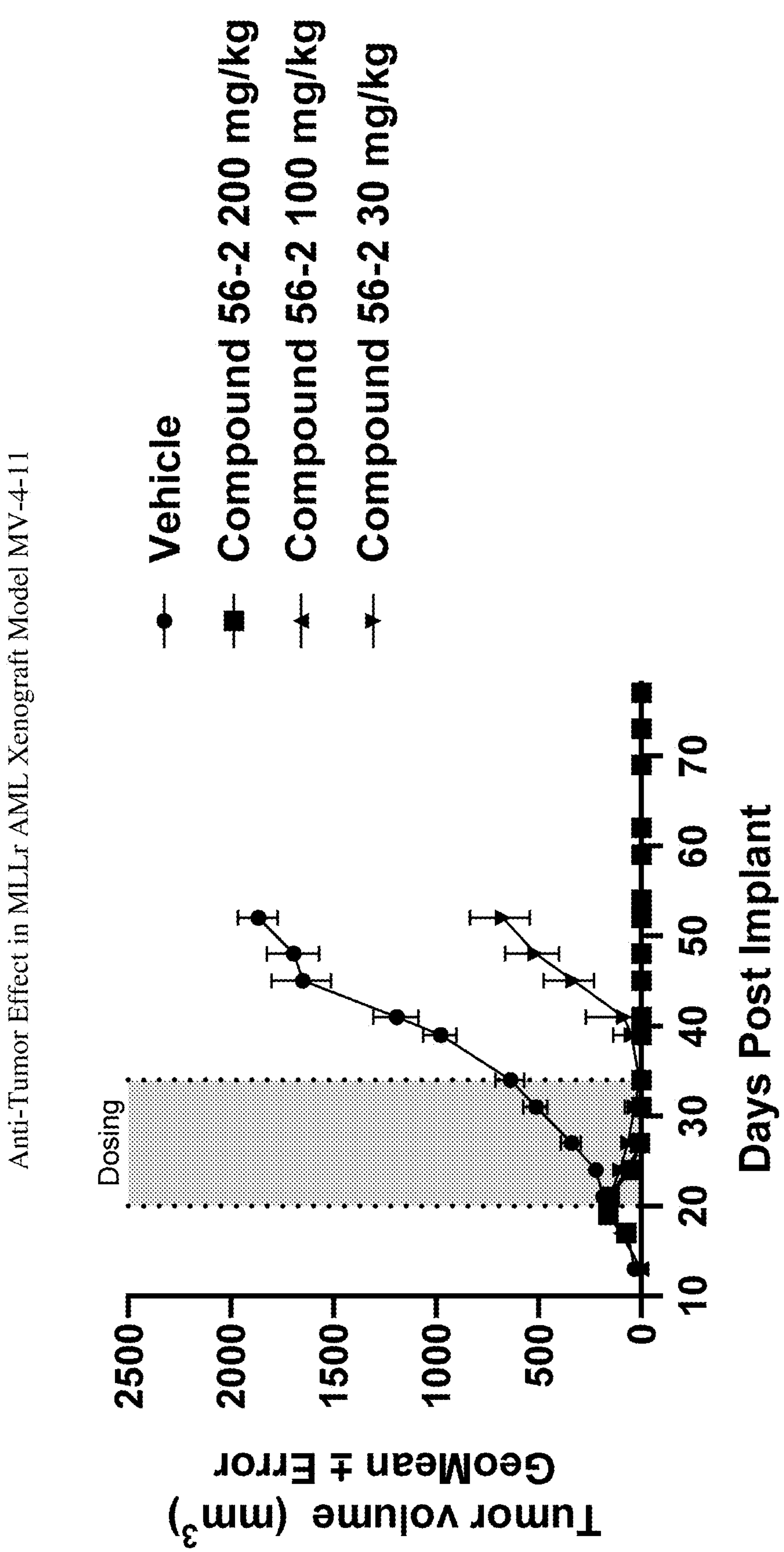
FIG. 1 illustrates the effect of treatment with a Menin inhibitor (the compound of Example 56-2) on tumor volume in MLLr AML Xenograft Model MV-4-11.

Many embodiments are detailed throughout the specification and will be apparent to a reader skilled in the art. The specification is not to be interpreted as being limited to any particular embodiment(s) described herein.

I. Definitions

With respect to the embodiments disclosed in this specification, the following terms have the meanings set forth below:

Reference to "a" or "an" means "one or more." Throughout, the plural and singular should be treated as interchangeable, other than the indication of number.

Unless the context requires otherwise, the words "comprise" or "comprises" or "comprising" are used on the basis and clear understanding that they are to be interpreted inclusively, rather than exclusively, and that Applicants intend each of those words to be so interpreted in construing this patent, including the claims below.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I).

The term "cyano" (alone or in combination with another term(s)) means —CN.

The term "alkyl" (alone or in combination with another term(s)) means a straight- or branched-chain saturated hydrocarbyl substituent (i.e., a substituent containing only carbon and hydrogen). Alkyl typically contains from 1 to about 20 carbon atoms, more typically from 1 to about 12 carbon atoms, even more typically from 1 to about 8 carbon atoms, and still even more typically from 1 to about 6 carbon atoms. Examples of such substituents include methyl, ethyl, propyl (including n-propyl and isopropyl), butyl (including n-butyl, isobutyl, sec-butyl, and tert-butyl), pentyl (including n-pentyl, isoamyl, and 2,2-dimethylpropyl), and hexyl.

The term "alkenyl" (alone or in combination with another term(s)) means a straight or branched chain saturated hydrocarbyl substituent (i.e., a substituent containing only carbon and hydrogen) containing one or more double bonds in the alkyl chain. Alkenyl typically contains from 2 to about 20 carbon atoms, more typically from 2 to about 12 carbon atoms, even more typically from 2 to about 8 carbon atoms, and still even more typically from 2 to about 6 carbon atoms. Examples of such substituents include ethylenyl, propylenyl (including n-propylenyl and isopropylenyl), butylenyl (including n-butylenyl, isobutylenyl, sec-butylenyl, and tert-butylenyl), pentylenyl (including n-pentylenyl), and hexylenyl.

The term "cycloalkyl" (alone or in combination with another term(s)) means a saturated carbocyclyl substituent containing from 3 to about 14 carbon ring atoms, more typically from 3 to about 12 carbon ring atoms, and even more typically from 3 to about 8 carbon ring atoms. A cycloalkyl includes a single carbon ring, which typically contains from 3 to 6 carbon ring atoms. Examples of single-ring cycloalkyls include cyclopropyl, cyclobutyl, cyclopentyl, and cyclohexyl.

The term "alkoxy" (alone or in combination with another term(s)) means an alkylether substituent, i.e., alkyl-O—. Examples of alkoxy include methoxy ($CH_3$—O—), ethoxy, n-propoxy, iso-propoxy, n-butoxy, iso-butoxy, sec-butoxy, and tert-butoxy. Thus, for example, the term "alkoxyalkyl" (alone or in combination with another term(s)) means alkyl substituted with alkoxy such as "methoxymethyl" which may be depicted as:

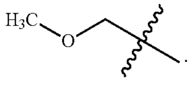

The term "heterocyclyl" (alone or in combination with another term(s)) means a saturated, partially saturated, or completely unsaturated (i.e., heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur in stable combinations known to those of skill in the art.

In some instances, the number of carbon atoms in a substituent (e.g., alkyl, cycloalkyl, etc.) is indicated by the prefix "$C_{x-y}$-", wherein x is the minimum and y is the maximum number of carbon atoms in the substituent. Thus, for example, "$C_{1-6}$-alkyl" refers to an alkyl substituent containing from 1 to 6 carbon atoms. Illustrating further, $C_{3-6}$-cycloalkyl refers to a cycloalkyl substituent containing from 3 to 6 carbon ring atoms.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Where there is more than one hydrogen replaced with halogens, the halogens may be the identical or different. Examples of haloalkyls include fluoromethyl, difluoromethyl, trifluoromethyl, difluoroethyl, 1,1,1-trifluoroethyl, pentafluoroethyl, difluoropropyl, heptafluoropropyl chloromethyl, dichloromethyl, trichloromethyl, difluorochloromethyl, dichlorofluoromethyl, and dichloropropyl.

The term "atropisomers" refers to stereoisomers resulting from hindered rotation about one or more single bonds, where the energy barrier to rotation is high enough to allow for the isolation of the conformers. Atropisomers are depicted in the chemical structures of the present disclosure by wedged bonds (solid or broken (hashed)) in aromatic rings in which the wedged bond is connected to the σ-bond around which axial rotation is hindered.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted," a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as "optionally substituted", the substituent may be either (1) not substituted, or (2) substituted. If a carbon of a substituent is described as optionally substituted with one or more of a list of substituents, one or more of the hydrogens on the carbon (to the extent there are any) may separately and/or together be replaced with an independently selected optional substituent. If a nitrogen of a substituent is described as optionally substituted with one or more of a list of substituents, one or more of the hydrogens on the nitrogen (to the extent there are any) may each be replaced with an independently selected optional substituent.

If substituents are described as being "independently selected" from a group, each substituent is selected independently of the other. Each substituent therefore may be identical to or different from the other substituent(s).

The term "pharmaceutically acceptable" is used adjectivally in this specification to mean that the modified noun is appropriate for use as a pharmaceutical product or as a part of a pharmaceutical product. For example, "pharmaceutically acceptable salts" are salts that are suitable for use in mammals, particularly humans, and include salts with an inorganic base, organic base, inorganic acid, organic acid, or basic or acidic amino acid that are suitable for use in mammals, particularly humans.

A "therapeutically effective amount" of a pharmacological agent is an amount that is sufficient to effect beneficial or desired results, including clinical results, and, as such, will depend upon the situation in which it is being administered. Where the pharmacological agent is being administered to treat cancer, for example, a therapeutically effective amount of the agent is an amount of the agent that is sufficient, either alone or in combination with additional therapies, to provide an anti-cancer effect in a subject as compared to the response obtained without administration of the agent.

The term "preventing" is readily understood by an ordinarily skilled physician and, with respect to treatment of a particular condition, can include is intended to have its normal meaning and includes primary prophylaxis to prevent the development of the condition and secondary prophylaxis whereby the condition has already developed and the patient is temporarily or permanently protected against exacerbation or worsening of the disease or the development of new symptoms associated with the condition.

The terms "treating" is readily understood by an ordinarily skilled physician and, with respect to treatment of a particular condition, can include (1) diminishing the extent or cause of the condition being treated, and/or (2) alleviating or ameliorating one or more symptoms associated with that condition. Treatment of cancer, for example, can include stabilizing (i.e., not worsening), delaying, or slowing the spread or progression of the cancer; prolonging survival as compared to expected survival if not receiving treatment; and/or otherwise ameliorating or palliating the cancer or the severity of the cancer, in whole or in part.

II. Compounds

A. Compounds of Formula (I)

In one embodiment, the present disclosure provides compounds having the structure of Formula (I):

(I)

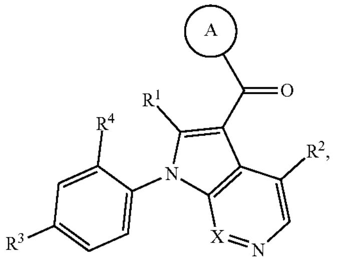

and pharmaceutically acceptable salts thereof, wherein:

$R^1$ is selected from the group consisting of hydrogen and methyl;

$R^2$ is hydrogen or fluoro;

$R^3$ is hydrogen or fluoro;

$R^4$ is selected from the group consisting of:

(a) —C(O)$NR^5R^6$;

(b) phenyl optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and (c) 5- or 6-membered ring heteroaryl having one, two, or three ring atoms independently selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

$R^5$ and $R^6$ are independently selected from $C_{1-4}$-alkyl and halo-$C_{1-4}$-alkyl; or $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl;

X is —C($R^9$)— or —N—;

$R^9$ is selected from the group consisting of hydrogen, fluorine, and methyl;

A is selected from the group consisting of:

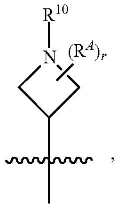
,
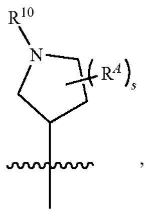
,
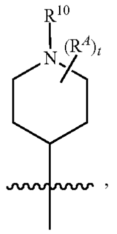
, and

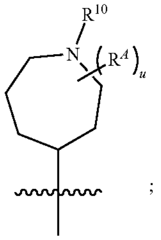
;

each $R^A$ substituent is optionally and independently selected from the group consisting of fluoro and $C_{1-4}$-alkyl;

r is 0, 1, or 2;

s is 0, 1, 2, or 3;

t is 0, 1, 2, 3, or 4;

u is 0, 1, 2, 3, 4, or 5;

$R^{10}$ is selected from the group consisting of $C_{1-10}$-alkyl, —$CH_2R^{11}$, or —C(O)$R^{12}$; wherein the $C_{1-10}$-alkyl is substituted with one or more —$NR^{13}R^{14}$.

$R^{11}$ is cyclohexyl optionally substituted with one or more substituents independently selected from the group consisting of $C_{1-4}$-alkyl, —$NR^{15}R^{16}$, and —N($R^{17}$)S(O)$_2R^{18}$;

$R^{12}$ is 5- to 10-membered ring heterocyclyl, wherein the heterocyclyl: (i) is a saturated or partially saturated monocyclic ring, bicyclic ring, or spirocyclic ring system, (ii) has one or two nitrogen ring atoms with the remaining ring atoms being carbon, and (iii) is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —N($R^{22}$)S(O)$_2R^{23}$;

$R^{13}$ and $R^{14}$ are independently selected from the group consisting of $C_{1-6}$-alkyl and $C_{1-6}$-alkoxy-$C_{1-6}$-alkyl;

and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), and pharmaceutically acceptable salts thereof, wherein the compound is an atropisomer.

In some embodiments, the present disclosure provides compounds of Formula (I) having the structure of Formula (I-A):

(I-A)

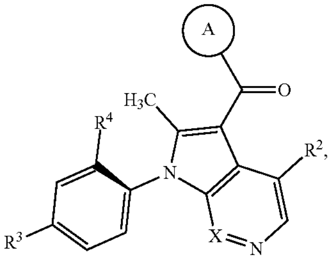

and pharmaceutically acceptable salts thereof, wherein $R^2$, $R^3$, $R^4$, A, and X, are as defined in the various embodiments described in this specification.

In some embodiments, the present disclosure provides compounds of Formula (I) having the structure of Formula (I-B):

(I-B)

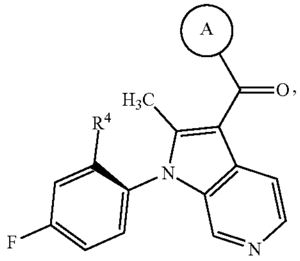

and pharmaceutically acceptable salts thereof, wherein $R^4$ and A are as defined in the various embodiments described in this specification.

In some embodiments, the present disclosure provides compounds of Formula (I) having the structure of Formula (I-C):

(I-C)

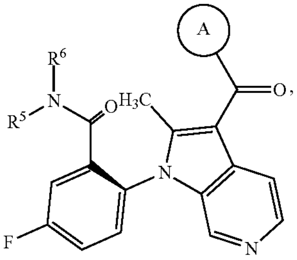

and pharmaceutically acceptable salts thereof, wherein $R^5$, $R^6$, and A are as defined in the various embodiments described in this specification.

In some embodiments, the present disclosure provides compounds of Formula (I) having the structure of Formula (I-D):

(I-D)

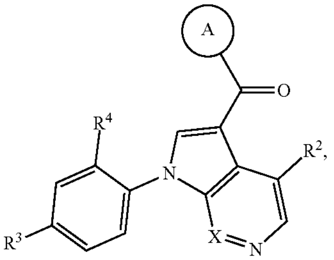

and pharmaceutically acceptable salts thereof, wherein $R^2$, $R^3$, $R^4$, A, and X, are as defined in the various embodiments described in this specification.

In some embodiments, the present disclosure provides compounds of Formula (I) having the structure of Formula (I-E):

(I-E)

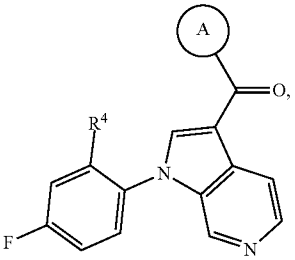

and pharmaceutically acceptable salts thereof, wherein $R^4$ and A are as defined in the various embodiments described in this specification.

In some embodiments, the present disclosure provides compounds of Formula (I) having the structure of Formula (I-F):

(I-F)

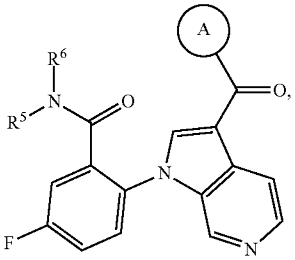

and pharmaceutically acceptable salts thereof, wherein $R^5$, $R^6$, and A are as defined in the various embodiments described in this specification.

X and $R^9$ Substituents

In some embodiments, the present disclosure provides compounds having the structure of Formula (I), Formula (I-A), or Formula (I-D), and pharmaceutically acceptable salts thereof, wherein X is —C($R^9$)—. In one aspect, $R^9$ is hydrogen. In another aspect, $R^9$ is fluoro. In another aspect, $R^9$ is methyl.

In some embodiments, the present disclosure provides compounds having the structure of Formula (I), Formula (I-A), or Formula (I-D), and pharmaceutically acceptable salts thereof, wherein X is —N—.

In some embodiments, the present disclosure provides compounds having the structure of Formula (I), Formula (I-A), or Formula (I-D), and pharmaceutically acceptable salts thereof, wherein X is —C($R^9$)— or —N—, and $R^9$ is hydrogen or fluoro.

$R^1$ Substituent

In some embodiments, the present disclosure provides compounds having the structure of Formula (I), and pharmaceutically acceptable salts thereof, wherein $R^1$ is hydrogen.

In some embodiments, the present disclosure provides compounds having the structure of Formula (I), and pharmaceutically acceptable salts thereof, wherein $R^1$ is methyl.

$R^2$ Substituent

In some embodiments, the present disclosure provides compounds having the structure of Formula (I), Formula (I-A), or Formula (I-D), and pharmaceutically acceptable salts thereof, wherein $R^2$ is hydrogen.

In some embodiments, the present disclosure provides compounds having the structure of Formula (I), Formula (I-A), or Formula (I-D), and pharmaceutically acceptable salts thereof, wherein $R^2$ is fluoro.

$R^3$ Substituents

In some embodiments, the present disclosure provides compounds having the structure of Formula (I), Formula (I-A), or Formula (I-D), and pharmaceutically acceptable salts thereof, wherein $R^3$ is hydrogen.

In some embodiments, the present disclosure provides compounds having the structure of Formula (I), Formula (I-A), or Formula (I-D), and pharmaceutically acceptable salts thereof, wherein $R^3$ is fluoro.

$R^4$=—C(O)$NR^5R^6$

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^4$ is —C(O)$NR^5R^6$.

$R^4$=—C(O)$NR^5R^6$ and $R^5$/$R^6$=$C_{1-4}$-Alkyl or Halo-$C_{1-4}$-alkyl

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^4$ is —C(O)$NR^5R^6$, and $R^5$ and $R^6$ are independently selected from $C_{1-4}$-alkyl and halo-$C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^4$ is —C(O)$NR^5R^6$, and $R^5$ and $R^6$ are independently selected from $C_{1-4}$-alkyl. In one aspect, $R^5$ and $R^6$ are independently selected from $C_{1-4}$-alkyl. In another aspect, at least one of $R^5$ and $R^6$ is methyl. In another aspect, at least one of $R^5$ and $R^6$ is ethyl. In another aspect, at least one of $R^5$ and $R^6$ is isopropyl. In another aspect, $R^5$ and $R^6$ are each ethyl. In another aspect, one of $R^5$ and $R^6$ is methyl and the other is isopropyl. In another aspect, one of $R^5$ and $R^6$ is ethyl and the other is isopropyl. In another aspect, $R^5$ and $R^6$ are each isopropyl. In another aspect, $R^5$ and $R^6$ are independently selected from ethyl and isopropyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^4$ is —C(O)$NR^5R^6$, and one of $R^5$ and $R^6$ is $C_{1-4}$-alkyl and the other is halo-$C_{1-4}$-alkyl. In one aspect, one of $R^5$ and $R^6$ is methyl. In another aspect, one of $R^5$ and $R^6$ is ethyl. In another aspect, one of $R^5$ and $R^6$ is isopropyl. In another aspect, one of $R^5$ and $R^6$ is trifluoroethyl. In another aspect, one of $R^5$ and $R^6$ is trifluoroisopropyl. In another aspect, one of $R^5$ and $R^6$ is ethyl and the other is trifluoroethyl. In another aspect, one of $R^5$ and $R^6$ is ethyl and the other is trifluoroisopropyl. In another aspect, one of $R^5$ and $R^6$ is isopropyl and the other is trifluoroethyl. In another aspect, one of $R^5$ and $R^6$ is isopropyl and the other is trifluoroisopropyl. In another aspect, $R^5$ is selected from ethyl and isopropyl, and $R^6$ is selected from trifluoroethyl and trifluoroisopropyl. In another aspect, $R^5$ and $R^6$ are independently selected from halo-$C_{1-4}$-alkyl. In another aspect, $R^5$ and $R^6$ are trifluoro-$C_{1-4}$-alkyl. In another aspect, $R^5$ and $R^6$ are independently selected from the group consisting of ethyl, isopropyl, trifluoroethyl, and trifluoroisopropyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^4$ is —C(O)$NR^5R^6$, and $R^5$ and $R^6$ are independently selected from $C_{1-4}$-alkyl and halo-$C_{1-4}$-alkyl wherein one or more hydrogen atoms of the $C_{1-4}$-alkyl and/or halo-$C_{1-4}$-alkyl substituents are deuterium. In one aspect, one or more hydrogen atoms of the $C_{1-4}$-alkyl substituent are deuterium. In another aspect, one or more hydrogen atoms of the halo-$C_{1-4}$-alkyl substituent are deuterium. In another aspect, $R^5$ and $R^6$ are each isopropyl wherein one or more hydrogen atoms of one or both isopropyl are deuterium. In another aspect, $R^5$ and $R^6$ are each isopropyl wherein all hydrogen atoms of one or both isopropyl are deuterium.

$R^4$=—C(O)$NR^5R^6$ and $R^5$/$R^6$ Together Form a Ring

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl. In one aspect, the 5- to 7-membered ring heterocyclyl is selected from the group consisting of optionally substituted pyrrolidinyl, piperidinyl, and morpholinyl. In another aspect, the 5- to 7-membered ring heterocyclyl is optionally substituted with one or two $C_{1-4}$-alkyl. In another aspect, the 5- to 7-membered ring heterocyclyl is optionally substituted with one or two methyl. In another aspect, the 5- to 7-membered ring heterocyclyl is optionally substituted with one or two halo-$C_{1-4}$-alkyl. In another aspect, the 5- to 7-membered ring heterocyclyl is optionally substituted with one or two trifluoromethyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^5$ and $R^6$, together with the nitrogen atom to which they are attached, form an optionally substituted pyrrolidinyl. In one aspect, the pyrrolidinyl is substituted with one or two methyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^5$ and $R^6$, together with the nitrogen atom to which they are attached, form an optionally substituted piperidinyl. In one aspect, the piperidinyl is substituted with one or two methyl.

In some embodiments, the present disclosure provides compounds having the structure Formula (I), Formula (I-A), Formula (I-B), Formula (I-C), Formula (I-D), Formula (I-E), or Formula (I-F), and pharmaceutically acceptable salts thereof, wherein $R^5$ and $R^6$, together with the nitrogen atom to which they are attached, form an optionally substituted morpholinyl. In one aspect, the morpholinyl is substituted with one or two methyl.

$R^4$=Phenyl

In some embodiments, the present disclosure provides compounds having the structure of Formula (I), Formula (I-A), Formula (I-B), Formula (I-D), or Formula (I-E), and pharmaceutically acceptable salts thereof, wherein $R^4$ is phenyl optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl. In one aspect, $R^4$ is phenyl optionally substituted with one to three substituents independently selected from fluoro, cyano, $C_{1-4}$-alkyl, and halo-$C_{1-4}$-alkyl. In another aspect, $R^4$ is phenyl optionally substituted with one to three fluoro. In another aspect, $R^4$ is phenyl optionally substituted with one to three cyano. In another aspect, $R^4$ is phenyl optionally substituted with one to three $C_{1-4}$-alkyl. In another aspect, $R^4$ is phenyl optionally substituted with one to three halo-$C_{1-4}$-alkyl. In another aspect, $R^4$ is phenyl optionally substituted with one to three $C_{3-4}$-cycloalkyl. In another aspect, $R^4$ is phenyl optionally substituted with one to three halo-$C_{3-4}$-cycloalkyl.

$R^4$=Heteroaryl

In some embodiments, the present disclosure provides compounds having the structure of Formula (I), Formula (I-A), Formula (I-B), Formula (I-D), or Formula (I-E), and pharmaceutically acceptable salts thereof, wherein $R^4$ is 5- or 6-membered ring heteroaryl having one, two, or three ring atoms independently selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl.

In some embodiments, the present disclosure provides compounds having the structure of Formula (I), Formula (I-A), Formula (I-B), Formula (I-D), or Formula (I-E), and pharmaceutically acceptable salts thereof, wherein $R^4$ is 5-membered ring heteroaryl having one or two ring atoms independently selected from nitrogen, oxygen, and sulfur with the remaining ring atoms being carbon, wherein the heteroaryl is optionally substituted with one to three substituents independently selected from the group consisting of fluoro, $C_{1-4}$-alkyl, halo-$C_{1-4}$-alkyl, $C_{3-4}$-cycloalkyl, and halo-$C_{3-4}$-cycloalkyl.

In some embodiments, the present disclosure provides compounds having the structure of Formula (I), Formula (I-A), Formula (I-B), Formula (I-D), or Formula (I-E), and pharmaceutically acceptable salts thereof, wherein $R^4$ is 6-membered ring heteroaryl having one or two ring atoms independently selected from nitrogen, oxygen, and sulfur with the remaining ring atoms being carbon, wherein the heteroaryl is optionally substituted with one to three substituents independently selected from the group consisting of fluoro, $C_{1-4}$-alkyl, halo-$C_{1-4}$-alkyl, $C_{3-4}$-cycloalkyl, and halo-$C_{3-4}$-cycloalkyl.

In some embodiments, the present disclosure provides compounds having the structure of Formula (I), Formula (I-A), Formula (I-B), Formula (I-D), or Formula (I-E), and pharmaceutically acceptable salts thereof, wherein $R^4$ is 5- or 6-membered ring heteroaryl selected from the group consisting of optionally substituted pyrazolyl, imidazolyl, thiazolyl, isothiazolyl, pyridinyl, pyrimidinyl, pyrazinyl, and pyridazinyl. In one aspect, the heteroaryl is selected from the group consisting of optionally substituted pyrazolyl, thiazolyl, pyridinyl, and pyrimidinyl. In another aspect, the heteroaryl is optionally substituted pyrazolyl. In another aspect, the heteroaryl is optionally substituted thiazolyl. In another aspect, the heteroaryl is optionally substituted pyridinyl. In another aspect, the heteroaryl is optionally substituted pyrimidinyl.

In some embodiments, the present disclosure provides compounds having the structure of Formula (I), Formula (I-A), Formula (I-B), Formula (I-D), or Formula (I-E), and pharmaceutically acceptable salts thereof, wherein the $R^4$ heteroaryl is optionally substituted with one to three substituents independently selected from the group consisting of $C_{1-4}$-alkyl, halo-$C_{1-4}$-alkyl, and $C_{3-4}$-cycloalkyl. In one aspect, the $R^4$ heteroaryl is optionally substituted with one or two substituents independently selected from the group consisting of $C_{1-4}$-alkyl and halo-$C_{1-4}$-alkyl. In another aspect, the $R^4$ heteroaryl is substituted with one or two fluoro. In another aspect, the $R^4$ heteroaryl is substituted with one or two cyano. In another aspect, the $R^4$ heteroaryl is substituted with one or two $C_{1-4}$-alkyl. In another aspect, the $R^4$ heteroaryl is substituted with one or two $C_{1-3}$-alkyl. In another aspect, the $R^4$ heteroaryl is substituted with methyl and isopropyl. In another aspect, the $R^4$ heteroaryl is substituted with one or two halo-$C_{1-4}$-alkyl. In another aspect, the $R^4$ heteroaryl is substituted with one or two fluoropropyl. In another aspect, the $R^4$ heteroaryl is substituted with one or two $C_{3-4}$-cycloalkyl. In another aspect, the $R^4$ heteroaryl is substituted with one or two cyclopropyl. In another aspect, the $R^4$ heteroaryl is substituted with one or two halo-$C_{3-4}$-cycloalkyl. In another aspect, the $R^4$ heteroaryl selected from the group consisting of optionally substituted pyrazolyl, imidazolyl, thiazolyl, isothiazolyl, pyridinyl, pyrimidinyl, pyrazinyl, and pyridazinyl.

$R^4$ Substituents

In further embodiments, the present disclosure provides compounds having the structure of Formula (I), Formula (I-A), Formula (I-B), Formula (I-D), or Formula (I-E), and pharmaceutically acceptable salts thereof, wherein $R^4$ is selected from the group consisting of:

(a) —C(O)NR$^5$R$^6$; and (b) 5- or 6-membered ring heteroaryl having one, two, or three ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

In further embodiments, the present disclosure provides compounds having the structure of Formula (I), Formula (I-A), Formula (I-B), Formula (I-D), or Formula (I-E), and pharmaceutically acceptable salts thereof, wherein $R^4$ is selected from the group consisting of:

(a) —C(O)$NR^5R^6$; and (b) 5-membered ring heteroaryl having one or two ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- or 6-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

In further embodiments, the present disclosure provides compounds having the structure of Formula (I), Formula (I-A), Formula (I-B), Formula (I-D), or Formula (I-E), and pharmaceutically acceptable salts thereof, wherein $R^4$ is selected from the group consisting of:

(a) —C(O)$NR^5R^6$; and (b) 6-membered ring heteroaryl having one or two ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- or 6-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

$R^A$ Substituent

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein r, s, t, and u are independently 0 or 1. In one aspect, r, s, t, and u are 1. In another aspect, r, s, t, and u are 0.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^A$ is fluoro.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^A$ is $C_{1-4}$-alkyl. In one aspect, $R^A$ is methyl. In another aspect, r, s, t, and u are 1, and $R^A$ is methyl.

A Ring

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein A is selected from the group consisting of:

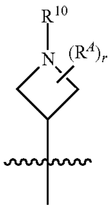, 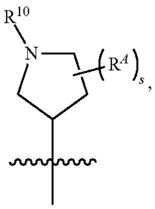, and 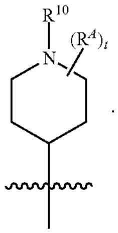.

In one aspect, A is selected from the group consisting of:

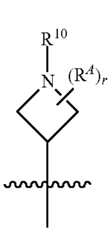 and 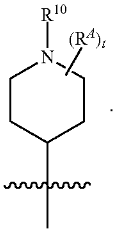.

In another aspect, A is selected from the group consisting of:

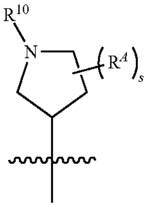 and 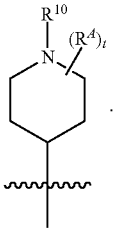.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein A is:

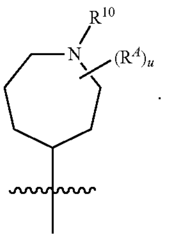.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein A is:

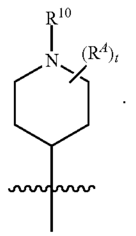

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein A is:

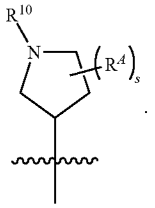

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein A is:

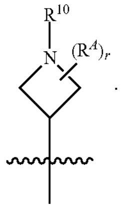

$R^{10}$=$C_{1-10}$-Alkyl

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is $C_{1-10}$-alkyl substituted with one or more —$NR^{13}R^{14}$; and $R^{13}$ and $R^{14}$ are independently selected from the group consisting of $C_{1-6}$-alkyl and $C_{1-6}$-alkoxy-$C_{1-6}$-alkyl. In one aspect, $R^{10}$ is $C_{1-10}$-alkyl substituted with —$NR^{13}R^{14}$; and $R^{13}$ and $R^{14}$ are independently selected from the group consisting of $C_{1-6}$-alkyl and $C_{1-6}$-alkoxy-$C_{1-6}$-alkyl. In another aspect, $R^{10}$ is $C_{1-10}$-alkyl substituted with —$NR^{13}R^{14}$; $R^{13}$ is $C_{1-3}$-alkyl; and $R^{14}$ is $C_{1-3}$-alkoxy-$C_{1-3}$-alkyl. In another aspect, $R^{10}$ is $C_{1-10}$-alkyl substituted with —$NR^{13}R^{14}$; $R^{13}$ is methyl; and $R^{14}$ is methoxyethyl.

$R^{10}$=—$CH_2R^{11}$

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$CH_2R^{11}$; $R^{11}$ is cyclohexyl optionally substituted with one or more substituents independently selected from the group consisting of $C_{1-4}$-alkyl, —$NR^{15}R^{16}$, and —$N(R^{17})S(O)_2R^{18}$; and $R^{15}$, $R^{16}$, $R^{17}$, and $R^{18}$ are independently selected from the group consisting of hydrogen and $C_{1-4}$-alkyl. In one aspect, $R^{11}$ is cyclohexyl optionally substituted with one or more $C_{1-4}$-alkyl. In another aspect, $R^{11}$ is cyclohexyl optionally substituted with one or more methyl. In another aspect, $R^{11}$ is cyclohexyl optionally substituted with one or more —$NR^{15}R^{16}$; and $R^{15}$ and $R^{16}$ are independently selected from the group consisting of hydrogen and $C_{1-4}$-alkyl. In another aspect, $R^{11}$ is cyclohexyl optionally substituted with one or more —$NR^{15}R^{16}$; and $R^{15}$ and $R^{16}$ are independently selected from the group consisting of hydrogen and methyl. In another aspect, $R^{11}$ is cyclohexyl optionally substituted with one or more —$N(R^{17})S(O)_2R^{18}$; and $R^{17}$ and $R^{18}$ are independently selected from the group consisting of hydrogen and $C_{1-4}$-alkyl. In another aspect, $R^{11}$ is cyclohexyl optionally substituted with one or more —$N(R^{17})S(O)_2R^{18}$; $R^{17}$ is hydrogen; and $R^{18}$ is $C_{1-4}$-alkyl. In another aspect, $R^{11}$ is cyclohexyl optionally substituted with one or more —$N(R^{17})S(O)_2R^{18}$; $R^{17}$ is hydrogen; and $R^{18}$ is methyl. In another aspect, the $R^{11}$ cyclohexyl is substituted at the para position.

$R^{10}$=—$C(O)R^{12}$

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$;

- $R^{12}$ is 5- to 10-membered ring heterocyclyl, wherein the heterocyclyl: (i) is a saturated or partially saturated monocyclic ring, bicyclic ring, or spirocyclic ring system, (ii) has one or two nitrogen ring atoms with the remaining ring atoms being carbon, and (iii) is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and
- $R^{19}$, $R^{20}$, $R^{21}$, $R^{22}$, and $R^{23}$ are independently selected from the group consisting of hydrogen and $C_{1-4}$-alkyl.

In one aspect, the $R^{12}$ heterocyclyl comprises a nitrogen ring atom adjacent to a carbon ring atom bonded to the carbonyl of the $R^{10}$ substituent.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is an optionally substituted, saturated or partially saturated monocyclic ring. In one aspect, the $R^{12}$ heterocyclyl is an optionally substituted saturated monocyclic ring. In another aspect, the $R^{12}$ heterocyclyl is an optionally substituted partially saturated monocyclic ring.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is an optionally substituted, saturated or partially saturated bicyclic ring. In one aspect, the $R^{12}$ heterocyclyl is an optionally substituted saturated bicyclic ring. In another aspect, the $R^{12}$ heterocyclyl is an optionally substituted saturated bicyclic ring. In another aspect, the bicyclic ring is a fused bicyclic ring. In another aspect, the bicyclic ring is a bridged bicyclic ring.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is an optionally substituted, saturated or partially saturated spirocyclic ring system. In one aspect, the $R^{12}$ heterocyclyl is an optionally substituted saturated spirocyclic ring system. In another aspect, the $R^{12}$ heterocyclyl is an optionally substituted partially saturated spirocyclic ring system In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 5-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 6-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 7-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 8-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 9-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ is optionally substituted 10-membered ring heterocyclyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is selected from the group consisting of:

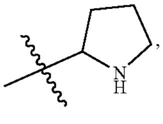,
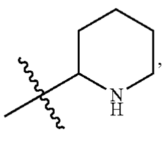,
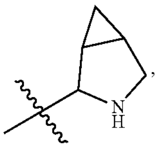,

-continued

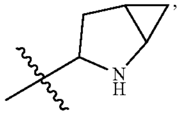,
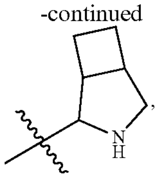,
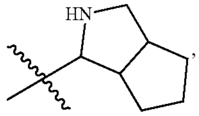,
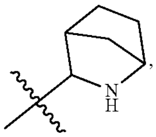,
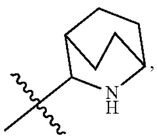,
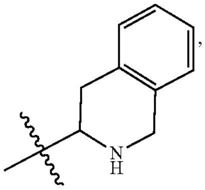,
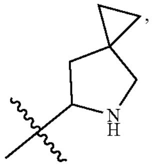, and
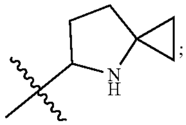;

wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is selected from the group consisting of:

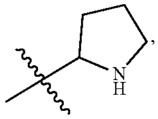,
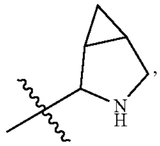,
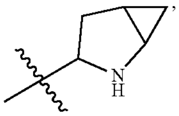,
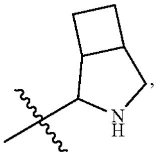,
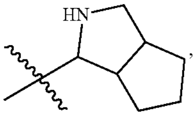,
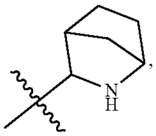,
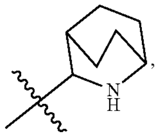,
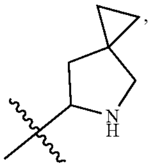, and
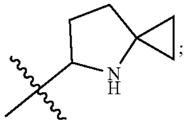;

and wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$- alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is selected from the group consisting of:

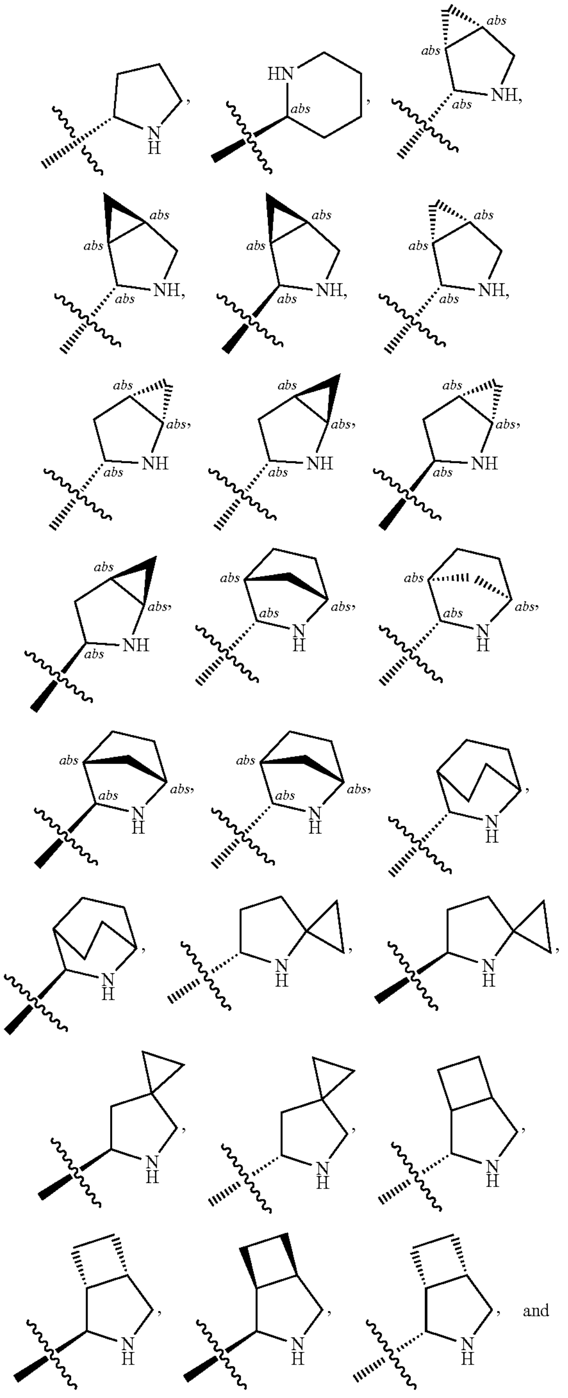

and

-continued

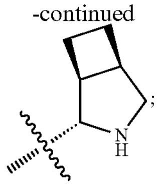

and wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the optionally substituted $R^{12}$ heterocyclyl is a monocyclic ring.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the optionally substituted $R^{12}$ heterocyclyl is a fused bicyclic ring.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the optionally substituted $R^{12}$ heterocyclyl is a bridged bicyclic ring.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the optionally substituted $R^{12}$ heterocyclyl is a spirocyclic ring system.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

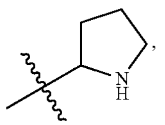 [SMILES: *C1CCCN1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

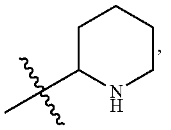 [SMILES: *C1CCCCN1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

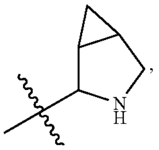 [SMILES: *C1NCC2CC21]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

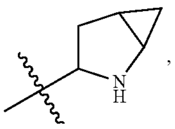 [SMILES: *C1CC2CC2N1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

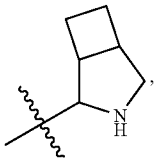 [SMILES: *C1NCC2CCC21]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

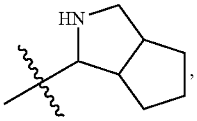 [SMILES: *C1NCC2CCCC21]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

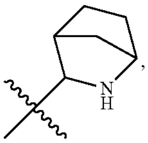 [SMILES: *C1NC2CCC1C2]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

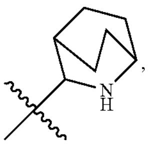 [SMILES: *C1NC2CCC1CC2]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

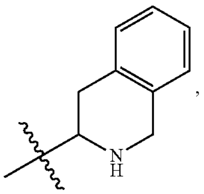 [SMILES: *C1Cc2ccccc2CN1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

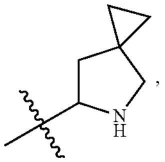 [SMILES: *C1CC2(CC2)CN1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is:

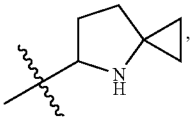

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and $R^{12}$ heterocyclyl is unsubstituted.

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —$C(O)R^{12}$, and the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, and —$OR^{19}$. In one aspect, the $R^{12}$ heterocyclyl is optionally substituted with one or more substituents independently selected from the group consisting of fluoro, methyl, halomethyl, methylenyl, and methoxy. In another aspect, the $R^{12}$ heterocyclyl is optionally substituted with one or more substituents independently selected from the group consisting of fluoro, methyl, trifluoromethyl, methylenyl, and methoxy. In another aspect, the $R^{12}$ heterocyclyl is optionally substituted with one or more substituents independently selected from the group consisting of fluoro, methyl, and methylenyl. In another aspect, the $R^{12}$ heterocyclyl is optionally substituted with one or more fluoro. In another aspect, the $R^{12}$ heterocyclyl is optionally substituted with one or more $C_{1-4}$-alkyl. In another aspect, the $R^{12}$ heterocyclyl is optionally substituted with one or more methyl. In another aspect, the $R^{12}$ heterocyclyl is optionally substituted with one or more halo-$C_{1-4}$-alkyl. In another aspect, the $R^{12}$ heterocyclyl is optionally substituted with one or more halomethyl. In another aspect, the $R^{12}$ heterocyclyl is optionally substituted with one or more trifluoromethyl. In another aspect, the $R^{12}$ heterocyclyl is optionally substituted with one or more $C_{1-4}$-alkenyl. In another aspect, the $R^{12}$ heterocyclyl is optionally substituted with one or more methenyl. In another aspect, the $R^{12}$ heterocyclyl is optionally substituted with one or more —$OR^{19}$; wherein $R^{19}$ is $C_{1-4}$-alkyl. In another aspect, the $R^{12}$ heterocyclyl is optionally substituted with one or more methoxy. In another aspect, the $R^{12}$ heterocyclyl is optionally substituted with one or more —$NR^{20}R^{21}$; wherein $R^{20}$ and $R^{21}$ are independently selected from the group consisting of hydrogen and $C_{1-4}$-alkyl. In another aspect, the $R^{12}$ heterocyclyl is optionally substituted with one or more —$NR^{20}R^{21}$; wherein $R^{20}$ and $R^{21}$ are independently selected from the group consisting of hydrogen and methyl. In another aspect, the $R^{12}$ heterocyclyl is optionally substituted with one or more —$N(R^{22})S(O)_2R^{23}$; wherein $R^{22}$ and $R^{23}$ are independently selected from the group consisting of hydrogen and $C_{1-4}$-alkyl. In another aspect, the $R^{12}$ heterocyclyl is optionally substituted with one or more —$N(R^{22})S(O)_2R^{23}$; wherein $R^{22}$ and $R^{23}$ are independently selected from the group consisting of hydrogen and methyl. In another aspect, In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is selected from the group consisting of:

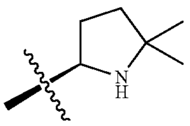
and
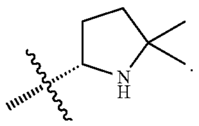

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is selected from the group consisting of:

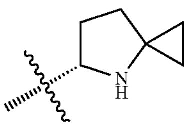
and
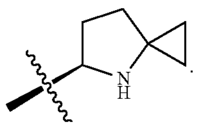

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is:

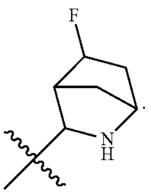 [SMILES: *C1NC2CC(F)C1C2]

In some embodiments, the present disclosure provides compounds having the structure of Formula (I), Formula (I-A), Formula (I-B), Formula (I-C), Formula (I-D), Formula (I-E), or Formula (I-F), and pharmaceutically acceptable salts thereof, wherein $R^{10}$ is —C(O)$R^{12}$, and the $R^{12}$ heterocyclyl is:

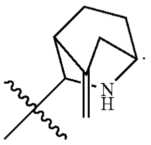 [SMILES: *C1NC2CCC1C(=C)C2]

In further aspects of the $R^{10}$ embodiments described above, A is:

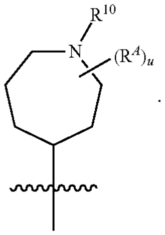

In one aspect, u is 0. In another aspect, u is 1 and $R^A$ is selected from the group consisting of fluoro and methyl. In another aspect, u is 1 and $R^A$ is fluoro. In another aspect, u is 1 and $R^A$ is methyl.

In further aspects of the $R^{10}$ embodiments described above, A is:

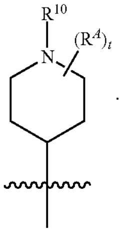

In one aspect, t is 0. In another aspect, t is 1 and $R^A$ is selected from the group consisting of fluoro and methyl. In another aspect, t is 1 and $R^A$ is fluoro. In another aspect, t is 1 and $R^A$ is methyl.

In further aspects of the $R^{10}$ embodiments described above, A is:

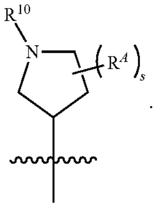

In one aspect, s is 0. In another aspect, s is 1 and $R^A$ is selected from the group consisting of fluoro and methyl. In another aspect, s is 1 and $R^A$ is fluoro. In another aspect, s is 1 and $R^A$ is methyl.

In further aspects of the $R^{10}$ embodiments described above, A is:

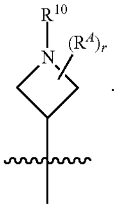

In one aspect, r is 0. In another aspect, r is 1 and $R^A$ is selected from the group consisting of fluoro and methyl. In another aspect, r is 1 and $R^A$ is fluoro. In another aspect, r is 1 and $R^A$ is methyl.

B. Additional Embodiments

In some embodiments, the present disclosure provides compounds having the structure of Formula (I), and pharmaceutically acceptable salts thereof, wherein the compound of Formula (I) has a structure selected from the group consisting of Formulae I-1 through Formula I-69:

Formula (I-1)

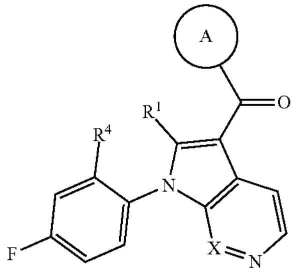

Formula (I-2)

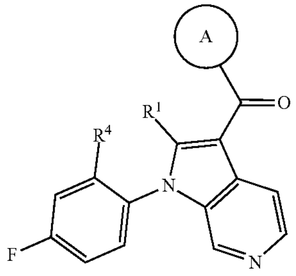

Formula (I-3)

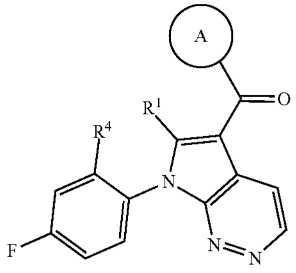

Formula (I-4)

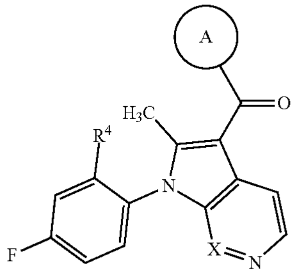

-continued

Formula (I-5)

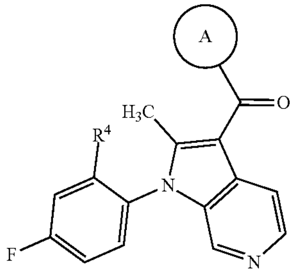

Formula (I-6)

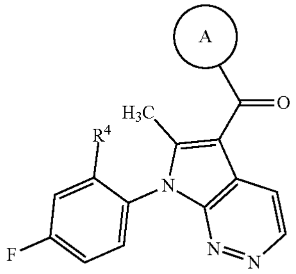

Formula (I-7)

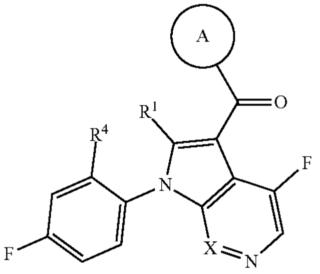

Formula (I-8)

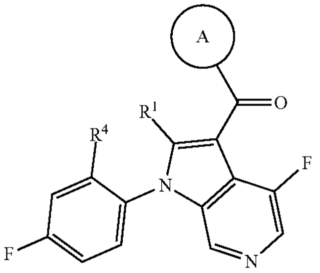

Formula (I-9)

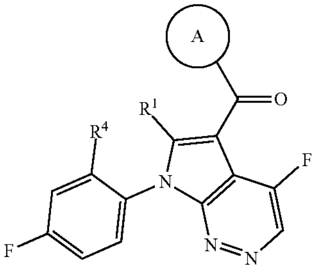

-continued
Formula (I-10)
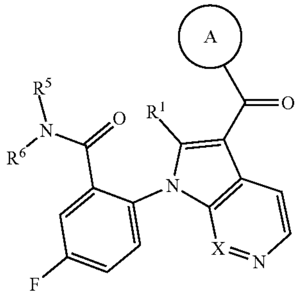
Formula (I-11)
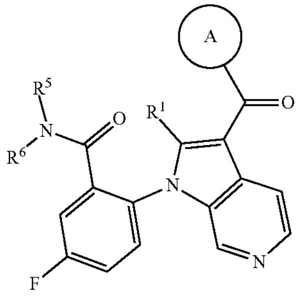
Formula (I-12)
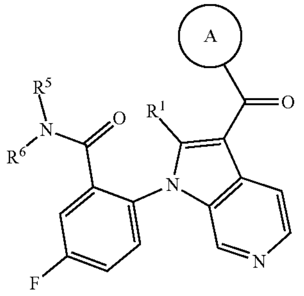
Formula (I-13)
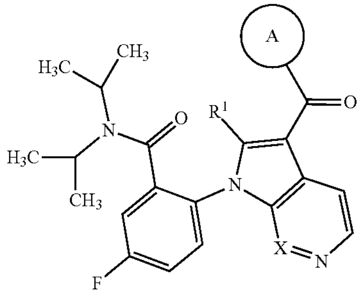
Formula (I-14)
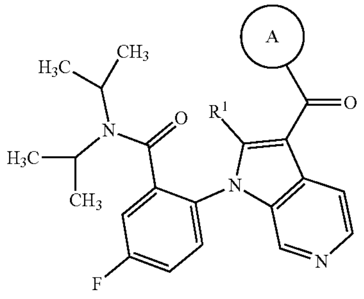
-continued
Formula (I-15)
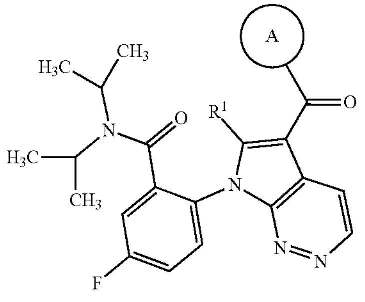
Formula (I-16)
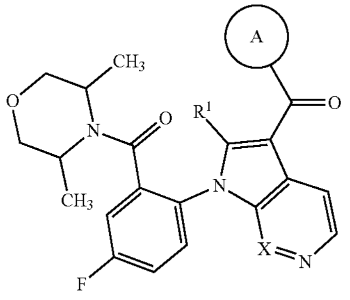
Formula (I-17)
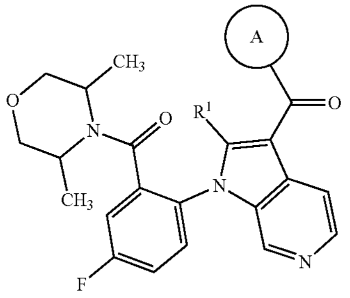
Formula (I-18)
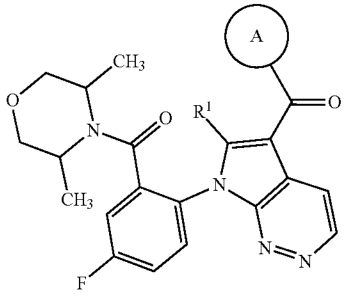
Formula (I-19)
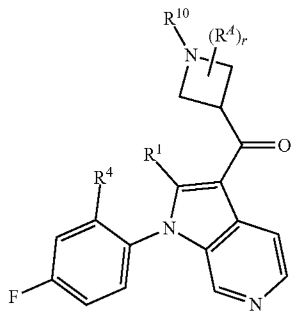

-continued
Formula (I-20)
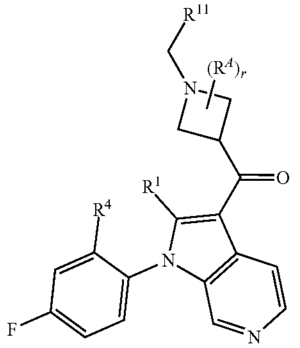
Formula (I-21)
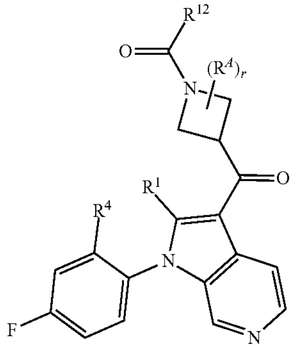
Formula (I-22)
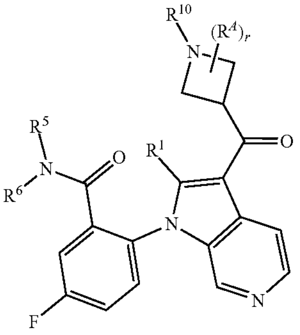
Formula (I-23)
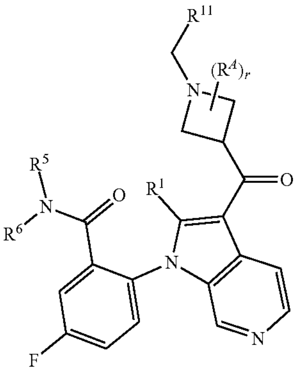
-continued
Formula (I-24)
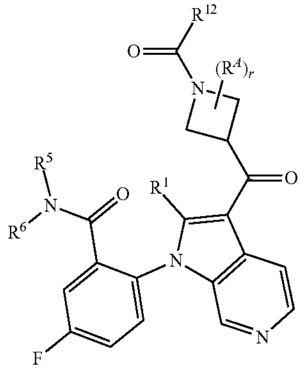
Formula (I-25)
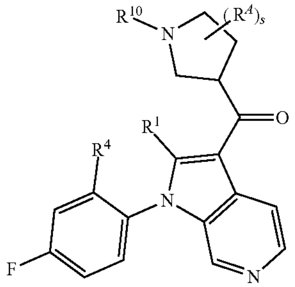
Formula (I-26)
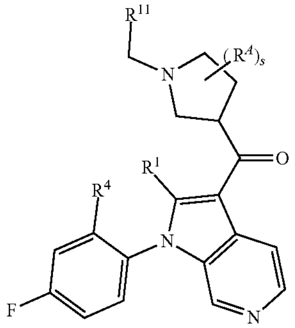
Formula (I-27)
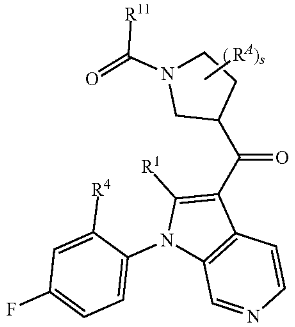
Formula (I-28)
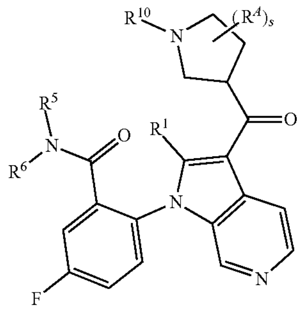

Formula (I-29)
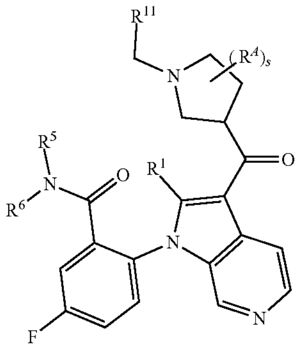
Formula (I-30)
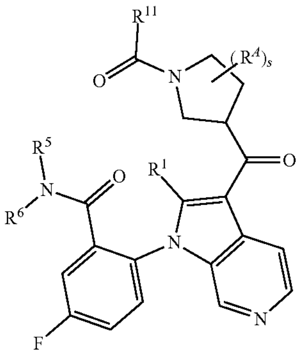
Formula (I-31)
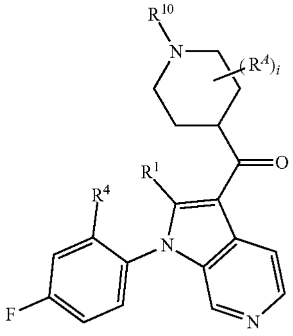
Formula (I-32)
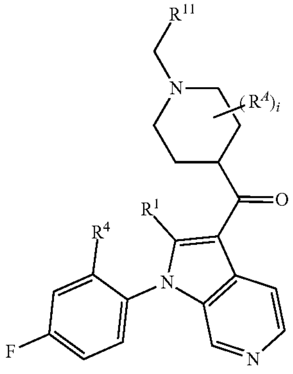
Formula (I-33)
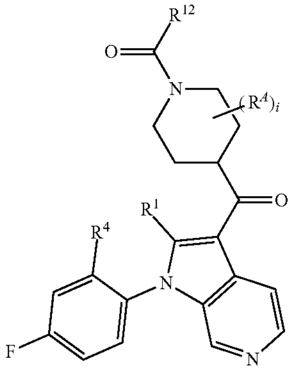
Formula (I-34)
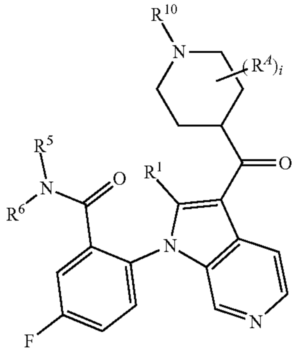
Formula (I-35)
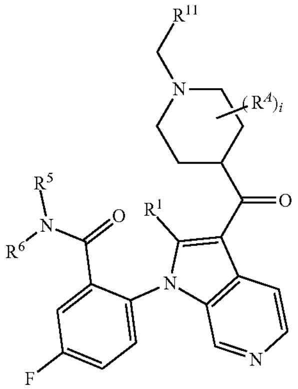
Formula (I-36)
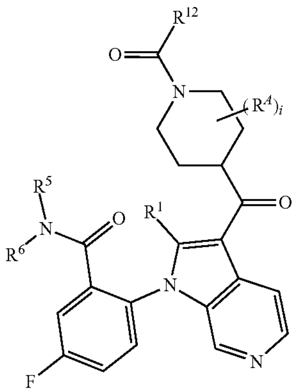

-continued
Formula (I-37)
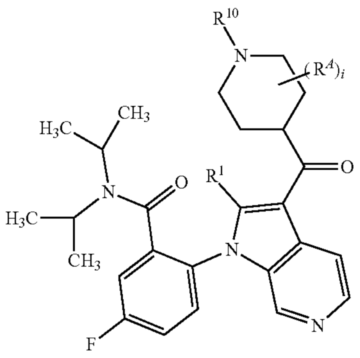
Formula (I-38)
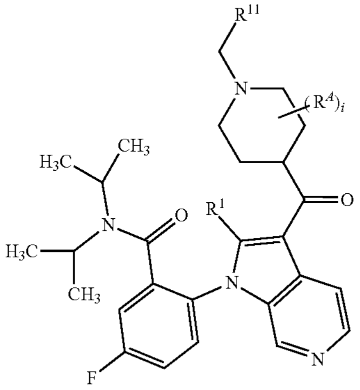
Formula (I-39)
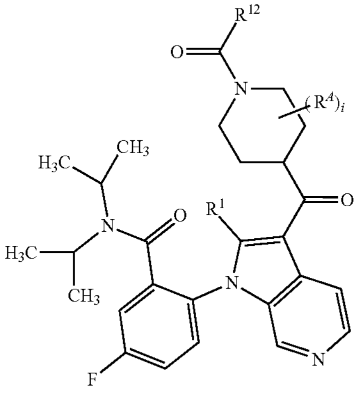
Formula (I-40)
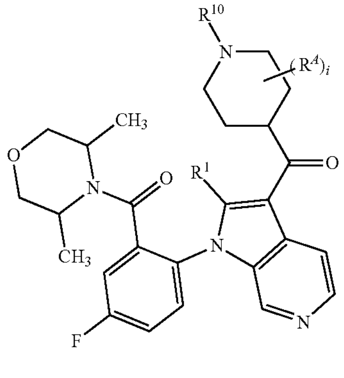
-continued
Formula (I-41)
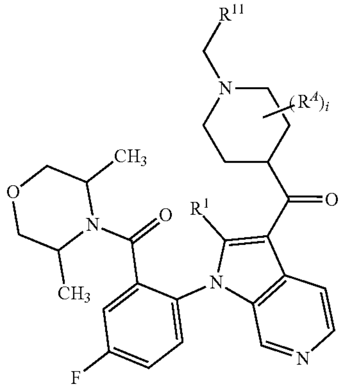
Formula (I-42)
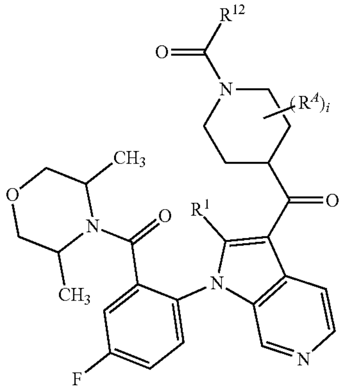
Formula (I-43)
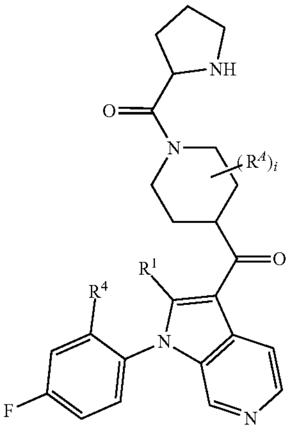
Formula (I-44)
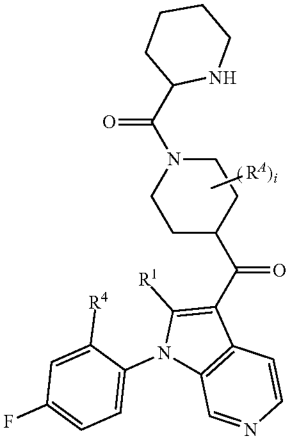

-continued
Formula (I-45)
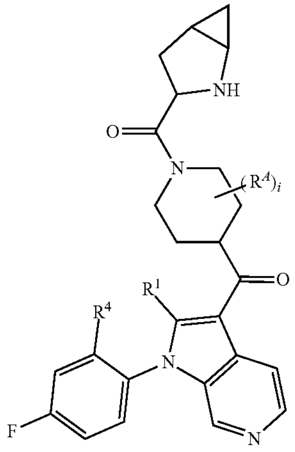
Formula (I-46)
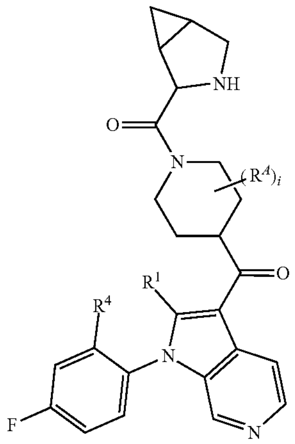
Formula (I-47)
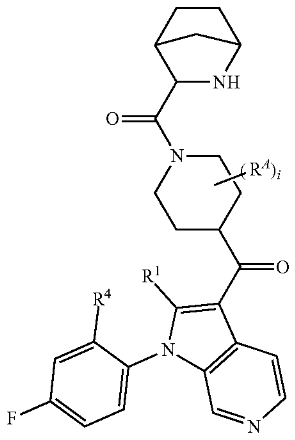
-continued
Formula (I-48)
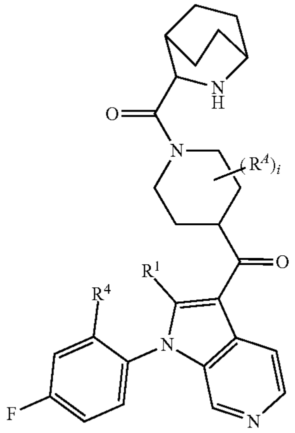
Formula (I-49)
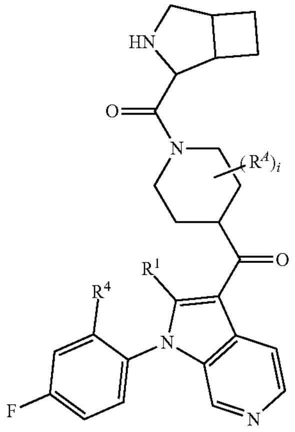
Formula (I-50)
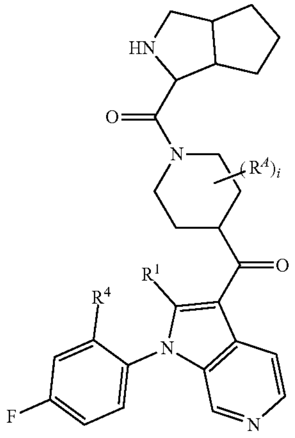

-continued
Formula (I-51)
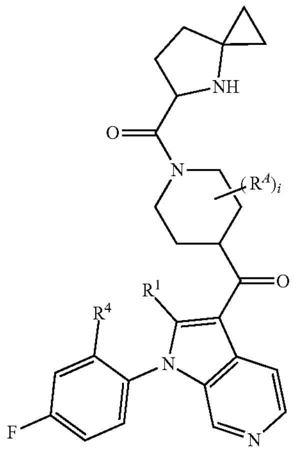
Formula (I-52)
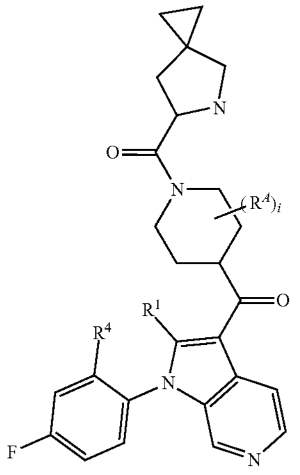
Formula (I-53)
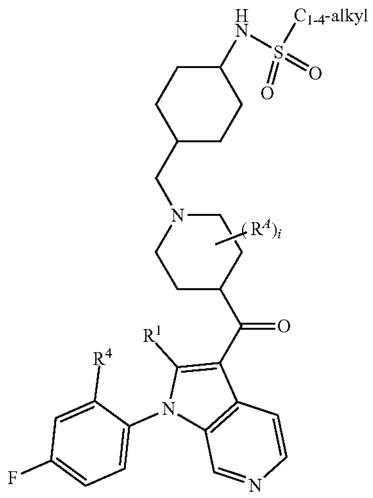
-continued
Formula (I-54)
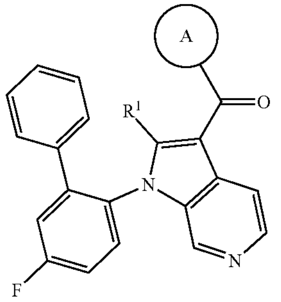
Formula (I-55)
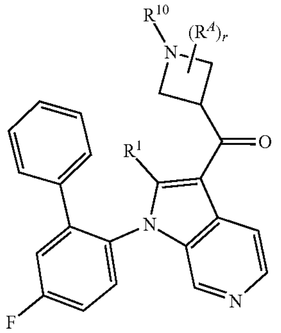
Formula (I-56)
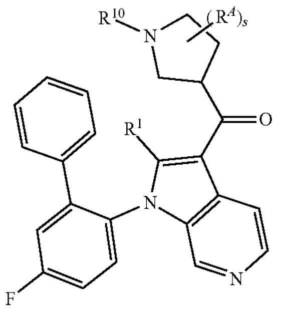
Formula (I-57)
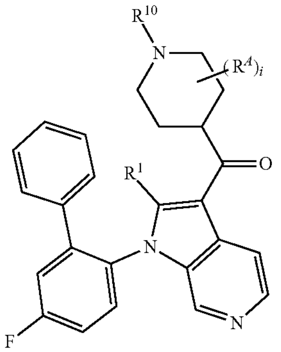
Formula (I-58)
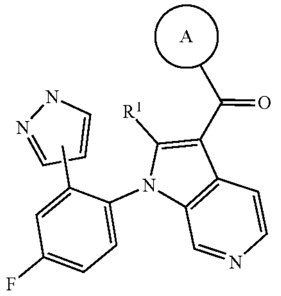

-continued
Formula (I-59)
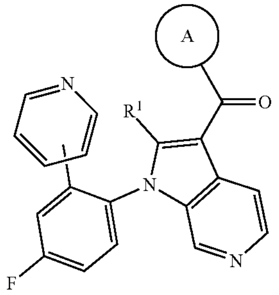
Formula (I-60)
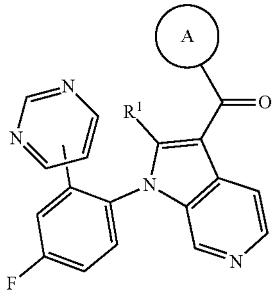
Formula (I-61)
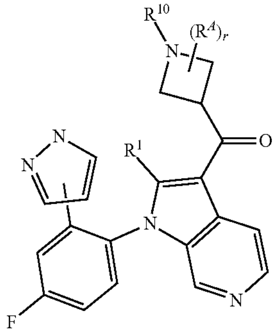
Formula (I-62)
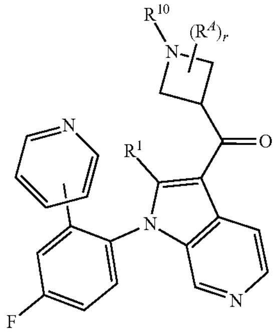
Formula (I-63)
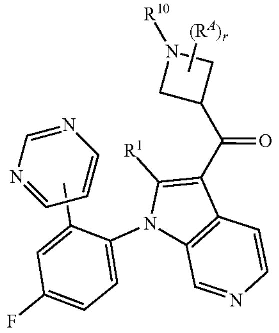
-continued
Formula (I-64)
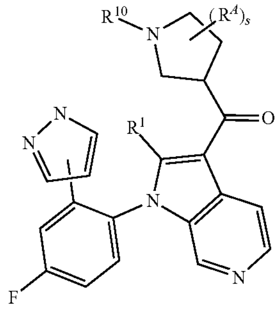
Formula (I-65)
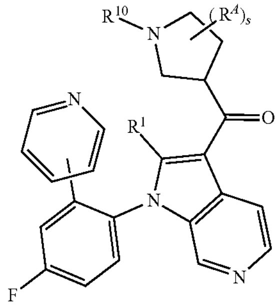
Formula (I-66)
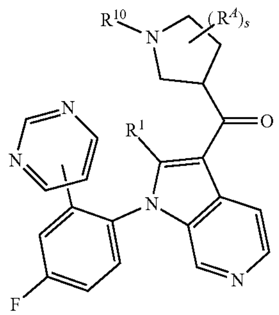
Formula (I-67)
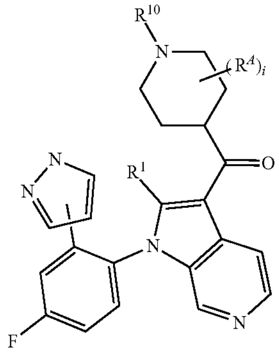

-continued

Formula (I-68)

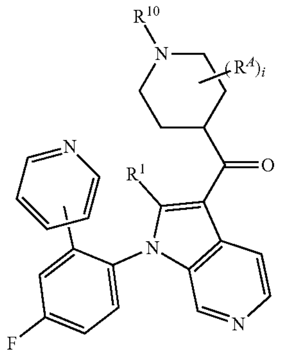

and

Formula (I-69)

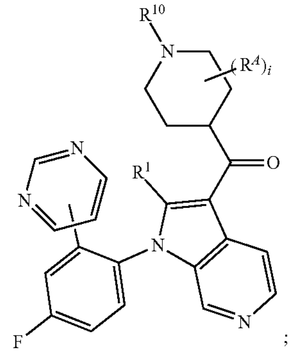

;

wherein, as applicable:

$R^1$, $R^4$, $R^5$, $R^6$, $R^{10}$, $R^{11}$, $R^{12}$, X, A, $R^A$, r, s, and t are as previously defined in this specification;

the $R^4$ phenyl present in the structures of Formula I-54 through Formula I-57 is optionally substituted with one or more substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

the $R^4$ pyrazolyl, pyridinyl, and pyrimidinyl present in the structures of Formula I-58 through Formula I-69 are optionally substituted with one or more substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

the $R^{11}$ cyclohexyl present in the structure of Formula I-53 is optionally substituted with one or more substituents independently selected from the group consisting of $C_{1-4}$-alkyl, $—NR^{15}R^{16}$, and $—N(R^{17})S(O)_2R^{18}$;

the $R^{12}$ heterocyclyl present in the structures of Formula I-43 through Formula I-52 is optionally substituted with one or more substituents independently selected from the group consisting of fluoro, $C_{1-4}$-alkyl, halo-$C_{1-4}$-alkyl, $C_{1-4}$-alkenyl, $—OR^{19}$, $—NR^{20}R^{21}$, and $—N(R^{22})S(O)_2R^{23}$; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

In one aspect, as applicable, $R^1$, $R^4$, $R^5$, $R^6$, $R^{10}$, $R^D$, $R^{12}$, and A are as previously defined in the specification; the $R^4$ phenyl present in the structures of Formula I-54 through Formula I-57 is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; the $R^4$ pyrazolyl, pyridinyl, and pyrimidinyl present in the structures of Formula I-58 through Formula I-69 are optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; X is $—C(R^9)—$; $R^9$ is hydrogen; $R^A$ is methyl; r, s, and t are independently 0 or 1; the $R^{11}$ cyclohexyl present in the structure of Formula I-53 is optionally substituted with one or more substituents independently selected from the group consisting of $C_{1-4}$-alkyl, $—NR^{15}R^{16}$, and $—N(R^{17})S(O)_2R^{18}$; the $R^{12}$ heterocyclyl present in the structures of Formula I-43 through Formula I-52 is optionally substituted with one or more substituents independently selected from the group consisting of fluoro, $C_{1-4}$-alkyl, halo-$C_{1-4}$-alkyl, $C_{1-4}$-alkenyl, $—OR^{19}$, $—NR^{20}R^{21}$, and $—N(R^{22})S(O)_2R^{23}$; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl. In another aspect, $R^1$ is methyl; r, s, and t are each 0; the structure is selected from Formula I-43 through Formula I-52; the $R^{12}$ heterocyclyl present in the structure is optionally substituted with one or more substituents independently selected from the group consisting of fluoro, $C_{1-4}$-alkyl, halo-$C_{1-4}$-alkyl, $C_{1-4}$-alkenyl, $—OR^{19}$, $—NR^{20}R^{21}$, and $—N(R^{22})S(O)_2R^{23}$; and $R^{19}$, $R^{20}$, $R^{21}$, $R^{22}$, and $R^{23}$ are independently selected from the group consisting of hydrogen and $C_{1-4}$-alkyl. In another aspect, $R^1$ is methyl; r, s, and t are each 0; the structure is selected from Formula I-43 through Formula I-52; and the $R^{12}$ heterocyclyl present in the structure is optionally substituted with one or more substituents independently selected from the group consisting of fluoro, $C_{1-4}$-alkyl, halo-$C_{1-4}$-alkyl, and $C_{1-4}$-alkenyl. In another aspect, $R^1$ is hydrogen; r, s, and t are each 0; the structure is selected from Formula I-43 through Formula I-52; the $R^{12}$ heterocyclyl present in the structure is optionally substituted with one or more substituents independently selected from the group consisting of fluoro, $C_{1-4}$-alkyl, halo-$C_{1-4}$-alkyl, $C_{1-4}$-alkenyl, $—OR^{19}$, $—NR^{20}R^{21}$, and $—N(R^{22})S(O)_2R^{23}$; and $R^{19}$, $R^{20}$, $R^{21}$, $R^{22}$, and $R^{23}$ are independently selected from the group consisting of hydrogen and $C_{1-4}$-alkyl. In another aspect, $R^1$ is hydrogen; r, s, and t are each 0; the structure is selected from Formula I-43 through Formula I-52; and the $R^{12}$ heterocyclyl present in the structure is optionally substituted with one or more substituents independently selected from the group consisting of fluoro, $C_{1-4}$-alkyl, halo-$C_{1-4}$-alkyl, and $C_{1-4}$-alkenyl. In another aspect, the compound is an atropisomer.

In some embodiments, the present disclosure provides compounds having the structure of Formula (I-5), and pharmaceutically acceptable salts thereof, wherein the compound has the structure of Formula I-B:

(I-B)

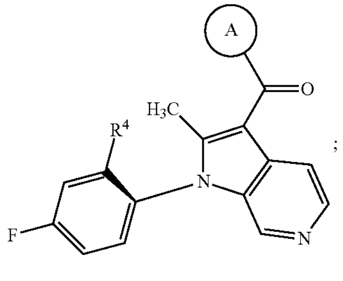

;

and $R^4$ and $R^A$ are as previously defined in the specification.

In some embodiments, the present disclosure provides compounds having the structure of Formula (I-33), and pharmaceutically acceptable salts thereof, wherein the compound has the structure of Formula I-33A:

(I-33A)

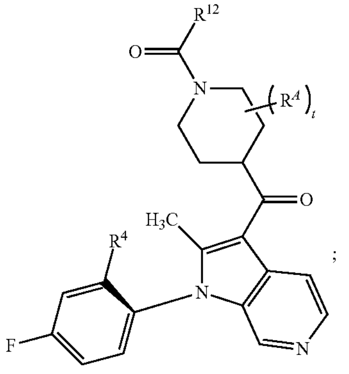

;

and $R^4$, $R^{12}$, $R^A$, and t are as previously defined in the specification. In one aspect, t is 0. In another aspect, t is 1.

In some embodiments, the present disclosure provides compounds of Formula (I), and pharmaceutically acceptable salts thereof, wherein the compound is selected from the group consisting of:

5-Fluoro-N,N-diisopropyl-2-(3-((S)-1-(((1r,4S)-4-(methylsulfonamido)-cyclohexyl)-methyl)pyrrolidine-3-carbonyl)-1H-pyrrolo[2,3-c]pyridin-1-yl)benzamide [Example 1];

2-(3-((S)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide [Example 2];

2-(3-((R)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide [Example 3];

5-Fluoro-N,N-diisopropyl-2-(3-((R)-1-(((1r,4R)-4-(methylsulfonamido)cyclohexyl)-methyl)pyrrolidine-3-carbonyl)-1H-pyrrolo[2,3-c]pyridin-1-yl)benzamide [Example 4];

2-(3-(1-((1R,3S,4S)-2-Azabicyclo[2.2.1]heptane-3-carbonyl)azetidine-3-carbonyl)-1H-pyrrolo[2,3-c]pyridin-1-yl)-5-fluoro-N,N-diisopropylbenzamide [Example 5];

(S)-2-(3-(1-(2-Azabicyclo[2.2.2]octane-3-carbonyl)azetidine-3-carbonyl)-1H-pyrrolo-[2,3-c]pyridin-1-yl)-5-fluoro-N,N-diisopropylbenzamide [Example 6];

5-Fluoro-2-(3-(1-((1S,3S,4S,5S)-5-fluoro-2-azabicyclo[2.2.1]heptane-3-carbonyl)-azetidine-3-carbonyl)-1H-pyrrolo[2,3-c]pyridin-1-yl)-N,N-diisopropylbenzamide [Example 7];

2-(3-(1-((1R,3S,4S)-2-Azabicyclo[2.2.1]heptane-3-carbonyl)azetidine-3-carbonyl)-1H-pyrrolo[2,3-c]pyridin-1-yl)-N-ethyl-5-fluoro-N-isopropylbenzamide [Example 8];

(S)-2-(3-(1-(2-Azabicyclo[2.2.2]octane-3-carbonyl)azetidine-3-carbonyl)-1H-pyrrolo-[2,3-c]pyridin-1-yl)-N-ethyl-5-fluoro-N-isopropylbenzamide [Example 9];

(1-((1R,3S,4S)-2-Azabicyclo[2.2.1]heptane-3-carbonyl)azetidin-3-yl)(1-(4-fluoro-2-(2-isopropylpyridin-3-yl)phenyl)-1H-pyrrolo[2,3-c]pyridin-3-yl)methanone [Example 10];

(1-((1R,3S,4S)-2-Azabicyclo[2.2.1]heptane-3-carbonyl)azetidin-3-yl)(1-(4-fluoro-2-(3-isopropylpyridin-4-yl)phenyl)-1H-pyrrolo[2,3-c]pyridin-3-yl)methanone 1·formic acid [Example 11];

(1-((1R,3S,4S)-2-Azabicyclo[2.2.1]heptane-3-carbonyl)azetidin-3-yl)(1-(4-fluoro-2-(4-isopropylthiazol-5-yl)phenyl)-1H-pyrrolo[2,3-c]pyridin-3-yl)methanone 1·formic acid [Example 12];

(1-((1R,3S,4S)-2-Azabicyclo[2.2.1]heptane-3-carbonyl)azetidin-3-yl)(1-(4-fluoro-2-(2-(2-fluoropropan-2-yl)pyridin-3-yl)phenyl)-1H-pyrrolo[2,3-c]pyridin-3-yl)methanone [Example 13];

2-(5-(1-((1R,3S,4S)-2-Azabicyclo[2.2.1]heptane-3-carbonyl)azetidine-3-carbonyl)-7H-pyrrolo[2,3-c]pyridazin-7-yl)-5-fluoro-N,N-diisopropylbenzamide 1·formic acid [Example 14];

2-(3-(1-((1R,3S,4S)-2-Azabicyclo[2.2.1]heptane-3-carbonyl)azetidine-3-carbonyl)-7-fluoro-1H-pyrrolo[2,3-c]pyridin-1-yl)-5-fluoro-N,N-diisopropylbenzamide [Example 15];

2-(3-(1-((1R,3S,4S)-2-Azabicyclo[2.2.1]heptane-3-carbonyl)piperidine-4-carbonyl)-1H-pyrrolo[2,3-c]pyridin-1-yl)-5-fluoro-N,N-diisopropylbenzamide [Example 16];

5-Fluoro-N,N-diisopropyl-2-(3-(1-(((1r,4r)-4-(methylsulfonamido)cyclohexyl)methyl)-piperidine-4-carbonyl)-1H-pyrrolo[2,3-c]pyridin-1-yl)benzamide [Example 17];

5-Fluoro-N,N-diisopropyl-2-(3-(1-((1S,3S,4R)-5-methylene-2-azabicyclo[2.2.2]octane-3-carbonyl)piperidine-4-carbonyl)-1H-pyrrolo[2,3-c]pyridin-1-yl)benzamide [Example 18];

2-(3-(1-((1S,2S,5R)-3-Azabicyclo[3.1.0]hexane-2-carbonyl)piperidine-4-carbonyl)-1H-pyrrolo[2,3-c]pyridin-1-yl)-5-fluoro-N,N-diisopropylbenzamide [Example 19];

(S)-2-(3-(1-(2-Azabicyclo[2.2.2]octane-3-carbonyl)piperidine-4-carbonyl)-1H-pyrrolo[2,3-c]pyridin-1-yl)-5-fluoro-N,N-diisopropylbenzamide [Example 20];

5-Fluoro-N,N-diisopropyl-2-(3-(1-((1S,3aR,6aS)-octahydrocyclopenta[c]pyrrole-1-carbonyl)piperidine-4-carbonyl)-1H-pyrrolo[2,3-c]pyridin-1-yl)benzamide [Example 21];

5-Fluoro-2-(3-(1-((1S,3S,4S,5S)-5-fluoro-2-azabicyclo[2.2.1]heptane-3-carbonyl)-piperidine-4-carbonyl)-1H-pyrrolo[2,3-c]pyridin-1-yl)-N,N-diisopropylbenzamide [Example 22];

rac-(R)-5-Fluoro-N,N-diisopropyl-2-(3-(1-(6-((2-methoxyethyl)(methyl)amino)-2-methylhexan-3-yl)piperidine-4-carbonyl)-1H-pyrrolo[2,3-c]pyridin-1-yl)benzamide [Example 23];

(S)-2-(3-(1-(4-Azaspiro[2.4]heptane-5-carbonyl)piperidine-4-carbonyl)-1H-pyrrolo[2,3-c]pyridin-1-yl)-5-fluoro-N,N-diisopropylbenzamide [Example 24];

rel-2-(3-(1-((1R,2R,5S)-3-Azabicyclo[3.2.0]heptane-2-carbonyl)piperidine-4-carbonyl)-1H-pyrrolo[2,3-c]pyridin-1-yl)-5-fluoro-N,N-diisopropylbenzamide [Example 25];

(S)-2-(3-(1-(5-Azaspiro[2.4]heptane-6-carbonyl)piperidine-4-carbonyl)-1H-pyrrolo[2,3-c]pyridin-1-yl)-5-fluoro-N,N-diisopropylbenzamide [Example 26];

(S)-2-(3-(1-(5,5-Dimethylpyrrolidine-2-carbonyl)piperidine-4-carbonyl)-1H-pyrrolo[2,3-c]pyridin-1-yl)-5-fluoro-N,N-diisopropylbenzamide [Example 27];

2-(3-(1-((1S,2S,5R)-3-Azabicyclo[3.1.0]hexane-2-carbonyl)piperidine-4-carbonyl)-1H-pyrrolo[2,3-c]pyridin-1-yl)-N-ethyl-5-fluoro-N-isopropylbenzamide [Example 28];

(S)-2-(3-(1-(2-Azabicyclo[2.2.2]octane-3-carbonyl)piperidine-4-carbonyl)-1H-pyrrolo[2,3-c]pyridin-1-yl)-N-ethyl-5-fluoro-N-isopropylbenzamide [Example 29];

N-Ethyl-5-fluoro-2-(3-(1-((1S,3S,4S,5S)-5-fluoro-2-azabicyclo[2.2.1]heptane-3-carbonyl)piperidine-4-carbonyl)-1H-pyrrolo[2,3-c]pyridin-1-yl)-N-isopropylbenzamide [Example 30];

2-(3-(1-((1R,3S,4S)-2-Azabicyclo[2.2.1]heptane-3-carbonyl)piperidine-4-carbonyl)-1H-pyrrolo[2,3-c]pyridin-1-yl)-N-ethyl-5-fluoro-N-isopropylbenzamide [Example 31];

(1-((1R,3S,4S)-2-Azabicyclo[2.2.1]heptane-3-carbonyl)piperidin-4-yl)(1-(2-((2R,5S)-2,5-dimethylpyrrolidine-1-carbonyl)-4-fluorophenyl)-1H-pyrrolo[2,3-c]pyridin-3-yl)methanone [Example 32];

(1-((1R,3S,4S)-2-Azabicyclo[2.2.1]heptane-3-carbonyl)piperidin-4-yl)(1-(2-((2R,6S)-2,6-dimethylpiperidine-1-carbonyl)-4-fluorophenyl)-1H-pyrrolo[2,3-c]pyridin-3-yl)methanone [Example 33];

(1-((1R,3S,4S)-2-Azabicyclo[2.2.1]heptane-3-carbonyl)piperidin-4-yl)(1-(2-((3R,5R)-3,5-dimethylmorpholine-4-carbonyl)-4-fluorophenyl)-1H-pyrrolo[2,3-c]pyridin-3-yl)methanone [Example 34];

(1-((1R,3S,4S)-2-Azabicyclo[2.2.1]heptane-3-carbonyl)piperidin-4-yl)(1-(2-((3R,5S)-3,5-dimethylmorpholine-4-carbonyl)-4-fluorophenyl)-1H-pyrrolo[2,3-c]pyridin-3-yl)methanone [Example 35];

(1-((1R,3S,4S)-2-Azabicyclo[2.2.1]heptane-3-carbonyl)piperidin-4-yl)(1-(4-fluoro-2-(1-isopropyl-1H-pyrazol-5-yl)phenyl)-1H-pyrrolo[2,3-c]pyridin-3-yl)methanone [Example 36];

(1-((1R,3S,4S)-2-Azabicyclo[2.2.1]heptane-3-carbonyl)piperidin-4-yl)(1-(4-fluoro-2-(4-isopropylpyrimidin-5-yl)phenyl)-1H-pyrrolo[2,3-c]pyridin-3-yl)methanone [Example 37];

(1-((1R,3S,4S)-2-Azabicyclo[2.2.1]heptane-3-carbonyl)piperidin-4-yl)(1-(4-fluoro-2-(2-isopropylpyridin-3-yl)phenyl)-1H-pyrrolo[2,3-c]pyridin-3-yl)methanone [Example 38];

(1-((1R,3S,4S)-2-Azabicyclo[2.2.1]heptane-3-carbonyl)piperidin-4-yl)(1-(5-fluoro-2'-isopropyl-[1,1'-biphenyl]-2-yl)-1H-pyrrolo[2,3-c]pyridin-3-yl)methanone [Example 39];

(1-((1R,3S,4S)-2-Azabicyclo[2.2.1]heptane-3-carbonyl)piperidin-4-yl)(1-(2-(4-cyclopropylpyrimidin-5-yl)-4-fluorophenyl)-1H-pyrrolo[2,3-c]pyridin-3-yl)methanone [Example 40];

(1-((1R,3S,4S)-2-Azabicyclo[2.2.1]heptane-3-carbonyl)piperidin-4-yl)(1-(4-fluoro-2-(4-isopropylpyridin-3-yl)phenyl)-1H-pyrrolo[2,3-c]pyridin-3-yl)methanone [Example 41];

(1-((1R,3S,4S)-2-Azabicyclo[2.2.1]heptane-3-carbonyl)piperidin-4-yl)(1-(4-fluoro-2-(4-isopropylthiazol-5-yl)phenyl)-1H-pyrrolo[2,3-c]pyridin-3-yl)methanone 1·formic acid [Example 42];

(1-((1S,2S,5R)-3-Azabicyclo[3.1.0]hexane-2-carbonyl)piperidin-4-yl)(1-(4-fluoro-2-(1-isopropyl-1H-pyrazol-5-yl)phenyl)-1H-pyrrolo[2,3-c]pyridin-3-yl)methanone 1·formic acid [Example 43];

2-(3-(1-((1R,3S,4S)-2-Azabicyclo[2.2.1]heptane-3-carbonyl)piperidine-4-carbonyl)-4-fluoro-1H-pyrrolo[2,3-c]pyridin-1-yl)-5-fluoro-N,N-diisopropylbenzamide 1·formic acid [Example 44];

2-(3-((R*)-1-((1R,3S,4S)-2-Azabicyclo[2.2.1]heptane-3-carbonyl)azepane-4-carbonyl)-1H-pyrrolo[2,3-c]pyridin-1-yl)-5-fluoro-N,N-diisopropylbenzamide 1·formic acid [Example 45];

2-(3-(1-((1R,3S,4S)-2-Azabicyclo[2.2.1]heptane-3-carbonyl)piperidine-4-carbonyl)-2-methyl-1H-pyrrolo[2,3-c]pyridin-1-yl)-N-ethyl-5-fluoro-N-isopropylbenzamide [Example 46];

2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-N-ethyl-5-fluoro-N-isopropylbenzamide [Example 47];

2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-N-ethyl-5-fluoro-N-isopropylbenzamide [Example 48-2];

(S)-2-(3-(1-(4-Azaspiro[2.4]heptane-5-carbonyl)piperidine-4-carbonyl)-2-methyl-1H-pyrrolo[2,3-c]pyridin-1-yl)-N-ethyl-5-fluoro-N-isopropylbenzamide [Example 49-2];

(S)-2-(3-(1-(5,5-Dimethylpyrrolidine-2-carbonyl)piperidine-4-carbonyl)-2-methyl-1H-pyrrolo[2,3-c]pyridin-1-yl)-N-ethyl-5-fluoro-N-isopropylbenzamide [Example 50-2];

2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N-isopropyl-N-(2,2,2-trifluoroethyl)benzamide [Example 51-2];

N-Ethyl-5-fluoro-N-isopropyl-2-(2-methyl-3-((2R*,4S*)-2-methyl-1-((S)-4-azaspiro[2.4]-heptane-5-carbonyl)piperidine-4-carbonyl)-1H-pyrrolo[2,3-c]pyridin-1-yl)benzamide [Example 52-1];

N-Ethyl-5-fluoro-N-isopropyl-2-(2-methyl-3-((2R*,4S*)-2-methyl-1-((S)-4-azaspiro[2.4]-heptane-5-carbonyl)piperidine-4-carbonyl)-1H-pyrrolo[2,3-c]pyridin-1-yl)benzamide [Example 52-2];

2-(3-((2R*,4S*)-1-((1S,2S,5R)-3-Azabicyclo[3.1.0]hexane-2-carbonyl)-2-methyl-piperidine-4-carbonyl)-2-methyl-1H-pyrrolo[2,3-c]pyridin-1-yl)-5-fluoro-N-isopropyl-N-(2,2,2-trifluoroethyl)benzamide [Example 53-3];

2-(3-((2R*,4S*)-1-((1S,2S,5R)-3-Azabicyclo[3.1.0]hexane-2-carbonyl)-2-methyl-piperidine-4-carbonyl)-2-methyl-1H-pyrrolo[2,3-c]pyridin-1-yl)-5-fluoro-N-isopropyl-N-(2,2,2-trifluoroethyl)benzamide [Example 53-4];

(1-((1S,2S,5R)-3-Azabicyclo[3.1.0]hexane-2-carbonyl)piperidin-4-yl)(1-(4-fluoro-2-(4-isopropylpyridin-3-yl)phenyl)-2-methyl-1H-pyrrolo[2,3-c]pyridin-3-yl)methanone [Example 54];

2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N,N-diisopropylbenzamide [Example 55-2];

(S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-diisopropylbenzamide [Example 56-2];

2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N-isopropyl-N—((R)-1,1,1-trifluoropropan-2-yl)benzamide [Example 57-1];

(1-((S)-4-Azaspiro[2.4]heptane-5-carbonyl)piperidin-4-yl)(1-(2-((3R,5R)-3,5-dimethylmorpholine-4-carbonyl)-4-fluorophenyl)-2-methyl-1H-pyrrolo[2,3-c]pyridin-3-yl)methanone [Example 58-2];

(S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-bis(propan-2-yl-$d_7$)benzamide [Example 59];

5-Fluoro-N,N-diisopropyl-2-(2-methyl-3-(1-((2S,5S)-5-methylpyrrolidine-2-carbonyl)piperidine-4-carbonyl)-1H-pyrrolo[2,3-c]pyridin-1-yl)benzamide [Example 60];

5-Fluoro-N,N-diisopropyl-2-(2-methyl-3-(1-((2S,5R)-5-methylpyrrolidine-2-carbonyl)piperidine-4-carbonyl)-1H-pyrrolo[2,3-c]pyridin-1-yl)benzamide [Example 61];

5-Fluoro-N,N-diisopropyl-2-(2-methyl-3-((2S,4RS)-2-methyl-1-((2S,5S)-5-methylpyrrolidine-2-carbonyl)piperidine-4-carbonyl)-1H-pyrrolo[2,3-c]pyridin-1-yl)benzamide [Example 62];

N-Ethyl-5-fluoro-N-isopropyl-2-(2-methyl-3-((2S,4RS)-2-methyl-1-((2S,5S)-5-methylpyrrolidine-2-carbonyl)piperidine-4-carbonyl)-1H-pyrrolo[2,3-c]pyridin-1-yl)benzamide [Example 63];

5-Fluoro-N,N-diisopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide [Example 64]; and N-Ethyl-5-fluoro-N-isopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide [Example 65].

C. Combination of Embodiments

Any embodiment of the compounds described in the present disclosure can be combined with any other suitable embodiment described herein to provide additional embodiments. For example, where one embodiment individually or collectively describes possible groups for $R^1$, $R^2$, $R^3$, and/or $R^4$ and a separate embodiment describes possible groups for A, it is understood that these embodiments can be combined to provide an additional embodiment describing the possible groups described for $R^1$, $R^2$, $R^3$, and/or $R^4$ together with the possible groups described for A. In other words, for any of the embodiments of the compounds described in the present disclosure, the A substituent can be as defined in any of the embodiments of A described in this specification.

D. Further Embodiments

In some embodiments, the compounds of the present disclosure have an $IC_{50}$ value for Menin binding below about 200 nM as measured in the fluorescence polarization assay described in Example 66 below. In one aspect, the $IC_{50}$ value is below about 100 nM. In another aspect, the $IC_{50}$ value is below about 50 nM. In another aspect, the $IC_{50}$ value is below about 25 nM.

In some embodiments, the compounds of the present disclosure inhibit MOLM-13 cellular proliferation as measured in the cellular proliferation assay described in Example 67 below. In one aspect, the compounds have an $IC_{50}$ value in the assay below about 300 nM. In another aspect, the $IC_{50}$ value is below about 150 nM. In another aspect, the $IC_{50}$ value is below about 75 nM.

In some embodiments, the compounds of the present disclosure inhibit MV4-11 cellular proliferation as measured in the cellular proliferation assay described in Example 67 below. In one aspect, the compounds have an $IC_{50}$ value in the assay below about 200 nM. In another aspect, the $IC_{50}$ value is below about 100 nM. In another aspect, the $IC_{50}$ value is below about 50 nM.

In some embodiments, the compounds of the present disclosure inhibit OCI-AML3 cellular proliferation as measured in the cellular proliferation assay described in Example 67 below. In one aspect, the compounds have an $IC_{50}$ value in the assay below about 500 nM. In another aspect, the $IC_{50}$ value is below about 300 nM. In another aspect, the $IC_{50}$ value is below about 150 nM. In another aspect, the $IC_{50}$ value is below about 75 nM.

In some embodiments, the compounds of the present disclosure do not significantly inhibit HEL cellular proliferation as measured in the cellular proliferation assay described in Example 67 below. In one aspect, the compounds have an $IC_{50}$ value in the assay greater than about 5 μM. In another aspect, the $IC_{50}$ value is greater than about 7 μM. In another aspect, the $IC_{50}$ value is greater than about 10 μM.

In some embodiments, the compounds of the present disclosure have a an $IC_{50}$ value for hERG inhibition greater than about 5 μM as measured in the hERG assay 1 (standard) described in Example 68 below. In one aspect, the $IC_{50}$ value is greater than about 10 μM. In another aspect, the $IC_{50}$ value is greater than about 25 μM. In another aspect, the $IC_{50}$ value is greater than about 40 μM.

In some embodiments, the compounds of the present disclosure are selective for Menin relative to the muscarinic M2 receptor. In one aspect, the compounds have a an $IC_{50}$ value greater than about 0.1 μM as measured in the muscarinic M2 receptor binding assay (assay 1) described in Example 69 below. In another aspect, the $IC_{50}$ value is greater than about 0.5 μM. In another aspect, the $IC_{50}$ value is greater than about 2.5 μM. In another aspect, the $IC_{50}$ value is greater than about 10 μM.

In some embodiments, the compounds of the present disclosure have a pharmaceutically acceptable metabolic stability measured as described for the human hepatocytes (HH) assay reported in Example 70 below. In one aspect, the compounds have an HH $CL_{int}$ value less than about 10 μL/min/1E6. In another aspect, the HH $CL_{int}$ value is less than about 5 μL/min/1E6. In another aspect, the HH $CL_{int}$ value is less than about 1 μL/min/1E6.

In some embodiments, the compounds of the present disclosure have a pharmaceutically acceptable Caco-2 AB intrinsic permeability measured as measured in the Caco-2 AB intrinsic permeability assay described in Example 71 below. In one aspect, the compounds have a Caco-2 intrinsic apparent permeability of at least about $0.2\times10^6$ cm/s. In another aspect, the compounds have a Caco-2 intrinsic apparent permeability of at least about $0.5\times10^6$ cm/s. In another aspect, the compounds have a Caco-2 intrinsic apparent permeability of at least about $1\times10^6$ cm/s. In another aspect, the compounds have a Caco-2 intrinsic apparent permeability of at least about $3\times10^6$ cm/s.

E. Salts

The compounds of the present disclosure may exist in salt form or in non-salt form (i.e., as a free base), and the present disclosure covers both salt forms and non-salt forms. The compounds may form acid addition salts or base addition salts. In general, an acid addition salt can be prepared using various inorganic or organic acids. Such salts can typically be formed by, for example, mixing the compound with an acid (e.g., a stoichiometric amount of an acid) using various methods known in the art. This mixing may occur in water, an organic solvent (e.g., ether, ethyl acetate, ethanol, methanol, isopropanol, or acetonitrile), or an aqueous/organic mixture. In another aspect, the acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example, J. Pharm. Sci. 1977 66, 1. Examples of pharmaceutically acceptable salts are also described in "Handbook of Pharmaceutical Salts: Properties, Selection, and Use" by Stahl and Wermuth (Wiley-VCH, Weinheim, Germany, 2002).

F. Isomers

The compounds and salts of the present disclosure may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g., chromatographic techniques and recrystallisation techniques). Where appropriate such isomers can be prepared by the application or adaptation of known methods. In some embodiments, a single stereoisomer is obtained by isolating it from a mixture of isomers (e.g., a racemate) using, for example, chiral chromatographic separation. In other embodiments, a single stereoisomer is obtained through direct synthesis from, for example, a chiral starting material.

A particular enantiomer of a compound described herein may be more active than other enantiomers of the same compound. In one embodiment, the compound, or a pharmaceutically acceptable salt thereof, is a single enantiomer being in an enantiomeric excess (% ee) of ≥90, ≥95%, ≥96%, ≥97, ≥98% or ≥99%. In one aspect, the single enantiomer is present in an enantiomeric excess (% ee) of ≥99%.

In another embodiment, the present disclosure relates to a pharmaceutical composition comprising a compound, or a pharmaceutically acceptable salt thereof, which is a single enantiomer being in an enantiomeric excess (% ee) of ≥90, ≥95%, ≥96%, ≥97, ≥98% or ≥99%, or a pharmaceutically acceptable salt thereof, in association with one or more pharmaceutically acceptable excipients. In one aspect, the single enantiomer is present in an enantiomeric excess (% ee) of ≥99%.

G. Additional Forms

The compounds and salts of the present disclosure may exist in various tautomeric forms and the specification encompasses all such tautomeric forms. "Tautomers" are structural isomers that exist in equilibrium resulting from the migration of a hydrogen atom.

The compounds of the present disclosure, and pharmaceutically acceptable salts thereof, may exist as solvates (such as a hydrates) as well as unsolvated forms, and the present specification covers all such solvates.

The compounds of the present disclosure, and pharmaceutically acceptable salts thereof, may exist in crystalline or amorphous form, and the present specification covers all such forms.

Compounds and salts of the present disclosure may be isotopically labeled (or "radio-labeled"). In that instance, one or more atoms are replaced by an atom having an atomic mass or mass number different from the atomic mass or mass number typically found in nature. The specification encompasses isotopically labelled forms of compounds disclosed herein. Examples of isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$ and $^{36}Cl$. The isotope that is used will depend on the specific application of that radio-labeled derivative. For example, for in vitro receptor labeling and competition assays, $^{3}H$ or $^{14}C$ are often useful. For radio-imaging applications, $^{11}C$ is often useful. In some embodiments, the radionuclide is $^{3}H$. In some embodiments, the radionuclide is $^{14}C$. In some embodiments, the radionuclide is $^{11}C$.

H. Intermediates

In some embodiments, the present disclosure provides additional compounds that are useful as intermediates for preparing the compounds of the present disclosure, and pharmaceutically acceptable salts thereof.

III. Methods of Use

The disclosed compounds of the present disclosure, and pharmaceutically acceptable salts thereof, are inhibitors of Menin activity.

In some embodiments, therefore, the present disclosure provides a method for treating or preventing a Menin-mediated condition in a subject in need thereof by administering to the subject a therapeutically effective amount of a compound of Formula I, or a pharmaceutically acceptable salt thereof.

In some embodiments, the present disclosure provides a method for treating or preventing a condition characterized by overexpression of Menin in a subject in need thereof by administering to the subject a therapeutically effective amount of a compound of Formula I, or a pharmaceutically acceptable salt thereof.

In some embodiments, the present disclosure provides a method for treating or preventing a cancer in a subject in need thereof by administering to the subject a therapeutically effective amount of a compound of Formula I, or a pharmaceutically acceptable salt thereof. In one aspect, the cancer is a hematological malignancy. In another aspect, the cancer is a solid tumor cancer.

In some embodiments, the present disclosure provides a method for treating or preventing a hematological malignancy in a subject in need thereof by administering to the subject a therapeutically effective amount of a compound of Formula I, or a pharmaceutically acceptable salt thereof, wherein the hematological malignancy is selected from the group consisting of leukemias, myeloma, Non-Hodgkin lymphoma (NHL), diffuse large B-cell lymphoma (DLBCL), myeloproliferative neoplasm (MPN), and myelodysplastic syndrome (MDS). In one aspect, the hematological malignancy is a leukemia. In another aspect, the hematological malignancy is mixed-lineage leukemia (MLL)-rearranged leukemia. In another aspect, the hematological malignancy is multiple myeloma. In another aspect, the hematological malignancy is Non-Hodgkin lymphoma. In another aspect, the hematological malignancy is diffuse large B-cell lymphoma (DLBCL). In another aspect, the hematological malignancy is myeloproliferative neoplasm. In another aspect, the hematological malignancy is myelodysplastic syndrome (MDS).

In some embodiments, the present disclosure provides a method for treating or preventing a leukemia in a subject in need thereof by administering to the subject a therapeutically effective amount of a compound of Formula I, or a pharmaceutically acceptable salt thereof, wherein the leukemia is selected from the group consisting of acute leukemia, chronic leukemia, myeloid leukemia, myelogeneous leukemia, lymphoblastic leukemia, lymphocytic leukemia, acute myelogeneous leukemia (AML), chronic myelogenous leukemia (CML), acute lymphoblastic leukemia (ALL), chronic lymphocytic leukemia (CLL), T cell prolymphocytic leukemia (T-PLL), large granular lymphocytic leukemia, hairy cell leukemia (HCL), mixed-lineage leukemia (MLL)-rearranged leukemia, mixed lineage leukemia-partial tandem duplication (MLL-PTD) leukemia, MLL-amplified leukemias, MLL-positive leukemias, NPM1-mutant acute myelogeneous leukemia (AML), NUP98-rearranged acute myelogeneous leukemia (AML), SETD2/RUNX1 mutant leukemia, and leukemia exhibiting an HOX/MEIS1 gene expression signature. In aspect, the leukemia is acute myeloid leukemia (AML). In another aspect, the leukemia is NPM1-mutant acute myeloid leukemia (AML). In another aspect, the leukemia is NUP98-rearranged acute myelogeneous leukemia (AML). In another aspect, the leukemia is acute lymphoblastic leukemia (ALL).

In some embodiments, the present disclosure provides a method for treating or preventing a solid tumor cancer in a subject in need thereof by administering to the subject a therapeutically effective amount of a compound of Formula I, or a pharmaceutically acceptable salt thereof, wherein the solid tumor cancer is selected from the group consisting of ovarian cancer, head and neck cancer, prostate cancer, lung cancer, breast cancer, pancreatic cancer, colorectal cancer, liver cancer, melanoma, glioblastoma, and sarcoma cancers. In one aspect, the solid tumor cancer is ovarian cancer. In another aspect, the solid tumor cancer is head and neck cancer. In another aspect, the solid tumor cancer is prostate cancer. In another aspect, the solid tumor cancer is lung cancer. In another aspect, the solid tumor cancer is breast cancer. In another aspect, the solid tumor cancer is pancreatic cancer. In another aspect, the solid tumor cancer is colorectal cancer. In another aspect, the solid tumor cancer is liver cancer. In another aspect, the solid tumor cancer is melanoma. In another aspect, the solid tumor cancer is glioblastoma. In another aspect, the solid tumor cancer is a sarcoma cancer.

In some embodiments, the compound of the present disclosure, or a pharmaceutically acceptable salt thereof, is administered as first line therapy.

In some embodiments, the compound of the present disclosure, or a pharmaceutically acceptable salt thereof, is administered as second line (or later) therapy.

In some embodiments, the subject to whom a therapeutically effective amount of a compound of the present disclosure, or a pharmaceutically acceptable salt thereof, is administered exhibits a partial response (PR) in response to such treatment.

In some embodiments, the subject to whom a therapeutically effective amount of a compound of the present disclosure, or a pharmaceutically acceptable salt thereof, is administered exhibits a complete response (CR) in response to such treatment.

In some embodiments, the subject to whom a therapeutically effective amount of a compound of the present disclosure, or a pharmaceutically acceptable salt thereof, is administered exhibits an improved progression free survival (PFS) in response to such treatment.

In some embodiments, the subject to whom a therapeutically effective amount of a compound of the present disclosure, or a pharmaceutically acceptable salt thereof, is administered exhibits an improved overall survival (OR) in response to such treatment.

The subject treated typically will be a human or non-human mammal, particularly a human. Suitable subjects can also include domestic or wild animals; companion animals (including dogs, cats, and the like); livestock (including horses, cows and other ruminants, pigs, poultry, rabbits, and the like); primates (including monkeys such as rhesus monkeys, cynomolgus (also known as crab-eating or long-tailed) monkeys, marmosets, tamarins, chimpanzees, macaques, and the like); and rodents (including rats, mice, gerbils, guinea pigs, and the like).

In some embodiments, the present disclosure provides the compounds of Formula I, or pharmaceutically acceptable salts thereof, for use as medicaments.

In some embodiments, the present disclosure provides for the use of the compounds of the Formula I, or pharmaceutically acceptable salts thereof, for treating or preventing a Menin-mediated condition as discussed above.

In some embodiments, the present disclosure provides for the use of the compounds of the Formula I, or pharmaceutically acceptable salts thereof, for the manufacture of medicaments for treating or preventing a Menin-mediated condition as discussed above.

IV. Combination Therapies and Fixed-Dose Combinations

The compounds of Formula I, or a pharmaceutically acceptable salt thereof, may be used in the methods described above as either as single pharmacological agents or in combination with other pharmacological agents or techniques. Such combination therapies may be achieved by way of the simultaneous, sequential, or separate dosing of the individual components of the treatment. These combination therapies (and corresponding combination products) employ the compounds of the present disclosure within the dosage ranges described in this application and the other pharmacological agent(s), typically within its approved dosage range(s).

In some embodiments, the present disclosure provides a combination suitable for use in the treatment of a condition selected from the previously discussed conditions, wherein the combination comprises a compound of Formula I, or a pharmaceutically acceptable salt thereof, and chemotherapy. In one aspect, the chemotherapy is induction chemotherapy. In another aspect, the chemotherapy is consolidation chemotherapy. In another aspect, the chemotherapy comprises administration of cytarabine. In another aspect, the chemotherapy comprises administration of cytarabine and an anthracycline. In another aspect, the chemotherapy comprises administration of cytarabine and an anthracycline selected from daunorubicin and idarubicin. In another aspect, the chemotherapy comprises administration of azacitidine. In another aspect, the chemotherapy comprises administration of all-trans-retinoic acid (ATRA) and arsenic trioxide or an anthracycline. In another aspect, the chemotherapy comprises administration of all-trans-retinoic acid (ATRA) and arsenic trioxide or an anthracycline selected from daunorubicin and idarubicin. In another aspect, the chemotherapy comprises administration of two or more agents selected from the group consisting of vincristine, cyclophosphamide, cytarabine, daunorubicin, etoposide, thioguanine, mercaptopurine. In another aspect, the chemotherapy further comprises administration of methotrexate and/or a steroid selected from the group consisting of prednisolone, dexamethasone, and hydrocortisone.

In some embodiments, the present disclosure provides a combination suitable for use in the treatment of a condition selected from the previously discussed conditions, wherein the combination comprises a compound of Formula I, or a pharmaceutically acceptable salt thereof, and radiation therapy.

In some embodiments, the present disclosure provides a combination suitable for use in the treatment of a condition selected from the previously discussed conditions, wherein the combination comprises a compound of Formula I, or a pharmaceutically acceptable salt thereof, and allogenic stem cell transplantation.

In some embodiments, the present disclosure provides a combination suitable for use in the treatment of a condition selected from the previously discussed conditions, wherein the combination comprises a compound of Formula I, or a pharmaceutically acceptable salt thereof, and CAR-T therapy.

In some embodiments, the present disclosure provides a combination suitable for use in the treatment of a condition selected from the previously discussed conditions, wherein the combination comprises a compound of Formula I, or a pharmaceutically acceptable salt thereof, and an epigenetic modulator. In one aspect, the epigenetic modulator is selected from the group consisting of ivosidenib and enasidenib.

In some embodiments, the present disclosure provides a combination suitable for use in the treatment of a condition selected from the previously discussed conditions, wherein the combination comprises a compound of Formula I, or a pharmaceutically acceptable salt thereof, and a tyrosine kinase inhibitor. In one aspect, the tyrosine kinase inhibitor is selected from the group consisting of adavosertib, dasatinib, erlotinib, gefitinib, imatinib, lapatinib, nilotinib, and sunitinib.

In some embodiments, the present disclosure provides a combination suitable for use in the treatment of a condition selected from the previously discussed conditions, wherein the combination comprises a compound of Formula I, or a pharmaceutically acceptable salt thereof, and a Bruton kinase inhibitor. In one aspect, the tyrosine kinase inhibitor is selected from the group consisting of acalabrutinib, ibrutinib, nemtabrutinib, orelabrutinib, pirtobrutinib, remibrutinib, tolebrutinib, and zanubrutinib.

In some embodiments, the present disclosure provides a combination suitable for use in the treatment of a condition selected from the previously discussed conditions, wherein the combination comprises a compound of Formula I, or a pharmaceutically acceptable salt thereof, and a BCL2 inhibitor. In one aspect, the BCL2 inhibitor is venetoclax.

In some embodiments, the present disclosure provides a combination suitable for use in the treatment of a condition selected from the previously discussed conditions, wherein the combination comprises a compound of Formula I, or a pharmaceutically acceptable salt thereof, and a CDK4/6 kinase inhibitor. In one aspect, the CDK4/6 inhibitor is selected from the group consisting of palbociclib, abemaciclib, ribociclib, lerociclib (G1T38), trilaciclib (G1T28), dalpiciclib (SHR-6390), and BPI-16350. In another aspect, the CDK4/6 inhibitor is selected from the group consisting of palbociclib, abemaciclib, ribociclib, and dalpiciclib.

In some embodiments, the present disclosure provides a combination suitable for use in the treatment of a condition selected from the previously discussed conditions, wherein the combination comprises a compound of Formula I, or a pharmaceutically acceptable salt thereof, and an isocitrate dehydrogenase-1 (IDH1) inhibitor. In one aspect, the IDH1 inhibitor is olutasidenib (Rezlidhia™).

In some embodiments, the present disclosure provides a combination suitable for use in the treatment of a condition selected from the previously discussed conditions, wherein the combination comprises a compound of Formula I, or a pharmaceutically acceptable salt thereof, and a bi-specific T-cell engager. In one aspect, the bi-specific T-cell engager is blinatumomab.

In some embodiments, the present disclosure provides a combination suitable for use in the treatment of a condition selected from the previously discussed conditions, wherein the combination comprises a compound of Formula I, or a pharmaceutically acceptable salt thereof, and a FLT3 inhibitor. In one aspect, the FLT3 inhibitor is gilteritinib.

In some embodiments, the present disclosure provides a combination suitable for use in the treatment of a condition selected from the previously discussed conditions, wherein the combination comprises a compound of Formula I, or a pharmaceutically acceptable salt thereof, and an XPO inhibitor.

In some embodiments, the present disclosure provides a combination suitable for use in the treatment of a condition selected from the previously discussed conditions, wherein the combination comprises a compound of Formula I, or a pharmaceutically acceptable salt thereof, and a chromatin regulator.

In some embodiments, the present disclosure provides a combination suitable for use in the treatment of a condition selected from the previously discussed conditions, wherein the combination comprises a compound of Formula I, or a pharmaceutically acceptable salt thereof, and an immunomodulatory agent from the class of IMids.

V. Pharmaceutical Compositions

The compounds of Formula I, and pharmaceutically acceptable salts thereof, may be administered as pharmaceutical compositions, comprising one or more pharmaceutically acceptable excipients. Therefore, in some embodiments the present disclosure provides pharmaceutical compositions comprising a compound of Formula I, or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth Edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. Compositions intended for oral use may contain, for example, one or more coloring, sweetening, flavoring and/or preservative agents.

The total daily dose will necessarily be varied depending upon the subject treated, the route of administration, any therapies being co-administered, and the severity of the illness being treated, and may include single or multiple doses. Specific dosages can be adjusted, for example, depending upon the condition being treated; the age, body weight, general health condition, sex, and diet of the subject; administration routes; dose intervals; excretion rate; and other drugs being co-administered to the subject. The compound of Formula I, or a pharmaceutically acceptable salt thereof, typically will be administered to a warm-blooded animal at a unit dose within the range 2.5 to 5000 mg/$m^2$ body area of the animal, or approximately 0.05 to 100 mg/kg, and this normally provides a therapeutically effective dose.

In some embodiments, the present disclosure provides pharmaceutical compositions for use in therapy, comprising a compound of Formula I, or a pharmaceutically acceptable salt thereof, and at least one pharmaceutically acceptable excipient.

In some embodiments, the present disclosure provides pharmaceutical compositions for use in the treatment of Menin-mediated condition, comprising a compound of Formula I, or a pharmaceutically acceptable salt thereof, and at least one pharmaceutically acceptable excipient. In one aspect, the Menin-mediated condition is a hematological malignancy. In another aspect, Menin-mediated condition is a solid tumor cancer.

VI. Kits

The present disclosure further provides kits comprising a unit dosage form comprising a compound of Formula I, or a pharmaceutically acceptable salt thereof, contained within a packaging material and a label or package insert which indicates that the unit dosage form can be used for treating one or more of the previously described conditions.

In some embodiments, the kit comprises a unit dosage form comprising a compound of Formula I, or a pharmaceutically acceptable salt thereof, contained within a packaging material and a label or package insert which indicates that the pharmaceutical composition can be used for treating a Menin-mediated condition. In one aspect, the Menin-mediated condition is a hematological malignancy. In another aspect, the Menin-mediated condition is a solid tumor cancer.

In some embodiments, kit comprises: (a) a first unit dosage form comprising a compound of Formula I, or a pharmaceutically acceptable salt thereof; (b) a second unit dosage form comprising a pharmacological agent selected from the group consisting of chemotherapeutic agents, epigenetic modulators, tyrosine kinases, Bruton kinase inhibitors, BCL2 inhibitors, CDK4/6 kinase inhibitors, isocitrate dehydrogenase-1 (IDH1) inhibitors, FLT3 inhibitors, XPO inhibitors, chromatin regulators, and EGFR inhibitors; (c) a container means for containing said first and second dosage forms; and (d) a label or package insert which indicates that the first unit dosage form and second unit dosage form can be used for treating an FAP-mediated condition.

VII. Methods of Preparation

The present disclosure further provides processes for the preparation of the compounds of Formula (I) and pharmaceutically acceptable salts thereof.

Schemes 1 to 14 below illustrate synthetic routes to compounds of Formula (I) wherein $R^1$, $R^2$, $R^3$, $R^4$, $R^5$, $R^6$, $R^{10}$, $R^{11}$, $R^{12}$, $R^{13}$, $R^{14}$, $R^A$ and X are as defined in formula (I), $X^2$ is a leaving group (e.g. I, Br, Cl or OTf), n and m determines the ring size of group A, defined in formula (I) (n=1 or 2 —$CH_2$— and m=1, 2 or 3 —$CH_2$—). One of skill in the art will appreciate that these methods are representative and are not inclusive of all possible methods for preparing the compounds of the present disclosure. The RX substituents in each Scheme are as defined for the compounds of the present disclosure unless otherwise stated. It is understood that the processes for preparation described in Schemes 1 to 14 can be performed starting from any enantiomer, or a racemic mixture, of compounds of the formula (1), (2), (4), (6), (7), (8), (9), (10), (12), (14), (15), (18), (20), (21), (22), (23), (25), (34), (35), (41), (43) or (44), to give compounds of Formula (I) or any stereoisomer of Formula (I). All starting materials are readily available or described in the 'Intermediate Compounds" section.

SCHEME 1

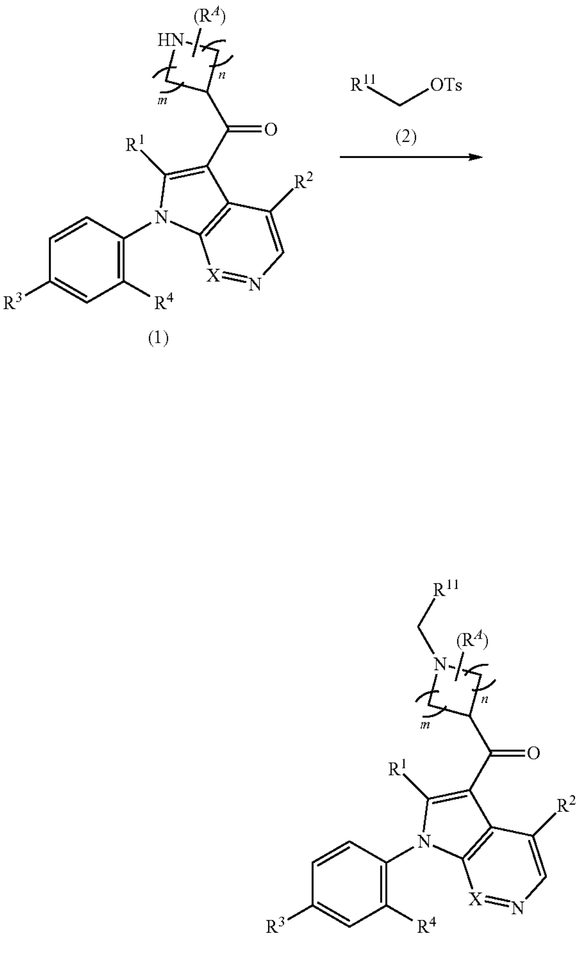

(1) (2) (3)

Scheme 1 illustrates synthetic routes to certain compounds of formula (3). A compound of formula (3) may be formed from compounds of formula (1) with a compound TsO—$R^{11}$ (2), wherein $R^{11}$ is as defined in Formula (I). The reaction may be performed in the presence of a base (such as $K_2CO_3$, etc.) in an organic solvent (such as MeCN, etc.) at a temperature of 80° C.

SCHEME 2

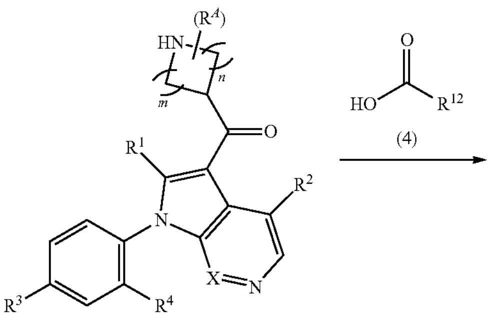

(1)

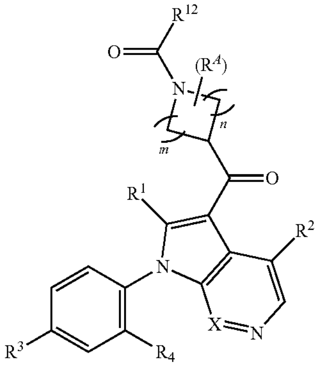

(5)

SCHEME 3

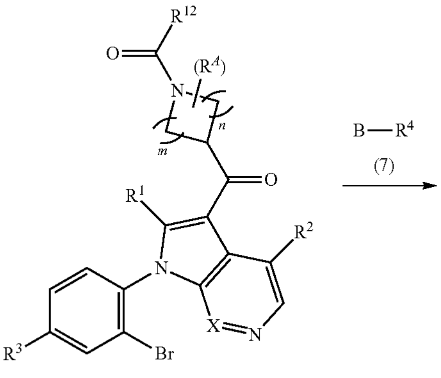

(6)

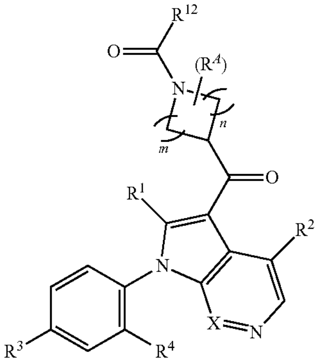

(5)

Scheme 2 illustrates synthetic routes to certain compounds of formula (5). A compound of formula (1) may be reacted with carboxylic acid $R^{12}$—COOH (4), wherein $R^{12}$ is as defined in Formula (I), to give a compound of formula (5). The reaction may be performed using suitable coupling reagents (such as HATU, HOBt/EDC, T3P, etc.) in the presence of a base (typically an organic base such as DIPEA, etc.) using a solvent (such as DCM, DMF, EtOAc, or mixtures thereof) and temperatures typically ranging from 0° C. to room temperature.

Compounds of formula (5) may contain a Boc-protected amine which may be removed with a suitable acid such as TFA or FA, neat or in solvent such as DCM. Alternatively, the reaction may be performed using acids such as HCl, MsOH or TsOH in a solvent (such as MeCN, 1,4-dioxane, IPA, or mixtures thereof) at temperatures typically ranging from 0° C. to 60° C.

Scheme 3 illustrates synthetic routes to certain compounds of formula (5). A compound of formula (5) may be formed by reacting a compound of formula (6) with a compound of formula B—$R^4$ (7), wherein B is a boronic acid or boronate ester, and wherein $R^4$ is selected from the group consisting of (b) and (c) as defined in Formula (I). The reaction may be catalyzed with a suitable Pd-reagent (such as $Pd(dppf)Cl_2$, etc.) in the presence of a base (such as $K_2CO_3$, etc.) in a suitable solvent (such as 1,4-dioxane, etc.), optionally in the presence of water, at temperatures ranging from 60° C. to 110° C.

Compounds of formula (5) may contain a Boc-protected amine which may be removed with a suitable acid such as TFA or FA, neat or in solvent such as DCM. Alternatively, the reaction may be performed using acids such as HCl in a solvent (such as MeCN, 1,4-dioxane, or mixtures thereof) at temperatures typically ranging from 0° C. to room temperature.

SCHEME 4

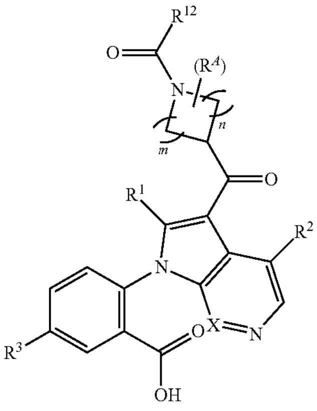

(8)

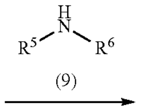

(9)

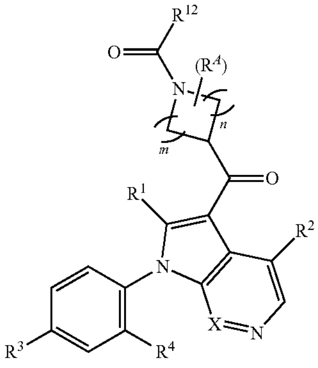

(5)

Scheme 4 illustrates additional synthetic routes to certain compounds of formula (5). A compound of formula (5) may be formed from compounds of formula (8) and amine H—$NR^5R^6$ (9), wherein $R^5$ and $R^6$ are as defined in Formula (I). The reaction may be performed using suitable coupling reagents (such as HATU, etc.) in the presence of a base (typically an organic base such as DIPEA, etc.) using a solvent (such as DCM, DMF, or mixtures thereof) and temperatures typically ranging from 0° C. to room temperature.

Compounds of formula (5) may contain a Boc-protected amine which may be removed with a suitable acid such as TFA, neat or in solvent such as DCM, at room temperature.

SCHEME 5

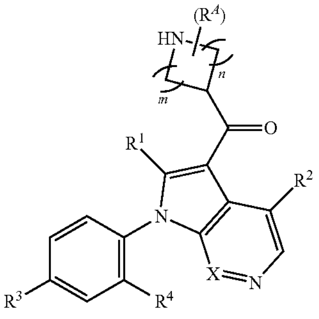

(1)

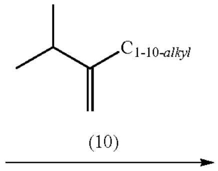

(10)

-continued

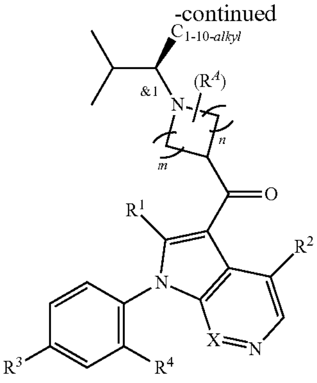

(11)

$X^2$—$R^{14}$ (12)

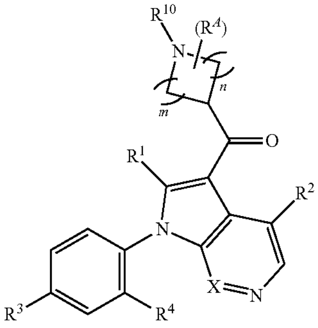

(13)

Scheme 5 illustrates synthetic routes to certain compounds of formula (13). A compound of formula (1) may be reacted with a compound of formula (10), wherein the structure represents $R^{10}$ consisting of $C_{1-10}$-alkyl, wherein the $C_{1-10}$-alkyl is substituted with one or more —$NR^{13}R^{14}$ as defined in Formula (I), to give a compound of formula (11). The reaction may be performed using suitable reducing agents (such as STAB, etc.) in the presence of $Ti(OiPr)_4$, using a solvent (such as such as DMF, etc.) at room temperature.

Compounds of formula (11) may contain a Boc-protected amine which may be removed with a suitable acid (such as HCl, etc.) in a solvent (such as 1,4-dioxane, etc.) at room temperature. The free amine may be reacted with a compound of formula (12), wherein $X^2$ is a leaving group (such as I, Br, Cl or OTf, etc.), and wherein $R^{14}$ is as defined in Formula (I), to give a compound of formula (13). The reaction may be performed in the presence of a base (such as $K_2CO_3$, NaI, etc.) using a solvent (such as DMF, etc.) at temperatures ranging from room temperature to 50° C.

SCHEME 6

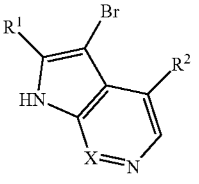

(14)

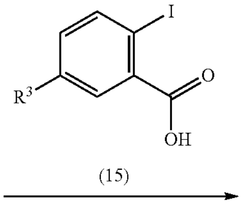

(15)

-continued

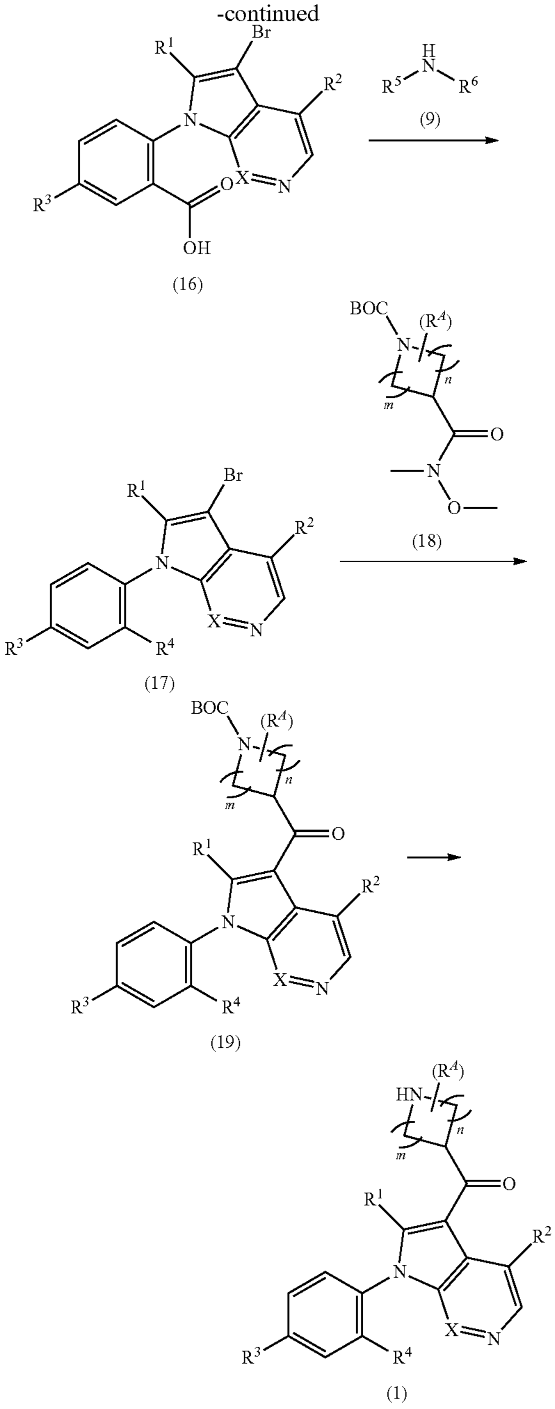

(16)

(9)

(18)

(17)

(19)

(1)

Scheme 6 illustrates synthetic routes to certain compounds of formula (1). A compound of formula (16) may be formed by reacting a compound of formula (14) with a compound of formula (15). The reaction may be catalyzed with a suitable Cu-reagent (such as Cu, CuI, etc.) in the presence of a base (such as $K_2CO_3$, $Cs_2CO_3$, etc.) in a suitable solvent (such as DMF, etc.) at temperatures ranging from 80° C. to 130° C.

A compound of formula (16) may be reacted with a compound of formula (9), wherein $R^5$ and $R^6$ are as defined in Formula (I), to give a compound of formula (17). The reaction may be performed using suitable coupling reagents (such as HATU, etc.) in the absence or presence of a base (typically an organic base such as DIPEA, etc.) using a solvent (such as DCM, DMF, or mixtures thereof) at room temperature.

A compound of formula (19) may be formed by treating a compound of formula (17) with a strong base (such as n-BuLi, etc.) and reacting this with a compound of formula (18), wherein the ring size (m, n) and $R^A$ are as defined in Formula (I), in a solvent (such as THF, etc.) and at a temperature typically ranging from −78° C. to room temperature.

A compound of formula (19) may be transformed into a compound of formula (1) with a suitable acid such as TFA, neat or in a solvent such as DCM, at room temperature.

SCHEME 7

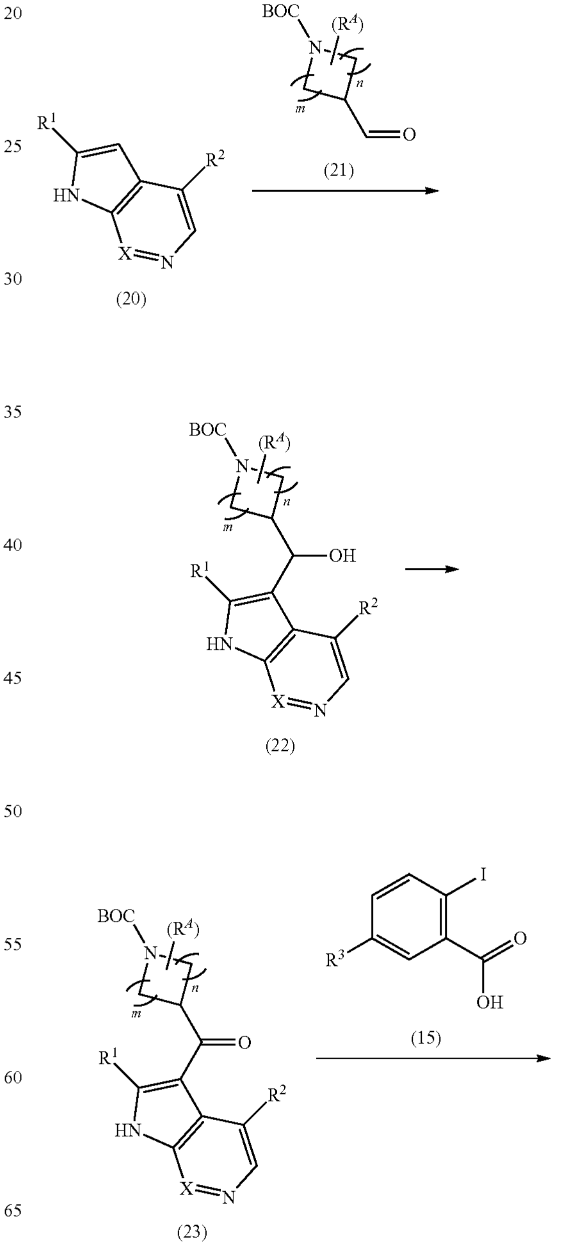

(20)

(21)

(22)

(23)

(15)

-continued

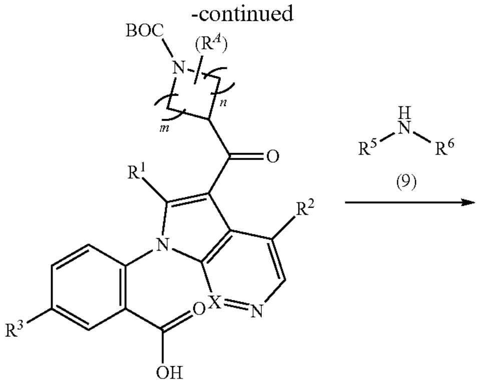

(9)

(24)

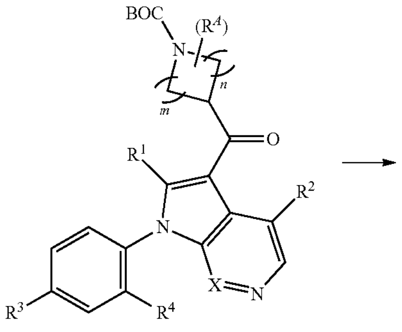

(19)

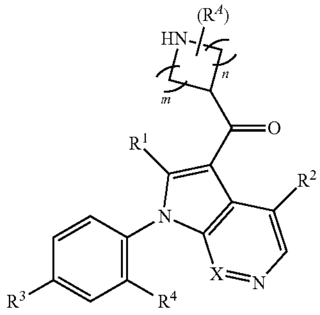

(1)

Scheme 7 illustrates additional synthetic routes to certain compounds of formula (1). A compound of formula (22) may be formed by reacting a compound of formula (20) with an aldehyde (21), wherein $R^A$, n and m are defined in Formula (I), in the presence of a base (such as KOH, KOt-Bu, etc.) in a suitable solvent (such as MeOH, EtOH, 1,4-dioxane, water, or mixtures thereof) and at temperatures typically ranging from 0° C. to 40° C.

A compound of formula (23) may be formed by reacting a compound formula (22) with a suitable oxidizing agent (such as $MnO_2$, TEMPO/PIDA, etc.) in a suitable solvent (such as 1,4-dioxane, DCM, etc.) and at temperatures typically ranging from room temperature to 100° C.

A compound of formula (24) may be formed by reacting a compound of formula (23) with a compound of formula (15). The reaction may be catalyzed with a suitable Cu-reagent (such as Cu, CuI, etc.) in the presence of a base (such as $K_2CO_3$, $Cs_2CO_3$, etc.) in a suitable solvent (such as DMF, etc.) at temperatures ranging from 60° C. to 100° C.

A compound of formula (24) may be reacted with a compound of formula (9), wherein $R^5$ and $R^6$ are as defined in Formula (I), to give a compound of formula (19). The reaction may be performed using suitable coupling reagents (such as HATU, T3P, etc.) in the absence or presence of a base (such as DIPEA, DMAP, etc.) using a solvent (such as DCM, DMF, or mixtures thereof) and at temperatures typically ranging from room temperature to 40° C.

A compound of formula (19) may be transformed into a compound of formula (1) with a suitable acid such as TFA or FA, neat or in solvent such as DCM. Alternatively, the reaction may be performed using a suitable acid (such as HCl, etc.) in a solvent such as 1,4-dioxane at room temperature.

SCHEME 8

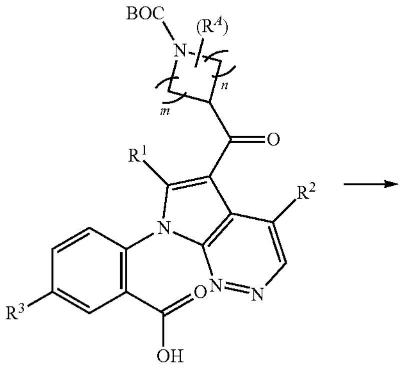

(25)

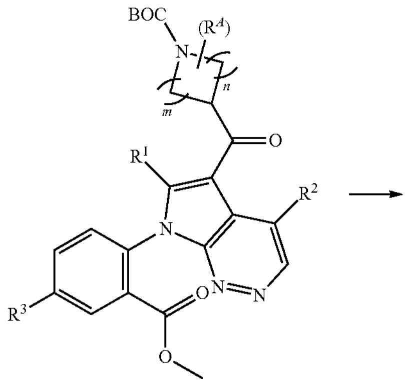

(26)

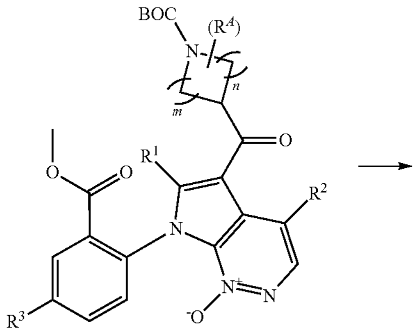

(27)

-continued

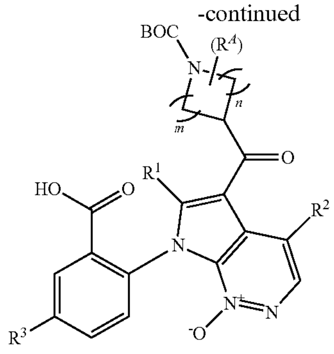

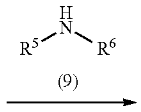

(9)

(28)

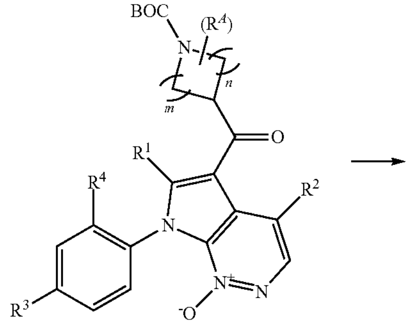

(29)

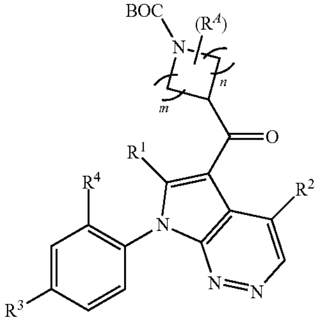

(30)

Scheme 8 illustrates synthetic routes to certain compounds of formula (30). A compound of formula (25) may be reacted with MeI to give a compound of formula (26). The reaction may be performed in the presence of a base (such as $K_2CO_3$, etc.) using a solvent (such as DMF, etc.) at room temperature.

A compound of formula (27) may be formed by reacting a compound of formula (26) with a suitable oxidizing agent (such as m-CPBA, etc.) using a solvent (such as DCM, etc.) at room temperature.

A compound of formula (28) may be formed by reacting a compound of formula (27) with a base (such as LiOH, etc.) in an organic solvent (such as THF, etc.), optionally in the presence of water, at room temperature.

A compound of formula (28) may be reacted with a compound of formula (9), wherein $R^5$ and $R^6$ are as defined in Formula (I), to give a compound of formula (29). The reaction may be performed using suitable coupling reagents (such as T3P, etc.) in the absence or presence of a base (such as DIPEA, etc.) using a solvent (such as DCM, DMF, or mixtures thereof) and at temperatures typically ranging from 0° C. to room temperature.

A compound of formula (30) may be formed by reacting a compound of formula (29) with a suitable reducing agent (such as iron and $NH_4Cl$, etc.) using a solvent (such as EtOH, water, or mixtures thereof) at a temperature of 80° C.

SCHEME 9

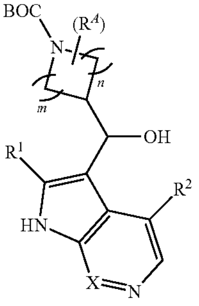

(22)

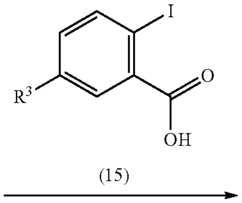

(15)

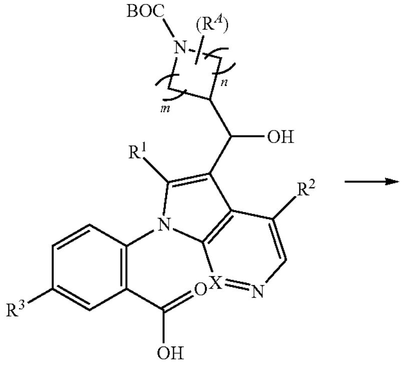

(31)

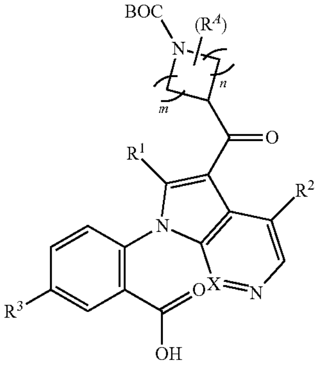

(24)

Scheme 9 illustrates synthetic routes to certain compounds of formula (24). A compound of formula (22) may be reacted with a compound of formula (15) to give a compound of formula (31). The reaction may be catalyzed with a suitable Cu-reagent (such as Cu, etc.) in the presence of a base (such as $K_2CO_3$, etc.) in a suitable solvent (such as DMF, etc.) at 80° C.

A compound of formula (24) may be formed by reacting a compound formula (31) with a suitable oxidizing agent (such as Dess-Martin periodinane, etc.) in a suitable solvent (such as DCM, etc.) at room temperature.

SCHEME 10

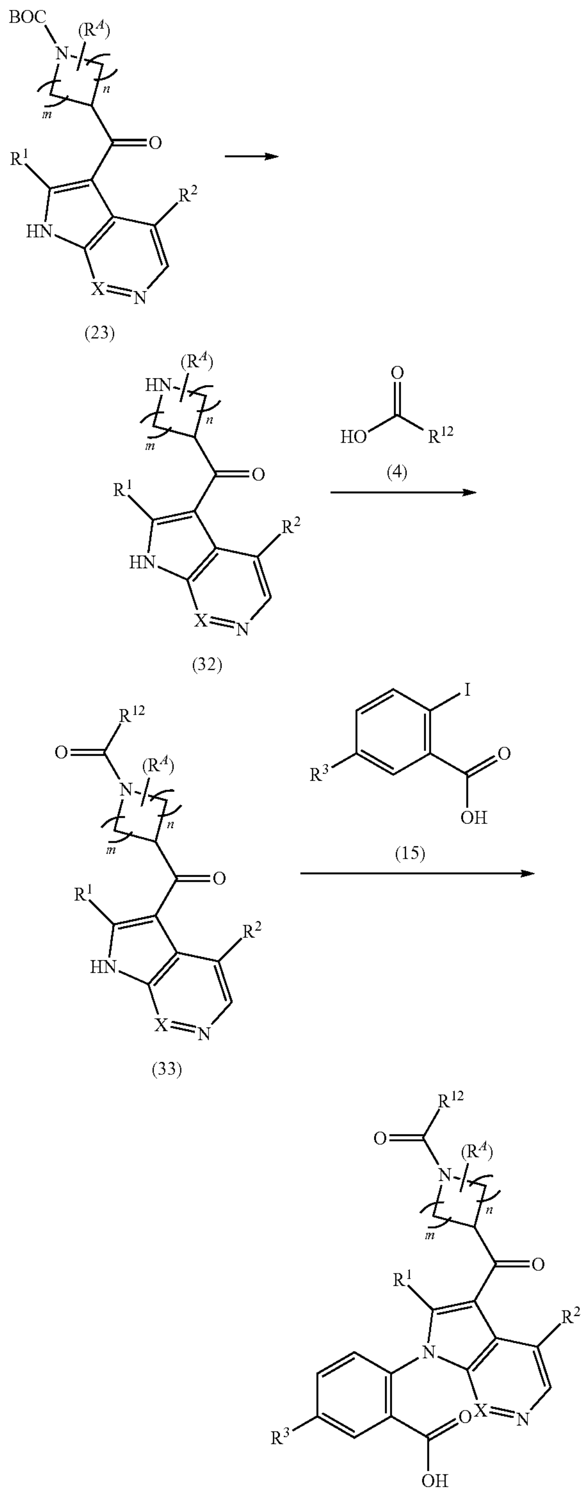

(23)

(32)

(4)

(33)

(15)

(8)

Scheme 10 illustrates synthetic routes to certain compounds of formula (8). A compound of formula (23) may be transformed into a compound of formula (32) with a suitable acid (such as HCl, etc.) in a solvent (such as 1,4-dioxane, MeCN, or mixtures thereof) at room temperature.

A compound of formula (32) may be reacted with carboxylic acid $R^{12}$—COOH (4), wherein $R^{12}$ is as defined in Formula (I), to give a compound of formula (33). The reaction may be performed using suitable coupling reagents (such as HOBt/EDC, etc.) in the presence of a base (typically an organic base such as DIPEA, etc.) using a solvent (such as DCM, DMF, or mixtures thereof) at room temperature.

A compound of formula (33) may be reacted with a compound of formula (15) to give a compound of formula (8). The reaction may be catalyzed with a suitable Cu-reagent (such as Cu, etc.) in the presence of a base (such as $K_2CO_3$, etc.) in a suitable solvent (such as DMF, etc.) at 80° C.

SCHEME 11

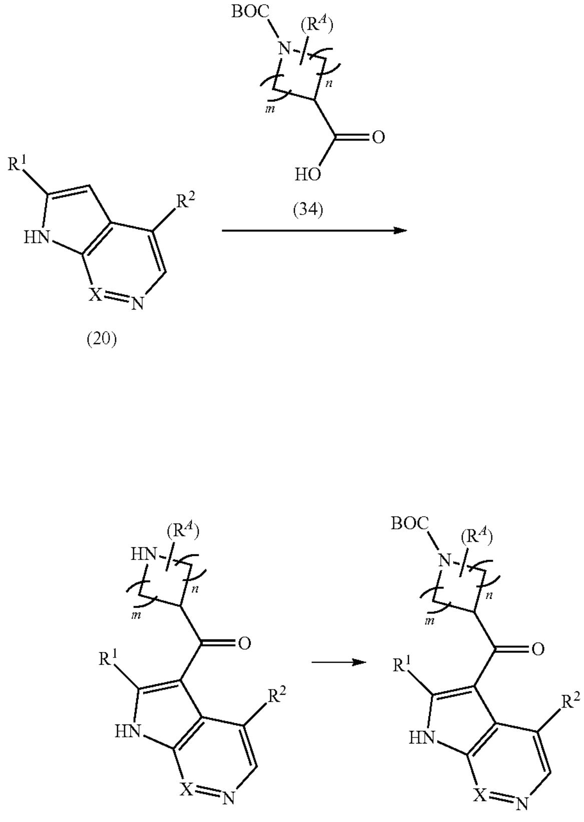

(34)

(20)

(32)

(23)

Scheme 11 illustrates additional synthetic routes to certain compounds of formula (23). A compound of formula (32) may be formed by reacting a compound of formula (34) with a suitable agent (such as $SOCl_2$, etc.) to form the acyl chloride, and reacting a compound of formula (20) with the acyl chloride in the presence of a Lewis acid (such as $AlCl_3$, etc.) in a suitable solvent (such as DCM, etc.) at temperatures typically ranging from 0° C. to room temperature.

A compound of formula (23) may be formed by reacting a compound of formula (32) with $Boc_2O$ in the presence of a base (such as TEA/DMAP, etc.) in a suitable solvent (such as DCM, etc.) at room temperature, followed by treating the obtained isolated product with a base such as NaOH in a suitable solvent (e.g. MeOH) at room temperature.

SCHEME 12

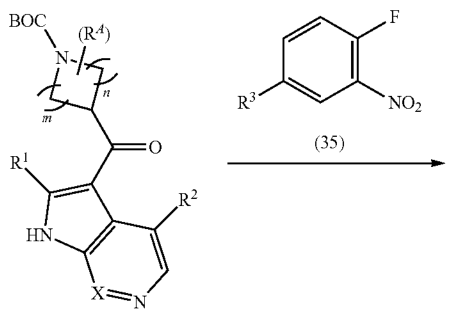

(23)

(35)

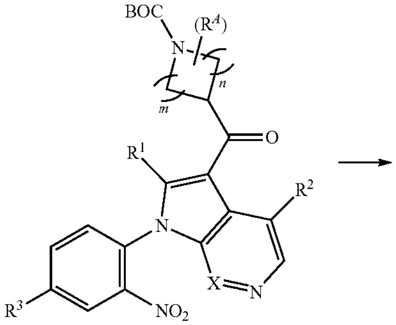

(36)

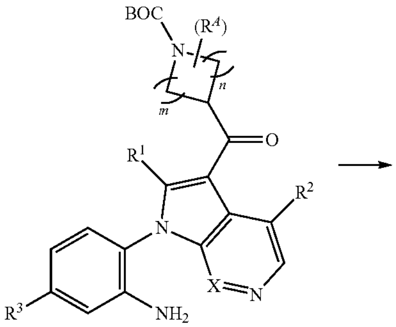

(37)

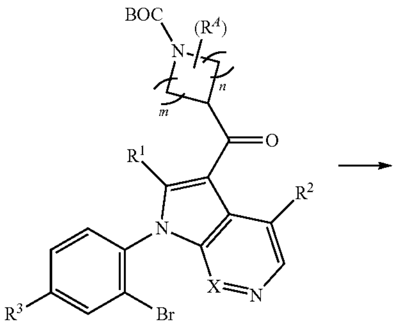

(38)

-continued

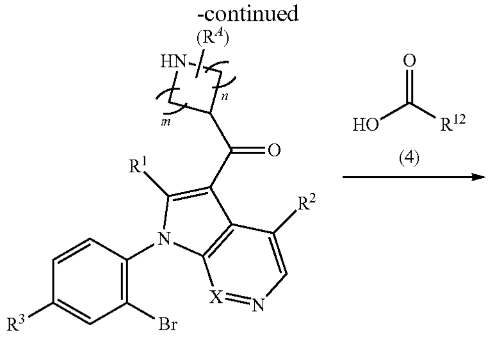

(39)

(4)

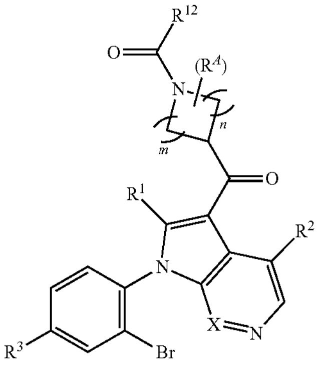

(6)

Scheme 12 illustrates synthetic routes to certain compounds of formula (6). A compound of formula (36) may be formed by reacting a compound of formula (23) with a compound of formula (35). The reaction may be performed in the presence of a base (such as $K_2CO_3$, etc.) using a solvent (such as DMF, etc.) at 80° C.

A compound of formula (36) may be transformed into a compound of formula (37) by reduction using a suitable reagent (such as iron/$NH_4Cl$, etc.) in a solvent (such as EtOH, EtOAc, water, or mixtures thereof) at 80° C.

A compound of formula (37) may be transformed into a compound of formula (38) by bromide formation using a suitable reagent (such as t-BuONO/$CuBr_2$, etc.) in a solvent (such as MeCN, etc.) at room temperature.

A compound of formula (39) may be formed by reacting a compound of formula (38) with a suitable acid (such as HCl, etc.) in a solvent (such as 1,4-dioxane, MeCN, or mixtures thereof) at room temperature.

A compound of formula (39) may be reacted with carboxylic acid $R^{12}$—COOH (4), wherein $R^{12}$ is as defined in Formula (I), to give a compound of formula (6). The reaction may be performed using suitable coupling reagents (such as T3P, etc.) in the presence of a base (typically an organic base such as DIPEA, etc.) using a solvent (such as DCM, EtOAc, or mixtures thereof) and temperatures typically ranging from 0° C. to room temperature.

SCHEME 13

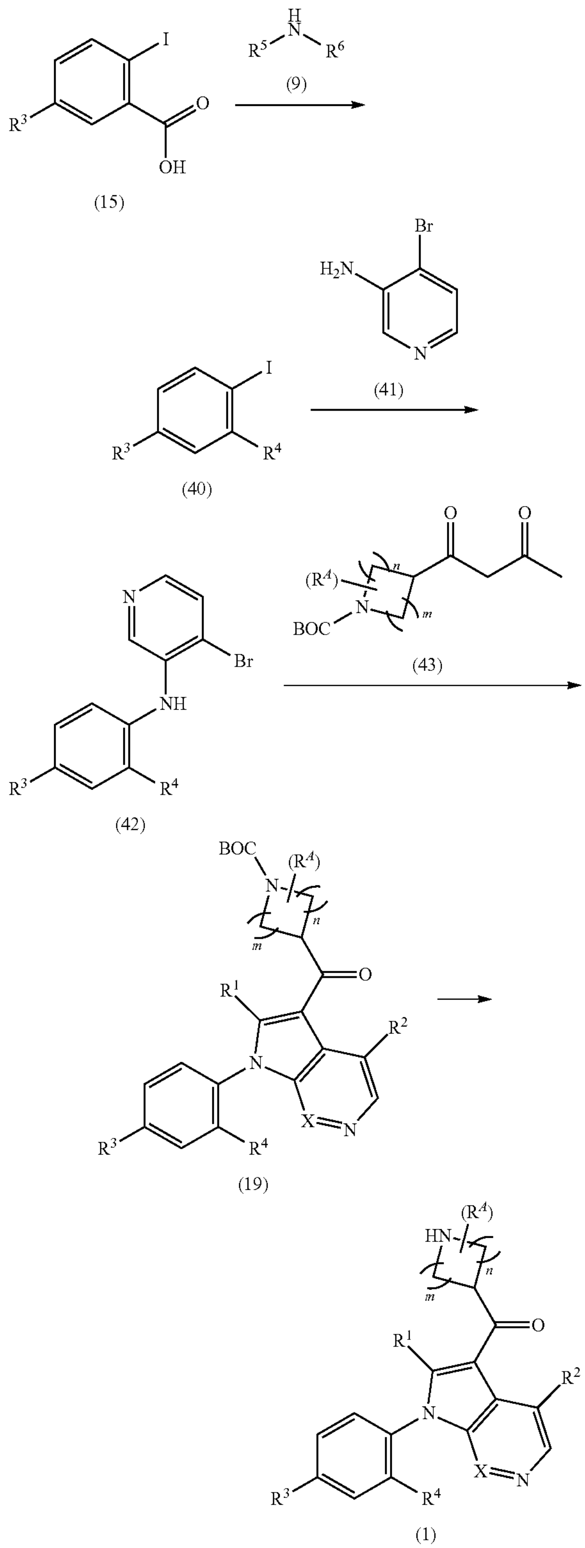

(15) (9) (40) (41) (42) (43) (19) (1)

Scheme 13 illustrates additional synthetic routes to certain compounds of formula (1). A compound of formula (40) may be formed from compounds of formula (15) and amine H—$NR^5R^6$ (9), wherein $R^5$ and $R^6$ are as defined in Formula (I). The reaction may be performed using suitable coupling reagents (such as T3P, etc.) in the presence or absence of a base (typically an organic base such as DIPEA, etc.) using a solvent (such as DCM, etc.) and temperatures typically ranging from 0° C. to room temperature. Alternatively, the reaction may be performed by reacting a compound of formula (15) with a suitable agent (such as $SOCl_2$, etc.) to form the acyl chloride, and reacting a compound of formula (9) with the acyl chloride in a suitable solvent (such as toluene, etc.) at temperatures typically ranging from 0° C. to 80° C.

A compound of formula (42) may be formed by reacting a compound of formula (40) with a compound of formula (41). The reaction may be catalyzed with a suitable Pd-reagent (such as $Pd_2dba_3$, etc.) with a suitable phosphine ligand (such as XantPhos, etc.) in the presence of a base (such as NaOtBu, $Cs_2CO_3$, etc.) in a suitable solvent (such as 1,4-dioxane, 2Me-THF, etc.) at 80° C.

A compound of formula (19) may be formed by reacting a compound of formula (42) with a compound of formula (43). The reaction may be catalyzed with a suitable Cu-reagent (such as CuO, etc.) in the presence of a base (such as $Cs_2CO_3$, etc.) in a suitable solvent (such as DMSO, etc.) at temperatures typically ranging from 100° C. to 110° C.

A compound of formula (19) may be transformed into a compound of formula (1) with a suitable acid (such as TFA, etc.) in a solvent (such as DCM, etc.) at room temperature.

SCHEME 14

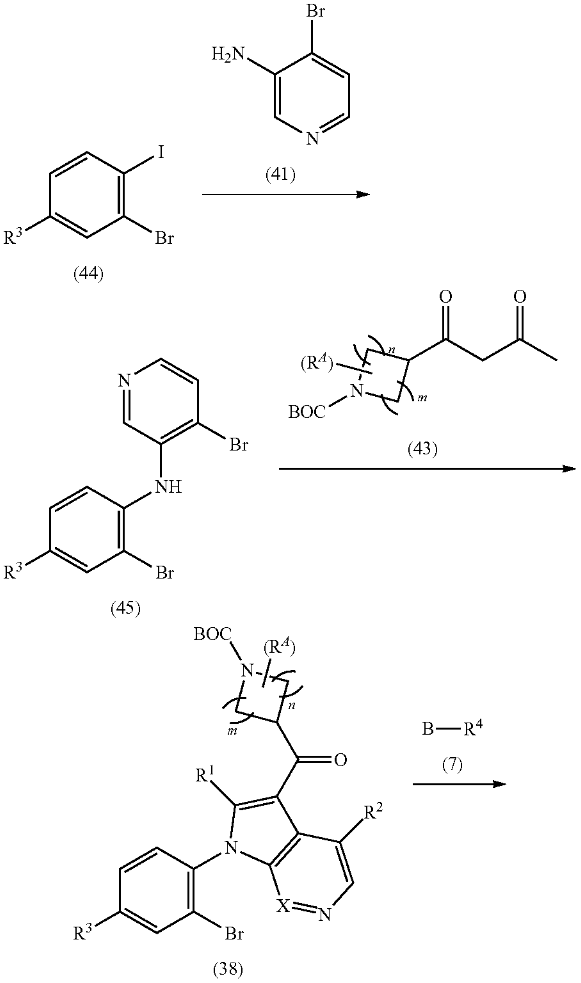

(44) (41) (45) (43) (38) (7)

-continued

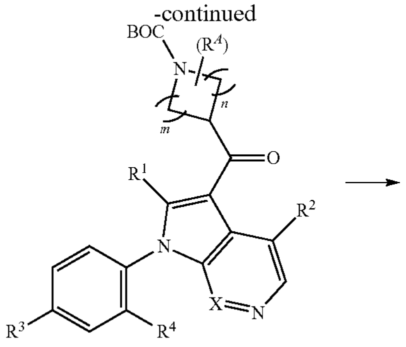

(19)

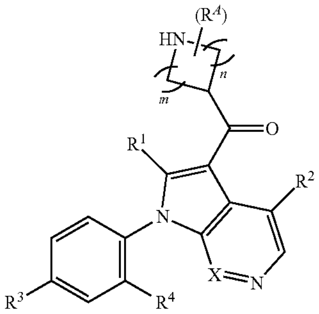

(1)

Scheme 14 illustrates synthetic routes to certain compounds of formula (1). A compound of formula (45) may be formed by reacting a compound of formula (44) with a compound of formula (41). The reaction may be catalyzed with a suitable Pd-reagent (such as $Pd_2dba_3$, etc.) with a suitable phosphine ligand (such as XantPhos, etc.) in the presence of a base (such as NaOtBu, etc.) in a suitable solvent (such as toluene, etc.) at 60° C.

A compound of formula (38) may be formed by reacting a compound of formula (45) with a compound of formula (43). The reaction may be catalyzed with a suitable Cu-reagent (such as CuO, etc.) in the presence of a base (such as $Cs_2CO_3$, etc.) in a suitable solvent (such as DMSO, etc.) at 80° C.

A compound of formula (19) may be formed by reacting a compound of formula (38) with a compound of formula B—$R^4$ (7), wherein B is a boronic acid or boronate ester, and wherein $R^4$ is selected from the group consisting of (b) and (c) as defined in Formula (I). The reaction may be catalyzed with a suitable Pd-reagent (such as Pd(dppf)$Cl_2$, etc.) in the presence of a base (such as $K_2CO_3$, etc.) in a suitable solvent (such as 1,4-dioxane, etc.), optionally in the presence of water, at 100° C.

A compound of formula (19) may be transformed into a compound of formula (1) with a suitable acid such as TFA in a solvent such as DCM. Alternatively, the reaction may be performed using acids such as HCl in a solvent such as 1,4-dioxane, MeCN, or mixtures thereof, at room temperature.

It should be understood that: (i) the organic reactions described in this disclosure are performed according to laboratory practice known to person skilled in the art; (ii) some of the reactions described in this disclosure may optionally be performed in different orders than laid out herein; (iii) chiral isomers of compounds in this disclosure can be resolved at any stage in the synthetic process using chiral resolving agents described in the literature and known to person skilled in the art, or using chiral chromatography methods described in the literature and known to person skilled in the art, or as described further in the Examples; (iv) additional and/or other protective groups may optionally be needed in some of the steps described above, and (v) a deprotection step therefore optionally may be performed, using method described in the literature and known to person skilled in the art. The protection and deprotection of functional groups is described in "Protective Groups in Organic Synthesis" 3rd Ed, T. W. Greene and P. G. M. Wutz, Wiley-Interscience (1999), which publication is incorporated herein by reference.

VIII. Examples

The following descriptions of experiments, procedures, examples, and intermediates are intended to exemplify embodiments of the disclosure and are in no way intended to be limiting. Other compounds of this disclosure may be prepared using the methods illustrated in these examples, either alone or in combination with techniques generally known in the art.

A. General Conditions

Unless otherwise stated:

(i) operations were carried out at room temperature (rt), i.e., in the range of 17 to 25° C. and under an atmosphere of an inert gas such as $N_2$ unless otherwise stated;

(ii) in general, the course of reactions was followed by thin layer chromatography (TLC) and/or analytical (ultra) high performance liquid chromatography (HPLC or UPLC) which was usually coupled to a mass spectrometer (LCMS);

(iii) when necessary, organic solutions were dried over anhydrous $Na_2SO_4$ or $MgSO_4$, or by using Kinesis TELOS® or Whatman™ Phase Separator, and work-up procedures were carried out using traditional phase separating techniques;

(iv) evaporations were carried out by rotary evaporation in vacuo or in a Genevac HT-4/EZ-2 or Biotage V10;

(v) unless otherwise stated, flash column chromatography was performed on straight phase silica, using either Acros Silica Gel (35-70 m silica, art. 240360010) or Orienda Silica Gel (38-60 m silica, art. F01-BK-1000), or pre-packed cartridges from Buchi (FlashPure, 35-45 m silica, 4-330 g) or Orienda (FlashPure, 38-60 m silica, 4-330 g), or on reversed phase silica using either pre-packed cartridges from Agela (Claricep Spherical C18 20-35 μm, 100 Δ, 120 g/branch, art. SO230120-0) or (Claricep Spherical C18 20-35 μm, 100 Δ, 330 g/branch, art. SO230330-0), manually or automated using a Buchi Pure, Biotage Isolera Four or Agela Cheetah II flash system;

(vi) unless otherwise stated, preparative TLC was performed on silica, using Xin Nuo Kun Yu Mountain preparative TLC GF254 (art. XN1997-2-3);

(vii) (a) chiral preparative HPLC and (a) chiral preparative SFC were performed using standard HPLC and SFC instruments, respectively, equipped with either a MS and/or UV triggered fraction collecting instrument, using either isocratic or a gradient of the mobile phase as described in the experimental section, and one of the following methods as described below;

HPLC Prep Methods: PrepMethod A: The compound was purified by preparative HPLC on a Luna® C18(2) column (5

μm, 150×21.2 mm ID) using a gradient of MeCN in $H_2O$ with 0.1% TFA as mobile phase; PrepMethod B: The compound was purified by preparative chiral HPLC on a Lux 5 m Cellulose-4 column (5 μm, 25×2.12 mm ID) using EtOH in hexane with 0.5% 2 M $NH_3$ in MeOH as mobile phase; PrepMethod C: The compound was purified by preparative HPLC on a Xselect CSH C18 OBD column (5 μm, 150×30 mm ID) using a gradient of MeCN in $H_2O$ with 0.1% FA; PrepMethod D: The compound was purified by preparative HPLC on a Atlantis Prep T3 OBD column (10 m, 250×19 mm ID) using a gradient of MeCN in $H_2O$ with 0.1% FA; PrepMethod E: The compound was purified by preparative HPLC on a Xselect CHS Prep C18 OBD column (5 μm, 250×19 mm ID) using a gradient of MeCN in $H_2O$ with 0.1% FA; PrepMethod F: The compound was purified by preparative HPLC on a Xbridge Shield RP18 OBD column (5 am, 150×30 mm ID) using a gradient of MeCN in $H_2O$ with 0.1% FA; PrepMethod G: The compound was purified by preparative HPLC on a Sunfire prep C18 column (5 am, 150×30 mm ID) using a gradient of MeCN in $H_2O$ with 0.1% FA; PrepMethod H: The compound was purified by preparative HPLC on a Chiralpak ID column (5 μm, 250×20 mm ID) using a gradient of EtOH in MTBE containing 0.5% 2 M $NH_3$ in MeOH; PrepMethod I: The compound was purified by preparative HPLC on a Waters CSH C18 OBD column (5 μm, 100×30 mm ID) using a gradient of MeCN in $H_2O$ with 0.3% $NH_4OH$; PrepMethod J: The compound was purified by preparative HPLC on a YMC-Actus Triart C18 ExRS column (5 μm, 150×30 mm ID) using a gradient of MeCN in $H_2O$ with 10 mM $NH_4HCO_3$+0.1% $NH_3{\cdot}H_2O$; PrepMethod K: The compound was purified by preparative HPLC on a Phenomenex Luna C18 column (5 μm, 150×21.2 mm ID) using a gradient of MeCN in $H_2O$ with 0.1% FA; SFC Prep Methods: PrepMethod SFC-A: The compound was purified by preparative SFC on a Chiralpak IG-3 column (3 μm, 50×4.6 mm ID) using MeOH with 0.1% DEA in $CO_2$ as mobile phase; PrepMethod SFC-B: The compound was purified by preparative SFC on a Enanticel C9-3 column (5 μm, 150×30 mm ID) using IPA with 0.1% DEA in $CO_2$ as mobile phase; PrepMethod SFC-C: The compound was purified by preparative SFC on a Chiralpak IG column (5 μm, 250×20 mm ID) using MeOH with 0.1% $NH_3$ in $CO_2$ as mobile phase; PrepMethod SFC-D: The compound was purified by preparative SFC on a YMC SZ column (5 μm, 250×20 mm ID) using MeOH with 0.1% $NH_3$ in $CO_2$ as mobile phase; PrepMethod SFC-E: The compound was purified by preparative SFC on a Regis (R,R)-Whelk-O column (5 μm, 250×20 mm ID) using MeOH with 0.1% $NH_3$ in $CO_2$ as mobile phase; PrepMethod SFC-F: The compound was purified by preparative SFC on a IK column (5 μm, 250×20 mm ID) using MeOH with 0.1% $NH_3$ in $CO_2$ as mobile phase; PrepMethod SFC-G: The compound was purified by preparative SFC on a YMC SB column (5 μm, 250×20 mm ID) using MeOH with 0.1% $NH_3$ in $CO_2$ as mobile phase;

Relevant fractions were collected, combined, and freeze-dried to give the purified compound or relevant fractions were collected, combined, and concentrated at reduced pressure, extracted with DCM or EtOAc in a basic work-up using sat. aq. $NaHCO_3$, and the organic phase was dried over $Na_2SO_4$ or $MgSO_4$, and then concentrated at reduced pressure to give the purified compound;

(viii) yields, where present, are not necessarily the maximum attainable, and when necessary, reactions were repeated if a larger amount of the reaction product was required;

(ix) where certain compounds were obtained as salts, for example a mono-hydrochloride salt or a di-hydrochloride salt, the stoichiometry of the salt was based on the number and nature of the basic groups in the compound or the stoichiometry is labelled as x. The exact stoichiometry of the salt was generally not determined, for example by means of elemental analysis data for hydrochloride and trifluoro acidic acid salts. The stoichiometry of formic acid salts was determined by H-NMR and rounded to an integer number;

(x) in general, the structures of the end-products of the Formula (I) were confirmed by nuclear magnetic resonance (NMR) and/or mass spectral techniques; proton NMR chemical shifts values were measured on the delta scale using Bruker Avance III 400, 500 spectrometer, operating at 1H frequency of 300, 400, 500 MHz. The experiments were typically recorded at 25° C. Chemical shifts are given in ppm with the solvent as internal standard. Protons on heteroatoms such as NH and OH are only reported when detected in NMR and can therefore be missing. In certain instances, protons can be masked by solvent peaks and will therefore either be missing and not reported or reported as multiplets overlapping with solvent. The following abbreviations have been used (and derivatives thereof, e.g., dd doublet of doublets, etc.): s, singlet; d, doublet; t, triplet; q, quartet; m, multiplet; br, broad; qn, quintet; p, pentet. In some cases, the structures of the end-products of the Formula (I) might appear as rotamers in the NMR-spectrum, in which instances only peaks of the major rotamer are reported. Electrospray mass spectral data were obtained using either an Agilent 1260 HPLC or an Agilent 1290 UPLC coupled to an Agilent single quadrupole mass spectrometer or a Shimadzu LC20XR HPLC or a Shimadzu LC40XR HPLC coupled to a Shimadzu single quadrupole mass spectrometer, or similar equipment, acquiring the positive ion data, and generally, only ions relating to the parent structure are reported;

(xi) intermediates were not necessarily fully purified but their structures and purities were assessed by TLC, analytical HPLC/UPLC, and/or NMR analysis and/or mass spectroscopy. In general, purities of intermediates are reported when found to be ≤85% by LC-UV (260±80 nm). The theoretical moles (th.) are reported for crude and impure starting materials;

(xii) specific optical rotation measurements were performed in a 2 dm polarimeter tube using a Bellingham and Stanley ADP400+ Polarimeter;

(xiii) unless stated otherwise compounds containing an asymmetrical carbon and/or sulfur atom were not resolved;

(xiv) in general Examples and Intermediate compounds are named using ChemDraw Professional version 21.0.0 from PerkinElmer. ChemDraw Professional version 21.0.0 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure. In general, chemical structures of Examples and Intermediates containing the label '&' at a stereocenter, means the configuration of such Example or Intermediate at that stereocenter is a mixture of both (R) and (S); and a label 'or' means the configuration of such Example or Intermediate at the stereocenter is either (R) or (S). Absolute, unspecified, '&', and 'or' stereocenters can all be present in a single structure.

In general for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

The compounds of the following Examples wherein the $R^1$ substituent is methyl (as well as the compounds of the corresponding Intermediates) may exist as a mixture of atropisomers or as a separated atropisomer. The bond around which axial rotation is hindered is the C—N σ-bond. Separated atropisomers are depicted in the Examples by wedged bonds (solid or broken (hashed)) in the phenyl ring connected to the C—N σ-bond around which axial rotation is hindered. A mixture of atropisomers is depicted in the Examples by non-wedged bonds in the phenyl ring connected to the C—N σ-bond around which axial rotation is hindered.

(xv) where reactions refer to being degassed or purged, this can be performed for example by purging the reaction solvent with a constant flow of nitrogen for a suitable period of time (for example 5 to 10 min);

(xvi) in addition to the ones mentioned above, the following abbreviations have been used:

$AlCl_3$=aluminum chloride;
aq.=aqueous;
ATP=adenosine triphosphate;
BAST=bis(2-methoxyethyl)aminosulfur trifluoride;
$BH_3$·THF=borane-tetrahydrofuran;
Boc=t-butyloxycarbonyl;
$Boc_2O$=di-tert-butyl dicarbonate;
C=Celsius;
$CDCl_3$=deuterated chloroform;
CDI=1,1'-carbonyldiimidazole;
CHO=Chinese hamster ovary;
$CO_2$=carbon dioxide;
$Cs_2CO_3$=cesium carbonate;
$CuBr_2$=copper(II) bromide;
CuI=copper(I) iodide;
CuO=copper(II) oxide;
DAST=diethylaminosulfur trifluoride;
DCM=dichloromethane;
DEA=diethylamine;
Dess-martin periodinane=1,1,1-Tris(acetyloxy)-1,1-dihydro-1,2-benziodoxol-3-(1H)-one;
DIPEA=N,N-diisopropylethylamine;
dm=diameter;
DMAP=2,6-dimethylaminopyridine;
DME=1,2-dimethoxyethane;
DMF=N,N-dimethylformamide;
DMSO=dimethylsulfoxide;
DMSO-$d_6$=deuterated dimethylsulfoxide;
EDC=N-(3-Dimethylaminopropyl)-N'-ethylcarbodiimide;
EDTA=ethylenediaminetetraacetic acid;
ee=enantiomeric excess;
EGTA=ethylene glycol-bis(3-aminoethyl ether)-N,N,N',N'-tetraacetic acid;
eq=equivalent;
ES=electrospray;
Et3N=triethylamine;
$Et_2O$=diethyl ether;
EtOAc=ethyl acetate;
EtOH=ethanol;
FA=formic acid;
g=gram;
GMF=glass micro fiber;
h=hour(s);
HATU=(dimethylamino)-N,N-dimethyl(3-oxido-1H-[1,2,3]triazolo[4,5-b]pyridinyl)-methaniminium hexafluorophosphate;
HCl=hydrochloric acid;
HBSS=Hepes-buffered saline solution;
HEPES=(4-(2-hydroxyethyl)-1-piperazineethanesulfonic acid);
hERG=human Ether-à-go-go-Related Gene;
HOBt=1-hydroxybenzotriazole;
$H_2O$=water;
HPLC=high-performance liquid chromatography;
IBMX=3-isobutyl-1-methylxanthine;
$IC_{50}$=half-maximum inhibitory concentration;
ID=inner diameter;
IPA=isopropanol;
$K_2CO_3$=potassium carbonate;
KCl=potassium chloride;
KF=potassium fluoride;
KOH=potassium hydroxide;
KOtBu=potassium tert-butoxide;
LCMS=liquid chromatography-mass spectrometry;
LiOH=lithium hydroxide;
M=molar;
m-CPBA=meta-chloroperoxybenzoic acid;
MeCN=acetonitrile;
MeI=methyl iodide;
MeMgBr=methylmagnesium bromide;
MeOD=deuterated methanol;
MeOH=methanol;
2Me-THF=2-methyltetrahydrofuran;
Mg=magnesium;
mg=milligram;
$MgSO_4$=magnesium sulfate;
MHz=megahertz;
min=minute(s);
mL=milliliter;
mm=millimeter;
mmol=millimole;
$MnO_2$=manganese dioxide;
MS=mass spectrometry;
MsOH=methanesulfonic acid;
MTBE=methyl tert-butyl ether;
m/z=mass spectrometry peak(s);
$NaBH_4$=sodium borohydride;
$Na_2CO_3$=sodium carbonate;
NaCl=sodium chloride;
NaOH=sodium hydroxide;
n-BuLi=n-butyl lithium;
NaH=sodium hydride;
$NaHCO_3$=sodium bicarbonate;
NaOtBu=sodium tert-butoxide;
$Na_2SO_4$=sodium sulfate;
$Na_2S_2O_3$=sodium thiosulfate;

$NH_3$=ammonia;
$NH_4Cl$=ammonium chloride;
$NH_4HCO_3$=ammonium bicarbonate;
NMDG=N-methyl-d-glucamine;
NMR=nuclear magnetic resonance;
OTf=trifluoromethanesulfonate;
Pd/C=palladium on carbon;
$Pd(dppf)Cl_2$=1,1'-bis(di-tert-butylphosphino)ferrocene palladium dichloride;
$Pd_2dba_3$=tris(dibenzylideneacetone)dipalladium(0);
$Pd_2dba_3·CHCl_3$=tris(dibenzylideneacetone)dipalladium-chloroform adduct;
PIDA=(diacetoxyiodo)benzene;
ppm=parts per million;
prep=preparative;
p-TsOH·$H_2O$=p-toluenesulfonic acid monohydrate;
PVDF=polyvinylidene difluoride;
quant.=quantitative;
rt=room temperature;
sat=saturated;
SCX=strong cation exchange;
SFC=supercritical fluid chromatography;
$SOCl_2$=thionyl chloride;
STAB=sodium triacetoxyborohydride;
tBu=tert-butyl;
t-BuONO=tert-butyl nitrite;
TEA=triethylamine;
TEMPO=(2,2,6,6-tetramethylpiperidin-1-yl)oxyl;
TFA=trifluoroacetic acid;
th.=theoretical;
THF=tetrahydrofuran;
$Ti(OiPr)_4$=titanium(IV) isopropoxide;
TLC=thin layer chromatography;
T3P=2,4,6-tripropyl-1,3,5,2,4,6-trioxatriphosphinane 2,4,6-trioxide;
Ts=tosyl;
TsCl=para-toluenesulfonyl chloride;
TsOH=para-toluenesulfonic acid;
μL=microliter;
μm=micrometer;
UPLC=ultra-performance liquid chromatography;
UV=ultraviolet; and
Xantphos=(9,9-dimethyl-9H-xanthene-4,5-diyl)bis(diphenylphosphane).

B. Intermediate Compounds

Intermediate 1: tert-Butyl (S)-3-(methoxy(methyl)carbamoyl)pyrrolidine-1-carboxylate

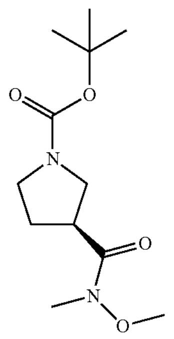 [SMILES: CON(C)C(=O)[C@H]1CCN(C(=O)OC(C)(C)C)C1]

CDI (1.66 g, 10.2 mmol) was added to a solution of (S)-1-(tert-butoxycarbonyl)pyrrolidine-3-carboxylic acid (2.00 g, 9.29 mmol) in DCM (60 mL) and THF (20 mL) at 0° C. The mixture was stirred at rt for 1 h before N,O-dimethylhydroxylamine hydrochloride (1.00 g, 10.2 mmol) was added. The mixture was stirred at rt overnight. The reaction mixture was diluted with water (40 mL) and extracted with DCM (3×40 mL). The combined organic layers were washed with brine, dried over $Na_2SO_4$, filtered, and concentrated to dryness. The residue was purified by straight phase flash chromatography on silica (gradient: 0-100% EtOAc in heptane) to give the title compound (2.01 g, 84%) as a colorless oil; MS m/z (ES+) $[M+H-tBu]^+$=203.1.

Intermediate 2: 2-(3-Bromo-H-pyrrolo[2,3-c]pyridin-1-yl)-5-fluorobenzoic acid

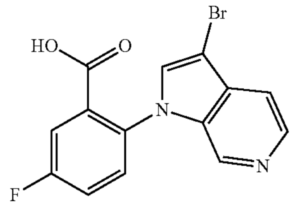 [SMILES: O=C(O)c1cc(F)ccc1-n1cc(Br)c2ccncc21]

Copper powder (387 mg, 6.09 mmol) was added to a deoxygenated solution of 5-fluoro-2-iodobenzoic acid (8.10 g, 30.5 mmol), 3-bromo-1H-pyrrolo[2,3-c]pyridine (6.00 g, 30.5 mmol) and $K_2CO_3$ (12.6 g, 91.4 mmol) in DMF (60 mL) and the reaction mixture was purged with $N_2$ for 5 minutes. The reaction mixture was stirred at 130° C. overnight. The reaction was allowed to reach rt and acidified to pH 1 with aq. HCl (6 M). The precipitate was collected by filtration, washed with water and dried under vacuum to give the title compound (6.73 g, 66%) as a beige solid; MS m/z (ES+) $[M+H]^+$=335.0/337.0.

Intermediate 3: 2-(3-Bromo-1H-pyrrolo[2,3-c]pyridin-1-yl)-5-fluoro-N,N-diisopropyl-benzamide

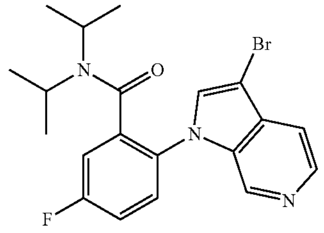 [SMILES: CC(C)N(C(=O)c1cc(F)ccc1-n1cc(Br)c2ccncc21)C(C)C]

Diisopropylamine (6.39 mL, 45.6 mmol) was added to a suspension of Intermediate 2 (5.09 g, 15.2 mmol) and HATU (6.35 g, 16.7 mmol) in DMF (20 mL). The resulting mixture was stirred at rt overnight. The reaction mixture was diluted with EtOAc (40 mL), and washed with aq. HCl (1 M, 40 mL) and sat. aq. $NaHCO_3$ (40 mL). The organic layer was washed with brine, dried over $Na_2SO_4$, filtered, and concentrated under reduced pressure. The residue was purified by straight phase flash chromatography on silica (gradient: 0-100% EtOAc in heptane) to give the title compound (5.57 g, 88%) as a beige solid; MS m/z (ES+) $[M+H]^+$=418.1/420.1.

Intermediate 4: tert-Butyl (S)-3-(1-(2-(diisopropylcarbamoyl)-4-fluorophenyl)-1H-pyrrolo[2,3-c]pyridine-3-carbonyl)pyrrolidine-1-carboxylate

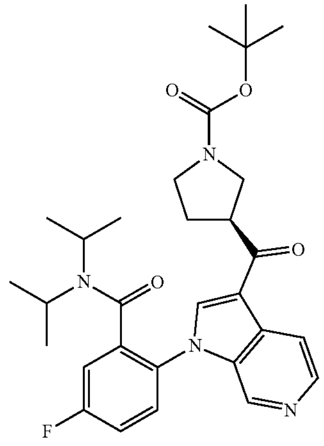 [SMILES: CC(C)N(C(=O)c1cc(F)ccc1-n1cc(C(=O)[C@H]2CCN(C(=O)OC(C)(C)C)C2)c2ccncc21)C(C)C]

n-BuLi (1.64 mL, 2.63 mmol, 1.6 M in hexane) was added dropwise to a suspension of Intermediate 3 (550 mg, 1.31 mmol) in THF (10 mL) at −78° C. under $N_2$. The mixture was stirred for 5-10 minutes at −78° C. before Intermediate 1 (577 mg, 2.24 mmol) in THF (2 mL) was added dropwise. The resulting mixture was stirred at −78° C. for 1 h. The reaction was quenched with cold sat. aq. $NH_4Cl$, allowed to return to rt and extracted with EtOAc (3×20 mL). The combined organic layers were washed with brine, dried over $Na_2SO_4$, filtered, and concentrated to dryness. The residue was purified by straight phase flash chromatography on silica (gradient: 0-5% MeOH in DCM), followed by preparative HPLC, PrepMethod A (gradient: 20-75%). Appropriate fractions were pooled, diluted with sat. aq. $NaHCO_3$ and extracted with EtOAc (2×20 mL). The combined organic layers were washed with brine, dried over $Na_2SO_4$, filtered, and concentrated under reduced pressure to give the title compound (223 mg, 32%) as an orange gum; MS m/z (ES+) $[M+H]^+$=537.3.

Intermediate 5a: (S)-5-Fluoro-N,N-diisopropyl-2-(3-(pyrrolidine-3-carbonyl)-1H-pyrrolo[2,3-c]pyridin-1-yl)benzamide 2,2,2-trifluoroacetic acid

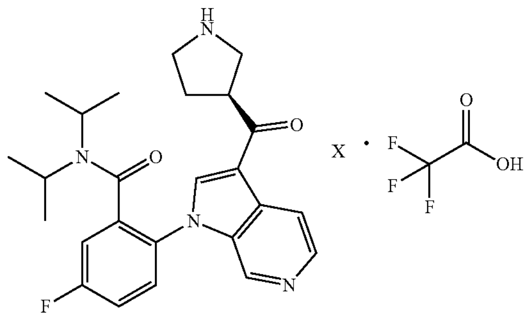

TFA (1 mL) was added to a solution of Intermediate 4 (223 mg, 0.36 mmol th.) in DCM (5 mL). The resulting mixture was stirred at rt for 30 minutes. The mixture was concentrated under reduced pressure to give the crude title compound in a quantitative yield (454 mg) as an orange solid; MS m/z (ES+) $[M+H]^+$=437.4.

Intermediate 5b: (S)-5-Fluoro-N,N-diisopropyl-2-(3-(pyrrolidine-3-carbonyl)-1H-pyrrolo[2,3-c]pyridin-1-yl)benzamide

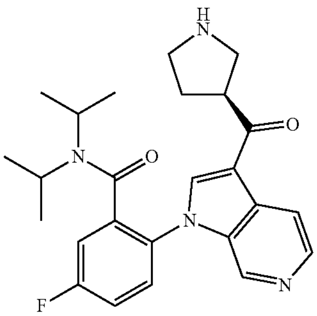 [SMILES: CC(C)N(C(=O)c1cc(F)ccc1-n1cc(C(=O)[C@H]2CCNC2)c2ccncc21)C(C)C]

TFA (1 mL) was added to a solution of Intermediate 4 (45.1 mg, 0.08 mmol) in DCM (5 mL). The resulting mixture was stirred at rt for 30 minutes. The mixture was concentrated under reduced pressure. The residue was dissolved in DCM (10 mL), washed with sat. aq. $NaHCO_3$ (10 mL) and brine. The organic layer was dried over $Na_2SO_4$, filtered, and concentrated under reduced pressure to give the title compound (35.6 mg, 97%) as a brown gum; MS m/z (ES+) $[M+H]^+$=437.3.

Intermediate 6: tert-Butyl (R)-3-(methoxy(methyl)carbamoyl)pyrrolidine-1-carboxylate

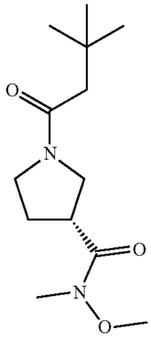 [SMILES: CON(C)C(=O)[C@@H]1CCN(C(=O)CC(C)(C)C)C1]

CDI (1.66 g, 10.2 mmol) was added to a solution of (R)-1-(tert-butoxycarbonyl)pyrrolidine-3-carboxylic acid (2.00 g, 9.29 mmol) in DCM (60 mL) and THF (20 mL) at 0° C. The resulting mixture was stirred at rt for 1 h before N,O-dimethylhydroxylamine hydrochloride (1.00 g, 10.2 mmol) was added. The reaction was stirred at rt overnight. The reaction mixture was diluted with water (40 mL) and extracted with DCM (3×40 mL). The combined organic layers were washed with brine, dried over $Na_2SO_4$, filtered, and concentrated under reduced pressure. The residue was purified by straight phase flash chromatography on silica (gradient: 0-100% EtOAc in heptane) to give the title compound (2.00 g, 83%) as a colorless liquid; MS m/z (ES+) $[M+H-tBu]^+$=203.2.

Intermediate 7: tert-Butyl (R)-3-(1-(2-(diisopropylcarbamoyl)-4-fluorophenyl)-1H-pyrrolo[2,3-c]pyridine-3-carbonyl)pyrrolidine-1-carboxylate

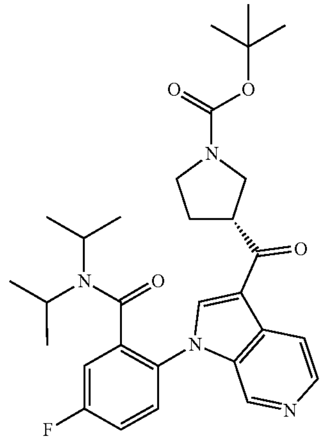 [SMILES: CC(C)N(C(=O)c1cc(F)ccc1-n1cc(C(=O)[C@@H]2CCN(C(=O)OC(C)(C)C)C2)c2ccncc21)C(C)C]

n-BuLi (1.64 mL, 2.63 mmol, 1.6 M in hexane) was added dropwise to a suspension of Intermediate 3 (550 mg, 1.31 mmol) in THF (10 mL) at −78° C. under $N_2$. The mixture was stirred for 5-10 minutes at −78° C. before Intermediate 6 (577 mg, 2.24 mmol) in THF (2 mL) was added dropwise. The resulting mixture was stirred at −78° C. for 1 h. The reaction was quenched with cold sat. aq. $NH_4Cl$, allowed to return to rt and extracted with EtOAc (3×20 mL). The combined organic layers were washed with brine, dried over $Na_2SO_4$, filtered, and concentrated to dryness. The residue was purified by straight phase flash chromatography on silica (gradient: 0-100% EtOAc in heptane). The residue was purified by preparative HPLC, PrepMethod A (gradient: 0-75%). Appropriate fractions were pooled, diluted with aq. NaOH (2 M) and extracted with EtOAc (2×20 mL). The combined organic layers were washed with brine, dried over $Na_2SO_4$, filtered, and concentrated under reduced pressure to give the title compound (227 mg, 32%) as an orange gum; MS m/z (ES+) $[M+H]^+$=537.3; $^1H$ NMR (400 MHz, $CDCl_3$) δ 0.12-0.20 (3H, m), 0.98-1.02 (3H, m), 1.05-1.13 (3H, m), 1.45-1.50 (12H, m), 2.13-2.22 (1H, m), 2.21-2.35 (1H, m), 3.21 (1H, dt), 3.39-3.49 (2H, m), 3.53-3.71 (3H, m), 3.71-3.80 (1H, m), 7.16-7.20 (1H, m), 7.27-7.36 (1H, m), 7.59 (1H, dd), 8.22-8.31 (1H, m), 8.30-8.37 (1H, m), 8.51 (1H, d), 8.64-8.72 (1H, m).

Intermediate 8a: (R)-5-Fluoro-N,N-diisopropyl-2-(3-(pyrrolidine-3-carbonyl)-1H-pyrrolo[2,3-c]pyridin-1-yl)benzamide hydrochloride

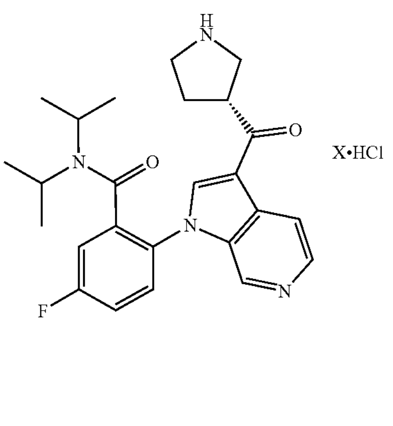

4 M HCl in 1,4-dioxane (2 mL) was added to Intermediate 7 (73.9 mg, 0.12 mmol th.) and the resulting mixture was stirred at rt for 30 minutes. The mixture was concentrated under reduced pressure to give the crude title compound in a quantitative yield (73.0 mg) as an orange solid; MS m/z (ES+) $[M+H]^+$=437.4.

Intermediate 8b: (R)-5-Fluoro-N,N-diisopropyl-2-(3-(pyrrolidine-3-carbonyl)-1H-pyrrolo[2,3-c]pyridin-1-yl)benzamide 2,2,2-trifluoroacetic acid

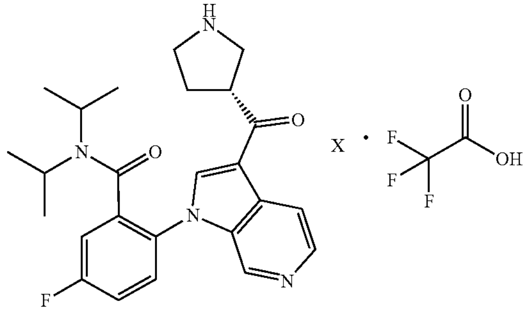

TFA (1 mL) was added to a solution of Intermediate 7 (105.6 mg, 0.18 mmol th.) in DCM (5 mL). The resulting mixture was stirred for at rt for 30 minutes. The mixture was concentrated under reduced pressure to give the crude title compound in a quantitative yield (152 mg) as an orange solid; MS m/z (ES+) $[M+H]^+$=437.4.

Intermediate 9: tert-Butyl 3-(hydroxy(1H-pyrrolo[2,3-c]pyridin-3-yl)methyl)azetidine-1-carboxylate

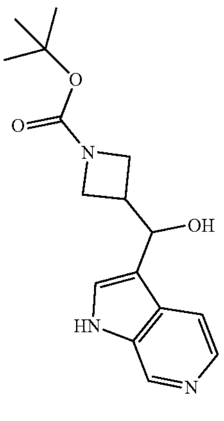 [SMILES: CC(C)(C)OC(=O)N1CC(C(O)c2c[nH]c3cnccc23)C1]

KOtBu (21.0 g, 187 mmol) was added in one portion to a solution of 1H-pyrrolo[2,3-c]pyridine (11.1 g, 93.7 mmol) in EtOH (100 mL) at 0° C. The reaction mixture was stirred at rt for 20 minutes before tert-butyl 3-formylazetidine-1-carboxylate (17.4 g, 93.7 mmol) was added dropwise over 2 minutes. The resulting mixture was stirred at rt overnight. The reaction mixture was diluted with aq. citric acid (340 mL, 1 M) and extracted with MTBE (340 mL). The pH was adjusted with solid NaOH to pH 8 and EtOAc (400 mL) was added. The formed precipitate was collected by filtration and dried to give the title compound (17.7 g, 62%) as a white solid. The organic layer of the filtrate was separated, and the water layer extracted with EtOAc (400 mL). The combined organic layers were washed with brine, dried over $Na_2SO_4$, filtered, and concentrated under reduced pressure. The residue was purified by straight phase flash chromatography on silica (gradient: 0-25% MeOH in DCM) to give the title compound (3.66 g, 13%) as a light yellow foam; MS m/z (ES+) $[M+H]^+$=304.2; $^1$H NMR (400 MHz, DMSO-$d_6$, 22° C.) δ 1.35 (9H, s), 2.89-3.03 (1H, m), 3.47-3.67 (1H, m), 3.64-3.96 (3H, m), 4.91 (1H, dd), 5.35 (1H, d), 7.47 (1H, s), 7.62 (1H, dd), 8.06 (1H, d), 8.69 (1H, d), 11.42 (1H, s).

Intermediate 10: tert-Butyl 3-(1H-pyrrolo[2,3-c]pyridine-3-carbonyl)azetidine-1-carboxylate

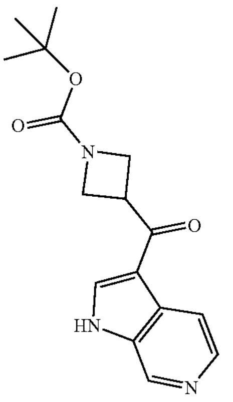 [SMILES: CC(C)(C)OC(=O)N1CC(C(=O)c2c[nH]c3cnccc23)C1]

A mixture of Intermediate 9 (17.7 g, 58.3 mmol) and $MnO_2$ (25.3 g, 291 mmol) in 1,4-dioxane (150 mL) was heated at 100° C. for 48 h. The reaction mixture was allowed to reach rt and stirring was stopped for 30 minutes before the solvent was carefully filtered over a Whatman 0.45 m PVDF w/GMF filter. The remaining solids were diluted with MeOH (100 mL) and filtered over a filter paper, followed by filtration over a Whatman 0.45 m PVDF w/GMF filter. The filtrate was filtered over a path of Celite® and the filtrate was concentrated under reduced pressure to give the title compound (14.3 g, 81%) as a brown solid; MS m/z (ES+) $[M+H]^+$=302.1; $^1$H NMR (400 MHz, DMSO-$d_6$, 22° C.) δ 1.31-1.43 (9H, m), 4.05 (4H, d), 4.25 (1H, tt), 8.06 (1H, dd), 8.28 (1H, d), 8.42 (1H, s), 8.83 (1H, s).

Intermediate 11: 2-(3-(1-(tert-Butoxycarbonyl)azetidine-3-carbonyl)-1H-pyrrolo[2,3-c]pyridin-1-yl)-5-fluorobenzoic acid

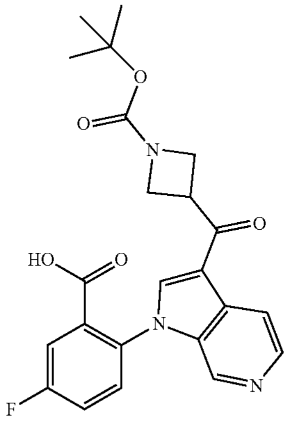 [SMILES: CC(C)(C)OC(=O)N1CC(C(=O)c2cn(-c3ccc(F)cc3C(=O)O)c3cnccc23)C1]

Copper powder (107 mg, 1.69 mmol) was added to a deoxygenated solution of 5-fluoro-2-iodobenzoic acid (2.25 g, 8.44 mmol), Intermediate 10 (2.54 g, 8.44 mmol) and $K_2CO_3$ (3.50 g, 25.3 mmol) in DMF (15 mL). The resulting mixture was purged with $N_2$ before the vial was sealed and heated at 100° C. overnight. The reaction mixture was diluted with water (20 mL) and acidified to pH 2 with aq. HCl (1 M). The precipitate was collected by filtration and dried under vacuum to give the crude title compound (2.98 g) as a yellow solid; MS m/z (ES+) $[M+H]^+$=440.1.

Intermediate 12: tert-Butyl 3-(1-(2-(diisopropylcarbamoyl)-4-fluorophenyl)-1H-pyrrolo[2,3-c]pyridine-3-carbonyl)azetidine-1-carboxylate

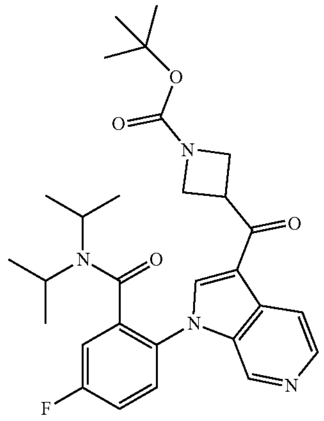 [SMILES: CC(C)N(C(=O)c1cc(F)ccc1-n1cc(C(=O)C2CN(C(=O)OC(C)(C)C)C2)c2ccncc21)C(C)C]

Diisopropylamine (3.01 mL, 21.8 mmol) was added to a mixture of Intermediate 11 (1.91 g, 4.35 mmol th.), HATU (2.48 g, 6.53 mmol) and DIPEA (1.14 mL, 6.53 mmol) in DMF (15 mL). The mixture was stirred at rt for 2 h. The reaction mixture was diluted with DCM (100 mL) and washed with sat. aq. $NaHCO_3$ (60 mL). The organic layer was washed with brine (60 mL), dried over $Na_2SO_4$, filtered, and concentrated under reduced pressure. The residue was purified by straight phase flash chromatography on silica (gradient: 0-100% EtOAc in heptane) to give the title compound (1.40 g, 62%) as a brown solid; MS m/z (ES+) $[M+H]^+$=523.2; $^1$H NMR (400 MHz, DMSO-$d_6$, 22° C.) δ 0.28 (3H, br s), 0.72 (3H, br s), 0.99 (3H, d), 1.28-1.35 (3H, m), 1.36-1.45 (9H, m), 3.17-3.28 (1H, m), 3.43-3.55 (1H, m), 3.91-4.16 (4H, m), 4.14-4.25 (1H, m), 7.50-7.60 (2H, m), 7.84 (1H, dd), 8.14 (1H, dd), 8.40 (1H, d), 8.45 (1H, s), 8.64 (1H, s).

Intermediate 13: 2-(3-(Azetidine-3-carbonyl)-1H-pyrrolo[2,3-c]pyridin-1-yl)-5-fluoro-N,N-diisopropylbenzamide

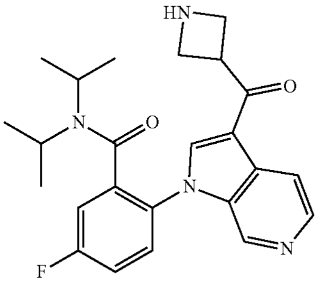 [SMILES: CC(C)N(C(=O)c1cc(F)ccc1-n1cc(C(=O)C2CNC2)c2ccncc21)C(C)C]

TFA (3 mL) was added to a solution of Intermediate 12 (1.40 g, 2.69 mmol) in DCM (15 mL). The resulting mixture was stirred at rt for 1 h. The mixture was concentrated under reduced pressure. The residue was dissolved in DCM (40 mL) and washed with sat. aq. $NaHCO_3$ (40 mL). The organic layer was washed with brine, dried over $Na_2SO_4$, filtered, and concentrated under reduced pressure to give the title compound (1.12 g, 99%) as a brown foam; MS m/z (ES+) $[M+H]^+$=423.2; $^1$H NMR (400 MHz, DMSO-$d_6$, 27° C.) δ 0.26 (3H, br s), 0.72 (3H, br s), 0.90-1.04 (3H, m), 1.20-1.41 (3H, m), 3.17-3.30 (2H, m), 3.39-3.55 (2H, m), 3.84-4.13 (3H, m), 4.26-4.40 (1H, m), 7.47-7.63 (2H, m), 7.82 (1H, dd), 8.11-8.21 (1H, m), 8.34-8.53 (2H, m), 8.65 (1H, s).

Intermediate 14: tert-Butyl 3-(1-(2-(ethyl(isopropyl)carbamoyl)-4-fluorophenyl)-1H-pyrrolo[2,3-c]pyridine-3-carbonyl)azetidine-1-carboxylate

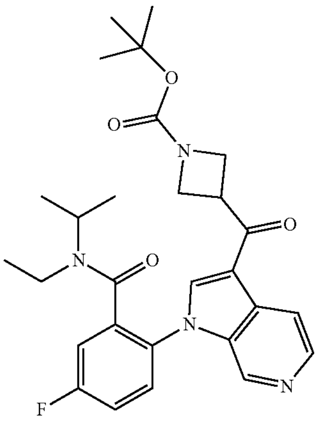 [SMILES: CCN(C(=O)c1cc(F)ccc1-n1cc(C(=O)C2CN(C(=O)OC(C)(C)C)C2)c2ccncc21)C(C)C]

N-Ethylpropan-2-amine (1.35 mL, 11.2 mmol) was added to a mixture of Intermediate 11 (2.46 g, 5.59 mmol, th.) and HATU (3.19 g, 8.38 mmol) in DMF (15 mL). The mixture was stirred at rt for 2 h. The reaction mixture was diluted with EtOAc (80 mL) and washed with sat. aq. $NaHCO_3$ (60 mL). The organic layer was washed with brine, dried over $Na_2SO_4$, filtered, and concentrated under reduced pressure. The residue was purified by straight phase flash chromatography on silica (gradient: 0-100% EtOAc in heptane) to give the title compound in a quantitative yield (3.20 g) as a yellow gum, which was used directly in the next step; MS m/z (ES+) $[M+H]^+$=509.2; $^1$H NMR (400 MHz, DMSO-$d_6$, 27° C.) δ 0.41 (3H, d), 0.92 (3H, dd), 1.18 (3H, t), 1.39 (9H, s), 2.75-2.85 (1H, m), 3.18-3.30 (1H, m), 3.54 (1H, p), 3.89-4.01 (2H, m), 4.06-4.16 (2H, m), 4.16-4.25 (1H, m), 7.53-7.64 (2H, m), 7.79-7.89 (1H, m), 8.14 (1H, d), 8.40 (1H, d), 8.48 (1H, s), 8.55-8.67 (1H, m).

Intermediate 15: 2-(3-(Azetidine-3-carbonyl)-1H-pyrrolo[2,3-c]pyridin-1-yl)-N-ethyl-5-fluoro-N-isopropylbenzamide

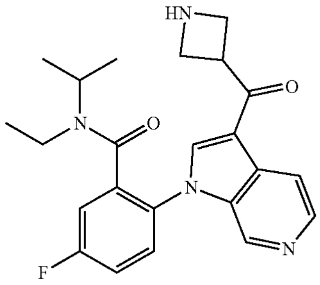 [SMILES: CCN(C(=O)c1cc(F)ccc1-n1cc(C(=O)C2CNC2)c2ccncc21)C(C)C]

TFA (6 mL) was added to a solution of Intermediate 14 (2.84 g, 5.58 mmol, th.) in DCM (20 mL). The resulting mixture was stirred at rt for 2 h. The mixture was quenched with sat. aq. $NaHCO_3$ and extracted with DCM (2×30 mL). The organic layer was washed with brine, dried over $Na_2SO_4$, filtered, and concentrated under reduced pressure to give the title compound (1.43 g, 63%) as an orange gum; MS m/z (ES+) $[M+H]^+$=409.1; $^1$H NMR (400 MHz, DMSO-$d_6$, 27° C.) δ 0.11-0.68 (6H, m), 0.84-1.03 (4H, m), 2.75-2.85 (1H, m), 3.17-3.29 (1H, m), 3.46-3.62 (1H, m), 4.10-4.30 (3H, m), 4.32-4.45 (1H, m), 7.50-7.66 (2H, m), 7.78-7.88 (1H, m), 8.11-8.19 (1H, m), 8.36-8.46 (1H, m), 8.50-8.68 (2H, m).

Intermediate 16: tert-Butyl 3-(1-(4-fluoro-2-nitrophenyl)-1H-pyrrolo[2,3-c]pyridine-3-carbonyl)azetidine-1-carboxylate

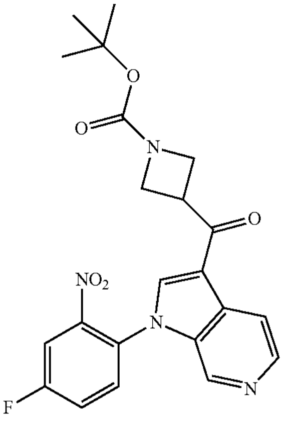

$K_2CO_3$ (23.4 g, 169 mmol) was added to a mixture of Intermediate 10 (17.0 g, 56.4 mmol) and 1,4-difluoro-2-nitrobenzene (9.87 g, 62.1 mmol) in DMF (170 mL). The resulting mixture was stirred at 80° C. for 16 h. The reaction mixture was quenched with water (300 mL) and extracted with EtOAc (2×125 mL). The combined organic layers were dried over $Na_2SO_4$, filtered, and concentrated to dryness. The residue was purified by straight phase flash chromatography on silica (gradient 0-100% EtOAc in petroleum ether) to give the title compound (10.0 g, 40%) as a yellow solid; MS m/z (ES+) $[M+H]^+$=441.1; $^1$H NMR (400 MHz, DMSO-$d_6$, 22° C.) δ 1.39 (9H, s), 4.04 (2H, br s), 4.12 (2H, br s), 4.16-4.25 (1H, m), 7.95-8.01 (1H, m), 8.06-8.11 (1H, m), 8.17-8.21 (1H, m), 8.40 (1H, dd), 8.45 (1H, d), 8.58 (1H, s), 8.71 (1H, s).

Intermediate 17: tert-Butyl 3-(1-(2-amino-4-fluorophenyl)-1H-pyrrolo[2,3-c]pyridine-3-carbonyl)azetidine-1-carboxylate

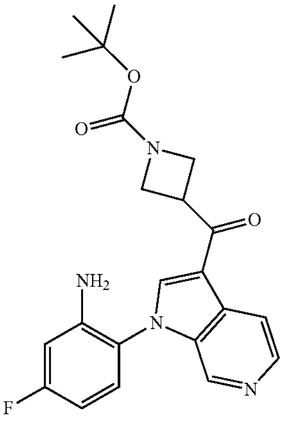 [SMILES: CC(C)(C)OC(=O)N1CC(C(=O)c2cn(-c3ccc(F)cc3[N+](=O)[O-])c3cnccc23)C1]

Iron powder (5.07 g, 90.8 mmol) was added to Intermediate 16 (10.0 g, 22.7 mmol) in EtOH (80 mL) followed by $NH_4Cl$ (4.86 g, 90.8 mmol) in water (20 mL). The resulting mixture was stirred at 80° C. for 2 h. The reaction mixture was filtered through Celite®. The filtrate was quenched with water (100 mL) and extracted with EtOAc (3×100 mL). The combined organic layers were dried over $Na_2SO_4$, filtered, and concentrated to dryness to give the title compound (9.30 g, 100%) as a pale yellow solid; MS m/z (ES+) $[M+H]^+$=411.2; $^1$H NMR (400 MHz, DMSO-$d_6$, 22° C.) δ 1.40 (9H, s), 4.06 (2H, br s), 4.12 (2H, br s), 4.17-4.34 (1H, m), 5.53 (2H, br s), 6.51 (1H, td), 6.70 (1H, dd), 7.27 (1H, dd), 8.20 (1H, d), 8.39-8.43 (2H, m), 8.54 (1H, s).

Intermediate 18: tert-Butyl 3-(1-(2-bromo-4-fluorophenyl)-1H-pyrrolo[2,3-c]pyridine-3-carbonyl)azetidine-1-carboxylate

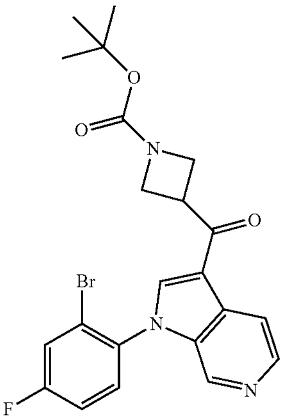 [SMILES: CC(C)(C)OC(=O)N1CC(C(=O)c2cn(-c3ccc(F)cc3Br)c3cnccc23)C1]

t-BuONO (4.00 mL, 33.6 mmol) was added to Intermediate 17 (9.20 g, 22.4 mmol) in MeCN (100 mL). The mixture was stirred at rt for 30 minutes before $CuBr_2$ (5.01 g, 22.4 mmol) was added. The resulting mixture was stirred at rt for 2 h. The reaction mixture was quenched with sat. aq. $NH_4Cl$ (100 mL) and extracted with EtOAc (3×100 mL). The combined organic layers were dried over $Na_2SO_4$, filtered, and concentrated to dryness. The residue was purified by straight phase flash chromatography on silica (gradient: 0-100% EtOAc in petroleum ether) to give the title compound (10.0 g, 94%) as a pale yellow solid; MS m/z (ES+) $[M+H]^+$=474.2/476.2.

Intermediate 19: Azetidin-3-yl(1-(2-bromo-4-fluorophenyl)-1H-pyrrolo[2,3-c]pyridin-3-yl)methanone hydrochloride

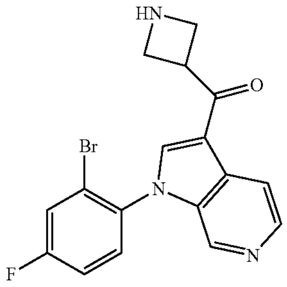

X•HCl

4 M HCl in 1,4-dioxane (20 mL) was added to a mixture of Intermediate 18 (8.00 g, 16.9 mmol) in 1,4-dioxane (60 mL). The resulting mixture was stirred at rt for 1 h. The reaction mixture was diluted with $Et_2O$ (100 mL) and filtered through Celite®. The filtrate was concentrated under reduced pressure to give crude the title compound as a pale yellow solid in a quantitative yield, which was used directly in the next step (7.20 g); MS m/z (ES+) $[M+H]^+$=374.0/376.0; $^1$H NMR (300 MHz, DMSO-$d_6$) δ 4.13-4.32 (4H, m), 4.43-4.66 (1H, m), 7.52-7.72 (1H, m), 7.83-7.98 (1H, m), 8.07 (1H, d), 8.20-8.46 (1H, m), 8.97-9.21 (1H, m), 9.36-9.72 (2H, m).

Intermediate 20: tert-Butyl (1R,3S,4S)-3-(3-(1-(2-bromo-4-fluorophenyl)-1H-pyrrolo[2,3-c]pyridine-3-carbonyl)azetidine-1-carbonyl)-2-azabicyclo[2.2.1]heptane-2-carboxylate

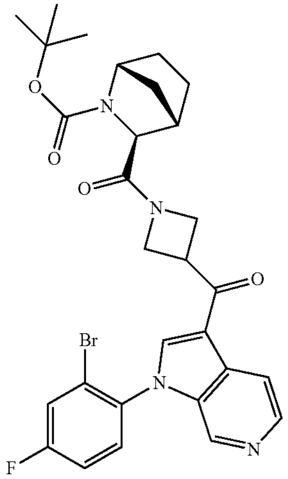 [SMILES: CC(C)(C)OC(=O)N1[C@@H]2CC[C@@H](C2)[C@H]1C(=O)N1CC(C(=O)c2cn(-c3ccc(F)cc3Br)c3cnccc23)C1]

T3P (36.7 g, 57.7 mmol, 50% in EtOAc) was added to a mixture of Intermediate 19 (7.20 g, 16.9 mmol th.), (1R,3S,4S)-2-(tert-butoxycarbonyl)-2-azabicyclo[2.2.1]heptane-3-carboxylic acid (4.64 g, 19.2 mmol) and DIPEA (13.4 mL, 77.0 mmol) in DCM (70 mL) at 0° C. under $N_2$. The resulting mixture was stirred at rt for 1 h. The reaction mixture was quenched with sat. aq. $NaHCO_3$ (50 mL) and extracted with DCM (3×100 mL). The combined organic layers were dried over $Na_2SO_4$, filtered, and concentrated to dryness. The residue was purified by straight phase flash chromatography on silica (gradient: 0-100% EtOAc in petroleum ether) to give the title compound (4.60 g, 46%) as a pale yellow solid; MS m/z (ES+) $[M+H]^+$=597.2/599.2.

Intermediate 21: tert-Butyl 3-(hydroxy(7H-pyrrolo[2,3-c]pyridazin-5-yl)methyl)azetidine-1-carboxylate

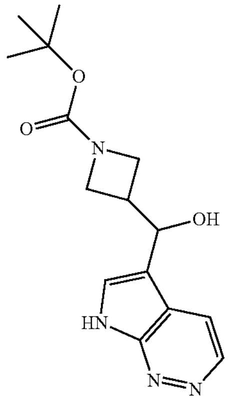 [SMILES: CC(C)(C)OC(=O)N1CC(C(O)c2c[nH]c3nnccc23)C1]

A mixture of KOH (4.14 g, 73.9 mmol) in MeOH (150 mL) was stirred at rt for 30 minutes before 7H-pyrrolo[2,3-c]pyridazine (4.40 g, 36.9 mmol) and tert-butyl 3-formylazetidine-1-carboxylate (13.7 g, 73.9 mmol) were added. The resulting mixture was stirred at rt for 4 days under $N_2$. The reaction mixture was diluted with water. The solvent was removed under reduced pressure and extracted with EtOAc (4×100 mL). The combined organic layers were dried over $Na_2SO_4$, filtered, and concentrated to dryness. The residue was purified by straight phase flash chromatography on silica (gradient: 0-10% MeOH in DCM) to give the title compound (11.0 g, 98%) as a pale yellow solid; MS m/z (ES+) $[M+H]^+$=305.2; $^1$H NMR (300 MHz, DMSO-$d_6$) δ 1.35 (9H, s), 2.95-3.06 (1H, m), 3.57-3.63 (1H, m), 3.73-3.79 (1H, m), 3.80-3.90 (2H, m), 4.93 (1H, d), 7.76 (1H, s), 7.92 (1H, d), 8.83 (1H, d).

Intermediate 22: tert-Butyl 3-(7H-pyrrolo[2,3-c]pyridazine-5-carbonyl)azetidine-1-carboxylate

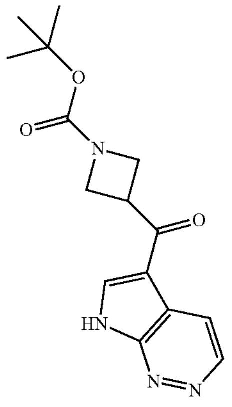 [SMILES: CC(C)(C)OC(=O)N1CC(C(=O)c2c[nH]c3nnccc23)C1]

Dess-Martin periodinane (8.36 g, 19.7 mmol) was added in one portion to a mixture of Intermediate 21 (3.00 g, 9.86 mmol) in DCM (45 mL) cooled to 0° C. under $N_2$. The resulting mixture was stirred at rt for 16 h. The reaction mixture was quenched with sat. aq. $NaHCO_3$ (150 mL) and $Na_2S_2O_3$ and extracted with DCM (3×125 mL). The combined organic layers were dried over $Na_2SO_4$, filtered, and concentrated to dryness. The crude product was purified by straight phase flash chromatography on silica (gradient: 0-10% MeOH in DCM) to give the title compound (1.00 g, 34%) as a yellow solid; MS m/z (ES+) $[M+H]^+$=303.2; $^1$H NMR (300 MHz, $CDCl_3$) δ 1.48 (9H, s), 4.01-4.17 (1H, m), 4.20-4.37 (4H, m), 8.38 (1H, s), 8.55 (1H, d), 9.18 (1H, d).

Intermediate 23: 2-(5-(1-(tert-Butoxycarbonyl)azetidine-3-carbonyl)-7H-pyrrolo[2,3-c]-pyridazin-7-yl)-5-fluorobenzoic acid

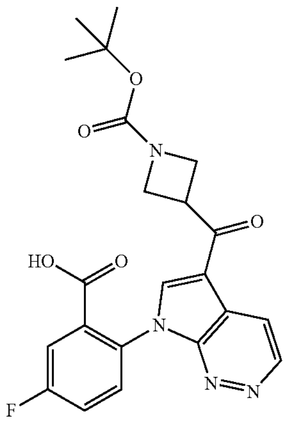 [SMILES: CC(C)(C)OC(=O)N1CC(C(=O)c2cn(-c3ccc(F)cc3C(=O)O)c3nnccc23)C1]

Copper powder (28.6 mg, 0.45 mmol) was added to a mixture of Intermediate 22 (680 mg, 2.25 mmol), 5-fluoro-2-iodobenzoic acid (598 mg, 2.25 mmol) and $Cs_2CO_3$ (2.20 g, 6.75 mmol) in DMF (8 mL) under $N_2$. The resulting mixture was stirred at 80° C. for 18 h. The reaction mixture was purified by reversed phase flash chromatography on a C18 column (gradient: 20-40% MeCN in water with 0.1% $NH_4HCO_3$). Appropriate fractions were pooled, concentrated to small amount and adjusted to pH 5 with aq. HCl. The resulting precipitate was filtered off and dried under vacuum to give the title compound (420 mg, 42%) as a yellow solid; MS m/z (ES+) $[M+H]^+$=441.2; $^1$H NMR (300 MHz, DMSO-$d_6$, 26° C.) δ 1.40 (9H, s), 4.00-4.08 (2H, m), 4.09-4.20 (2H, m), 4.21-4.36 (1H, m), 7.76-7.82 (1H, m), 7.83-7.94 (2H, m), 8.36 (1H, d), 9.02 (1H, s), 9.15 (1H, d), 13.32 (1H, br s).

Intermediate 24: tert-Butyl 3-(7-(4-fluoro-2-(methoxycarbonyl)phenyl)-7H-pyrrolo[2,3-c]-pyridazine-5-carbonyl)azetidine-1-carboxylate

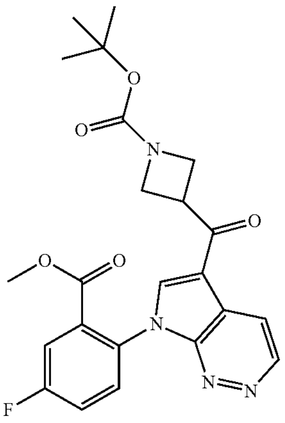 [SMILES: COC(=O)c1cc(F)ccc1-n1cc(C(=O)C2CN(C(=O)OC(C)(C)C)C2)c2ccnnc21]

MeI (267 mg, 1.88 mmol) was added to a mixture of Intermediate 23 (830 mg, 1.88 mmol) and $K_2CO_3$ (781 mg, 5.65 mmol) in DMF (15 mL) under $N_2$. The resulting mixture was stirred at rt for 1 h. The reaction mixture was quenched with water (50 mL) and extracted with EtOAc (3×50 mL). The combined organic layers were dried over $Na_2SO_4$, filtered, and concentrated to dryness. The crude product was purified by straight phase flash chromatography on silica (gradient: 60-100% EtOAc in petroleum ether) to give the title compound (580 mg, 68%) as a white solid; MS m/z (ES+) $[M+H]^+$=455.2; $^1$H NMR (300 MHz, DMSO-$d_6$, 26° C.) δ 1.40 (9H, s), 3.46 (3H, s), 4.02-4.12 (2H, m), 4.12-4.19 (2H, m), 4.20-4.37 (1H, m), 7.76-7.88 (1H, m), 7.89-7.99 (2H, m), 8.38 (1H, d), 9.03 (1H, s), 9.16 (1H, d).

Intermediate 25: 5-(1-(tert-Butoxycarbonyl)azetidine-3-carbonyl)-7-(4-fluoro-2-(methoxy-carbonyl)phenyl)-7H-pyrrolo[2,3-c]pyridazine 1-oxide

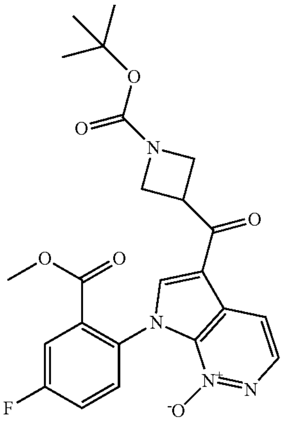

m-CPBA (740 mg, 4.29 mmol) was added to a mixture of Intermediate 24 (650 mg, 1.43 mmol) in DCM (7 mL) under $N_2$. The resulting mixture was stirred at rt for 1 h. The reaction mixture was poured into sat. aq. $Na_2S_2O_3$ (25 mL) and extracted with EtOAc (3×25 mL). The combined organic layers were dried over $Na_2SO_4$, filtered, and concentrated to dryness. The crude product was purified by straight phase flash chromatography on silica (gradient: 0-100% EtOAc in petroleum ether) to give the title compound (660 mg, 98%) as a white solid; MS m/z (ES+) [M+H]+=471.2; $^1$H NMR (300 MHz, DMSO-$d_6$, 24° C.) δ 1.39 (9H, s), 3.59 (3H, s), 4.00-4.07 (2H, m), 4.09-4.16 (2H, m), 4.16-4.28 (1H, m), 7.78-7.90 (2H, m), 7.91-7.96 (1H, m), 8.31 (1H, d), 8.44 (1H, d), 8.80 (1H, s).

Intermediate 26: 5-(1-(tert-Butoxycarbonyl)azetidine-3-carbonyl)-7-(2-carboxy-4-fluorophenyl)-7H-pyrrolo[2,3-c]pyridazine 1-oxide

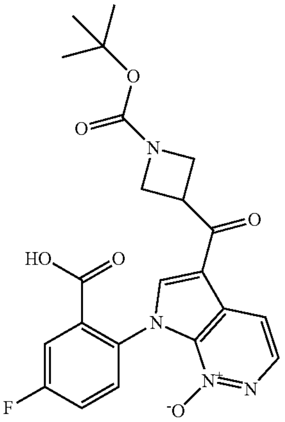

LiOH (163 mg, 6.80 mmol) in water (3 mL) was added to a mixture of Intermediate 25 (640 mg, 1.36 mmol) in THF (6 mL). The resulting mixture was stirred at rt for 1 h. The solvent was removed under reduced pressure. The residue was acidified with aq. HCl (2 M). The resulting suspension was filtered off and dried under vacuum to give the title compound (500 mg, 81%) as a white solid; MS m/z (ES+) $[M+H]^+$=457.2; $^1$H NMR (300 MHz, DMSO-$d_6$, 24° C.) δ 1.39 (9H, s), 3.93-4.06 (2H, m), 4.06-4.16 (2H, m), 4.17-4.28 (1H, m), 7.62-7.79 (2H, m), 7.84 (1H, dd), 8.29 (1H, d), 8.42 (1H, d), 8.77 (1H, s).

Intermediate 27: 5-(1-(tert-Butoxycarbonyl)azetidine-3-carbonyl)-7-(2-(diisopropylcarbamoyl)-4-fluorophenyl)-7H-pyrrolo[2,3-c]pyridazine 1-oxide

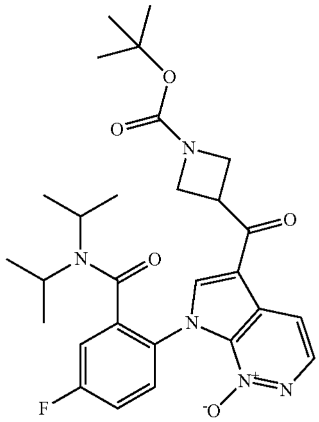

T3P (1.88 g, 2.96 mmol, 50% in EtOAc) was added dropwise to a mixture of Intermediate 26 (450 mg, 0.99 mmol), DIPEA (861 μL, 4.93 mmol) and diisopropylamine (798 mg, 7.89 mmol) in DCM (8 mL) cooled to 0° C. under $N_2$. The resulting mixture was stirred at rt for 4 h. The reaction mixture was quenched with sat. aq. $NaHCO_3$ (50 mL) and extracted with DCM (3×25 mL). The combined organic layers were dried over $Na_2SO_4$, filtered, and concentrated to dryness. The residue was purified by preparative TLC on silica (DCM:MeOH 10:1) to give the title compound (440 mg, 83%) as a white solid; MS m/z (ES+) $[M+Na]^+$=562.3; $^1$H NMR (300 MHz, DMSO-$d_6$, 26° C.) δ 0.52 (3H, d), 0.87 (3H, d), 1.07 (3H, d), 1.34 (3H, d), 1.39 (9H, s), 3.27-3.37 (1H, m), 3.45-3.64 (1H, m), 3.92-4.24 (5H, m), 7.50-7.59 (2H, m), 7.82 (1H, dd), 8.32 (1H, d), 8.44 (1H, d), 8.55 (1H, s).

Intermediate 28: tert-butyl 3-(7-(2-(Diisopropylcarbamoyl)-4-fluorophenyl)-7H-pyrrolo[2,3-c]pyridazine-5-carbonyl)azetidine-1-carboxylate

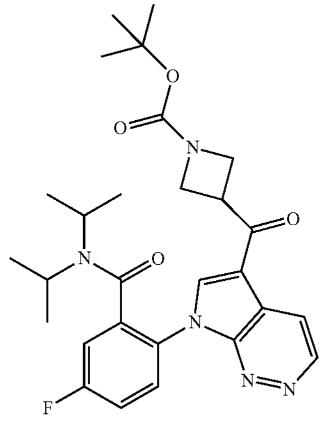 [SMILES: CC(C)N(C(=O)c1cc(F)ccc1-n1cc(C(=O)C2CN(C(=O)OC(C)(C)C)C2)c2ccnnc21)C(C)C]

Iron powder (174 mg, 3.11 mmol) was added to a mixture of Intermediate 27 (420 mg, 0.78 mmol) and $NH_4Cl$ (167 mg, 3.11 mmol) in EtOH (8 mL) and water (2 mL) under $N_2$. The resulting mixture was stirred at 80° C. for 5 h. The reaction mixture was filtered through Celite®. The filtrate was diluted with water (50 mL) and extracted with EtOAc (3×25 mL). The combined organic layers were dried over $Na_2SO_4$, filtered, and concentrated to dryness to give the title compound (360 mg, 88%) as a yellow solid; MS m/z (ES+) $[M+H]^+$=524.3; $^1$H NMR (300 MHz, DMSO-$d_6$, 26° C.) δ 0.52 (3H, d), 0.87 (3H, d), 1.07 (3H, d), 1.34 (3H, d), 1.39 (9H, s), 3.27-3.37 (1H, m), 3.45-3.64 (1H, m), 3.92-4.24 (5H, m), 7.50-7.59 (2H, m), 7.82 (1H, dd), 8.32 (1H, d), 8.44 (1H, d), 8.55 (1H, s).

Intermediate 29: 2-(5-(Azetidine-3-carbonyl)-7H-pyrrolo[2,3-c]pyridazin-7-yl)-5-fluoro-N,N-diisopropylbenzamide

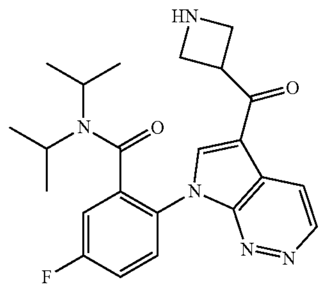 [SMILES: CC(C)N(C(=O)c1cc(F)ccc1-n1cc(C(=O)C2CNC2)c2ccnnc21)C(C)C]

FA (5 mL) was added to Intermediate 28 (200 mg, 0.38 mmol) and stirred at rt for 1 h. The solvent was removed under reduced pressure. The residue was suspended in sat. aq. $NaHCO_3$ (50 mL) and extracted with DCM (3×25 mL). The combined organic layers were dried over $Na_2SO_4$, filtered, and concentrated to dryness to give the title compound as a yellow solid in a quantitative yield, which was used directly in the next step in Example 14a (220 mg); MS m/z (ES+) $[M+H]^+$=424.2; $^1$H NMR (300 MHz, $CDCl_3$, 23° C.) δ 0.20 (3H, d), 0.95-1.04 (6H, m), 1.45 (3H, d), 3.16-3.26 (1H, m), 3.59-3.71 (1H, m), 3.86-3.94 (2H, m), 4.07-4.16 (2H, m), 4.23-4.35 (1H, m), 7.15 (1H, dd), 7.28-7.37 (1H, m), 7.73 (1H, dd), 8.34 (1H, s), 8.48 (1H, d), 9.20 (1H, d).

Intermediate 30: tert-butyl 3-((7-Fluoro-1H-pyrrolo[2,3-c]pyridin-3-yl)(hydroxy)methyl)-azetidine-1-carboxylate

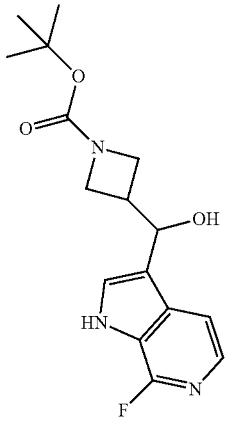 [SMILES: CC(C)(C)OC(=O)N1CC(C(O)c2c[nH]c3c(F)nccc23)C1]

KOH (824 mg, 14.7 mmol) was added to a solution of 7-fluoro-1H-pyrrolo[2,3-c]pyridine (1.00 g, 7.35 mmol) and tert-butyl 3-formylazetidine-1-carboxylate (1.36 g, 7.35 mmol) in MeOH (15 mL). The reaction mixture was stirred at rt for 18 h. Another aliquot of tert-butyl 3-formylazetidine-1-carboxylate (408 mg, 2.20 mmol) was added, after which the mixture was stirred at rt for 24 h. The mixture was concentrated under reduced pressure. The residue was taken up in water (50 mL) and extracted with EtOAc (2×100 mL). The combined organic layers were washed with brine (50 mL), passed through a phase separator and concentrated under reduced pressure. The crude product was purified by straight phase flash chromatography on silica (gradient: 0-10% MeOH in DCM) to afford the title compound (1.83 g, 78%) as a yellow foam; MS m/z (ES+) $[M+H]^+$=322.0; $^1$H NMR (400 MHz, $CDCl_3$, 22° C.) δ 1.44 (9H, s), 2.12 (1H, d), 3.00-3.14 (1H, m), 3.60-3.69 (1H, m), 3.89 (1H, t), 3.99 (1H, dd), 4.08 (1H, t), 5.12 (1H, dd), 7.32 (1H, d), 7.52 (1H, dd), 7.79 (1H, dd), 8.98 (1H, s).

Intermediate 31: 2-(3-((1-(tert-Butoxycarbonyl)azetidin-3-yl)(hydroxy)methyl)-7-fluoro-1H-pyrrolo[2,3-c]pyridin-1-yl)-5-fluorobenzoic acid

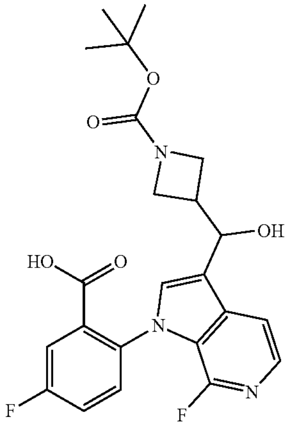

Copper powder (106 mg, 1.66 mmol) was added to a deoxygenated solution of 5-fluoro-2-iodobenzoic acid (1.77 g, 6.65 mmol), Intermediate 30 (1.78 g, 5.54 mmol), and $K_2CO_3$ (4.59 g, 33.2 mmol) in DMF (20 mL). The resulting mixture was purged with $N_2$ and stirred and heated at 80° C. for 4 h. The reaction mixture was diluted with water and acidified with aq. HCl (1 M) to pH 2. The formed precipitate was collected by filtration, washed with water and lyophilized from $MeCN/H_2O$ to give the crude title compound (2.51 g) as a light brown solid, which was used directly in the next step; MS m/z (ES+) $[M+H]^+$=460.5; $^1$H NMR (400 MHz, DMSO-$d_6$, 22° C.) δ 1.20-1.45 (9H, m), 2.93-3.07 (1H, m), 3.55-3.67 (1H, m), 3.67-3.99 (3H, m), 4.85-5.04 (1H, m), 5.34-5.77 (1H, m), 7.10-7.54 (1H, m), 7.57-7.66 (2H, m), 7.64-7.74 (2H, m), 7.72-7.86 (1H, m), 13.30 (1H, br s).

Intermediate 32: 2-(3-(1-(tert-Butoxycarbonyl)azetidine-3-carbonyl)-7-fluoro-1H-pyrrolo[2,3-c]pyridin-1-yl)-5-fluorobenzoic acid

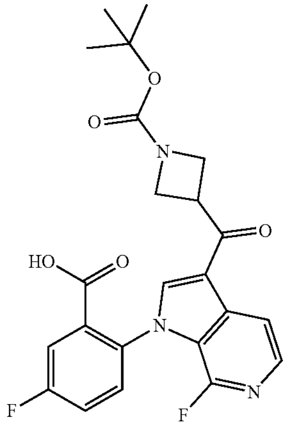 [SMILES: CC(C)(C)OC(=O)N1CC(C(=O)c2cn(-c3ccc(F)cc3C(=O)O)c3c(F)nccc23)C1]

Dess-Martin periodinane (609 mg, 1.44 mmol) was added to a solution of Intermediate 31 (600 mg, 0.94 mmol th.) in DCM (12 mL). The resulting mixture was stirred at rt for 45 minutes. The reaction mixture was diluted with EtOAc (40 mL) and washed with sat. aq. $Na_2S_2O_3$ (10 mL), sat. aq. $Na_2CO_3$ (10 mL), and brine (10 mL). The organic layer was passed through a phase separator and concentrated under reduced pressure to give the crude title compound (670 mg) as a brown solid, which was used directly in the next step; MS m/z (ES+) $[M+H]^+$=458.1.

Intermediate 33: tert-Butyl 3-(1-(2-(diisopropylcarbamoyl)-4-fluorophenyl)-7-fluoro-1H-pyrrolo[2,3-c]pyridine-3-carbonyl)azetidine-1-carboxylate

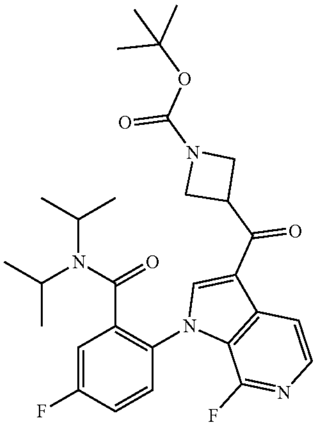 [SMILES: CC(C)N(C(=O)c1cc(F)ccc1-n1cc(C(=O)C2CN(C(=O)OC(C)(C)C)C2)c2ccnc(F)c21)C(C)C]

T3P (1.81 mL, 2.84 mmol, 50% in DCM) was added to a solution of Intermediate 32 (650 mg, 0.99 mmol th.), diisopropylamine (1.20 mL, 8.53 mmol) and DMAP (87.0 mg, 0.71 mmol) in DCM (10 mL). The reaction mixture was stirred at rt for 3 h. The mixture was diluted with EtOAc (50 mL) and washed with water (20 mL) and brine (20 mL). The organic layer was passed through a phase separator and concentrated to dryness. The residue was purified by straight phase flash chromatography on silica (gradient: 0-65% EtOAc in heptane) to afford the title compound (114 mg, 21%) as a white solid; MS m/z (ES+) $[M+H]^+$=541.2; $^1$H NMR (400 MHz, $CDCl_3$, 22° C.) δ 0.35 (3H, d), 0.95-1.12 (6H, m), 1.52 (3H, s), 1.55 (9H, s), 3.13-3.27 (1H, m), 3.52-3.64 (1H, m), 3.95-4.01 (1H, m), 4.11-4.31 (4H, m), 7.04-7.14 (1H, m), 7.42-7.51 (1H, m), 7.54-7.61 (1H, m), 8.01 (1H, dd), 8.05 (1H, s), 8.21-8.28 (1H, m).

Intermediate 34: 2-(3-(Azetidine-3-carbonyl)-7-fluoro-1H-pyrrolo[2,3-c]pyridin-1-yl)-5-fluoro-N,N-diisopropylbenzamide

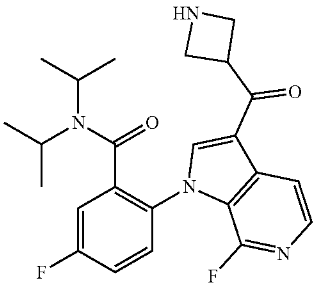 [SMILES: CC(C)N(C(=O)c1cc(F)ccc1-n1cc(C(=O)C2CNC2)c2ccnc(F)c21)C(C)C]

TFA (238 L) was added to a solution of Intermediate 33 (105 mg, 0.19 mmol) in DCM (3 mL). The resulting mixture was stirred at rt for 1 h. The mixture was quenched with sat. aq. $NaHCO_3$ and extracted with DCM (2×30 mL). The combined organic layers were passed through a phase separator and concentrated under reduced pressure to give the crude title compound (89.0 mg) as a yellow foam which was used directly in the next step (Example 15a); MS m/z (ES+) $[M+H]^+$=441.1; $^1H$ NMR (400 MHz, $CDCl_3$, 22° C.) δ 0.31-0.47 (3H, m), 1.00 (3H, d), 1.04 (3H, d), 1.44 (3H, d), 3.13-3.28 (1H, m), 3.50-3.64 (1H, m), 3.79-3.94 (2H, m), 4.00-4.15 (2H, m), 4.17-4.31 (1H, m), 7.09 (1H, dd), 7.21-7.25 (1H, m), 7.42-7.51 (1H, m), 7.99 (1H, dd), 8.00-8.08 (1H, m), 8.18-8.35 (1H, m).

Intermediate 35: tert-Butyl 4-(hydroxy(1H-pyrrolo[2,3-c]pyridin-3-yl)methyl)piperidine-1-carboxylate

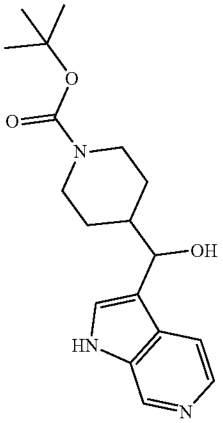 [SMILES: CC(C)(C)OC(=O)N1CCC(C(O)c2c[nH]c3cnccc23)CC1]

KOH (17.5 g, 312 mmol) was added to a solution of 1H-pyrrolo[2,3-c]pyridine (18.5 g, 156 mmol) and tert-butyl 4-formylpiperidine-1-carboxylate (33.3 g, 156 mmol) in MeOH (300 mL). The reaction was stirred at rt for 24 h. Additional tert-butyl 4-formylpiperidine-1-carboxylate (13.3 g, 62.4 mmol) was added, and the stirring was continued at rt overnight. The reaction mixture was concentrated under reduced pressure. The residue was dissolved in EtOAc (600 mL) and diluted with water (400 mL). The formed precipitate during the extraction was collected by filtration, washed with EtOAc (50 mL) and dried under vacuum to give the title compound (22.0 g, 42%) as a white solid. The organic layer of the filtrate was separated, and the water layer extracted with EtOAc (100 mL). The combined organic layers were washed with brine, dried over $Na_2SO_4$, filtered, and concentrated to dryness. The residue was purified by straight phase flash chromatography on silica (gradient: 0-25% MeOH in DCM). Appropriate fractions were concentrated under reduced pressure to give the title compound (17.6 g, 34%) as a yellow foam; MS m/z (ES+) $[M+H]^+$=332.2.

Intermediate 36: tert-Butyl 4-(1H-pyrrolo[2,3-c]pyridine-3-carbonyl)piperidine-1-carboxylate

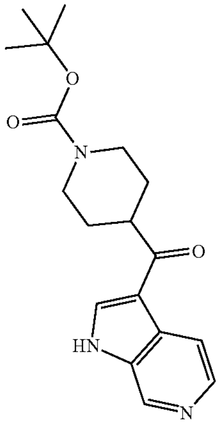 [SMILES: CC(C)(C)OC(=O)N1CCC(C(=O)c2c[nH]c3cnccc23)CC1]

$MnO_2$ (23.1 g, 265 mmol) was added to a solution of Intermediate 35 (17.6 g, 53.1 mmol) in 1,4-dioxane (150 mL) and the mixture was stirred and heated at 100° C. for 48 h. The reaction mixture was allowed to reach rt and stirring was stopped so the precipitate could sink to the bottom overnight. The supernatant was carefully filtered over a Whatman 0.45 m PVDF w/GMF filter. The filtrate was concentrated under reduced pressure to give the crude title compound (16.4 g) as a brown foam; MS m/z (ES+) $[M+H]^+$=330.1; $^1H$ NMR (400 MHz, DMSO-$d_6$, 22° C.) δ 1.41 (9H, s), 1.46-1.55 (2H, m), 1.76 (2H, d), 2.89 (2H, br s), 3.38-3.46 (1H, m), 4.01 (2H, d), 8.05 (1H, dd), 8.28 (1H, d), 8.63 (1H, s), 8.83 (1H, d), 12.46 (1H, br s).

Intermediate 37: 2-(3-(1-(tert-Butoxycarbonyl)piperidine-4-carbonyl)-1H-pyrrolo[2,3-c]-pyridin-1-yl)-5-fluorobenzoic acid

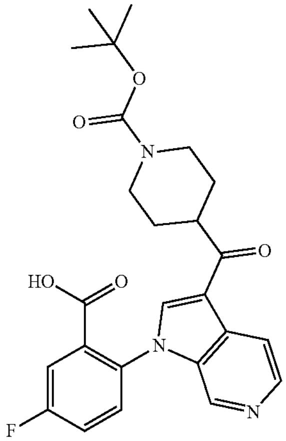 [SMILES: CC(C)(C)OC(=O)N1CCC(C(=O)c2cn(-c3ccc(F)cc3C(=O)O)c3cnccc23)CC1]

Copper powder (270 mg, 4.25 mmol) was added to a deoxygenated solution of 5-fluoro-2-iodobenzoic acid (5.65 g, 21.3 mmol), Intermediate 36 (7.00 g, 16.8 mmol th.) and $K_2CO_3$ (8.81 g, 63.8 mmol) in DMF (60 mL). The resulting mixture was purged with $N_2$ and stirred and heated at 80° C. overnight. The reaction mixture was diluted with water (100 mL) and acidified with aq. HCl (1 M) to pH 2. The formed precipitate was collected by filtration and dried under vacuum to give the crude title compound (9.80 g) as a yellow solid which was used directly in the next step; MS m/z (ES+) $[M+H]^+$=468.1.

Intermediate 38: tert-Butyl 4-(1-(2-(diisopropylcarbamoyl)-4-fluorophenyl)-1H-pyrrolo[2,3-c]-pyridine-3-carbonyl)piperidine-1-carboxylate

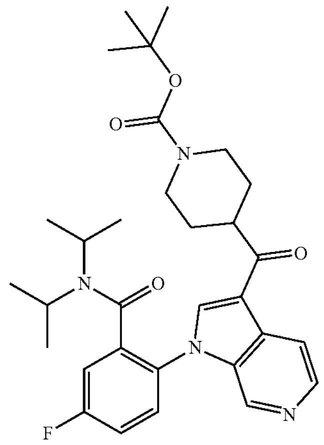 [SMILES: CC(C)N(C(=O)c1cc(F)ccc1-n1cc(C(=O)C2CCN(C(=O)OC(C)(C)C)CC2)c2ccncc21)C(C)C]

Diisopropylamine (14.7 mL, 105 mmol) was added to a mixture of Intermediate 37 (9.80 g, 16.8 mmol th.) and HATU (12.0 g, 31.4 mmol) in DMF (60 mL) and was stirred at rt overnight. The reaction mixture was diluted with EtOAc (400 mL) and washed with aq. HCl (200 mL, 1 M) and sat. aq. $NaHCO_3$ (200 mL). The organic layer was washed with brine (200 mL), dried over $Na_2SO_4$, filtered, and concentrated under reduced pressure. The residue was purified by straight phase flash chromatography on silica (gradient: 0-100% EtOAc in heptane) to give the title compound (7.23 g, 78%) as an orange foam; MS m/z (ES+) $[M+H]^+$=551.3; $^1H$ NMR (400 MHz, DMSO-$d_6$, 22° C.) δ 0.09-0.87 (6H, m), 1.04 (3H, d), 1.31 (3H, d), 1.41 (9H, s), 1.46-1.57 (2H, m), 1.75-1.88 (2H, m), 2.87 (2H, br s), 3.20-3.32 (1H, m), 3.40-3.52 (1H, m), 3.54-3.61 (1H, m), 3.97-4.05 (2H, m), 7.56-7.69 (2H, m), 7.95 (1H, dd), 8.53-8.65 (2H, m), 8.95-9.53 (2H, m).

Intermediate 39: 5-Fluoro-N,N-diisopropyl-2-(3-(piperidine-4-carbonyl)-1H-pyrrolo[2,3-c]-pyridin-1-yl)benzamide

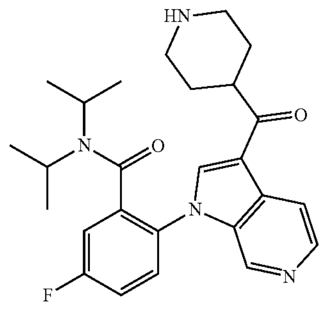 [SMILES: CC(C)N(C(=O)c1cc(F)ccc1-n1cc(C(=O)C2CCNCC2)c2ccncc21)C(C)C]

TFA (10 mL) was added to a solution of Intermediate 38 (9.12 g, 16.6 mmol) in DCM (50 mL). The resulting mixture was stirred at rt for 3 h. The mixture was quenched with sat. aq. $NaHCO_3$ and extracted with DCM (3×100 mL). The combined organic layers were washed with brine, dried over $Na_2SO_4$, filtered, and concentrated under reduced pressure to give the title compound (7.27 g, 98%) as a yellow solid; MS m/z (ES+) $[M+H]^+$=451.2; $^1H$ NMR (400 MHz, DMSO-$d_6$, 22° C.) δ 0.27 (3H, br s), 0.73 (3H, br s), 0.99 (3H, d), 1.33 (3H, d), 1.64-1.94 (4H, m), 2.79-2.98 (2H, m), 3.09-3.28 (3H, m), 3.37-3.56 (3H, m), 7.45-7.66 (2H, m), 7.85 (1H, dd), 8.01-8.20 (1H, m), 8.32-8.48 (1H, m), 8.64 (2H, s).

Intermediate 40: tert-Butyl 4-(1-(2-(ethyl(isopropyl)carbamoyl)-4-fluorophenyl)-1H-pyrrolo[2,3-c]pyridine-3-carbonyl)piperidine-1-carboxylate

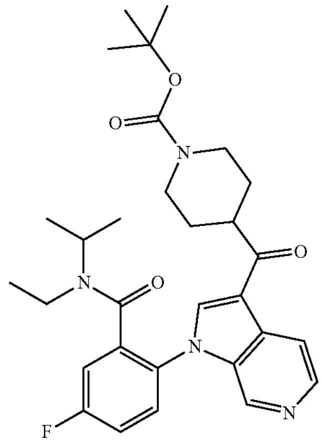 [SMILES: CCN(C(=O)c1cc(F)ccc1-n1cc(C(=O)C2CCN(C(=O)OC(C)(C)C)CC2)c2ccncc21)C(C)C]

N-Ethylpropan-2-amine (1.52 mL, 12.5 mmol) was added to a mixture of Intermediate 37 (1.75 g, 2.51 mmol th.) and HATU (1.43 g, 3.76 mmol) in DMF (15 mL) and was stirred at rt overnight. The reaction mixture was diluted with EtOAc (100 mL) and washed sequentially with aq. HCl (50 mL, 1 M), sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-100% EtOAc in heptane) to give the title compound (1.12 g, 83%) as a yellow gum; MS m/z (ES+) $[M+H]^+$=537.2; $^1H$ NMR (400 MHz, DMSO-$d_6$, 22° C.) δ 0.23-0.57 (6H, m), 0.98 (3H, d), 1.41 (9H, s), 1.45-1.55 (2H, m), 1.72-1.83 (2H, m), 2.75-2.82 (2H, m), 3.23-3.30 (1H, m), 3.38-3.43 (1H, m), 3.50-3.58 (1H, m), 3.94-4.07 (2H, m), 7.55-7.63 (2H, m), 7.80-7.90 (1H, m), 7.95 (1H, s), 8.10-8.14 (1H, m), 8.33-8.40 (1H, m), 8.54-8.72 (2H, m).

Intermediate 41: N-Ethyl-5-fluoro-N-isopropyl-2-(3-(piperidine-4-carbonyl)-1H-pyrrolo[2,3-c]pyridin-1-yl)benzamide

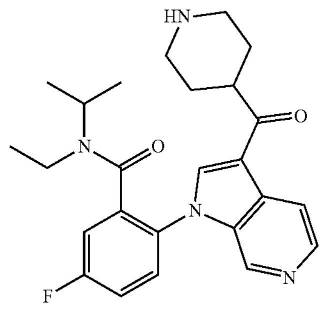 [SMILES: CCN(C(=O)c1cc(F)ccc1-n1cc(C(=O)C2CCNCC2)c2ccncc21)C(C)C]

TFA (2 mL) was added to a solution of Intermediate 40 (1.12 g, 2.09 mmol) in DCM (10 mL). The resulting mixture was stirred at rt for 1 h. The reaction mixture was concentrated under reduced pressure. The residue was dissolved in EtOAc (50 mL) and washed with sat. aq. $NaHCO_3$ (50 mL). The organic layer was washed with brine (50 mL), dried over $Na_2SO_4$, filtered, and concentrated under reduced pressure to give the title compound (574 mg, 63%) as a yellow gum; MS m/z (ES+) $[M+H]^+$=437.2.

Intermediate 42: Piperidin-4-yl(1H-pyrrolo[2,3-c]pyridin-3-yl)methanone hydrochloride

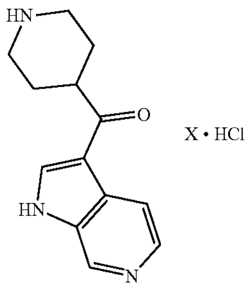

X • HCl

4 M HCl in 1,4-dioxane (35 mL) was added to a solution of Intermediate 10 (4.00 g, 12.1 mmol) in MeCN (5 mL). The resulting reaction mixture was stirred at rt for 4 h. The reaction mixture was concentrated under reduced pressure to give the crude title compound (3.23 g) as a beige solid; MS m/z (ES+) $[M+H]^+$=230.5.

Intermediate 43: tert-Butyl (1R,3S,4S)-3-(4-(1H-pyrrolo[2,3-c]pyridine-3-carbonyl)piperidine-1-carbonyl)-2-azabicyclo[2.2.1]heptane-2-carboxylate

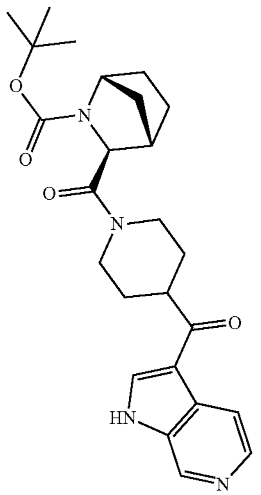 [SMILES: CC(C)(C)OC(=O)N1[C@@H]2CC[C@@H](C2)[C@H]1C(=O)N1CCC(C(=O)c2c[nH]c3cnccc23)CC1]

Intermediate 42 (3.23 g, 12.1 mmol, th.) was added to a stirred solution of (1R,3S,4S)-2-(tert-butoxycarbonyl)-2-azabicyclo[2.2.1]heptane-3-carboxylic acid (3.22 g, 13.4 mmol), EDC (2.79 g, 14.6 mmol), HOBt (2.23 g, 14.6 mmol) and DIPEA (4.24 mL, 24.3 mmol) in a mixture of DCM (25 mL) and DMF (25 mL). The resulting mixture was stirred at rt overnight. The reaction mixture was diluted with sat. aq. $NaHCO_3$ and extracted with DCM. The combined organic layers were dried over $Na_2SO_4$, filtered, and concentrated under reduced pressure. The residue was purified by straight phase flash chromatography on silica (gradient: 0-10% MeOH in DCM) to give the title compound (3.04 g, 55%) as an orange gum.

Intermediate 44: 2-(3-(1-((1R,3S,4S)-2-(tert-Butoxycarbonyl)-2-azabicyclo[2.2.1]heptane-3-carbonyl)piperidine-4-carbonyl)-1H-pyrrolo[2,3-c]pyridin-1-yl)-5-fluorobenzoic acid

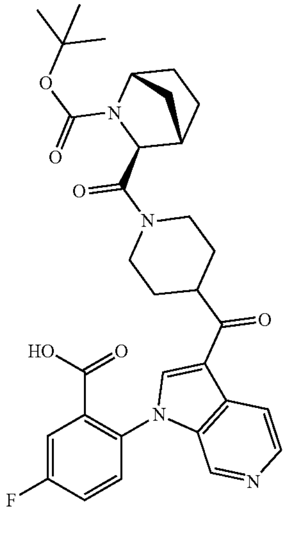 [SMILES: CC(C)(C)OC(=O)N1[C@@H]2CC[C@@H](C2)[C@H]1C(=O)N1CCC(C(=O)c2cn(-c3ccc(F)cc3C(=O)O)c3cnccc23)CC1]

Copper powder (85.0 mg, 1.34 mmol) was added to a deoxygenated solution of 5-fluoro-2-iodobenzoic acid (1.79 g, 6.71 mmol), Intermediate 43 (3.04 g, 6.71 mmol) and $K_2CO_3$ (2.78 g, 20.1 mmol) in DMF (20 mL). The resulting mixture was purged with $N_2$ before the vial was sealed and stirred at 80° C. overnight. The reaction mixture was diluted with water (40 mL) and acidified with aq. HCl (1 M) to pH 2. The formed precipitate was collected by filtration and dried under vacuum. Solid NaCl was added, and the water layer was extracted with EtOAc (3×50 mL). The combined organic layers were washed with brine, dried over $Na_2SO_4$, filtered, combined with the precipitate and concentrated under reduced pressure to give the title compound (3.27 g, 82%) as an orange foam; MS m/z (ES+) $[M+H]^+$=591.2.

Intermediate 45: tert-Butyl 4-(1-(4-fluoro-2-nitrophenyl)-1H-pyrrolo[2,3-c]pyridine-3-carbonyl)piperidine-1-carboxylate

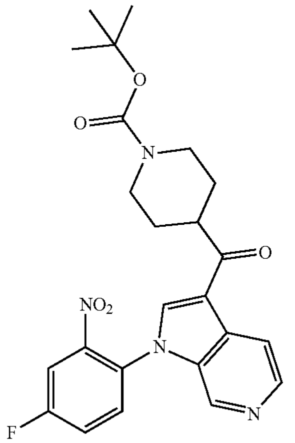 [SMILES: CC(C)(C)OC(=O)N1CCC(C(=O)c2cn(-c3ccc(F)cc3[N+](=O)[O-])c3cnccc23)CC1]

$K_2CO_3$ (2.60 g, 18.8 mmol) was added to a mixture of Intermediate 36 (3.10 g, 9.41 mmol) and 1,4-difluoro-2-nitrobenzene (1.80 g, 11.3 mmol) in DMF (40 mL). The resulting mixture was stirred at 80° C. for 1 h. The reaction mixture was diluted with EtOAc (50 mL) and washed sequentially with sat. aq. $NaHCO_3$ (50 mL) and brine (50 mL). The organic layer was dried over $Na_2SO_4$, filtered, and concentrated to dryness. The residue was purified by straight phase flash chromatography on silica (gradient 0-100% EtOAc in heptane) to give the title compound (1.91 g, 43%) as an orange solid; MS m/z (ES+) $[M+H]^+$=469.1; $^1$H NMR (400 MHz, $CDCl_3$, 22° C.) δ 1.48 (9H, s), 1.79-1.94 (4H, m), 2.75-2.96 (2H, m), 3.10-3.20 (1H, m), 4.21 (2H, br s), 7.57-7.65 (1H, m), 7.69 (1H, dd), 7.93 (1H, s), 7.98 (1H, dd), 8.28 (1H, d), 8.48 (1H, s), 8.52 (1H, d).

Intermediate 46: tert-Butyl 4-(1-(2-amino-4-fluorophenyl)-1H-pyrrolo[2,3-c]pyridine-3-carbonyl)piperidine-1-carboxylate

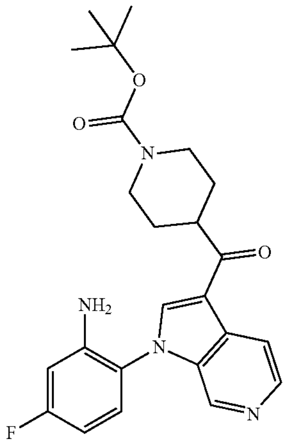

Iron powder (387 mg, 6.94 mmol) and $NH_4Cl$ (371 mg, 6.94 mmol) were added to Intermediate 45 (325 mg, 0.69 mmol) in a mixture of EtOH (16 mL), EtOAc (6 mL) and water (6 mL). The resulting mixture was stirred at 80° C. for 2 h. The reaction mixture was filtered through Celite® and the Celite was rinsed with EtOAc. The filtrate was washed sequentially with aq. $NaHCO_3$ (5%) and brine. The organic layer was dried over $Na_2SO_4$, filtered, and concentrated to dryness. The residue was purified by straight phase flash chromatography on silica (gradient 0-100% EtOAc in heptane) to give the title compound (196 mg, 64%) as a light yellow solid; MS m/z (ES+) $[M+H]^+$=439.6; $^1$H NMR (400 MHz, $CDCl_3$, 22° C.) δ 1.48 (9H, s), 1.76-1.95 (4H, m), 2.76-2.96 (2H, m), 3.10-3.23 (1H, m), 3.80 (2H, s), 4.21 (2H, br s), 6.55-6.69 (2H, m), 7.19 (1H, dd), 7.95 (1H, s), 8.27 (1H, dd), 8.49 (1H, d), 8.54 (1H, d).

Intermediate 47: tert-Butyl 4-(1-(2-bromo-4-fluorophenyl)-1H-pyrrolo[2,3-c]pyridine-3-carbonyl)piperidine-1-carboxylate

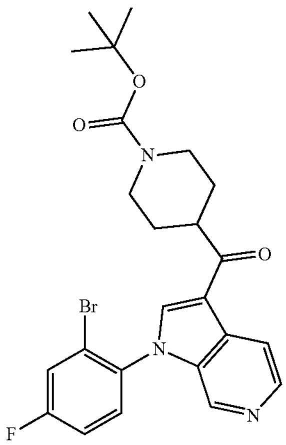

t-BuONO (203 mL, 1.71 mmol) was added to a mixture of Intermediate 46 (500 mg, 1.14 mmol) in MeCN (5 mL)

under $N_2$. The mixture was stirred at rt for 20 minutes before $CuBr_2$ (280 mg, 1.25 mmol) in MeCN (1 mL) was added dropwise. The resulting mixture was stirred at rt overnight. The reaction mixture was diluted with EtOAc (50 mL) and washed with sat. aq. $NaHCO_3$ (50 mL) and brine (50 mL). The organic layer was dried over $Na_2SO_4$, filtered, and concentrated to dryness. The residue was purified by straight phase flash chromatography on silica (gradient: 0-100% EtOAc in heptane) to give the title compound (413 mg, 72%) as a white solid; MS m/z (ES+) $[M+H]^+$=502.0/504.0; $^1$H NMR (400 MHz, $CDCl_3$, 22° C.) δ 1.48 (9H, s), 1.76-1.98 (4H, m), 2.72-2.97 (2H, m), 3.12-3.25 (1H, m), 4.21 (2H, br s), 7.27-7.33 (1H, m), 7.52 (1H, dd), 7.60 (1H, dd), 7.95 (1H, s), 8.29 (1H, d), 8.47-8.57 (2H, m).

Intermediate 48: (1-(2-Bromo-4-fluorophenyl)-1H-pyrrolo[2,3-c]pyridin-3-yl)(piperidin-4-yl)methanone di-hydrochloride

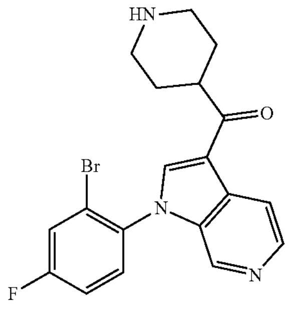

2•HCl

4 M HCl in 1,4-dioxane (2 mL) was added to a solution of Intermediate 47 (410 mg, 0.82 mmol) in MeCN (4 mL). The resulting mixture was stirred at rt for 1 h. The reaction mixture was concentrated under reduced pressure to give the crude title compound (409 mg) as a white solid; MS m/z (ES+) $[M+H]^+$=402.0/404.0.

Intermediate 49: tert-Butyl (1R,3S,4S)-3-(4-(1-(2-bromo-4-fluorophenyl)-1H-pyrrolo[2,3-c]-pyridine-3-carbonyl)piperidine-1-carbonyl)-2-azabicyclo[2.2.1]heptane-2-carboxylate

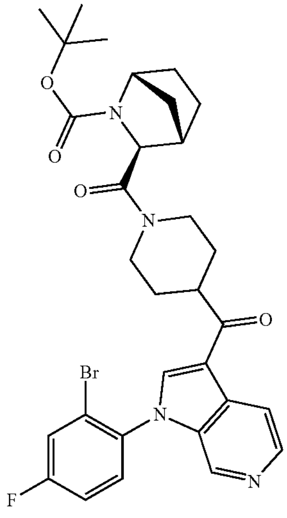 [SMILES: CC(C)(C)OC(=O)N1[C@@H]2CC[C@@H](C2)[C@H]1C(=O)N1CCC(C(=O)c2cn(-c3ccc(F)cc3Br)c3cnccc23)CC1]

T3P (1.54 mL, 2.58 mmol, 50% in EtOAc) was added dropwise to a solution of Intermediate 48 (409 mg, 0.82 mmol, th.), (1R,3S,4S)-2-(tert-butoxycarbonyl)-2-azabicyclo[2.2.1]heptane-3-carboxylic acid (498 mg, 2.06 mmol) and DIPEA (1.50 mL, 8.60 mmol) in a mixture of EtOAc (5 mL) and DCM (1 mL). The resulting mixture was stirred at rt overnight. The reaction mixture was diluted with EtOAc (25 mL) and sat. aq. $NaHCO_3$ (25 mL) and was stirred vigorously for 10 minutes. The organic layer was separated and washed with brine (25 mL), dried over $Na_2SO_4$, filtered, and concentrated to dryness. The crude product was purified by straight phase flash chromatography on silica (gradient: 0-100% EtOAc in heptane) to give the title compound (438 mg, 86%) as a white solid; MS m/z (ES+) $[M+H]^+$=625.1/627.1; $^1$H NMR (400 MHz, $CDCl_3$, 22° C.) δ 1.19-1.31 (1H, m), 1.33-1.55 (10H, m), 1.64-1.68 (1H, m), 1.71-1.83 (2H, m), 1.88-2.17 (4H, m), 2.43-2.61 (1H, m), 2.73-3.02 (1H, m), 3.12-3.39 (2H, m), 3.49 (1H, d), 3.91-4.16 (2H, m), 4.26-4.44 (1H, m), 4.53-4.76 (1H, m), 7.27-7.35 (1H, m), 7.48-7.57 (1H, m), 7.57-7.65 (1H, m), 7.91-7.99 (1H, m), 8.24-8.32 (1H, m), 8.49 (1H, d), 8.52 (1H, d).

Intermediate 50: tert-Butyl (1S,2S,5R)-2-(4-(1-(2-bromo-4-fluorophenyl)-1H-pyrrolo[2,3-c]-pyridine-3-carbonyl)piperidine-1-carbonyl)-3-azabicyclo[3.1.0]hexane-3-carboxylate

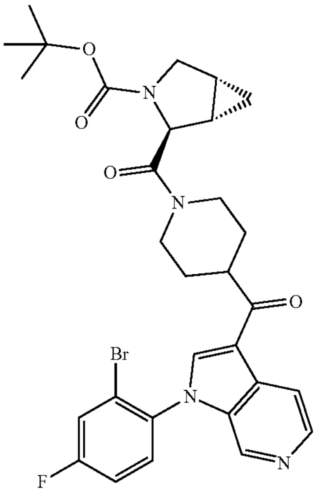 [SMILES: CC(C)(C)OC(=O)N1C[C@@H]2C[C@@H]2[C@H]1C(=O)N1CCC(C(=O)c2cn(-c3ccc(F)cc3Br)c3cnccc23)CC1]

T3P (1.90 g, 2.98 mmol, 50% in EtOAc) was added to a solution of Intermediate 48 (400 mg, 0.99 mmol), (1S,2S,5R)-3-(tert-butoxycarbonyl)-3-azabicyclo[3.1.0]hexane-2-carboxylic acid (226 mg, 0.99 mmol) and DIPEA (868 μL, 4.97 mmol) in DCM (5 mL) under $N_2$. The resulting mixture was stirred at rt for 2 h. The reaction mixture was quenched with sat. aq. $NaHCO_3$ (20 mL) and extracted with DCM (3×20 mL). The combined organic layers were dried over $Na_2SO_4$, filtered, and concentrated to dryness. The crude product was purified by straight phase flash chromatography on silica (gradient: 0-100% EtOAc in petroleum ether) to give the title compound (520 mg, 86%) as a pale yellow solid; MS m/z (ES+) $[M+H]^+$=611.1/613.1; $^1$H NMR (300 MHz, DMSO-$d_6$, 24° C.) δ 0.18-0.39 (1H, m), 0.67-0.78 (1H, m), 0.81-0.90 (1H, m), 1.29-1.41 (9H, m), 1.48-1.65 (3H, m), 1.66-1.78 (1H, m), 1.92 (2H, d), 2.64-2.93 (1H, m), 3.21-3.31 (1H, m), 3.40-3.68 (2H, m), 4.07-4.22 (1H, m), 4.37-4.70 (2H, m), 7.60 (1H, td), 7.92 (1H, dd), 8.01 (1H, dd), 8.13-8.22 (1H, m), 8.41 (1H, dd), 8.47 (1H, s), 8.91-8.98 (1H, m).

Intermediate 51: tert-Butyl 4-((4-fluoro-1H-pyrrolo[2,3-c]pyridin-3-yl)(hydroxy)methyl)-piperidine-1-carboxylate

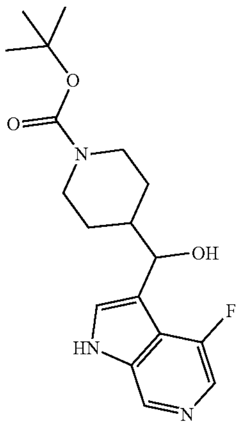 [SMILES: CC(C)(C)OC(=O)N1CCC(C(O)c2c[nH]c3cncc(F)c23)CC1]

KOH (437 mg, 7.79 mmol) was added to a mixture of tert-butyl 4-formylpiperidine-1-carboxylate (1.66 g, 7.79 mmol) and 4-fluoro-1H-pyrrolo[2,3-c]pyridine (530 mg, 3.89 mmol) in EtOH (20 mL) under $N_2$. The reaction was stirred at 40° C. for 2 h. The reaction mixture was diluted with EtOAc (150 mL) and washed with sat. aq. $NH_4Cl$ (2×75 mL). The organic layer was dried over $Na_2SO_4$, filtered, and concentrated to dryness. The residue was purified by straight phase flash chromatography on silica (gradient: 0-5% MeOH in DCM) to give the title compound in a quantitative yield (2.35 g) as a white solid; MS m/z (ES+) $[M+H]^+$=350.1; $^1H$ NMR (300 MHz, DMSO-$d_6$, 23° C.) δ 1.02-1.17 (2H, m), 1.26-1.34 (1H, m), 1.37 (9H, s), 1.76-1.87 (2H, m), 2.61 (2H, br s), 3.85-4.00 (2H, m), 4.65-4.73 (1H, m), 5.11 (1H, d), 7.52 (1H, d), 7.99 (1H, d), 8.59 (1H, d), 11.80 (1H, s).

Intermediate 52: tert-Butyl 4-(4-fluoro-1H-pyrrolo[2,3-c]pyridine-3-carbonyl)piperidine-1-carboxylate

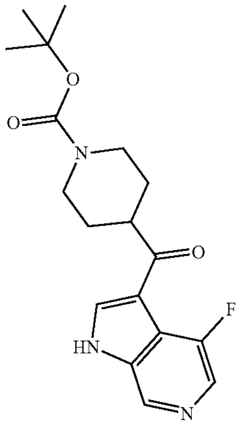 [SMILES: CC(C)(C)OC(=O)N1CCC(C(=O)c2c[nH]c3cncc(F)c23)CC1]

$MnO_2$ (1.62 g, 18.6 mmol) was added to a mixture of Intermediate 51 (1.30 g, 3.72 mmol, th.) in 1,4-dioxane (25 mL) under $N_2$. The reaction mixture was heated at 100° C. for 16 h. The reaction mixture was filtered through Celite®, and the filtrate was concentrated under reduced pressure. The residue was diluted with EtOAc (100 mL) and washed with water (3×25 mL). The organic layer was dried over $Na_2SO_4$, filtered, and concentrated to dryness. The residue was purified by straight phase flash chromatography on silica (gradient: 0-60% EtOAc in petroleum ether) to give the title compound (1.02 g, 79%) as a white solid; MS m/z (ES+) $[M+Na]^+$=370.1; $^1H$ NMR (300 MHz, DMSO-$d_6$, 22° C.) δ 1.42 (9H, s), 1.44-1.56 (2H, m), 1.69-1.86 (2H, m), 2.76-3.00 (2H, m), 3.41-3.58 (1H, m), 3.90-4.13 (2H, m), 8.19 (1H, d), 8.67 (1H, s), 8.69 (1H, d), 12.77 (1H, s).

Intermediate 53: 2-(3-(1-(tert-Butoxycarbonyl)piperidine-4-carbonyl)-4-fluoro-1H-pyrrolo[2,3-c]pyridin-1-yl)-5-fluorobenzoic acid

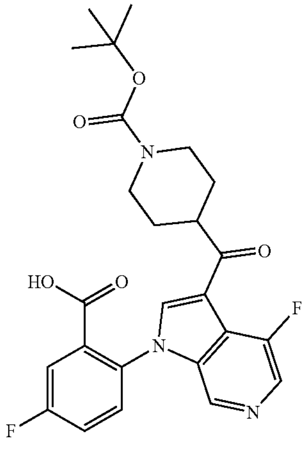 [SMILES: CC(C)(C)OC(=O)N1CCC(C(=O)c2cn(-c3ccc(F)cc3C(=O)O)c3cncc(F)c23)CC1]

CuI (107 mg, 0.56 mmol) was added to a mixture of 5-fluoro-2-iodobenzoic acid (750 mg, 2.82 mmol), Intermediate 52 (980 mg, 2.82 mmol) and $Cs_2CO_3$ (2.76 g, 8.46 mmol) in DMF (15 mL). The resulting mixture was stirred at 60° C. for 8 h. The reaction mixture was purified by reversed phase flash chromatography on a C18 column (gradient: 0-40% MeOH in water containing 5% $NH_4HCO_3$) to give the title compound (1.00 g, 73%) as a white solid; MS m/z (ES+) $[M+H]^+$=486.2.

Intermediate 54: tert-Butyl 4-(1-(2-(diisopropylcarbamoyl)-4-fluorophenyl)-4-fluoro-1H-pyrrolo[2,3-c]pyridine-3-carbonyl)piperidine-1-carboxylate

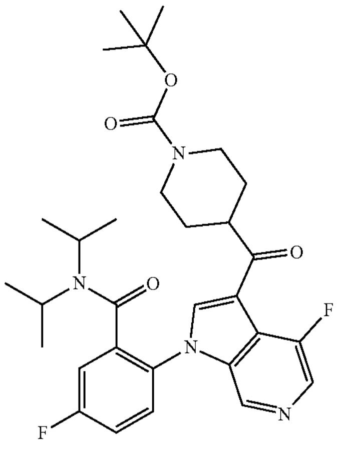 [SMILES: CC(C)N(C(=O)c1cc(F)ccc1-n1cc(C(=O)C2CCN(C(=O)OC(C)(C)C)CC2)c2c(F)cncc21)C(C)C]

T3P (3.93 g, 6.18 mmol, 50% in EtOAc) was added to a mixture of Intermediate 53 (500 mg, 1.03 mmol), DIPEA (1.80 mL, 10.3 mmol) and diisopropylamine (1.45 mL, 10.3 mmol) in DCM (5 mL). The mixture was stirred at rt for 6 h. The reaction mixture was poured into sat. aq. $NH_4Cl$ (75 mL) and extracted with EtOAc (3×25 mL). The combined organic layers were dried over $Na_2SO_4$, filtered, and concentrated under reduced pressure. The residue was purified by straight phase flash chromatography on silica (gradient: 0-70% EtOAc in petroleum ether) to give the title compound (463 mg, 79%) as a white solid; MS m/z (ES+) $[M+H]^+$=569.2; $^1$H NMR (300 MHz, DMSO-$d_6$, 24° C.) δ 0.36 (3H, br s), 0.75 (3H, br s), 1.02 (3H, d), 1.33 (3H, d), 1.42 (9H, s), 1.46-1.54 (2H, m), 1.70-1.86 (2H, m), 2.86 (2H, br s), 3.21-3.31 (1H, m), 3.36-3.51 (1H, m), 3.51-3.58 (1H, m), 3.94-4.06 (2H, m), 7.52-7.61 (2H, m), 7.82-7.93 (1H, m), 8.31 (1H, d), 8.48 (1H, s), 8.69 (1H, s).

Intermediate 55: 5-Fluoro-2-(4-fluoro-3-(piperidine-4-carbonyl)-1H-pyrrolo[2,3-c]pyridin-1-yl)-N,N-diisopropylbenzamide di-hydrochloride

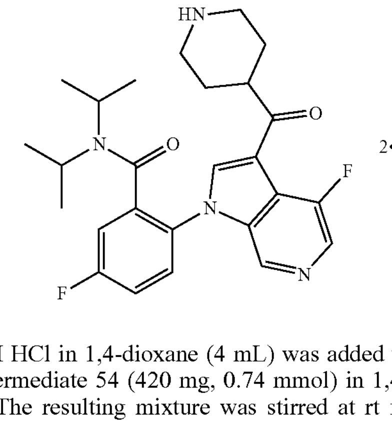

2•HCl

4 M HCl in 1,4-dioxane (4 mL) was added to a solution of Intermediate 54 (420 mg, 0.74 mmol) in 1,4-dioxane (4 mL). The resulting mixture was stirred at rt for 1 h. The mixture was diluted with $Et_2O$. The formed precipitate was collected by filtration, washed with $Et_2O$ (150 mL) and dried under vacuum to give the title compound (300 mg, 75%) as a white solid; MS m/z (ES+) $[M+H]^+$=469.2; $^1$H NMR (300 MHz, DMSO-$d_6$, 24° C.) δ 0.03-0.98 (6H, m), 1.03 (3H, d), 1.32 (3H, d), 1.80-2.02 (4H, m), 2.92-3.06 (2H, m), 3.22-3.36 (3H, m), 3.57 (3H, s), 7.54-7.64 (2H, m), 7.78-7.98 (1H, m), 8.50 (1H, d), 8.71 (1H, s), 8.82-9.06 (2H, m), 9.12-9.33 (1H, m).

Intermediate 56: tert-Butyl 4-(hydroxy(1H-pyrrolo[2,3-c]pyridin-3-yl)methyl)azepane-1-carboxylate

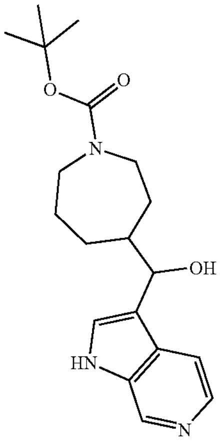 [SMILES: CC(C)(C)OC(=O)N1CCCC(C(O)c2c[nH]c3cnccc23)CC1]

KOH (475 mg, 8.46 mmol) was added to a solution of 1H-pyrrolo[2,3-c]pyridine (500 mg, 4.23 mmol) and tert-butyl 4-formylazepane-1-carboxylate (1.44 g, 6.35 mmol) in EtOH (25 mL) under $N_2$. The reaction was stirred at 60° C. for 8 h. The reaction mixture was diluted with DCM (100 mL) and washed sequentially with sat. aq. $NH_4Cl$ (50 mL) and water (25 mL). The organic layer was dried over $Na_2SO_4$, filtered, and concentrated to dryness. The residue was purified by straight phase flash chromatography on silica (gradient: 0-10% MeOH in DCM) to give the title compound (1.35 g, 92%) as a white solid; MS m/z (ES+) $[M+H]^+$=346.2; $^1$H NMR (300 MHz, DMSO-$d_6$, 26° C.) δ 1.00-1.16 (1H, m), 1.23-1.43 (11H, m), 1.69-1.88 (2H, m), 3.08-3.22 (3H, m), 3.31-3.44 (3H, m), 4.57-4.77 (1H, m), 4.96-5.13 (1H, m), 7.41-7.44 (1H, m), 7.57 (1H, d), 8.03 (1H, d), 8.69 (1H, s), 11.41 (1H, s).

Intermediate 57: tert-Butyl 4-(1H-pyrrolo[2,3-c]pyridine-3-carbonyl)azepane-1-carboxylate

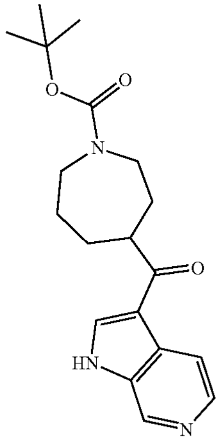 [SMILES: CC(C)(C)OC(=O)N1CCCC(C(=O)c2c[nH]c3cnccc23)CC1]

$MnO_2$ (1.01 g, 11.6 mmol) was added to a solution of Intermediate 56 (800 mg, 2.32 mmol) in 1,4-dioxane (25 mL) under $N_2$. The resulting mixture was stirred and heated at 100° C. for 8 h. The crude product was purified by straight phase flash chromatography on silica (gradient: 0-10% MeOH in DCM) to give the title compound (770 mg, 97%) as a white solid; MS m/z (ES+) [M+H]+=344.2; $^1$H NMR (300 MHz, DMSO-$d_6$) δ 1.43 (9H, s), 1.47-1.53 (1H, m), 1.61-1.80 (2H, m), 1.83-1.97 (3H, m), 3.19-3.31 (2H, m), 3.37-3.45 (2H, m), 3.49-3.73 (1H, m), 8.00-8.11 (1H, m), 8.28 (1H, d), 8.52 (1H, d), 8.84 (1H, s), 12.42 (1H, s).

Intermediate 58: 2-(3-(1-(tert-Butoxycarbonyl)azepane-4-carbonyl)-1H-pyrrolo[2,3-c]pyridin-1-yl)-5-fluorobenzoic acid

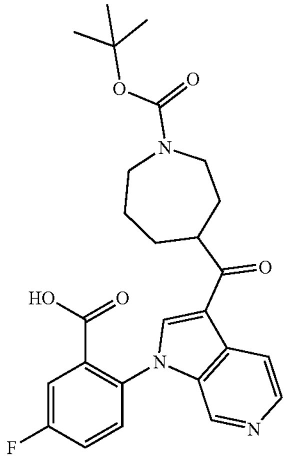 [SMILES: CC(C)(C)OC(=O)N1CCCC(C(=O)c2cn(-c3ccc(F)cc3C(=O)O)c3cnccc23)CC1]

CuI (84.0 mg, 0.44 mmol) was added to a deoxygenated solution of 5-fluoro-2-iodobenzoic acid (589 mg, 2.21 mmol), Intermediate 57 (760 mg, 2.21 mmol) and $Cs_2CO_3$ (2.16 g, 6.64 mmol) in DMF (25 mL). The resulting mixture was stirred and heated at 60° C. for 8 h. The crude product was purified by reversed phase flash chromatography on a C18 column (gradient: 0-50% MeOH in water) to give the title compound (980 mg, 92%) as a yellow solid; MS m/z (ES+) $[M+H]^+$=482.2; $^1$H NMR (300 MHz, DMSO-$d_6$) δ 1.40-1.44 (9H, m), 1.45-1.56 (1H, m), 1.63-1.80 (2H, m), 1.81-1.99 (3H, m), 3.14-3.26 (1H, m), 3.30-3.43 (3H, m), 3.56-3.71 (2H, m), 7.45-7.58 (1H, m), 7.62-7.75 (2H, m), 8.07-8.22 (2H, br s), 8.42 (1H, m), 8.68 (1H, s).

Intermediate 59: tert-Butyl 4-(1-(2-(diisopropylcarbamoyl)-4-fluorophenyl)-1H-pyrrolo[2,3-c]-pyridine-3-carbonyl)azepane-1-carboxylate

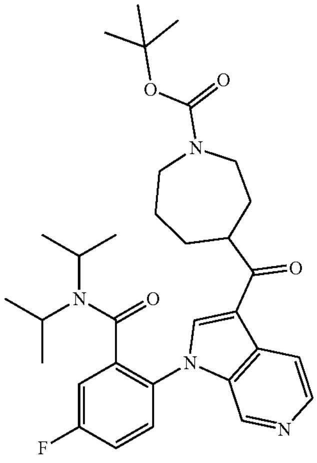 [SMILES: CC(C)N(C(=O)c1cc(F)ccc1-n1cc(C(=O)C2CCCN(C(=O)OC(C)(C)C)CC2)c2ccncc21)C(C)C]

HATU (2.25 g, 5.92 mmol) was added to a mixture of Intermediate 58 (950 mg, 1.97 mmol), diisopropylamine (1.94 mL, 13.8 mmol) and DIPEA (2.41 mL, 13.8 mmol) in DCM (25 mL) and the mixture was stirred at rt for 6 h. The reaction mixture was diluted with DCM (100 mL) and washed with sat. aq. $NH_4Cl$ (2×50 mL). The organic layer was dried over $Na_2SO_4$, filtered, and concentrated under reduced pressure. The residue was purified by straight phase flash chromatography on silica (gradient: 0-5% MeOH in DCM) to give the title compound (472 mg, 42%) as a yellow solid; MS m/z (ES+) $[M+H]^+$=565.5; $^1$H NMR (300 MHz, DMSO-$d_6$, 23° C.) δ 0.28 (2H, br s), 0.79 (3H, br s), 0.99 (3H, d), 1.26 (4H, m), 1.34 (3H, d), 1.38-1.47 (9H, m), 1.60-1.69 (1H, m), 1.84-1.94 (2H, m), 3.16-3.29 (3H, m), 3.38-3.67 (4H, m), 7.49-7.59 (2H, m), 7.74-7.92 (1H, m), 8.11-8.19 (1H, m), 8.38 (1H, d), 8.47-8.60 (1H, m), 8.65 (1H, s).

Intermediate 60: 2-(3-(Azepane-4-carbonyl)-1H-pyrrolo[2,3-c]pyridin-1-yl)-5-fluoro-N,N-diisopropylbenzamide hydrochloride

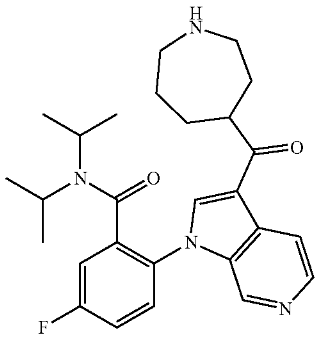

X•HCl

4 M HCl in 1,4-dioxane (3 mL) was added to a solution of Intermediate 59 (440 mg, 0.78 mmol) in 1,4-dioxane (9 mL). The resulting mixture was stirred at rt for 4 h. The mixture was concentrated under reduced pressure, washed with $Et_2O$ and filtered to give the title compound (294 mg, 74%) as a white solid; MS m/z (ES+) $[M+H]^+$=465.5; $^1$H NMR (300 MHz, DMSO-$d_6$, 27° C.) δ 0.64 (3H, br s), 0.97-1.12 (3H, m), 1.27-1.34 (6H, m), 1.64-2.20 (6H, m), 3.06-3.37 (5H, m), 3.59-3.79 (2H, m), 7.56-7.74 (2H, m), 7.91-8.02 (1H, m), 8.52-8.73 (2H, m), 9.08-9.53 (3H, m).

Intermediate 61: 2-Methyl-1-tosyl-1H-pyrrolo[2,3-c]pyridine

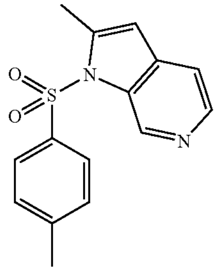 [SMILES: Cc1ccc(S(=O)(=O)n2c(C)cc3ccncc32)cc1]

NaH (11.2 g, 279 mmol, 60% dispersion in mineral oil) was added portion wise at 0° C. to a stirred solution of 6-azaindole (30.0 g, 254 mmol) in dry THF (1.5 L). The ice-bath was removed after 10 minutes and the resulting suspension was stirred at rt for 1 h before 4-methylbenzenesulfonyl chloride (53.3 g, 279 mmol) was added in one portion. The reaction mixture was stirred at rt for 1 h. The mixture was cooled to −78° C. and n-BuLi (238 mL, 381 mmol, 6 M in hexane) was added in one portion. The mixture was stirred at −78° C. for 1 h. MeI (23.7 mL, 381 mmol) was added, and the stirred mixture was allowed to reach rt over a period of 1 h. The reaction mixture was quenched with water (500 mL) and the organic solvent was concentrated to dryness. The aqueous layer was extracted with EtOAc (4×300 mL). The combined organic layers were washed with brine (2×250 mL), dried over $Na_2SO_4$, filtered, and concentrated under reduced pressure to give the crude title compound (80.0 g) as a brown solid, which was used directly in the next step; MS m/z (ES+) $[M+H]^+$=287.0; $^1$H NMR (400 MHz, MeOD, 22° C.) δ 2.37 (3H, s), 2.64 (3H, d), 6.52-6.57 (1H, m), 7.36 (2H, d), 7.50 (1H, dd), 7.71-7.80 (2H, m), 8.26 (1H, d), 9.28 (1H, s).

Intermediate 62: 2-Methyl-1H-pyrrolo[2,3-c]pyridine

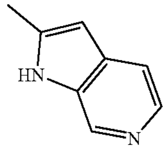

KOH (92.0 g, 1.40 mol) was added to a suspension of Intermediate 61 (80.0 g, 254 mmol, th.) in MeOH (1 L) and the mixture was stirred at 40° C. overnight. The reaction mixture was diluted with water (500 mL) and the organic solvent was concentrated under reduced pressure. The aqueous layer was extracted with EtOAc (3×500 mL). The combined organic layers were washed with brine (500 mL), dried over $Na_2SO_4$, filtered, and concentrated under reduced pressure to give the crude title compound (36.8 g) as an orange solid; MS m/z (ES+) $[M+H]^+$=133.1; $^1$H NMR (400 MHz, MeOD, 22° C.) δ 2.48 (3H, d), 6.22-6.27 (1H, m), 7.43 (1H, dd), 7.97 (1H, d), 8.51 (1H, s).

Intermediate 63: tert-Butyl 4-(hydroxy(2-methyl-1H-pyrrolo[2,3-c]pyridin-3-yl)methyl)-piperidine-1-carboxylate

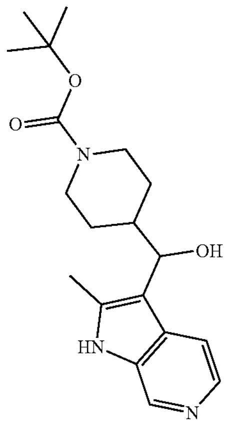 [SMILES: Cc1[nH]c2cnccc2c1C(O)C1CCN(C(=O)OC(C)(C)C)CC1]

tert-Butyl 4-formylpiperidine-1-carboxylate (39.7 mL, 205 mmol) was added to Intermediate 62 (26.0 g, 157 mmol th.) in a mixture of 1,4-dioxane (500 mL) and water (100 mL), followed by KOH (20.8 g, 315 mmol). The resulting mixture was stirred at rt for 24 h. The reaction mixture was concentrated under reduced pressure. The residue was diluted in water (500 mL) and extracted with EtOAc (3×500 mL). The combined organic layers were washed with brine (250 mL), dried over $Na_2SO_4$, filtered, and concentrated under reduced pressure to give the title compound (36.8 g, 68%) as a beige solid; MS m/z (ES+) $[M+H]^+$=346.6; $^1$H NMR (400 MHz, MeOD, 22° C.) δ 1.03 (1H, qd), 1.18-1.29 (2H, m), 1.42 (9H, s), 2.04-2.21 (2H, m), 2.46 (3H, s), 2.62 (1H, br s), 2.76 (1H, br s), 3.93-4.02 (1H, m), 4.10-4.20 (1H, m), 4.62 (1H, d), 7.63-7.69 (1H, m), 7.98 (1H, d), 8.50 (1H, s).

Intermediate 64: tert-Butyl 4-(2-methyl-1H-pyrrolo[2,3-c]pyridine-3-carbonyl)piperidine-1-carboxylate

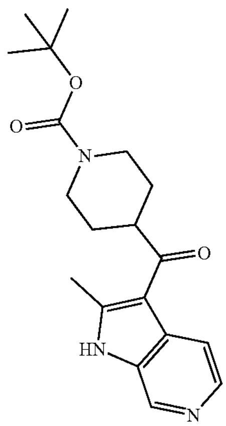 [SMILES: Cc1[nH]c2cnccc2c1C(=O)C1CCN(C(=O)OC(C)(C)C)CC1]

TEMPO (5.15 g, 32.9 mmol) and water (3.6 mL, 198 mmol) were added to a mixture of Intermediate 63 (22.8 g, 65.9 mmol) and PIDA (42.4 g, 132 mmol) in DCM (340 mL). The resulting mixture was stirred at rt for 1 h. The mixture was diluted with sat. aq. $NaHCO_3$ (50 mL) and stirred for 10 minutes. The organic layer was separated, and the aqueous layer extracted with DCM (150 mL). The combined organic layers were concentrated under reduced pressure. The residue was filtered through silica and rinsed sequentially with heptane (2×100 mL), heptane/DCM (7:3), DCM/MeOH (75:25) and MeOH (500 mL). The filtrate was concentrated under reduced pressure. The residue was purified by straight phase flash chromatography on silica (gradient: 0-10% MeOH in DCM) to give the title compound (18.7 g, 83%) as a beige solid after co-evaporation with toluene (3×50 mL); MS m/z (ES+) $[M+H]^+$=344.6; $^1$H NMR (400 MHz, MeOD, 22° C.) δ 1.50 (9H, s), 1.67 (2H, m), 1.89-1.98 (2H, m), 2.81 (3H, s), 3.07 (2H, br s), 3.47 (1H, tt), 4.13-4.22 (2H, m), 7.91-7.98 (1H, m), 8.27 (1H, d), 8.69 (1H, s).

Intermediate 65: 2-(3-(1-(tert-Butoxycarbonyl)piperidine-4-carbonyl)-2-methyl-1H-pyrrolo[2,3-c]pyridin-1-yl)-5-fluorobenzoic acid

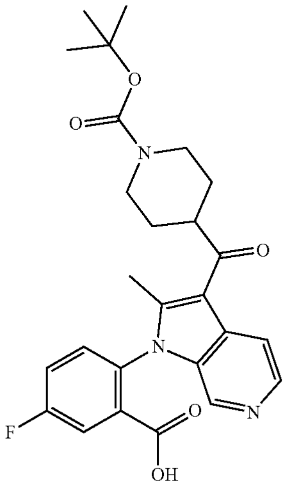 [SMILES: Cc1c(C(=O)C2CCN(C(=O)OC(C)(C)C)CC2)c2ccncc2n1-c1ccc(F)cc1C(=O)O]

Copper powder (339 mg, 5.33 mmol) was added to a deoxygenated solution of 5-fluoro-2-iodobenzoic acid (9.45 g, 35.5 mmol), Intermediate 64 (6.10 g, 17.8 mmol) and $K_2CO_3$ (8.59 g, 62.2 mmol) in DMF (72 mL). The resulting mixture was purged with $N_2$ and stirred and heated at 100° C. overnight. The reaction mixture was diluted with water (100 mL) and EtOAc (200 mL), filtered, and the filtrate was acidified with aq. HCl (6 M) to pH 2. The filtrate was saturated with solid NaCl and extracted with EtOAc (3×100 mL). The combined organic layers were concentrated under reduced pressure. The residue was purified by straight phase flash chromatography on silica (gradient: 0-100% EtOAc in heptane followed by 0-10% MeOH in DCM) to give the title compound (7.91 g, 92%) as a brown solid; MS m/z (ES+) $[M+H]^+$=482.1.

Intermediate 66 (Mixture of Atropisomers): tert-Butyl 4-(1-(2-(ethyl(isopropyl)carbamoyl)-4-fluorophenyl)-2-methyl-1H-pyrrolo[2,3-c]pyridine-3-carbonyl)piperidine-1-carboxylate

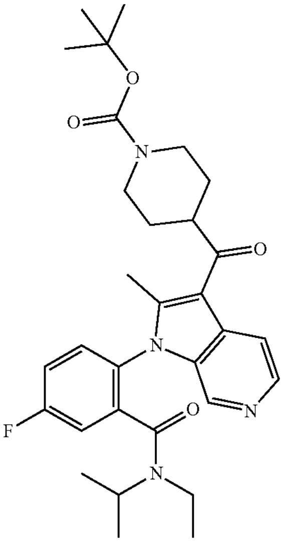 [SMILES: CCN(C(=O)c1cc(F)ccc1-n1c(C)c(C(=O)C2CCN(C(=O)OC(C)(C)C)CC2)c2ccncc21)C(C)C]

DIPEA (1.45 mL, 8.31 mmol) and N-ethylpropan-2-amine (2.51 mL, 20.8 mmol) were added to a mixture of Intermediate 65 (2.00 g, 4.15 mmol), HATU (1.74 g, 4.57 mmol) and DMAP (101 mg, 0.83 mmol) in DMF (6 mL). The resulting mixture was stirred at rt overnight. The reaction mixture was diluted with sat. aq. $NaHCO_3$ (100 mL) and extracted with EtOAc (3×50 mL). The combined organic layers were washed with brine (100 mL), dried over $Na_2SO_4$, filtered, and concentrated under reduced pressure. The residue was purified by straight phase flash chromatography on silica (gradient: 0-100% EtOAc in heptane) to give the title compound (2.13 g, 93%) as a brown gum which was used directly in the next step; MS m/z (ES+) $[M+H]^+$=551.3; $^1$H NMR (400 MHz, DMSO-$d_6$, 22° C.) δ 0.12-0.46 (5H, m), 0.57-0.79 (2H, m), 0.95-1.08 (3H, m), 1.37-1.56 (10H, m), 1.81 (2H, d), 2.73 (3H, s), 3.01 (2H, br s), 3.12-3.25 (1H, m), 3.38-3.52 (2H, m), 3.62-3.74 (1H, m), 4.00 (2H, br s), 7.55-7.63 (2H, m), 7.71-7.80 (1H, m), 7.84-7.94 (1H, m), 8.25-8.42 (2H, m).

Intermediate 67 (Mixture of Atropisomers): N-Ethyl-5-fluoro-N-isopropyl-2-(2-methyl-3-(piperidine-4-carbonyl)-1H-pyrrolo[2,3-c]pyridin-1-yl) benzamide

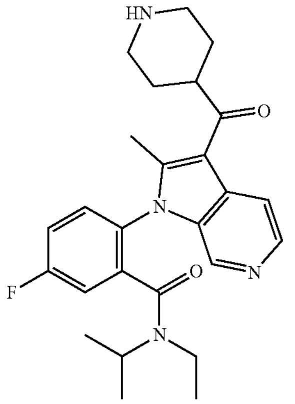 [SMILES: CCN(C(=O)c1cc(F)ccc1-n1c(C)c(C(=O)C2CCNCC2)c2ccncc21)C(C)C]

TFA (4 mL) was added to a solution of Intermediate 66 (2.13 g, 3.44 mmol th.) in DCM (20 mL). The resulting mixture was stirred at rt for 1 h. The mixture was concentrated under reduced pressure. The residue was quenched with sat. aq. $NaHCO_3$ and extracted with DCM (3×30 mL). The combined organic layers were washed with brine, dried over $Na_2SO_4$, filtered, and concentrated under reduced pressure to give the crude title compound (1.04 g, LC-UV purity 87%) as a brown gum; MS m/z (ES+) $[M+H]^+$=451.2; $^1H$ NMR (400 MHz, DMSO-$d_6$, 22° C.) δ 0.15-0.47 (4H, m), 0.54-0.80 (2H, m), 0.92-1.11 (3H, m), 1.07-1.37 (2H, m), 1.64-1.85 (2H, m), 1.94 (2H, d), 2.51 (3H, s), 2.69-2.80 (2H, m), 3.05-3.23 (3H, m), 3.49-3.57 (1H, m), 3.65-3.75 (1H, m), 7.55-7.65 (2H, m), 7.70-7.81 (1H, m), 7.88-7.98 (1H, m), 8.26-8.40 (2H, m).

Intermediate 68 (Mixture of Atropisomers): tert-Butyl 4-(1-(4-fluoro-2-(isopropyl(2,2,2-trifluoroethyl)carbamoyl)phenyl)-2-methyl-1H-pyrrolo[2,3-c]pyridine-3-carbonyl)piperidine-1-carboxylate

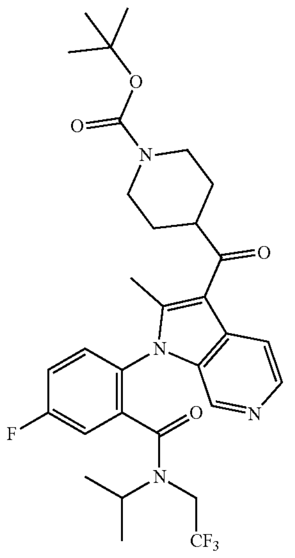 [SMILES: Cc1c(C(=O)C2CCN(C(=O)OC(C)(C)C)CC2)c2ccncc2n1-c1ccc(F)cc1C(=O)N(CC(F)(F)F)C(C)C]

T3P (3.71 mL, 6.23 mmol, 50% in EtOAc) was added to a mixture of Intermediate 65 (1.00 g, 2.08 mmol), N-(2,2,2-trifluoroethyl)propan-2-amine HCl (738 mg, 4.15 mmol) and DIPEA (2.13 mL, 12.5 mmol) in EtOAc (8 mL). The mixture was stirred at 40° C. for 4 days. The reaction mixture was diluted with sat. aq. $NaHCO_3$ (40 mL) and extracted sequentially with EtOAc (2×50 mL) and DCM (2×20 mL). The organic layers were washed with brine (100 mL), dried over $Na_2SO_4$, filtered, combined and concentrated under reduced pressure. The residue was purified by straight phase flash chromatography on silica (gradient: 0-10% MeOH in DCM) to give the title compound (581 mg, 46%) as an orange foam; MS m/z (ES+) $[M+H]^+$=605.3; $^1H$ NMR (400 MHz, DMSO-$d_6$, 23° C.) δ 0.37 (2H, br s), 0.76-1.12 (4H, m), 1.41 (9H, s), 1.44-1.59 (2H, m), 1.81 (2H, d), 2.45 (3H, s), 3.03 (2H, br s), 3.36-3.48 (1H, m), 3.70-3.86 (2H, m), 3.89-4.11 (3H, m), 7.58-7.69 (2H, m), 7.72-7.82 (1H, m), 7.90 (1H, br s), 8.34 (2H, br s).

Intermediate 69 (Mixture of Atropisomers): 5-Fluoro-N-isopropyl-2-(2-methyl-3-(piperidine-4-carbonyl)-1H-pyrrolo[2,3-c]pyridin-1-yl)-N-(2,2,2-trifluoroethyl)benzamide

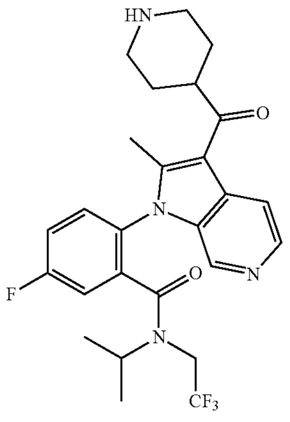 [SMILES: Cc1c(C(=O)C2CCNCC2)c2ccncc2n1-c1ccc(F)cc1C(=O)N(CC(F)(F)F)C(C)C]

TFA (2 mL) was added to a solution of Intermediate 68 (581 mg, 0.96 mmol) in DCM (10 mL). The resulting mixture was stirred at rt for 1 h. The mixture was concentrated under reduced pressure. The residue was quenched with sat. aq. $NaHCO_3$ and extracted with DCM (3×30 mL). The combined organic layers were washed with brine, dried over $Na_2SO_4$, filtered, and concentrated under reduced pressure to give the title compound (419 mg, 86%) as a brown foam; MS m/z (ES+) $[M+H]^+$=505.2; $^1H$ NMR (400 MHz, DMSO-$d_6$, 22° C.) δ 0.35 (2H, br s), 0.71-1.09 (4H, m), 1.35-1.96 (5H, m), 2.46 (3H, s), 2.65-3.19 (4H, m), 3.70-4.11 (3H, m), 7.60-7.69 (2H, m), 7.71-7.80 (1H, m), 7.81-7.89 (1H, m), 8.23-8.46 (2H, m).

Intermediate 70: rel-(2-Methyl-1H-pyrrolo[2,3-c]pyridin-3-yl)((2R,4R)-2-methylpiperidin-4-yl)methanone

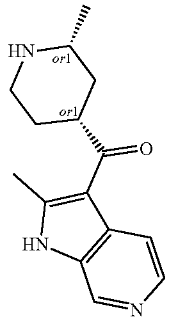 [SMILES: Cc1[nH]c2cnccc2c1C(=O)[C@@H]1CCN[C@H](C)C1]

rel-(2R,4R)-1-(tert-Butoxycarbonyl)-2-methylpiperidine-4-carboxylic acid (10.0 g, 41.1 mmol) was added to $SOCl_2$ (50 mL) at 0° C. under $N_2$. The resulting mixture was stirred at rt for 1 h. The solvent was removed under reduced pressure. The residue was dissolved in DCM (200 mL) and added dropwise to a mixture of Intermediate 62 (5.43 g, 41.1 mmol) and anhydrous $AlCl_3$ (38.4 g, 288 mmol) in DCM (200 mL) under $N_2$. The resulting mixture was stirred at rt for 2 h. The reaction mixture was poured into MeOH (100 mL) and the solvent was removed under reduced pressure. The residue was purified by straight phase flash chromatography on silica (gradient: 0-10% 0.7 M $NH_3$ in MeOH in DCM) to give the title compound in a quantitative yield (11.0 g) as a yellow solid; MS m/z (ES+) $[M+H]^+$=258.3.

Intermediate 71: rel-tert-butyl 3-((2R,4R)-1-(tert-butoxycarbonyl)-2-methylpiperidine-4-carbonyl)-2-methyl-1H-pyrrolo[2,3-c]pyridine-1-carboxylate

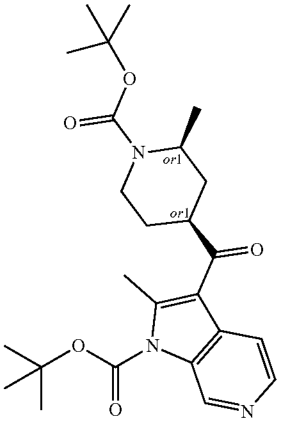 [SMILES: Cc1c(C(=O)[C@H]2CCN(C(=O)OC(C)(C)C)[C@@H](C)C2)c2ccncc2n1C(=O)OC(C)(C)C]

A solution of $Boc_2O$ (29.8 mL, 128 mmol) in DCM (50 mL) was added slowly to a stirred mixture of $Et_3N$ (29.8 mL, 214 mmol), DMAP (1.04 g, 8.55 mmol) and Intermediate 70 (11.0 g, 41.1 mmol, th.) in DCM (100 mL) under $N_2$. The resulting mixture was stirred at rt for 16 h. The reaction mixture was poured into sat. aq. $NaHCO_3$ (150 mL) and extracted with DCM (2×100 mL). The combined organic layers were dried over $Na_2SO_4$, filtered, and concentrated under reduced pressure. The residue was purified by straight phase flash chromatography on silica (gradient: 0-50% EtOAc in petroleum ether) to give the title compound (7.00 g, 37%); MS m/z ES+$[M+H]^+$=458.4; $^1H$ NMR (300 MHz, DMSO-$d_6$, 25° C.) δ 0.94 (1H, d), 1.19 (2H, d), 1.39-1.41 (9H, m), 1.68 (9H, s), 2.79-2.84 (3H, m), 2.93-3.20 (2H, m), 3.42-3.62 (2H, m), 3.65-3.75 (1H, m), 3.84-3.96 (1H, m), 3.96-4.06 (1H, m), 4.19-4.52 (1H, m), 7.75-7.90 (1H, m), 8.33-8.51 (1H, m), 9.27 (1H, s).

Intermediate 72: rel-tert-Butyl (2R,4S)-2-methyl-4-(2-methyl-1H-pyrrolo[2,3-c]pyridine-3-carbonyl)piperidine-1-carboxylate

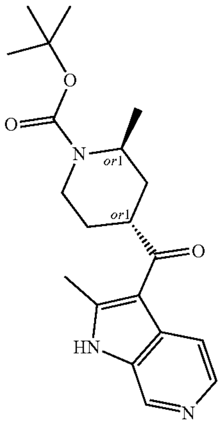 [SMILES: Cc1[nH]c2cnccc2c1C(=O)[C@@H]1CCN(C(=O)OC(C)(C)C)[C@@H](C)C1]

NaOH (1.22 g, 30.6 mmol) was added to a solution of Intermediate 71 (7.00 g, 15.3 mmol) in MeOH (60 mL) under $N_2$. The resulting mixture was stirred at rt for 16 h. The reaction mixture was poured into sat. aq. $NaHCO_3$ (150 mL) and extracted with EtOAc (3×100 mL). The combined organic layers were dried over $Na_2SO_4$, filtered, and concentrated under reduced pressure. The residue was purified by preparative SFC, PrepMethod SFC-A, to give the title compound (2.50 g, 46%) as a white solid; MS m/z ES+$[M+H]^+$=358.1; $^1H$ NMR (300 MHz, DMSO-$d_6$, 25° C.) δ 1.26 (3H, d), 1.41 (9H, s), 1.45-1.66 (2H, m), 1.67-1.84 (2H, m), 2.73 (3H, s), 2.92-3.18 (1H, m), 3.38-3.58 (1H, m), 3.92 (1H, d), 4.39 (1H, br s), 7.81-7.86 (1H, m), 8.26 (1H, d), 8.73 (1H, s), 12.43 (1H, br s).

Intermediate 73: rel-2-(3-((2R,4S)-1-(tert-Butoxycarbonyl)-2-methylpiperidine-4-carbonyl)-2-methyl-1H-pyrrolo[2,3-c]pyridin-1-yl)-5-fluorobenzoic acid

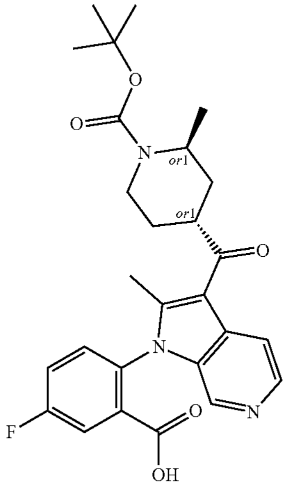 [SMILES: Cc1c(C(=O)[C@@H]2CCN(C(=O)OC(C)(C)C)[C@@H](C)C2)c2ccncc2n1-c1ccc(F)cc1C(=O)O]

Copper powder (711 mg, 11.2 mmol) was added to a deoxygenated solution of 5-fluoro-2-iodobenzoic acid (2.23 g, 8.39 mmol), Intermediate 72 (2.00 g, 5.60 mmol) and $K_2CO_3$ (2.71 g, 19.6 mmol) in DMF (30 mL). The resulting mixture was purged with $N_2$ and stirred at 100° C. for 2 h. The reaction mixture was purified by reversed phase flash chromatography on a C18 column (gradient: 0-80% MeOH in water containing 0.5% $NH_4HCO_3$) to give the title compound (1.80 g, 65%) as a yellow solid; MS m/z (ES+) $[M+H]^+$=496.4.

Intermediates 74-1, 74-2, 74-3 and 74-4 (separated atropisomers, single isomers): rel-tert-Butyl (2R, 4S)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carboxylate

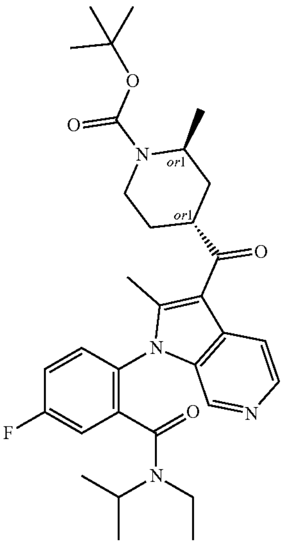

seperated isomers 74-1 to 74-4

HATU (2.84 g, 7.47 mmol) was added to a mixture of Intermediate 73 (1.85 g, 3.73 mmol), N-ethylpropan-2-amine (651 mg, 7.47 mmol) and DIPEA (1.96 mL, 11.2 mmol) in DCM (20 mL) under $N_2$. The mixture was stirred at rt for 2 h. The reaction mixture was diluted with sat. aq. $NaHCO_3$ (50 mL) and extracted with DCM (3×50 mL). The combined organic layers were dried over $Na_2SO_4$, filtered, combined and concentrated under reduced pressure. The residue was purified by straight phase flash chromatography on silica (gradient: 0-70% EtOAc in petroleum ether). The residue was purified by preparative chiral HPLC, Prep-Method B (isocratic: 15%), to give the title compound intermediate 74-1 as first eluting product (250 mg, 12%) as a white solid; MS m/z (ES+) $[M+H]^+$=565.4; $^1$H NMR (400 MHz, DMSO-$d_6$, 21° C.) δ 0.11-0.30 (1H, m), 0.38-0.44 (3H, m), 0.59 (1H, br s), 0.66-0.79 (1H, m), 0.98-1.10 (3H, m), 1.27 (3H, d), 1.42 (9H, s), 1.45-1.53 (1H, m), 1.55-1.67 (1H, m), 1.68-1.77 (1H, m), 1.81 (1H, d), 2.63-2.84 (1H, m), 3.08 (1H, br s), 3.13-3.27 (1H, m), 3.50-3.62 (1H, m), 3.64-3.76 (1H, m), 3.92 (1H, d), 4.40 (1H, br s), 7.55-7.63 (2H, m), 7.71-7.83 (1H, m), 7.84-7.92 (1H, m), 8.31-8.36 (2H, m); and intermediate 74-2 as second eluting product (200 mg, 9%) as a white solid; MS m/z (ES+) $[M+H]^+$=565.3; $^1$H NMR (400 MHz, DMSO-$d_6$, 20° C.) δ 0.12-0.26 (1H, m), 0.39-0.45 (3H, m), 0.62 (1H, br s), 0.68-0.76 (1H, m), 0.99-1.11 (3H, m), 1.25 (3H, d), 1.41 (9H, s), 1.44-1.63 (2H, m), 1.67-1.75 (1H, m), 1.81 (1H, d), 2.69-2.78 (1H, m), 3.07 (1H, br s), 3.14-3.25 (1H, m), 3.52-3.62 (1H, m), 3.67-3.75 (1H, m), 3.93 (1H, d), 4.32-4.42 (1H, m), 7.56-7.62 (2H, m), 7.73-7.79 (1H, m), 7.88-7.92 (1H, m), 8.31-8.35 (2H, m); and intermediate 74-3 as third eluting product (200 mg, 9%) as a white solid; MS m/z (ES+) $[M+H]^+$=565.4; $^1$H NMR (400 MHz, DMSO-$d_6$, 23° C.) δ 0.14-0.30 (1H, m), 0.38-0.45 (3H, m), 0.60 (1H, br s), 0.67-0.78 (1H, m), 0.96-1.10 (3H, m), 1.22-1.35 (3H, m), 1.42 (9H, s), 1.43-1.51 (1H, m), 1.55-1.67 (1H, m), 1.68-1.77 (1H, m), 1.81 (1H, d), 2.64-2.80 (1H, m), 3.08 (1H, br s), 3.13-3.27 (1H, m), 3.50-3.61 (1H, m), 3.64-3.76 (1H, m), 3.92 (1H, d), 4.40 (1H, br s), 7.55-7.62 (2H, m), 7.70-7.82 (1H, m), 7.86-7.93 (1H, m), 8.31-8.37 (2H, m); and intermediate 74-4 as fourth eluting product (200 mg, 9%) as a white solid; MS m/z (ES+) $[M+H]^+$=565.4; $^1$H NMR (400 MHz, DMSO-$d_6$, 23° C.) δ 0.10-0.29 (1H, m), 0.39-0.47 (3H, m), 0.61 (1H, br s), 0.67-0.79 (1H, m), 0.93-1.11 (3H, m), 1.25 (3H, d), 1.42 (9H, s), 1.44-1.62 (2H, m), 1.66-1.76 (1H, m), 1.81 (1H, d), 2.72-2.81 (1H, m), 3.07 (1H, br s), 3.13-3.25 (1H, m), 3.48-3.63 (1H, m), 3.67-3.76 (1H, m), 3.93 (1H, d), 4.37 (1H, br s), 7.56-7.62 (2H, m), 7.73-7.80 (1H, m), 7.84-7.93 (1H, m), 8.31-8.36 (2H, m).

Intermediate 75 (Single Atropisomer, Single Isomer): rel-N-Ethyl-5-fluoro-N-isopropyl-2-(2-methyl-3-((2R,4S)-2-methylpiperidine-4-carbonyl)-1H-pyrrolo[2,3-c]pyridin-1-yl)benzamide

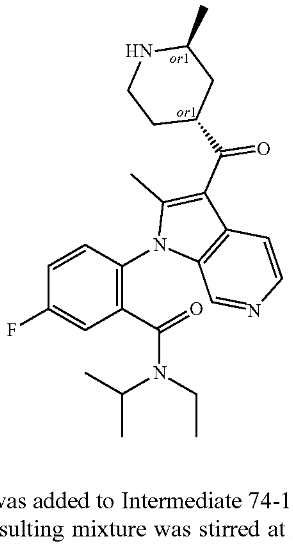

FA (5 mL) was added to Intermediate 74-1 (250 mg, 0.44 mmol). The resulting mixture was stirred at rt for 1 h. The mixture was concentrated under reduced pressure. The residue was quenched with sat. aq. $NaHCO_3$ (50 mL) and extracted with DCM (4×50 mL). The combined organic layers were dried over $Na_2SO_4$, filtered, and concentrated under reduced pressure to give the title compound (187 mg, 91%) as a pale yellow solid; MS m/z (ES+) $[M+H]^+$=465.2; $^1$H NMR (300 MHz, DMSO-$d_6$, 21° C.) δ 0.08-0.21 (1H, m), 0.34-0.42 (3H, m), 0.60-0.86 (2H, m), 0.97-1.08 (6H, m), 1.09-1.31 (1H, m), 1.33-1.52 (1H, m), 1.75 (2H, br s), 1.82-2.00 (1H, m), 2.65-2.81 (2H, m), 2.86-3.00 (1H, m), 3.20-3.41 (1H, m), 3.52-3.63 (1H, m), 3.63-3.75 (1H, m), 7.54-7.62 (2H, m), 7.71-7.84 (2H, m), 8.25-8.37 (2H, m).

Intermediate 76 (Single Atropisomer, Single Isomer): rel-N-Ethyl-5-fluoro-N-isopropyl-2-(2-methyl-3-((2R,4S)-2-methylpiperidine-4-carbonyl)-1H-pyrrolo[2,3-c]pyridin-1-yl)benzamide

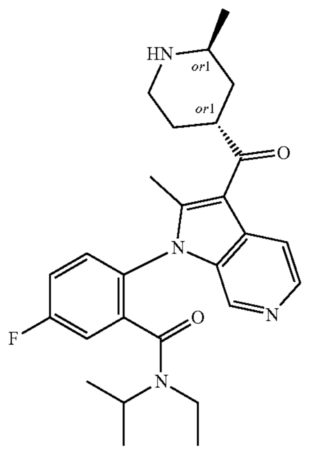 [SMILES: CCN(C(=O)c1cc(F)ccc1-n1c(C)c(C(=O)[C@@H]2CCN[C@@H](C)C2)c2ccncc21)C(C)C]

FA (5 mL) was added to Intermediate 74-2 (190 mg, 0.34 mmol). The resulting mixture was stirred at rt for 1 h. The mixture was concentrated under reduced pressure. The residue was quenched with sat. aq. $NaHCO_3$ (50 mL) and extracted with DCM (4×50 mL). The combined organic layers were dried over $Na_2SO_4$, filtered, and concentrated under reduced pressure to give the crude title compound (180 mg) as a pale yellow solid; MS m/z (ES+) $[M+H]^+$ =465.2; $^1$H NMR (300 MHz, DMSO-$d_6$, 21° C.) δ 0.10-0.18 (1H, m), 0.36-0.44 (3H, m), 0.60-0.74 (1H, m), 0.82-0.91 (1H, m), 0.93-1.09 (6H, m), 1.20-1.30 (1H, m), 1.40-1.58 (1H, m), 1.75 (1H, m), 1.78-1.95 (2H, m), 2.66-2.74 (1H, m), 2.76-2.88 (2H, m), 3.19-3.34 (1H, m), 3.53-3.63 (1H, m), 3.64-3.74 (1H, m), 7.53-7.63 (2H, m), 7.70-7.85 (2H, m), 8.24-8.37 (2H, m).

Intermediate 77 (Single Atropisomer, Single Isomer): rel-N-Ethyl-5-fluoro-N-isopropyl-2-(2-methyl-3-((2R,4S)-2-methylpiperidine-4-carbonyl)-1H-pyrrolo[2,3-c]pyridin-1-yl)benzamide

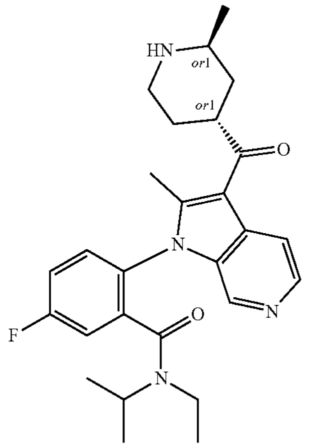 [SMILES: CCN(C(=O)c1cc(F)ccc1-n1c(C)c(C(=O)[C@@H]2CCN[C@@H](C)C2)c2ccncc21)C(C)C]

FA (5 mL) was added to Intermediate 74-3 (200 mg, 0.35 mmol). The resulting mixture was stirred at rt for 1 h. The mixture was concentrated under reduced pressure. The residue was quenched with sat. aq. $NaHCO_3$ (50 mL) and extracted with DCM (4×50 mL). The combined organic layers were dried over $Na_2SO_4$, filtered, and concentrated under reduced pressure to give the crude title compound (180 mg) as a yellow solid; MS m/z (ES+) $[M+H]^+$=465.3; $^1$H NMR (300 MHz, DMSO-$d_6$, 21° C.) δ 0.10-0.19 (1H, m), 0.35-0.44 (3H, m), 0.58-0.77 (1H, m), 0.78-0.90 (1H, m), 0.95-1.08 (6H, m), 1.18-1.30 (1H, m), 1.32-1.50 (1H, m), 1.76 (2H, br s), 1.85-1.95 (1H, m), 2.65-2.78 (2H, m), 2.86-2.99 (1H, m), 3.14-3.32 (1H, m), 3.54-3.62 (1H, m), 3.63-3.74 (1H, m), 7.54-7.64 (2H, m), 7.70-7.89 (2H, m), 8.25-8.36 (2H, m).

Intermediate 78 (Single Atropisomer, Single Isomer): rel-N-Ethyl-5-fluoro-N-isopropyl-2-(2-methyl-3-((2R,4S)-2-methylpiperidine-4-carbonyl)-1H-pyrrolo[2,3-c]pyridin-1-yl)benzamide

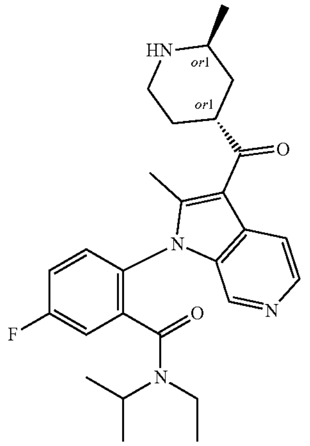 [SMILES: CCN(C(=O)c1cc(F)ccc1-n1c(C)c(C(=O)[C@@H]2CCN[C@@H](C)C2)c2ccncc21)C(C)C]

FA (5 mL) was added to Intermediate 74-4 (210 mg, 0.37 mmol). The resulting mixture was stirred at rt for 1 h. The mixture was concentrated under reduced pressure. The residue was quenched with sat. aq. $NaHCO_3$ (50 mL) and extracted with DCM (4×50 mL). The combined organic layers were dried over $Na_2SO_4$, filtered, and concentrated under reduced pressure to give the crude title compound (180 mg) as a yellow solid; MS m/z (ES+) $[M+H]^+$=465.4; $^1$H NMR (300 MHz, DMSO-$d_6$, 21° C.) δ 0.09-0.18 (1H, m), 0.35-0.44 (3H, m), 0.68-0.75 (1H, m), 0.83-0.92 (1H, m), 0.94-1.08 (6H, m), 1.20-1.26 (1H, m), 1.40-1.56 (1H, m), 1.63-1.77 (1H, m), 1.78-1.95 (2H, m), 2.72-2.87 (3H, m), 3.15-3.30 (1H, m), 3.53-3.64 (1H, m), 3.64-3.73 (1H, m), 7.54-7.63 (2H, m), 7.71-7.84 (2H, m), 8.25-8.37 (2H, m).

Intermediates 79-1, 79-2, 79-3 and 79-4 (separated atropisomers, single isomers): rel-tert-Butyl (2R, 4S)-4-(1-(4-fluoro-2-(isopropyl(2,2,2-trifluoroethyl) carbamoyl)phenyl)-2-methyl-1H-pyrrolo[2,3-c]pyridine-3-carbonyl)-2-methylpiperidine-1-carboxylate

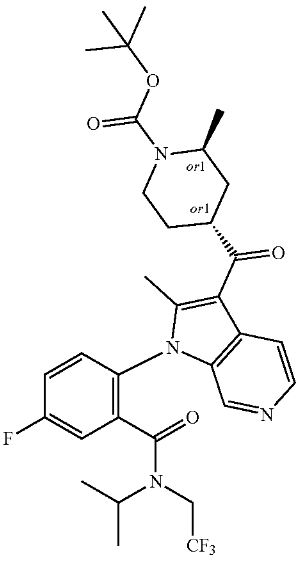

separated isomers 79-1 to 79-4

T3P (8.59 g, 13.5 mmol, 50% in EtOAc) was added to a mixture of Intermediate 73 (2.23 g, 4.50 mmol), N-(2,2,2-trifluoroethyl)propan-2-amine (3.18 g, 22.5 mmol) and DIPEA (4.72 mL, 27.0 mmol) in DCM (20 mL) under $N_2$. The mixture was stirred at rt for 45 h. The reaction mixture was concentrated under reduced pressure. The residue was diluted with DCM (300 mL) and washed with water (3×100 mL). The organic layer was dried over $Na_2SO_4$, filtered, combined, and concentrated under reduced pressure. The residue was purified by straight phase flash chromatography (gradient: 0-100% EtOAc in petroleum ether), followed by preparative SFC, PrepMethod SFC-B (isocratic 15%) to give the title compound intermediate 79-1 as first eluting product (35.0 mg, 1%) as a white solid; MS m/z (ES+) $[M+H]^+$=619.3; $^1$H NMR (400 MHz, DMSO-$d_6$, 22° C.) δ 0.35-0.43 (2H, m), 0.80-0.88 (1H, m), 1.03-1.11 (3H, m), 1.25 (3H, d), 1.42 (9H, s), 1.47-1.64 (2H, m), 1.67-1.75 (1H, m), 1.76-1.85 (1H, m), 2.41-2.48 (3H, m), 3.01-3.29 (1H, m), 3.50-3.62 (1H, m), 3.67-3.87 (2H, m), 3.93 (1H, d), 3.98-4.13 (1H, m), 4.37 (1H, br s), 7.59-7.69 (2H, m), 7.73-7.81 (1H, m), 7.89 (1H, d), 8.29-8.35 (1H, m), 8.39 (1H, s); and intermediate 79-2 as second eluting product (80.0 mg, 3%) as a white solid; MS m/z (ES+) $[M+H]^+$=619.3; $^1$H NMR (400 MHz, DMSO-$d_6$, 22° C.) δ 0.34-0.40 (2H, m), 0.84-0.92 (1H, m), 1.01-1.11 (3H, m), 1.24-1.27 (3H, m), 1.42 (9H, s), 1.44-1.52 (1H, m), 1.57-1.67 (1H, m), 1.67-1.75 (1H, m), 1.76-1.88 (1H, m), 2.47 (3H, s), 3.07 (1H, br s), 3.48-3.61 (1H, m), 3.69-3.85 (2H, m), 3.91 (1H, d), 3.99-4.17 (1H, m), 4.39 (1H, br s), 7.61-7.69 (2H, m), 7.74-7.82 (1H, m), 7.90 (1H, d), 8.33 (1H, d), 8.39 (1H, s); and intermediate 79-3 as third eluting product (80.0 mg, 3%) as a white solid; MS m/z (ES+) $[M+H]^+$=619.3; $^1$H NMR (400 MHz, DMSO-$d_6$, 22° C.) δ 0.32-0.42 (2H, m), 0.83-0.91 (1H, m), 1.02-1.08 (3H, m), 1.26 (3H, d), 1.42 (9H, s), 1.46-1.52 (1H, m), 1.61-1.67 (1H, m), 1.69-1.77 (1H, m), 1.78-1.86 (1H, m), 2.47 (3H, s), 3.00-3.15 (1H, m), 3.49-3.61 (1H, m), 3.71-3.87 (2H, m), 3.92 (1H, d), 3.99-4.13 (1H, m), 4.41 (1H, br s), 7.62-7.69 (2H, m), 7.73-7.81 (1H, m), 7.90 (1H, d), 8.34 (1H, d), 8.39 (1H, s); and intermediate 79-4 as fourth eluting product (80.0 mg, 3%) as a white solid; MS m/z (ES+) $[M+H]^+$=619.3; $^1$H NMR (400 MHz, DMSO-$d_6$, 22° C.) δ 0.37-0.45 (2H, m), 0.79-0.91 (1H, m), 1.01-1.14 (3H, m), 1.25 (3H, d), 1.42 (9H, s), 1.47-1.60 (2H, m), 1.69-1.75 (1H, m), 1.77-1.90 (1H, m), 2.42-2.48 (3H, m), 3.10 (1H, br s), 3.51-3.65 (1H, m), 3.71-3.88 (2H, m), 3.89-3.98 (1H, m), 4.01-4.12 (1H, m), 4.40 (1H, br s), 7.61-7.68 (2H, m), 7.74-7.82 (1H, m), 7.86-7.94 (1H, m), 8.29-8.43 (2H, m).

Intermediate 80 (Single Atropisomer, Single Isomer): rel-5-Fluoro-N-isopropyl-2-(2-methyl-3-((2R, 4S)-2-methylpiperidine-4-carbonyl)-1H-pyrrolo[2,3-c]pyridin-1-yl)-N-(2,2,2-trifluoroethyl)benzamide

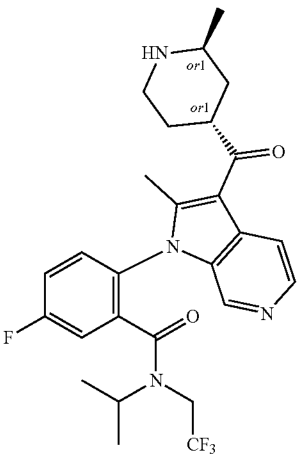 [SMILES: Cc1c(C(=O)[C@@H]2CCN[C@@H](C)C2)c2ccncc2n1-c1ccc(F)cc1C(=O)N(CC(F)(F)F)C(C)C]

FA (2 mL) was added to a solution of Intermediate 79-1 (35.0 mg, 0.06 mmol). The resulting mixture was stirred at rt for 2 h. The mixture was concentrated under reduced pressure. The residue was quenched with sat. aq. $NaHCO_3$ and extracted with DCM. The combined organic layers were dried over $Na_2SO_4$, filtered, and concentrated under reduced pressure to give the crude title compound (36.6 mg) as an off-white solid, which was used directly in the next step (Example 53-1a); MS m/z (ES+) $[M+H]^+$=519.2.

Intermediate 81 (Single Atropisomer, Single Isomer): rel-5-Fluoro-N-isopropyl-2-(2-methyl-3-((2R, 4S)-2-methylpiperidine-4-carbonyl)-1H-pyrrolo[2,3-c]pyridin-1-yl)-N-(2,2,2-trifluoroethyl)benzamide

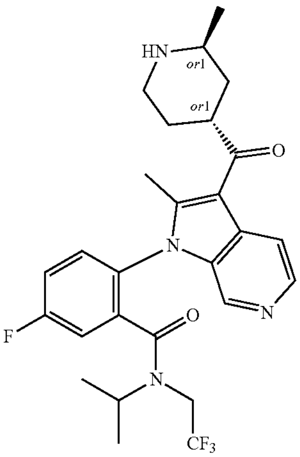 [SMILES: Cc1c(C(=O)[C@@H]2CCN[C@@H](C)C2)c2ccncc2n1-c1ccc(F)cc1C(=O)N(CC(F)(F)F)C(C)C]

FA (2 mL) was added to a solution of Intermediate 79-2 (80.0 mg, 0.13 mmol). The resulting mixture was stirred at rt for 2 h. The mixture was concentrated under reduced pressure. The residue was quenched with sat. aq. $NaHCO_3$ and extracted with DCM. The combined organic layers were dried over $Na_2SO_4$, filtered, and concentrated under reduced pressure to give the crude title compound (76.6 mg) as an off-white solid, which was used directly in the next step (Example 53-2a); MS m/z (ES+) $[M+H]^+$=519.2.

Intermediate 82 (Single Atropisomer, Single Isomer): rel-5-Fluoro-N-isopropyl-2-(2-methyl-3-((2R, 4S)-2-methylpiperidine-4-carbonyl)-1H-pyrrolo[2,3-c]pyridin-1-yl)-N-(2,2,2-trifluoroethyl)benzamide

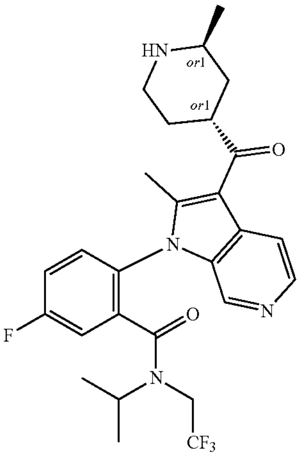 [SMILES: Cc1c(C(=O)[C@@H]2CCN[C@@H](C)C2)c2ccncc2n1-c1ccc(F)cc1C(=O)N(CC(F)(F)F)C(C)C]

FA (2 mL) was added to a solution of Intermediate 79-3 (75.0 mg, 0.12 mmol). The resulting mixture was stirred at rt for 2 h. The mixture was concentrated under reduced pressure. The residue was quenched with sat. aq. $NaHCO_3$ and extracted with DCM. The combined organic layers were dried over $Na_2SO_4$, filtered, and concentrated under reduced pressure to give the crude title compound (75.0 mg) as an off-white gum, which was used directly in the next step (Example 53-3a); MS m/z (ES+) $[M+H]^+$=519.2.

Intermediate 83 (Single Atropisomer, Single Isomer): rel-5-Fluoro-N-isopropyl-2-(2-methyl-3-((2R, 4S)-2-methylpiperidine-4-carbonyl)-1H-pyrrolo[2,3-c]pyridin-1-yl)-N-(2,2,2-trifluoroethyl)benzamide

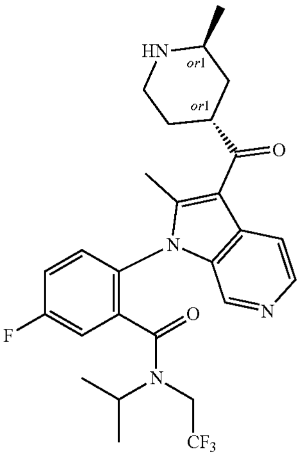 [SMILES: Cc1c(C(=O)[C@@H]2CCN[C@@H](C)C2)c2ccncc2n1-c1ccc(F)cc1C(=O)N(CC(F)(F)F)C(C)C]

FA (2 mL) was added to a solution of Intermediate 79-4 (80.0 mg, 0.13 mmol). The resulting mixture was stirred at rt for 2 h. The mixture was concentrated under reduced pressure. The residue was quenched with sat. aq. $NaHCO_3$ and extracted with DCM. The combined organic layers were dried over $Na_2SO_4$, filtered, and concentrated under reduced pressure to give the crude title compound (76.3 mg) as an off-white solid, which was used directly in the next step (Example 53-4a); MS m/z (ES+) $[M+H]^+$=519.2.

Intermediate 84: tert-Butyl 4-(3-oxobutanoyl)piperidine-1-carboxylate

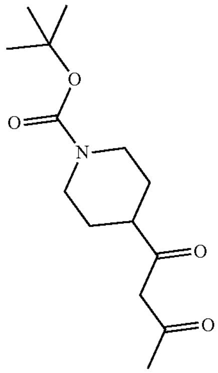 [SMILES: CC(=O)CC(=O)C1CCN(C(=O)OC(C)(C)C)CC1]

NaH (3.52 g, 88.0 mmol, 60% dispersion in mineral oil) was added to a cooled solution of tert-butyl 4-acetylpiperidine-1-carboxylate (9.50 mL, 44.0 mmol) in THF (100 mL) at 0° C. under $N_2$. The reaction mixture was allowed to reach rt and stirred for 1 h before EtOAc (8.59 mL, 88.0 mmol) was added. The resulting mixture was stirred at 40° C. for 3 h. The reaction mixture was poured into water (150 mL) and sat. aq. $NH_4Cl$ (200 mL) and extracted with EtOAc (3×200 mL). The combined organic layers were dried over $Na_2SO_4$, filtered, and concentrated under reduced pressure. The residue was purified by straight phase flash chromatography on silica (gradient: 0-40% EtOAc in heptane) to give the title compound (8.50 g, 72%) as a beige solid; MS m/z (ES+) $[M+H-tBu]^+$=213.9; $^1H$ NMR (400 MHz, $CDCl_3$, 22° C.) δ 1.45-1.47 (9H, m), 1.57 (2H, m), 1.81 (2H, d), 2.07 (3H, s), 2.33 (1H, tt), 2.69-2.82 (2H, m), 4.05-4.23 (2H, m), 5.53 (1H, s), 15.54 (1H, br s).

Intermediate 85: 4-Bromo-N-(2-bromo-4-fluorophenyl)pyridin-3-amine

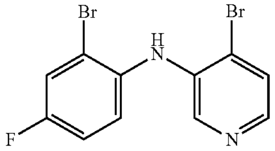 [SMILES: Fc1ccc(Nc2cnccc2Br)c(Br)c1]

$Pd_2dba_3 \cdot CHCl_3$ (3.44 g, 3.32 mmol) was added to a deoxygenated mixture of 2-bromo-4-fluoro-1-iodobenzene (10.0 g, 33.2 mmol), 4-bromopyridin-3-amine (5.75 g, 33.2 mmol), XantPhos (3.85 g, 6.65 mmol) and NaOtBu (6.39 g, 66.5 mmol) in toluene (150 mL). The mixture was purged with $N_2$ for 10 minutes and stirred at 60° C. for 4 h under $N_2$. The reaction mixture was diluted with EtOAc and washed with water and brine. The organic layer was dried over $Na_2SO_4$, filtered, and concentrated under reduced pressure. The residue was purified by straight phase flash chromatography on silica (gradient: 10-20% EtOAc in heptane) to give the title compound (8.04 g, 70%) as a white solid; MS m/z (ES+) $[M+H]^+$=344.9/346.9; $^1H$ NMR (400 MHz, DMSO-$d_6$, 22° C.) δ 7.08-7.19 (1H, m), 7.19-7.30 (1H, m), 7.50 (1H, s), 7.61-7.72 (2H, m), 7.89 (1H, s), 7.96 (1H, d).

Intermediate 86: tert-Butyl 4-(1-(2-bromo-4-fluorophenyl)-2-methyl-1H-pyrrolo[2,3-c]-pyridine-3-carbonyl)piperidine-1-carboxylate

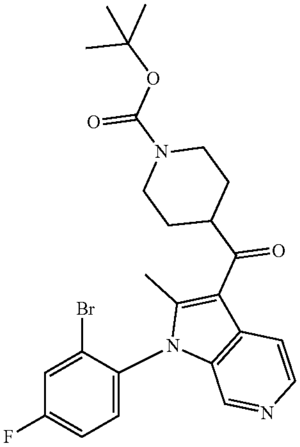 [SMILES: Cc1c(C(=O)C2CCN(C(=O)OC(C)(C)C)CC2)c2ccncc2n1-c1ccc(F)cc1Br]

CuO (144 mg, 1.81 mmol) was added to a deoxygenated mixture of Intermediate 84 (1.95 g, 7.23 mmol), Intermediate 85 (1.25 g, 3.61 mmol) and $Cs_2CO_3$ (589 mg, 1.81 mmol) in DMSO (20 mL). The resulting mixture was purged with $N_2$ for additional 10 minutes and was stirred at 80° C. for 48 h. The mixture was diluted with EtOAc and washed with water and brine. The organic layer was dried over $Na_2SO_4$, filtered, and concentrated under reduced pressure. The residue was purified by straight phase flash chromatography on silica (gradient: 0-10% MeOH in DCM) to give the title compound (514 mg, 28%) as a brown solid; MS m/z (ES+) $[M+H]^+$=516.0/518.0; $^1H$ NMR (400 MHz, DMSO-$d_6$, 22° C.) δ 1.35-1.47 (9H, m), 1.47-1.62 (2H, m), 1.87 (2H, d), 2.47 (3H, s), 3.03 (2H, br s), 3.42-3.54 (1H, m), 4.00 (2H, d), 7.54-7.66 (1H, m), 7.83 (1H, dd), 7.95 (1H, d), 8.02 (1H, dd), 8.20 (1H, s), 8.38 (1H, d).

Intermediate 87 (Mixture of Atropisomers): tert-Butyl 4-(1-(4-fluoro-2-(4-isopropylpyridin-3-yl)phenyl)-2-methyl-1H-pyrrolo[2,3-c]pyridine-3-carbonyl)piperidine-1-carboxylate

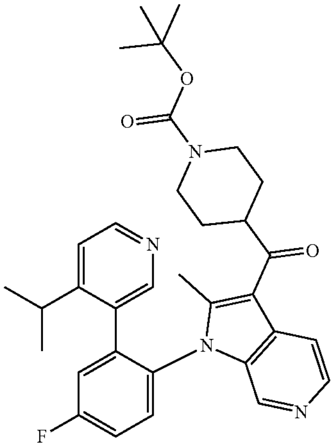 [SMILES: Cc1c(C(=O)C2CCN(C(=O)OC(C)(C)C)CC2)c2ccncc2n1-c1ccc(F)cc1-c1cnccc1C(C)C]

$Pd(dppf)Cl_2$ (31.9 mg, 0.04 mmol) was added to a deoxygenated solution of Intermediate 86 (225 mg, 0.44 mmol), Intermediate 121 (108 mg, 0.44 mmol, th.) and aq. $K_2CO_3$ (440 μL, 0.88 mmol, 2 M) in 1,4-dioxane (2.3 mL) under $N_2$. The resulting mixture was stirred at 100° C. for 1.5 h. The reaction mixture concentrated in the presence of silica and purified by straight phase flash chromatography on silica (gradient: 0-100% EtOAc in heptane) to give the title compound (70.0 mg, 29%) as a yellow oil; MS m/z (ES+) $[M+H]^+$=557.2.

Intermediate 88 (Mixture of Atropisomers): (1-(4-Fluoro-2-(4-isopropylpyridin-3-yl)phenyl)-2-methyl-1H-pyrrolo[2,3-c]pyridin-3-yl)(piperidin-4-yl)methanone

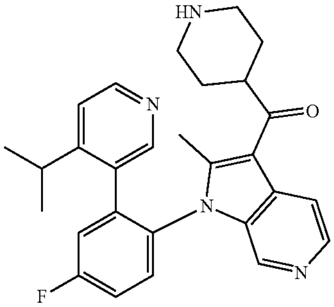 [SMILES: Cc1c(C(=O)C2CCNCC2)c2ccncc2n1-c1ccc(F)cc1-c1cnccc1C(C)C]

TFA (414 L) was added to a solution of Intermediate 87 (70.0 mg, 0.13 mmol) in DCM (1 mL). The resulting mixture was stirred at rt for 1 h. The mixture was quenched with sat. aq. $NaHCO_3$ (50 mL) and extracted with EtOAc (3×50 mL). The combined organic layers were dried over $Na_2SO_4$, filtered, and concentrated under reduced pressure to give the title compound (50.6 mg, 88%) as an off-white solid; MS m/z (ES+) $[M+H]^+$=457.2.

Intermediate 89: 5-Fluoro-2-iodo-N,N-diisopropylbenzamide

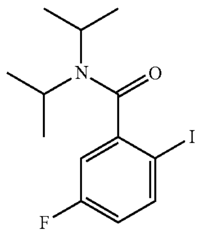 [SMILES: CC(C)N(C(=O)c1cc(F)ccc1I)C(C)C]

T3P (198 mL, 338 mmol, 50% in DCM) was added to a stirred solution of 5-fluoro-2-iodobenzoic acid (75.0 g, 282 mmol) and diisopropylamine (199 mL, 1.41 mol) in DCM (450 mL). The resulting mixture was stirred at rt overnight. The reaction mixture was washed sequentially with sat. aq. $NaHCO_3$ and brine. The organic layer was dried over $Na_2SO_4$, filtered, and concentrated under reduced pressure. The residue was dissolved in EtOAc, filtered through a short plug of silica and rinsed with EtOAc. The filtrate was concentrated under reduced pressure to give the crude title compound (40.0 g) as a beige solid. The silica plug was rinsed with DCM:MeOH (3:1) and the filtrate was concentrated under reduced pressure to give the crude title compound (63.0 g) as a brown solid; MS m/z (ES+) $[M+H]^+$ =350.0; $^1H$ NMR (400 MHz, DMSO-$d_6$, 22° C.) δ 1.06 (3H, d), 1.21 (3H, d), 1.46 (6H, t), 3.41 (1H, p), 3.57 (1H, p), 7.03 (1H, td), 7.20 (1H, dd), 7.87 (1H, dd).

Intermediate 90: 2-((4-Bromopyridin-3-yl)amino)-5-fluoro-N,N-diisopropylbenzamide

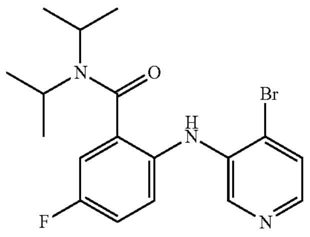 [SMILES: CC(C)N(C(=O)c1cc(F)ccc1Nc1cnccc1Br)C(C)C]

$Pd_2dba_3 \cdot CHCl_3$ (5.34 g, 10.3 mmol) was added to a deoxygenated mixture of Intermediate 89 (36.0 g, 103 mmol, th.), 4-bromopyridin-3-amine (21.4 g, 124 mmol), XantPhos (5.97 g, 10.3 mmol) and $Cs_2CO_3$ (101 g, 309 mmol) in 2-MeTHF (360 mL). The mixture was purged with $N_2$ for additional 5 minutes and stirred at 80° C. overnight. The reaction mixture was filtered over Celite® and the Celite was rinsed with EtOAc. The filtrate was concentrated under reduced pressure. The residue was purified by straight phase flash chromatography on silica (gradient: 0-100% EtOAc in heptane). Appropriate fractions were combined and concentrated under reduced pressure. The residue was dissolved in DCM and washed sequentially with aq. N-acetyl-cysteine (2%) and brine. The organic layer was dried over $Na_2SO_4$, filtered, and concentrated under reduced pressure to give the title compound (23.6 g, 58%) as a yellow solid; MS m/z (ES+) $[M+H]^+$=394.0/396.0; $^1H$ NMR (400 MHz, DMSO-$d_6$, 22° C.) δ 0.80-1.50 (12H, m), 3.67 (2H, s), 7.00 (1H, s), 7.19 (1H, dd), 7.26 (1H, td), 7.35 (1H, dd), 7.62 (1H, d), 7.88 (1H, d), 8.06 (1H, s).

Intermediate 91 (Mixture of Atropisomers): tert-Butyl 4-(1-(2-(diisopropylcarbamoyl)-4-fluorophenyl)-2-methyl-1H-pyrrolo[2,3-c]pyridine-3-carbonyl)piperidine-1-carboxylate

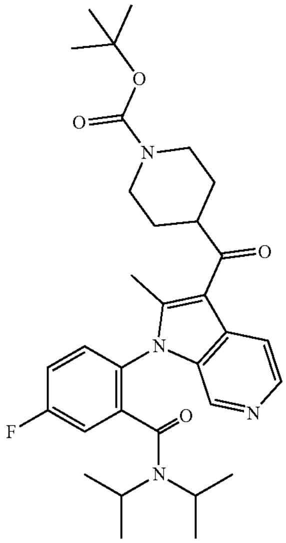 [SMILES: Cc1c(C(=O)C2CCN(C(=O)OC(C)(C)C)CC2)c2ccncc2n1-c1ccc(F)cc1C(=O)N(C(C)C)C(C)C]

CuO (171 mg, 2.16 mmol) was added to a deoxygenated mixture of Intermediate 84 (1.37 g, 5.07 mmol), Intermediate 90 (1.00 g, 2.54 mmol) and $Cs_2CO_3$ (1.16 g, 3.55 mmol) in DMSO (18 mL). The resulting mixture was purged with $N_2$ for additional 10 minutes and was stirred at 110° C. for 6 h. Above procedure was carried out 16 times. The reaction mixtures were combined, diluted with EtOAc (500 mL) and water (500 mL) and filtered. The organic layer of the filtrate was separated and washed with water (300 mL) and brine (500 mL). The organic layer was dried over $Na_2SO_4$, filtered, and concentrated under reduced pressure. The residue was purified by straight phase flash chromatography on silica (gradient: 20-100% EtOAc in heptane) to give the title compound (17.9 g, 78%) as a brown foam; MS m/z (ES+) $[M+H]^+$=565.3; $^1H$ NMR (400 MHz, DMSO-$d_6$, 27° C.) δ 0.41 (3H, br s), 0.53-0.77 (3H, m), 0.98-1.13 (3H, m), 1.26 (3H, d), 1.41 (11H, s), 1.73-1.89 (2H, m), 3.02 (2H, br s), 3.13-3.27 (1H, m), 3.38-3.54 (1H, m), 3.68 (1H, br s), 3.87-4.01 (2H, m), 7.16-9.27 (6H, m).

Intermediate 92 (Mixture of Atropisomers): 5-Fluoro-N,N-diisopropyl-2-(2-methyl-3-(piperidine-4-carbonyl)-1H-pyrrolo[2,3-c]pyridin-1-yl) benzamide

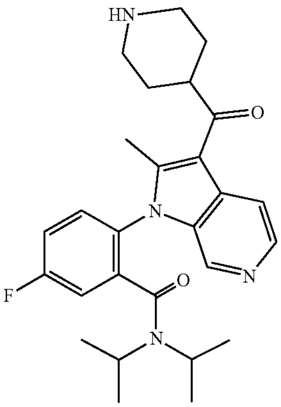 [SMILES: Cc1c(C(=O)C2CCNCC2)c2ccncc2n1-c1ccc(F)cc1C(=O)N(C(C)C)C(C)C]

TFA (25 mL) was added to a solution of Intermediate 91 (17.0 g, 30.2 mmol) in DCM (95 mL). The resulting mixture was stirred at rt for 4 h. The mixture was diluted with DCM (400 mL) and quenched with sat. aq. $NaHCO_3$ (200 mL). The organic layer was separated, and the water layer extracted with DCM (200 mL). The combined organic layers were washed with brine (200 mL), dried over $Na_2SO_4$, filtered, and concentrated under reduced pressure to give the crude title compound in a quantitative yield (14.9 g) as a beige foam; MS m/z (ES+) $[M+H]^+$=465.3; $^1$H NMR (400 MHz, DMSO-$d_6$, 22° C.) δ 0.41 (3H, d), 0.50-0.75 (3H, m), 0.95-1.17 (3H, m), 1.26 (3H, d), 1.57-1.83 (2H, m), 1.90 (2H, br s), 2.94-3.11 (2H, m), 3.12-3.26 (3H, m), 3.43-3.58 (2H, m), 3.61-3.78 (1H, m), 7.46-7.63 (2H, m), 7.65-7.79 (1H, m), 7.83-8.00 (1H, m), 8.32 (2H, s).

Intermediate 93: (R)-1,1,1-Trifluoro-N-isopropylpropan-2-amine hydrochloride

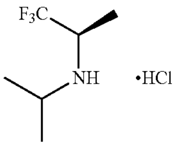

A mixture of (R)-1,1,1-trifluoropropan-2-amine (5.00 g, 44.2 mmol) and dry acetone (6.55 mL, 88.4 mmol) in a mixture of dry DCM (30 mL) and acetic acid (2 mL) was stirred at rt for 2 h in the presence of molecular sieves (3 Å). $NaBH_4$ (3.35 g, 88.4 mmol) was added and stirred at rt overnight. The mixture was filtered through Celite® and 4 M HCl in 1,4-dioxane (15 mL) was added to the filtrate. The solvents were concentrated to dryness and the residue partitioned between $Et_2O$ (150 mL) and aq. NaOH (150 mL, 1 M). The organic layer was washed with brine, dried over $Na_2SO_4$, filtered, treated with 4 M HCl in 1,4-dioxane (15 mL) and concentrated under reduced pressure. The product was lyophilized from 1,4-dioxane/$H_2O$ to give the title compound (6.15 g, 73%) as a white solid; MS m/z (ES+) $[M+H]^+$=156.1; $^1$H NMR (400 MHz, MeOD, 22° C.) δ 1.38 (3H, d), 1.43 (3H, d), 1.55 (3H, d), 3.64 (1H, hept), 4.37 (1H, hept).

Intermediate 94: (R)-5-Fluoro-2-iodo-N-isopropyl-N-(1,1,1-trifluoropropan-2-yl)benzamide

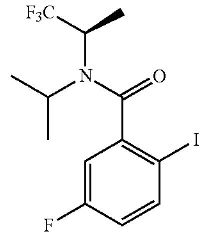 [SMILES: CC(C)N(C(=O)c1cc(F)ccc1I)[C@H](C)C(F)(F)F]

$SOCl_2$ (3.93 mL, 54.1 mmol) was added to 5-fluoro-2-iodobenzoic acid (600 mg, 2.26 mmol) in a sealed microwave tube. The resulting mixture was stirred at 70° C. for 2 h. The reaction mixture was concentrated under reduced pressure to yield the acyl chloride. A solution of Intermediate 93 (1.08 g, 5.64 mmol) in toluene (15 mL) was washed with aq. NaOH (4 mL, 2 M). The organic layer was dried over $Na_2SO_4$, filtered, and added to a cooled solution of the acyl chloride at 0° C. After addition was complete, the mixture was stirred at 80° C. overnight. The reaction mixture was concentrated under reduced pressure. The residue was taken up in DCM (20 mL) and sat. aq. $NaHCO_3$ (15 mL). The aqueous layer was extracted with DCM (3×10 mL). The combined organic layers were passed through a phase separator and concentrated under reduced pressure. The residue was purified by straight phase flash chromatography on silica (gradient: 0-20% EtOAc in heptane) to give the title compound (468 mg, 52%) as a yellow solid; MS m/z (ES+) $[M+H]^+$=404.0; $^1$H NMR (400 MHz, $CDCl_3$, 22° C.) δ 1.05-1.85 (9H, m), 3.61-3.78 (1H, m), 3.81-4.04 (1H, m), 6.77-7.02 (2H, m), 7.69-7.88 (1H, m).

Intermediate 95: (R)-2-((4-Bromopyridin-3-yl) amino)-5-fluoro-N-isopropyl-N-(1,1,1-trifluoropropan-2-yl)benzamide

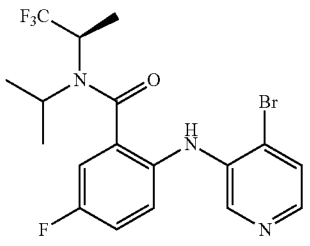 [SMILES: CC(C)N(C(=O)c1cc(F)ccc1Nc1cnccc1Br)[C@H](C)C(F)(F)F]

$Pd_2dba_3{\cdot}CHCl_3$ (120 mg, 0.12 mmol) was added to a deoxygenated mixture of Intermediate 94 (468 mg, 1.16 mmol), 4-bromopyridin-3-amine (603 mg, 3.48 mmol), XantPhos (134 mg, 0.23 mmol) and NaOtBu (335 mg, 3.48 mmol) in dry 1,4-dioxane (7 mL). The mixture was purged with $N_2$ and stirred at 80° C. for 6 h. The reaction mixture was filtered over Celite® and the filtrate was concentrated under reduced pressure. The residue was purified by straight phase flash chromatography on silica (gradient: 0-100%

EtOAc in heptane) to give the title compound (320 mg, 62%) as a light brown oil; MS m/z (ES+) $[M+H]^+$=448.0/450.0; $^1$H NMR (400 MHz, $CDCl_3$, 22° C.) δ 1.01-1.31 (3H, m), 1.34-1.59 (6H, m), 3.50-4.49 (2H, m), 6.15-7.05 (2H, m), 7.10 (1H, td), 7.34-7.42 (1H, m), 7.46 (1H, d), 7.94 (1H, d), 8.33 (1H, br s).

Intermediate 96 (Mixture of Atropisomers): tert-Butyl (R)-4-(1-(4-fluoro-2-(isopropyl(1,1,1-trifluoropropan-2-yl)carbamoyl)phenyl)-2-methyl-1H-pyrrolo[2,3-c]pyridine-3-carbonyl)-piperidine-1-carboxylate

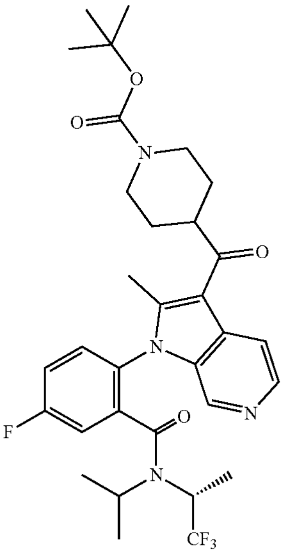 [SMILES: Cc1c(C(=O)C2CCN(C(=O)OC(C)(C)C)CC2)c2ccncc2n1-c1ccc(F)cc1C(=O)N(C(C)C)[C@H](C)C(F)(F)F]

CuO (46.8 mg, 0.59 mmol) was added to a deoxygenated mixture of Intermediate 84 (559 mg, 2.07 mmol), Intermediate 95 (310 mg, 0.69 mmol) and $Cs_2CO_3$ (315 mg, 0.97 mmol) in DMSO (5 mL). The resulting mixture was purged with $N_2$ and stirred at 110° C. for 18 h. The mixture was diluted with EtOAc (50 mL) and washed with water (25 mL). The organic layer was passed through a phase separator and concentrated under reduced pressure. The residue was purified by straight phase flash chromatography on silica (gradient: 0-100% EtOAc in heptane) to give the title compound (280 mg, 65%) as a yellow oil; MS m/z (ES+) $[M+H]^+$=619.6; $^1$H NMR (400 MHz, $CDCl_3$, 22° C.) δ 0.39-0.49 (1H, m), 0.59 (1H, d), 0.72 (1H, d), 0.83-1.19 (3H, m), 1.33-1.54 (11H, m), 1.65-2.01 (4H, m), 2.57-2.66 (2H, m), 2.88-3.11 (2H, m), 3.16-3.52 (3H, m), 3.70-3.99 (2H, m), 4.12-4.30 (2H, m), 7.06-7.23 (1H, m), 7.27-7.50 (2H, m), 7.73-7.91 (1H, m), 8.11-8.35 (1H, m), 8.35-8.56 (1H, m).

Intermediate 97 (Mixture of Atropisomers): (R)-5-Fluoro-N-isopropyl-2-(2-methyl-3-(piperidine-4-carbonyl)-1H-pyrrolo[2,3-c]pyridin-1-yl)-N-(1,1,1-trifluoropropan-2-yl)-benzamide hydrochloride

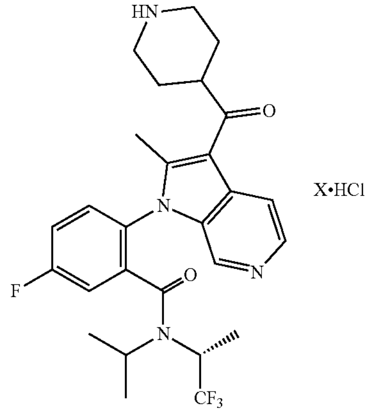

X•HCl

4 M HCl in 1,4-dioxane (1 mL) was added to a solution of Intermediate 96 (266 mg, 0.43 mmol) in MeCN (5 mL). The resulting mixture was stirred at rt for 1.5 h. The reaction mixture was concentrated under reduced pressure to give the crude title compound (239 mg); MS m/z (ES+) $[M+H]^+$= 519.2.

Intermediate 98: ((3R,5R)-3,5-Dimethylmorpholino)(5-fluoro-2-iodophenyl)methanone

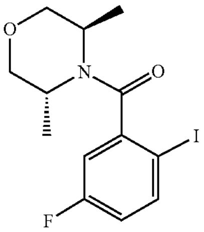 [SMILES: C[C@@H]1COC[C@@H](C)N1C(=O)c1cc(F)ccc1I]

T3P (91.0 mL, 152 mmol, 50% in DCM) was added to a stirred solution of 5-fluoro-2-iodobenzoic acid (27.0 g, 102 mmol), (3R,5R)-3,5-dimethylmorpholine hydrochloride (18.5 g, 122 mmol) and DIPEA (70.7 mL, 122 mmol) in DCM (360 mL) at 0° C. The resulting mixture was stirred at rt overnight. The reaction mixture was washed with 50% sat. aq. $NaHCO_3$ (2×360 mL) and brine (180 mL). The organic layer was dried over $Na_2SO_4$, filtered, and concentrated under reduced pressure. The residue was dissolved in DCM, filtered through silica and the silica was washed with heptane:EtOAc (1:1, 2×1 L). The filtrate was concentrated under reduced pressure. The residue was taken up in EtOAc (150 mL) and washed sequentially with sat. aq. $NaHCO_3$ (2×150 mL) and brine (100 mL). The organic layer was dried over $Na_2SO_4$, filtered, and concentrated under reduced pressure to give the title compound (27.7 g, 75%); MS m/z (ES+) $[M+H]^+$=364.0; $^1$H NMR (400 MHz, $CDCl_3$, 22° C.) δ 1.06-1.38 (3H, m), 1.57-1.63 (3H, m), 3.45 (1H, br s), 3.60 (2H, d), 3.76-4.39 (3H, m), 6.85 (1H, td), 6.93-7.12 (1H, m), 7.62-7.85 (1H, m).

Intermediate 99: (2-((4-Bromopyridin-3-yl)amino)-5-fluorophenyl)((3R,5R)-3,5-dimethyl-morpholino) methanone

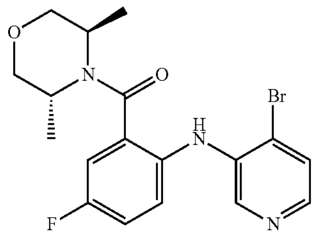 [SMILES: C[C@@H]1COC[C@@H](C)N1C(=O)c1cc(F)ccc1Nc1cnccc1Br]

$Pd_2dba_3 \cdot CHCl_3$ (2.00 g, 1.93 mmol) was added to a deoxygenated mixture of Intermediate 98 (14.0 g, 38.6 mmol), 4-bromopyridin-3-amine (8.00 g, 46.3 mmol), Xant-Phos (2.23 g, 3.85 mmol) and $Cs_2CO_3$ (37.7 g, 116 mmol) in 2-MeTHF (128 mL). The mixture was purged with $N_2$ for additional 5 minutes and stirred at 80° C. overnight. The reaction mixture was diluted with EtOAc, filtered over Celite® and the Celite was rinsed with EtOAc. The filtrate was washed with water and brine. The organic layer was dried over $Na_2SO_4$, filtered, and concentrated under reduced pressure. The residue was purified by straight phase flash chromatography on silica (gradient: 5-50% EtOAc in heptane) to give the title compound (10.1 g, 64%) as a yellow gum; MS m/z (ES+) $[M+H]^+$=408.0/410.0; $^1H$ NMR (400 MHz, DMSO-$d_6$, 22° C.) δ 0.96 (6H, d), 3.22-3.33 (2H, m), 3.61-3.74 (2H, m), 3.79 (2H, dd), 7.20-7.40 (3H, m), 7.53 (1H, s), 7.62 (1H, d), 7.89 (1H, d), 7.99 (1H, s).

Intermediate 100 (Mixture of Atropisomers): tert-Butyl 4-(1-(2-((3R,5R)-3,5-dimethyl-morpholine-4-carbonyl)-4-fluorophenyl)-2-methyl-1H-pyrrolo[2,3-c]pyridine-3-carbonyl)-piperidine-1-carboxylate

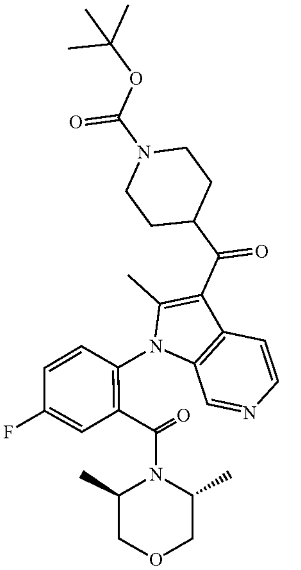 [SMILES: Cc1c(C(=O)C2CCN(C(=O)OC(C)(C)C)CC2)c2ccncc2n1-c1ccc(F)cc1C(=O)N1[C@H](C)COC[C@H]1C]

CuO (103 mg, 1.29 mmol) was added to a deoxygenated mixture of Intermediate 84 (818 mg, 3.04 mmol), Intermediate 99 (620 mg, 1.52 mmol) and $Cs_2CO_3$ (692 mg, 2.13 mmol) in DMSO (19 mL). The resulting mixture was purged with $N_2$ for 5 minutes and was stirred at 90° C. overnight. Above procedure was carried out 5 times. The reaction mixtures were combined, diluted with EtOAc and washed with water. The organic layer was dried over $Na_2SO_4$, filtered, and concentrated under reduced pressure. The residue was purified by straight phase flash chromatography on silica (gradient: 0-100% EtOAc in heptane) to give the title compound (2.10 g, 48%) as a brown solid; MS m/z (ES+) $[M+H]^+$=579.3; $^1H$ NMR (400 MHz, DMSO-$d_6$, 22° C.) δ 0.57 (2H, br s), 0.87-1.2 (3H, m), 1.20-1.29 (1H, m), 1.42 (9H, s), 1.45-1.65 (2H, m), 1.75-1.93 (2H, m), 2.05-2.35 (1H, m), 2.41 (2H, s), 2.56 (1H, s), 2.80-3.23 (4H, m), 3.35-3.73 (4H, m), 3.82-4.07 (2H, m), 7.58-7.68 (1H, m), 7.69-7.74 (1H, m), 7.75-7.84 (1H, m), 7.88-8.07 (1H, m), 8.08-8.85 (2H, m).

Intermediate 101 (Mixture of Atropisomers): (1-(2-((3R,5R)-3,5-Dimethylmorpholine-4-carbonyl)-4-fluorophenyl)-2-methyl-1H-pyrrolo[2,3-c]pyridin-3-yl)(piperidin-4-yl)methanone hydrochloride

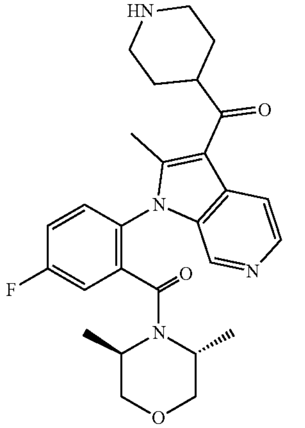

X•HCl

4 M HCl in 1,4-dioxane (8.15 mL) was added to a solution of Intermediate 100 (1.89 g, 3.26 mmol) in MeCN (40 mL). The resulting mixture was stirred at rt for 1.5 h. The mixture was concentrated under reduced pressure to give the crude title compound (1.68 g) as a brown solid; MS m/z (ES+) $[M+H]^+$=479.2; $^1H$ NMR (400 MHz, DMSO-$d_6$, 22° C.) δ 0.32-0.79 (2H, m), 0.80-1.37 (3H, m), 1.59-2.21 (5H, m), 2.54 (2H, s), 2.64-2.96 (2H, m), 3.10-3.39 (5H, m), 3.41-3.49 (1H, m), 3.61-3.92 (4H, m), 7.63-7.76 (1H, m), 7.76-7.83 (1H, m), 7.83-7.93 (1H, m), 8.26-8.94 (2H, m), 8.95-9.17 (1H, m), 9.25-9.48 (1H, m).

Intermediate 102: Methyl (1r,4r)-4-(methylsulfonamido)cyclohexane-1-carboxylate

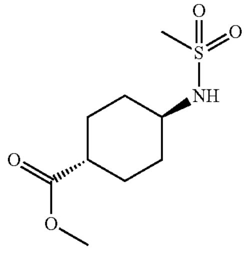

Methanesulfonic anhydride (36.6 g, 210 mmol) was added to methyl (1r,4r)-4-aminocyclohexane-1-carboxylate (22.0 g, 140 mmol) and $Et_3N$ (39.0 mL, 280 mmol) in DCM (300 mL) cooled to 0° C. under $N_2$. The resulting mixture was stirred at rt for 2 h. The reaction mixture was poured into sat. aq. $NH_4Cl$ (300 mL) and extracted with DCM (3×150 mL). The combined organic layers were dried over $Na_2SO_4$, filtered, and concentrated to dryness. The residue was purified by straight phase flash chromatography on silica (gradient: 0-40% EtOAc in DCM) to give the title compound (30.0 g, 91%) as a white solid; $^1H$ NMR (300 MHz, $CDCl_3$, 24° C.) δ 1.22-1.37 (2H, m), 1.46-1.61 (2H, m), 2.00-2.30 (5H, m), 2.98 (3H, s), 3.20-3.33 (1H, m), 3.67 (3H, s), 4.67 (1H, d).

Intermediate 103: N-((1r,4r)-4-(Hydroxymethyl) cyclohexyl)methanesulfonamide

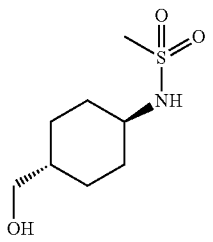

$BH_3$·THF (127 mL, 128 mmol, 1 M) was added to Intermediate 102 (15.0 g, 63.8 mmol) in THF (150 mL) cooled to 0° C. under $N_2$. The resulting mixture was stirred at rt for 1 h. The reaction mixture was added slowly to sat. aq. $NaHCO_3$ (200 mL) and extracted with DCM (5×100 mL). The combined organic layers were dried over $Na_2SO_4$, filtered, and concentrated to dryness to give the title compound (11.0 g, 83%) as a white solid; $^1H$ NMR (300 MHz, $CDCl_3$, 25° C.) δ 0.97-1.15 (2H, m), 1.18-1.35 (2H, m), 1.37-1.54 (1H, m), 1.81-1.90 (2H, m), 1.93 (1H, s), 2.02-2.20 (2H, m), 2.98 (3H, s), 3.15-3.32 (1H, m), 3.38-3.53 (2H, m), 4.73 (1H, d).

Intermediate 104: ((1r,4r)-4-(Methylsulfonamido)cyclohexyl)methyl 4-methylbenzenesulfonate

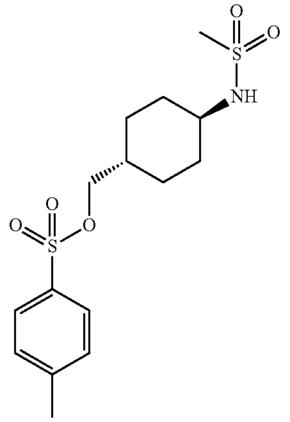 [SMILES: Cc1ccc(S(=O)(=O)OC[C@H]2CC[C@H](NS(C)(=O)=O)CC2)cc1]

DMAP (660 mg, 5.40 mmol) was added to a cooled mixture of Intermediate 103 (11.2 g, 54.0 mmol), TsCl (15.5 g, 81.1 mmol) and $Et_3N$ (22.6 mL, 162 mmol) in DCM (200 mL) at 0° C. under $N_2$. The resulting mixture was stirred at rt for 6 h. The solvent was removed under reduced pressure. The residue was purified by straight phase flash chromatography on silica (gradient: 0-60% EtOAc in petroleum ether) to give the title compound (19.0 g, 97%) as a white solid; MS m/z (ES+) $[M+Na]^+$=384.2; $^1H$ NMR (300 MHz, $CDCl_3$, 25° C.) δ 0.98-1.31 (4H, m), 1.57-1.71 (1H, m), 1.76-1.85 (2H, m), 2.04-2.12 (2H, m), 2.47 (3H, s), 2.97 (3H, s), 3.15-3.29 (1H, m), 3.83 (2H, d), 4.35 (1H, d), 7.34-7.40 (2H, m), 7.75-7.83 (2H, m).

Intermediate 105: 2-(tert-Butyl) 3-ethyl (1S,3S,4S,5S)-5-fluoro-2-azabicyclo[2.2.1]heptane-2,3-dicarboxylate

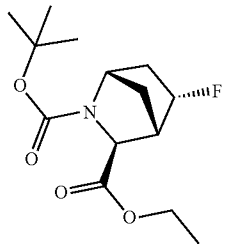 [SMILES: CCOC(=O)[C@@H]1[C@@H]2C[C@@H](C[C@@H]2F)N1C(=O)OC(C)(C)C]

DAST (56.5 mg, 0.35 mmol) was added to a mixture of 2-(tert-butyl) 3-ethyl (1S,3S,4S)-5-hydroxy-2-azabicyclo[2.2.1]heptane-2,3-dicarboxylate and 2-(tert-butyl) 3-ethyl (1S,3S,4R)-6-hydroxy-2-azabicyclo[2.2.1]heptane-2,3-dicarboxylate [synthesis described in US 20200157114 A1] (100 mg, 0.35 mmol) in DCM (1 mL) at 0° C. The mixture was stirred at rt overnight. The reaction mixture was quenched with sat. aq. $NaHCO_3$ (50 mL) and extracted with EtOAc (3×50 mL). The combined organic layers were dried over $Na_2SO_4$, filtered, and concentrated under reduced pressure. The residue was purified by straight phase flash chromatography on silica (gradient: 0-50% EtOAc in heptane) to give the title compound (60.0 mg, 60%) as a yellow oil as first eluting product; MS m/z (ES+) $[M+H-tBu]^+$=232.1; $^1H$ NMR (400 MHz, DMSO-$d_6$, 22° C.) δ 1.16-1.23 (3H, m), 1.27-1.43 (9H, m), 1.46-1.55 (1H, m), 1.56-1.73 (1H, m), 1.73-1.86 (1H, m), 1.88-2.17 (1H, m), 2.64-2.79 (1H, m), 3.61 (1H, d), 4.03-4.27 (3H, m), 4.55-4.84 (1H, m); and the undesired fluorinated isomer as second eluting product (33.0 mg, 33%).

Intermediate 106: (1S,3S,4S,5S)-2-(tert-Butoxycarbonyl)-5-fluoro-2-azabicyclo[2.2.1]heptane-3-carboxylic acid

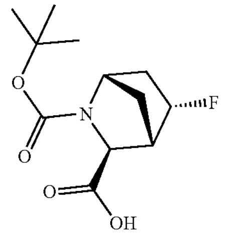 [SMILES: CC(C)(C)OC(=O)N1[C@H]2C[C@@H]([C@H]1C(=O)O)[C@@H](F)C2]

Aq. NaOH (940 μL, 0.94 mmol, 1 M) was added to a solution of Intermediate 105 (60.0 mg, 0.21 mmol) in 1,4-dioxane (2 mL). The mixture was stirred at rt for 1 h. The reaction mixture was acidified with aq. HCl (1 M, 10 mL) and extracted with EtOAc (3×20 mL). The combined organic layers were dried over $Na_2SO_4$, filtered, and concentrated under reduced pressure to give the title compound (41.0 mg, 76%) as a colorless gum; MS m/z (ES+) $[M+H-tBu]^+$=204.0.

Intermediate 107:
2-(Prop-1-en-2-yl)pyridin-3-amine

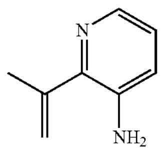

$Pd(dppf)Cl_2$ (2.85 g, 3.89 mmol) was added to 2-chloropyridin-3-amine (10.0 g, 77.8 mmol), isopropenylboronic acid pinacol ester (14.4 g, 85.6 mmol) and $K_2CO_3$ (32.3 g, 233 mmol) in a mixture of 1,4-dioxane (240 mL) and water (60 mL) under $N_2$. The resulting mixture was stirred at 80° C. for 16 h. The reaction mixture was poured into water (200 mL) and extracted with EtOAc (2×125 mL). The combined organic layers were dried over $Na_2SO_4$, filtered, and concentrated to dryness. The crude product was purified by straight phase flash chromatography on silica (gradient: 0-30% EtOAc in petroleum ether) to give the title compound (10.0 g, 96%) as a yellow oil; MS m/z (ES+) $[M+H]^+$=135.2; $^1H$ NMR (300 MHz, DMSO-$d_6$) δ 2.07 (3H, s), 5.03 (2H, s), 5.25-5.31 (1H, m), 5.35-5.45 (1H, m), 6.91-6.99 (1H, m), 7.05 (1H, dd), 7.79 (1H, dd).

Intermediate 108: 2-Isopropylpyridin-3-amine

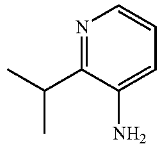

Pd/C (10.2 g, 9.61 mmol, 10%) was added to a mixture of Intermediate 107 (12.9 g, 96.1 mmol) in MeOH (500 mL). The mixture was stirred under hydrogen atmosphere at rt for 4 h. The reaction mixture was filtered through Celite®. The filtrate was concentrated under reduced pressure to give the title compound (12.0 g, 92%) as an orange liquid; MS m/z (ES+) $[M+H]^+$=137.3; $^1H$ NMR (300 MHz, DMSO-$d_6$, 24° C.) δ 1.15 (6H, d), 3.06-3.20 (1H, m), 5.02 (2H, s), 6.83-6.93 (2H, m), 7.74 (1H, dd).

Intermediate 109: 3-Bromo-2-isopropylpyridine

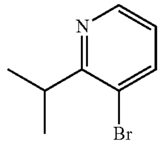

t-BuONO (3.49 mL, 29.4 mmol) was added to Intermediate 108 (2.00 g, 14.7 mmol) in MeOH (70 mL) under $N_2$. The mixture was stirred at rt for 30 minutes before $CuBr_2$ (3.28 g, 14.7 mmol) was added. The resulting mixture was stirred at rt for 16 h. The reaction mixture was quenched with sat. aq. $NaHCO_3$ (100 mL) and extracted with EtOAc (3×50 mL). The combined organic layers were dried over $Na_2SO_4$, filtered, and concentrated to dryness. The crude product was purified by straight phase flash chromatography on silica (gradient: 0-4% EtOAc in petroleum ether) to give the title compound (1.29 g, 44%) as a yellow liquid; MS m/z (ES+) $[M+H]^+$=200.0/202.0; $^1H$ NMR (300 MHz, $CDCl_3$, 23° C.) δ1.30 (6H, d), 3.58 (1H, hept), 7.00 (1H, dd), 7.82 (1H, dd), 8.52 (1H, dd).

Intermediate 110: 2-Isopropyl-3-(4,4,5,5-tetramethyl-1,3,2-dioxaborolan-2-yl)pyridine

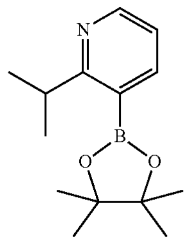 [SMILES: CC(C)c1ncccc1B1OC(C)(C)C(C)(C)O1]

n-BuLi (3.21 mL, 8.04 mmol, 2.5 M in hexane) was added dropwise to a mixture of Intermediate 109 (1.34 g, 6.70 mmol) and isopropyl pinacol borate (1.64 mL, 8.04 mmol) in THF (23 mL) cooled to −78° C. over a period of 5 minutes under $N_2$. The resulting mixture was stirred at −78° C. for 1 h followed by stirring at rt for 1 h. The reaction mixture was poured into brine (50 mL) and extracted with EtOAc (4×75 mL). The combined organic layers were dried over $MgSO_4$, filtered, and concentrated to dryness. The crude product was purified by straight phase flash chromatography on silica (gradient: 0-40% EtOAc in petroleum ether) to give the title compound (1.20 g, 73%) as a yellow oil; MS m/z (ES+) $[M+H]^+$=248.1.

Intermediate 111:
3-(Prop-1-en-2-yl)pyridin-4-amine

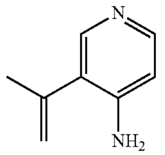

$Pd(dppf)Cl_2$ (4.23 g, 5.78 mmol) was added to 3-bromopyridin-4-amine (10.0 g, 57.8 mmol), isopropenylboronic acid pinacol ester (9.71 g, 57.8 mmol) and $K_2CO_3$ (24.0 g, 173 mmol) in a mixture of 1,4-dioxane (200 mL) and water (50 mL) under $N_2$. The resulting mixture was stirred at 90° C. for 16 h. The reaction mixture was concentrated under reduced pressure. The residue was diluted with EtOAc (1 L) and washed with water (2×500 mL). The organic layer was dried over $Na_2SO_4$, filtered, and concentrated to dryness. The crude product was purified by straight phase flash chromatography on silica (gradient: 0-50% EtOAc in DCM) to give the title compound (5.00 g, 65%) as a black oil; MS m/z (ES+) $[M+H]^+$=135.2; $^1$H NMR (300 MHz, $CDCl_3$, 24° C.) δ 2.01 (3H, s), 4.90-5.08 (1H, m), 5.19-5.38 (1H, m), 5.72 (2H, s), 6.61 (1H, s), 8.01 (2H, br s).

Intermediate 112: 3-Isopropylpyridin-4-amine

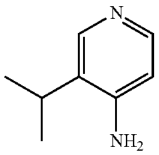

Pd/C (3.97 g, 3.73 mmol, 10%) was added to a mixture of Intermediate 111 (5.00 g, 37.3 mmol) in MeOH (100 mL). The mixture was stirred under hydrogen atmosphere at rt for 16 h. The reaction mixture was filtered through Celite® and the filtrate was concentrated under reduced pressure to give the title compound (5.00 g, 99%) as a grey oil; MS m/z (ES+) $[M+H]^+$=137.1; $^1$H NMR (300 MHz, $CDCl_3$, 24° C.) δ 1.30 (6H, d), 2.84 (1H, hept), 4.30 (2H, s), 6.50 (1H, d), 8.08 (1H, d), 8.19 (1H, s).

Intermediate 113: 4-Bromo-3-isopropylpyridine

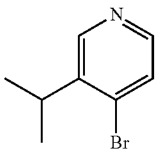

t-BuONO (5.40 mL, 45.0 mmol) was added to Intermediate 112 (4.09 g, 30.0 mmol) in MeOH (100 mL) under $N_2$. The mixture was stirred at rt for 10 minutes before $CuBr_2$ (7.37 g, 33.0 mmol) was added. The resulting mixture was stirred at rt for 16 h. The reaction mixture was poured into sat. aq. $NaHCO_3$ (200 mL) and extracted with EtOAc (3×150 mL). The combined organic layers were dried over $MgSO_4$, filtered, and concentrated to dryness. The crude product was purified by straight phase flash chromatography on silica (gradient: 0-20% EtOAc in petroleum ether) to give the title compound (1.00 g, 17%) as a pale yellow liquid; MS m/z (ES+) $[M+H]^+$=199.9/201.9; $^1$H NMR (400 MHz, $CDCl_3$, 0° C.) δ 1.34 (6H, d), 3.37 (1H, hept), 7.53 (1H, s), 7.88-8.97 (2H, m).

Intermediate 114: 3-Isopropyl-4-(4,4,5,5-tetramethyl-1,3,2-dioxaborolan-2-yl)pyridine

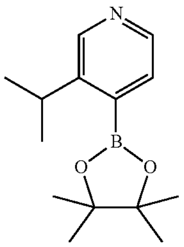 [SMILES: CC(C)c1cnccc1B1OC(C)(C)C(C)(C)O1]

n-BuLi (3.54 mL, 8.84 mmol, 2.5 M in hexane) was added dropwise to a mixture of Intermediate 113 (1.36 g, 6.80 mmol) and isopropyl pinacol borate (1.80 mL, 8.84 mmol) in THF (25 mL) at −78° C. under $N_2$. The resulting mixture was stirred at −78° C. for 1 h followed by stirring at rt for 2 h. The reaction mixture was poured into brine (50 mL) and extracted with EtOAc (4×75 mL). The combined organic layers were dried over $MgSO_4$, filtered, and concentrated to dryness. The crude product was purified by straight phase flash chromatography on silica (gradient: 0-40% EtOAc in petroleum ether) to give the title compound (500 mg, 30%) as a white solid; MS m/z (ES+) $[M+H]^+$=248.1; $^1$H NMR (400 MHz, $CDCl_3$, 0° C.) δ 1.31 (6H, d), 1.38 (12H, s), 3.58 (1H, hept), 7.56 (1H, d), 8.45 (1H, d), 8.61 (1H, s).

Intermediate 115: Methyl 4-((tert-butoxycarbonyl)(methyl)amino)butanoate

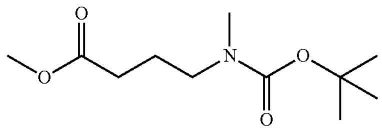 [SMILES: COC(=O)CCCN(C)C(=O)OC(C)(C)C]

$Boc_2O$ (27.5 g, 126 mmol) was added to a mixture of methyl 4-(methylamino)butanoate (15.0 g, 114 mmol) and DMAP (4.19 g, 34.3 mmol) in DCM (100 mL). The resulting mixture was stirred at rt for 1 h. The reaction mixture was diluted with DCM (50 mL) and washed with brine (3×100 mL). The organic layer was dried over $Na_2SO_4$, filtered, and concentrated to dryness to give the title compound (20.6 g, 78%) as a yellow oil; MS m/z (ES+) $[M+H]^+$=232.1.

Intermediate 116: tert-Butyl methyl(5-methyl-4-oxohexyl)carbamate

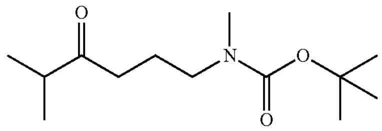 [SMILES: CC(C)C(=O)CCCN(C)C(=O)OC(C)(C)C]

Isopropylmagnesium chloride (130 mL, 259 mmol, 2 M in THF) was added dropwise to Intermediate 115 (20.0 g, 86.5 mmol) in THF (80 mL) at −78° C. under $N_2$. The resulting mixture was stirred at rt for 2 h. The reaction mixture was quenched with sat. aq. $NaHCO_3$ (100 mL) and extracted with DCM (3×100 mL). The combined organic layers were dried over $Na_2SO_4$, filtered, and concentrated to dryness. The crude product was purified by straight phase flash chromatography on silica (gradient: 0-20% EtOAc in petroleum ether) to give the title compound (5.00 g, 24%) as a yellow oil; MS m/z (ES+) $[M+H]^+$=244.1; $^1$H NMR (300 MHz, DMSO-$d_6$, 22° C.) δ 1.00 (6H, d), 1.39 (9H, s), 1.57-1.70 (2H, m), 2.44 (2H, t), 2.53-2.67 (1H, m), 2.74 (3H, s), 3.12 (2H, t).

Intermediate 117: rel-(1R,2R,5S)-3-(tert-Butoxycarbonyl)-3-azabicyclo[3.2.0]heptane-2-carboxylic acid

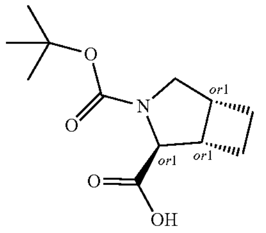 [SMILES: CC(C)(C)OC(=O)N1C[C@@H]2CC[C@@H]2[C@H]1C(=O)O]

$Boc_2O$ (170 mg, 0.78 mmol) was added to a mixture of rel-(1S,2S,5R)-3-azabicyclo[3.2.0]heptane-2-carboxylic acid (100 mg, 0.71 mmol) and sat. aq. $NaHCO_3$ (2 mL) in 1,4-dioxane (2 mL). The resulting mixture was stirred at rt overnight. The reaction mixture was acidified with aq. HCl (1 M, 20 mL) and extracted with DCM (3×20 mL). The combined organic layers were washed with brine, dried over $Na_2SO_4$, filtered, and concentrated under reduced pressure to give the title compound (171 mg, 100%) as a colorless gum; MS m/z ES+[M+H−tBu]$^+$186.1; $^1$H NMR (400 MHz, DMSO-$d_6$, 22° C.) δ 1.36-1.47 (9H, m), 1.60-1.84 (2H, m), 2.09-2.31 (2H, m), 2.83-3.00 (2H, m), 3.35-3.45 (2H, m), 4.09 (1H, d), 12.61 (1H, br s).

Intermediate 118: 4-(Prop-1-en-2-yl)pyridin-3-amine

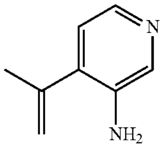

$Pd(dppf)Cl_2$ (4.27 g, 5.83 mmol) was added to a mixture of 4-chloropyridin-3-amine (15.0 g, 117 mmol), isopropenylboronic acid pinacol ester (21.6 g, 128 mmol) and $K_2CO_3$ (48.4 g, 350 mmol) in 1,4-dioxane (200 mL) and water (50 mL) under $N_2$. The resulting mixture was stirred at 80° C. for 16 h. The reaction mixture was poured into water (200 mL) and extracted with EtOAc (2×125 mL). The combined organic layers were dried over $Na_2SO_4$, filtered, and concentrated to dryness. The crude product was purified by straight phase flash chromatography on silica (gradient: 50-100% EtOAc in petroleum ether) to give the title compound (12.9 g, 82%) as a yellow oil; MS m/z (ES+) [M+H]$^+$=135.3.

Intermediate 119: 4-Isopropylpyridin-3-amine

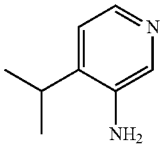

Pd/C (8.72 g, 8.20 mmol, 10%) was added to Intermediate 118 (11.0 g, 82.0 mmol) in MeOH (150 mL). The mixture was stirred under hydrogen atmosphere at rt for 16 h. The reaction mixture was filtered through Celite® and the filtrate was concentrated under reduced pressure to give the crude title compound (7.00 g) as a yellow oil; MS m/z (ES+) [M+H]$^+$=137.1; $^1$H NMR (300 MHz, $CDCl_3$, 25° C.) δ 1.28 (6H, d), 2.90 (1H, hept), 3.64 (2H, s), 7.05 (1H, d), 8.03 (1H, d), 8.06 (1H, s).

Intermediate 120: 3-Bromo-4-isopropylpyridine

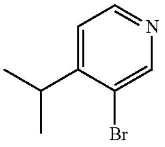

t-BuONO (6.60 mL, 55.1 mmol) was added dropwise to a mixture of Intermediate 119 (5.00 g, 36.7 mmol, th.) and $CuBr_2$ (7.90 g, 55.1 mmol) in MeCN (300 mL) at 0° C. under $N_2$. The resulting mixture was stirred at 60° C. for 16 h. The reaction mixture was filtered through Celite®, and the filtrate was concentrated under reduced pressure. The residue was purified by straight phase flash chromatography on silica (gradient: 0-30% EtOAc in petroleum ether) to give the title compound (1.50 g, 20%) as a yellow oil; MS m/z (ES+) [M+H]$^+$=200.0/202.0.

Intermediate 121: 4-Isopropyl-3-(4,4,5,5-tetramethyl-1,3,2-dioxaborolan-2-yl)pyridine

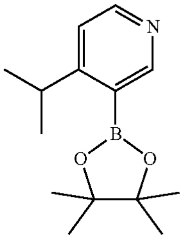 [SMILES: CC(C)c1ccncc1B1OC(C)(C)C(C)(C)O1]

n-BuLi (3.12 mL, 7.80 mmol, 2.5 M in hexane) was added dropwise to a mixture of Intermediate 120 (1.30 g, 6.50 mmol) and isopropyl pinacol borate (1.59 mL, 7.80 mmol) in THF (20 mL) at −78° C. under $N_2$. The resulting mixture was stirred at −78° C. for 1 h followed by stirring at rt for 1 h. The reaction mixture was poured into brine (25 mL) and extracted with EtOAc (3×50 mL). The combined organic layers were dried over $MgSO_4$, filtered, and concentrated to dryness to give the crude title compound (1.60 g) as an orange oil; MS m/z (ES+) [M+H]$^+$=248.1.

Intermediate 122: 4-Isopropyl-5-(4,4,5,5-tetramethyl-1,3,2-dioxaborolan-2-yl)thiazole

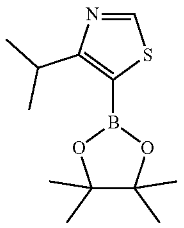 [SMILES: CC(C)c1ncsc1B1OC(C)(C)C(C)(C)O1]

n-BuLi (2.60 mL, 6.50 mmol, 2.5 M in hexane) was added dropwise to a mixture of 5-bromo-4-isopropylthiazole (1.03 g, 5.00 mmol) and isopropyl pinacol borate (1.43 mL, 7.00 mmol) in THF (20 mL) at −78° C. under $N_2$. The resulting mixture was stirred at −78° C. for 1 h followed by stirring at rt for 1 h. The reaction mixture was poured into brine (25 mL) and extracted with EtOAc (200 mL). The organic layer was dried over $MgSO_4$, filtered, and concentrated to dryness to give the title compound (1.03 g, 81%) as a pale yellow oil, which was used directly in the next step; MS m/z (ES+) $[M+H]^+$=254.1; $^1H$ NMR (400 MHz, $CDCl_3$) δ 1.32 (6H, d), 1.35 (12H, s), 3.63-3.79 (1H, m), 8.90 (1H, s).

Intermediate 123: 2-(3-Bromopyridin-2-yl)propan-2-ol

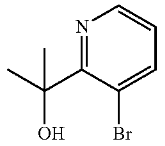

MeMgBr (4.63 mL, 13.9 mmol, 3 M in THF) was added to methyl 3-bromopicolinate (1.00 g, 4.63 mmol) in THF (25 mL) at −78° C. under $N_2$. The resulting mixture was stirred at −78° C. for 2 h. The reaction mixture was concentrated under reduced pressure. The residue was diluted with DCM (200 mL) and washed with sat. $NH_4Cl$ (3×75 mL). The organic layer was dried over $Na_2SO_4$, filtered, and concentrated to dryness. The crude product was purified by straight phase flash chromatography on silica (gradient: 0-3% EtOAc in petroleum ether) to give the title compound (830 mg, 83%) as a yellow solid; MS m/z (ES+) $[M+H]^+$=216.2/218.2.

Intermediate 124: 3-Bromo-2-(2-fluoropropan-2-yl)pyridine

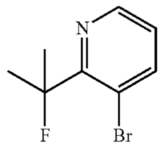

BAST (2.13 mL, 11.5 mmol) was added to Intermediate 123 (830 mg, 3.84 mmol) in DCM (25 mL) under $N_2$. The resulting mixture was stirred at rt for 2 h. The reaction mixture was concentrated under reduced pressure. The residue was diluted with DCM (200 mL) and washed with water (100 mL). The organic layer was dried over $Na_2SO_4$, filtered, and concentrated to dryness. The crude product was purified by straight phase flash chromatography on silica (gradient: 0-3% EtOAc in petroleum ether) to give the title compound (560 mg, 67%) as a yellow solid; MS m/z (ES+) $[M+H]^+$=217.9; $^1H$ NMR (300 MHz, DMSO-$d_6$, 26° C.) δ 1.73 (3H, s), 1.80 (3H, s), 7.32 (1H, dd), 8.12 (1H, dd), 8.53 (1H, d).

Intermediate 125: 2-(2-Fluoropropan-2-yl)-3-(4,4,5,5-tetramethyl-1,3,2-dioxaborolan-2-yl)-pyridine

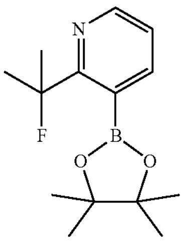 [SMILES: CC(C)(F)c1ncccc1B1OC(C)(C)C(C)(C)O1]

n-BuLi (1.23 mL, 3.08 mmol, 2.5 M in hexane) was added dropwise to a mixture of Intermediate 124 (560 mg, 2.57 mmol) and isopropyl pinacol borate (629 μL, 3.08 mmol) in THF (10 mL) at −78° C. under $N_2$. The resulting mixture was stirred at −78° C. for 1 h followed by stirring at rt for 1 h. The reaction mixture was poured into brine (25 mL) and extracted with EtOAc (3×50 mL). The combined organic layers were dried over $MgSO_4$, filtered, and concentrated to dryness to give the title compound (500 mg, 73%) as a yellow oil; MS m/z (ES+) $[M+H]^+$=266.2; $^1H$ NMR (400 MHz, DMSO-$d_6$, 25° C.) δ 1.28 (12H, s), 1.65 (6H, d), 7.27 (1H, dd), 7.74 (1H, dd), 8.47-8.59 (1H, m).

Intermediate 126: 5-Fluoro-2-iodo-N,N-bis(propan-2-yl-$d_7$)benzamide

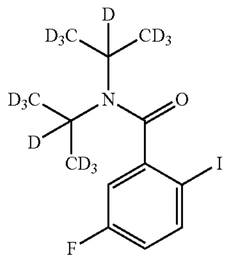 [SMILES: [2H]C([2H])([2H])C([2H])(N(C(=O)c1cc(F)ccc1I)C([2H])(C([2H])([2H])[2H])C([2H])([2H])[2H])C([2H])([2H])[2H]]

T3P (3.87 mL, 6.51 mmol, 50% in DCM) was added at 0° C. to a stirred solution of 5-fluoro-2-iodobenzoic acid (1.15 g, 4.34 mmol), bis(propan-2-yl-$d_7$)amine (697 μL, 4.34 mol), and DIPEA (3.02 mL, 17.4 mmol) in EtOAc (5 mL). The resulting mixture was stirred at rt overnight. The reaction mixture was diluted with water (75 mL) and stirred for 30 minutes. The organic solvent was removed under reduced pressure. The formed precipitate was filtered off, washed with water, and dried under reduced pressure to give the title compound (100 mg, 6%) as a white solid; MS m/z (ES+) $[M+H]^+$=364.0; $^1H$ NMR (400 MHz, DMSO-$d_6$, 22° C.) δ 7.03 (1H, td), 7.20 (1H, dd), 7.87 (1H, dd).

Intermediate 127: 2-((4-Bromopyridin-3-yl)amino)-5-fluoro-N,N-bis(propan-2-yl-$d_7$)benzamide

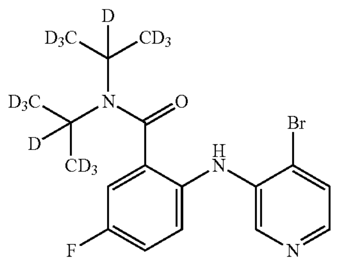 [SMILES: [2H]C([2H])([2H])C([2H])(N(C(=O)c1cc(F)ccc1Nc1cnccc1Br)C([2H])(C([2H])([2H])[2H])C([2H])([2H])[2H])C([2H])([2H])[2H]]

Intermediate 126 (100 mg, 0.28 mmol) was added to a mixture of 4-bromopyridin-3-amine (57.2 mg, 0.33 mmol), XantPhos (15.9 mg, 0.03 mmol), and $Cs_2CO_3$ (269 mg, 0.83 mmol) in 2-MeTHF (1 mL). The resulting suspension was purged with $N_2$ for 5 minutes before $Pd_2dba_3 \cdot CHCl_3$ (14.3 mg, 0.01 mmol) was added. The mixture was purged with $N_2$ for additional 5 minutes and stirred at 80° C. overnight. The reaction mixture was diluted with EtOAc (25 mL) and washed sequentially with aq. 2% N-acetyl-cysteine (2×25 mL) and sat. aq. $NaHCO_3$ (25 mL). The organic layer was dried over $Na_2SO_4$, filtered, and concentrated under reduced pressure. The residue was purified by straight phase flash chromatography on silica (gradient: 0-100% EtOAc in heptane) to give the title compound (65.0 mg, 58%) as a colorless oil; MS m/z (ES+) $[M+H]^+$=408.0/409.9; $^1$H NMR (400 MHz, DMSO-$d_6$, 22° C.) δ 6.95 (1H, s), 7.19 (1H, dd), 7.25 (1H, td), 7.35 (1H, dd), 7.59 (1H, d), 7.87 (1H, d), 8.08 (1H, s).

Intermediate 128 (Mixture of Atropisomers): tert-Butyl 4-(1-(2-(bis(propan-2-yl-$d_7$)carbamoyl)-4-fluorophenyl)-2-methyl-1H-pyrrolo[2,3-c]pyridine-3-carbonyl)piperidine-1-carboxylate

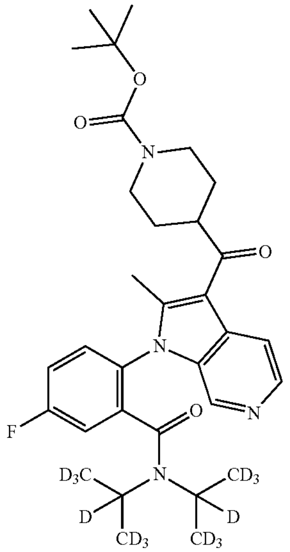 [SMILES: [2H]C([2H])([2H])C([2H])(N(C(=O)c1cc(F)ccc1-n1c(C)c(C(=O)C2CCN(C(=O)OC(C)(C)C)CC2)c2ccncc21)C([2H])(C([2H])([2H])[2H])C([2H])([2H])[2H])C([2H])([2H])[2H]]

CuO (10.8 mg, 0.14 mmol) was added to a deoxygenated mixture of Intermediate 84 (129 mg, 0.48 mmol), Intermediate 127 (65.0 mg, 0.16 mmol), and $Cs_2CO_3$ (72.6 mg, 0.22 mmol) in DMSO (1 mL). The resulting mixture was purged with $N_2$ for additional 3 minutes and was stirred at 100° C. overnight. The reaction mixture was diluted with EtOAc (5 mL) and washed with water (5 mL). The organic layer dried over $Na_2SO_4$, filtered, and concentrated under reduced pressure. The residue was purified by straight phase flash chromatography on silica (gradient: 0-100% EtOAc in heptane) to give the title compound (80.0 mg, 87%) as a brown dry film; MS m/z (ES+) $[M+H]^+$=579.4; $^1$H NMR (400 MHz, DMSO-$d_6$, 22° C.) δ 1.21-1.31 (1H, m), 1.36-1.52 (10H, m), 1.81 (2H, br s), 3.02 (2H, br s), 3.37-3.53 (1H, m), 3.80-4.10 (2H, m), 7.41-7.63 (2H, m), 7.64-7.79 (1H, m), 7.93 (1H, br s), 8.37 (2H, br s).

Intermediate 129 (Mixture of Atropisomers): 5-Fluoro-2-(2-methyl-3-(piperidine-4-carbonyl)-1H-pyrrolo[2,3-c]pyridin-1-yl)-N,N-bis(propan-2-yl-$d_7$)benzamide

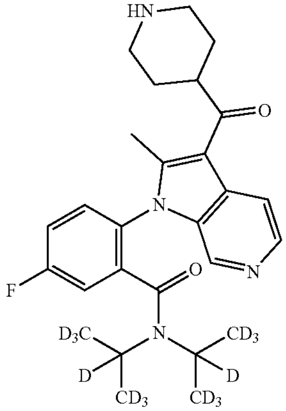 [SMILES: [2H]C([2H])([2H])C([2H])(N(C(=O)c1cc(F)ccc1-n1c(C)c(C(=O)C2CCNCC2)c2ccncc21)C([2H])(C([2H])([2H])[2H])C([2H])([2H])[2H])C([2H])([2H])[2H]]

TFA (1 mL) was added to a solution of Intermediate 128 (80.0 mg, 0.14 mmol) in DCM (5 mL). The resulting mixture was stirred at rt for 2 hours. The reaction mixture was concentrated under reduced pressure. The residue was diluted with DCM (5 mL) and quenched with sat. aq. $NaHCO_3$ (5 mL). The organic layer was separated by passing through a phase separator and concentrated under reduced pressure to give the crude, and the water layer extracted with DCM (200 mL). The combined organic layers were washed with brine (200 mL), dried over $Na_2SO_4$, filtered, and concentrated under reduced pressure to give the crude title compound, which was used directly in the next step (Example 59a).

Intermediate 130: tert-butyl (2S,4RS)-4-cyano-2-methylpiperidine-1-carboxylate

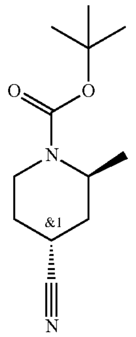 [SMILES: C[C@H]1C[C@H](C#N)CCN1C(=O)OC(C)(C)C]

KOtBu (10.4 g, 92.2 mmol) was added to a solution of 1-((isocyanomethyl)sulfonyl)-4-methylbenzene (9.83 g, 46.1 mmol) and tert-butyl (S)-2-methyl-4-oxopiperidine-1-carboxylate (6.00 g, 30.7 mmol) in DME (184 mL) and EtOH (3.6 mL) at −10° C. The resulting mixture was stirred at −10° C. for 2 h and then at rt overnight. The reaction mixture was diluted with EtOAc (30 mL) and washed sequentially with water (30 mL) and brine. The organic layer was dried over $Na_2SO_4$, filtered, and concentrated under reduced pressure. The residue was purified by straight phase flash chromatography on silica (gradient: 0-60% EtOAc in heptane) to give the title compound (1.15 g, 17%) as a yellow oil; MS m/z (ES+) $[M-Boc]^+$=125.2; $^1H$ NMR (400 MHz, DMSO-$d_6$, 22° C.) δ 1.06 (3H, d), 1.39 (9H, d), 1.44-1.52 (1H, m), 1.72 (1H, td), 1.85 (1H, ddt), 1.90-1.98 (1H, m), 2.81 (1H, td), 3.08 (1H, tt), 3.81 (1H, ddd), 4.25-4.35 (1H, m).

Intermediate 131: tert-butyl (2S,4RS)-4-acetyl-2-methylpiperidine-1-carboxylate

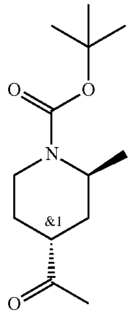 [SMILES: CC(=O)[C@@H]1CCN(C(=O)OC(C)(C)C)[C@@H](C)C1]

MeMgBr (6.74 mL, 20.2 mmol, 3 M in $Et_2O$) was added dropwise to Intermediate 130 (2.27 g, 10.1 mmol) in DME (30 mL) at rt. The resulting mixture was stirred at rt overnight. The reaction mixture was quenched with aq. HCl (1M, 10 mL), diluted with sat. $NH_4Cl$ (100 mL) and extracted with EtOAc (2×100 mL). The combined organics were washed with brine (100 mL), dried over $Na_2SO_4$, filtered, and concentrated to dryness. The crude product was purified by straight phase flash chromatography on silica (gradient: 0-75% EtOAc in heptane) to give the title compound (1.62 g, 66%) as a light yellow oil; MS m/z (ES+) $[M-tBu]^+$=186.1; $^1H$ NMR (400 MHz, DMSO-$d_6$, 22° C.) δ 1.08 (3H, dd), 1.13-1.26 (1H, m), 1.39 (9H, s), 1.41-1.53 (1H, m), 1.63-1.74 (1H, m), 1.74-1.89 (1H, m), 2.11 (3H, s), 2.65-2.76 (1H, m), 2.76-2.92 (1H, m), 3.78-3.91 (1H, m), 4.25-4.45 (1H, m).

Intermediate 132: tert-butyl (2S,4RS)-2-methyl-4-(3-oxobutanoyl)piperidine-1-carboxylate

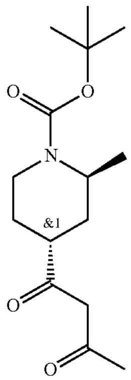 [SMILES: CC(=O)CC(=O)[C@@H]1CCN(C(=O)OC(C)(C)C)[C@@H](C)C1]

NaH (635 mg, 15.9 mmol, 60% dispersion in mineral oil) was added to Intermediate 131 (1.92 g, 7.94 mmol) in THF (25 mL) at 0° C. The resulting mixture was stirred at rt for 1 h before EtOAc (1.55 mL, 15.9 mmol) was added. The resulting mixture was stirred at 55° C. for 3 h. The reaction mixture was quenched with water (150 mL) and extracted with EtOAc (2×100 mL). The combined organics were washed with brine (100 mL), dried over $Na_2SO_4$, filtered, and concentrated under reduced pressure. The crude product was purified by straight phase flash chromatography on silica (gradient: 0-40% EtOAc in heptane) to give the title compound (1.68 g, 75%) as a yellow gum; MS m/z (ES+) $[M-tBu]^+$=228.1; $^1H$ NMR (400 MHz, DMSO-$d_6$, 22° C.) δ 1.02-1.14 (3H, m), 1.15-1.35 (1H, m), 1.39 (9H, d), 1.42-1.59 (1H, m), 1.61-1.98 (2H, m), 2.05 (2H, s), 2.13 (1H, s), 2.56-2.68 (1H, m), 2.73-2.95 (1H, m), 3.73-3.79 (1H, m), 3.80-3.91 (1H, m), 4.24-4.44 (1H, m), 5.76 (1H, s).

Intermediate 133 (Mixture of Atropisomers): tert-butyl (2S,4RS)-4-(1-(2-(diisopropylcarbamoyl)-4-fluorophenyl)-2-methyl-1H-pyrrolo[2,3-c]pyridine-3-carbonyl)-2-methylpiperidine-1-carboxylate

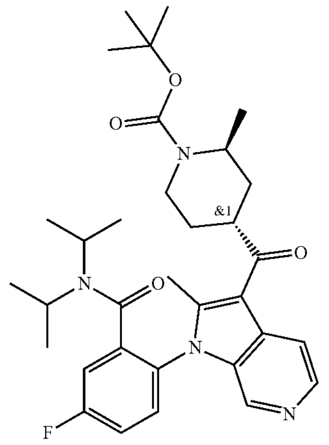 [SMILES: Cc1c(C(=O)[C@@H]2CCN(C(=O)OC(C)(C)C)[C@@H](C)C2)c2ccncc2n1-c1ccc(F)cc1C(=O)N(C(C)C)C(C)C]

CuCl (67.8 mg, 0.69 mmol) was added to a deoxygenated mixture of Intermediate 132 (1.29 g, 4.57 mmol), Intermediate 90 (900 mg, 2.28 mmol) and $Cs_2CO_3$ (1.12 g, 3.42 mmol) in DMF (26 mL). The resulting mixture was purged with $N_2$ for additional 1 minute and was stirred at 100° C. overnight. The reaction mixture was filtered and washed with EtOAc (100 mL). The filtrate was washed sequentially with a mixture of water and brine (100 mL, 1:1), brine (100 mL), dried over $Na_2SO_4$, filtered, and concentrated under reduced pressure. The residue was purified by straight phase flash chromatography on silica (gradient: 20-100% EtOAc in heptane) to give the title compound (1.00 g, 76%) as a brown dry film; MS m/z (ES+) $[M+H]^+$=579.4.

Intermediate 134 (Mixture of Atropisomers): 5-fluoro-N,N-diisopropyl-2-(2-methyl-3-((2S,4RS)-2-methylpiperidine-4-carbonyl)-1H-pyrrolo[2,3-c]pyridin-1-yl)benzamide

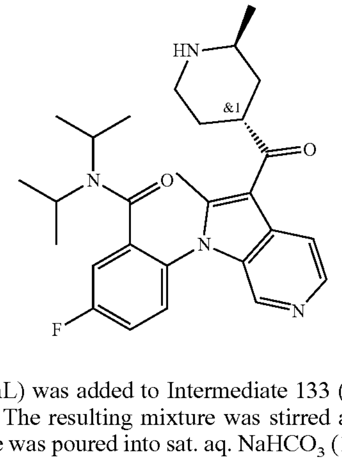

FA (10 mL) was added to Intermediate 133 (1.00 g, 1.46 mmol, th.). The resulting mixture was stirred at rt for 3 h. The mixture was poured into sat. aq. $NaHCO_3$ (100 mL) and solid $NaHCO_3$ was added until the pH>8. The water layer was diluted with sat. NaOH (50 mL, 2M) and saturated with solid NaCl before it was extracted with DCM (100 mL). The organic layer was washed with brine, dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (561 mg, 80%) as a light yellow dry film; MS m/z (ES+) $[M+H]^+$=479.3; $^1$H NMR (400 MHz, DMSO-$d_6$, 22° C.) δ 0.34-0.45 (3H, m), 0.49-0.74 (3H, m), 1.00-1.10 (3H, m), 1.13-1.29 (6H, m), 1.69-1.87 (1H, m), 1.87-2.10 (3H, m), 2.53 (3H, s), 2.75-3.12 (3H, m), 3.18-3.26 (1H, m), 3.28-3.58 (1H, m), 3.61-3.81 (2H, m), 7.43-7.63 (2H, m), 7.65-7.78 (1H, m), 7.78-7.96 (1H, m), 8.23-8.40 (2H, m).

Intermediate 135: N-ethyl-5-fluoro-2-iodo-N-isopropylbenzamide

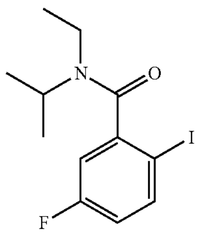 [SMILES: CCN(C(=O)c1cc(F)ccc1I)C(C)C]

T3P (28.7 mL, 45.1 mmol, 50% in DCM) was added to a stirred solution of 5-fluoro-2-iodobenzoic acid (10.0 g, 37.6 mmol) and N-ethylpropan-2-amine (22.8 mL, 188 mol) in DCM (104 mL). The resulting mixture was stirred at rt overnight. The reaction mixture was diluted with DCM and washed with sat. aq. $NaHCO_3$. The combined organic layers were dried over $Na_2SO_4$, filtered, and concentrated under reduced pressure. The residue was purified by straight phase flash chromatography on silica (gradient: 0-100% EtOAc in cyclohexane) to give the title compound (6.54 g, 52%) as a white solid; MS m/z (ES+) $[M+H]^+$=336.0; $^1$H NMR (400 MHz, $CDCl_3$, 22° C.) δ 1.02-1.12 (3H, m), 1.27-1.37 (6H, m), 2.95-3.22 (1H, m), 3.29 (1H, dq), 3.59 (1H, ddt), 6.77-6.85 (1H, m), 6.94 (1H, ddd), 7.75 (1H, ddd).

Intermediate 136: 2-((4-bromopyridin-3-yl)amino)-N-ethyl-5-fluoro-N-isopropylbenzamide

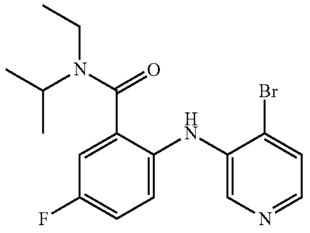 [SMILES: CCN(C(=O)c1cc(F)ccc1Nc1cnccc1Br)C(C)C]

$Pd_2dba_3 \cdot CHCl_3$ (154 mg, 0.15 mmol) was added to a deoxygenated mixture of Intermediate 135 (1.00 g, 2.98 mmol), 4-bromopyridin-3-amine (619 mg, 3.58 mmol), XantPhos (173 mg, 0.30 mmol) and $Cs_2CO_3$ (2.92 g, 8.95 mmol) in 2-MeTHF (11 mL). The mixture was purged with $N_2$ and stirred at 80° C. overnight. The reaction mixture was filtered and diluted with EtOAc (100 mL). The organic layer was washed sequentially with 2% (w/w %) aq. N-acetyl cysteine (100 mL), sat. aq. $NaHCO_3$ (100 mL) and brine (100 mL). The organic layer was dried over $Na_2SO_4$, filtered, and concentrated under reduced pressure. The residue was purified by straight phase flash chromatography on silica (gradient: 0-100% EtOAc in heptane). Appropriate fractions were combined and concentrated under reduced pressure. The residue was dissolved in EtOAc (50 mL) and washed sequentially with 2% aq. N-acetyl-cysteine (50 mL), sat. aq. $NaHCO_3$ (50 mL) and brine (50 mL). The organic layer was dried over $Na_2SO_4$, filtered, and concentrated under reduced pressure to give the title compound (599 mg, 53%) as a beige solid; MS m/z (ES+) $[M+H]^+$=380.1/382.1; $^1H$ NMR (400 MHz, DMSO-$d_6$, 22° C.) δ 0.93 (3H, t), 0.97-1.13 (6H, m), 3.08-3.31 (2H, m), 3.66-3.84 (1H, m), 7.05-7.33 (4H, m), 7.59 (1H, d), 7.88 (1H, d), 8.07 (1H, s).

Intermediate 137 (Mixture of Atropisomers): tert-butyl (2S,4RS)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carboxylate

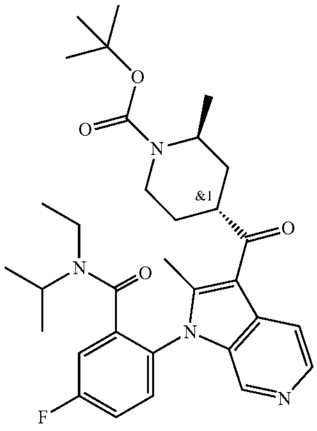 [SMILES: CCN(C(=O)c1cc(F)ccc1-n1c(C)c(C(=O)[C@@H]2CCN(C(=O)OC(C)(C)C)[C@@H](C)C2)c2ccncc21)C(C)C]

CuCl (46.7 mg, 0.47 mmol) was added to a deoxygenated mixture of Intermediate 132 (891 mg, 3.15 mmol), Intermediate 136 (598 mg, 1.57 mmol) and $Cs_2CO_3$ (769 mg, 2.36 mmol) in DMF (18 mL). The resulting mixture was purged with $N_2$ for additional 1 minute and was stirred at 100° C. overnight. The reaction mixture was filtered and washed with EtOAc (100 mL). The filtrate was washed with brine (100 mL), dried over $Na_2SO_4$, filtered, and concentrated under reduced pressure. The residue was purified by straight phase flash chromatography on silica (gradient: 20-100% EtOAc in heptane) to give the title compound (499 mg, 56%) as a brown dry film; MS m/z (ES+) $[M+H]^+$=565.3.

Intermediate 138 (Mixture of Atropisomers): N-ethyl-5-fluoro-N-isopropyl-2-(2-methyl-3-((2S,4RS)-2-methylpiperidine-4-carbonyl)-1H-pyrrolo[2,3-c]pyridin-1-yl)benzamide

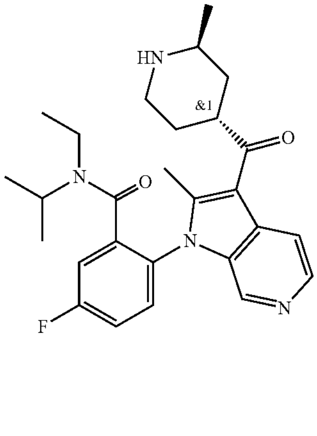 [SMILES: CCN(C(=O)c1cc(F)ccc1-n1c(C)c(C(=O)[C@@H]2CCN[C@@H](C)C2)c2ccncc21)C(C)C]

FA (5 mL) was added to Intermediate 137 (499 mg, 0.74 mmol, th.). The resulting mixture was stirred at rt for 3 h. The mixture was poured into sat. aq. $NaHCO_3$ (100 mL) and solid $NaHCO_3$ was added until the pH was >8. The water layer was diluted with sat. NaOH (50 mL, 2M) and saturated with solid NaCl before it was extracted with DCM (100 mL). The organic layer was washed with brine, dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (321 mg, 93%) as a light yellow dry film; MS m/z (ES+) $[M+H]^+$=465.3; $^1H$ NMR (400 MHz, DMSO-$d_6$, 22° C.) δ 0.09-0.23 (1H, m), 0.28-0.47 (4H, m), 0.51-0.79 (2H, m), 0.93-1.15 (6H, m), 1.47-1.70 (1H, m), 1.72-2.02 (3H, m), 2.41-2.48 (1H, m), 2.51-2.57 (2H, m), 2.66-3.03 (3H, m), 3.05-3.15 (1H, m), 3.18-3.30 (1H, m), 3.41-3.74 (2H, m), 7.51-7.65 (2H, m), 7.70-7.80 (1H, m), 7.80-7.90 (1H, m), 8.25-8.38 (2H, m).

C. Final Compounds

Example 1: 5-Fluoro-N,N-diisopropyl-2-(3-((S)-1-(((1r,4S)-4-(methylsulfonamido)-cyclohexyl)methyl) pyrrolidine-3-carbonyl)-1H-pyrrolo[2,3-c]pyridin-1-yl)benzamide

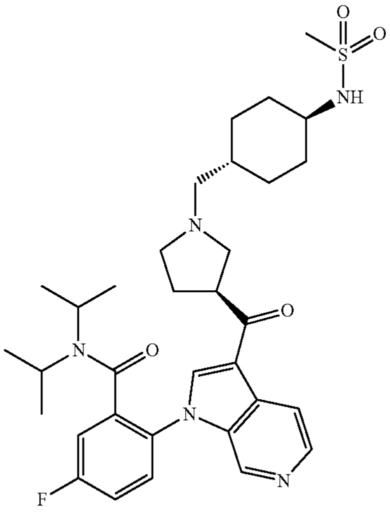 [SMILES: CC(C)N(C(=O)c1cc(F)ccc1-n1cc(C(=O)[C@H]2CCN(C[C@H]3CC[C@H](NS(C)(=O)=O)CC3)C2)c2ccncc21)C(C)C]

Intermediate 104 (33.6 mg, 0.09 mmol) was added to a suspension of Intermediate 5a (99.3 mg, 0.10 mmol th.) and $K_2CO_3$ (64.3 mg, 0.47 mmol) in MeCN (1 mL). The resulting mixture was stirred at 80° C. overnight. The reaction mixture was diluted with water (10 mL) and extracted with EtOAc (3×10 mL). The combined organic layers were washed with brine, dried over $Na_2SO_4$, filtered, and concentrated under reduced pressure. The residue was purified by straight phase flash chromatography on silica (gradient: 0-10% MeOH in DCM). Appropriate fractions were pooled and concentrated under reduced pressure. The product was lyophilized from MeCN/$H_2O$ to give the title compound (26.7 mg, 44%) as an orange solid; MS m/z (ES+) $[M+H]^+$=626.3; $^1H$ NMR (400 MHz, DMSO-$d_6$, 22° C.) δ 0.28 (3H, br s), 0.75 (3H, br s), 0.83-0.95 (2H, m), 0.99 (3H, d), 1.10-1.25 (2H, m), 1.33 (3H, t), 1.72-1.92 (4H, m), 1.93-2.13 (2H, m), 2.18 (2H, br s), 2.30-2.46 (2H, m), 2.55-2.69 (1H, m), 2.88 (3H, br s), 2.94-3.08 (2H, m), 3.18-3.27 (1H, m), 3.31 (1H, br s), 3.44-3.56 (1H, m), 3.80 (1H, br s), 6.94-7.03 (1H, m), 7.48-7.58 (2H, m), 7.78-7.88 (1H, m), 8.14 (1H, d), 8.37 (1H, d), 8.56 (1H, s), 8.63 (1H, s).

Example 2: 2-(3-((S)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide

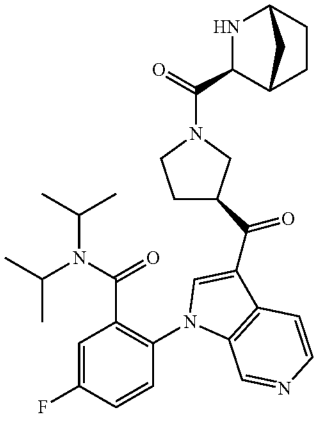 [SMILES: CC(C)N(C(=O)c1cc(F)ccc1-n1cc(C(=O)[C@H]2CCN(C(=O)[C@H]3N[C@@H]4CC[C@H]3C4)C2)c2ccncc21)C(C)C]

Step a) tert-Butyl (1R,3S,4S)-3-((S)-3-(1-(2-(diisopropylcarbamoyl)-4-fluorophenyl)-1H-pyrrolo[2,3-c]pyridine-3-carbonyl)pyrrolidine-1-carbonyl)-2-azabicyclo[2.2.1]heptane-2-carboxylate

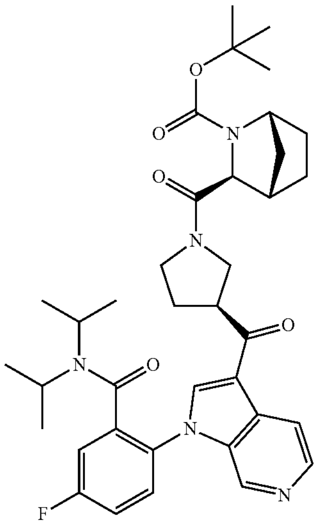 [SMILES: CC(C)N(C(=O)c1cc(F)ccc1-n1cc(C(=O)[C@H]2CCN(C(=O)[C@@H]3[C@H]4CC[C@H](C4)N3C(=O)OC(C)(C)C)C2)c2ccncc21)C(C)C]

Intermediate 5b (35.6 mg, 0.08 mmol) was added to a solution of (1R,3S,4S)-2-(tert-butoxycarbonyl)-2-azabicyclo[2.2.1]heptane-3-carboxylic acid (21.7 mg, 0.09 mmol), EDC (18.8 mg, 0.10 mmol), HOBt (15.0 mg, 0.10 mmol) and DIPEA (28.5 µl, 0.16 mmol) in DCM (1 mL). The resulting mixture was stirred at rt for 2 h. The reaction mixture was diluted with sat. aq. $NaHCO_3$ (20 mL) and extracted with DCM (3×20 mL). The combined organic layers were washed with brine, dried over $Na_2SO_4$, filtered, and concentrated under reduced pressure. The residue was purified by straight phase flash chromatography on silica (gradient: 0-10% MeOH in DCM) to give the title compound (43.3 mg, 80%) as an orange gum; MS m/z (ES+) $[M+H]^+$=660.4.

Step b) 2-(3-((S)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide (Example 2)

TFA (1 mL) was added to a solution of tert-butyl (1R,3S,4S)-3-((S)-3-(1-(2-(diisopropylcarbamoyl)-4-fluorophenyl)-1H-pyrrolo[2,3-c]pyridine-3-carbonyl)pyrrolidine-1-carbonyl)-2-azabicyclo[2.2.1]heptane-2-carboxylate from Step a) (43.3 mg, 0.07 mmol) in DCM (5 mL). The mixture was stirred at rt for 30 minutes. The reaction mixture was concentrated under reduced pressure. The residue was purified by preparative HPLC, PrepMethod A, (gradient: 0-50%). Appropriate fractions were pooled, diluted with aq. NaOH (2 M) and extracted with EtOAc (2×20 mL). The combined organic layers were washed with brine, dried over $Na_2SO_4$, filtered, and concentrated under reduced pressure. The product was lyophilized from $MeCN/H_2O$ to give the title compound (27.8 mg, 76%) as a white solid; MS m/z (ES+) $[M+H]^+$=560.3; $^1H$ NMR (400 MHz, DMSO-$d_6$, 22° C.) δ 0.27 (3H, br s), 0.74 (3H, br s), 0.95-1.02 (3H, m), 1.15-1.19 (1H, m), 1.22-1.3 (2H, m), 1.33 (3H, d), 1.36-1.42 (1H, m), 1.45-1.53 (2H, m), 2.04-2.31 (2H, m), 2.55 (1H, s), 3.19-3.31 (2H, m), 3.41-3.58 (4H, m), 3.60-3.69 (1H, m), 3.71-3.79 (1H, m), 3.85-4.11 (2H, m), 7.52-7.59 (2H, m), 7.83-7.89 (1H, m), 8.11-8.16 (1H, m), 8.37-8.41 (1H, m), 8.63-8.73 (2H, m).

Example 3: 2-(3-((R)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide

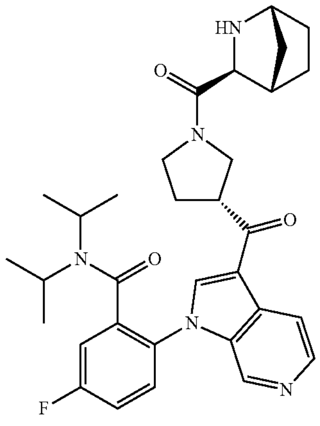 [SMILES: CC(C)N(C(=O)c1cc(F)ccc1-n1cc(C(=O)[C@@H]2CCN(C(=O)[C@H]3N[C@@H]4CC[C@H]3C4)C2)c2ccncc21)C(C)C]

Step a) tert-Butyl (1R,3S,4S)-3-((R)-3-(1-(2-(diisopropylcarbamoyl)-4-fluorophenyl)-1H-pyrrolo[2,3-c]pyridine-3-carbonyl)pyrrolidine-1-carbonyl)-2-azabicyclo[2.2.1]heptane-2-carboxylate

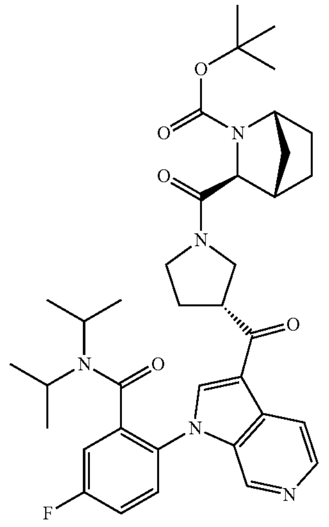 [SMILES: CC(C)N(C(=O)c1cc(F)ccc1-n1cc(C(=O)[C@@H]2CCN(C(=O)[C@@H]3[C@H]4CC[C@H](C4)N3C(=O)OC(C)(C)C)C2)c2ccncc21)C(C)C]

Intermediate 8a (73.0 mg, 0.11 mmol th.) was added to a solution of (1R,3S,4S)-2-(tert-butoxycarbonyl)-2-azabicyclo[2.2.1]heptane-3-carboxylic acid (30.3 mg, 0.13 mmol), EDC (26.3 mg, 0.14 mmol), HOBt (21.0 mg, 0.14 mmol) and DIPEA (40.0 μl, 0.23 mmol) in DCM (1 mL). The resulting mixture was stirred at rt for 2 h. The reaction mixture was diluted with sat. aq. $NaHCO_3$ (20 mL) and extracted with DCM (3×20 mL). The combined organic layers were washed with brine, dried over $Na_2SO_4$, filtered, and concentrated under reduced pressure. The residue was purified by straight phase flash chromatography on silica (gradient: 0-10% MeOH in DCM) to give the title compound (67.4 mg, 89%) as an orange gum; MS m/z (ES+) $[M+H]^+$=660.4.

Step b) 2-(3-((R)-1-((1R,3S,4S)-2-Azabicyclo[2.2.1]heptane-3-carbonyl)pyrrolidine-3-carbonyl)-1H-pyrrolo[2,3-c]pyridin-1-yl)-5-fluoro-N,N-diisopropylbenzamide (Example 3)

TFA (1 mL) was added to a solution of tert-butyl (1R,3S,4S)-3-((R)-3-(1-(2-(diisopropylcarbamoyl)-4-fluorophenyl)-1H-pyrrolo[2,3-c]pyridine-3-carbonyl)pyrrolidine-1-carbonyl)-2-azabicyclo[2.2.1]heptane-2-carboxylate from Step a) (67.4 mg, 0.10 mmol) in DCM (5 mL). The mixture was stirred at rt for 30 minutes. The mixture was concentrated under reduced pressure. The residue was purified by preparative HPLC, PrepMethod A, (gradient: 0-75%). Appropriate fractions were pooled, diluted with sat. aq. $NaHCO_3$ (20 mL) and extracted with EtOAc (2×20 mL). The combined organic layers were washed with brine, dried over $Na_2SO_4$, filtered, and concentrated under reduced pressure. The product was lyophilized from MeCN/$H_2O$ to give the title compound (30.4 mg, 53%) as an off-white solid; MS m/z (ES+) $[M+H]^+$=560.3; $^1H$ NMR (400 MHz, DMSO-$d_6$, 22° C.) δ 0.27 (3H, br s), 0.75 (3H, br s), 0.99 (3H, dd), 1.16-1.25 (2H, m), 1.28-1.36 (4H, m), 1.36-1.45 (2H, m), 1.46-1.55 (2H, m), 2.01-2.34 (3H, m), 3.20-3.26 (1H, m), 3.40-3.58 (4H, m), 3.62-3.70 (1H, m), 3.72-3.80 (1H, m), 3.87-4.11 (2H, m), 7.51-7.59 (2H, m), 7.82-7.89 (1H, m), 8.14 (1H, d), 8.37-8.41 (1H, m), 8.63-8.72 (2H, m).

Example 4: 5-Fluoro-N,N-diisopropyl-2-(3-((R)-1-(((1r,4R)-4-(methylsulfonamido)-cyclohexyl)methyl)pyrrolidine-3-carbonyl)-1H-pyrrolo[2,3-c]pyridin-1-yl)benzamide

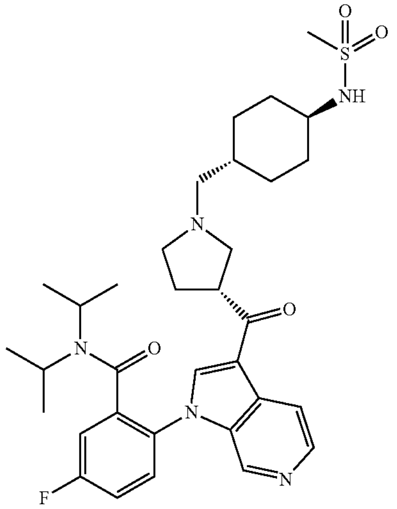 [SMILES: CC(C)N(C(=O)c1cc(F)ccc1-n1cc(C(=O)[C@@H]2CCN(C[C@H]3CC[C@H](NS(C)(=O)=O)CC3)C2)c2ccncc21)C(C)C]

A suspension of Intermediate 8b (152 mg, 0.18 mmol th.) and $K_2CO_3$ (122 mg, 0.88 mmol) in MeCN (1 mL) was stirred at rt for 30 minutes before Intermediate 104 (63.9 mg, 0.18 mmol) was added. The resulting mixture was stirred at 80° C. overnight. The reaction mixture was diluted with water (20 mL) and extracted with EtOAc (3×20 mL). The combined organic layers were washed with brine, dried over $Na_2SO_4$, filtered, and concentrated under reduced pressure. The residue was purified by preparative HPLC, PrepMethod A, (gradient: 0-50%). Appropriate fractions were pooled, diluted with sat. aq. $NaHCO_3$ and extracted with EtOAc (2×20 mL). The combined organic layers were washed with brine, dried over $Na_2SO_4$, filtered, and concentrated under reduced pressure. The product was lyophilized from MeCN/$H_2O$ to give the title compound (35.9 mg, 33%) as an off-white solid; MS m/z (ES+) $[M+H]^+$=626.3; $^1H$ NMR (400 MHz, DMSO-$d_6$, 22° C.) δ 0.29 (3H, br s), 0.76 (3H, br s), 0.84-0.94 (2H, m), 0.99 (3H, d), 1.12-1.22 (2H, m), 1.34 (3H, t), 1.74-2.13 (7H, m), 2.15-2.44 (4H, m), 2.57-2.68 (1H, m), 2.88 (3H, s), 2.96-3.08 (2H, m), 3.19-3.28 (1H, m), 3.48 (1H, br s), 3.80 (1H, br s), 6.95-7.01 (1H, m), 7.49-7.57 (2H, m), 7.78-7.85 (1H, m), 8.14 (1H, d), 8.37 (1H, d), 8.56 (1H, s), 8.63 (1H, s).

Example 5: 2-(3-(1-((1R,3S,4S)-2-Azabicyclo[2.2.1]heptane-3-carbonyl)azetidine-3-carbonyl)-1H-pyrrolo[2,3-c]pyridin-1-yl)-5-fluoro-N,N-diisopropylbenzamide

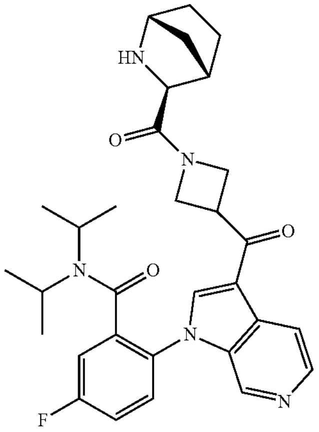 [SMILES: CC(C)N(C(=O)c1cc(F)ccc1-n1cc(C(=O)C2CN(C(=O)[C@H]3N[C@@H]4CC[C@H]3C4)C2)c2ccncc21)C(C)C]

Step a) tert-Butyl (1R,3S,4S)-3-(3-(1-(2-(diisopropylcarbamoyl)-4-fluorophenyl)-1H-pyrrolo[2,3-c]pyridine-3-carbonyl)azetidine-1-carbonyl)-2-azabicyclo[2.2.1]heptane-2-carboxylate

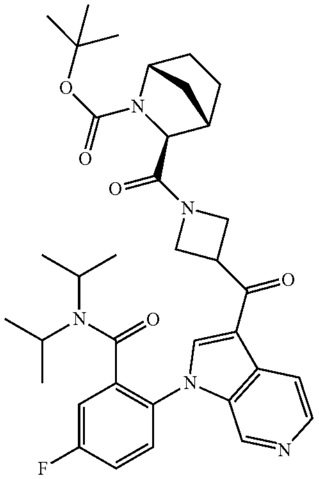 [SMILES: CC(C)N(C(=O)c1cc(F)ccc1-n1cc(C(=O)C2CN(C(=O)[C@@H]3[C@H]4CC[C@H](C4)N3C(=O)OC(C)(C)C)C2)c2ccncc21)C(C)C]

Intermediate 13 (880 mg, 2.08 mmol) was added to a solution of (1R,3S,4S)-2-(tert-butoxycarbonyl)-2-azabicyclo[2.2.1]heptane-3-carboxylic acid (503 mg, 2.08 mmol), EDC (479 mg, 2.50 mmol), HOBt (383 mg, 2.50 mmol) and DIPEA (728 µl, 4.17 mmol) in DMF (8 mL). The resulting mixture was stirred at rt overnight. The reaction mixture was diluted with EtOAc (50 mL) and washed with aq. HCl (50 mL, 1 M), sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-10% MeOH in DCM) to give the title compound (883 mg, 66%) as a brown foam; MS m/z (ES+) $[M+H]^+$=646.3; $^1H$ NMR (400 MHz, DMSO-$d_6$, 27° C.) δ 0.31 (3H, br s), 0.72 (3H, br s), 0.99 (3H, d), 1.10-1.42 (12H, m), 1.41-1.51 (2H, m), 1.51-1.71 (2H, m), 1.86-2.02 (1H, m), 2.54-2.60 (1H, m), 3.15-3.32 (2H, m), 3.49 (1H, s), 3.58-3.72 (1H, m), 3.89-4.61 (6H, m), 7.44-7.69 (2H, m), 7.76-7.92 (1H, m), 8.06-8.18 (1H, m), 8.36-8.56 (2H, m), 8.64 (1H, s).

Step b) 2-(3-(1-((1R,3S,4S)-2-Azabicyclo[2.2.1]heptane-3-carbonyl)azetidine-3-carbonyl)-1H-pyrrolo[2,3-c]pyridin-1-yl)-5-fluoro-N,N-diisopropylbenzamide (Example 5)

TFA (2 mL) was added to a solution of tert-butyl (1R,3S,4S)-3-(3-(1-(2-(diisopropylcarbamoyl)-4-fluorophenyl)-1H-pyrrolo[2,3-c]pyridine-3-carbonyl)azetidine-1-carbonyl)-2-azabicyclo[2.2.1]heptane-2-carboxylate from Step a) (880 mg, 1.36 mmol) in DCM (10 mL). The mixture was stirred at rt for 1 h. The mixture was concentrated under reduced pressure. The residue was taken up in DCM (50 mL) and washed with sat. aq. $NaHCO_3$ (50 mL). The organic layer was washed with brine, dried over $Na_2SO_4$, filtered, and concentrated under reduced pressure. The residue was purified by straight phase flash chromatography on silica (gradient: 0-20% 0.7 M $NH_3$ in MeOH in DCM). The crude product was purified by preparative HPLC, PrepMethod A, (gradient: 0-75%). Appropriate fractions were pooled, diluted with sat. aq. $NaHCO_3$ and extracted with EtOAc (2×30 mL). The combined organic layers were washed with brine, dried over $Na_2SO_4$, filtered, and concentrated under reduced pressure. The product was lyophilized from MeCN/$H_2O$ to give the title compound (437 mg, 59%) as an off-white solid; MS m/z (ES+) $[M+H]^+$=546.3; $^1H$ NMR (400 MHz, DMSO-$d_6$, 27° C.) δ 0.31 (3H, br s), 0.73 (3H, br s), 0.99 (3H, d), 1.13 (1H, d), 1.25 (1H, d), 1.33 (4H, d), 1.49 (2H, d), 2.39-2.49 (2H, m), 3.12-3.18 (1H, m), 3.23 (1H, s), 3.39 (1H, br s), 3.44-3.56 (1H, m), 3.95-4.07 (1H, m), 4.08-4.21 (1H, m), 4.22-4.37 (2H, m), 4.38-4.59 (2H, m), 7.50-7.60 (2H, m), 7.79-7.89 (1H, m), 8.12-8.18 (1H, m), 8.37-8.44 (1H, m), 8.43-8.52 (1H, m), 8.65 (1H, s).

Example 6: (S)-2-(3-(1-(2-Azabicyclo[2.2.2]octane-3-carbonyl)azetidine-3-carbonyl)-1H-pyrrolo[2,3-c]pyridin-1-yl)-5-fluoro-N,N-diisopropylbenzamide

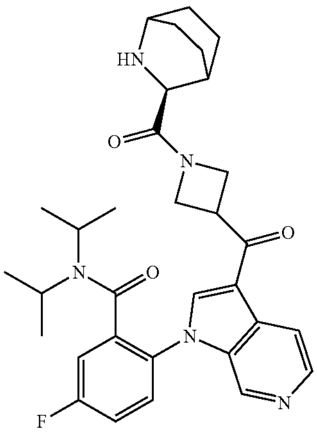 [SMILES: CC(C)N(C(=O)c1cc(F)ccc1-n1cc(C(=O)C2CN(C(=O)[C@H]3NC4CCC3CC4)C2)c2ccncc21)C(C)C]

Step a) tert-Butyl (S)-3-(3-(1-(2-(diisopropylcarbamoyl)-4-fluorophenyl)-1H-pyrrolo[2,3-c]pyridine-3-carbonyl)azetidine-1-carbonyl)-2-azabicyclo[2.2.2]octane-2-carboxylate

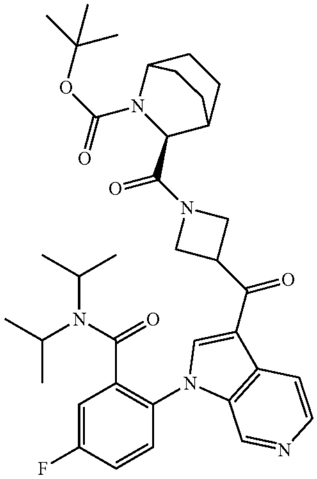 [SMILES: CC(C)N(C(=O)c1cc(F)ccc1-n1cc(C(=O)C2CN(C(=O)[C@@H]3C4CCC(CC4)N3C(=O)OC(C)(C)C)C2)c2ccncc21)C(C)C]

Intermediate 13 (120 mg, 0.28 mmol) was added to a solution of (S)-2-(tert-butoxycarbonyl)-2-azabicyclo[2.2.2]octane-3-carboxylic acid (72.5 mg, 0.28 mmol), EDC (65.3 mg, 0.34 mmol), HOBt (52.2 mg, 0.34 mmol) and DIPEA (100 μL, 0.57 mmol) in DMF (2 mL). The resulting mixture was stirred at rt overnight. The reaction mixture was diluted with EtOAc (50 mL) and washed sequentially with aq. HCl (50 mL, 1 M), sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-10% MeOH in DCM) to give the title compound (137 mg, 73%) as a yellow foam; MS m/z (ES+) $[M+H]^+$=660.3.

Step b) (S)-2-(3-(1-(2-Azabicyclo[2.2.2]octane-3-carbonyl)azetidine-3-carbonyl)-1H-pyrrolo[2,3-c]pyridin-1-yl)-5-fluoro-N,N-diisopropylbenzamide (Example 6)

TFA (1 mL) was added to a solution of tert-butyl (S)-3-(3-(1-(2-(diisopropylcarbamoyl)-4-fluorophenyl)-1H-pyrrolo[2,3-c]pyridine-3-carbonyl)azetidine-1-carbonyl)-2-azabicyclo[2.2.2]octane-2-carboxylate from Step a) (137 mg, 0.21 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ and extracted with EtOAc (2×30 mL). The combined organic layers were washed with brine, dried over $Na_2SO_4$, filtered, and concentrated under reduced pressure. The product was lyophilized from MeCN/$H_2O$ to give the title compound (48.0 mg, 41%) as a white solid; MS m/z (ES+) $[M+H]^+$=560.3; $^1$H NMR (400 MHz, DMSO-$d_6$, 27° C.) δ 0.30 (3H, br s), 0.73 (3H, br s), 0.99 (3H, d), 1.33 (3H, d), 1.41-1.50 (2H, m), 1.53-1.84 (6H, m), 2.84 (1H, s), 3.15-3.28 (2H, m), 3.43-3.58 (1H, m), 3.64 (1H, s), 3.98-4.35 (4H, m), 4.36-4.60 (2H, m), 7.47-7.59 (2H, m), 7.77-7.89 (1H, m), 8.14 (1H, d), 8.41 (1H, d), 8.42-8.52 (1H, m), 8.64 (1H, s).

Example 7: 5-Fluoro-2-(3-(1-((1S,3S,4S,5S)-5-fluoro-2-azabicyclo[2.2.1]heptane-3-carbonyl)azetidine-3-carbonyl)-1H-pyrrolo[2,3-c]pyridin-1-yl)-N,N-diisopropylbenzamide

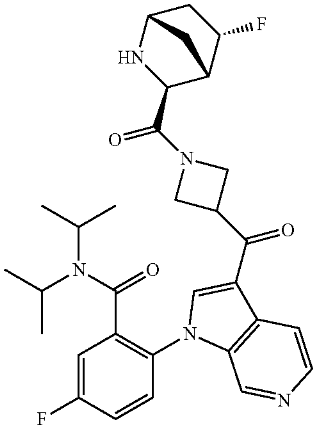 [SMILES: CC(C)N(C(=O)c1cc(F)ccc1-n1cc(C(=O)C2CN(C(=O)[C@H]3N[C@H]4C[C@@H]3[C@@H](F)C4)C2)c2ccncc21)C(C)C]

Step a) tert-Butyl (1S,3S,4S,5S)-3-(3-(1-(2-(diisopropylcarbamoyl)-4-fluorophenyl)-1H-pyrrolo[2,3-c]pyridine-3-carbonyl)azetidine-1-carbonyl)-5-fluoro-2-azabicyclo[2.2.1]heptane-2-carboxylate

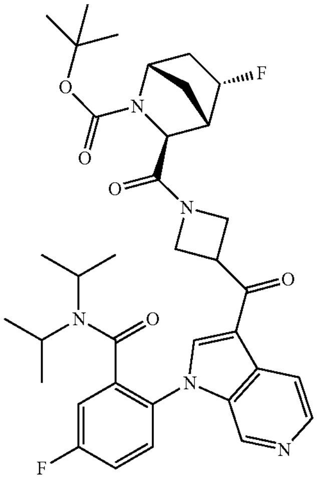 [SMILES: CC(C)N(C(=O)c1cc(F)ccc1-n1cc(C(=O)C2CN(C(=O)[C@@H]3[C@@H]4C[C@@H](C[C@@H]4F)N3C(=O)OC(C)(C)C)C2)c2ccncc21)C(C)C]

Intermediate 13 (85.3 mg, 0.20 mmol) was added to a solution of Intermediate 106 (52.3 mg, 0.20 mmol), EDC (38.7 mg, 0.20 mmol), HOBt (37.1 mg, 0.24 mmol) and DIPEA (141 L, 0.81 mmol) in DMF (1.5 mL). The resulting mixture was stirred at rt overnight. The reaction mixture was diluted with EtOAc (50 mL) and washed sequentially with aq. HCl (50 mL, 1 M) and sat. aq. $NaHCO_3$ (50 mL). The organic layer was washed with brine, dried over $Na_2SO_4$, filtered, and concentrated under reduced pressure to give the crude title compound (133 mg) as an orange oil; MS m/z (ES+) $[M+H]^+$=664.3.

Step b) 5-Fluoro-2-(3-(1-((1S,3S,4S,5S)-5-fluoro-2-azabicyclo[2.2.1]heptane-3-carbonyl)azetidine-3-carbonyl)-1H-pyrrolo[2,3-c]pyridin-1-yl)-N,N-diisopropylbenzamide (Example 7)

TFA (1 mL) was added to a solution of tert-butyl (1S,3S,4S,5S)-3-(3-(1-(2-(diisopropylcarbamoyl)-4-fluorophenyl)-1H-pyrrolo[2,3-c]pyridine-3-carbonyl)azetidine-1-carbonyl)-5-fluoro-2-azabicyclo[2.2.1]heptane-2-carboxylate from Step a) (133 mg, 0.20 mmol th.) in DCM (5 mL). The resulting mixture was stirred at rt for 1 h. The mixture was diluted with sat. aq. $NaHCO_3$ (25 mL) and extracted with EtOAc (3×25 mL). The combined organic layers were washed with brine, dried over $Na_2SO_4$, filtered, and concentrated under reduced pressure. The residue was purified by preparative HPLC, PrepMethod A, (gradient: 0-75%). Appropriate fractions were pooled, diluted with sat. aq. $NaHCO_3$ and extracted with EtOAc (2×30 mL). The combined organic layers were washed with brine, dried over $Na_2SO_4$, filtered, and concentrated under reduced pressure. The product was lyophilized from $MeCN/H_2O$ to give the title compound (19.8 mg, 18%) as a white solid; MS m/z (ES+) $[M+H]^+$=564.2; $^1H$ NMR (400 MHz, DMSO-$d_6$, 22° C.) δ 0.30 (2H, br s), 0.71 (3H, br s), 0.99 (3H, d), 1.26-1.39 (6H, m), 1.86-2.02 (1H, m), 2.69-2.84 (1H, m), 3.23 (1H, hept), 3.31 (1H, s), 3.41 (1H, s), 3.45-3.56 (1H, m), 3.64-3.76 (1H, m), 3.96-4.09 (1H, m), 4.10-4.23 (1H, m), 4.24-4.42 (2H, m), 4.43-4.58 (1H, m), 5.02-5.30 (1H, m), 7.49-7.59 (2H, m), 7.80-7.88 (1H, m), 8.12-8.19 (1H, m), 8.41 (1H, d), 8.44-8.55 (1H, m), 8.65 (1H, s).

Example 8: 2-(3-(1-((1R,3S,4S)-2-Azabicyclo[2.2.1]heptane-3-carbonyl)azetidine-3-carbonyl)-1H-pyrrolo[2,3-c]pyridin-1-yl)-N-ethyl-5-fluoro-N-isopropylbenzamide

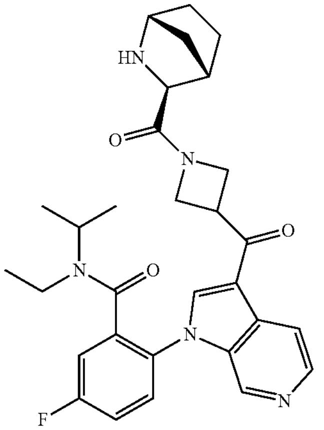 [SMILES: CCN(C(=O)c1cc(F)ccc1-n1cc(C(=O)C2CN(C(=O)[C@H]3N[C@@H]4CC[C@H]3C4)C2)c2ccncc21)C(C)C]

Step a) tert-Butyl (1R,3S,4S)-3-(3-(1-(2-(ethyl(isopropyl)carbamoyl)-4-fluorophenyl)-1H-pyrrolo[2,3-c]pyridine-3-carbonyl)azetidine-1-carbonyl)-2-azabicyclo[2.2.1]heptane-2-carboxylate

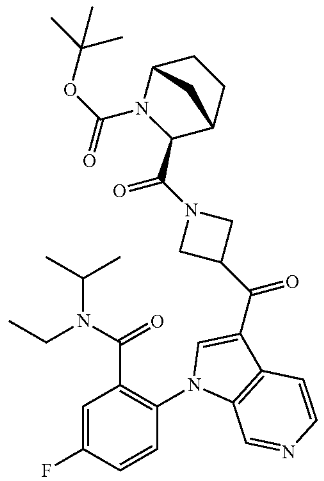 [SMILES: CCN(C(=O)c1cc(F)ccc1-n1cc(C(=O)C2CN(C(=O)[C@@H]3[C@H]4CC[C@H](C4)N3C(=O)OC(C)(C)C)C2)c2ccncc21)C(C)C]

Intermediate 15 (97.2 mg, 0.24 mmol) was added to a solution of (1R,3S,4S)-2-(tert-butoxycarbonyl)-2-azabicyclo[2.2.1]heptane-3-carboxylic acid (57.4 mg, 0.24 mmol), EDC (54.7 mg, 0.29 mmol), HOBt (43.7 mg, 0.29 mmol) and DIPEA (83.0 μl, 0.48 mmol) in DMF (2 mL). The resulting mixture was stirred at rt overnight. The reaction mixture was diluted with EtOAc (50 mL) and washed with sat. aq. $NaHCO_3$ (40 mL). The organic layer was washed with brine, dried over $Na_2SO_4$, filtered, and concentrated under reduced pressure. The residue was purified by straight phase flash chromatography on silica (gradient: 0-10% MeOH in DCM) to give the title compound (106 mg, 71%) as a yellow gum; MS m/z (ES+) $[M+H]^+$=632.3.

Step b) 2-(3-(1-((1R,3S,4S)-2-Azabicyclo[2.2.1]heptane-3-carbonyl)azetidine-3-carbonyl)-1H-pyrrolo[2,3-c]pyridin-1-yl)-N-ethyl-5-fluoro-N-isopropylbenzamide (Example 8)

TFA (1 mL) was added to a solution of tert-butyl (1R,3S,4S)-3-(3-(1-(2-(ethyl(isopropyl)carbamoyl)-4-fluorophenyl)-1H-pyrrolo[2,3-c]pyridine-3-carbonyl)azetidine-1-carbonyl)-2-azabicyclo[2.2.1]heptane-2-carboxylate from Step a) (106 mg, 0.17 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine, dried over $Na_2SO_4$, filtered, and concentrated under reduced pressure. The product was lyophilized from $MeCN/H_2O$ to give the title compound (26.7 mg, 30%) as a white solid; MS m/z (ES+) $[M+H]^+$=532.3; $^1H$ NMR (400 MHz, DMSO-$d_6$, 22° C.) δ 0.13-0.75 (6H, m), 0.76-1.02 (4H, m), 1.13-1.20 (1H, m), 1.22-1.29 (1H, m), 1.36 (2H, d), 1.51 (2H, d), 2.45 (1H, s), 2.74-2.87 (1H, m), 3.20-3.30 (2H, m), 3.46 (1H, s), 3.49-3.59 (1H, m), 3.93-4.08 (1H, m), 4.11-4.23 (1H, m), 4.25-4.56 (3H, m), 7.55-7.66 (2H, m), 7.80-7.91 (1H, m), 8.11-8.18 (1H, m), 8.41 (1H, d), 8.51 (1H, s), 8.58-8.69 (1H, m).

Example 9: (S)-2-(3-(1-(2-Azabicyclo[2.2.2]octane-3-carbonyl)azetidine-3-carbonyl)-1H-pyrrolo[2,3-c]pyridin-1-yl)-N-ethyl-5-fluoro-N-isopropylbenzamide

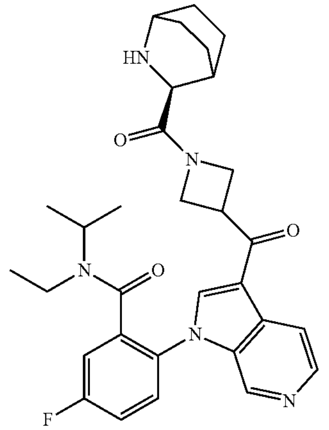 [SMILES: CCN(C(=O)c1cc(F)ccc1-n1cc(C(=O)C2CN(C(=O)[C@H]3NC4CCC3CC4)C2)c2ccncc21)C(C)C]

Step a) tert-Butyl (S)-3-(3-(1-(2-(ethyl(isopropyl)carbamoyl)-4-fluorophenyl)-1H-pyrrolo[2,3-c]pyridine-3-carbonyl)azetidine-1-carbonyl)-2-azabicyclo[2.2.2]octane-2-carboxylate

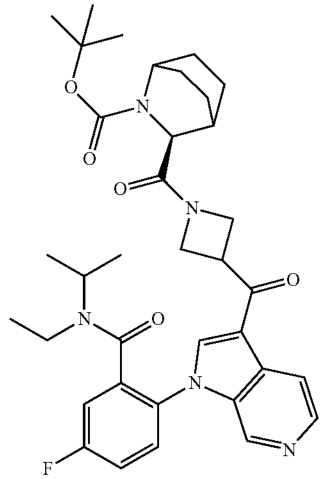 [SMILES: CCN(C(=O)c1cc(F)ccc1-n1cc(C(=O)C2CN(C(=O)[C@@H]3C4CCC(CC4)N3C(=O)OC(C)(C)C)C2)c2ccncc21)C(C)C]

Intermediate 15 (155 mg, 0.38 mmol) was added to a solution of (S)-2-(tert-butoxycarbonyl)-2-azabicyclo[2.2.2]octane-3-carboxylic acid (97.0 mg, 0.38 mmol), EDC (87.0 mg, 0.46 mmol), HOBt (69.7 mg, 0.46 mmol) and DIPEA (133 μl, 0.48 mmol) in DMF (2 mL). The resulting mixture was stirred at rt overnight. The reaction mixture was diluted with EtOAc (50 mL) and washed sequentially with aq. HCl (50 mL, 1 M) and sat. aq. $NaHCO_3$ (50 mL). The organic layer was washed with brine, dried over $Na_2SO_4$, filtered, and concentrated under reduced pressure. The residue was purified by straight phase flash chromatography on silica (gradient: 0-10% MeOH in DCM) to give the title compound (132 mg, 54%) as a yellow gum; MS m/z (ES+) $[M+H]^+$=646.3.

Step b) (S)-2-(3-(1-(2-Azabicyclo[2.2.2]octane-3-carbonyl)azetidine-3-carbonyl)-1H-pyrrolo[2,3-c]pyridin-1-yl)-N-ethyl-5-fluoro-N-isopropylbenzamide (Example 9)

TFA (1 mL) was added to a solution of tert-butyl (S)-3-(3-(1-(2-(ethyl(isopropyl)carbamoyl)-4-fluorophenyl)-1H-pyrrolo[2,3-c]pyridine-3-carbonyl)azetidine-1-carbonyl)-2-azabicyclo[2.2.2]octane-2-carboxylate from Step a) (132 mg, 0.20 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine, dried over $Na_2SO_4$, filtered, and concentrated under reduced pressure. The product was lyophilized from $MeCN/H_2O$ to give the title compound (23.9 mg, 21%) as a white solid; MS m/z (ES+) $[M+H]^+$=546.2; $^1H$ NMR (400 MHz, DMSO-$d_6$, 27° C.) δ 0.17-0.65 (6H, m), 0.85-0.99 (3H, m), 1.42-1.52 (3H, m), 1.55-1.62 (2H, m), 1.63-1.77 (3H, m), 1.83 (1H, d), 2.75-2.94 (2H, m), 3.47-3.59 (1H, m), 3.72 (1H, s), 3.87-4.33 (5H, m), 4.41-4.59 (2H, m), 7.52-7.64 (2H, m), 7.80-7.89 (1H, m), 8.10-8.18 (1H, m), 8.37-8.44 (1H, m), 8.48 (1H, s), 8.63 (1H, s).

Example 10: (1-((1R,3S,4S)-2-Azabicyclo[2.2.1]heptane-3-carbonyl)azetidin-3-yl)(1-(4-fluoro-2-(2-isopropylpyridin-3-yl)phenyl)-1H-pyrrolo[2,3-c]pyridin-3-yl)methanone

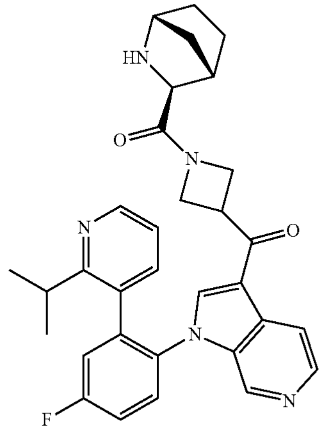 [SMILES: CC(C)c1ncccc1-c1cc(F)ccc1-n1cc(C(=O)C2CN(C(=O)[C@H]3N[C@@H]4CC[C@H]3C4)C2)c2ccncc21]

Step a) tert-Butyl (1R,3S,4S)-3-(3-(1-(4-fluoro-2-(2-isopropylpyridin-3-yl)phenyl)-1H-pyrrolo[2,3-c]pyridine-3-carbonyl)azetidine-1-carbonyl)-2-azabicyclo[2.2.1]heptane-2-carboxylate

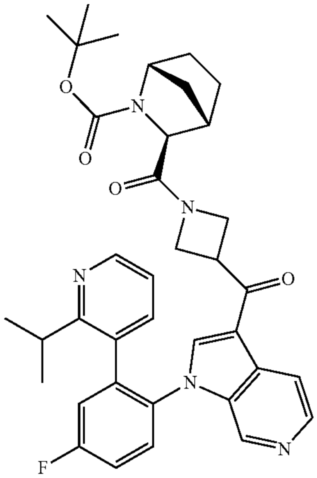 [SMILES: CC(C)c1ncccc1-c1cc(F)ccc1-n1cc(C(=O)C2CN(C(=O)[C@@H]3[C@H]4CC[C@H](C4)N3C(=O)OC(C)(C)C)C2)c2ccncc21]

Pd(dppf)$Cl_2$ (61.2 mg, 0.08 mmol) was added to Intermediate 20 (500 mg, 0.84 mmol), Intermediate 110 (414 mg, 1.67 mmol) and $K_2CO_3$ (347 mg, 2.51 mmol) in a mixture of 1,4-dioxane (5 mL) and water (1.25 mL) under $N_2$. The resulting mixture was stirred at 60° C. for 3 h. The reaction mixture was concentrated under reduced pressure. The residue was diluted with DCM (75 mL) and washed with water (100 mL). The organic layer was dried over $Na_2SO_4$, filtered, and concentrated to dryness. The crude product was purified by straight phase flash chromatography on silica (gradient: 0-80% EtOAc in petroleum ether) to give the title compound (400 mg, 75%) as a yellow solid; MS m/z (ES+) $[M+H]^+$=638.5; $^1$H NMR (300 MHz, DMSO-$d_6$, 23° C.) δ 0.47 (2H, br s), 0.90-1.11 (3H, m), 1.24-1.44 (11H, m), 1.45-1.57 (3H, m), 1.59-1.79 (3H, m), 1.87-1.98 (1H, m), 2.63-2.85 (1H, m), 3.21-3.41 (1H, m), 3.51-3.79 (2H, m), 4.11-4.19 (1H, m), 4.23-4.52 (2H, m), 7.03-7.28 (1H, m), 7.48-7.57 (1H, m), 7.62 (1H, td), 7.66-7.82 (1H, m), 7.88-7.96 (1H, m), 7.97-8.10 (1H, m), 8.28-8.48 (3H, m), 8.53-8.70 (1H, m).

Step b) (1-((1R,3S,4S)-2-Azabicyclo[2.2.1]heptane-3-carbonyl)azetidin-3-yl)(1-(4-fluoro-2-(2-isopropylpyridin-3-yl)phenyl)-1H-pyrrolo[2,3-c]pyridin-3-yl)methanone (Example 10)

FA (5 mL) was added to tert-butyl (1R,3S,4S)-3-(3-(1-(4-fluoro-2-(2-isopropylpyridin-3-yl)phenyl)-1H-pyrrolo[2,3-c]pyridine-3-carbonyl)azetidine-1-carbonyl)-2-azabicyclo[2.2.1]heptane-2-carboxylate from Step a) (400 mg, 0.63 mmol) under $N_2$. The resulting mixture was stirred at rt for 3 h. The solvent was removed under reduced pressure. The residue was quenched with sat. aq. $NaHCO_3$ (100 mL) and extracted with DCM (2×25 mL). The organic layer was dried over $Na_2SO_4$, filtered, and concentrated to dryness. The crude product was purified by preparative HPLC, Prep-Method C, (gradient: 2-20%). Appropriate fractions were pooled and concentrated under reduced pressure. The residue was diluted with DCM (100 mL) and washed with sat. aq. $NaHCO_3$ (20 mL). The organic layer was dried over $Na_2SO_4$, filtered, and concentrated to dryness to give the title compound (105 mg, 31%); MS m/z (ES+) $[M+H]^+$=538.3; $^1$H NMR (400 MHz, DMSO-$d_6$, 23° C.) δ 0.40 (2H, br s), 0.97 (3H, d), 1.09-1.18 (1H, m), 1.24 (1H, d), 1.31-1.61 (4H, m), 2.32-2.49 (1H, m), 2.55-2.88 (2H, m), 3.03-3.22 (1H, m), 3.23-3.36 (1H, m), 3.91-4.15 (3H, m), 4.20-4.46 (2H, m), 7.05-7.26 (1H, m), 7.54 (1H, dd), 7.62 (1H, td), 7.71-7.84 (1H, m), 7.86-7.95 (1H, m), 7.96-8.08 (1H, m), 8.26-8.46 (3H, m), 8.59 (1H, s).

Example 11: (1-((1R,3S,4S)-2-Azabicyclo[2.2.1]heptane-3-carbonyl)azetidin-3-yl)(1-(4-fluoro-2-(3-isopropylpyridin-4-yl)phenyl)-1H-pyrrolo[2,3-c]pyridin-3-yl)methanone 1·formic acid

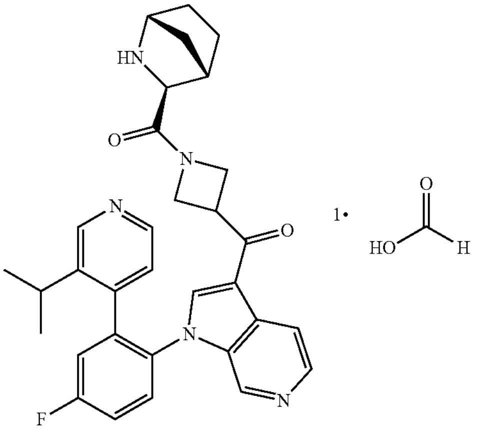 [SMILES: CC(C)c1cnccc1-c1cc(F)ccc1-n1cc(C(=O)C2CN(C(=O)[C@H]3N[C@@H]4CC[C@H]3C4)C2)c2ccncc21 ; O=CO]

Step a) tert-Butyl (1R,3S,4S)-3-(3-(1-(4-fluoro-2-(3-isopropylpyridin-4-yl)phenyl)-1H-pyrrolo[2,3-c]pyridine-3-carbonyl)azetidine-1-carbonyl)-2-azabicyclo[2.2.1]heptane-2-carboxylate

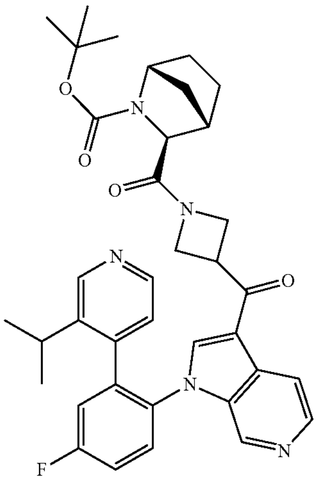 [SMILES: CC(C)c1cnccc1-c1cc(F)ccc1-n1cc(C(=O)C2CN(C(=O)[C@@H]3[C@H]4CC[C@H](C4)N3C(=O)OC(C)(C)C)C2)c2ccncc21]

Pd(dppf)$Cl_2$ (24.5 mg, 0.03 mmol) was added to Intermediate 20 (200 mg, 0.33 mmol), Intermediate 114 (248 mg, 1.00 mmol) and $K_2CO_3$ (139 mg, 1.00 mmol) in a mixture of 1,4-dioxane (3 mL) and water (750 μL) under $N_2$. The resulting mixture was stirred at 60° C. for 1 h. The reaction mixture was concentrated under reduced pressure. The residue was diluted with EtOAc (100 mL) and washed with sat. aq. $NH_4Cl$ (2×75 mL). The organic layer was dried over $Na_2SO_4$, filtered, and concentrated to dryness. The crude product was purified by preparative TLC on silica (EtOAc) to give the title compound (110 mg, 52%) as a yellow solid; MS m/z (ES+) $[M+H]^+$=638.3.

Step b) (1-((1R,3S,4S)-2-Azabicyclo[2.2.1]heptane-3-carbonyl)azetidin-3-yl)(1-(4-fluoro-2-(3-isopropylpyridin-4-yl)phenyl)-1H-pyrrolo[2,3-c]pyridin-3-yl)methanone 0.6·formic acid (Example 11)

FA (1 mL) was added to tert-butyl (1R,3S,4S)-3-(3-(1-(4-fluoro-2-(3-isopropylpyridin-4-yl)phenyl)-1H-pyrrolo[2,3-c]pyridine-3-carbonyl)azetidine-1-carbonyl)-2-azabicyclo[2.2.1]heptane-2-carboxylate from Step a) (100 mg, 0.16 mmol) under $N_2$. The resulting mixture was stirred at rt for 3 h. The solvent was removed under reduced pressure. The residue was quenched with sat. aq. $NaHCO_3$ (50 mL) and extracted with DCM (2×25 mL). The organic layer was dried over $Na_2SO_4$, filtered, and concentrated to dryness. The crude product was purified by preparative HPLC, Prep-Method D, (gradient: 5-30%). Appropriate fractions were pooled and concentrated under reduced pressure to give the title compound (24.1 mg, 27%); MS m/z (ES+) $[M+H]^+$=538.4; $^1H$ NMR (400 MHz, DMSO-$d_6$, 26° C.) δ 0.52 (2H, br s), 0.95-1.09 (3H, m), 1.18-1.38 (3H, m), 1.39-1.74 (4H, m), 3.31 (1H, br s), 3.50-3.66 (2H, m), 4.00-4.19 (3H, m), 4.23-4.53 (2H, m), 7.23-7.47 (2H, m), 7.50-7.57 (1H, m), 7.64 (1H, td), 7.88-7.98 (1H, m), 8.01-8.09 (1H, m), 8.20 (1H, s), 8.26-8.45 (3H, m), 8.56-8.68 (1H, m).

Example 12: (1-((1R,3S,4S)-2-Azabicyclo[2.2.1]heptane-3-carbonyl)azetidin-3-yl)(1-(4-fluoro-2-(4-isopropylthiazol-5-yl)phenyl)-1H-pyrrolo[2,3-c]pyridin-3-yl)methanone 1·formic acid

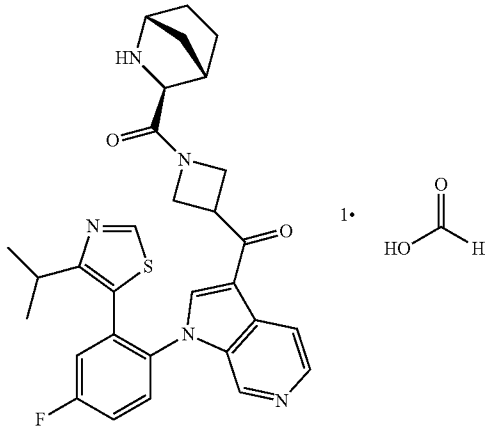 [SMILES: CC(C)c1ncsc1-c1cc(F)ccc1-n1cc(C(=O)C2CN(C(=O)[C@H]3N[C@@H]4CC[C@H]3C4)C2)c2ccncc21 ; O=CO]

Step a) tert-Butyl (1R,3S,4S)-3-(3-(1-(4-fluoro-2-(4-isopropylthiazol-5-yl)phenyl)-1H-pyrrolo[2,3-c]pyridine-3-carbonyl)azetidine-1-carbonyl)-2-azabicyclo[2.2.1]heptane-2-carboxylate

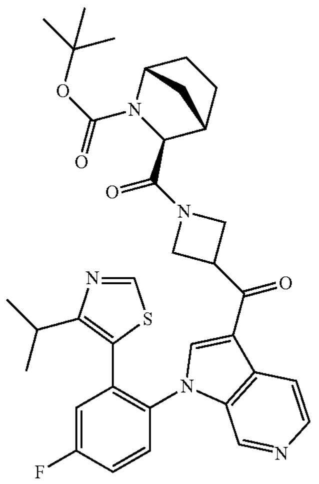 [SMILES: CC(C)c1ncsc1-c1cc(F)ccc1-n1cc(C(=O)C2CN(C(=O)[C@@H]3[C@H]4CC[C@H](C4)N3C(=O)OC(C)(C)C)C2)c2ccncc21]

$Pd(dppf)Cl_2$ (18.4 mg, 0.03 mmol) was added to Intermediate 20 (150 mg, 0.25 mmol), Intermediate 122 (127 mg, 0.50 mmol) and $K_2CO_3$ (104 mg, 0.75 mmol) in a mixture of 1,4-dioxane (1 mL) and water (250 μL) under $N_2$. The resulting mixture was stirred at 60° C. for 16 h. The reaction mixture was concentrated under reduced pressure. The residue was diluted with DCM (50 mL) and washed with water (50 mL). The organic layer was dried over $Na_2SO_4$, filtered, and concentrated to dryness. The crude product was purified by preparative TLC on silica (EtOAc) to give the title compound (100 mg, 62%) as a yellow solid; MS m/z (ES+) $[M+H]^+$=644.4.

Step b) (1-((1R,3S,4S)-2-Azabicyclo[2.2.1]heptane-3-carbonyl)azetidin-3-yl)(1-(4-fluoro-2-(4-isopropylthiazol-5-yl)phenyl)-1H-pyrrolo[2,3-c]pyridin-3-yl)methanone 1·formic acid (Example 12)

FA (1 mL) was added to tert-butyl (1R,3S,4S)-3-(3-(1-(4-fluoro-2-(4-isopropylthiazol-5-yl)phenyl)-1H-pyrrolo[2,3-c]pyridine-3-carbonyl)azetidine-1-carbonyl)-2-azabicyclo[2.2.1]heptane-2-carboxylate from Step a) (100 mg, 0.16 mmol) under $N_2$. The resulting mixture was stirred at rt for 1 h. The solvent was removed under reduced pressure. The residue was quenched with sat. aq. $NaHCO_3$ (50 mL) and extracted with DCM (2×25 mL). The organic layer was dried over $Na_2SO_4$, filtered, and concentrated to dryness. The crude product was purified by preparative HPLC, Prep-Method E, (gradient: 10-40%). Appropriate fractions were pooled and concentrated under reduced pressure to give the title compound (27.8 mg, 29%); MS m/z (ES+) $[M+H]^+$=544.3; $^1H$ NMR (400 MHz, DMSO-$d_6$, 23° C.) δ 0.79-1.22 (6H, m), 1.37-1.48 (2H, m), 1.49-1.57 (1H, m), 1.59-1.66 (3H, m), 2.59-2.69 (1H, m), 2.84-2.96 (1H, m), 3.69 (1H, d), 3.84 (1H, d), 4.08-4.25 (3H, m), 4.37-4.54 (1H, m), 7.55 (1H, dd), 7.63 (1H, td), 7.86-7.92 (1H, m), 8.06-8.09 (1H, m), 8.27 (1H, s), 8.35 (1H, d), 8.37-8.52 (2H, m), 8.84 (1H, d).

Example 13: (1-((1R,3S,4S)-2-Azabicyclo[2.2.1]heptane-3-carbonyl)azetidin-3-yl)(1-(4-fluoro-2-(2-(2-fluoropropan-2-yl)pyridin-3-yl)phenyl)-1H-pyrrolo[2,3-c]pyridin-3-yl)methanone

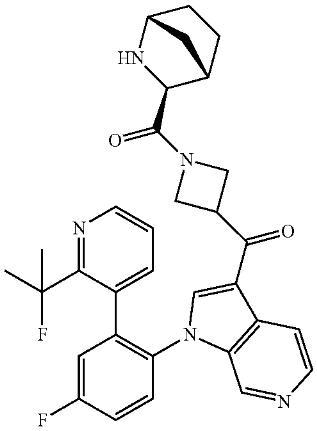 [SMILES: CC(C)(F)c1ncccc1-c1cc(F)ccc1-n1cc(C(=O)C2CN(C(=O)[C@H]3N[C@@H]4CC[C@H]3C4)C2)c2ccncc21]

Step a) tert-Butyl (1R,3S,4S)-3-(3-(1-(4-fluoro-2-(2-(2-fluoropropan-2-yl)pyridin-3-yl)phenyl)-1H-pyrrolo[2,3-c]pyridine-3-carbonyl)azetidine-1-carbonyl)-2-azabicyclo[2.2.1]-heptane-2-carboxylate

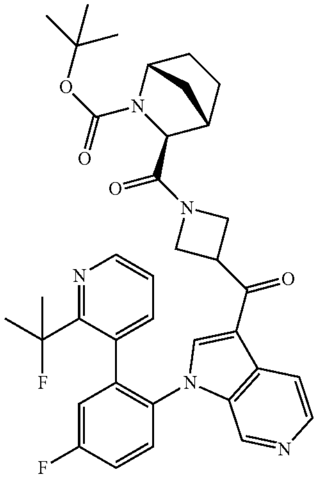 [SMILES: CC(C)(C)OC(=O)N1[C@@H]2CC[C@@H](C2)[C@H]1C(=O)N1CC(C(=O)c2cn(-c3ccc(F)cc3-c3cccnc3C(C)(C)F)c3cnccc23)C1]

$Pd(dppf)Cl_2$ (18.4 mg, 0.03 mmol) was added to Intermediate 20 (150 mg, 0.25 mmol), Intermediate 125 (399 mg, 1.51 mmol) and $K_2CO_3$ (104 mg, 0.75 mmol) in a mixture of 1,4-dioxane (3 mL) and water (750 μL) under $N_2$. The resulting mixture was stirred at 60° C. for 16 h. The reaction mixture was concentrated under reduced pressure. The residue was diluted with DCM (125 mL) and washed with water (2×75 mL). The organic layer was dried over $Na_2SO_4$, filtered, and concentrated to dryness. The crude product was purified by preparative TLC on silica (EtOAc) to give the title compound (80.0 mg) as a yellow solid which was used directly in the next step; MS m/z (ES+) $[M+H]^+$=656.3.

Step b) (1-((1R,3S,4S)-2-Azabicyclo[2.2.1]heptane-3-carbonyl)azetidin-3-yl)(1-(4-fluoro-2-(2-(2-fluoropropan-2-yl)pyridin-3-yl)phenyl)-1H-pyrrolo[2,3-c]pyridin-3-yl)-methanone (Example 13)

FA (1 mL) was added to tert-butyl (1R,3S,4S)-3-(3-(1-(4-fluoro-2-(2-(2-fluoropropan-2-yl)pyridin-3-yl)phenyl)-1H-pyrrolo[2,3-c]pyridine-3-carbonyl)azetidine-1-carbonyl)-2-azabicyclo[2.2.1]heptane-2-carboxylate from Step a) (80.0 mg) under $N_2$. The resulting mixture was stirred at rt for 1 h. The solvent was removed under reduced pressure. The residue was quenched with sat. aq. $NaHCO_3$ (50 mL) and extracted with DCM (2×25 mL). The organic layer was dried over $Na_2SO_4$, filtered, and concentrated to dryness. The crude product was purified by preparative HPLC, Prep-Method F, (gradient: 0-22%). Appropriate fractions were pooled and concentrated under reduced pressure. The residue was quenched with sat. aq. $NaHCO_3$ (10 mL) and extracted with DCM (2×25 mL). The combined organic layers were dried over $Na_2SO_4$, filtered, and concentrated to dryness to give the title compound (13.4 mg, 10% over two steps); MS m/z (ES+) $[M+H]^+$=556.2; $^1H$ NMR (400 MHz, DMSO-$d_6$, 26° C.) δ 0.99-1.18 (3H, m), 1.19-1.29 (2H, m), 1.31-1.42 (2H, m), 1.47-1.55 (3H, m), 1.55-1.61 (2H, m), 2.37-2.46 (1H, m), 3.07-3.18 (1H, m), 3.35-3.40 (1H, m), 3.93-4.19 (3H, m), 4.21-4.47 (2H, m), 7.19-7.30 (1H, m), 7.48-7.54 (2H, m), 7.71-7.85 (2H, m), 7.99-8.03 (1H, m), 8.26 (1H, s), 8.29-8.35 (1H, m), 8.40-8.46 (1H, m), 8.52 (1H, s).

Example 14: 2-(5-(1-((1R,3S,4S)-2-Azabicyclo[2.2.1]heptane-3-carbonyl)azetidine-3-carbonyl)-7H-pyrrolo[2,3-c]pyridazin-7-yl)-5-fluoro-N,N-diisopropylbenzamide 1·formic acid

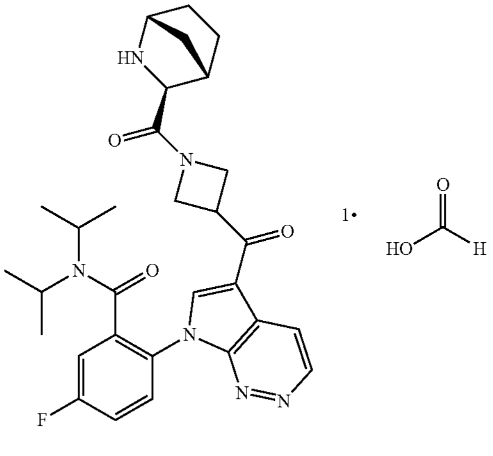 [SMILES: CC(C)N(C(=O)c1cc(F)ccc1-n1cc(C(=O)C2CN(C(=O)[C@H]3N[C@@H]4CC[C@H]3C4)C2)c2ccnnc21)C(C)C ; O=CO]

Step a) tert-Butyl (1R,3S,4S)-3-(3-(7-(2-(diisopropylcarbamoyl)-4-fluorophenyl)-7H-pyrrolo[2,3-c]pyridazine-5-carbonyl)azetidine-1-carbonyl)-2-azabicyclo[2.2.1]heptane-2-carboxylate

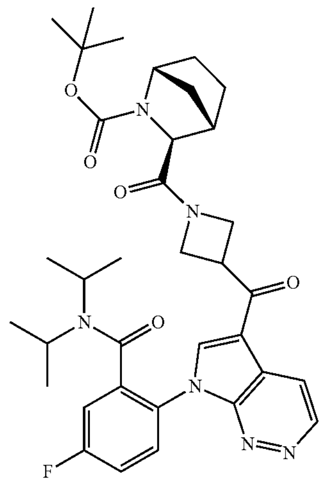

T3P (721 mg, 1.13 mmol, 50% in EtOAc) was added to a mixture of Intermediate 29 (160 mg, 0.38 mmol th.), (1R,3S,4S)-2-(tert-butoxycarbonyl)-2-azabicyclo[2.2.1]heptane-3-carboxylic acid (109 mg, 0.45 mmol) and DIPEA (198 μL, 1.13 mmol) in DCM (5 mL) at 0° C. under $N_2$. The resulting mixture was stirred at rt for 1 h. The reaction mixture was quenched with water (50 mL) and extracted with DCM (3×25 mL). The combined organic layers were dried over $Na_2SO_4$, filtered, and concentrated to dryness. The residue was purified by preparative TLC on silica (EtOAc) to give the title compound (165 mg, 68%) as a pale yellow solid; MS m/z (ES+) $[M+H]^+$=647.4; $^1$H NMR (300 MHz, $CDCl_3$, 23° C.) δ 0.14-0.33 (3H, m), 0.97-1.07 (6H, m), 1.42-1.44 (2H, m), 1.45-1.47 (9H, m), 1.52-1.93 (4H, m), 2.06-2.15 (1H, m), 2.19-2.55 (3H, m), 2.58-2.91 (2H, m), 3.14-3.31 (1H, m), 3.57-3.78 (2H, m), 4.18-4.26 (1H, m), 4.27-4.34 (1H, m), 4.36-4.80 (2H, m), 7.08-7.21 (1H, m), 7.30-7.39 (1H, m), 7.69-7.79 (1H, m), 8.25-8.42 (1H, m), 8.42-8.53 (1H, m), 9.18-9.27 (1H, m).

Step b) 2-(5-(1-((1R,3S,4S)-2-Azabicyclo[2.2.1]heptane-3-carbonyl)azetidine-3-carbonyl)-7H-pyrrolo[2,3-c]pyridazin-7-yl)-5-fluoro-N,N-diisopropylbenzamide 1·formic acid (Example 14)

FA (4 mL) was added to tert-butyl (1R,3S,4S)-3-(3-(7-(2-(diisopropylcarbamoyl)-4-fluorophenyl)-7H-pyrrolo[2,3-c]pyridazine-5-carbonyl)azetidine-1-carbonyl)-2-azabicyclo[2.2.1]heptane-2-carboxylate from Step a) (133 mg, 0.21 mmol). The resulting mixture was stirred at rt for 1 h. The solvent was removed under reduced pressure. The residue was quenched with sat. aq. $NaHCO_3$ (50 mL) and extracted with DCM (3×25 mL). The combined organic layers were dried over $Na_2SO_4$, filtered, and concentrated to dryness. The crude product was purified by preparative HPLC, Prep-Method G (gradient: 8-29%) to give the title compound (86.8 mg, 69%) as a pale yellow solid; MS m/z (ES+) $[M+H]^+$=547.3; $^1$H NMR (400 MHz, DMSO-$d_6$, 26° C.) δ 0.33-0.52 (3H, m), 0.67-0.79 (3H, m), 1.02-1.13 (3H, m), 1.28-1.35 (4H, m), 1.36-1.50 (2H, m), 1.51-1.64 (3H, m), 2.53-2.66 (1H, m), 3.19-3.33 (1H, m), 3.57-3.73 (2H, m), 3.99-4.29 (2H, m), 4.30-4.42 (2H, m), 4.44-4.67 (2H, m), 7.48-7.55 (1H, m), 7.58 (1H, td), 7.89 (1H, dd), 8.28 (1H, s), 8.34-8.41 (1H, m), 8.78-8.84 (1H, m), 9.19 (1H, d).

Example 15: 2-(3-(1-((1R,3S,4S)-2-Azabicyclo[2.2.1]heptane-3-carbonyl)azetidine-3-carbonyl)-7-fluoro-1H-pyrrolo[2,3-c]pyridin-1-yl)-5-fluoro-N,N-diisopropylbenzamide

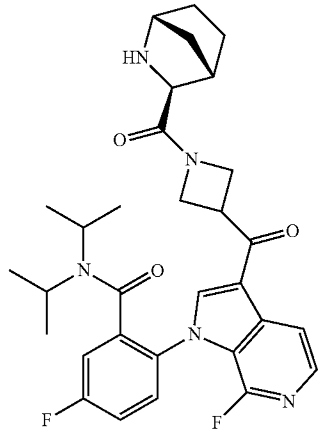 [SMILES: CC(C)N(C(=O)c1cc(F)ccc1-n1cc(C(=O)C2CN(C(=O)[C@H]3N[C@@H]4CC[C@H]3C4)C2)c2ccnc(F)c21)C(C)C]

Step a) tert-Butyl (1R,3S,4S)-3-(3-(1-(2-(diisopropylcarbamoyl)-4-fluorophenyl)-7-fluoro-1H-pyrrolo[2,3-c]pyridine-3-carbonyl)azetidine-1-carbonyl)-2-azabicyclo[2.2.1]-heptane-2-carboxylate

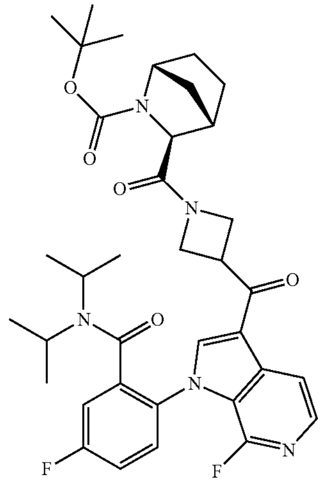 [SMILES: CC(C)N(C(=O)c1cc(F)ccc1-n1cc(C(=O)C2CN(C(=O)[C@@H]3[C@H]4CC[C@H](C4)N3C(=O)OC(C)(C)C)C2)c2ccnc(F)c21)C(C)C]

Intermediate 34 (86.0 mg, 0.14 mmol th.) was added to a solution of (1R,3S,4S)-2-(tert-butoxycarbonyl)-2-azabicyclo[2.2.1]heptane-3-carboxylic acid (56.5 mg, 0.23 mmol), HATU (97.0 mg, 0.25 mmol) and DIPEA (102 μL, 0.59 mmol) in DMF (4 mL). The reaction mixture was stirred at rt for 1 h. The mixture was diluted with EtOAc (50 mL), washed with sat. aq. $NaHCO_3$ (20 mL) and brine (2×20 mL). The organic layer was passed through a phase separator and concentrated under reduced pressure. The residue was purified by straight phase flash chromatography on silica (gradient: 0-80% EtOAc in heptane) to afford the title compound (68.0 mg, 74%) as a colorless solid; MS m/z (ES+)

[M+Na]$^+$=686.3; $^1$H NMR (400 MHz, $CDCl_3$, 22° C.) δ 0.31-0.44 (3H, m), 0.93-1.11 (6H, m), 1.24-1.34 (3H, m), 1.40-1.48 (12H, m), 1.60-1.81 (3H, m), 1.99-2.13 (1H, m), 3.14-3.28 (1H, m), 3.53-3.65 (1H, m), 3.70-3.86 (1H, m), 3.97-4.11 (1H, m), 4.13-4.35 (3H, m), 4.50-4.82 (2H, m), 7.10 (1H, d), 7.18-7.28 (1H, m), 7.42-7.53 (1H, m), 7.97-8.13 (2H, m), 8.19-8.28 (1H, m).

Step b) 2-(3-(1-((1R,3S,4S)-2-Azabicyclo[2.2.1]heptane-3-carbonyl)azetidine-3-carbonyl)-7-fluoro-1H-pyrrolo[2,3-c]pyridin-1-yl)-5-fluoro-N,N-diisopropylbenzamide (Example 15)

TFA (117 L) was added to a solution of tert-butyl (1R,3S,4S)-3-(3-(1-(2-(diisopropylcarbamoyl)-4-fluorophenyl)-7-fluoro-1H-pyrrolo[2,3-c]pyridine-3-carbonyl)azetidine-1-carbonyl)-2-azabicyclo[2.2.1]heptane-2-carboxylate from Step a) (68.0 mg, 0.10 mmol) in DCM (3 mL). The mixture was stirred at rt for 6 h. The mixture was diluted with EtOAc (30 mL), washed sequentially with sat. aq. $NaHCO_3$ (10 mL) and brine (5 mL). The organic layer was passed through a phase separator and concentrated under reduced pressure. The residue was purified by preparative HPLC, PrepMethod A, (gradient: 0-75%). Appropriate fractions were pooled, diluted with EtOAc and washed with sat. aq. $NaHCO_3$ and brine. The organic layer was passed through a phase separator and concentrated under reduced pressure. The product was lyophilized from MeCN/$H_2O$ to give the title compound (11.7 mg, 20%) as a colorless solid; MS m/z (ES+) [M+H]$^+$=564.3. $^1$H NMR (400 MHz, $CDCl_3$, 22° C.) δ 0.28-0.46 (3H, m), 0.96-1.02 (2H, m), 1.02-1.09 (3H, m), 1.17-1.33 (2H, m), 1.45 (5H, d), 1.54-1.62 (3H, m), 2.43-2.59 (1H, m), 3.15-3.34 (2H, m), 3.52-3.65 (2H, m), 4.02-4.66 (6H, m), 7.10 (1H, dt), 7.21-7.31 (1H, m), 7.42-7.54 (1H, m), 7.99-8.14 (2H, m), 8.19-8.28 (1H, m).

Example 16: 2-(3-(1-((1R,3S,4S)-2-Azabicyclo[2.2.1]heptane-3-carbonyl)piperidine-4-carbonyl)-1H-pyrrolo[2,3-c]pyridin-1-yl)-5-fluoro-N,N-diisopropylbenzamide

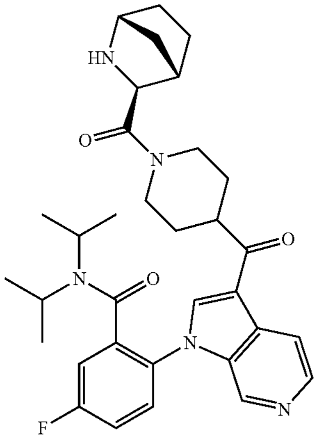 [SMILES: CC(C)N(C(=O)c1cc(F)ccc1-n1cc(C(=O)C2CCN(C(=O)[C@H]3N[C@@H]4CC[C@H]3C4)CC2)c2ccncc21)C(C)C]

Step a) tert-Butyl (1R,3S,4S)-3-(4-(1-(2-(diisopropylcarbamoyl)-4-fluorophenyl)-1H-pyrrolo[2,3-c]pyridine-3-carbonyl)piperidine-1-carbonyl)-2-azabicyclo[2.2.1]heptane-2-carboxylate

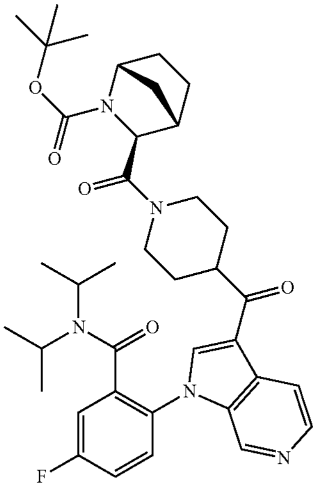 [SMILES: CC(C)N(C(=O)c1cc(F)ccc1-n1cc(C(=O)C2CCN(C(=O)[C@@H]3[C@H]4CC[C@H](C4)N3C(=O)OC(C)(C)C)CC2)c2ccncc21)C(C)C]

Intermediate 39 (1.00 g, 1.78 mmol th., LC-UV purity 80%) was added to a solution of (1R,3S,4S)-2-(tert-butoxycarbonyl)-2-azabicyclo[2.2.1]heptane-3-carboxylic acid (428 mg, 1.78 mmol), EDC (408 mg, 2.13 mmol), HOBt (326 mg, 2.13 mmol) and DIPEA (620 μL, 3.55 mmol) in DMF (15 mL). The resulting mixture was stirred at rt overnight. The reaction mixture was diluted with EtOAc (50 mL) and washed sequentially with aq. HCl (50 mL, 1 M) and sat. aq. $NaHCO_3$ (50 mL). The organic layer was washed with brine (50 mL), dried over $Na_2SO_4$, filtered, and concentrated under reduced pressure. The residue was purified by straight phase flash chromatography on silica (gradient: 0-5% MeOH in DCM) to give the title compound in a quantitative yield (1.33 g) as a light yellow foam; MS m/z (ES+) [M+H]$^+$=674.3; $^1$H NMR (400 MHz, DMSO-$d_6$, 22° C.) δ 0.31 (3H, br s), 0.73 (3H, br s), 0.99 (3H, d), 1.10-1.25 (2H, m), 1.27-1.41 (12H, m), 1.45-1.70 (6H, m), 1.70-1.90 (3H, m), 2.63-2.75 (1H, m), 3.11-3.28 (2H, m), 3.43-3.55 (2H, m), 3.97-4.16 (3H, m), 4.32-4.52 (1H, m), 7.51-7.60 (2H, m), 7.80-7.88 (1H, m), 8.09-8.17 (1H, m), 8.34-8.40 (1H, m), 8.60-8.75 (2H, m).

Step b) 2-(3-(1-((1R,3S,4S)-2-Azabicyclo[2.2.1]heptane-3-carbonyl)piperidine-4-carbonyl)-1H-pyrrolo[2,3-c]pyridin-1-yl)-5-fluoro-N,N-diisopropylbenzamide (Example 16)

TFA (5 mL) was added to a solution of tert-butyl (1R,3S,4S)-3-(4-(1-(2-(diisopropylcarbamoyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (926 mg, 1.37 mmol th.) in DCM (25 mL). The mixture was stirred at rt for 2 h. The mixture was concentrated under reduced pressure. The residue was dissolved in DCM (100 mL), washed sequentially with sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-20% 0.7 M $NH_3$ in MeOH in DCM) to give the title compound (691 mg, 88%) as a light yellow gum; MS m/z (ES+) $[M+H]^+$=574.3; $^1H$ NMR (400 MHz, DMSO-$d_6$, 22° C.) δ 0.28 (3H, br s), 0.74 (3H, br s), 0.99 (3H, d), 1.20-1.30 (2H, m), 1.33 (3H, d), 1.40-1.58 (5H, m), 1.59-1.73 (1H, m), 1.76-1.92 (2H, m), 2.42-2.47 (1H, m), 2.73-2.86 (1H, m), 3.13-3.27 (3H, m), 3.44-3.66 (4H, m), 3.88-4.02 (1H, m), 4.34-4.49 (1H, m), 7.48-7.61 (2H, m), 7.79-7.91 (1H, m), 8.07-8.17 (1H, m), 8.38 (1H, d), 8.58-8.75 (2H, m).

Example 17: 5-Fluoro-N,N-diisopropyl-2-(3-(1-(((1r,4r)-4-(methylsulfonamido)cyclohexyl)-methyl) piperidine-4-carbonyl)-1H-pyrrolo[2,3-c]pyridin-1-yl)benzamide

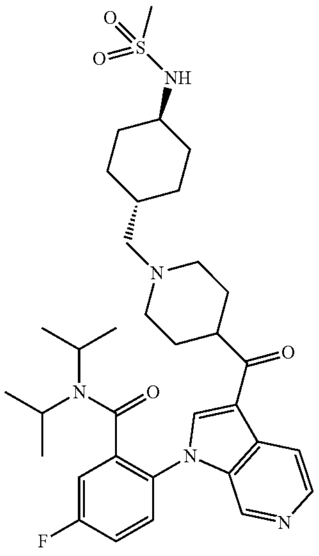 [SMILES: CC(C)N(C(=O)c1cc(F)ccc1-n1cc(C(=O)C2CCN(C[C@H]3CC[C@H](NS(C)(=O)=O)CC3)CC2)c2ccncc21)C(C)C]

A suspension of Intermediate 39 (35.0 mg, 0.08 mmol) and $K_2CO_3$ (53.7 mg, 0.39 mmol) in MeCN (1 mL) was stirred at rt for 30 minutes before Intermediate 104 (28.1 mg, 0.08 mmol) was added. The reaction mixture was stirred at 80° C. overnight. The reaction mixture was diluted with water (20 mL) and extracted with EtOAc (3×20 mL). The combined organic layers were washed with brine, dried over $Na_2SO_4$, filtered, and concentrated under reduced pressure. The residue was purified by preparative HPLC, PrepMethod A, (gradient: 0-50%). Appropriate fractions were pooled, diluted with sat. aq. $NaHCO_3$ (20 mL) and extracted with EtOAc (2×20 mL). The combined organic layers were washed with brine, dried over $Na_2SO_4$, filtered, and concentrated under reduced pressure. The product was lyophilized from MeCN/$H_2O$ to give the title compound (12.5 mg, 25%) as a white solid; MS m/z (ES+) $[M+H]^+$=640.4; $^1H$ NMR (400 MHz, DMSO-$d_6$, 22° C.) δ 0.30 (3H, br s), 0.76 (3H, br s), 0.83-0.94 (2H, m), 0.99 (3H, d), 1.13-1.26 (3H, m), 1.32 (3H, d), 1.36-1.44 (1H, m), 1.61-1.80 (6H, m), 1.86-2.00 (4H, m), 2.07 (2H, d), 2.82-2.87 (1H, m), 2.89 (3H, s), 2.99-3.16 (2H, m), 3.20-3.27 (1H, m), 3.45-3.54

(1H, m), 6.98 (1H, d), 7.49-7.58 (2H, m), 7.84 (1H, dd), 8.09-8.16 (1H, m), 8.37 (1H, d), 8.56 (1H, s), 8.64 (1H, s).

Example 18: 5-Fluoro-N,N-diisopropyl-2-(3-(1-((1S,3S,4R)-5-methylene-2-azabicyclo[2.2.2]-octane-3-carbonyl)piperidine-4-carbonyl)-1H-pyrrolo[2,3-c]pyridin-1-yl)benzamide

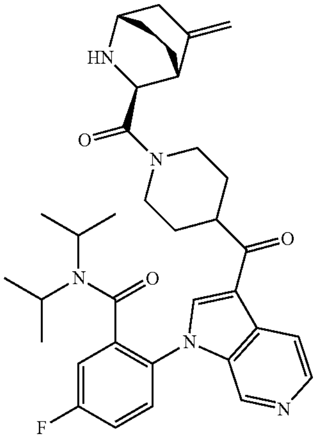 [SMILES: C=C1C[C@@H]2CC[C@H]1[C@@H](C(=O)N1CCC(C(=O)c3cn(-c4ccc(F)cc4C(=O)N(C(C)C)C(C)C)c4cnccc34)CC1)N2]

Step a) tert-Butyl (1S,3S,4R)-3-(4-(1-(2-(diisopropylcarbamoyl)-4-fluorophenyl)-1H-pyrrolo[2,3-c]pyridine-3-carbonyl)piperidine-1-carbonyl)-5-methylene-2-azabicyclo[2.2.2]-octane-2-carboxylate

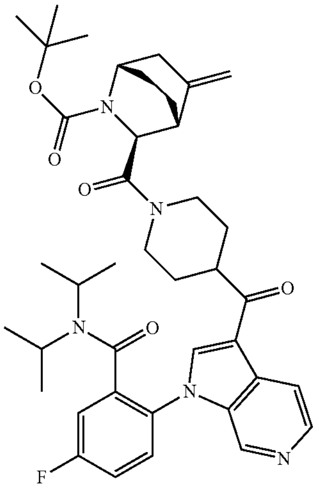 [SMILES: C=C1C[C@@H]2CC[C@H]1[C@@H](C(=O)N1CCC(C(=O)c3cn(-c4ccc(F)cc4C(=O)N(C(C)C)C(C)C)c4cnccc34)CC1)N2C(=O)OC(C)(C)C]

Intermediate 39 (70.0 mg, 0.16 mmol) was added to a solution of (1S,3S,4R)-2-(tert-butoxycarbonyl)-5-methylene-2-azabicyclo[2.2.2]octane-3-carboxylic acid [synthesis described in US 20200157114 A1](41.5 mg, 0.16 mmol), EDC (35.7 mg, 0.19 mmol), HOBt (28.6 mg, 0.19 mmol) and DIPEA (54.3 μl, 0.31 mmol) in DMF (1 mL). The resulting mixture was stirred at rt overnight. The reaction mixture was diluted with EtOAc and washed with aq. HCl (1 M) and sat. aq. $NaHCO_3$. The organic layer was washed with brine, dried over $Na_2SO_4$, filtered, and concentrated under reduced pressure. The residue was purified by straight phase flash chromatography on silica (gradient: 0-5% MeOH in DCM) to give the title compound (75.3 mg, 69%) as a colorless gum; MS m/z (ES+) $[M+H]^+$=700.4.

Step b) 5-Fluoro-N,N-diisopropyl-2-(3-(1-((1S,3S,4R)-5-methylene-2-azabicyclo[2.2.2]-octane-3-carbonyl)piperidine-4-carbonyl)-1H-pyrrolo[2,3-c]pyridin-1-yl)benzamide (Example 18)

TFA (500 μL) was added to a solution of tert-butyl (1S,3S,4R)-3-(4-(1-(2-(diisopropylcarbamoyl)-4-fluorophenyl)-1H-pyrrolo[2,3-c]pyridine-3-carbonyl)piperidine-1-carbonyl)-5-methylene-2-azabicyclo[2.2.2]octane-2-carboxylate from Step a) (75.3 mg, 0.11 mmol) in DCM (3 mL). The mixture was stirred at rt for 30 minutes. The reaction mixture was concentrated under reduced pressure. The residue was dissolved in EtOAc (20 mL) and washed with sat. aq. $NaHCO_3$ (20 mL). The organic layer was washed with brine (20 mL), dried over $Na_2SO_4$, filtered, and concentrated under reduced pressure. The product was lyophilized from $MeCN/H_2O$ to give the title compound (38.7 mg, 60%) as a white solid; MS m/z (ES+) $[M+H]^+$=600.3; $^1H$ NMR (400 MHz, DMSO-$d_6$, 22° C.) δ 0.29 (3H, br s), 0.67-0.86 (3H, m), 0.99 (3H, d), 1.33 (3H, d), 1.38-1.75 (7H, m), 1.77-1.94 (2H, m), 2.22-2.44 (3H, m), 2.75-2.87 (1H, m), 3.05 (1H, s), 3.15-3.27 (2H, m), 3.44-3.54 (2H, m), 3.70-3.84 (1H, m), 3.89-3.98 (1H, m), 4.44-4.56 (1H, m), 4.74 (1H, s), 4.93 (1H, s), 7.51-7.58 (2H, m), 7.83-7.89 (1H, m), 8.09-8.15 (1H, m), 8.38 (1H, d), 8.61-8.72 (2H, m).

Example 19: 2-(3-(1-((1S,2S,5R)-3-Azabicyclo[3.1.0]hexane-2-carbonyl)piperidine-4-carbonyl)-1H-pyrrolo[2,3-c]pyridin-1-yl)-5-fluoro-N,N-diisopropylbenzamide

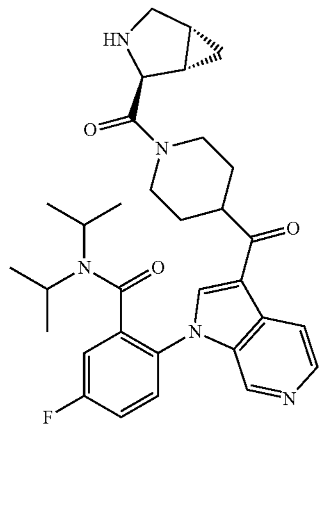 [SMILES: CC(C)N(C(=O)c1cc(F)ccc1-n1cc(C(=O)C2CCN(C(=O)[C@H]3NC[C@@H]4C[C@@H]43)CC2)c2ccncc21)C(C)C]

Step a) tert-Butyl (1S,2S,5R)-2-(4-(1-(2-(diisopropylcarbamoyl)-4-fluorophenyl)-1H-pyrrolo[2,3-c]pyridine-3-carbonyl)piperidine-1-carbonyl)-3-azabicyclo[3.1.0]hexane-3-carboxylate

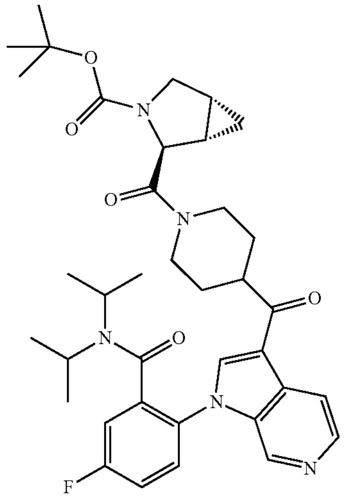 [SMILES: CC(C)N(C(=O)c1cc(F)ccc1-n1cc(C(=O)C2CCN(C(=O)[C@@H]3[C@H]4C[C@H]4CN3C(=O)OC(C)(C)C)CC2)c2ccncc21)C(C)C]

Intermediate 39 (1.00 g, 1.78 mmol th., LC-UV purity 80%) was added to a solution of (1S,2S,5R)-3-(tert-butoxycarbonyl)-3-azabicyclo[3.1.0]hexane-2-carboxylic acid (404 mg, 1.78 mmol), EDC (408 mg, 2.13 mmol), HOBt (326 mg, 2.13 mmol) and DIPEA (620 μl, 3.55 mmol) in DMF (15 mL). The resulting mixture was stirred at rt overnight. The reaction mixture was diluted with EtOAc (50 mL) and washed sequentially with aq. HCl (50 mL, 1 M) and sat. aq. $NaHCO_3$ (50 mL). The organic layer was washed with brine (50 mL), dried over $Na_2SO_4$, filtered, and concentrated under reduced pressure. The residue was purified by straight phase flash chromatography on silica (gradient: 0-10% MeOH in DCM) to give the title compound (1.14 g, 97%) as an orange foam; MS m/z (ES+) $[M+H]^+$=660.3; $^1H$ NMR (400 MHz, DMSO-$d_6$, 22° C.) δ 0.11-0.45 (4H, m), 0.60-0.85 (4H, m), 0.99 (3H, d), 1.28-1.41 (12H, m), 1.43-1.74 (4H, m), 1.80-1.94 (2H, m), 2.75-2.86 (1H, m), 3.19-3.29 (2H, m), 3.36-3.56 (4H, m), 4.03-4.17 (1H, m), 4.34-4.52 (1H, m), 4.54-4.66 (1H, m), 7.51-7.59 (2H, m), 7.86 (1H, dd), 8.10-8.17 (1H, m), 8.37 (1H, dd), 8.61-8.74 (2H, m).

Step b) 2-(3-(1-((1S,2S,5R)-3-Azabicyclo[3.1.0]hexane-2-carbonyl)piperidine-4-carbonyl)-1H-pyrrolo[2,3-c]pyridin-1-yl)-5-fluoro-N,N-diisopropylbenzamide (Example 19)

TFA (5 mL) was added to a solution of tert-butyl (1S,2S,5R)-2-(4-(1-(2-(diisopropylcarbamoyl)-4-fluorophenyl)-1H-pyrrolo[2,3-c]pyridine-3-carbonyl)piperidine-1-carbonyl)-3-azabicyclo[3.1.0]hexane-3-carboxylate from Step a) (1.14 g, 1.73 mmol) in DCM (25 mL). The mixture was stirred at rt for 2 h. The mixture was concentrated under reduced pressure. The residue was dissolved in DCM (100 mL), washed sequentially with sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-20% 0.7 M $NH_3$ in MeOH in DCM). The product was lyophilized from $MeCN/H_2O$ to give the title compound (731 mg, 76%) as a light orange solid; MS m/z (ES+) $[M+H]^+$=560.4; $^1$H NMR (400 MHz, DMSO-$d_6$, 22° C.) δ 0.15-0.55 (5H, m), 0.74 (3H, br s), 0.99 (3H, d), 1.33 (3H, d), 1.36-1.56 (3H, m), 1.57-1.74 (1H, m), 1.74-1.89 (2H, m), 2.64-2.79 (2H, m), 2.84-2.94 (1H, m), 3.00-3.28 (3H, m), 3.41-3.56 (2H, m), 3.88 (1H, t), 4.07-4.20 (1H, m), 4.36-4.49 (1H, m), 7.48-7.60 (2H, m), 7.86 (1H, dd), 8.13 (1H, dd), 8.37 (1H, d), 8.58-8.74 (2H, m).

Example 20: (S)-2-(3-(1-(2-Azabicyclo[2.2.2]octane-3-carbonyl)piperidine-4-carbonyl)-1H-pyrrolo[2,3-c]pyridin-1-yl)-5-fluoro-N,N-diisopropylbenzamide

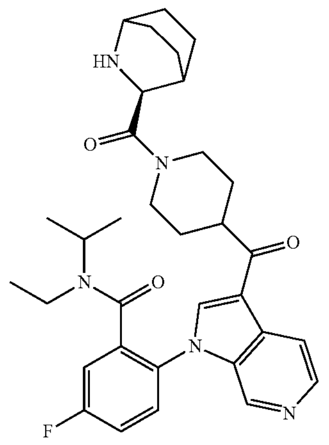 [SMILES: CCN(C(=O)c1cc(F)ccc1-n1cc(C(=O)C2CCN(C(=O)[C@H]3NC4CCC3CC4)CC2)c2ccncc21)C(C)C]

Step a) tert-Butyl (S)-3-(4-(1-(2-(diisopropylcarbamoyl)-4-fluorophenyl)-1H-pyrrolo[2,3-c]pyridine-3-carbonyl)piperidine-1-carbonyl)-2-azabicyclo[2.2.2]octane-2-carboxylate

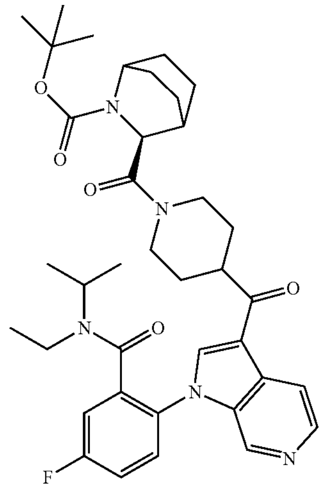 [SMILES: CCN(C(=O)c1cc(F)ccc1-n1cc(C(=O)C2CCN(C(=O)[C@@H]3C4CCC(CC4)N3C(=O)OC(C)(C)C)CC2)c2ccncc21)C(C)C]

Intermediate 39 (1.00 g, 1.78 mmol th., LC-UV purity 80%) was added to a solution of (S)-2-(tert-butoxycarbonyl)-2-azabicyclo[2.2.2]octane-3-carboxylic acid (453 mg, 1.78 mmol), EDC (408 mg, 2.13 mmol), HOBt (326 mg, 2.13 mmol) and DIPEA (620 μl, 3.55 mmol) in DMF (15 mL). The resulting mixture was stirred at rt overnight. The reaction mixture was diluted with EtOAc (50 mL) and washed sequentially with aq. HCl (50 mL, 1 M) and sat. aq. $NaHCO_3$ (50 mL). The organic layer was washed with brine (50 mL), dried over $Na_2SO_4$, filtered, and concentrated under reduced pressure. The residue was purified by straight phase flash chromatography on silica (gradient: 0-10% MeOH in DCM) to give the title compound (1.07 g, 87%) as an orange gum; MS m/z (ES+) $[M+H]^+$=688.3; $^1$H NMR (400 MHz, DMSO-$d_6$, 22° C.) δ 0.30 (3H, br s), 0.73 (3H, br s), 0.99 (3H, d), 1.28-1.43 (14H, m), 1.43-1.58 (4H, m), 1.58-1.76 (4H, m), 1.76-2.01 (4H, m), 3.09-3.28 (2H, m), 3.42-3.56 (2H, m), 3.91-4.09 (2H, m), 4.43-4.58 (2H, m), 7.50-7.59 (2H, m), 7.85 (1H, dd), 8.12 (1H, d), 8.37 (1H, dd), 8.61-8.73 (2H, m).

Step b) (S)-2-(3-(1-(2-Azabicyclo[2.2.2]octane-3-carbonyl)piperidine-4-carbonyl)-1H-pyrrolo[2,3-c]pyridin-1-yl)-5-fluoro-N,N-diisopropylbenzamide (Example 20)

TFA (5 mL) was added to a solution of tert-butyl (S)-3-(4-(1-(2-(diisopropylcarbamoyl)-4-fluorophenyl)-1H-pyrrolo[2,3-c]pyridine-3-carbonyl)piperidine-1-carbonyl)-2-azabicyclo[2.2.2]octane-2-carboxylate from Step a) (1.07 g, 1.55 mmol) in DCM (25 mL). The mixture was stirred at rt for 2 h. The mixture was concentrated under reduced pressure. The residue was dissolved in DCM (100 mL), washed sequentially with sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-20% 0.7 M $NH_3$ in MeOH in DCM). The pooled and concentrated product fractions were purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine (30 mL), dried over $Na_2SO_4$, filtered, and concentrated under reduced pressure. The product was lyophilized from MeCN/$H_2O$ to give the title compound (550 mg, 60%) as a light yellow solid; MS m/z (ES+) $[M+H]^+$=588.4; $^1$H NMR (400 MHz, DMSO-$d_6$, 22° C.) δ 0.29 (3H, br s), 0.73 (3H, br s), 0.99 (3H, d), 1.33 (3H, d), 1.37-1.66 (7H, m), 1.65-1.95 (6H, m), 2.72-2.90 (1H, m), 2.99 (1H, br s), 3.07-3.29 (3H, m), 3.42-3.57 (2H, m), 3.80-3.96 (1H, m), 3.96-4.13 (1H, m), 4.41-4.57 (1H, m), 7.47-7.64 (2H, m), 7.85 (1H, dd), 8.04-8.20 (1H, m), 8.38 (1H, d), 8.55-8.78 (2H, m).

Example 21: 5-Fluoro-N,N-diisopropyl-2-(3-(1-((1S,3aR,6aS)-octahydrocyclopenta[c]pyrrole-1-carbonyl)piperidine-4-carbonyl)-1H-pyrrolo[2,3-c]pyridin-1-yl)benzamide

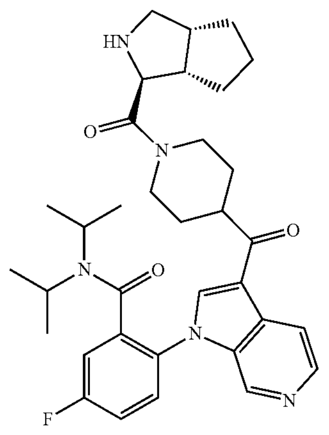 [SMILES: CC(C)N(C(=O)c1cc(F)ccc1-n1cc(C(=O)C2CCN(C(=O)[C@H]3NC[C@@H]4CCC[C@@H]43)CC2)c2ccncc21)C(C)C]

Step a) tert-Butyl (1S,3aR,6aS)-1-(4-(1-(2-(diisopropylcarbamoyl)-4-fluorophenyl)-1H-pyrrolo[2,3-c]pyridine-3-carbonyl)piperidine-1-carbonyl)hexahydrocyclopenta[c]pyrrole-2(1H)-carboxylate

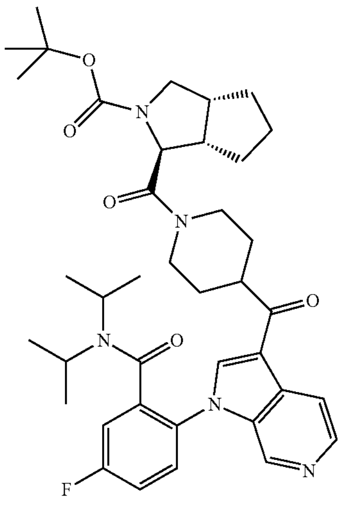 [SMILES: CC(C)N(C(=O)c1cc(F)ccc1-n1cc(C(=O)C2CCN(C(=O)[C@@H]3[C@H]4CCC[C@H]4CN3C(=O)OC(C)(C)C)CC2)c2ccncc21)C(C)C]

Intermediate 39 (70.0 mg, 0.16 mmol) was added to a solution of (1S,3aR,6aS)-2-(tert-butoxycarbonyl)octahydrocyclopenta[c]pyrrole-1-carboxylic acid (39.7 mg, 0.16 mmol), EDC (35.7 mg, 0.19 mmol), HOBt (28.6 mg, 0.19 mmol) and DIPEA (54.0 μl, 0.31 mmol) in DMF (1 mL). The resulting mixture was stirred at rt overnight. The reaction mixture was diluted with EtOAc (20 mL) and washed sequentially with aq. HCl (20 mL, 1 M) and sat. aq. $NaHCO_3$ (20 mL). The organic layer was washed with brine (20 mL), dried over $Na_2SO_4$, filtered, and concentrated under reduced pressure. The residue was purified by straight phase flash chromatography on silica (gradient: 0-5% MeOH in DCM) to give the title compound (81.0 mg, 76%) as a brown gum; MS m/z (ES+) [M+H]+=688.4.

Step b) 5-Fluoro-N,N-diisopropyl-2-(3-(1-((1S,3aR,6aS)-octahydrocyclopenta[c]-pyrrole-1-carbonyl)piperidine-4-carbonyl)-1H-pyrrolo[2,3-c]pyridin-1-yl)benzamide (Example 21)

TFA (500 μL) was added to a solution of tert-butyl (1S,3aR,6aS)-1-(4-(1-(2-(diisopropylcarbamoyl)-4-fluorophenyl)-1H-pyrrolo[2,3-c]pyridine-3-carbonyl)piperidine-1-carbonyl)hexahydrocyclopenta[c]pyrrole-2(1H)-carboxylate from Step a) (81.0 mg, 0.12 mmol) in DCM (3 mL). The mixture was stirred at rt for 30 minutes. The mixture was concentrated under reduced pressure. The residue was purified by preparative HPLC, PrepMethod A, (gradient: 0-50%). Appropriate fractions were pooled, diluted with sat. aq. $NaHCO_3$ (20 mL) and extracted with EtOAc (20 mL). The organic layer was washed with brine (20 mL), dried over $Na_2SO_4$, filtered, and concentrated under reduced pressure. The product was lyophilized from MeCN/$H_2O$ to give the title compound (35.3 mg, 51%) as a white solid; MS m/z (ES+) $[M+H]^+$=588.4; $^1H$ NMR (400 MHz, DMSO-$d_6$, 22° C.) δ 0.28 (3H, br s), 0.74 (3H, br s), 0.99 (3H, d), 1.33 (4H, d), 1.39-1.66 (7H, m), 1.68-1.91 (4H, m), 2.33-2.42 (1H, m), 2.69-2.82 (1H, m), 3.13-3.29 (4H, m), 3.46-3.55 (2H, m), 3.59-3.67 (1H, m), 4.02-4.14 (1H, m), 4.41-4.49 (1H, m), 7.51-7.59 (2H, m), 7.83-7.89 (1H, m), 8.12 (1H, d), 8.38 (1H, d), 8.62-8.71 (2H, m).

Example 22: 5-Fluoro-2-(3-(1-((1S,3S,4S,5S)-5-fluoro-2-azabicyclo[2.2.1]heptane-3-carbonyl)piperidine-4-carbonyl)-1H-pyrrolo[2,3-c]pyridin-1-yl)-N,N-diisopropylbenzamide

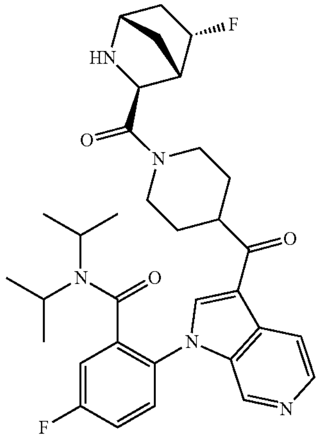 [SMILES: CC(C)N(C(=O)c1cc(F)ccc1-n1cc(C(=O)C2CCN(C(=O)[C@H]3N[C@H]4C[C@@H]3[C@@H](F)C4)CC2)c2ccncc21)C(C)C]

Step a) tert-Butyl (1S,3S,4S,5S)-3-(4-(1-(2-(diisopropylcarbamoyl)-4-fluorophenyl)-1H-pyrrolo[2,3-c]pyridine-3-carbonyl)piperidine-1-carbonyl)-5-fluoro-2-azabicyclo[2.2.1]heptane-2-carboxylate

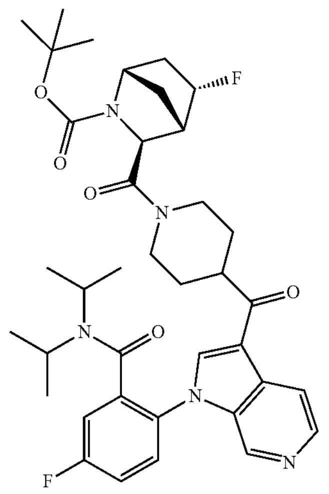 [SMILES: CC(C)N(C(=O)c1cc(F)ccc1-n1cc(C(=O)C2CCN(C(=O)[C@@H]3[C@@H]4C[C@@H](C[C@@H]4F)N3C(=O)OC(C)(C)C)CC2)c2ccncc21)C(C)C]

Intermediate 39 (100 mg, 0.18 mmol th., LC-UV purity 80%) was added to a solution of Intermediate 106 (46.0 mg, 0.18 mmol), EDC (41.0 mg, 0.21 mmol), HOBt (32.6 mg, 0.21 mmol) and DIPEA (62.0 µl, 0.36 mmol) in DMF (1.5 mL). The resulting mixture was stirred at rt overnight. The reaction mixture was diluted with EtOAc (40 mL), washed sequentially with aq. HCl (20 mL, 1 M), sat. aq. $NaHCO_3$ (40 mL) and brine (40 mL). The organic layer was dried over $Na_2SO_4$, filtered, and concentrated under reduced pressure. The residue was purified by straight phase flash chromatography on silica (gradient: 0-10% MeOH in DCM) to give the title compound (101 mg, 82%) as a yellow oil; MS m/z (ES+) $[M+H]^+$=692.8.

Step b) 5-Fluoro-2-(3-(1-((1S,3S,4S,5S)-5-fluoro-2-azabicyclo[2.2.1]heptane-3-carbonyl)piperidine-4-carbonyl)-1H-pyrrolo[2,3-c]pyridin-1-yl)-N,N-diisopropylbenzamide (Example 22)

TFA (480 µL) was added to a solution of tert-butyl (1S,3S,4S,5S)-3-(4-(1-(2-(diisopropylcarbamoyl)-4-fluorophenyl)-1H-pyrrolo[2,3-c]pyridine-3-carbonyl)piperidine-1-carbonyl)-5-fluoro-2-azabicyclo[2.2.1]heptane-2-carboxylate from Step a) (101 mg, 0.15 mmol) in DCM (3 mL). The mixture was stirred at rt for 1 h. The mixture was poured into sat. aq. $NaHCO_3$ (25 mL) and extracted with EtOAc (3×25 mL). The combined organic layers were concentrated under reduced pressure. The residue was purified by preparative HPLC, PrepMethod A, (gradient: 0-75%). Appropriate fractions were pooled, diluted with sat. aq. $NaHCO_3$ (20 mL) and extracted with EtOAc (20 mL). The organic layer was washed with brine (20 mL), dried over $Na_2SO_4$, filtered, and concentrated under reduced pressure. The product was lyophilized from MeCN/$H_2O$ to give the title compound (29.0 mg, 34%) as a white solid; MS m/z (ES+) $[M+H]^+$=592.3; $^1$H NMR (400 MHz, $CDCl_3$, 27° C.) δ 0.29 (2H, br s), 0.73 (3H, br s), 0.99 (3H, d), 1.19-1.25 (1H, m), 1.27-1.33 (5H, m), 1.40-1.57 (1H, m), 1.57-1.74 (1H, m), 1.74-2.02 (3H, m), 2.66-2.88 (2H, m), 3.13-3.27 (3H, m), 3.39-3.55 (3H, m), 3.79-3.97 (2H, m), 4.34-4.50 (1H, m), 5.03-5.17 (1H, m), 5.18-5.31 (OH, m), 7.45-7.61 (2H, m), 7.85 (1H, dd), 8.12 (1H, dd), 8.37 (1H, d), 8.55-8.72 (2H, m).

Example 23: rac-(R)-5-Fluoro-N,N-diisopropyl-2-(3-(1-(6-((2-methoxyethyl)(methyl)amino)-2-methylhexan-3-yl)piperidine-4-carbonyl)-1H-pyrrolo[2,3-c]pyridin-1-yl)benzamide

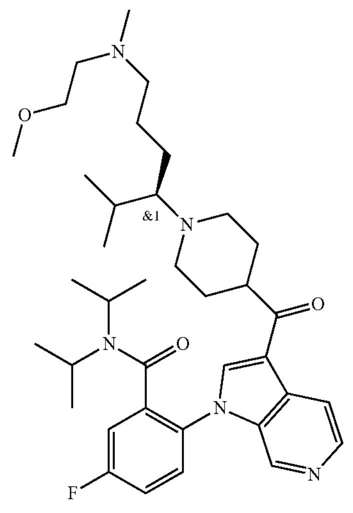 [SMILES: COCCN(C)CCC[C@H](C(C)C)N1CCC(C(=O)c2cn(-c3ccc(F)cc3C(=O)N(C(C)C)C(C)C)c3cnccc23)CC1]

Step a) rac-tert-Butyl (R)-(4-(4-(1-(2-(diisopropylcarbamoyl)-4-fluorophenyl)-1H-pyrrolo[2,3-c]pyridine-3-carbonyl)piperidin-1-yl)-5-methylhexyl)(methyl)carbamate

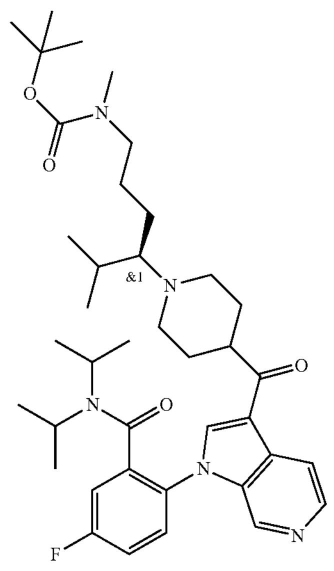 [SMILES: CC(C)[C@@H](CCCN(C)C(=O)OC(C)(C)C)N1CCC(C(=O)c2cn(-c3ccc(F)cc3C(=O)N(C(C)C)C(C)C)c3cnccc23)CC1]

Intermediate 39 (400 mg, 0.89 mmol) was added to a mixture of $Ti(OiPr)_4$ (303 mg, 1.07 mmol), Intermediate 116 (324 mg, 1.33 mmol) in DMF (10 mL). The resulting mixture was stirred at rt for 18 h before STAB (2.26 g, 10.7 mmol) was added. The mixture was stirred at rt for 6 h. The reaction mixture was diluted with DCM (50 mL) and washed sequentially with sat. aq. $NaHCO_3$ (2×50 mL) and brine (50 mL). The organic layer was dried over $Na_2SO_4$, filtered, and concentrated to dryness. The crude product was purified by straight phase flash chromatography on silica (gradient: 0-10% MeOH in DCM) to give the title compound (150 mg, 25%) as a yellow solid; MS m/z (ES+) $[M+H]^+$=678.4; $^1H$ NMR (300 MHz, DMSO-$d_6$, 29° C.) δ 0.29 (3H, br s), 0.72-0.80 (3H, m), 0.81-0.97 (7H, m), 1.00 (3H, d), 1.24 (4H, br s), 1.30-1.36 (4H, m), 1.40 (9H, s), 1.46-1.53 (1H, m), 1.57-1.68 (2H, m), 1.70-1.83 (2H, m), 2.07-2.18 (1H, m), 2.65-2.92 (5H, m), 3.11-3.30 (3H, m), 3.41-3.57 (2H, m), 7.43-7.65 (2H, m), 7.84 (1H, dd), 8.11-8.16 (1H, m), 8.38 (1H, d), 8.51-8.61 (1H, m), 8.64 (1H, s).

Step b) rac-(R)-5-Fluoro-N,N-diisopropyl-2-(3-(1-(2-methyl-6-(methylamino)hexan-3-yl)piperidine-4-carbonyl)-1H-pyrrolo[2,3-c]pyridin-1-yl)benzamide

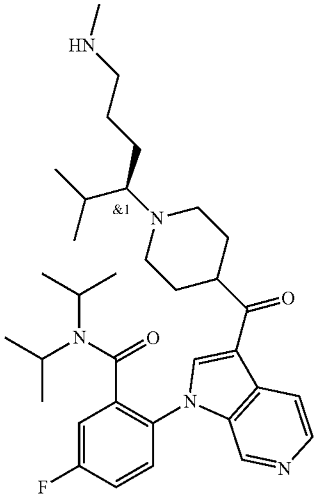 [SMILES: CNCCC[C@H](C(C)C)N1CCC(C(=O)c2cn(-c3ccc(F)cc3C(=O)N(C(C)C)C(C)C)c3cnccc23)CC1]

4 M HCl in 1,4-dioxane (2 mL) was added to rac-tert-butyl (R)-(4-(4-(1-(2-(diisopropylcarbamoyl)-4-fluorophenyl)-1H-pyrrolo[2,3-c]pyridine-3-carbonyl)piperidin-1-yl)-5-methylhexyl)(methyl)carbamate from Step a) (150 mg, 0.22 mmol). The resulting mixture was stirred at rt for 1 h. The reaction mixture was poured into sat. aq. $NaHCO_3$ (25 mL) and extracted with DCM (3×25 mL). The combined organic layers were dried over $Na_2SO_4$, filtered, and concentrated to dryness to give the title compound (90.0 mg, 70%) as a yellow solid; MS m/z (ES+) $[M+H]^+$=578.4; $^1H$ NMR (300 MHz, DMSO-$d_6$, 29° C.) δ 0.30 (3H, br s), 0.74-0.81 (3H, m), 0.84-0.93 (6H, m), 1.00 (3H, d), 1.34 (4H, m), 1.44-1.54 (2H, m), 1.56-1.68 (3H, m), 1.69-1.87 (3H, m), 2.06-2.18 (1H, m), 2.43 (2H, s), 2.63-2.92 (4H, m), 3.04-3.18 (2H, m), 3.22-3.30 (2H, m), 3.45-3.59 (2H, m), 7.47-7.61 (2H, m), 7.80-7.90 (1H, m), 8.08-8.18 (1H, m), 8.38 (1H, d), 8.54 (1H, s), 8.65 (1H, s).

Step c) rac-(R)-5-Fluoro-N,N-diisopropyl-2-(3-(1-(6-((2-methoxyethyl)(methyl)amino)-2-methylhexan-3-yl)piperidine-4-carbonyl)-1H-pyrrolo[2,3-c]pyridin-1-yl)benzamide (Example 23)

1-Iodo-2-methoxyethane (29.0 mg, 0.16 mmol) was added to rac-(R)-5-fluoro-N,N-diisopropyl-2-(3-(1-(2-methyl-6-(methylamino)hexan-3-yl)piperidine-4-carbonyl)-1H-pyrrolo[2,3-c]pyridin-1-yl)benzamide from Step b) (90.0 mg, 0.16 mmol), NaI (11.7 mg, 0.08 mmol) and $K_2CO_3$ (108 mg, 0.78 mmol) in DMF (2 mL). The resulting mixture was stirred at 50° C. for 16 h. The reaction mixture was diluted with DCM (25 mL) and washed with brine (2×25 mL). The organic layer was dried over $Na_2SO_4$, filtered, and concentrated to dryness. The crude product was purified by preparative HPLC, PrepMethod G (gradient: 4-15%). Appropriate fractions were pooled and concentrated under reduced pressure to give the title compound (16.0 mg, 16%); MS m/z (ES+) $[M+H]^+$=636.4; $^1H$ NMR (400 MHz, DMSO-$d_6$, 46° C.) δ 0.32 (3H, br s), 0.69-0.82 (3H, m), 0.88 (6H, dd), 0.99 (3H, d), 1.20-1.29 (2H, m), 1.33 (3H, d), 1.39-1.51 (2H, m), 1.54-1.66 (2H, m), 1.67-1.79 (3H, m), 2.03-2.12 (1H, m), 2.17 (3H, s), 2.27-2.37 (2H, m), 2.41-2.49 (3H, m), 2.55-2.61 (1H, m), 2.72-2.85 (2H, m), 3.06-3.17 (1H, m), 3.20-3.28 (4H, m), 3.40 (2H, t), 3.45-3.56 (1H, m), 7.48-7.59 (2H, m), 7.84 (1H, dd), 8.13 (1H, d), 8.37 (1H, d), 8.53-8.61 (1H, m), 8.64 (1H, s).

Example 24: (S)-2-(3-(1-(4-Azaspiro[2.4]heptane-5-carbonyl)piperidine-4-carbonyl)-1H-pyrrolo[2,3-c]pyridin-1-yl)-5-fluoro-N,N-diisopropylbenzamide

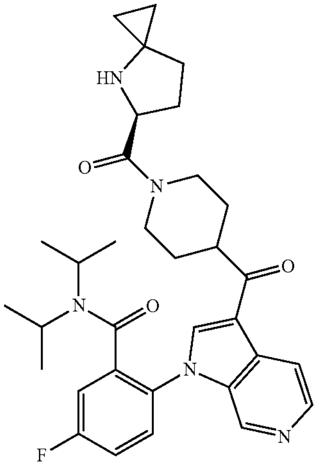 [SMILES: CC(C)N(C(=O)c1cc(F)ccc1-n1cc(C(=O)C2CCN(C(=O)[C@@H]3CCC4(CC4)N3)CC2)c2ccncc21)C(C)C]

Step a) tert-Butyl (S)-5-(4-(1-(2-(diisopropylcarbamoyl)-4-fluorophenyl)-1H-pyrrolo[2,3-c]pyridine-3-carbonyl)piperidine-1-carbonyl)-4-azaspiro[2.4]heptane-4-carboxylate

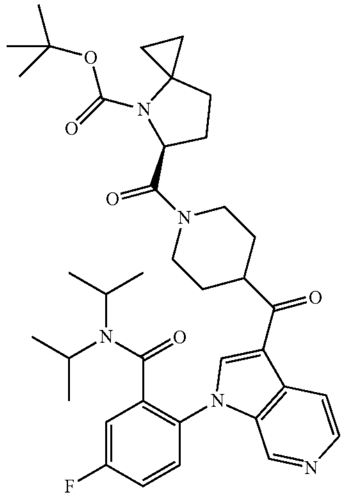 [SMILES: CC(C)N(C(=O)c1cc(F)ccc1-n1cc(C(=O)C2CCN(C(=O)[C@@H]3CCC4(CC4)N3C(=O)OC(C)(C)C)CC2)c2ccncc21)C(C)C]

Intermediate 39 (71.4 mg, 0.16 mmol) was added to a solution of (S)-4-(tert-butoxycarbonyl)-4-azaspiro[2.4]heptane-5-carboxylic acid (38.2 mg, 0.16 mmol), EDC (36.5 mg, 0.19 mmol), HOBt (29.1 mg, 0.19 mmol) and DIPEA (55.0 μl, 0.32 mmol) in DMF (2 mL). The resulting mixture was stirred at rt overnight. The reaction mixture was diluted with EtOAc (40 mL), washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (89.8 mg, 84%) as an orange gum; MS m/z (ES+) $[M+H]^+$=674.3.

Step b) (S)-2-(3-(1-(4-Azaspiro[2.4]heptane-5-carbonyl)piperidine-4-carbonyl)-1H-pyrrolo[2,3-c]pyridin-1-yl)-5-fluoro-N,N-diisopropylbenzamide (Example 24)

TFA (1 mL) was added to a solution of tert-butyl (S)-5-(4-(1-(2-(diisopropylcarbamoyl)-4-fluorophenyl)-1H-pyrrolo[2,3-c]pyridine-3-carbonyl)piperidine-1-carbonyl)-4-azaspiro[2.4]heptane-4-carboxylate from Step a) (89.8 mg, 0.13 mmol) in DCM (5 mL). The mixture was stirred at rt for 1 h. The mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by straight phase flash chromatography on silica (gradient: 0-25% 0.7 M $NH_3$ in MeOH in DCM). The product was lyophilized from MeCN/$H_2O$ to give the title compound (17.8 mg, 23%) as a light yellow solid; MS m/z (ES+) $[M+H]^+$=574.3; $^1H$ NMR (400 MHz, DMSO-$d_6$, 22° C.) δ 0.13-0.37 (3H, m), 0.41-0.50 (1H, m), 0.50-0.61 (1H, m), 0.65-0.88 (4H, m), 0.99 (3H, d), 1.33 (3H, d), 1.40-1.66 (3H, m), 1.66-1.91 (4H, m), 2.15-2.28 (1H, m), 2.68-2.82 (1H, m), 2.87-3.07 (1H, m), 3.07-3.29 (2H, m), 3.41-3.62 (2H, m), 3.90-4.12 (2H, m), 4.36-4.50 (1H, m), 7.45-7.62 (2H, m), 7.86 (1H, dd), 8.12 (1H, d), 8.37 (1H, d), 8.57-8.77 (2H, m).

Example 25: rel-2-(3-(1-((1R,2R,5S)-3-Azabicyclo[3.2.0]heptane-2-carbonyl)piperidine-4-carbonyl)-1H-pyrrolo[2,3-c]pyridin-1-yl)-5-fluoro-N,N-diisopropylbenzamide

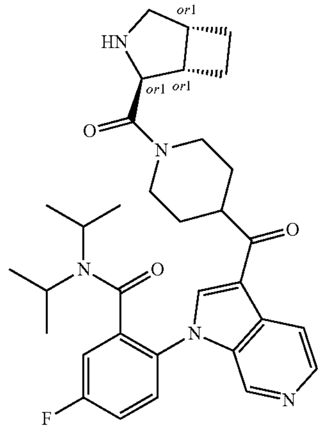 [SMILES: CC(C)N(C(=O)c1cc(F)ccc1-n1cc(C(=O)C2CCN(C(=O)[C@H]3NC[C@@H]4CC[C@@H]43)CC2)c2ccncc21)C(C)C]

Step a) rel-tert-Butyl (1R,2R,5S)-2-(4-(1-(2-(diisopropylcarbamoyl)-4-fluorophenyl)-1H-pyrrolo[2,3-c]pyridine-3-carbonyl)piperidine-1-carbonyl)-3-azabicyclo[3.2.0]heptane-3-carboxylate

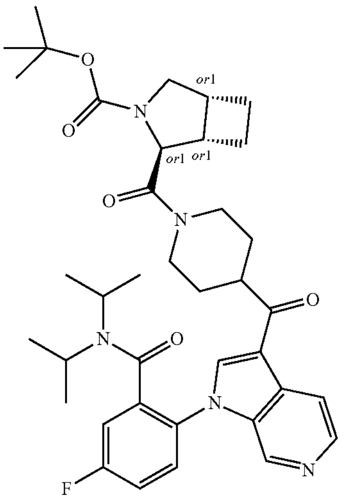 [SMILES: CC(C)N(C(=O)c1cc(F)ccc1-n1cc(C(=O)C2CCN(C(=O)[C@@H]3[C@H]4CC[C@H]4CN3C(=O)OC(C)(C)C)CC2)c2ccncc21)C(C)C]

Intermediate 39 (100 mg, 0.22 mmol) was added to a solution of Intermediate 117 (53.6 mg, 0.22 mmol), EDC (51.1 mg, 0.27 mmol), HOBt (40.8 mg, 0.27 mmol) and DIPEA (78.0 μl, 0.32 mmol) in DMF (2 mL). The resulting mixture was stirred at rt overnight. The reaction mixture was diluted with EtOAc (40 mL), washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (107 mg, 72%) as a colorless gum; MS m/z (ES+) $[M+H]^+$=674.3.

Step b) rel-2-(3-(1-((1R,2R,5S)-3-Azabicyclo[3.2.0]heptane-2-carbonyl)piperidine-4-carbonyl)-1H-pyrrolo[2,3-c]pyridin-1-yl)-5-fluoro-N,N-diisopropylbenzamide (Example 25)

TFA (1 mL) was added to a solution of rel-tert-butyl (1R,2R,5S)-2-(4-(1-(2-(diisopropylcarbamoyl)-4-fluorophenyl)-1H-pyrrolo[2,3-c]pyridine-3-carbonyl)piperidine-1-carbonyl)-3-azabicyclo[3.2.0]heptane-3-carboxylate from Step a) (107 mg, 0.16 mmol) in DCM (5 mL). The mixture was stirred at rt for 1 h. The mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by straight phase flash chromatography on silica (gradient: 0-25% 0.7 M $NH_3$ in MeOH in DCM). The product was lyophilized from $MeCN/H_2O$ to give the title compound (23.8 mg, 26%) as a light yellow solid; MS m/z (ES+) $[M+H]^+$=574.3; $^1H$ NMR (400 MHz, DMSO-$d_6$, 22° C.) δ 0.27 (3H, br s), 0.73 (3H, br s), 0.99 (3H, d), 1.33 (3H, d), 1.37-1.52 (1H, m), 1.57-1.88 (5H, m), 2.02-2.28 (2H, m), 2.65-2.91 (4H, m), 3.04-3.26 (3H, m), 3.42-3.56 (2H, m), 3.79-3.91 (1H, m), 3.98-4.14 (1H, m), 4.31-4.45 (1H, m), 7.48-7.61 (2H, m), 7.85 (1H, dd), 8.09-8.17 (1H, m), 8.38 (1H, d), 8.57-8.73 (2H, m).

Example 26: (S)-2-(3-(1-(5-Azaspiro[2.4]heptane-6-carbonyl)piperidine-4-carbonyl)-1H-pyrrolo[2,3-c]pyridin-1-yl)-5-fluoro-N,N-diisopropylbenzamide

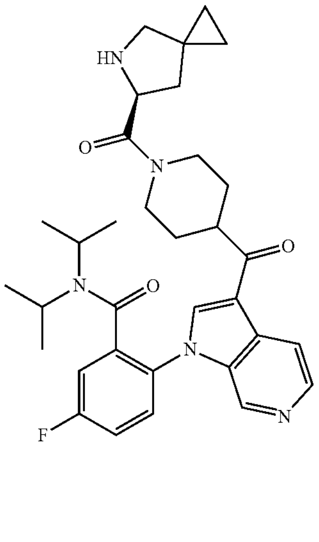 [SMILES: CC(C)N(C(=O)c1cc(F)ccc1-n1cc(C(=O)C2CCN(C(=O)[C@@H]3CC4(CC4)CN3)CC2)c2ccncc21)C(C)C]

Step a) tert-Butyl (S)-6-(4-(1-(2-(diisopropylcarbamoyl)-4-fluorophenyl)-1H-pyrrolo[2,3-c]pyridine-3-carbonyl)piperidine-1-carbonyl)-5-azaspiro[2.4]heptane-5-carboxylate

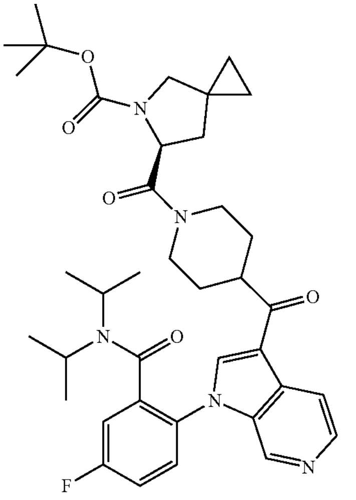 [SMILES: CC(C)N(C(=O)c1cc(F)ccc1-n1cc(C(=O)C2CCN(C(=O)[C@@H]3CC4(CC4)CN3C(=O)OC(C)(C)C)CC2)c2ccncc21)C(C)C]

Intermediate 39 (100 mg, 0.22 mmol) was added to a solution of (S)-5-(tert-butoxycarbonyl)-5-azaspiro[2.4]heptane-6-carboxylic acid (53.6 mg, 0.22 mmol), EDC (51.1 mg, 0.27 mmol), HOBt (40.8 mg, 0.27 mmol) and DIPEA (78.0 μl, 0.32 mmol) in DMF (2 mL). The resulting mixture was stirred at rt overnight. The reaction mixture was diluted with EtOAc (40 mL), washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (102 mg, 68%) as a colorless gum; MS m/z (ES+) $[M+H]^+$=674.3.

Step b) (S)-2-(3-(1-(5-Azaspiro[2.4]heptane-6-carbonyl)piperidine-4-carbonyl)-1H-pyrrolo[2,3-c]pyridin-1-yl)-5-fluoro-N,N-diisopropylbenzamide (Example 26)

TFA (1 mL) was added to a solution of tert-butyl (S)-6-(4-(1-(2-(diisopropylcarbamoyl)-4-fluorophenyl)-1H-pyrrolo[2,3-c]pyridine-3-carbonyl)piperidine-1-carbonyl)-5-azaspiro[2.4]heptane-5-carboxylate from Step a) (102 mg, 0.15 mmol) in DCM (5 mL). The mixture was stirred at rt for 1 h. The mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by straight phase flash chromatography on silica (gradient: 0-25% 0.7 M $NH_3$ in MeOH in DCM). The product was lyophilized from $MeCN/H_2O$ to give the title compound (65.8 mg, 76%) as a yellow solid; MS m/z (ES+) $[M+H]^+$=574.3; $^1H$ NMR (400 MHz, DMSO-$d_6$, 22° C.) δ 0.30 (3H, br s), 0.42-0.57 (3H, m), 0.56-0.66 (1H, m), 0.73 (3H, br s), 0.99 (3H, d), 1.33 (3H, d), 1.38-1.72 (3H, m), 1.74-1.88 (2H, m), 1.98-2.07 (1H, m), 2.62-2.69 (1H, m), 2.71-2.82 (1H, m), 2.86 (1H, d), 3.03-3.18 (1H, m), 3.19-3.27 (1H, m), 3.42-3.56 (2H, m), 3.90-

4.05 (1H, m), 4.03-4.16 (1H, m), 4.39-4.50 (1H, m), 7.50-7.59 (2H, m), 7.85 (1H, dd), 8.12 (1H, t), 8.37 (1H, d), 8.60-8.73 (2H, m).

Example 27: (S)-2-(3-(1-(5,5-Dimethylpyrrolidine-2-carbonyl)piperidine-4-carbonyl)-1H-pyrrolo[2,3-c]pyridin-1-yl)-5-fluoro-N,N-diisopropylbenzamide

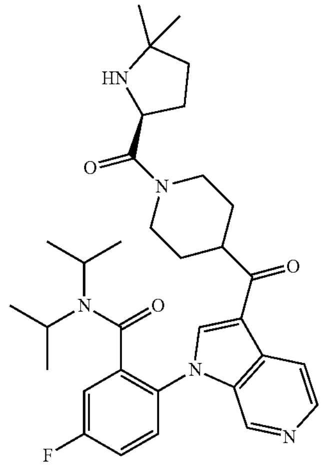 [SMILES: CC(C)N(C(=O)c1cc(F)ccc1-n1cc(C(=O)C2CCN(C(=O)[C@@H]3CCC(C)(C)N3)CC2)c2ccncc21)C(C)C]

Step a) tert-Butyl (S)-5-(4-(1-(2-(diisopropylcarbamoyl)-4-fluorophenyl)-1H-pyrrolo[2,3-c]pyridine-3-carbonyl)piperidine-1-carbonyl)-2,2-dimethylpyrrolidine-1-carboxylate

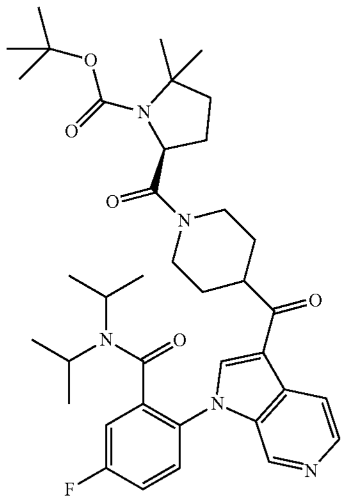 [SMILES: CC(C)N(C(=O)c1cc(F)ccc1-n1cc(C(=O)C2CCN(C(=O)[C@@H]3CCC(C)(C)N3C(=O)OC(C)(C)C)CC2)c2ccncc21)C(C)C]

Intermediate 39 (100 mg, 0.22 mmol) was added to a solution of (S)-1-(tert-butoxycarbonyl)-5,5-dimethylpyrrolidine-2-carboxylic acid (54.0 mg, 0.22 mmol), EDC (51.1 mg, 0.27 mmol), HOBt (40.8 mg, 0.27 mmol) and DIPEA (78.0 μl, 0.32 mmol) in DMF (2 mL). The resulting mixture was stirred at rt overnight. The reaction mixture was diluted with EtOAc (40 mL), washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (131 mg, 87%) as a colorless gum; MS m/z (ES+) $[M+H]^+$=676.3.

Step b) (S)-2-(3-(1-(5,5-Dimethylpyrrolidine-2-carbonyl)piperidine-4-carbonyl)-1H-pyrrolo[2,3-c]pyridin-1-yl)-5-fluoro-N,N-diisopropylbenzamide (Example 27)

TFA (1 mL) was added to a solution of tert-butyl (S)-5-(4-(1-(2-(diisopropylcarbamoyl)-4-fluorophenyl)-1H-pyrrolo[2,3-c]pyridine-3-carbonyl)piperidine-1-carbonyl)-2,2-dimethylpyrrolidine-1-carboxylate from Step a) (131 mg, 0.19 mmol) in DCM (5 mL). The mixture was stirred at rt for 1 h. The mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by straight phase flash chromatography on silica (gradient: 0-10% 0.7 M $NH_3$ in MeOH in DCM). The product was lyophilized from MeCN/$H_2O$ to give the title compound (70.2 mg, 63%) as a light yellow solid; MS m/z (ES+) $[M+H]^+$=576.3; $^1H$ NMR (400 MHz, DMSO-$d_6$, 22° C.) δ 0.29 (3H, br s), 0.74 (3H, br s), 0.99 (3H, d), 1.10 (3H, s), 1.17-1.27 (3H, m), 1.33 (3H, d), 1.37-1.53 (2H, m), 1.55-1.75 (3H, m), 1.76-1.90 (2H, m), 2.17-2.30 (1H, m), 2.71-2.85 (1H, m), 3.08-3.27 (2H, m), 3.43-3.56 (2H, m), 3.93-4.17 (2H, m), 4.38-4.49 (1H, m), 7.50-7.60 (2H, m), 7.86 (1H, dd), 8.13 (1H, dd), 8.38 (1H, d), 8.60-8.72 (2H, m).

Example 28: 2-(3-(1-((1S,2S,5R)-3-Azabicyclo[3.1.0]hexane-2-carbonyl)piperidine-4-carbonyl)-1H-pyrrolo[2,3-c]pyridin-1-yl)-N-ethyl-5-fluoro-N-isopropylbenzamide

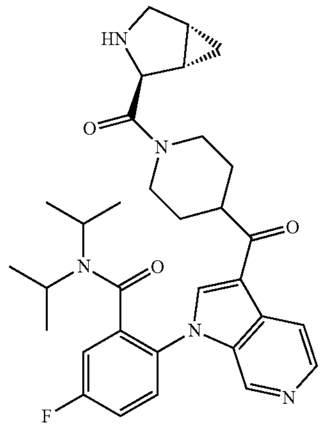 [SMILES: CC(C)N(C(=O)c1cc(F)ccc1-n1cc(C(=O)C2CCN(C(=O)[C@H]3NC[C@@H]4C[C@@H]43)CC2)c2ccncc21)C(C)C]

Step a) tert-Butyl (1S,2S,5R)-2-(4-(1-(2-(ethyl(isopropyl)carbamoyl)-4-fluorophenyl)-1H-pyrrolo[2,3-c]pyridine-3-carbonyl)piperidine-1-carbonyl)-3-azabicyclo[3.1.0]hexane-3-carboxylate

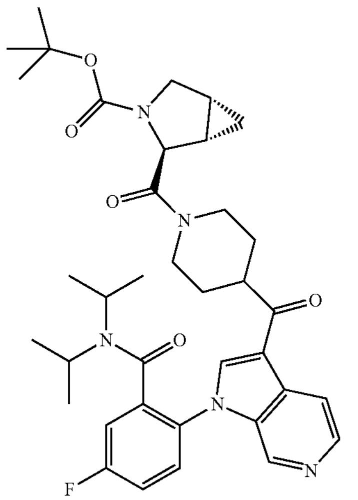 [SMILES: CC(C)N(C(=O)c1cc(F)ccc1-n1cc(C(=O)C2CCN(C(=O)[C@@H]3[C@H]4C[C@H]4CN3C(=O)OC(C)(C)C)CC2)c2ccncc21)C(C)C]

Intermediate 41 (94.0 mg, 0.22 mmol) was added to a solution of (1S,2S,5R)-3-(tert-butoxycarbonyl)-3-azabicyclo[3.1.0]hexane-2-carboxylic acid (48.9 mg, 0.22 mmol), EDC (49.5 mg, 0.26 mmol), HOBt (39.6 mg, 0.26 mmol) and DIPEA (75.0 μl, 0.43 mmol) in DMF (2 mL). The resulting mixture was stirred at rt overnight. The reaction mixture was diluted with EtOAc (20 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (119 mg, 85%) as a yellow gum; MS m/z (ES+) $[M+H]^+$=646.3.

Step b) 2-(3-(1-((1S,2S,5R)-3-Azabicyclo[3.1.0]hexane-2-carbonyl)piperidine-4-carbonyl)-1H-pyrrolo[2,3-c]pyridin-1-yl)-N-ethyl-5-fluoro-N-isopropylbenzamide (Example 28)

TFA (1 mL) was added to a solution of tert-butyl (1S,2S,5R)-2-(4-(1-(2-(ethyl(isopropyl)carbamoyl)-4-fluorophenyl)-1H-pyrrolo[2,3-c]pyridine-3-carbonyl)piperidine-1-carbonyl)-3-azabicyclo[3.1.0]hexane-3-carboxylate from Step a) (119 mg, 0.18 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (20 mL) and extracted with EtOAc (2×20 mL). The combined organic layers were washed with brine, dried over $Na_2SO_4$, filtered, and concentrated under reduced pressure. The product was lyophilized from $MeCN/H_2O$ to give the title compound (18.6 mg, 19%) as an off-white solid; MS m/z (ES+) $[M+H]^+$=546.2; $^1H$ NMR (400 MHz, DMSO-$d_6$, 22° C.) δ 0.29-0.56 (6H, m), 0.82-0.93 (1H, m), 0.98 (2H, d), 1.31-1.77 (5H, m), 1.77-1.93 (2H, m), 2.65-2.87 (3H, m), 2.90-3.30 (4H, m), 3.36-3.58 (3H, m), 3.99 (1H, d), 4.06-4.19 (1H, m), 4.42 (1H, br s), 7.53-7.65 (2H, m), 7.81-7.91 (1H, m), 8.08-8.15 (1H, m), 8.34-8.41 (1H, m), 8.59-8.78 (2H, m).

Example 29: (S)-2-(3-(1-(2-Azabicyclo[2.2.2]octane-3-carbonyl)piperidine-4-carbonyl)-1H-pyrrolo[2,3-c]pyridin-1-yl)-N-ethyl-5-fluoro-N-isopropylbenzamide

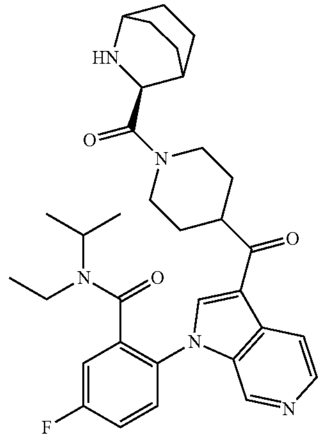 [SMILES: CCN(C(=O)c1cc(F)ccc1-n1cc(C(=O)C2CCN(C(=O)[C@H]3NC4CCC3CC4)CC2)c2ccncc21)C(C)C]

Step a) tert-Butyl (S)-3-(4-(1-(2-(ethyl(isopropyl)carbamoyl)-4-fluorophenyl)-1H-pyrrolo[2,3-c]pyridine-3-carbonyl)piperidine-1-carbonyl)-2-azabicyclo[2.2.2]octane-2-carboxylate

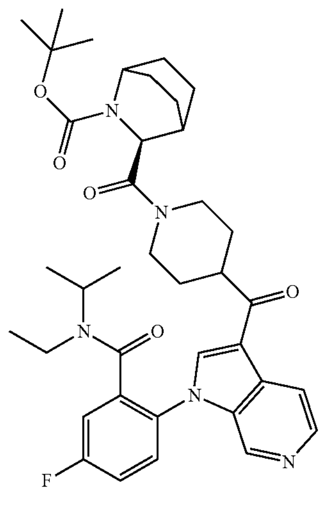 [SMILES: CCN(C(=O)c1cc(F)ccc1-n1cc(C(=O)C2CCN(C(=O)[C@@H]3C4CCC(CC4)N3C(=O)OC(C)(C)C)CC2)c2ccncc21)C(C)C]

Intermediate 41 (135 mg, 0.31 mmol) was added to a solution of (S)-2-(tert-butoxycarbonyl)-2-azabicyclo[2.2.2]octane-3-carboxylic acid (79.0 mg, 0.31 mmol), EDC (71.1 mg, 0.37 mmol), HOBt (56.8 mg, 0.37 mmol) and DIPEA (108 μl, 0.62 mmol) in DMF (2 mL). The resulting mixture was stirred at rt overnight. The reaction mixture was diluted with EtOAc (20 mL) and washed sequentially with aq. HCl (20 mL), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (35.4 mg, 17%) as an orange solid; MS m/z (ES+) $[M+H]^+$=674.3.

Step b) (S)-2-(3-(1-(2-Azabicyclo[2.2.2]octane-3-carbonyl)piperidine-4-carbonyl)-1H-pyrrolo[2,3-c]pyridin-1-yl)-N-ethyl-5-fluoro-N-isopropylbenzamide (Example 29)

TFA (1 mL) was added to a solution of tert-butyl (S)-3-(4-(1-(2-(ethyl(isopropyl)carbamoyl)-4-fluorophenyl)-1H-pyrrolo[2,3-c]pyridine-3-carbonyl)piperidine-1-carbonyl)-2-azabicyclo[2.2.2]octane-2-carboxylate from Step a) (35.4 mg, 0.05 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (20 mL) and extracted with EtOAc (2×20 mL). The combined organic layers were washed with brine, dried over $Na_2SO_4$, filtered, and concentrated under reduced pressure. The product was lyophilized from $MeCN/H_2O$ to give the title compound (17.1 mg, 57%) as a white solid; MS m/z (ES+) $[M+H]^+$=574.3; $^1$H NMR (400 MHz, DMSO-$d_6$, 22° C.) δ 0.29-0.52 (4H, m), 0.54-0.93 (3H, m), 0.98 (2H, d), 1.38-1.71 (8H, m), 1.73-1.89 (5H, m), 2.73-2.87 (2H, m), 2.96 (1H, br s), 3.10-3.30 (3H, m), 3.44-3.60 (2H, m), 3.80-4.07 (2H, m), 4.44-4.56 (1H, m), 7.53-7.65 (2H, m), 7.81-7.91 (1H, m), 8.08-8.15 (1H, m), 8.34-8.39 (1H, m), 8.56-8.75 (2H, m).

Example 30: N-Ethyl-5-fluoro-2-(3-(1-((1S,3S,4S,5S)-5-fluoro-2-azabicyclo[2.2.1]heptane-3-carbonyl)piperidine-4-carbonyl)-1H-pyrrolo[2,3-c]pyridin-1-yl)-N-isopropylbenzamide

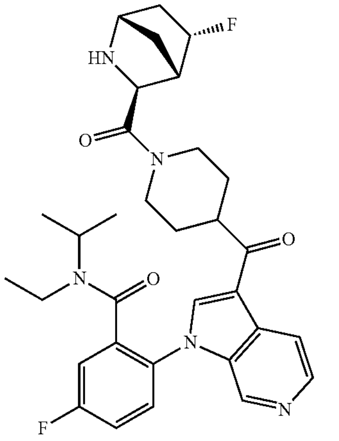 [SMILES: CCN(C(=O)c1cc(F)ccc1-n1cc(C(=O)C2CCN(C(=O)[C@H]3N[C@H]4C[C@@H]3[C@@H](F)C4)CC2)c2ccncc21)C(C)C]

Step a) tert-Butyl (1S,3S,4S,5S)-3-(4-(1-(2-(ethyl(isopropyl)carbamoyl)-4-fluorophenyl)-1H-pyrrolo[2,3-c]pyridine-3-carbonyl)piperidine-1-carbonyl)-5-fluoro-2-azabicyclo[2.2.1]heptane-2-carboxylate

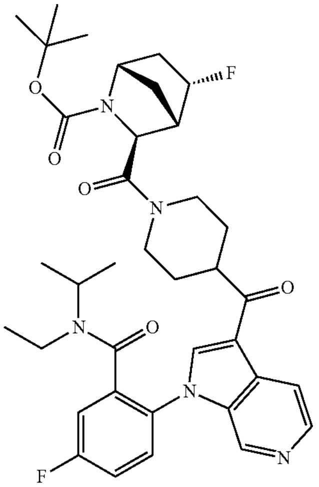 [SMILES: CCN(C(=O)c1cc(F)ccc1-n1cc(C(=O)C2CCN(C(=O)[C@@H]3[C@@H]4C[C@@H](C[C@@H]4F)N3C(=O)OC(C)(C)C)CC2)c2ccncc21)C(C)C]

Intermediate 41 (100 mg, 0.23 mmol) was added to a solution of Intermediate 106 (59.4 mg, 0.23 mmol), EDC (35.6 mg, 0.23 mmol), HOBt (42.1 mg, 0.27 mmol) and DIPEA (80.0 μl, 0.46 mmol) in DMF (2 mL). The resulting mixture was stirred at rt overnight. The reaction mixture was diluted with EtOAc (50 mL) and washed sequentially with aq. HCl (50 mL, 1 M), sat. aq. $NaHCO_3$ (50 mL) and brine (50 mL). The organic layer was dried over $Na_2SO_4$, filtered, and concentrated under reduced pressure to give the crude title compound (161 mg) as a yellow oil, which was used directly in the next step; MS m/z (ES+) $[M+H]^+$=678.3.

Step b) N-Ethyl-5-fluoro-2-(3-(1-((1S,3S,4S,5S)-5-fluoro-2-azabicyclo[2.2.1]heptane-3-carbonyl)piperidine-4-carbonyl)-1H-pyrrolo[2,3-c]pyridin-1-yl)-N-isopropylbenzamide (Example 30)

TFA (1 mL) was added to a solution of tert-butyl (1S,3S,4S,5S)-3-(4-(1-(2-(ethyl(isopropyl)carbamoyl)-4-fluorophenyl)-1H-pyrrolo[2,3-c]pyridine-3-carbonyl)piperidine-1-carbonyl)-5-fluoro-2-azabicyclo[2.2.1]heptane-2-carboxylate from Step a) (161 mg, 0.23 mmol th.) in DCM (4 mL). The mixture was stirred at rt for 1 h. The mixture was poured into sat. aq. $NaHCO_3$ (25 mL) and extracted with EtOAc (3×25 mL). The combined organic layers were concentrated under reduced pressure. The residue was purified by preparative HPLC, PrepMethod A, (gradient: 0-75%). Appropriate fractions were pooled, diluted with sat. aq. $NaHCO_3$ (20 mL) and extracted with EtOAc (2×20 mL). The combined organic layers were washed with brine, dried over $Na_2SO_4$, filtered, and concentrated under reduced pressure. The product was lyophilized from $MeCN/H_2O$ to give the title compound (34.1 mg, 26%) as a white solid; MS m/z (ES+) $[M+H]^+$=578.3; $^1$H NMR (400 MHz, DMSO-$d_6$, 22° C.) δ 0.33-0.57 (4H, m), 0.78-0.94 (2H, m), 0.98 (2H, d), 1.24-1.34 (3H, m), 1.43-1.59 (1H, m), 1.59-1.75 (1H, m), 1.78-2.05 (3H, m), 2.69-2.84 (3H, m), 3.14-3.29 (2H, m), 3.45-3.63 (3H, m), 3.81-3.98 (2H, m), 4.37-4.50 (1H, m), 5.05-5.20 (1H, m), 5.25 (1H, br s), 7.53-7.65 (2H, m), 7.81-7.90 (1H, m), 8.10-8.16 (1H, m), 8.34-8.41 (1H, m), 8.56-8.65 (1H, m), 8.72 (1H, br s).

Example 31: 2-(3-(1-((1R,3S,4S)-2-Azabicyclo[2.2.1]heptane-3-carbonyl)piperidine-4-carbonyl)-1H-pyrrolo[2,3-c]pyridin-1-yl)-N-ethyl-5-fluoro-N-isopropylbenzamide

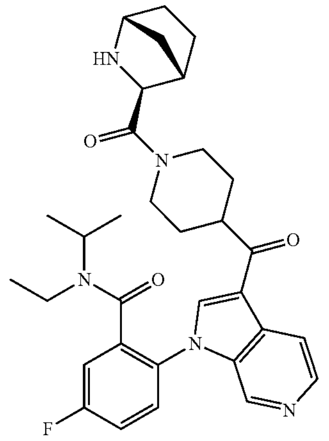 [SMILES: CCN(C(=O)c1cc(F)ccc1-n1cc(C(=O)C2CCN(C(=O)[C@H]3N[C@@H]4CC[C@H]3C4)CC2)c2ccncc21)C(C)C]

Step a) tert-Butyl (1R,3S,4S)-3-(4-(1-(2-(ethyl(isopropyl)carbamoyl)-4-fluorophenyl)-1H-pyrrolo[2,3-c]pyridine-3-carbonyl)piperidine-1-carbonyl)-2-azabicyclo[2.2.1]heptane-2-carboxylate

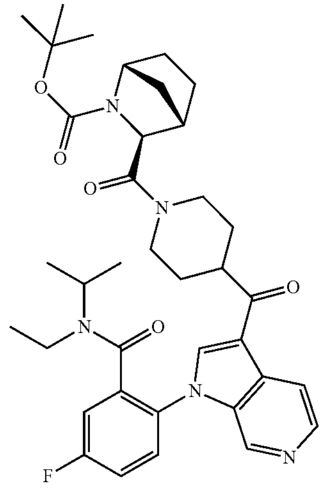 [SMILES: CCN(C(=O)c1cc(F)ccc1-n1cc(C(=O)C2CCN(C(=O)[C@@H]3[C@H]4CC[C@H](C4)N3C(=O)OC(C)(C)C)CC2)c2ccncc21)C(C)C]

N-Ethylpropan-2-amine (20.6 μL, 0.17 mmol) was added to a mixture of Intermediate 44 (100 mg, 0.17 mmol), HATU (70.8 mg, 0.19 mmol) and DIPEA (89.0 μL, 0.51 mmol) in DMF (1 mL). The mixture was stirred at rt overnight. The reaction mixture was diluted with EtOAc (20 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (65.8 mg, 59%) as a yellow gum; MS m/z (ES+) $[M+H]^+$=660.4.

Step b) 2-(3-(1-((1R,3S,4S)-2-Azabicyclo[2.2.1]heptane-3-carbonyl)piperidine-4-carbonyl)-1H-pyrrolo[2,3-c]pyridin-1-yl)-N-ethyl-5-fluoro-N-isopropylbenzamide (Example 31)

TFA (1 mL) was added to a solution of tert-butyl (1R,3S,4S)-3-(4-(1-(2-(ethyl(isopropyl)carbamoyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (65.8 mg, 0.10 mmol) in DCM (5 mL). The mixture was stirred at rt for 1 h. The mixture was concentrated under reduced pressure. The residue was purified by preparative HPLC, PrepMethod A, (gradient: 0-50%). Appropriate fractions were pooled, diluted with sat. aq. $NaHCO_3$ (20 mL) and extracted with EtOAc (2×20 mL). The combined organic layers were washed with brine (20 mL), dried over $Na_2SO_4$, filtered, and concentrated under reduced pressure. The product was lyophilized from $MeCN/H_2O$ to give the title compound (23.4 mg, 42%) as a white solid; MS m/z (ES+) $[M+H]^+$=560.3; $^1H$ NMR (400 MHz, DMSO-$d_6$, 22° C.) δ 0.16-0.75 (6H, m), 0.83-0.93 (1H, m), 0.98 (2H, d), 1.09-1.29 (3H, m), 1.31-1.56 (5H, m), 1.57-1.74 (1H, m), 1.75-1.93 (2H, m), 2.36-2.46 (1H, m), 2.69-2.85 (2H, m), 3.09-3.28 (2H, m), 3.41-3.63 (4H, m), 3.87-4.05 (1H, m), 4.33-4.51 (1H, m), 7.52-7.65 (2H, m), 7.80-7.92 (1H, m), 8.04-8.18 (1H, m), 8.32-8.42 (1H, m), 8.54-8.65 (1H, m), 8.71 (1H, br s).

Example 32: (1-((1R,3S,4S)-2-Azabicyclo[2.2.1]heptane-3-carbonyl)piperidin-4-yl)(1-(2-((2R,5S)-2,5-dimethylpyrrolidine-1-carbonyl)-4-fluorophenyl)-1H-pyrrolo[2,3-c]pyridin-3-yl)methanone

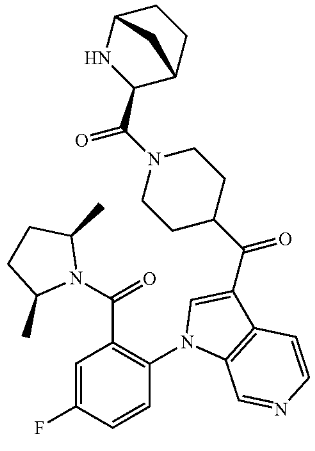 [SMILES: C[C@@H]1CC[C@H](C)N1C(=O)c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(2-((2R,5S)-2,5-dimethylpyrrolidine-1-carbonyl)-4-fluorophenyl)-1H-pyrrolo[2,3-c]pyridine-3-carbonyl)piperidine-1-carbonyl)-2-azabicyclo[2.2.1]heptane-2-carboxylate

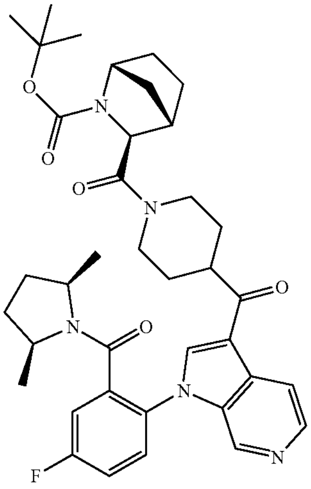 [SMILES: C[C@@H]1CC[C@H](C)N1C(=O)c1cc(F)ccc1-n1cc(C(=O)C2CCN(C(=O)[C@@H]3[C@H]4CC[C@H](C4)N3C(=O)OC(C)(C)C)CC2)c2ccncc21]

(2S,5R)-2,5-Dimethylpyrrolidine HCl (25.3 mg, 0.19 mmol) was added to a mixture of Intermediate 44 (100 mg, 0.17 mmol), HATU (70.8 mg, 0.19 mmol) and DIPEA (89.0 μL, 0.51 mmol) in DCM (1 mL). The mixture was stirred at rt overnight. The reaction mixture was diluted with EtOAc (20 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (86.9 mg, 76%) as a yellow gum; MS m/z (ES+) $[M+H]^+$=672.4.

Step b) (1-((1R,3S,4S)-2-Azabicyclo[2.2.1]heptane-3-carbonyl)piperidin-4-yl)(1-(2-((2R,5S)-2,5-dimethylpyrrolidine-1-carbonyl)-4-fluorophenyl)-1H-pyrrolo[2,3-c]pyridin-3-yl)methanone (Example 32)

TFA (1 mL) was added to a solution of tert-butyl (1R,3S,4S)-3-(4-(1-(2-((2R,5S)-2,5-dimethylpyrrolidine-1-carbonyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (86.9 mg, 0.13 mmol) in DCM (5 mL). The reaction mixture was stirred at rt for 1 h. The mixture was concentrated under reduced pressure. The residue was purified by preparative HPLC, PrepMethod A, (gradient: 0-50%). Appropriate fractions were pooled, diluted with sat. aq. $NaHCO_3$ (20 mL) and extracted with EtOAc (2×20 mL). The combined organic layers were washed with brine (20 mL), dried over $Na_2SO_4$, filtered, and concentrated under reduced pressure. The product was lyophilized from MeCN/$H_2O$ to give the title compound (25.5 mg, 35%) as a white solid; MS m/z (ES+) $[M+H]^+$=572.3; $^1H$ NMR (400 MHz, DMSO-$d_6$, 22° C.) δ 0.79-0.98 (3H, m), 1.07 (3H, d), 1.14-1.28 (3H, m), 1.33-1.55 (7H, m), 1.59-1.76 (2H, m), 1.78-1.94 (2H, m), 2.42 (1H, d), 2.70-2.85 (1H, m), 3.10-3.25 (1H, m), 3.40-3.73 (6H, m), 3.87-4.06 (1H, m), 4.34-4.51 (1H, m), 7.59 (1H, td), 7.66 (1H, dd), 7.89 (1H, dd), 8.13 (1H, dd), 8.38 (1H, d), 8.60 (1H, s), 8.64-8.74 (1H, m).

Example 33: (1-((1R,3S,4S)-2-Azabicyclo[2.2.1]heptane-3-carbonyl)piperidin-4-yl)(1-(2-((2R,6S)-2,6-dimethylpiperidine-1-carbonyl)-4-fluorophenyl)-1H-pyrrolo[2,3-c]pyridin-3-yl)methanone

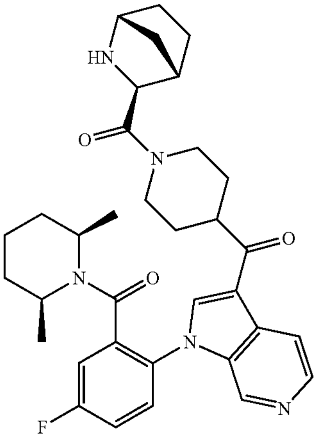 [SMILES: C[C@@H]1CCC[C@H](C)N1C(=O)c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(2-((2R,6S)-2,6-dimethylpiperidine-1-carbonyl)-4-fluorophenyl)-1H-pyrrolo[2,3-c]pyridine-3-carbonyl)piperidine-1-carbonyl)-2-azabicyclo[2.2.1]heptane-2-carboxylate

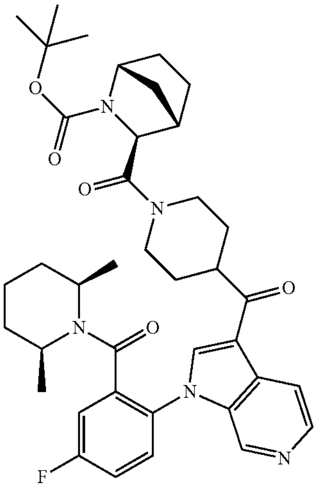 [SMILES: C[C@@H]1CCC[C@H](C)N1C(=O)c1cc(F)ccc1-n1cc(C(=O)C2CCN(C(=O)[C@@H]3[C@H]4CC[C@H](C4)N3C(=O)OC(C)(C)C)CC2)c2ccncc21]

(2S,6R)-2,6-Dimethylpiperidine (46.0 mg, 0.40 mmol) was added to a mixture of Intermediate 44 (120 mg, 0.20 mmol), HATU (170 mg, 0.44 mmol) and DIPEA (212 μL, 1.22 mmol) in DMF (1 mL). The mixture was stirred at rt overnight. The reaction mixture was diluted with DCM (40 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (116 mg, 84%) as a brown gum; MS m/z (ES+) $[M+H]^+$=686.2.

Step b) (1-((1R,3S,4S)-2-Azabicyclo[2.2.1]heptane-3-carbonyl)piperidin-4-yl)(1-(2-((2R,6S)-2,6-dimethylpiperidine-1-carbonyl)-4-fluorophenyl)-1H-pyrrolo[2,3-c]pyridin-3-yl)methanone (Example 33)

TFA (1 mL) was added to a solution of tert-butyl (1R,3S,4S)-3-(4-(1-(2-((2R,6S)-2,6-dimethylpiperidine-1-carbonyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (116 mg, 0.17 mmol) in DCM (5 mL). The mixture was stirred at rt for 2 h. The mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine (30 mL), dried over $Na_2SO_4$, filtered, and concentrated under reduced pressure. The product was lyophilized from MeCN/$H_2O$ to give the title compound (44.9 mg, 45%) as a light yellow solid; MS m/z (ES+) $[M+H]^+$=586.3; $^1H$ NMR (400 MHz, DMSO-$d_6$, 22° C.) δ 0.46 (2H, br s), 0.73-0.90 (1H, m), 0.90-1.18 (6H, m), 1.17-1.39 (4H, m), 1.39-1.75 (7H, m), 1.85 (2H, br s), 2.43-2.51 (1H, m), 2.80 (1H, br s), 3.13-3.29 (1H, m), 3.41-3.83 (5H, m), 3.90-4.03 (1H, m), 4.14 (1H, br s), 4.43 (1H, t), 7.60 (1H, td), 7.68 (1H, dd), 7.86-7.99 (1H, m), 8.10-8.22 (1H, m), 8.37-8.48 (1H, m), 8.59-8.79 (2H, m).

Example 34: (1-((1R,3S,4S)-2-Azabicyclo[2.2.1]heptane-3-carbonyl)piperidin-4-yl)(1-(2-((3R,5R)-3,5-dimethylmorpholine-4-carbonyl)-4-fluorophenyl)-1H-pyrrolo[2,3-c]pyridin-3-yl)methanone

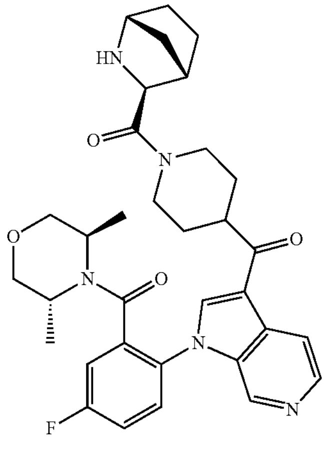 [SMILES: C[C@@H]1COC[C@@H](C)N1C(=O)c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(2-((3R,5R)-3,5-dimethylmorpholine-4-carbonyl)-4-fluorophenyl)-1H-pyrrolo[2,3-c]pyridine-3-carbonyl)piperidine-1-carbonyl)-2-azabicyclo[2.2.1]heptane-2-carboxylate

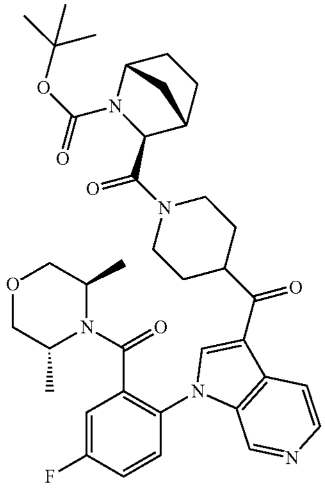 [SMILES: C[C@@H]1COC[C@@H](C)N1C(=O)c1cc(F)ccc1-n1cc(C(=O)C2CCN(C(=O)[C@@H]3[C@H]4CC[C@H](C4)N3C(=O)OC(C)(C)C)CC2)c2ccncc21]

(3R,5R)-3,5-Dimethylmorpholine HCl (61.2 mg, 0.40 mmol) was added to a mixture of Intermediate 44 (120 mg, 0.20 mmol), HATU (170 mg, 0.44 mmol) and DIPEA (212 μL, 1.22 mmol) in DMF (1 mL). The mixture was stirred at rt overnight. The reaction mixture was diluted with DCM (40 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (111 mg, 79%) as a brown gum; MS m/z (ES+) $[M+H]^+$=688.3.

Step b) (1-((1R,3S,4S)-2-Azabicyclo[2.2.1]heptane-3-carbonyl)piperidin-4-yl)(1-(2-((3R,5R)-3,5-dimethylmorpholine-4-carbonyl)-4-fluorophenyl)-1H-pyrrolo[2,3-c]pyridin-3-yl)methanone (Example 34)

TFA (1 mL) was added to a solution of tert-butyl (1R,3S,4S)-3-(4-(1-(2-((3R,5R)-3,5-dimethylmorpholine-4-carbonyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (111 mg, 0.16 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine (30 mL), dried over $Na_2SO_4$, filtered, and concentrated under reduced pressure. The product was lyophilized from MeCN/$H_2O$ to give the title compound (25.2 mg, 27%) as a light yellow solid; MS m/z (ES+) $[M+H]^+$=588.3; $^1H$ NMR (400 MHz, DMSO-$d_6$, 22° C.) δ 0.07-1.15 (6H, m), 1.16-1.34 (3H, m), 1.39-1.58 (5H, m), 1.60-1.76 (1H, m), 1.79-1.94 (2H, m), 2.16-2.49 (2H, m), 2.70-2.83 (1H, m), 3.07-3.26 (2H, m), 3.37-3.62 (7H, m), 3.89-4.04 (1H, m), 4.37-4.51 (1H, m), 7.59-7.69 (1H, m), 7.71 (1H, dd), 7.80-7.94 (1H, m), 8.16 (1H, d), 8.33-9.03 (3H, m).

Example 35: (1-((1R,3S,4S)-2-Azabicyclo[2.2.1]heptane-3-carbonyl)piperidin-4-yl)(1-(2-((3R,5S)-3,5-dimethylmorpholine-4-carbonyl)-4-fluorophenyl)-1H-pyrrolo[2,3-c]pyridin-3-yl)methanone

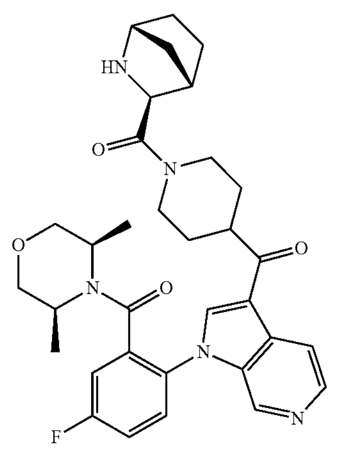 [SMILES: C[C@@H]1COC[C@H](C)N1C(=O)c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(2-((3R,5S)-3,5-dimethylmorpholine-4-carbonyl)-4-fluorophenyl)-1H-pyrrolo[2,3-c]pyridine-3-carbonyl)piperidine-1-carbonyl)-2-azabicyclo[2.2.1]heptane-2-carboxylate

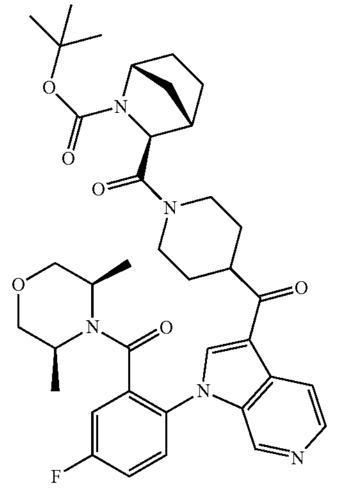 [SMILES: C[C@@H]1COC[C@H](C)N1C(=O)c1cc(F)ccc1-n1cc(C(=O)C2CCN(C(=O)[C@@H]3[C@H]4CC[C@H](C4)N3C(=O)OC(C)(C)C)CC2)c2ccncc21]

(3S,5R)-3,5-Dimethylmorpholine HCl (77.0 mg, 0.50 mmol) was added to a mixture of Intermediate 44 (150 mg, 0.25 mmol), HATU (386 mg, 1.02 mmol) and DIPEA (266 µL, 1.52 mmol) in DMF (1 mL). The mixture was stirred at rt overnight. The reaction mixture was diluted with DCM (40 mL) and washed sequentially with aq. HCl (2×20 mL, 1 M), sat. aq. $NaHCO_3$ (2×20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (114 mg, 65%) as a brown gum; MS m/z (ES+) $[M+H]^+$=688.3.

Step b) (1-((1R,3S,4S)-2-Azabicyclo[2.2.1]heptane-3-carbonyl)piperidin-4-yl)(1-(2-((3R,5S)-3,5-dimethylmorpholine-4-carbonyl)-4-fluorophenyl)-1H-pyrrolo[2,3-c]pyridin-3-yl)methanone (Example 35)

TFA (1 mL) was added to a solution of tert-butyl (1R,3S,4S)-3-(4-(1-(2-((3R,5S)-3,5-dimethylmorpholine-4-carbonyl)-4-fluorophenyl)-1H-pyrrolo[2,3-c]pyridine-3-carbonyl)piperidine-1-carbonyl)-2-azabicyclo[2.2.1]heptane-2-carboxylate from Step a) (114 mg, 0.17 mmol) in DCM (5 mL). The mixture was stirred at rt for 1 h. The mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine (30 mL), dried over $Na_2SO_4$, filtered, and concentrated under reduced pressure. The product was lyophilized from MeCN/$H_2O$ to give the title compound (24.6 mg, 25%) as a white solid; MS m/z (ES+) $[M+H]^+$=588.3; $^1H$ NMR (400 MHz, DMSO-$d_6$, 22° C.) δ 0.54-1.27 (9H, m), 1.38-1.56 (5H, m), 1.58-1.72 (1H, m), 1.86 (2H, br s), 2.29-2.47 (2H, m), 2.73-3.29 (4H, m), 3.37-3.84 (6H, m), 3.95 (1H, t), 4.34-4.48 (1H, m), 7.54-7.75 (2H, m), 7.84-7.97 (1H, m), 8.15 (1H, d), 8.40 (1H, dd), 8.51-8.87 (2H, m).

Example 36: (1-((1R,3S,4S)-2-Azabicyclo[2.2.1]heptane-3-carbonyl)piperidin-4-yl)(1-(4-fluoro-2-(1-isopropyl-1H-pyrazol-5-yl)phenyl)-1H-pyrrolo[2,3-c]pyridin-3-yl)methanone

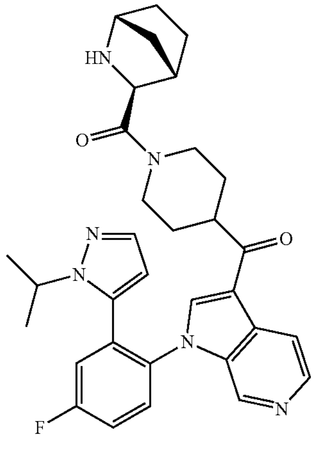 [SMILES: CC(C)n1nccc1-c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(4-fluoro-2-(1-isopropyl-1H-pyrazol-5-yl)phenyl)-1H-pyrrolo[2,3-c]pyridine-3-carbonyl)piperidine-1-carbonyl)-2-azabicyclo[2.2.1]heptane-2-carboxylate

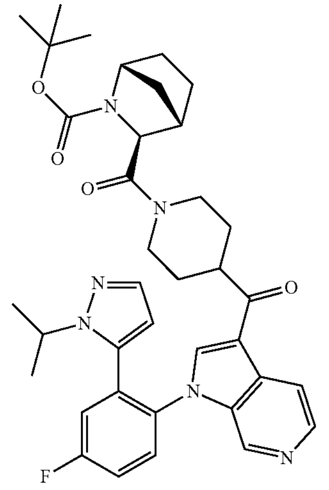 [SMILES: CC(C)n1nccc1-c1cc(F)ccc1-n1cc(C(=O)C2CCN(C(=O)[C@@H]3[C@H]4CC[C@H](C4)N3C(=O)OC(C)(C)C)CC2)c2ccncc21]

$Pd(dppf)Cl_2$ (5.85 mg, 0.01 mmol) was added to a degassed solution of Intermediate 49 (50.0 mg, 0.08 mmol), (1-isopropyl-1H-pyrazol-5-yl)boronic acid (14.8 mg, 1.67 mmol) and aq. $K_2CO_3$ (120 µL, 0.24 mmol, 2 M) in 1,4-dioxane (1 mL) under $N_2$. The resulting mixture was stirred at 90° C. for 1.5 h. The reaction mixture was purified by straight phase flash chromatography on silica (gradient: 0-10% MeOH in DCM) to give the title compound (41.3 mg, 79%) as a yellow oil; MS m/z (ES+) $[M+H]^+$=655.2.

Step b) (1-((1R,3S,4S)-2-Azabicyclo[2.2.1]heptane-3-carbonyl)piperidin-4-yl)(1-(4-fluoro-2-(1-isopropyl-1H-pyrazol-5-yl)phenyl)-1H-pyrrolo[2,3-c]pyridin-3-yl)methanone (Example 36)

4 M HCl in 1,4-dioxane (153 L) was added to tert-butyl (1R,3S,4S)-3-(4-(1-(4-fluoro-2-(1-isopropyl-1H-pyrazol-5-yl)phenyl)-1H-pyrrolo[2,3-c]pyridine-3-carbonyl)piperidine-1-carbonyl)-2-azabicyclo[2.2.1]heptane-2-carboxylate from Step a) (40.0 mg, 0.06 mmol) in MeCN (1 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc (20 mL), and washed sequentially with sat. aq. $NaHCO_3$ (30 mL) and brine (30 mL). The organic layer was dried over $Na_2SO_4$, filtered, and concentrated under reduced pressure. The product was lyophilized from $MeCN/H_2O$ to give the title compound (16.6 mg, 49%) as a white solid; MS m/z (ES+) $[M+H]^+$=555.3; $^1H$ NMR (400 MHz, DMSO-$d_6$, 22° C.) δ 1.02 (6H, br s), 1.16-1.31 (3H, m), 1.31-1.69 (7H, m), 1.69-1.82 (2H, m), 2.64-2.81 (1H, m), 3.13 (1H, dd), 3.53 (2H, dd), 3.94 (1H, t), 4.18 (1H, dt), 4.42 (1H, t), 6.14-6.22 (1H, m), 7.31-7.36 (1H, m), 7.59 (1H, dd), 7.67 (1H, td), 7.95 (1H, dd), 8.03 (1H, dd), 8.32 (1H, dd), 8.55 (1H, s), 8.67 (1H, s).

Example 37: (1-((1R,3S,4S)-2-Azabicyclo[2.2.1]heptane-3-carbonyl)piperidin-4-yl)(1-(4-fluoro-2-(4-isopropylpyrimidin-5-yl)phenyl)-1H-pyrrolo[2,3-c]pyridin-3-yl)methanone

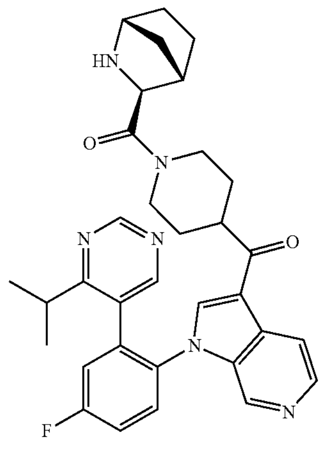 [SMILES: CC(C)c1ncncc1-c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(4-fluoro-2-(4-isopropylpyrimidin-5-yl)phenyl)-1H-pyrrolo[2,3-c]pyridine-3-carbonyl)piperidine-1-carbonyl)-2-azabicyclo[2.2.1]heptane-2-carboxylate

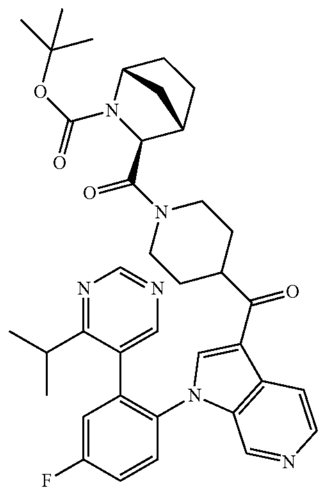 [SMILES: CC(C)c1ncncc1-c1cc(F)ccc1-n1cc(C(=O)C2CCN(C(=O)[C@@H]3[C@H]4CC[C@H](C4)N3C(=O)OC(C)(C)C)CC2)c2ccncc21]

$Pd(dppf)Cl_2$ (17.6 mg, 0.02 mmol) was added to a degassed solution of Intermediate 49 (150 mg, 0.24 mmol), (4-isopropylpyrimidin-5-yl)boronic acid (119 mg, 0.72 mmol) and aq. $K_2CO_3$ (480 µL, 0.96 mmol, 2 M) in 1,4-dioxane (5 mL) under $N_2$. The resulting mixture was stirred at 110° C. for 2 h. The reaction mixture was diluted with EtOAc (20 mL) and washed with water. The organic layer was dried over $Na_2SO_4$, filtered, and concentrated to dryness. The residue was purified by straight phase flash chromatography on silica (gradient: 0-7.5% MeOH in DCM) to give the title compound (122 mg, 76%) as a yellow oil; MS m/z (ES+) $[M+H]^+$=667.3.

Step b) (1-((1R,3S,4S)-2-Azabicyclo[2.2.1]heptane-3-carbonyl)piperidin-4-yl)(1-(4-fluoro-2-(4-isopropylpyrimidin-5-yl)phenyl)-1H-pyrrolo[2,3-c]pyridin-3-yl)methanone (Example 37)

TFA (1 mL) was added to tert-butyl (1R,3S,4S)-3-(4-(1-(4-fluoro-2-(4-isopropylpyrimidin-5-yl)phenyl)-1H-pyrrolo[2,3-c]pyridine-3-carbonyl)piperidine-1-carbonyl)-2-azabicyclo[2.2.1]heptane-2-carboxylate from Step a) (122 mg, 0.18 mmol) in DCM (4 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc and washed with sat. aq. $NaHCO_3$. The organic layer was dried over $Na_2SO_4$, filtered, and concentrated under reduced pressure. The product was lyophilized from $MeCN/H_2O$ to give the title compound (83.0 mg, 80%) as a white solid; MS m/z (ES+) $[M+H]^+$=567.3; $^1$H NMR (400 MHz, DMSO-$d_6$, 22° C.) δ 0.35 (2H, br s), 0.99 (4H, t), 1.19-1.33 (3H, m), 1.35-1.83 (9H, m), 2.64-2.80 (2H, m), 3.06-3.19 (1H, m), 3.52-3.71 (2H, m), 3.85-3.99 (1H, m), 4.33-4.48 (1H, m), 7.61-7.73 (2H, m), 7.90-8.04 (2H, m), 8.31 (1H, d), 8.53-8.83 (3H, m), 8.96 (1H, br s).

Example 38: (1-((1R,3S,4S)-2-Azabicyclo[2.2.1]heptane-3-carbonyl)piperidin-4-yl)(1-(4-fluoro-2-(2-isopropylpyridin-3-yl)phenyl)-1H-pyrrolo[2,3-c]pyridin-3-yl)methanone

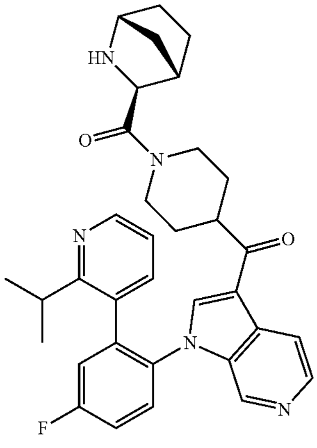 [SMILES: CC(C)c1ncccc1-c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(4-fluoro-2-(2-isopropylpyridin-3-yl)phenyl)-1H-pyrrolo[2,3-c]pyridine-3-carbonyl)piperidine-1-carbonyl)-2-azabicyclo[2.2.1]heptane-2-carboxylate

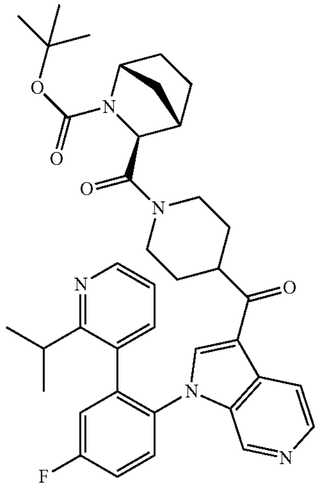 [SMILES: CC(C)c1ncccc1-c1cc(F)ccc1-n1cc(C(=O)C2CCN(C(=O)[C@@H]3[C@H]4CC[C@H](C4)N3C(=O)OC(C)(C)C)CC2)c2ccncc21]

Pd(dppf)$Cl_2$ (5.85 mg, 0.01 mmol) was added to a degassed solution of Intermediate 49 (50.0 mg, 0.08 mmol), (2-isopropylpyridin-3-yl)boronic acid HCl (32.2 mg, 0.16 mmol) and aq. $K_2CO_3$ (200 μL, 0.40 mmol, 2 M) in 1,4-dioxane (1 mL) under $N_2$. The resulting mixture was stirred at 110° C. for 1.5 h. The reaction mixture was diluted with MeOH (20 mL), silica gel was added and the mixture was concentrated under reduced pressure. The resulting silica powder with absorbed crude product was applied on a silica flash cartridge and the product was purified by straight phase flash chromatography on silica (gradient: 0-10% MeOH in DCM) to give the title compound (45.0 mg, 85%) as a yellow oil; MS m/z (ES+) $[M+H]^+$=666.2.

Step b) (1-((1R,3S,4S)-2-Azabicyclo[2.2.1]heptane-3-carbonyl)piperidin-4-yl)(1-(4-fluoro-2-(2-isopropylpyridin-3-yl)phenyl)-1H-pyrrolo[2,3-c]pyridin-3-yl)methanone (Example 38)

4 M HCl in 1,4-dioxane (169 L) was added to a mixture of tert-butyl (1R,3S,4S)-3-(4-(1-(4-fluoro-2-(2-isopropylpyridin-3-yl)phenyl)-1H-pyrrolo[2,3-c]pyridine-3-carbonyl)piperidine-1-carbonyl)-2-azabicyclo[2.2.1]heptane-2-carboxylate from Step a) (45.0 mg, 0.07 mmol) in MeCN (1 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc (20 mL) and washed sequentially with sat. aq. $NaHCO_3$ (20 mL) and brine (20 mL). The organic layer was dried over $Na_2SO_4$, filtered, and concentrated under reduced pressure. The product was lyophilized from $MeCN/H_2O$ to give the title compound (20.6 mg, 54%) as a white solid; MS m/z (ES+) $[M+H]^+$=566.3; $^1$H NMR (400 MHz, DMSO-$d_6$, 22° C.) δ 0.15 (3H, br s), 0.87-1.06 (3H, m), 1.12-1.29 (3H, m), 1.32-1.45 (2H, m), 1.46-1.54 (3H, m), 1.55-1.79 (2H, m), 2.29-2.48 (2H, m), 2.53-2.81 (2H, m), 3.11 (1H, p), 3.40-3.51 (2H, m), 3.78-3.99 (1H, m), 4.40 (1H, t), 7.16 (1H, br s), 7.54 (1H, dd), 7.61 (1H, td), 7.76

(1H, br s), 7.92 (1H, dd), 7.98 (1H, dd), 8.25-8.33 (1H, m), 8.40 (1H, s), 8.5-8.57 (1H, m), 8.55-8.63 (1H, m).

Example 39: (1-((1R,3S,4S)-2-Azabicyclo[2.2.1]heptane-3-carbonyl)piperidin-4-yl)(1-(5-fluoro-2'-isopropyl-[1,1'-biphenyl]-2-yl)-1H-pyrrolo[2,3-c]pyridin-3-yl)methanone

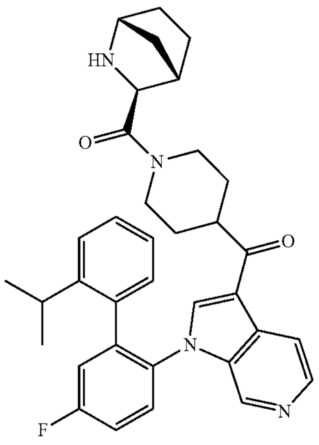 [SMILES: CC(C)c1ccccc1-c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(5-fluoro-2'-isopropyl-[1,1'-biphenyl]-2-yl)-1H-pyrrolo[2,3-c]pyridine-3-carbonyl)piperidine-1-carbonyl)-2-azabicyclo[2.2.1]heptane-2-carboxylate

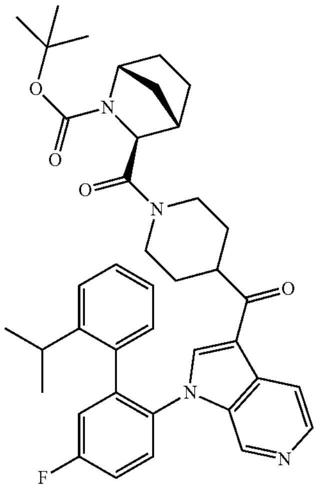 [SMILES: CC(C)c1ccccc1-c1cc(F)ccc1-n1cc(C(=O)C2CCN(C(=O)[C@@H]3[C@H]4CC[C@H](C4)N3C(=O)OC(C)(C)C)CC2)c2ccncc21]

$Pd(dppf)Cl_2$ (5.85 mg, 0.01 mmol) was added to a degassed solution of Intermediate 49 (50.0 mg, 0.08 mmol), (2-isopropylphenyl)boronic acid (26.2 mg, 0.16 mmol) and aq. $K_2CO_3$ (120 L, 0.24 mmol, 2 M) in 1,4-dioxane (1 mL) at rt under $N_2$. The resulting mixture was stirred at 110° C. for 1.5 h. The reaction mixture was diluted with MeOH (20 mL), concentrated in the presence of silica and purified by straight phase flash chromatography on silica (gradient: 0-100% EtOAc in heptane) to give the title compound (39.3 mg, 74%) as a yellow oil; MS m/z (ES+) $[M+H]^+$=665.2.

Step b) (1-((1R,3S,4S)-2-Azabicyclo[2.2.1]heptane-3-carbonyl)piperidin-4-yl)(1-(5-fluoro-2'-isopropyl-[1,1'-biphenyl]-2-yl)-1H-pyrrolo[2,3-c]pyridin-3-yl)methanone (Example 39)

4 M HCl in 1,4-dioxane (148 L) was added to a mixture of tert-butyl (1R,3S,4S)-3-(4-(1-(5-fluoro-2'-isopropyl-[1,1'-biphenyl]-2-yl)-1H-pyrrolo[2,3-c]pyridine-3-carbonyl)piperidine-1-carbonyl)-2-azabicyclo[2.2.1]heptane-2-carboxylate from Step a) (39.3 mg, 0.06 mmol) in MeCN (1 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc (20 mL) and washed sequentially with sat. aq. $NaHCO_3$ (20 mL) and brine (20 mL). The organic layer was dried over $Na_2SO_4$, filtered, and concentrated under reduced pressure. The product was lyophilized from $MeCN/H_2O$ to give the title compound (14.8 mg, 44%) as a white solid; MS m/z (ES+) $[M+H]^+$=565.3; $^1H$ NMR (400 MHz, DMSO-$d_6$, 22° C.) δ 0.32-0.67 (3H, m), 0.88-1.04 (3H, m), 1.14-1.31 (3H, m), 1.32-1.72 (9H, m), 2.41 (1H, br s), 2.61-2.75 (1H, m), 3.00-3.15 (1H, m), 3.51-3.67 (2H, m), 3.82-4.00 (1H, m), 4.31-4.45 (1H, m), 7.09-7.20 (2H, m), 7.20-7.26 (1H, m), 7.26-7.37 (1H, m), 7.45 (1H, dd), 7.57 (1H, td), 7.90 (1H, dd), 7.98 (1H, dd), 8.30 (1H, dd), 8.36-8.42 (1H, m), 8.59-8.63 (1H, m).

Example 40: (1-((1R,3S,4S)-2-Azabicyclo[2.2.1]heptane-3-carbonyl)piperidin-4-yl)(1-(2-(4-cyclopropylpyrimidin-5-yl)-4-fluorophenyl)-1H-pyrrolo[2,3-c]pyridin-3-yl)methanone

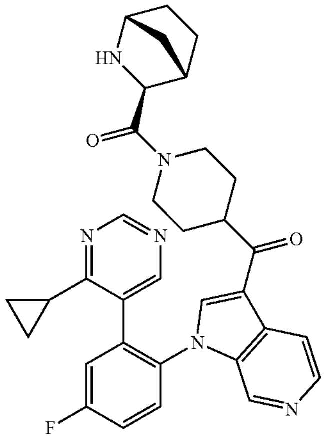 [SMILES: O=C(c1cn(-c2ccc(F)cc2-c2cncnc2C2CC2)c2cnccc12)C1CCN(C(=O)[C@H]2N[C@@H]3CC[C@H]2C3)CC1]

Step a) tert-Butyl (1R,3S,4S)-3-(4-(1-(2-(4-cyclopropylpyrimidin-5-yl)-4-fluorophenyl)-1H-pyrrolo[2,3-c]pyridine-3-carbonyl)piperidine-1-carbonyl)-2-azabicyclo[2.2.1]heptane-2-carboxylate

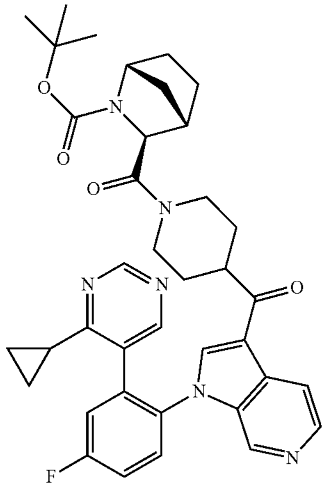 [SMILES: CC(C)(C)OC(=O)N1[C@@H]2CC[C@@H](C2)[C@H]1C(=O)N1CCC(C(=O)c2cn(-c3ccc(F)cc3-c3cncnc3C3CC3)c3cnccc23)CC1]

$Pd(dppf)Cl_2$ (5.85 mg, 0.01 mmol) was added to a degassed solution of Intermediate 49 (50.0 mg, 0.08 mmol), (4-cyclopropylpyrimidin-5-yl)boronic acid (26.2 mg, 0.16 mmol) and aq. $K_2CO_3$ (120 μL, 0.24 mmol, 2 M) in 1,4-dioxane (1 mL) under $N_2$. The resulting mixture was stirred at 110° C. for 1.5 h. The reaction mixture was diluted with MeOH (20 mL), absorbed on silica and purified by straight phase flash chromatography on silica (gradient: 0-100% EtOAc in heptane followed by 0-10% MeOH in DCM) to give the title compound (44.6 mg, 84%) as a yellow oil; MS m/z (ES+) $[M+H]^+$=665.3.

Step b) (1-((1R,3S,4S)-2-Azabicyclo[2.2.1]heptane-3-carbonyl)piperidin-4-yl)(1-(2-(4-cyclopropylpyrimidin-5-yl)-4-fluorophenyl)-1H-pyrrolo[2,3-c]pyridin-3-yl)methanone (Example 40)

4 M HCl in 1,4-dioxane (168 L) was added to a solution of tert-butyl (1R,3S,4S)-3-(4-(1-(2-(4-cyclopropylpyrimidin-5-yl)-4-fluorophenyl)-1H-pyrrolo[2,3-c]pyridine-3-carbonyl)piperidine-1-carbonyl)-2-azabicyclo[2.2.1]heptane-2-carboxylate from Step a) (44.6 mg, 0.07 mmol) in MeCN (1 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc (20 mL) and washed sequentially with sat. aq. $NaHCO_3$ (20 mL) and brine (20 mL). The organic layer was dried over $Na_2SO_4$, filtered, and concentrated under reduced pressure. The product was lyophilized from $MeCN/H_2O$ to give the title compound to give the title compound (8.90 mg, 23%) as a white solid; MS m/z (ES+) $[M+H]^+$=565.3; $^1H$ NMR (400 MHz, DMSO-$d_6$, 22° C.) δ 0.75-1.06 (3H, m), 1.13-1.29 (3H, m), 1.32-1.58 (6H, m), 1.57-1.82 (3H, m), 2.28-2.46 (2H, m), 2.60-2.77 (1H, m), 3.01-3.17 (1H, m), 3.41-3.51 (3H, m), 3.86-4.03 (1H, m), 4.29-4.51 (1H, m), 7.67 (1H, td), 7.74 (1H, dd), 7.92-8.08 (2H, m), 8.25-8.37 (1H, m), 8.64 (2H, d), 8.71-8.90 (2H, m).

Example 41: (1-((1R,3S,4S)-2-Azabicyclo[2.2.1]heptane-3-carbonyl)piperidin-4-yl)(1-(4-fluoro-2-(4-isopropylpyridin-3-yl)phenyl)-1H-pyrrolo[2,3-c]pyridin-3-yl)methanone

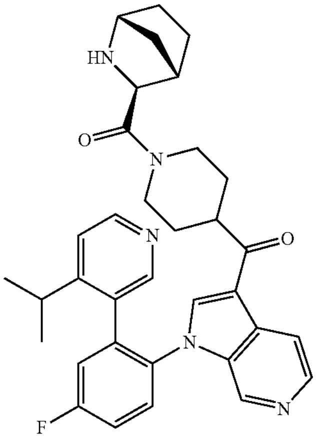 [SMILES: CC(C)c1ccncc1-c1cc(F)ccc1-n1cc(C(=O)C2CCN(C(=O)[C@H]3N[C@@H]4CC[C@H]3C4)CC2)c2ccncc21]

Step a) tert-Butyl (1R,3S,4S)-3-(4-(1-(4-fluoro-2-(4-isopropylpyridin-3-yl)phenyl)-1H-pyrrolo[2,3-c]pyridine-3-carbonyl)piperidine-1-carbonyl)-2-azabicyclo[2.2.1]heptane-2-carboxylate

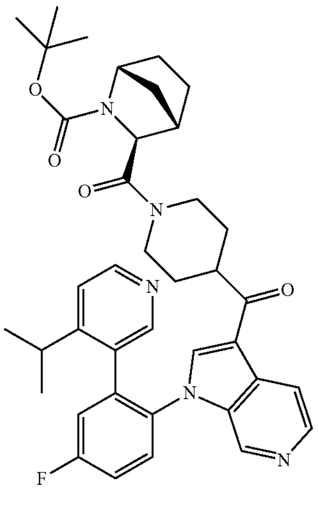 [SMILES: CC(C)c1ccncc1-c1cc(F)ccc1-n1cc(C(=O)C2CCN(C(=O)[C@@H]3[C@H]4CC[C@H](C4)N3C(=O)OC(C)(C)C)CC2)c2ccncc21]

$Pd(dppf)Cl_2$ (5.85 mg, 0.01 mmol) was added to a degassed solution of Intermediate 49 (50.0 mg, 0.08 mmol), (4-isopropylpyridin-3-yl)boronic acid (19.8 mg, 0.08 mmol) and aq. $K_2CO_3$ (120 μL, 0.24 mmol, 2 M) in 1,4-dioxane (1 mL) under $N_2$. The resulting mixture was stirred at 110° C. for 2 h. The reaction mixture was diluted with MeOH (20 mL), absorbed on silica and purified by straight phase flash chromatography on silica (gradient: 0-12.5% MeOH in DCM) to give the title compound (45.5 mg, 85%) as a purple oil; MS m/z (ES+) $[M+H]^+$=666.2.

Step b) (1-((1R,3S,4S)-2-Azabicyclo[2.2.1]heptane-3-carbonyl)piperidin-4-yl)(1-(4-fluoro-2-(4-isopropylpyridin-3-yl)phenyl)-1H-pyrrolo[2,3-c]pyridin-3-yl)methanone (Example 41)

4 M HCl in 1,4-dioxane (171 L) was added to a solution of tert-butyl (1R,3S,4S)-3-(4-(1-(4-fluoro-2-(4-isopropylpyridin-3-yl)phenyl)-1H-pyrrolo[2,3-c]pyridine-3-carbonyl)piperidine-1-carbonyl)-2-azabicyclo[2.2.1]heptane-2-carboxylate from Step a) (45.5 mg, 0.07 mmol) in MeCN (1 mL). The resulting mixture was stirred at rt for 1 h. The reaction mixture was concentrated under reduced pressure. The residue was purified by preparative HPLC, PrepMethod A, (gradient: 0-75%). Appropriate fractions were pooled, diluted with EtOAc (20 mL) and washed sequentially with sat. aq. $NaHCO_3$ (20 mL) and brine (20 mL). The organic layer was dried over $Na_2SO_4$, filtered, and concentrated under reduced pressure. The product was lyophilized from $MeCN/H_2O$ to give the title compound (6.00 mg, 16%) as a white solid; MS m/z (ES+) $[M+H]^+$=566.3; $^1H$ NMR (400 MHz, DMSO-$d_6$, 22° C.) δ 0.91-1.03 (3H, m), 1.21-1.27 (1H, m), 1.31 (3H, s), 1.35-1.76 (9H, m), 2.52-2.60 (2H, m), 2.64-2.83 (2H, m), 3.03-3.22 (2H, m), 3.62-3.80 (2H, m), 3.84-3.94 (1H, m), 4.30-4.45 (1H, m), 7.14-7.22 (1H, m), 7.55-7.60 (1H, m), 7.63 (1H, td), 7.91-7.96 (1H, m), 7.98 (1H, dd), 8.27-8.32 (1H, m), 8.30-8.38 (1H, m), 8.41-8.63 (3H, m).

Example 42: (1-((1R,3S,4S)-2-Azabicyclo[2.2.1]heptane-3-carbonyl)piperidin-4-yl)(1-(4-fluoro-2-(4-isopropylthiazol-5-yl)phenyl)-1H-pyrrolo[2,3-c]pyridin-3-yl)methanone 1·formic acid

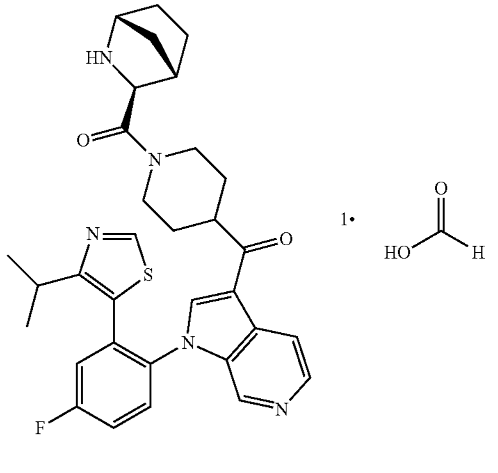 [SMILES: CC(C)c1ncsc1-c1cc(F)ccc1-n1cc(C(=O)C2CCN(C(=O)[C@H]3N[C@@H]4CC[C@H]3C4)CC2)c2ccncc21 ; O=CO]

Step a) tert-Butyl (1R,3S,4S)-3-(4-(1-(4-fluoro-2-(4-isopropylthiazol-5-yl)phenyl)-1H-pyrrolo[2,3-c]pyridine-3-carbonyl)piperidine-1-carbonyl)-2-azabicyclo[2.2.1]heptane-2-carboxylate

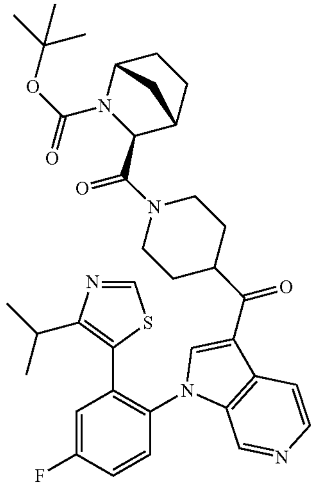 [SMILES: CC(C)c1ncsc1-c1cc(F)ccc1-n1cc(C(=O)C2CCN(C(=O)[C@@H]3[C@H]4CC[C@H](C4)N3C(=O)OC(C)(C)C)CC2)c2ccncc21]

Pd(dppf)$Cl_2$ (27.9 mg, 0.04 mmol) was added to a mixture of Intermediate 49 (200 mg, 0.38 mmol), Intermediate 122 (193 mg, 0.76 mmol) and $K_2CO_3$ (158 mg, 1.14 mmol, 2 M) in 1,4-dioxane (2 mL) and water (500 μL) under $N_2$. The resulting mixture was stirred at 60° C. for 3 h. The reaction mixture was concentrated under reduced pressure. The residue was diluted with DCM (100 mL) and washed with water (100 mL). The organic layer was dried over $Na_2SO_4$, filtered, and concentrated to dryness. The residue was purified by preparative TLC on silica (EtOAc) to give the title compound (110 mg, 43%) as a yellow solid; MS m/z (ES+) $[M+H]^+$=672.4.

Step b) (1-((1R,3S,4S)-2-Azabicyclo[2.2.1]heptane-3-carbonyl)piperidin-4-yl)(1-(4-fluoro-2-(4-isopropylthiazol-5-yl)phenyl)-1H-pyrrolo[2,3-c]pyridin-3-yl)methanone 1·formic acid (Example 42)

tert-Butyl (1R,3S,4S)-3-(4-(1-(4-fluoro-2-(4-isopropylthiazol-5-yl)phenyl)-1H-pyrrolo[2,3-c]pyridine-3-carbonyl)piperidine-1-carbonyl)-2-azabicyclo[2.2.1]heptane-2-carboxylate from Step a) (100 mg, 0.15 mmol) was added to FA (2 mL) under $N_2$. The resulting mixture was stirred at rt for 3 hours. The reaction mixture was concentrated under reduced pressure. The residue was quenched with sat. aq. $NaHCO_3$ (50 mL) and extracted with DCM (2×25 mL). The combined organic layers were dried over $Na_2SO_4$, filtered, and concentrated under reduced pressure. The residue was purified by preparative HPLC, PrepMethod G (gradient: 4-18%). Appropriate fractions were pooled and concentrated under reduced pressure to give the title compound (36.1 mg, 39%); MS m/z (ES+) $[M+H]^+$=572.3; $^1H$ NMR (400 MHz, DMSO-$d_6$) δ 1.02 (6H, br s), 1.34-1.51 (3H, m), 1.64 (5H, br s), 1.68-1.85 (2H, m), 2.55-2.66 (1H, m), 2.75-2.85 (1H, m), 2.86-2.96 (1H, m), 3.13-3.26 (1H, m), 3.36-3.46 (1H, m), 3.84-3.92 (2H, m), 3.95-4.11 (1H, m), 4.38 (1H, t), 7.55 (1H, dd), 7.63 (1H, td), 7.91 (1H, dd), 8.05 (1H, dd), 8.26-8.40 (2H, m), 8.43 (1H, s), 8.64 (1H, s), 8.85 (1H, s).

Example 43: (1-((1S,2S,5R)-3-Azabicyclo[3.1.0]hexane-2-carbonyl)piperidin-4-yl)(1-(4-fluoro-2-(1-isopropyl-1H-pyrazol-5-yl)phenyl)-1H-pyrrolo[2,3-c]pyridin-3-yl)methanone 1·formic acid

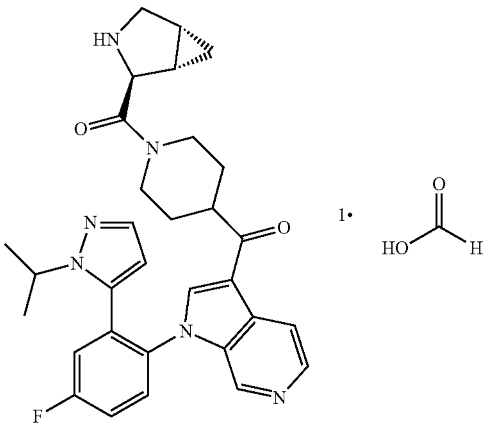 [SMILES: CC(C)n1nccc1-c1cc(F)ccc1-n1cc(C(=O)C2CCN(C(=O)[C@H]3NC[C@@H]4C[C@@H]43)CC2)c2ccncc21 ; O=CO]

Step a) tert-Butyl (1S,2S,5R)-2-(4-(1-(4-fluoro-2-(1-isopropyl-1H-pyrazol-5-yl)phenyl)-1H-pyrrolo[2,3-c]pyridine-3-carbonyl)piperidine-1-carbonyl)-3-azabicyclo[3.1.0]hexane-3-carboxylate

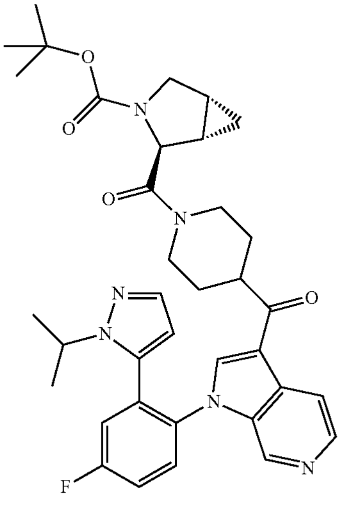 [SMILES: CC(C)n1nccc1-c1cc(F)ccc1-n1cc(C(=O)C2CCN(C(=O)[C@@H]3[C@H]4C[C@H]4CN3C(=O)OC(C)(C)C)CC2)c2ccncc21]

Pd(dppf)$C_2$ (23.9 mg, 0.03 mmol) was added to a degassed solution of Intermediate 50 (200 mg, 0.33 mmol), 1-isopropyl-5-(4,4,5,5-tetramethyl-1,3,2-dioxaborolan-2-yl)-1H-pyrazole (116 mg, 0.49 mmol) and $K_2CO_3$ (136 mg, 0.98 mmol) in a mixture of 1,4-dioxane (8 mL) and water (2 mL) under $N_2$. The resulting mixture was stirred at 60° C. for 1 h. The reaction mixture was quenched with sat. aq. $NaHCO_3$ (50 mL) and extracted with EtOAc (3×25 mL). The combined organic layers were dried over $Na_2SO_4$, filtered, and concentrated under reduced pressure. The residue was purified by preparative TLC on silica (DCM: MeOH, 10:1) to give the title compound (150 mg, 72%) as a white solid; MS m/z (ES+) $[M+H]^+$=641.3.

Step b) (1-((1S,2S,5R)-3-Azabicyclo[3.1.0]hexane-2-carbonyl)piperidin-4-yl)(1-(4-fluoro-2-(1-isopropyl-1H-pyrazol-5-yl)phenyl)-1H-pyrrolo[2,3-c]pyridin-3-yl)methanone 1·formic acid (Example 43)

4 M HCl in 1,4-dioxane (1 mL) was added to tert-butyl (1S,2S,5R)-2-(4-(1-(4-fluoro-2-(1-isopropyl-1H-pyrazol-5-yl)phenyl)-1H-pyrrolo[2,3-c]pyridine-3-carbonyl)piperidine-1-carbonyl)-3-azabicyclo[3.1.0]hexane-3-carboxylate from Step a) (130 mg, 0.20 mmol). The reaction mixture was stirred at rt for 1 h. The reaction mixture was poured into sat. aq. $NaHCO_3$ (25 mL) and extracted with DCM (3×15 mL). The combined organic layers were dried over $Na_2SO_4$, filtered, and concentrated under reduced pressure. The residue was purified by preparative HPLC, PrepMethod G (gradient: 3-15%). Appropriate fractions were pooled and concentrated under reduced pressure to give the title compound (52.0 mg, 44%); MS m/z (ES+) $[M+H]^+$=541.3; $^1H$ NMR (300 MHz, DMSO-$d_6$, 24° C.) δ 0.37-0.48 (1H, m), 0.51-0.63 (1H, m), 1.02 (6H, s), 1.27-1.99 (6H, m), 2.64-2.77 (1H, m), 2.85-2.97 (1H, m), 2.99-3.26 (2H, m), 3.32-3.45 (1H, m), 4.00-4.26 (3H, m), 4.37-4.49 (1H, m), 6.18 (1H, d), 7.34 (1H, d), 7.59 (1H, dd), 7.64-7.72 (1H, m), 7.96 (1H, dd), 8.04 (1H, d), 8.25 (1H, s), 8.32 (1H, d), 8.56 (1H, s), 8.66 (1H, s).

Example 44: 2-(3-(1-((1R,3S,4S)-2-Azabicyclo[2.2.1]heptane-3-carbonyl)piperidine-4-carbonyl)-4-fluoro-1H-pyrrolo[2,3-c]pyridin-1-yl)-5-fluoro-N,N-diisopropylbenzamide 1·formic acid

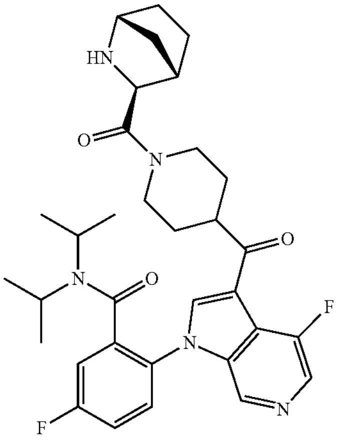

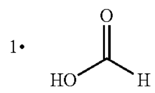

Step a) tert-Butyl (1R,3S,4S)-3-(4-(1-(2-(diisopropylcarbamoyl)-4-fluorophenyl)-4-fluoro-1H-pyrrolo[2,3-c]pyridine-3-carbonyl)piperidine-1-carbonyl)-2-azabicyclo[2.2.1]-heptane-2-carboxylate

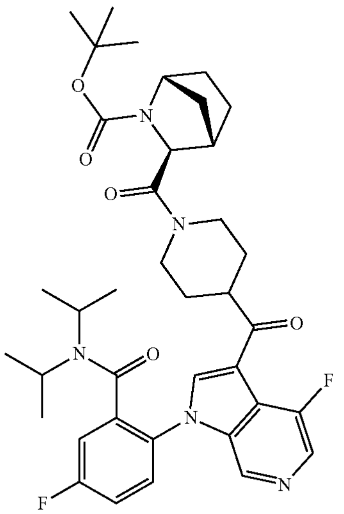 [SMILES: CC(C)N(C(=O)c1cc(F)ccc1-n1cc(C(=O)C2CCN(C(=O)[C@@H]3[C@H]4CC[C@H](C4)N3C(=O)OC(C)(C)C)CC2)c2c(F)cncc21)C(C)C]

T3P (3.10 g, 4.88 mmol, 50% in EtOAc) was added to a mixture of Intermediate 55 (440 mg, 0.81 mmol), (1R,3S,4S)-2-(tert-butoxycarbonyl)-2-azabicyclo[2.2.1]heptane-3-carboxylic acid (235 mg, 0.98 mmol) and DIPEA (840 mg, 6.50 mmol) in DCM (5 mL). The resulting mixture was stirred at rt for 6 h. The reaction mixture was poured into sat. $NH_4Cl$ (100 mL) and extracted with DCM (3×25 mL). The combined organic layers were dried over $Na_2SO_4$, filtered, and concentrated to dryness to give the title compound (476 mg, 85%); MS m/z (ES+) $[M+H]^+$=692.3; $^1H$ NMR (300 MHz, DMSO-$d_6$, 24° C.) δ 0.42 (2H, br s), 0.78 (2H, br s), 1.03 (3H, d), 1.28-1.37 (9H, m), 1.40 (5H, s), 1.47-1.69 (6H, m), 1.71-1.95 (4H, m), 2.39-2.47 (1H, m), 2.55-2.85 (2H, m), 3.09-3.32 (2H, m), 3.48-3.57 (2H, m), 4.08-4.19 (2H, m), 4.29-4.53 (1H, m), 7.49-7.63 (2H, m), 7.84-7.94 (1H, m), 8.29-8.33 (1H, m), 8.48 (1H, s), 8.72 (1H, s).

Step b) 2-(3-(1-((1R,3S,4S)-2-Azabicyclo[2.2.1]heptane-3-carbonyl)piperidine-4-carbonyl)-4-fluoro-1H-pyrrolo[2,3-c]pyridin-1-yl)-5-fluoro-N,N-diisopropylbenzamide FA (4 mL) was added to tert-butyl (1R,3S,4S)-3-(4-(1-(2-(diisopropylcarbamoyl)-4-fluorophenyl)-4-fluoro-1H-pyrrolo[2,3-c]pyridine-3-carbonyl)piperidine-1-carbonyl)-2-azabicyclo[2.2.1]heptane-2-carboxylate from Step a) (400 mg, 0.58 mmol). The resulting mixture was stirred at rt for 3 h. The reaction mixture was poured into sat. aq. $NaHCO_3$ (100 mL) and extracted with DCM (3×25 mL). The combined organic layers were dried over $Na_2SO_4$, filtered, and concentrated to dryness. The crude product was purified by preparative HPLC, PrepMethod G (gradient: 5-26%) to give the title compound (170 mg, 47%) as a white solid; MS m/z (ES+) [M+H]+=592.3; $^1H$ NMR (400 MHz, DMSO-$d_6$, 26° C.) δ 0.39 (3H, br s), 0.77 (3H, br s), 1.02 (3H, d), 1.29-1.43 (5H, m), 1.45-1.73 (6H, m), 1.76-1.98 (2H, m), 2.53-2.65 (1H, m), 2.74-2.95 (1H, m), 3.15-3.34 (2H, m), 3.48-3.64 (2H, m), 3.72-3.84 (1H, m), 3.85-4.10 (2H, m), 4.31-4.51 (1H, m), 7.49-7.63 (2H, m), 7.82-7.93 (1H, m), 8.31 (1H, s), 8.50 (1H, s), 8.73 (1H, s).

Example 45: 2-(3-((R*)-1-((1R,3S,4S)-2-Azabicyclo[2.2.1]heptane-3-carbonyl)azepane-4-carbonyl)-1H-pyrrolo[2,3-c]pyridin-1-yl)-5-fluoro-N,N-diisopropylbenzamide 1·formic acid

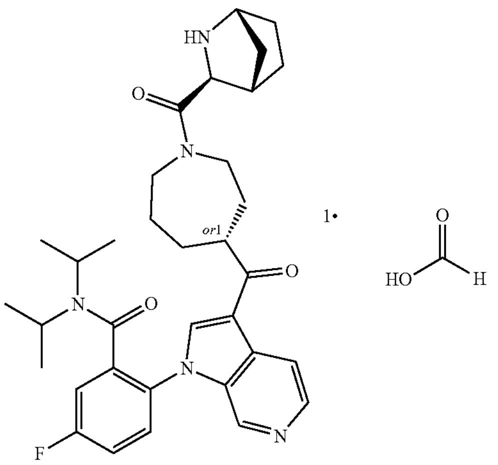 [SMILES: CC(C)N(C(=O)c1cc(F)ccc1-n1cc(C(=O)[C@@H]2CCCN(C(=O)[C@H]3N[C@@H]4CC[C@H]3C4)CC2)c2ccncc21)C(C)C ; O=CO]

Step a) tert-Butyl (1R,3S,4S)-3-((R*)-4-(1-(2-(diisopropylcarbamoyl)-4-fluorophenyl)-HH-pyrrolo[2,3-c]pyridine-3-carbonyl)azepane-1-carbonyl)-2-azabicyclo[2.2.1]heptane-2-carboxylate

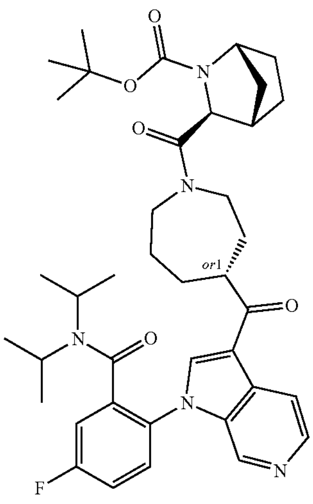 [SMILES: CC(C)N(C(=O)c1cc(F)ccc1-n1cc(C(=O)[C@@H]2CCCN(C(=O)[C@@H]3[C@H]4CC[C@H](C4)N3C(=O)OC(C)(C)C)CC2)c2ccncc21)C(C)C]

T3P (1.07 g, 1.68 mmol, 50% in EtOAc) was added to a solution of Intermediate 60 (260 mg, 0.56 mmol), (1R,3S,4S)-2-(tert-butoxycarbonyl)-2-azabicyclo[2.2.1]heptane-3-carboxylic acid (176 mg, 0.73 mmol) and DIPEA (293 μL, 1.68 mmol) in DCM (15 mL). The resulting mixture was stirred at rt for 8 h. The reaction mixture was diluted with EtOAc (50 mL) and washed sequentially with sat. $NH_4Cl$ (25 mL) and water (25 mL). The organic layer was dried over $Na_2SO_4$, filtered, and concentrated under reduced pressure. The residue was purified by preparative HPLC, PrepMethod H (isocratic: 10%) to give the title compound (74.0 mg, 19%) as a white solid; MS m/z (ES+) $[M+H]^+$=688.5.

Step b) 2-(3-((R*)-1-((1R,3S,4S)-2-Azabicyclo[2.2.1]heptane-3-carbonyl)azepane-4-carbonyl)-1H-pyrrolo[2,3-c]pyridin-1-yl)-5-fluoro-N,N-diisopropylbenzamide 1·formic acid (Example 45)

FA (1.5 mL) was added to a solution of tert-butyl (1R,3S,4S)-3-((R*)-4-(1-(2-(diisopropylcarbamoyl)-4-fluorophenyl)-1H-pyrrolo[2,3-c]pyridine-3-carbonyl)azepane-1-carbonyl)-2-azabicyclo[2.2.1]heptane-2-carboxylate from Step a) (74.0 mg, 0.11 mmol). The mixture was stirred at rt for 1 h. The mixture was diluted with DCM (50 mL) and washed with sat. aq. $NaHCO_3$ (50 mL). The organic layer was dried over $Na_2SO_4$, filtered, and concentrated under reduced pressure. The residue was purified by preparative HPLC, PrepMethod G (gradient: 4-20%). Appropriate fractions were pooled and concentrated under reduced pressure to give the title compound (17.0 mg, 24%); MS m/z (ES+) $[M+H]^+$=588.3; $^1H$ NMR (400 MHz, DMSO-$d_6$, 24° C.) δ 0.04-0.56 (3H, m), 0.58-0.86 (3H, m), 0.91-1.10 (3H, m), 1.19-1.34 (3H, m), 1.34-1.53 (3H, m), 1.53-1.69 (5H, m), 1.75-1.97 (3H, m), 2.00-2.18 (1H, m), 2.67 (1H, d), 3.02-3.43 (3H, m), 3.43-3.51 (1H, m), 3.58-3.75 (2H, m), 3.77-3.95 (2H, m), 4.00-4.23 (1H, m), 7.46-7.61 (2H, m), 7.75-7.89 (1H, m), 8.09-8.17 (1H, m), 8.26 (1H, s), 8.33-8.42 (1H, m), 8.51-8.60 (1H, m), 8.60-8.67 (1H, m).

Example 46: 2-(3-(1-((1R,3S,4S)-2-Azabicyclo[2.2.1]heptane-3-carbonyl)piperidine-4-carbonyl)-2-methyl-1H-pyrrolo[2,3-c]pyridin-1-yl)-N-ethyl-5-fluoro-N-isopropylbenzamide (Mixture of Atropisomers)

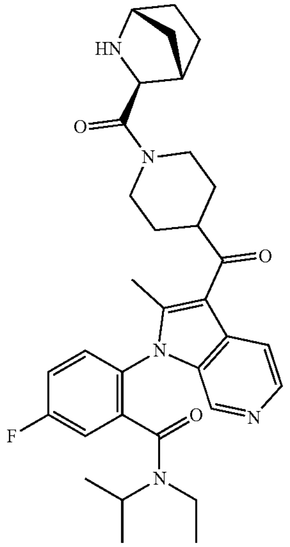 [SMILES: CCN(C(=O)c1cc(F)ccc1-n1c(C)c(C(=O)C2CCN(C(=O)[C@H]3N[C@@H]4CC[C@H]3C4)CC2)c2ccncc21)C(C)C]

Step a) tert-Butyl (1R,3S,4S)-3-(4-(1-(2-(ethyl(isopropyl)carbamoyl)-4 fluorophenyl)-2-2-carboxylate (Mixture of Atropisomers)

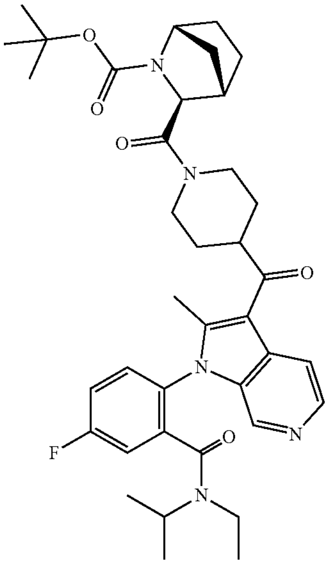 [SMILES: CCN(C(=O)c1cc(F)ccc1-n1c(C)c(C(=O)C2CCN(C(=O)[C@@H]3[C@H]4CC[C@H](C4)N3C(=O)OC(C)(C)C)CC2)c2ccncc21)C(C)C]

Intermediate 67 hydrochloride (489.3 mg, 0.24 mmol th.) was added to a solution of (1R,3S,4S)-2-(tert-butoxycarbonyl)-2-azabicyclo[2.2.1]heptane-3-carboxylic acid (116 mg, 0.48 mmol), EDC (116 mg, 0.60 mmol), HOBt (92.0 mg, 0.60 mmol) and DIPEA (211 μL, 1.21 mmol) in DMF (2 mL). The resulting mixture was stirred at rt overnight. The reaction mixture was diluted with EtOAc (50 mL) and washed sequentially with aq. HCl (50 mL, 1 M), sat. aq. $NaHCO_3$ (50 mL) and brine (50 mL). The organic layer was dried over $Na_2SO_4$, filtered, and concentrated under reduced pressure. The residue was purified by straight phase flash chromatography on silica (gradient: 0-5% MeOH in DCM) to give the title compound (126 mg) as a light yellow foam which was used directly in the next step; MS m/z (ES+) $[M+H]^+$=674.3.

Step b) 2-(3-(1-((1R,3S,4S)-2-Azabicyclo[2.2.1]heptane-3-carbonyl)piperidine-4-carbonyl)-2-methyl-1H-pyrrolo[2,3-c]pyridin-1-yl)-N-ethyl-5-fluoro-N-isopropylbenzamide (Mixture of Atropisomers) (Example 46)

TFA (1 mL) was added to a solution of tert-butyl (1R,3S,4S)-3-(4-(1-(2-(ethyl(isopropyl)carbamoyl)-4-fluorophenyl)-2-methyl-1H-pyrrolo[2,3-c]pyridine-3-carbonyl)piperidine-1-carbonyl)-2-azabicyclo[2.2.1]heptane-2-carboxylate from Step a) (126 mg) in DCM (5 mL). The mixture was stirred at rt for 1 h. The reaction mixture was concentrated under reduced pressure. The residue was purified by preparative HPLC, PrepMethod A, (gradient: 0-75%). Appropriate fractions were pooled, diluted with sat. aq. $NaHCO_3$ (30 mL) and extracted with EtOAc (2×30 mL). The combined organic layers were washed with brine, dried over $Na_2SO_4$, filtered, and concentrated under reduced pressure. The product was lyophilized from MeCN/$H_2O$ to give the title compound (10.6 mg, 8% over two steps) as a white solid; MS m/z (ES+) $[M+H]^+$=574.3; $^1H$ NMR (400 MHz, DMSO-$d_6$, 22° C.) δ 0.12-0.27 (1H, m), 0.31-0.48 (4H, m), 0.55-0.78 (2H, m), 0.95-1.09 (3H, m), 1.18-1.32 (3H, m), 1.40-1.70 (6H, m), 1.82-1.97 (2H, m), 2.41-2.46 (1H, m), 2.52-2.57 (3H, m), 2.64-2.79 (1H, m), 2.92-3.05 (1H, m), 3.20 (1H, dd), 3.48-3.65 (3H, m), 3.65-3.76 (1H, m), 3.85-3.99 (1H, m), 4.26-4.45 (1H, m), 7.53-7.65 (2H, m), 7.70-7.80 (1H, m), 7.85-7.96 (1H, m), 8.28-8.39 (2H, m).

Example 47: 2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-N-ethyl-5-fluoro-N-isopropylbenzamide (Mixture of Atropisomers)

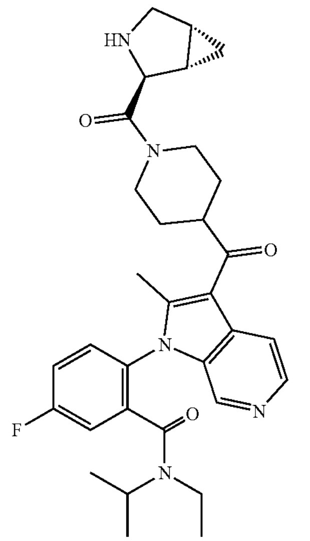 [SMILES: CCN(C(=O)c1cc(F)ccc1-n1c(C)c(C(=O)C2CCN(C(=O)[C@H]3NC[C@@H]4C[C@@H]43)CC2)c2ccncc21)C(C)C]

Step a) tert-Butyl (1S,2S,5R)-2-(4-(1-(2-(ethyl(isopropyl)carbamoyl)-4-fluorophenyl)-2-methyl-1H-pyrrolo[2,3-c]pyridine-3-carbonyl)piperidine-1-carbonyl)-3-azabicyclo[3.1.0]-hexane-3-carboxylate (Mixture of Atropisomers)

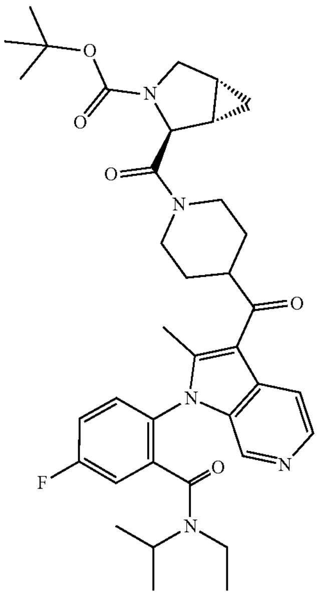 [SMILES: CCN(C(=O)c1cc(F)ccc1-n1c(C)c(C(=O)C2CCN(C(=O)[C@@H]3[C@H]4C[C@H]4CN3C(=O)OC(C)(C)C)CC2)c2ccncc21)C(C)C]

Intermediate 67 (611 mg, 1.17 mmol th.) was added to a solution of (1S,2S,5R)-3-(tert-butoxycarbonyl)-3-azabicyclo[3.1.0]hexane-2-carboxylic acid (294 mg, 1.29 mmol), EDC (270 mg, 1.41 mmol), HOBt (216 mg, 1.41 mmol) and DIPEA (410 μL, 2.35 mmol) in DMF (5 mL). The resulting mixture was stirred at rt overnight. The reaction mixture was diluted with DCM (40 mL) and washed sequentially with aq. HCl (20 mL, 1 M), sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (590 mg, 76%) as a yellow gum; MS m/z (ES+) $[M+H]^+$=660.5.

Step b) 2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-N-ethyl-5-fluoro-N-isopropylbenzamide (Mixture of Atropisomers) (Example 47)

TFA (2 mL) was added to a solution of tert-butyl (1S,2S,5R)-2-(4-(1-(2-(ethyl-(isopropyl)carbamoyl)-4-fluorophenyl)-2-methyl-1H-pyrrolo[2,3-c]pyridine-3-carbonyl)-piperidine-1-carbonyl)-3-azabicyclo[3.1.0]hexane-3-carboxylate from Step a) (590 mg, 0.89 mmol) in DCM (10 mL). The mixture was stirred at rt for 1 h. The mixture was concentrated under reduced pressure. The mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by straight phase flash chromatography on silica (gradient: 0-20% 0.7 M $NH_3$ in MeOH in DCM). The product was lyophilized from MeCN/$H_2O$ to give the title compound (340 mg, 68%) as a light orange solid; MS m/z (ES+) $[M+H]^+$=560.3; $^1$H NMR (400 MHz, DMSO-$d_6$, 22° C.) δ 0.12-0.34 (2H, m), 0.34-0.51 (5H, m), 0.55-0.77 (2H, m), 0.95-1.09 (3H, m), 1.32-1.51 (3H, m), 1.56-1.74 (1H, m), 1.79-1.94 (2H, m), 2.48 (3H, s), 2.65-2.80 (2H, m), 2.83-2.94 (2H, m), 3.13-3.27 (1H, m), 3.46-3.59 (1H, m), 3.62-3.75 (1H, m), 3.88 (1H, d), 4.10 (1H, br s), 4.27-4.44 (1H, m), 7.54-7.65 (2H, m), 7.70-7.80 (1H, m), 7.83-7.97 (1H, m), 8.27-8.38 (2H, m).

Examples 48-1 and 48-2: 2-(3-(1-((1S,2S,5R)-3-Azabicyclo[3.1.0-]hexane-2-carbonyl)piperidine-4-carbonyl)-2-methyl-1H-pyrrolo[2,3-c]pyridin-1-yl)-N-ethyl-5-fluoro-N-isopropylbenzamide (Separated Atropisomers)

48-1

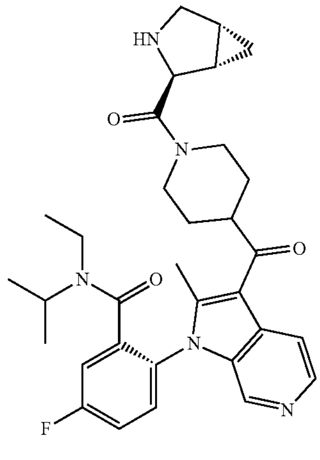

-continued 48-2

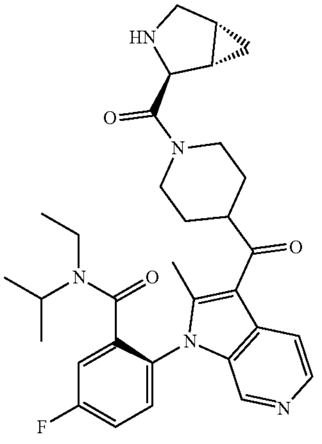

Example 47 (180 mg, 0.32 mmol) was purified by preparative SFC, PrepMethod SFC-C, to give the title compound Example 48-1 as first eluting product (84.2 mg, 47%); MS m/z (ES+) $[M+H]^+$=560.2; $^1H$ NMR (500 MHz, DMSO-$d_6$, 27° C.) δ 0.15-0.32 (2H, m), 0.36-0.48 (5H, m), 0.58-0.78 (2H, m), 0.97-1.07 (3H, m), 1.33-1.47 (3H, m), 1.65 (1H, br s), 1.79-1.94 (2H, m), 2.68-2.76 (2H, m), 2.82-2.92 (2H, m), 3.15-3.24 (1H, m), 3.44-3.58 (1H, m), 3.65-3.74 (1H, m), 3.84 (1H, s), 4.04-4.16 (1H, m), 4.27-4.41 (1H, m), 7.54-7.62 (2H, m), 7.69-7.78 (1H, m), 7.84-7.95 (1H, m), 8.29-8.36 (2H, m); and Example 48-2 as second eluting product (85.7 mg, 48%); MS m/z (ES+) $[M+H]^+$=560.3; $^1H$ NMR (500 MHz, DMSO-$d_6$, 27° C.) δ 0.16-0.33 (2H, m), 0.36-0.49 (5H, m), 0.57-0.78 (2H, m), 0.97-1.09 (3H, m), 1.33-1.49 (3H, m), 1.56-1.75 (1H, m), 1.79-1.94 (2H, m), 2.68-2.77 (2H, m), 2.83-2.93 (2H, m), 3.22 (1H, dd), 3.45-3.58 (1H, m), 3.65-3.75 (1H, m), 3.85 (1H, d), 4.04-4.17 (1H, m), 4.35 (1H, d), 7.54-7.62 (2H, m), 7.70-7.79 (1H, m), 7.84-7.94 (1H, m), 8.28-8.36 (2H, m).

Examples 49-1 and 49-2: (S)-2-(3-(1-(4-Azaspiro[2.4]heptane-5-carbonyl)piperidine-4-carbonyl)-2-methyl-1H-pyrrolo[2,3-c]pyridin-1-yl)-N-ethyl-5-fluoro-N-isopropylbenzamide (Separated Atropisomers)

49-1

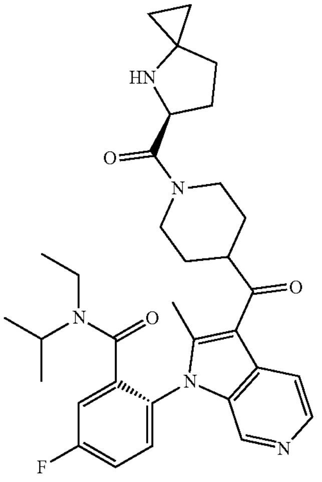

-continued 49-2

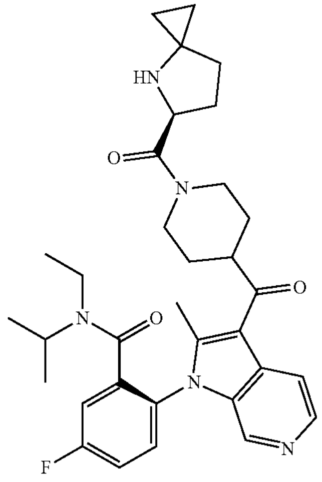

Step a) tert-Butyl (S)-5-(4-(1-(2-(ethyl(isopropyl)carbamoyl)-4-fluorophenyl)-2-methyl-1H-pyrrolo[2,3-c]pyridine-3-carbonyl)piperidine-1-carbonyl)-4-azaspiro[2.4]heptane-4-carboxylate (Mixture of Atropisomers)

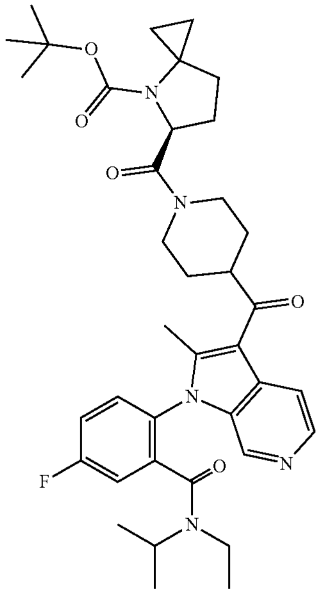 [SMILES: CCN(C(=O)c1cc(F)ccc1-n1c(C)c(C(=O)C2CCN(C(=O)[C@@H]3CCC4(CC4)N3C(=O)OC(C)(C)C)CC2)c2ccncc21)C(C)C]

Intermediate 67 (356 mg, 0.71 mmol th.) was added to a solution of (S)-4-(tert-butoxycarbonyl)-4-azaspiro[2.4]heptane-5-carboxylic acid (189 mg, 0.78 mmol), EDC (164 mg, 0.85 mmol), HOBt (131 mg, 0.85 mmol) and DIPEA (249 μL, 1.42 mmol) in DCM (2 mL). The resulting mixture was stirred at rt for 2 h. The reaction mixture was diluted with DCM (40 mL) and washed with sat. aq. $NaHCO_3$ (20 mL). The organic layer was washed with brine (20 mL), dried over $Na_2SO_4$, filtered, and concentrated under reduced pressure. The residue was purified by straight phase flash chromatography on silica (gradient: 0-10% MeOH in DCM) to give the title compound (476 mg, 99%) as a yellow gum which was used directly in the next step; MS m/z (ES+) $[M+H]^+$=674.3.

Step b) (S)-2-(3-(1-(4-Azaspiro[2.4]heptane-5-carbonyl)piperidine-4-carbonyl)-2-methyl-1H-pyrrolo[2,3-c]pyridin-1-yl)-N-ethyl-5-fluoro-N-isopropylbenzamide rotational (separated Atropisomers) (Examples 49-1 and 49-2)

p-TsOH·$H_2O$ (343 mg, 1.80 mmol) was added to a solution of tert-butyl (S)-5-(4-(1-(2-(ethyl(isopropyl)carbamoyl)-4-fluorophenyl)-2-methyl-1H-pyrrolo[2,3-c]pyridine-3-carbonyl)piperidine-1-carbonyl)-4-azaspiro[2.4]heptane-4-carboxylate from Step a) (476 mg, 0.63 mmol th.) in IPA (3.5 mL). The mixture was stirred at 60° C. overnight. The reaction mixture was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by preparative HPLC, PrepMethod A, (gradient: 0-75%) followed by preparative SFC, PrepMethod SFC-D to afford the separated atropisomers. Both atropisomers were further purified by preparative HPLC, PrepMethod I (gradient: 30-60%) to give the title compound Example 49-1 as first eluting product in SFC (65.8 mg, 17%); MS m/z (ES+) $[M+H]^+$=574.3; $^1$H NMR (500 MHz, $CDCl_3$, 27° C.) δ 0.32-0.40 (1H, m), 0.48 (2H, dd), 0.56-0.68 (4H, m), 0.70 (1H, d), 0.78-0.92 (2H, m), 1.01-1.14 (3H, m), 1.54-1.63 (1H, m), 1.66-1.79 (1H, m), 1.79-2.08 (5H, m), 2.22-2.35 (1H, m), 2.55-2.67 (3H, m), 2.70-3.05 (3H, m), 3.08-3.48 (3H, m), 3.62-3.87 (1H, m), 3.97-4.09 (2H, m), 4.50-4.59 (1H, m), 7.16-7.26 (1H, m), 7.30-7.37 (1H, m), 7.38-7.45 (1H, m), 7.70-7.82 (1H, m), 8.20-8.27 (1H, m), 8.37-8.43 (1H, m); and Example 49-2 as second eluting product in SFC (61.3 mg, 18%); MS m/z (ES+) $[M+H]^+$=574.3; $^1$H NMR (500 MHz, $CDCl_3$, 27° C.) δ 0.34-0.42 (1H, m), 0.44-0.54 (2H, m), 0.59-0.76 (5H, m), 0.81-0.93 (2H, m), 1.02-1.16 (3H, m), 1.55-1.65 (1H, m), 1.73 (1H, q), 1.83-2.07 (5H, m), 2.25-2.34 (1H, m), 2.56-2.70 (3H, m), 2.75-3.05 (3H, m), 3.12-3.45 (3H, m), 3.63-3.89 (1H, m), 3.99-4.10 (2H, m), 4.49-4.64 (1H, m), 7.19-7.27 (1H, m), 7.32-7.37 (1H, m), 7.40-7.45 (1H, m), 7.74-7.81 (1H, m), 8.23-8.29 (1H, m), 8.40-8.45 (1H, m).

Examples 50-1 and 50-2: (S)-2-(3-(1-(5,5-Dimethylpyrrolidine-2-carbonyl)piperidine-4-carbonyl)-2-methyl-1H-pyrrolo[2,3-c]pyridin-1-yl)-N-ethyl-5-fluoro-N-isopropylbenzamide (Separated Atropisomers)

50-1

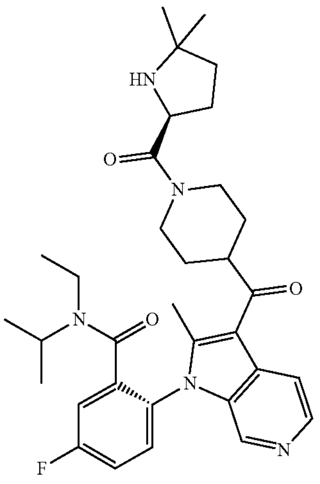

-continued 50-2

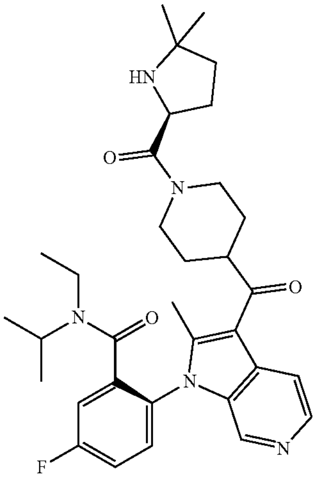

Step a) tert-Butyl (S)-5-(4-(1-(2-(ethyl(isopropyl)carbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate (Mixture of Atropisomers)

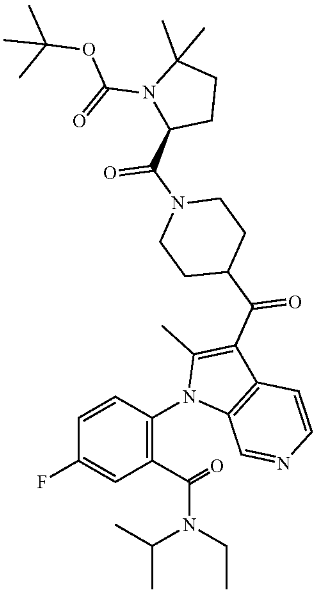 [SMILES: CCN(C(=O)c1cc(F)ccc1-n1c(C)c(C(=O)C2CCN(C(=O)[C@@H]3CCC(C)(C)N3C(=O)OC(C)(C)C)CC2)c2ccncc21)C(C)C]

Intermediate 67 (350 mg, 0.71 mmol th.) was added to a solution of (S)-1-(tert-butoxycarbonyl)-5,5-dimethylpyrrolidine-2-carboxylic acid (190 mg, 0.78 mmol), EDC (164 mg, 0.85 mmol), HOBt (131 mg, 0.85 mmol) and DIPEA (249 μL, 1.42 mmol) in DCM (2 mL). The resulting mixture was stirred at rt for 2 h. The reaction mixture was diluted with DCM (20 mL) and washed with sat. aq. $NaHCO_3$ (20 mL). The organic layer was passed through a phase separator, dried over $Na_2SO_4$, filtered, and concentrated under reduced pressure. The residue was purified by straight phase flash chromatography on silica (gradient: 0-10% MeOH in DCM) to give the title compound (470 mg, 98%) as a yellow gum which was used directly in the next step; MS m/z (ES+) $[M+H]^+$=676.3.

Step b) (S)-2-(3-(1-(5,5-Dimethylpyrrolidine-2-carbonyl)piperidine-4-carbonyl)-2-methyl-1H-pyrrolo[2,3-c]pyridin-1-yl)-N-ethyl-5-fluoro-N-isopropyl-benzamide (Separated Atropisomers) (Examples 50-1 and 50-2)

TFA (2 mL) was added to a solution of tert-butyl (S)-5-(4-(1-(2-(ethyl(isopropyl)-carbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate from Step a) (470 mg, 0.63 mmol th.) in DCM (10 mL). The reaction mixture was stirred at rt for 1 h. The mixture was concentrated under reduced pressure. The residue was quenched with sat. aq. $NaHCO_3$ (30 mL) and extracted with DCM (2×30 mL). The combined organic layers were washed with brine (30 mL), dried over $Na_2SO_4$, filtered, and concentrated under reduced pressure. The residue was purified by preparative HPLC, PrepMethod A, (gradient: 0-75%), followed by preparative SFC, PrepMethod SFC-D to afford the separated atropisomers. Both atropisomers were further purified by preparative HPLC, PrepMethod I (gradient: 30-60%) to give the title compound Example 50-1 as first eluting product in SFC (66.6 mg, 18%); MS m/z (ES+) $[M+H]^+$=576.4; $^1H$ NMR (500 MHz, $CDCl_3$, 27° C.) δ 0.40-0.52 (2H, m), 0.56-0.66 (2H, m), 0.68-0.74 (1H, m), 0.83 (1H, t), 1.03-1.10 (3H, m), 1.14 (3H, s), 1.30 (3H, s), 1.45-1.56 (1H, m), 1.64-1.76 (2H, m), 1.76-1.94 (2H, m), 1.95-2.05 (2H, m), 2.17-2.28 (1H, m), 2.30-2.46 (1H, m), 2.57-2.66 (3H, m), 2.71-2.84 (1H, m), 2.93-3.03 (1H, m), 3.09-3.46 (3H, m), 3.61-3.86 (1H, m), 3.96-4.03 (1H, m), 4.02-4.09 (1H, m), 4.47-4.61 (1H, m), 7.17-7.25 (1H, m), 7.29-7.37 (1H, m), 7.37-7.46 (1H, m), 7.70-7.81 (1H, m), 8.20-8.27 (1H, m), 8.37-8.43 (1H, m); and Example 50-2 as second eluting product in SFC (65.6 mg, 18%); MS m/z (ES+) $[M+H]^+$=576.7; $^1H$ NMR (500 MHz, $CDCl_3$, 27° C.) δ 0.50 (2H, dd), 0.58-0.76 (3H, m), 0.82-0.87 (1H, m), 1.03-1.16 (6H, m), 1.31 (3H, s), 1.45-1.57 (1H, m), 1.66-2.08 (6H, m), 2.18-2.29 (1H, m), 2.56-2.72 (4H, m), 2.74-2.86 (1H, m), 2.94-3.05 (1H, m), 3.18-3.47 (3H, m), 3.63-3.88 (1H, m), 3.95-4.04 (1H, m), 4.04-4.11 (1H, m), 4.50-4.60 (1H, m), 7.18-7.26 (1H, m), 7.30-7.38 (1H, m), 7.38-7.46 (1H, m), 7.72-7.84 (1H, m), 8.21-8.29 (1H, m), 8.39-8.44 (1H, m).

Examples 51-1 and 51-2: 2-(3-(1-((1S,2S,5R)-3-Azabicyclo[3.1.0]hexane-2-carbonyl)-piperidine-4-carbonyl)-2-methyl-1H-pyrrolo[2,3-c]pyridin-1-yl)-5-fluoro-N-isopropyl-N-(2,2,2-trifluoroethyl) benzamide (Separated Atropisomers)

51-1

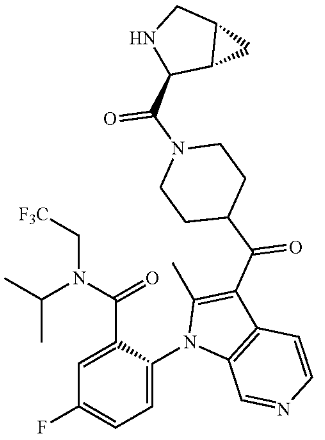

-continued 51-2

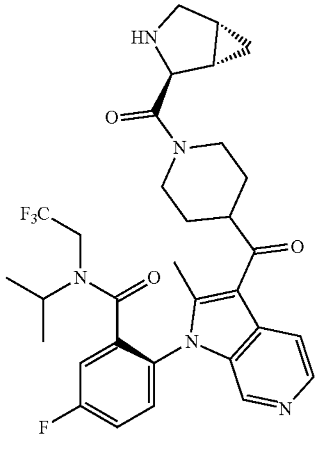

Step a) tert-Butyl (1S,2S,5R)-2-(4-(1-(4-fluoro-2-(isopropyl(2,2,2-trifluoroethyl)-carbamoyl)phenyl)-2-methyl-1H-pyrrolo[2,3-c]pyridine-3-carbonyl) piperidine-1-carbonyl)-3-azabicyclo[3.1.0]hexane-3-carboxylate (Mixture of Atropisomers)

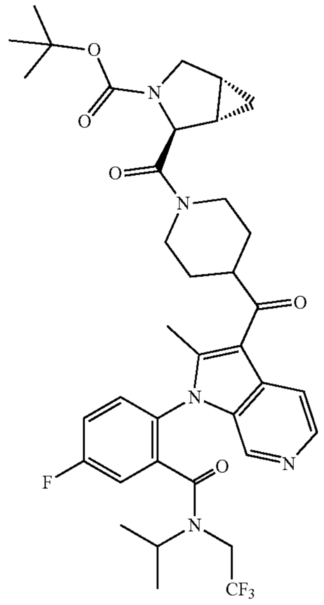 [SMILES: Cc1c(C(=O)C2CCN(C(=O)[C@@H]3[C@H]4C[C@H]4CN3C(=O)OC(C)(C)C)CC2)c2ccncc2n1-c1ccc(F)cc1C(=O)N(CC(F)(F)F)C(C)C]

Intermediate 69 (315 mg, 0.62 mmol) was added to a solution of (1S,2S,5R)-3-(tert-butoxycarbonyl)-3-azabicyclo[3.1.0]hexane-2-carboxylic acid (156 mg, 0.69 mmol), EDC (144 mg, 0.75 mmol), HOBt (115 mg, 0.75 mmol) and DIPEA (218 μL, 1.25 mmol) in DMF (2 mL). The resulting mixture was stirred at rt overnight. The reaction mixture was diluted with DCM (20 mL) and washed with sat. aq. $NaHCO_3$ (20 mL). The organic layer was passed through a phase separator and concentrated under reduced pressure. The residue was purified by straight phase flash chromatography on silica (gradient: 0-10% MeOH in DCM) to give the title compound in a quantitative yield (461 mg) as a yellow gum, which was used directly in the next step; MS m/z (ES+) $[M+H]^+$=714.2.

Step b) 2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N-isopropyl-N-(2,2,2-trifluoroethyl)benzamide (Separated Atropisomers) (Examples 51-1 and 51-2)

TFA (1 mL) was added to a solution of tert-butyl (1S,2S,5R)-2-(4-(1-(4-fluoro-2-(isopropyl(2,2,2-trifluoroethyl)carbamoyl)phenyl)-2-methyl-1H-pyrrolo[2,3-c]pyridine-3-carbonyl)piperidine-1-carbonyl)-3-azabicyclo[3.1.0]hexane-3-carboxylate from Step a) (461 mg, 0.62 mmol) in DCM (5 mL). The mixture was stirred at rt for 2 h. The mixture was concentrated under reduced pressure. The residue was quenched with sat. aq. $NaHCO_3$ and diluted with DCM. The organic layer was passed through a phase separator and concentrated under reduced pressure. The residue was purified by straight phase flash chromatography on silica (gradient: 0-20% 0.7 M $NH_3$ in MeOH in DCM). The crude product was purified by preparative HPLC, PrepMethod A, (gradient: 0-75%), followed by preparative SFC, PrepMethod SFC-E, to give the title compound Example 51-1 as first eluting product (97.3 mg, 25%); MS m/z (ES+) $[M+H]^+$=614.3; $^1$H NMR (500 MHz, DMSO-$d_6$, 27° C.) δ 0.32-0.45 (3H, m), 0.51 (1H, td), 0.80-1.13 (4H, m), 1.39-1.54 (3H, m), 1.61-1.74 (1H, m), 1.82-1.95 (2H, m), 2.48 (3H, s), 2.82 (1H, t), 2.87-3.02 (2H, m), 3.46-3.56 (2H, m), 3.72-3.87 (2H, m), 3.95-4.14 (3H, m), 4.27-4.43 (1H, m), 7.61-7.70 (2H, m), 7.74-7.81 (1H, m), 7.91 (1H, s), 8.18-8.44 (2H, m); and Example 51-2 as second eluting product (99.2 mg, 26%); MS m/z (ES+) $[M+H]^+$=614.3; $^1$H NMR (500 MHz, DMSO-$d_6$, 27° C.) δ 0.25-0.5 (4H, m), 0.77-1.13 (4H, m), 1.32-1.78 (4H, m), 1.78-1.96 (2H, m), 2.47 (3H, s), 2.68-2.79 (1H, m), 2.82-2.97 (2H, m), 3.17 (1H, s), 3.44-3.58 (1H, m), 3.63-3.89 (3H, m), 3.98-4.18 (2H, m), 4.24-4.41 (1H, m), 7.6-7.68 (2H, m), 7.72-7.8 (1H, m), 7.84-7.95 (1H, m), 8.19-8.41 (2H, m).

Example 52-1: N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer)

52-1

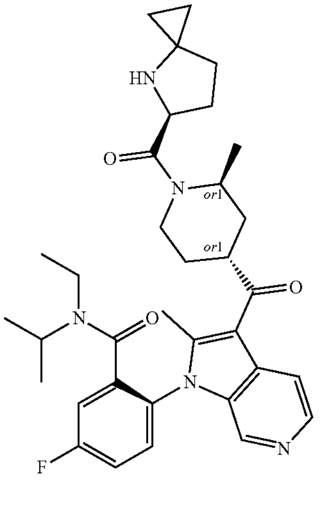

Step a) tert-Butyl (S)-5-((2R*,4S*)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate (Single Atropisomer, Single Isomer)

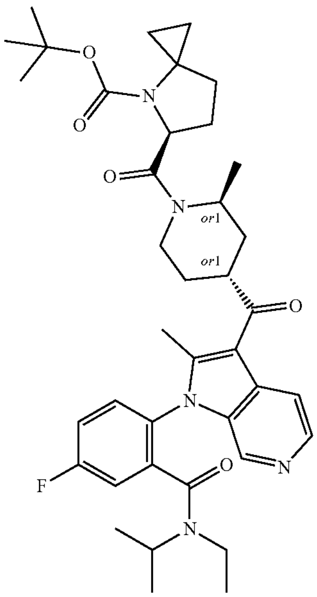 [SMILES: CCN(C(=O)c1cc(F)ccc1-n1c(C)c(C(=O)[C@@H]2CCN(C(=O)[C@@H]3CCC4(CC4)N3C(=O)OC(C)(C)C)[C@@H](C)C2)c2ccncc21)C(C)C]

T3P (247 mg, 0.39 mmol, 50% in EtOAc) was added to a mixture of Intermediate 75 (60.0 mg, 0.13 mmol), (S)-4-(tert-butoxycarbonyl)-4-azaspiro[2.4]heptane-5-carboxylic acid (46.7 mg, 0.19 mmol) and DIPEA (68.0 μL, 0.39 mmol) in DCM (500 μL) under $N_2$. The resulting mixture was stirred at rt for 3 h. The reaction mixture was diluted with water (20 mL) and extracted with DCM (3×20 mL). The combined organic layers were dried over $Na_2SO_4$, filtered, and concentrated to dryness. The residue was purified by preparative TLC on silica (EtOAc) to give the title compound (72.0 mg, 81%) as a white solid; MS m/z (ES+) $[M+H]^+$=688.4.

Step b) N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer) (Example 52-1)

FA (2 mL) was added to tert-butyl (S)-5-((2R*,4S*)-4-(1-(2-(ethyl(isopropyl)-carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate from Step a) (60.0 mg, 0.09 mmol). The resulting mixture was stirred at rt for 1 h. The reaction mixture was concentrated under reduced pressure. The residue was quenched with sat. aq. $NaHCO_3$ (20 mL) and extracted with DCM (4×25 mL). The combined organic layers were dried over $Na_2SO_4$, filtered, and concentrated to dryness. The crude product was purified by preparative HPLC, PrepMethod J (gradient: 37-47%) to give the title compound (25.0 mg, 49%) as a white solid; MS m/z (ES+) $[M+H]^+$=588.4; $^1$H NMR (400 MHz, DMSO-$d_6$, 22° C.) δ 0.15-0.27 (1H, m), 0.31-0.37 (1H, m), 0.37-0.47 (4H, m), 0.52-0.60 (1H, m), 0.67-0.80 (2H, m), 0.98-1.10 (3H, m), 1.27 (2H, d), 1.41 (2H, d), 1.50-1.62 (2H, m), 1.69-1.92 (5H, m), 2.11-2.30 (1H, m), 2.65-2.79 (1H, m), 2.90-3.02 (1H, m), 3.13-3.26 (1H, m), 3.64-3.76 (2H, m), 3.82-4.08 (2H, m), 4.37-4.55 (1H, m), 4.81-4.92 (1H, m), 7.54-7.63 (2H, m), 7.69-7.80 (1H, m), 7.86-7.96 (1H, m), 8.29-8.41 (2H, m).

Example 52-2: N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer)

52-2

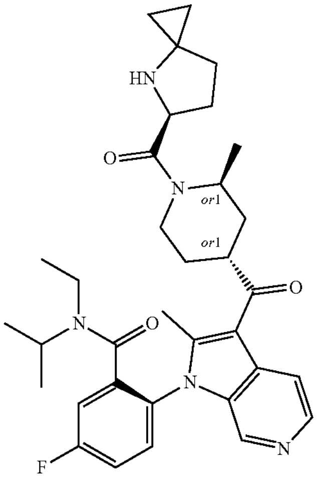

Step a) tert-Butyl (S)-5-((2R*,4S*)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate (Single Atropisomer, Single Isomer)

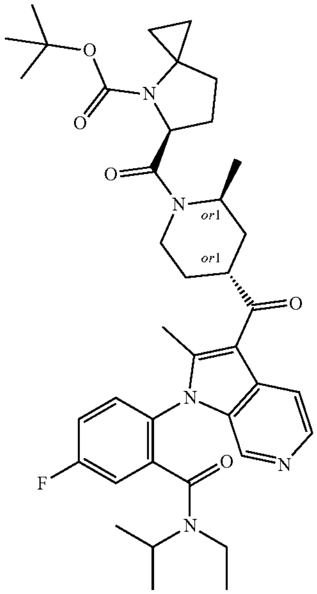 [SMILES: CCN(C(=O)c1cc(F)ccc1-n1c(C)c(C(=O)[C@@H]2CCN(C(=O)[C@@H]3CCC4(CC4)N3C(=O)OC(C)(C)C)[C@@H](C)C2)c2ccncc21)C(C)C]

T3P (247 mg, 0.39 mmol, 50% in EtOAc) was added to a mixture of Intermediate 76 (60.0 mg, 0.13 mmol th.), (S)-4-(tert-butoxycarbonyl)-4-azaspiro[2.4]heptane-5-carboxylic acid (46.7 mg, 0.19 mmol) and DIPEA (68.0 μL, 0.39 mmol) in DCM (500 μL) under $N_2$. The resulting mixture was stirred at rt for 3 h. The reaction mixture was diluted with water (20 mL) and extracted with DCM (4×20 mL). The combined organic layers were dried over $Na_2SO_4$, filtered, and concentrated to dryness. The residue was purified by preparative TLC on silica (EtOAc) to give the title compound (80.0 mg, 90%) as a white solid; MS m/z (ES+) $[M+H]^+$=688.4.

Step b) N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer) (Example 52-2)

FA (2 mL) was added to tert-butyl (S)-5-((2R*,4S*)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate from Step a) (60.0 mg, 0.09 mmol). The resulting mixture was stirred at rt for 1 h. The reaction mixture was concentrated under reduced pressure. The residue was quenched with sat. aq. $NaHCO_3$ (25 mL) and extracted with DCM (4×25 mL). The combined organic layers were dried over $Na_2SO_4$, filtered, and concentrated to dryness. The crude product was purified by preparative HPLC, PrepMethod J (gradient: 37-52%) to give the title compound (21.0 mg, 41%) as a white solid; MS m/z (ES+) $[M+H]^+$=588.3; $^1$H NMR (400 MHz, DMSO-$d_6$, 22° C.) δ 0.13-0.26 (1H, m), 0.29-0.37 (1H, m), 0.39-0.49 (4H, m), 0.54-0.66 (1H, m), 0.68-0.79 (2H, m), 0.92-1.11 (3H, m), 1.25 (2H, d), 1.38 (2H, d), 1.47-1.58 (2H, m), 1.59-1.91 (5H, m), 2.14-2.30 (1H, m), 2.66-2.80 (1H, m), 2.93-3.05 (1H, m), 3.13-3.26 (1H, m), 3.57-3.81 (2H, m), 3.82-4.03 (2H, m), 4.30-4.48 (1H, m), 4.76-4.87 (1H, m), 7.52-7.65 (2H, m), 7.70-7.81 (1H, m), 7.84-7.97 (1H, m), 8.25-8.41 (2H, m).

Example 52-3: N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer)

52-3

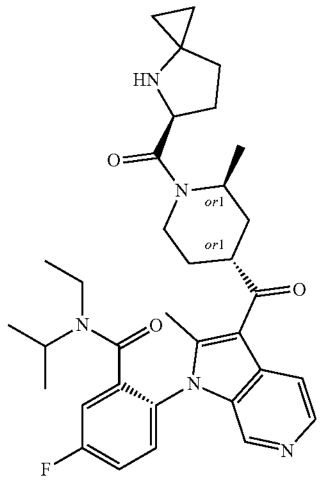

Step a) tert-Butyl (S)-5-((2R*,4S*)-4-(1-(2-(ethyl (isopropyl)carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate (Single Atropisomer, Single Isomer)

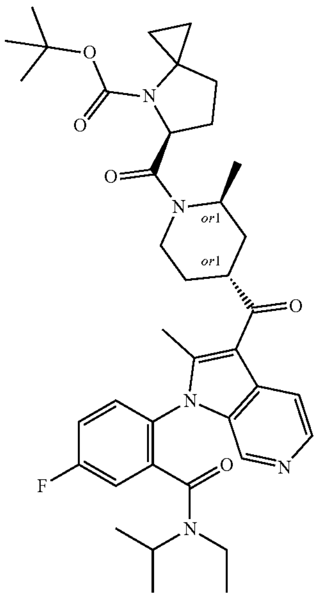 [SMILES: CCN(C(=O)c1cc(F)ccc1-n1c(C)c(C(=O)[C@@H]2CCN(C(=O)[C@@H]3CCC4(CC4)N3C(=O)OC(C)(C)C)[C@@H](C)C2)c2ccncc21)C(C)C]

T3P (247 mg, 0.39 mmol, 50% in EtOAc) was added to a solution of Intermediate 77 (60.0 mg, 0.13 mmol th.), (S)-4-(tert-butoxycarbonyl)-4-azaspiro[2.4]heptane-5-carboxylic acid (46.7 mg, 0.19 mmol) and DIPEA (68.0 μL, 0.39 mmol) in DCM (500 μL) under $N_2$. The resulting mixture was stirred at rt for 3 h. The reaction mixture was diluted with water (20 mL) and extracted with DCM (3×20 mL). The combined organic layers were dried over $Na_2SO_4$, filtered, and concentrated to dryness. The residue was purified by preparative TLC on silica (EtOAc) to give the title compound (75.0 mg, 84%) as a white solid; MS m/z (ES+) $[M+H]^+$=688.4.

Step b) N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer) (Example 52-3)

FA (2 mL) was added to tert-butyl (S)-5-((2R*,4S*)-4-(1-(2-(ethyl(isopropyl)-carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate from Step a) (60.0 mg, 0.09 mmol). The resulting mixture was stirred at rt for 1 h. The reaction mixture was concentrated under reduced pressure. The residue was quenched with sat. aq. $NaHCO_3$ (25 mL) and extracted with DCM (4×25 mL). The combined organic layers were dried over $Na_2SO_4$, filtered, and concentrated to dryness. The crude product was purified by preparative HPLC, PrepMethod J (gradient: 37-47%) to give the title compound (23.0 mg, 45%) as a white solid; MS m/z (ES+) $[M+H]^+$=588.3; $^1$H NMR (400 MHz, DMSO-$d_6$, 22° C.) δ 0.22 (1H, br s), 0.29-0.36 (1H, m), 0.41 (4H, d), 0.53-0.61 (1H, m), 0.65-0.80 (2H, m), 0.97-1.10 (3H, m), 1.27 (2H, d), 1.40 (2H, d), 1.47-1.93 (7H, m), 2.14-2.32 (1H, m), 2.66-2.80 (1H, m), 2.89-3.05 (1H, m), 3.15-3.26 (1H, m), 3.61-3.76 (2H, m), 3.83-4.03 (2H, m), 4.32-4.46 (1H, m), 4.78-4.88 (1H, m), 7.55-7.64 (2H, m), 7.70-7.79 (1H, m), 7.85-7.97 (1H, m), 8.29-8.38 (2H, m).

Example 52-4: N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)benzamide (Single Atropisomer, Single Isomer)

52-4

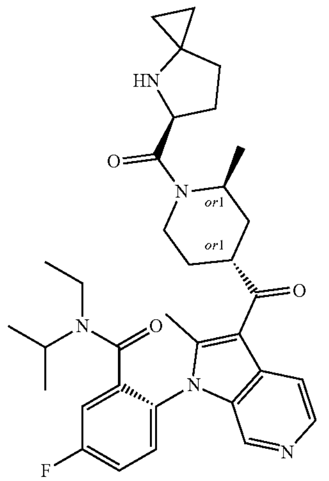

Step a) tert-Butyl (S)-5-((2R*,4S*)-4-(1-(2-(ethyl (isopropyl)carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate (Single Atropisomer, Single Isomer)

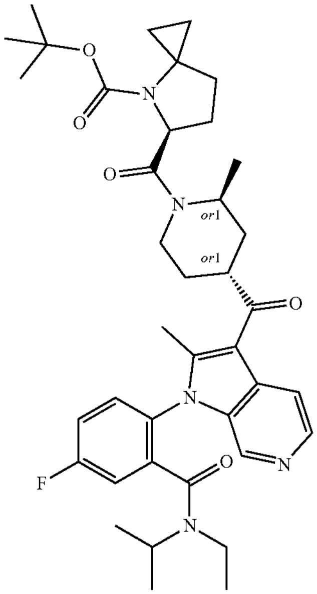 [SMILES: CCN(C(=O)c1cc(F)ccc1-n1c(C)c(C(=O)[C@@H]2CCN(C(=O)[C@@H]3CCC4(CC4)N3C(=O)OC(C)(C)C)[C@@H](C)C2)c2ccncc21)C(C)C]

T3P (247 mg, 0.39 mmol, 50% in EtOAc) was added to a solution of Intermediate 78 (60.0 mg, 0.13 mmol th.), (S)-4-(tert-butoxycarbonyl)-4-azaspiro[2.4]heptane-5-carboxylic acid (46.7 mg, 0.19 mmol) and DIPEA (68.0 μL, 0.39 mmol) in DCM (500 μL) under $N_2$. The resulting mixture was stirred at rt for 3 h. The reaction mixture was diluted with water (20 mL) and extracted with DCM (3×20 mL). The combined organic layers were dried over $Na_2SO_4$, filtered, and concentrated to dryness. The residue was purified by preparative TLC on silica (EtOAc) to give the title compound (73.0 mg, 82%) as a white solid; MS m/z (ES+) $[M+H]^+$=688.4.

Step b) N-Ethyl-5-fluoro-N-isopropyl-2-(2-methyl-3-((2R*,4S*)-2-methyl-1-((S)-4-azaspiro[2.4]heptane-5-carbonyl)piperidine-4-carbonyl)-1H-pyrrolo[2,3-c]pyridin-1-yl)-benzamide (Single Atropisomer, Single Isomer) (Example 52-4)

FA (2 mL) was added to tert-butyl (S)-5-((2R*,4S*)-4-(1-(2-(ethyl(isopropyl)-carbamoyl)-4-fluorophenyl)-2-methyl-1H-pyrrolo[2,3-c]pyridine-3-carbonyl)-2-methylpiperidine-1-carbonyl)-4-azaspiro[2.4]heptane-4-carboxylate from Step a) (60.0 mg, 0.09 mmol). The resulting mixture was stirred at rt for 1 h. The reaction mixture was concentrated under reduced pressure. The residue was quenched with sat. aq. $NaHCO_3$ (25 mL) and extracted with DCM (4×25 mL). The combined organic layers were dried over $Na_2SO_4$, filtered, and concentrated to dryness. The crude product was purified by preparative HPLC, PrepMethod J (gradient: 37-47%) to give the title compound (18.0 mg, 35%) as a white solid; MS m/z (ES+) $[M+H]^+$=588.4; $^1H$ NMR (400 MHz, DMSO-$d_6$, 22° C.) δ 0.14-0.25 (1H, m), 0.30-0.38 (1H, m), 0.38-0.50 (4H, m), 0.53-0.61 (1H, m), 0.65-0.76 (2H, m), 0.97-1.12 (4H, m), 1.26 (2H, d), 1.40 (1H, d), 1.51-1.65 (2H, m), 1.66-1.94 (4H, m), 1.96-2.38 (2H, m), 2.64-2.80 (1H, m), 2.92-3.02 (1H, m), 3.13-3.25 (1H, m), 3.64-3.79 (2H, m), 3.83-4.03 (2H, m), 4.38-4.54 (1H, m), 4.77-4.91 (1H, m), 7.55-7.63 (2H, m), 7.73-7.84 (1H, m), 7.87-7.98 (1H, m), 8.25-8.38 (2H, m).

Example 53-1: 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer)

53-1

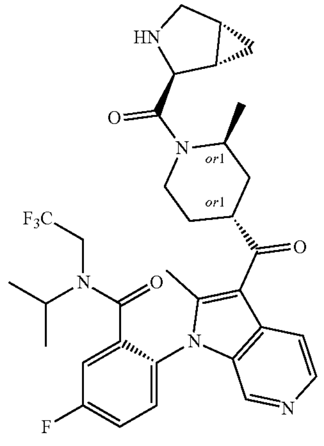

Step a) tert-Butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate (Single Atropisomer, Single Isomer)

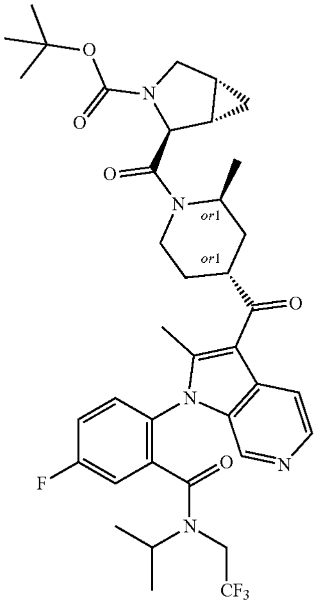 [SMILES: Cc1c(C(=O)[C@@H]2CCN(C(=O)[C@@H]3[C@H]4C[C@H]4CN3C(=O)OC(C)(C)C)[C@@H](C)C2)c2ccncc2n1-c1ccc(F)cc1C(=O)N(CC(F)(F)F)C(C)C]

T3P (63.0 μL, 0.11 mmol, 50% in EtOAc) and DIPEA (61.0 μL, 0.35 mmol) were added dropwise to a solution of Intermediate 80 (36.6 mg, 0.06 mmol th.), (1S,2R,5R)-3-(tert-butoxycarbonyl)-3-azabicyclo[3.1.0]hexane-2-carboxylic acid (24.1 mg, 0.11 mmol) in DCM (2 mL). The resulting mixture was stirred at rt overnight. The reaction mixture was diluted with DCM and sat. aq. $NaHCO_3$ and was stirred vigorously for 10 minutes. The water layer was extracted with DCM. The combined organic layers were washed with brine, dried over $Na_2SO_4$, filtered, and concentrated to dryness. The residue was purified by straight phase flash chromatography on silica (gradient: 40-100% EtOAc in heptane) to give the title compound in a quantitative yield (85.0 mg) as a white solid, which was used directly in the next step; MS m/z (ES+) $[M+H]^+$=728.3.

Step b) 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer) (Example 53-1)

FA (2 mL) was added to tert-butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate from Step a) (85.0 mg, 0.06 mmol th.). The resulting mixture was stirred at rt for 2 h. The reaction mixture was concentrated under reduced pressure. The residue was quenched with sat. aq. $NaHCO_3$ and extracted with DCM. The combined organic layers were washed with brine, dried over $Na_2SO_4$, filtered, and concentrated to dryness. The residue was purified by straight phase flash chromatography on silica (gradient: 0-10% 0.7 M $NH_3$ in MeOH in DCM) to give the title compound (11.0 mg, 29%) as a white solid; MS m/z (ES+) $[M+H]^+$=628.3; $^1$H NMR (400 MHz, DMSO-$d_6$, 22° C.) δ 0.25-0.33 (1H, m), 0.33-0.41 (2H, m), 0.42-0.49 (1H, m), 0.81-0.86 (1H, m), 1.02-1.07 (3H, m), 1.23-1.24 (2H, m), 1.38-1.46 (3H, m), 1.60-1.86 (4H, m), 2.46 (3H, s), 2.69-2.78 (1H, m), 2.77-2.97 (2H, m), 3.42-3.50 (1H, m), 3.57-3.69 (1H, m), 3.76-3.85 (2H, m), 3.93-4.11 (2H, m), 4.40-4.59 (1H, m), 4.77 (1H, br s), 7.60-7.69 (2H, m), 7.73-7.81 (1H, m), 7.87-7.94 (1H, m), 8.29-8.42 (2H, m).

Example 53-2: 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer)

53-2

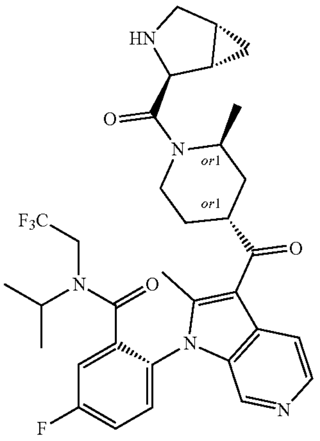

Step a) tert-Butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate (Single Atropisomer, Single Isomer)

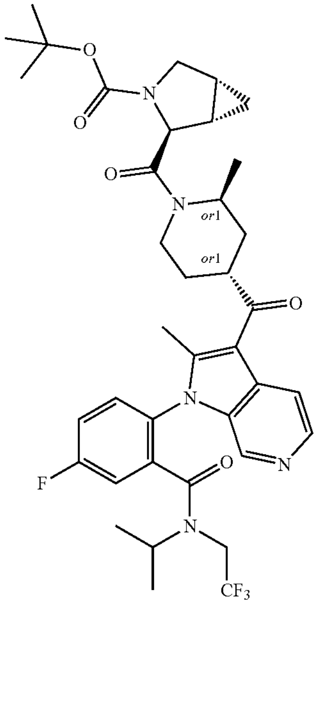 [SMILES: Cc1c(C(=O)[C@@H]2CCN(C(=O)[C@@H]3[C@H]4C[C@H]4CN3C(=O)OC(C)(C)C)[C@@H](C)C2)c2ccncc2n1-c1ccc(F)cc1C(=O)N(CC(F)(F)F)C(C)C]

T3P (132 μL, 0.22 mmol, 50% in EtOAc) and DIPEA (126 μL, 0.72 mmol) were added dropwise to a solution of Intermediate 81 (76.6 mg, 0.13 mmol th.), (1S,2R,5R)-3-(tert-butoxycarbonyl)-3-azabicyclo[3.1.0]hexane-2-carboxylic acid (50.4 mg, 0.22 mmol) in DCM (2 mL). The resulting mixture was stirred at rt overnight. The reaction mixture was diluted with DCM and sat. aq. $NaHCO_3$ and was stirred vigorously for 10 minutes. The water layer was extracted with DCM. The combined organic layers were washed with brine, dried over $Na_2SO_4$, filtered, and concentrated to dryness. The residue was purified by straight phase flash chromatography on silica (gradient: 40-100% EtOAc in heptane) to give the title compound in a quantitative yield (112 mg) as a white solid, which was used directly in the next step.

Step b) 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer) (Example 53-2)

FA (2 mL) was added to tert-butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate from Step a) (112 mg, 0.13 mmol th.). The resulting mixture was stirred at rt for 2 h. The reaction mixture was concentrated under reduced pressure. The residue was quenched with sat. aq. $NaHCO_3$ and extracted with DCM. The combined organic layers were washed with brine, dried over $Na_2SO_4$, filtered, and concentrated to dryness. The residue was purified by straight phase flash chromatography on silica (gradient: 0-10% 0.7 M $NH_3$ in MeOH in DCM) to give the title compound (24.4 mg, 30%) as a white solid; MS m/z (ES+) $[M+H]^+$=628.3; $^1$H NMR (400 MHz, DMSO-$d_6$, 22° C.) δ 0.25-0.33 (1H, m), 0.37 (2H, s), 0.39-0.52 (1H, m), 0.85 (1H, br s), 0.99-1.11 (3H, m), 1.25 (2H, d), 1.35-1.42 (3H, m), 1.50-1.67 (1H, m), 1.69-1.89 (3H, m), 2.47 (3H, s), 2.74 (1H, d), 2.86-2.97 (2H, m), 3.36-3.42 (1H, m), 3.57-3.69 (1H, m), 3.76-3.87 (2H, m), 3.94-4.15 (2H, m), 4.34-4.56 (1H, m), 4.78-4.89 (1H, m), 7.60-7.69 (2H, m), 7.72-7.79 (1H, m), 7.85-7.96 (1H, m), 8.34 (1H, d), 8.39 (1H, s).

Example 53-3: 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer)

53-3

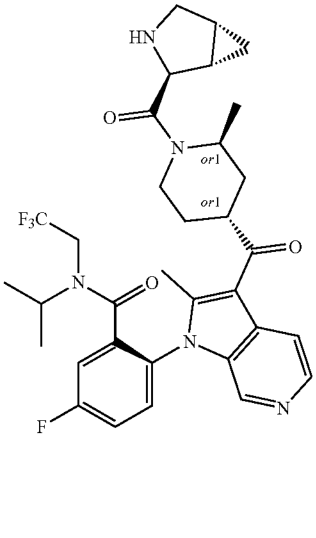

Step a) tert-Butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate (Single Atropisomer, Single Isomer)

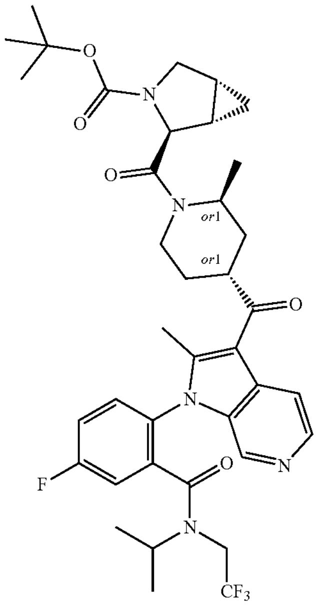 [SMILES: Cc1c(C(=O)[C@@H]2CCN(C(=O)[C@@H]3[C@H]4C[C@H]4CN3C(=O)OC(C)(C)C)[C@@H](C)C2)c2ccncc2n1-c1ccc(F)cc1C(=O)N(CC(F)(F)F)C(C)C]

T3P (129 μL, 0.22 mmol, 50% in EtOAc) and DIPEA (126 μL, 0.72 mmol) were added dropwise to Intermediate 82 (75.0 mg, 0.12 mmol th.), (1S,2R,5R)-3-(tert-butoxycarbonyl)-3-azabicyclo[3.1.0]hexane-2-carboxylic acid (49.3 mg, 0.22 mmol) in DCM (1.2 mL). The resulting mixture was stirred at rt overnight. The reaction mixture was diluted with DCM and sat. aq. $NaHCO_3$ and was stirred vigorously for 10 minutes. The water layer was extracted with DCM. The combined organic layers were washed with brine, dried over $Na_2SO_4$, filtered, and concentrated to dryness. The residue was purified by straight phase flash chromatography on silica (gradient: 40-100% EtOAc in heptane) to give the title compound in a quantitative yield (148 mg) as a white solid, which was used directly in the next step; MS m/z (ES+) $[M+H]^+$=728.3.

Step b) 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer) (Example 53-3)

FA (2 mL) was added to tert-butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate from Step a) (148 mg, 0.12 mmol th.). The resulting mixture was stirred at rt for 2 h. The reaction mixture was concentrated under reduced pressure. The residue was quenched with sat. aq. $NaHCO_3$ and extracted with DCM. The combined organic layers were washed with brine, dried over $Na_2SO_4$, filtered, and concentrated to dryness. The residue was purified by straight phase flash chromatography on silica (gradient: 0-10% 0.7 M $NH_3$ in MeOH in DCM) to give the title compound (29.7 mg, 39%) as a white solid; MS m/z (ES+) $[M+H]^+$=628.2; $^1H$ NMR (400 MHz, DMSO-$d_6$, 22° C.) δ 0.26-0.33 (1H, m), 0.33-0.43 (2H, m), 0.39-0.50 (1H, m), 0.85 (1H, br s), 0.98-1.15 (3H, m), 1.23 (2H, d), 1.36-1.46 (3H, m), 1.52-1.66 (1H, m), 1.67-1.90 (3H, m), 2.47 (3H, s), 2.70-2.78 (1H, m), 2.80-2.98 (2H, m), 3.35-3.42 (1H, m), 3.58-3.72 (1H, m), 3.75-3.85 (2H, m), 3.92-4.11 (2H, m), 4.35-4.66 (1H, m), 4.71-4.87 (1H, m), 7.60-7.69 (2H, m), 7.72-7.80 (1H, m), 7.85-7.95 (1H, m), 8.30-8.37 (1H, m), 8.39 (1H, s).

Example 53-4: 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer)

53-4

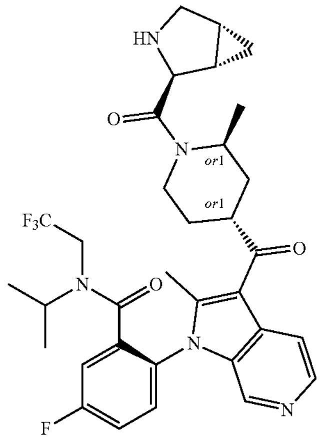

Step a) tert-Butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate (Single Atropisomer, Single Isomer)

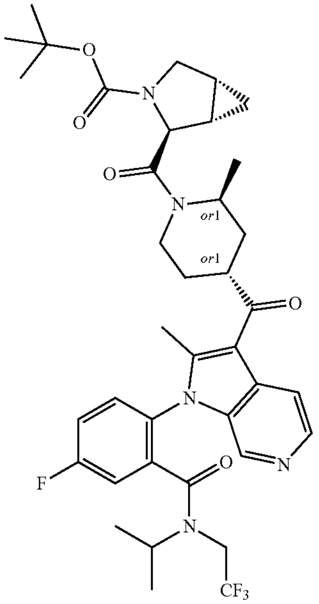 [SMILES: Cc1c(C(=O)[C@@H]2CCN(C(=O)[C@@H]3[C@H]4C[C@H]4CN3C(=O)OC(C)(C)C)[C@@H](C)C2)c2ccncc2n1-c1ccc(F)cc1C(=O)N(CC(F)(F)F)C(C)C]

T3P (131 μL, 0.22 mmol, 50% in EtOAc) and DIPEA (128 μL, 0.74 mmol) were added dropwise to a solution of Intermediate 83 (76.3 mg, 0.13 mmol th.), (1S,2R,5R)-3-(tert-butoxycarbonyl)-3-azabicyclo[3.1.0]hexane-2-carboxylic acid (50.2 mg, 0.22 mmol) in DCM (1.2 mL). The resulting mixture was stirred at rt overnight. The reaction mixture was diluted with DCM and sat. aq. $NaHCO_3$ and was stirred vigorously for 10 minutes. The water layer was extracted with DCM. The combined organic layers were washed with brine, dried over $Na_2SO_4$, filtered, and concentrated to dryness. The residue was purified by straight phase flash chromatography on silica (gradient: 40-100% EtOAc in heptane) to give the title compound in a quantitative yield (149 mg) as a white solid, which was used directly in the next step; MS m/z (ES+) $[M+H]^+$=728.3.

Step b) 2-(3-((2R*,4S*)-1-((1S,2S,5R)-3-Azabicyclo[3.1.0]hexane-2-carbonyl)-2-methylpiperidine-4-carbonyl)-2-methyl-1H-pyrrolo[2,3-c]pyridin-1-yl)-5-fluoro-N-isopropyl-N-(2,2,2-trifluoroethyl)benzamide (Single Atropisomer, Single Isomer) (Example 53-4)

FA (2 mL) was added to tert-butyl (1S,2S,5R)-2-((2R*,4S*)-4-(1-(4-fluoro-2-(isopropyl(2,2,2-trifluoroethyl)carbamoyl)phenyl)-2-methyl-1H-pyrrolo[2,3-c]pyridine-3-carbonyl)-2-methylpiperidine-1-carbonyl)-3-azabicyclo[3.1.0]hexane-3-carboxylate from Step a) (149 mg, 0.13 mmol th.). The resulting mixture was stirred at rt for 2 h. The reaction mixture was concentrated under reduced pressure. The residue was quenched with sat. aq. $NaHCO_3$ and extracted with DCM. The combined organic layers were washed with brine, dried over $Na_2SO_4$, filtered, and concentrated to dryness. The residue was purified by straight phase flash chromatography on silica (gradient: 0-10% 0.7 M $NH_3$ in MeOH in DCM) to give the title compound (34.1 mg, 41%) as a white solid; MS m/z (ES+) $[M+H]^+$=628.3; $^1H$ NMR (400 MHz, DMSO-$d_6$, 22° C.) δ 0.26-0.35 (1H, m), 0.38 (2H, s), 0.40-0.49 (1H, m), 0.80-0.87 (1H, m), 1.02-1.08 (3H, m), 1.22-1.24 (2H, m), 1.38-1.55 (4H, m), 1.61-1.87 (3H, m), 2.46 (3H, s), 2.69-2.79 (1H, m), 2.82-3.02 (2H, m), 3.39-3.52 (1H, m), 3.59-3.71 (1H, m), 3.75-3.88 (2H, m), 3.94-4.14 (2H, m), 4.37-4.53 (1H, m), 4.71-4.92 (1H, m), 7.60-7.69 (2H, m), 7.74-7.80 (1H, m), 7.91 (1H, d), 8.29-8.37 (1H, m), 8.39 (1H, s).

Example 54: (1-((1S,2S,5R)-3-Azabicyclo[3.1.0]hexane-2-carbonyl)piperidin-4-yl)(1-(4-fluoro-2-(4-isopropylpyridin-3-yl)phenyl)-2-methyl-1H-pyrrolo[2,3-c]pyridin-3-yl)methanone (Mixture of Atropisomers)

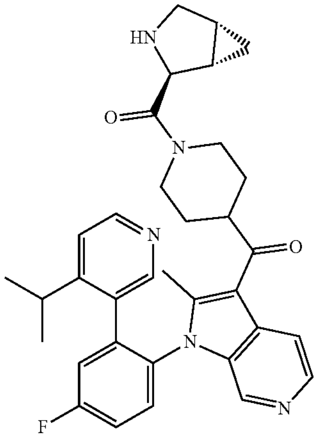 [SMILES: Cc1c(C(=O)C2CCN(C(=O)[C@H]3NC[C@@H]4C[C@@H]43)CC2)c2ccncc2n1-c1ccc(F)cc1-c1cnccc1C(C)C]

Step a) tert-Butyl (1S,2S,5R)-2-(4-(1-(4-fluoro-2-(4-isopropylpyridin-3-yl)phenyl)-2-methyl-1H-pyrrolo[2,3-c]pyridine-3-carbonyl)piperidine-1-carbonyl)-3-azabicyclo[3.1.0]-hexane-3-carboxylate (Mixture of Atropisomers)

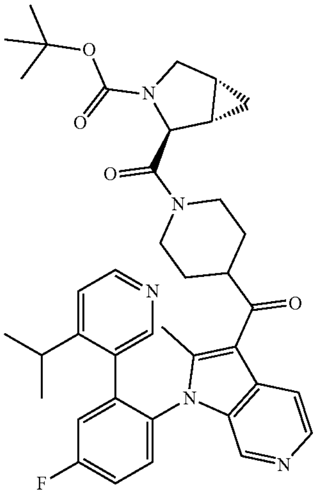 [SMILES: Cc1c(C(=O)C2CCN(C(=O)[C@@H]3[C@H]4C[C@H]4CN3C(=O)OC(C)(C)C)CC2)c2ccncc2n1-c1ccc(F)cc1-c1cnccc1C(C)C]

T3P (99.0 μL, 0.17 mmol, 50% in EtOAc) and DIPEA (97.0 μL, 0.55 mmol) were added dropwise to a solution of Intermediate 88 (50.6 mg, 0.11 mmol) and (1S,2R,5R)-3-(tert-butoxycarbonyl)-3-azabicyclo[3.1.0]hexane-2-carboxylic acid (37.8 mg, 0.17 mmol) in DCM (2 mL). The resulting mixture was stirred at rt overnight. The reaction mixture was diluted with DCM and sat. aq. $NaHCO_3$ and stirred vigorously for 10 minutes. The water layer was extracted with DCM. The combined organic layers were washed with brine, dried over $Na_2SO_4$, filtered, and concentrated to dryness. The residue was purified by straight phase flash chromatography on silica (gradient: 40-100% EtOAc in heptane) to give the title compound in a quantitative yield (91.6 mg) as a white solid, which was used directly in the next step; MS m/z (ES+) $[M+H]^+$=666.3.

Step b) (1-((1S,2S,5R)-3-Azabicyclo[3.1.0]hexane-2-carbonyl)piperidin-4-yl)(1-(4-fluoro-2-(4-isopropylpyridin-3-yl)phenyl)-2-methyl-1H-pyrrolo[2,3-c]pyridin-3-yl)methanone (Mixture of Atropisomers) (Example 54)

FA (2 mL) was added to tert-butyl (1S,2S,5R)-2-(4-(1-(4-fluoro-2-(4-isopropylpyridin-3-yl)phenyl)-2-methyl-1H-pyrrolo[2,3-c]pyridine-3-carbonyl)piperidine-1-carbonyl)-3-azabicyclo[3.1.0]hexane-3-carboxylate from Step a) (91.6 mg, 0.11 mmol th.). The resulting mixture was stirred at rt for 2 h. The reaction mixture was concentrated under reduced pressure. The residue was quenched with sat. aq. $NaHCO_3$ and extracted with DCM. The combined organic layers were washed with brine, dried over $Na_2SO_4$, filtered, and concentrated to dryness. The residue was purified by straight phase flash chromatography on silica (gradient: 0-10% 0.7 M $NH_3$ in MeOH in DCM) to give the title compound (19.4 mg, 31%) as an off-white solid; MS m/z (ES+) $[M+H]^+$=566.3; $^1H$ NMR (400 MHz, DMSO-$d_6$, 22° C.) δ 0.27-0.35 (1H, m), 0.43-0.51 (1H, m), 0.68 (2H, dd), 0.95-1.00 (1H, m), 1.09 (3H, d), 1.34-1.47 (3H, m), 1.50-1.63 (1H, m), 1.70-1.83 (2H, m), 2.42 (1H, s), 2.52 (3H, s), 2.60-2.72 (1H, m), 2.72-2.80 (2H, m), 2.86-2.93 (1H, m), 3.39-3.47 (1H, m), 3.86-3.94 (1H, m), 4.01-4.11 (1H, m), 4.26-4.38 (1H, m), 7.13-7.27 (1H, m), 7.51-7.58 (1H, m), 7.59-7.67 (1H, m), 7.76-7.85 (2H, m), 8.09-8.18 (1H, m), 8.19-8.30 (3H, m), 8.43 (1H, s).

Examples 55-1 and 55-2: 2-(3-(1-((1S,2S,5R)-3-Azabicyclo[3.1.0]-hexane-2-carbonyl)-piperidine-4-carbonyl)-2-methyl-1H-pyrrolo[2,3-c]pyridin-1-yl)-5-fluoro-N,N-diisopropylbenzamide (Separated Atropisomers)

55-1

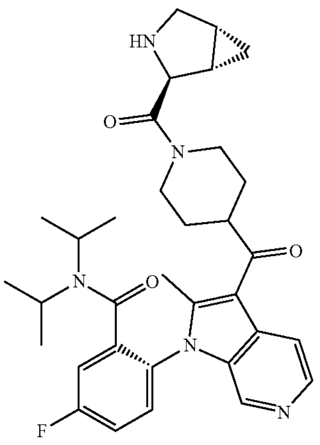

55-2

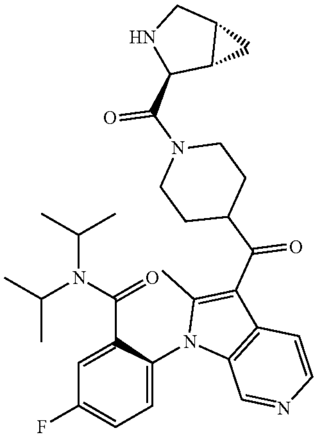

Step a) tert-Butyl (1S,2S,5R)-2-(4-(1-(2-(diisopropylcarbamoyl)-4-fluorophenyl)-2-methyl-1H-pyrrolo[2,3-c]pyridine-3-carbonyl)piperidine-1-carbonyl)-3-azabicyclo[3.1.0]-hexane-3-carboxylate (Mixture of Atropisomers)

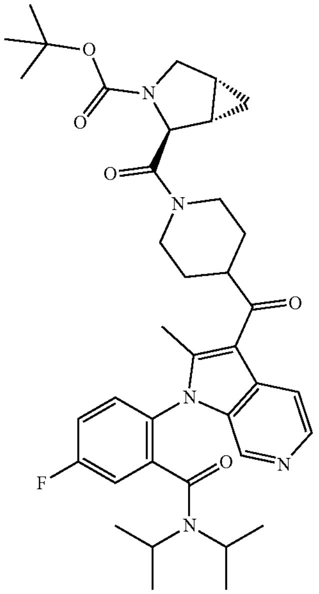 [SMILES: Cc1c(C(=O)C2CCN(C(=O)[C@@H]3[C@H]4C[C@H]4CN3C(=O)OC(C)(C)C)CC2)c2ccncc2n1-c1ccc(F)cc1C(=O)N(C(C)C)C(C)C]

Intermediate 92 (357 mg, 0.77 mmol th.) was added to a solution of (1S,2S,5R)-3-(tert-butoxycarbonyl)-3-azabicyclo[3.1.0]hexane-2-carboxylic acid (192 mg, 0.85 mmol), EDC (177 mg, 0.92 mmol), HOBt (141 mg, 0.92 mmol) and DIPEA (402 μL, 2.31 mmol) in DMF (5 mL). The resulting mixture was stirred at rt overnight. The reaction mixture was diluted with EtOAc and washed sequentially with sat. aq. $NaHCO_3$ and brine. The organic layer was dried over $Na_2SO_4$, filtered, and concentrated under reduced pressure. The residue was purified by straight phase flash chromatography on silica (gradient: 0-100% EtOAc in heptane) to give the title compound (392 mg, 76%); MS m/z (ES+) $[M+H]^+$= 674.3; $^1H$ NMR (400 MHz, DMSO-$d_6$, 22° C.) δ 0.19-0.33 (1H, m), 0.33-0.46 (3H, m), 0.60 (2H, d), 0.64-0.79 (2H, m), 0.96-1.11 (3H, m), 1.27 (3H, d), 1.32 (5H, d), 1.37 (3H, s), 1.41-1.57 (3H, m), 1.57-1.71 (1H, m), 1.81-1.96 (2H, m), 3.11-3.28 (2H, m), 3.36-3.50 (3H, m), 3.53-3.62 (1H, m), 3.63-3.72 (1H, m), 4.02-4.15 (2H, m), 4.25-4.48 (1H, m), 4.51-4.66 (1H, m), 7.48-7.62 (2H, m), 7.68-7.8 (1H, m), 7.85-7.98 (1H, m), 8.26-8.4 (2H, m).

Step b) 2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N,N-diisopropylbenzamide (separated Atropisomers) (Examples 55-1 and 55-2)

FA (4 mL) was added to tert-butyl (1S,2S,5R)-2-(4-(1-(2-(diisopropylcarbamoyl)-4-fluorophenyl)-2-methyl-1H-pyrrolo[2,3-c]pyridine-3-carbonyl)piperidine-1-carbonyl)-3-azabicyclo[3.1.0]hexane-3-carboxylate from Step a) (392 mg, 0.58 mmol). The mixture was stirred at rt for 4 h. The mixture was quenched with sat. aq. $NaHCO_3$ (30 mL) and extracted with EtOAc. The combined organic layers were washed with brine, dried over $Na_2SO_4$, filtered, and concentrated under reduced pressure. The residue was purified straight phase flash chromatography on silica (gradient: 0-10% 0.7 M $NH_3$ in MeOH in DCM). The residue was purified by preparative SFC, PrepMethod SFC-C to give the title compound Example 55-1 as first eluting product (84.9 mg, 25%); MS m/z (ES+) $[M+H]^+$=574.3; $^1H$ NMR (500 MHz, DMSO-$d_6$, 27° C.) δ 0.30 (1H, d), 0.37-0.49 (4H, m), 0.66 (3H, dd), 1.01-1.11 (3H, m), 1.22-1.31 (3H, m), 1.33-1.50 (3H, m), 1.66 (1H, br s), 1.79-1.94 (2H, m), 2.52 (3H, s), 2.69-2.76 (1H, m), 2.82-2.94 (2H, m), 3.12-3.24 (2H, m), 3.43-3.58 (1H, m), 3.64-3.73 (1H, m), 3.85 (1H, s), 4.05-4.15 (1H, m), 4.34 (1H, dd), 7.48-7.60 (2H, m), 7.67-7.78 (1H, m), 7.84-7.95 (1H, m), 8.27-8.39 (2H, m); and Example 55-2 as second eluting product (90.2 mg, 27%); MS m/z (ES+) $[M+H]^+$=574.3; $^1H$ NMR (500 MHz, DMSO-$d_6$, 27° C.) δ 0.25-0.35 (1H, m), 0.38-0.49 (4H, m), 0.56-0.74 (3H, m), 1.01-1.11 (3H, m), 1.22-1.31 (3H, m), 1.34-1.51 (3H, m), 1.54-1.75 (1H, m), 1.77-1.94 (2H, m), 2.52 (3H, s), 2.73 (1H, dd), 2.83-2.93 (2H, m), 3.14-3.26 (2H, m), 3.43-3.60 (1H, m), 3.62-3.73 (1H, m), 3.85 (1H, d), 4.03-4.16 (1H, m), 4.34 (1H, d), 7.48-7.61 (2H, m), 7.67-7.78 (1H, m), 7.84-7.96 (1H, m), 8.26-8.40 (2H, m).

Examples 56-1 and 56-2: (S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-diisopropylbenzamide (Separated Atropisomers)

56-1

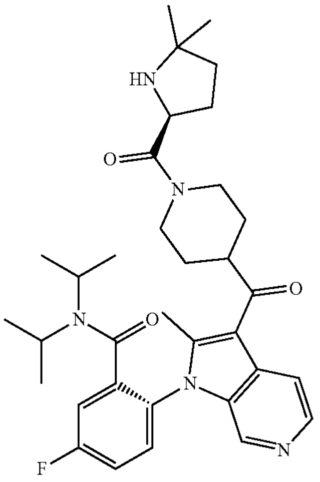

56-2

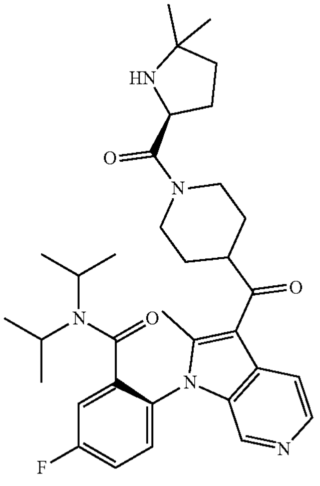

Step a) tert-Butyl (S)-5-(4-(1-(2-(diisopropylcarbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate (Mixture of Atropisomers)

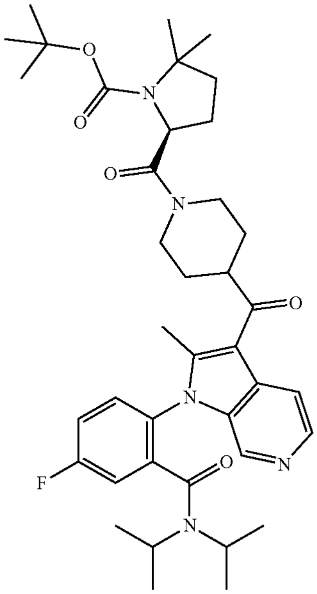 [SMILES: Cc1c(C(=O)C2CCN(C(=O)[C@@H]3CCC(C)(C)N3C(=O)OC(C)(C)C)CC2)c2ccncc2n1-c1ccc(F)cc1C(=O)N(C(C)C)C(C)C]

Intermediate 92 (11.2 g, 24.0 mmol th.) was added to a solution of (S)-1-(tert-butoxycarbonyl)-5,5-dimethylpyrrolidine-2-carboxylic acid (5.90 g, 24.2 mmol), EDC (5.53 g, 28.8 mmol), HOBt (4.41 g, 28.8 mmol) and DIPEA (8.39 mL, 48.0 mmol) in DCM (120 mL). The resulting mixture was stirred at rt overnight. The reaction mixture was diluted with DCM (200 mL) and washed sequentially with sat. aq. $NaHCO_3$ (300 mL) and brine (300 mL). The organic layer was dried over $Na_2SO_4$, filtered, and concentrated under reduced pressure. The residue was purified by straight phase flash chromatography on silica (gradient: 0-10% MeOH in DCM) to give the title compound (14.2 g, 86%) as a beige foam; MS m/z (ES+) $[M+H]^+$=690.3; $^1H$ NMR (400 MHz, DMSO-$d_6$, 22° C.) δ 0.34-0.49 (3H, m), 0.52-0.76 (3H, m), 0.99-1.13 (3H, m), 1.21-1.35 (12H, m), 1.37-1.48 (7H, m), 1.52-1.93 (6H, m), 2.14 (1H, br s), 2.51 (3H, s), 2.79-3.01 (1H, m), 3.12-3.32 (2H, m), 3.41-3.61 (1H, m), 3.63-3.74 (1H, m), 3.98 (1H, d), 4.23-4.47 (1H, m), 4.64-4.78 (1H, m), 7.46-7.62 (2H, m), 7.67-7.80 (1H, m), 7.83-7.97 (1H, m), 8.26-8.39 (2H, m).

Step b) (S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-diisopropylbenzamide (separated atropisomer) (Examples 56-1 and 56-2)

TFA (15 mL) was added to a solution of tert-butyl (S)-5-(4-(1-(2-(diisopropyl-carbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate from Step a) (14.1 g, 20.5 mmol) in DCM (90 mL). The reaction mixture was stirred at rt for 2 h. The mixture was quenched with sat. aq. $NaHCO_3$ (800 mL) and extracted with DCM (2×400 mL). The combined organic layers were washed with brine (400 mL), dried over $Na_2SO_4$, filtered, and concentrated under reduced pressure. The residue was purified straight phase flash chromatography on silica (gradient: 0-15% 0.7 M $NH_3$ in MeOH in DCM). The residue was purified by preparative SFC, PrepMethod SFC-F to give the title compound Example 56-1 as first eluting product (4.82 g, 40%); MS m/z (ES+) $[M+H]^+$=590.3; $^1H$ NMR (500 MHz, DMSO-$d_6$, 27° C.) δ 0.33-0.48 (3H, m), 0.56-0.76 (3H, m), 1.04 (3H, s), 1.08 (3H, d), 1.18 (3H, s), 1.27 (3H, d), 1.30-1.70 (5H, m), 1.80-1.95 (2H, m), 2.10-2.25 (1H, m), 2.27-2.37 (1H, m), 2.53 (3H, s), 2.89-3.03 (1H, m), 3.18-3.29 (2H, m), 3.43-3.61 (1H, m), 3.63-3.75 (1H, m), 3.92-4.04 (2H, m), 4.28-4.44 (1H, m), 7.48-7.62 (2H, m), 7.66-7.79 (1H, m), 7.83-7.96 (1H, m), 8.26-8.41 (2H, m);

$[\alpha]_D^{26}$ − 36.3(c 0.223, MeOH);

and Example 56-2 as second eluting product (4.42 g, 37%) as an off-white solid; MS m/z (ES+) $[M+H]^+$=590.4; 1H (500 MHz, DMSO-$d_6$, 27° C.) δ 0.42 (3H, d), 0.56-0.77 (3H, m), 1.02-1.11 (6H, m), 1.20 (3H, d), 1.27 (3H, d), 1.33-1.73 (5H, m), 1.82-1.94 (2H, m), 2.13-2.27 (1H, m), 2.53 (3H, s), 2.96 (1H, q), 3.14-3.28 (2H, m), 3.46-3.61 (1H, m), 3.69 (1H, p), 3.91-4.06 (2H, m), 4.28-4.42 (1H, m), 7.48-7.60 (2H, m), 7.67-7.78 (1H, m), 7.83-7.95 (1H, m), 8.25-8.40 (2H, m);

$[\alpha]_D^{26}$ − 8.2(c 0.223, MeOH).

Examples 57-1 and 57-2: 2-(3-(1-((1S,2S,5R)-3-Azabicyclo[3.1.0-]hexane-2-carbonyl)-piperidine-4-carbonyl)-2-methyl-1H-pyrrolo[2,3-c]pyridin-1-yl)-5-fluoro-N-isopropyl-N—((R)-1,1,1-trifluoropropan-2-yl)benzamide (Separated Atropisomers)

57-1

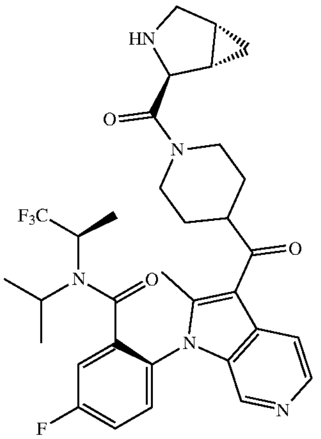

-continued 57-2

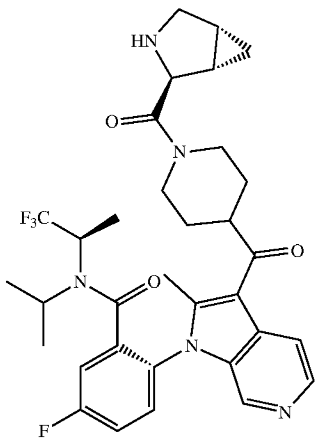

Step a) tert-Butyl (1S,2S,5R)-2-(4-(1-(4-fluoro-2-(isopropyl((R)-1,1,1-trifluoropropan-2-yl)carbamoyl)phenyl)-2-methyl-1H-pyrrolo[2,3-c]pyridine-3-carbonyl)piperidine-1-carbonyl)-3-azabicyclo[3.1.0]hexane-3-carboxylate (Mixture of Atropisomers)

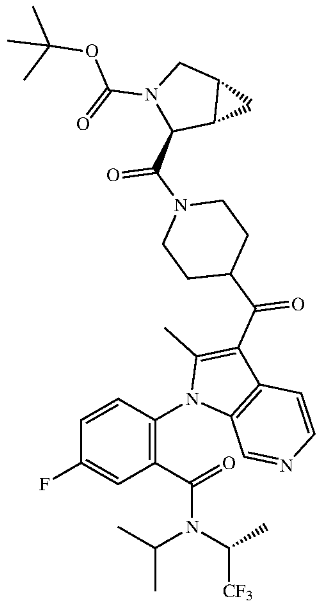 [SMILES: Cc1c(C(=O)C2CCN(C(=O)[C@@H]3[C@H]4C[C@H]4CN3C(=O)OC(C)(C)C)CC2)c2ccncc2n1-c1ccc(F)cc1C(=O)N(C(C)C)[C@H](C)C(F)(F)F]

Intermediate 97 (119 mg, 0.21 mmol th.) was added to a solution of (2S,4R)-1-(tert-butoxycarbonyl)-4-ethylpyrrolidine-2-carboxylic acid (73.0 mg, 0.30 mmol), HATU (130 mg, 0.34 mmol) and DIPEA (112 μL, 0.64 mmol) in DMF (2 mL). The resulting mixture was stirred at rt overnight. The reaction mixture was diluted with EtOAc and washed sequentially with sat. aq. $NaHCO_3$ and brine. The organic layer was dried over $Na_2SO_4$, filtered, and concentrated under reduced pressure. The residue was purified by straight phase flash chromatography on silica (gradient: 40-100%

EtOAc in heptane followed by 0-10% MeOH in DCM) to give the title compound (152 mg, 97%); MS m/z (ES+) $[M+H]^+$=728.3; $^1$H NMR (400 MHz, DMSO-$d_6$, 22° C.) δ 0.17-0.32 (1H, m), 0.33-0.58 (2H, m), 0.63 (1H, d), 0.67-0.89 (2H, m), 0.90-1.13 (2H, m), 1.13-1.30 (2H, m), 1.32 (5H, s), 1.37 (3H, s), 1.40-1.48 (2H, m), 1.49-1.75 (2H, m), 1.83-2.03 (2H, m), 2.58-2.79 (2H, m), 2.91-3.12 (1H, m), 3.36-3.5 (3H, m), 3.51-3.66 (1H, m), 3.75-3.97 (1H, m), 3.98-4.39 (2H, m), 4.39-4.67 (2H, m), 7.23-7.69 (2H, m), 7.71-7.86 (1H, m), 7.88-8.01 (1H, m), 8.28-8.66 (2H, m).

Step b) 2-(3-(1-((1S,2S,5R)-3-Azabicyclo[3.1.0]hexane-2-carbonyl)piperidine-4-carbonyl)-2-methyl-1H-pyrrolo[2,3-c]pyridin-1-yl)-5-fluoro-N-isopropyl-N—((R)-1,1,1-trifluoropropan-2-yl)benzamide (separated atropisomer) (Examples 57-1 and 57-2)

4 M HCl in 1,4-dioxane (522 L) was added to a solution of tert-butyl (1S,2S,5R)-2-(4-(1-(4-fluoro-2-(isopropyl((R)-1,1,1-trifluoropropan-2-yl)carbamoyl)phenyl)-2-methyl-1H-pyrrolo[2,3-c]pyridine-3-carbonyl)piperidine-1-carbonyl)-3-azabicyclo[3.1.0]hexane-3-carboxylate from Step a) (152 mg, 0.21 mmol) in MeCN (1 mL). The mixture was stirred at rt for 1.5 h. The mixture was concentrated under reduced pressure. The residue was purified by preparative HPLC, PrepMethod K (gradient: 16-22%). Appropriate fractions were pooled, concentrated under reduced pressure, dissolved in EtOAc and washed sequentially with sat. aq. $NaHCO_3$ and brine. The organic layer was dried over $Na_2SO_4$, filtered, and concentrated under reduced pressure. The product was lyophilized from MeCN/$H_2O$ to give the title compound Example 57-1 as first eluting product (32.6 mg, 25%); MS m/z (ES+) $[M+H]^+$=628.3; $^1$H NMR (400 MHz, DMSO-$d_6$, 22° C.) δ 0.20-0.42 (3H, m), 0.42-0.49 (1H, m), 0.49-0.81 (1H, m), 0.90-1.05 (1H, m), 1.10 (2H, d), 1.20-1.30 (1H, m), 1.31-1.50 (5H, m), 1.53-1.77 (1H, m), 1.78-1.96 (2H, m), 2.48 (3H, s), 2.52-2.64 (2H, m), 2.68-2.77 (1H, m), 2.82-2.95 (2H, m), 3.45-3.83 (2H, m), 3.82-4.02 (2H, m), 4.09 (1H, t), 4.25-4.41 (1H, m), 7.35-7.70 (2H, m), 7.75 (1H, dd), 7.91 (1H, d), 8.23-8.42 (2H, m); and Example 57-2 as second eluting product (50.0 mg, 38%); MS m/z (ES+) $[M+H]^+$=628.4; $^1$H NMR (400 MHz, DMSO-$d_6$, 22° C.) δ 0.19-0.36 (1H, m), 0.36-0.50 (2H, m), 0.50-0.57 (1H, m), 0.57-0.87 (3H, m), 1.00-1.17 (1H, m), 1.19-1.31 (2H, m), 1.31-1.54 (3H, m), 1.56-1.73 (1H, m), 1.77-2.02 (2H, m), 2.48 (3H, s), 2.64-2.77 (1H, m), 2.80-2.97 (2H, m), 3.16-3.33 (2H, m), 3.44-3.60 (1H, m), 3.60-3.99 (2H, m), 3.99-4.64 (3H, m), 7.19-7.53 (1H, m), 7.55-7.74 (1H, m), 7.74-7.89 (1H, m), 7.89-8.05 (1H, m), 8.18-8.72 (2H, m).

Examples 58-1 and 58-2: (1-((S)-4-Azaspiro[2.4]heptane-5-carbonyl)piperidin-4-yl)(1-(2-((3R,5R)-3,5-dimethylmorpholine-4-carbonyl)-4-fluorophenyl)-2-methyl-1H-pyrrolo[2,3-c]pyridin-3-yl)methanone (Separated Atropisomers)

58-1

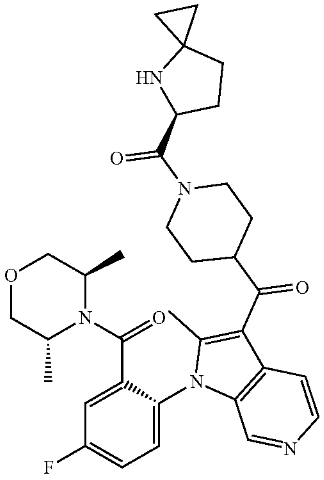

58-2

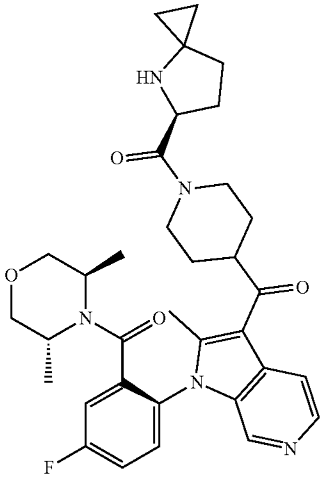

Step a) tert-Butyl (S)-5-(4-(1-(2-((3R,5R)-3,5-dimethylmorpholine-4-carbonyl)-4-fluorophenyl)-2-methyl-1H-pyrrolo[2,3-c]pyridine-3-carbonyl)piperidine-1-carbonyl)-4-azaspiro[2.4]heptane-4-carboxylate (Mixture of Atropisomers)

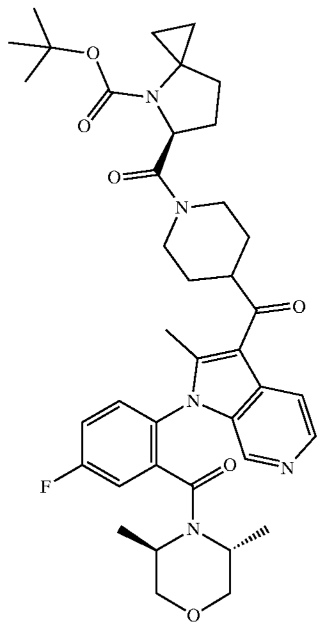 [SMILES: Cc1c(C(=O)C2CCN(C(=O)[C@@H]3CCC4(CC4)N3C(=O)OC(C)(C)C)CC2)c2ccncc2n1-c1ccc(F)cc1C(=O)N1[C@H](C)COC[C@H]1C]

To a solution of Intermediate 101 (1.68 g, 3.26 mmol th.) and DIPEA (5.68 mL, 32.6 mmol) in DCM (20 mL) was added (S)-4-(tert-butoxycarbonyl)-4-azaspiro[2.4]heptane-5-carboxylic acid (866 mg, 3.59 mmol), followed by T3P (2.88 mL, 4.89 mmol, 50% in EtOAc). The resulting mixture was stirred at rt overnight. The reaction mixture was diluted with EtOAc and washed with sat. aq. $NaHCO_3$ and brine. The organic layer was dried over $Na_2SO_4$, filtered, and concentrated under reduced pressure. The residue was purified by straight phase flash chromatography on silica (gradient: 0-100% EtOAc in heptane followed by 0-10% MeOH in DCM) to give the title compound (1.97 g, 86%) as a pale yellow solid; MS m/z (ES+) $[M+H]^+$=702.3; $^1$H NMR (400 MHz, DMSO-$d_6$, 22° C.) δ 0.34-0.69 (4H, m), 0.82-1.25 (4H, m), 1.31 (9H, s), 1.40-1.61 (3H, m), 1.61-1.81 (3H, m), 1.81-2.07 (4H, m), 2.10-2.35 (2H, m), 2.41 (2H, d), 2.56 (1H, d), 2.80-3.20 (2H, m), 3.21-3.31 (1H, m), 3.35-3.75 (4H, m), 3.95-4.12 (1H, m), 4.26-4.51 (1H, m), 4.68-4.89 (1H, m), 7.59-7.70 (1H, m), 7.68-7.76 (1H, m), 7.74-7.84 (1H, m), 7.88-8.05 (1H, m), 8.15-8.51 (2H, m).

Step b) (1-((S)-4-Azaspiro[2.4]heptane-5-carbonyl)piperidin-4-yl)(1-(2-((3R,5R)-3,5-dimethylmorpholine-4-carbonyl)-4-fluorophenyl)-2-methyl-1H-pyrrolo[2,3-c]pyridin-3-yl)methanone (separated atropisomer) (Examples 58-1 and 58-2)

p-TsOH·$H_2O$ (2.30 g, 12.1 mmol) was added to a solution of tert-butyl (S)-5-(4-(1-(2-((3R,5R)-3,5-dimethylmorpholine-4-carbonyl)-4-fluorophenyl)-2-methyl-1H-pyrrolo[2,3-c]pyridine-3-carbonyl)piperidine-1-carbonyl)-4-azaspiro[2.4]heptane-4-carboxylate from Step a) (2.83 g, 4.03 mmol) in IPA (35 mL). The mixture was stirred at 60° C. overnight. The mixture was quenched with sat. aq. $NaHCO_3$ and extracted with EtOAc. The combined organic layers were washed with brine, dried over $Na_2SO_4$, filtered, and concentrated under reduced pressure. The residue was purified straight phase flash chromatography on silica (gradient: 0-10% 0.7 M $NH_3$ in MeOH in DCM), followed by preparative SFC, PrepMethod SFC-G (gradient: 45-55%) to give the title compound Example 58-1 as first eluting product (614 mg, 25%) as a pale yellow solid; MS m/z (ES+) $[M+H]^+$=602.4; $^1$H NMR (400 MHz, DMSO-$d_6$, 27° C.) δ 0.19 (2H, br s), 0.29-0.39 (1H, m), 0.42-0.50 (1H, m), 0.51-0.62 (1H, m), 0.66-0.75 (1H, m), 0.76-1.32 (3H, m), 1.39-1.68 (3H, m), 1.68-1.82 (2H, m), 1.82-2.01 (2H, m), 2.08-2.42 (2H, m), 2.57 (3H, s), 2.75-3.19 (3H, m), 3.31-3.69 (6H, m), 3.88-4.14 (2H, m), 4.28-4.50 (1H, m), 7.64 (1H, td), 7.70 (1H, dd), 7.76 (1H, dd), 7.92 (1H, t), 8.21 (1H, s), 8.33 (1H, d);

$$[\alpha]_D^{26} - 60.2(c\ 0.225,\ \text{MeOH});$$

and Example 58-2 as second eluting product (774 mg, 32%) as a pale yellow solid; MS m/z (ES+) $[M+H]^+$=602.3; $^1$H NMR (500 MHz, DMSO-$d_6$, 27° C.) δ 0.34 (1H, ddd), 0.47 (1H, ddd), 0.56 (1H, ddd), 0.54-0.59 (3H, m), 0.68-0.75 (1H, m), 0.95-1.28 (3H, m), 1.41-1.70 (2H, m), 1.51-1.58 (1H, m), 1.72-1.77 (1H, m), 1.72-1.78 (1H, m), 1.82-1.97 (2H, m), 1.98-2.07 (1H, m), 2.18-2.26 (1H, m), 2.43 (3H, s), 2.94-3.02 (1H, m), 3.09 (1H, br s), 3.26-3.39 (1H, m), 3.39-3.48 (2H, m), 3.54-3.60 (1H, m), 3.93-4.00 (1H, m), 3.97-4.06 (1H, m), 4.39 (1H, br d), 7.64 (1H, td), 7.71 (1H, dd), 7.80 (1H, dd), 7.99 (1H, d), 8.41 (1H, d), 8.44 (1H, s);

$$[\alpha]_D^{26} - 37.5(c\ 0.212,\ \text{MeOH}).$$

Example 59: (S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-bis(propan-2-yl-$d_7$)benzamide (Mixture of Atropisomers)

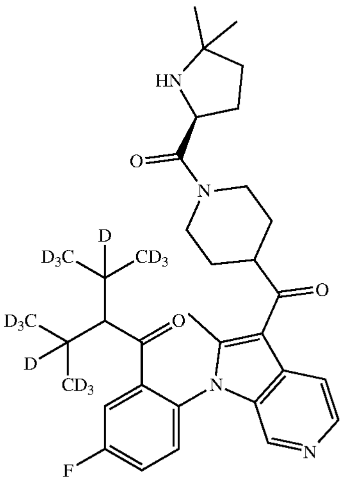 [SMILES: [2H]C([2H])([2H])C([2H])(C(C(=O)c1cc(F)ccc1-n1c(C)c(C(=O)C2CCN(C(=O)[C@@H]3CCC(C)(C)N3)CC2)c2ccncc21)C([2H])(C([2H])([2H])[2H])C([2H])([2H])[2H])C([2H])([2H])[2H]]

Step a) tert-Butyl (S)-5-(4-(1-(2-(bis(propan-2-yl-$d_7$)carbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate (Mixture of Atropisomers)

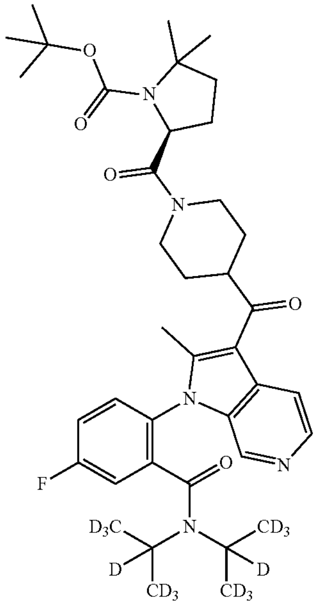 [SMILES: [2H]C([2H])([2H])C([2H])(N(C(=O)c1cc(F)ccc1-n1c(C)c(C(=O)C2CCN(C(=O)[C@@H]3CCC(C)(C)N3C(=O)OC(C)(C)C)CC2)c2ccncc21)C([2H])(C([2H])([2H])[2H])C([2H])([2H])[2H])C([2H])([2H])[2H]]

T3P (112 μL, 0.19 mmol, 50% in EtOAc) was added to a solution of (S)-1-(tert-butoxycarbonyl)-5,5-dimethylpyrrolidine-2-carboxylic acid (29.0 mg, 0.12 mmol), Intermediate 129 (0.13 mmol th.), and DIPEA (219 μL, 1.25 mmol) in EtOAc (1 mL). The resulting mixture was stirred at rt overnight. The reaction mixture was diluted with EtOAc (20 mL) and washed with sat. aq. $NaHCO_3$ (10 mL). The organic layer was dried over $Na_2SO_4$, filtered, and concentrated under reduced pressure to give the crude title compound (90.0 mg) as a brown dry film which was used directly in the next step; MS m/z (ES+) $[M+H]^+$=704.5.

Step b) (S)-2-(3-(1-(5,5-Dimethylpyrrolidine-2-carbonyl)piperidine-4-carbonyl)-2-methyl-1H-pyrrolo[2,3-c]pyridin-1-yl)-5-fluoro-N,N-bis(propan-2-yl-$d_7$)benzamide (Mixture of Atropisomers) (Example 59)

MsOH (25 μL, 0.38 mmol) was added to a solution of tert-butyl (S)-5-(4-(1-(2-(bis(propan-2-yl-$d_7$)carbamoyl)-4-fluorophenyl)-2-methyl-1H-pyrrolo[2,3-c]pyridine-3-carbonyl)piperidine-1-carbonyl)-2,2-dimethylpyrrolidine-1-carboxylate from Step a) (90.0 mg, 0.13 mmol) in IPA (2 mL). The reaction mixture was stirred at 60° C. overnight. The mixture was diluted with DCM (5 mL) and washed sequentially with sat. aq. $NaHCO_3$ (5 mL) and brine (2 mL). The organic layer was dried over $Na_2SO_4$, filtered, and concentrated under reduced pressure. The residue was purified straight phase flash chromatography on silica (gradient: 0-20% 0.7 M $NH_3$ in MeOH in DCM). Appropriate fractions were pooled and concentrated under reduced pressure. The product was lyophilized from $MeCN/H_2O$ to give the title compound (43.0 mg, 56%); MS m/z (ES+) $[M+H]^+$=604.5; $^1H$ NMR (400 MHz, DMSO-$d_6$, 22° C.) δ 1.03 (3H, s), 1.18 (3H, s), 1.24-1.71 (5H, m), 1.75-1.96 (2H, m), 2.09-2.27

(1H, m), 2.83-3.07 (1H, m), 3.28 (1H, s), 3.45-3.64 (1H, m), 3.81-4.13 (2H, m), 4.36 (1H, t), 7.40-7.64 (2H, m), 7.64-7.82 (1H, m), 7.82-8.01 (1H, m), 8.22-8.44 (2H, m).

Example 60: 5-Fluoro-N,N-diisopropyl-2-(2-methyl-3-(1-((2S,5S)-5-methylpyrrolidine-2-carbonyl)piperidine-4-carbonyl)-1H-pyrrolo[2,3-c]pyridin-1-yl)benzamide (Mixture of Atropisomers)

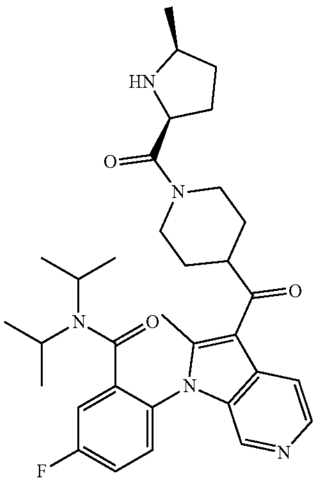 [SMILES: Cc1c(C(=O)C2CCN(C(=O)[C@@H]3CC[C@H](C)N3)CC2)c2ccncc2n1-c1ccc(F)cc1C(=O)N(C(C)C)C(C)C]

Step a) tert-butyl (2S,5S)-2-(4-(1-(2-(diisopropylcarbamoyl)-4-fluorophenyl)-2-methyl-1H-pyrrolo[2,3-c]pyridine-3-carbonyl)piperidine-1-carbonyl)-5-methylpyrrolidine-1-carboxylate (Mixture of Atropisomers)

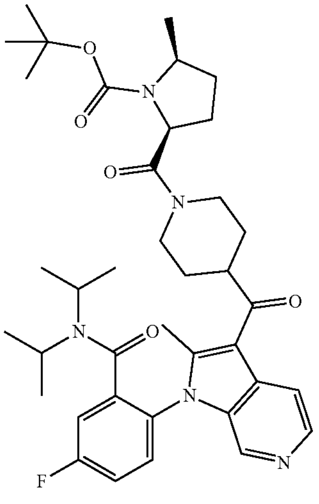 [SMILES: Cc1c(C(=O)C2CCN(C(=O)[C@@H]3CC[C@H](C)N3C(=O)OC(C)(C)C)CC2)c2ccncc2n1-c1ccc(F)cc1C(=O)N(C(C)C)C(C)C]

Intermediate 92 (250 mg, 0.54 mmol) was added to a solution of (2S,5S)-1-(tert-butoxycarbonyl)-5-methylpyrrolidine-2-carboxylic acid (123 mg, 0.54 mmol), EDC (124 mg, 0.65 mmol), HOBt (99.0 mg, 0.65 mmol) and DIPEA (188 μL, 1.08 mmol) in DCM (2 mL). The resulting mixture was stirred at rt overnight. The reaction mixture was diluted with DCM (20 mL) and washed sequentially with sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (353 mg, 97%) as a yellow gum; MS m/z (ES+) $[M+H]^+$=676.4.

Step b) 5-fluoro-N,N-diisopropyl-2-(2-methyl-3-(1-((2S,5S)-5-methylpyrrolidine-2-carbonyl)piperidine-4-carbonyl)-1H-pyrrolo[2,3-c]pyridin-1-yl)benzamide (Mixture of Atropisomers) (Example 60)

TFA (1 mL) was added to a solution of tert-butyl (2S,5S)-2-(4-(1-(2-(diisopropyl-carbamoyl)-4-fluorophenyl)-2-methyl-1H-pyrrolo[2,3-c]pyridine-3-carbonyl)piperidine-1-carbonyl)-5-methylpyrrolidine-1-carboxylate from Step a) (353 mg, 0.52 mmol) in DCM (5 mL). The mixture was stirred at rt for 1 h. The mixture was quenched with sat. aq. $NaHCO_3$ (20 mL) stirred vigorously with DCM (2×10 mL) for 10 min. The organic layers were separated through a phase separator. The combined organic layers were concentrated under reduced pressure. The residue was purified by straight phase flash chromatography on silica (gradient: 0-15% 0.7 M $NH_3$ in MeOH in DCM). Appropriate fractions were pooled and concentrated under reduced pressure. The product was lyophilized from $MeCN/H_2O$ to give the title compound (244 mg, 81%) as a light yellow solid; MS m/z (ES+) $[M+H]^+$=576.4; $^1H$ NMR (400 MHz, DMSO-$d_6$, 22° C.) δ 0.30-0.50 (3H, m), 0.50-0.78 (3H, m), 0.98-1.16 (3H, m), 1.16-1.36 (7H, m), 1.38-1.69 (2H, m), 1.69-1.81 (1H, m), 1.82-2.01 (3H, m), 2.11-2.28 (1H, m), 2.52 (3H, s), 2.94-3.06 (1H, m), 3.16-3.26 (2H, m), 3.34-3.40 (2H, m), 3.51-3.63 (1H, m), 3.63-3.78 (1H, m), 3.89 (1H, s), 4.13-4.44 (2H, m), 7.45-7.63 (2H, m), 7.65-7.81 (1H, m), 7.83-7.99 (1H, m), 8.23-8.43 (2H, m).

Example 61: 5-Fluoro-N,N-diisopropyl-2-(2-methyl-3-(1-((2S,5R)-5-methylpyrrolidine-2-carbonyl)piperidine-4-carbonyl)-1H-pyrrolo[2,3-c]pyridin-1-yl)benzamide (Mixture of Atropisomers)

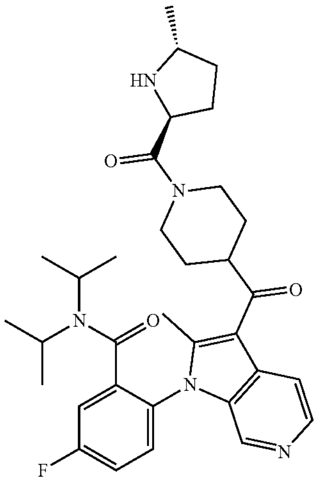 [SMILES: Cc1c(C(=O)C2CCN(C(=O)[C@@H]3CC[C@@H](C)N3)CC2)c2ccncc2n1-c1ccc(F)cc1C(=O)N(C(C)C)C(C)C]

Step a) tert-butyl (2S,5R)-2-(4-(1-(2-(diisopropyl-carbamoyl)-4-fluorophenyl)-2-methyl-1H-pyrrolo[2,3-c]pyridine-3-carbonyl)piperidine-1-carbonyl)-5-methylpyrrolidine-1-carboxylate (Mixture of Atropisomers)

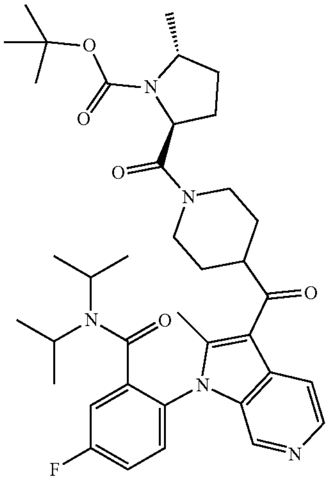 [SMILES: Cc1c(C(=O)C2CCN(C(=O)[C@@H]3CC[C@@H](C)N3C(=O)OC(C)(C)C)CC2)c2ccncc2n1-c1ccc(F)cc1C(=O)N(C(C)C)C(C)C]

Intermediate 92 (250 mg, 0.54 mmol) was added to a solution of (2S,5R)-1-(tert-butoxycarbonyl)-5-methylpyrrolidine-2-carboxylic acid (123 mg, 0.54 mmol), EDC (124 mg, 0.65 mmol), HOBt (99.0 mg, 0.65 mmol) and DIPEA (188 μL, 1.08 mmol) in DCM (2 mL). The resulting mixture was stirred at rt overnight. The reaction mixture was diluted with DCM (20 mL) and washed sequentially with sat. aq. $NaHCO_3$ (20 mL) and brine (20 mL). The organic layer was dried over $Na_2SO_4$, filtered, and concentrated under reduced pressure. The residue was purified by straight phase flash chromatography on silica (gradient: 0-10% MeOH in DCM) to give the title compound (329 mg, 90%) as a light yellow foam; MS m/z (ES+) $[M+H]^+$=676.4.

Step b) 5-fluoro-N,N-diisopropyl-2-(2-methyl-3-(1-((2S,5R)-5-methylpyrrolidine-2-carbonyl)piperidine-4-carbonyl)-1H-pyrrolo[2,3-c]pyridin-1-yl)benzamide (Mixture of Atropisomers) (Example 61)

TFA (1 mL) was added to a solution of tert-butyl (2S,5R)-2-(4-(1-(2-(diisopropyl-carbamoyl)-4-fluorophenyl)-2-methyl-1H-pyrrolo[2,3-c]pyridine-3-carbonyl)piperidine-1-carbonyl)-5-methylpyrrolidine-1-carboxylate from Step a) (329 mg, 0.49 mmol) in DCM (5 mL). The mixture was stirred at rt for 1 h. The mixture was quenched with sat. aq. $NaHCO_3$ (20 mL) stirred vigorously with DCM (2×10 mL) for 10 min. The organic layers were separated through a phase separator. The combined organic layers were concentrated under reduced pressure. The residue was purified by straight phase flash chromatography on silica (gradient: 0-15% 0.7 M $NH_3$ in MeOH in DCM). Appropriate fractions were pooled and concentrated under reduced pressure. The product was lyophilized from $MeCN/H_2O$ to give the title compound (216 mg, 77%) as a light yellow solid; MS m/z (ES+) $[M+H]^+$=576.3; $^1H$ NMR (400 MHz, DMSO-$d_6$, 22° C.) δ 0.41 (3H, d), 0.52-0.74 (3H, m), 0.99-1.13 (6H, m), 1.26 (3H, d), 1.29-1.38 (1H, m), 1.38-1.71 (3H, m), 1.77-1.95 (3H, m), 2.14-2.29 (1H, m), 2.52 (3H, s), 2.89-3.03 (1H, m), 3.13-3.29 (2H, m), 3.36-3.60 (2H, m), 3.62-3.74

(1H, m), 3.88-4.03 (1H, m), 4.04-4.18 (1H, m), 4.27-4.43 (1H, m), 7.46-7.62 (2H, m), 7.67-7.79 (1H, m), 7.81-7.97 (1H, m), 8.23-8.42 (2H, m).

Example 62: 5-Fluoro-N,N-diisopropyl-2-(2-methyl-3-((2S,4RS)-2-methyl-1-((2S,5S)-5-methylpyrrolidine-2-carbonyl)piperidine-4-carbonyl)-1H-pyrrolo[2,3-c]pyridin-1-yl)benzamide (Mixture of Atropisomers)

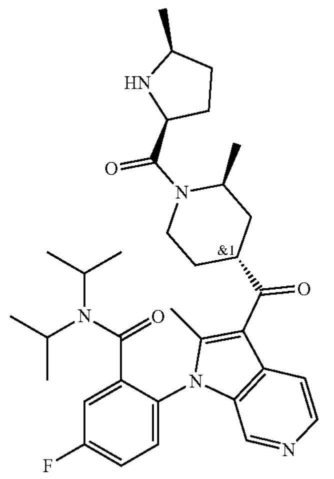 [SMILES: Cc1c(C(=O)[C@@H]2CCN(C(=O)[C@@H]3CC[C@H](C)N3)[C@@H](C)C2)c2ccncc2n1-c1ccc(F)cc1C(=O)N(C(C)C)C(C)C]

Step a) tert-butyl (2S,5S)-2-((2S,4RS)-4-(1-(2-(diisopropylcarbamoyl)-4-fluorophenyl)-2-methyl-1H-pyrrolo[2,3-c]pyridine-3-carbonyl)-2-methylpiperidine-1-carbonyl)-5-methyl-pyrrolidine-1-carboxylate (Mixture of Atropisomers)

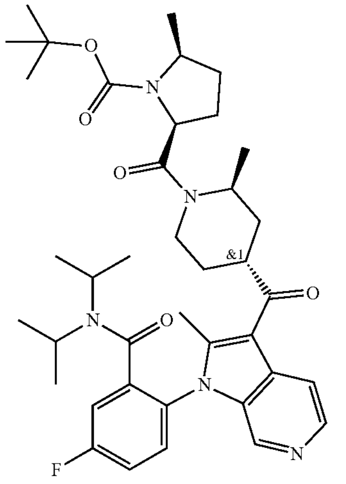 [SMILES: Cc1c(C(=O)[C@@H]2CCN(C(=O)[C@@H]3CC[C@H](C)N3C(=O)OC(C)(C)C)[C@@H](C)C2)c2ccncc2n1-c1ccc(F)cc1C(=O)N(C(C)C)C(C)C]

Intermediate 134 (280 mg, 0.59 mmol) was added to a solution of (2S,5S)-1-(tert-butoxycarbonyl)-5-methylpyrrolidine-2-carboxylic acid (134 mg, 0.59 mmol), EDC (135 mg, 0.70 mmol), HOBt (108 mg, 0.70 mmol) and DIPEA (204 µL, 1.17 mmol) in DCM (4 mL). The resulting mixture was stirred at rt for 4 h. Additional (2S,5S)-1-(tert-butoxycarbonyl)-5-methylpyrrolidine-2-carboxylic acid (134 mg, 0.59 mmol), EDC (135 mg, 0.70 mmol), HOBt (108 mg, 0.70 mmol) and DIPEA (204 µL, 1.17 mmol) were added and the mixture was stirred at rt for another 2 h. The reaction mixture was diluted with DCM (10 mL) and was stirred vigorously with sat. aq. $NaHCO_3$ (10 mL) for 10 min. The organic layer was passed over a phase separator and concentrated under reduced pressure. The residue was purified by straight phase flash chromatography on silica (gradient: 0-10% MeOH in DCM) to give the title compound (359 mg, 89%) as a light yellow foam; MS m/z (ES+) $[M+H]^+$=690.4.

Step b) 5-fluoro-N,N-diisopropyl-2-(2-methyl-3-((2S,4RS)-2-methyl-1-((2S,5S)-5-methylpyrrolidine-2-carbonyl)piperidine-4-carbonyl)-1H-pyrrolo[2,3-c]pyridine-1-yl)benzamide (Mixture of Atropisomers) (Example 62)

FA (7 mL) was added to a solution of tert-butyl (2S,5S)-2-((2S,4RS)-4-(1-(2-(diisopropylcarbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate from Step a) (359 mg, 0.52 mmol). The mixture was stirred at rt for 5 h. The mixture was quenched with sat. aq. $NaHCO_3$ (50 mL) and extracted with DCM (50 mL). The organic layer was dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (218 mg, 71%) as a white solid; MS m/z (ES+) $[M+H]^+$=590.4; $^1H$ NMR (400 MHz, DMSO-$d_6$, 22° C.) δ 0.42 (3H, dd), 0.51-0.78 (3H, m), 0.94-1.11 (4H, m), 1.10-1.19 (4H, m), 1.20-1.32 (5H, m), 1.34-1.44 (1H, m), 1.45-1.60 (1H, m), 1.62-1.78 (2H, m), 1.78-1.92 (2H, m), 1.95-2.17 (1H, m), 2.51-2.59 (3H, m), 2.93-3.06 (1H, m), 3.14-3.26 (1H, m), 3.55-3.85 (3H, m), 3.85-4.03 (1H, m), 4.32-4.48 (1H, m), 4.77-4.89 (1H, m), 7.46-7.62 (2H, m), 7.65-7.79 (1H, m), 7.85-7.97 (1H, m), 8.24-8.41 (2H, m).

Example 63: N-Ethyl-5-fluoro-N-isopropyl-2-(2-methyl-3-((2S,4RS)-2-methyl-1-((2S,5S)-5-methylpyrrolidine-2-carbonyl)piperidine-4-carbonyl)-1H-pyrrolo[2,3-c]pyridin-1-yl)benzamide (Mixture of Atropisomers)

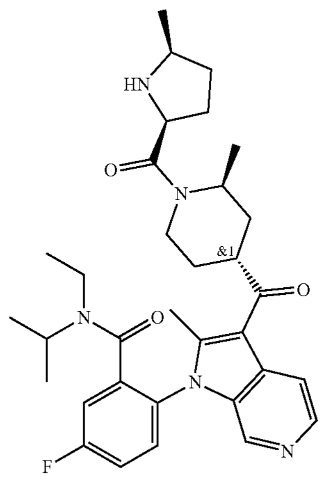 [SMILES: CCN(C(=O)c1cc(F)ccc1-n1c(C)c(C(=O)[C@@H]2CCN(C(=O)[C@@H]3CC[C@H](C)N3)[C@@H](C)C2)c2ccncc21)C(C)C]

Step a) tert-butyl (2S,5S)-2-((2S,4RS)-4-(1-(2-(ethyl (isopropyl)carbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate (Mixture of Atropisomers)

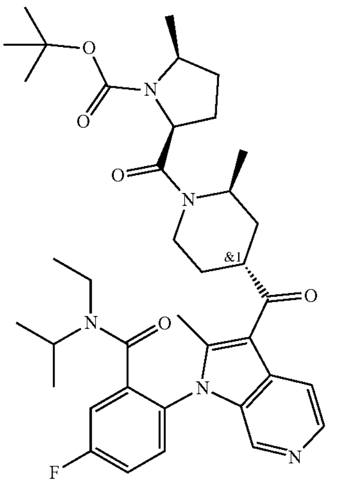 [SMILES: CCN(C(=O)c1cc(F)ccc1-n1c(C)c(C(=O)[C@@H]2CCN(C(=O)[C@@H]3CC[C@H](C)N3C(=O)OC(C)(C)C)[C@@H](C)C2)c2ccncc21)C(C)C]

Intermediate 138 (160 mg, 0.34 mmol) was added to a solution of (2S,5S)-1-(tert-butoxycarbonyl)-5-methylpyrrolidine-2-carboxylic acid (79.0 mg, 0.34 mmol), EDC (79.0 mg, 0.41 mmol), HOBt (63.3 mg, 0.41 mmol) and DIPEA (120 μL, 0.69 mmol) in DCM (3 mL). The resulting mixture was stirred at rt for 4 h. Additional (2S,5S)-1-(tert-butoxycarbonyl)-5-methylpyrrolidine-2-carboxylic acid (79.0 mg, 0.34 mmol), EDC (79.0 mg, 0.41 mmol), HOBt (63.3 mg, 0.41 mmol) and DIPEA (120 μL, 0.69 mmol) were added and the mixture was stirred at rt for another 2 h. The reaction mixture was diluted with DCM (10 mL) and was stirred vigorously with sat. aq. $NaHCO_3$ (10 mL) for 10 min. The organic layer was passed over a phase separator and concentrated under reduced pressure. The residue was purified by straight phase flash chromatography on silica (gradient: 0-10% MeOH in DCM) to give the title compound (227 mg, 97%) as a light yellow gum; MS m/z (ES+) $[M+H]^+$=676.4.

Step b) N-ethyl-5-fluoro-N-isopropyl-2-(2-methyl-3-((2S,4RS)-2-methyl-1-((2S,5S)-5-methylpyrrolidine-2-carbonyl)piperidine-4-carbonyl)-1H-pyrrolo [2,3-c]pyridin-1-yl)benzamide (Mixture of Atropisomers) (Example 63)

FA (5 mL) was added to a solution of tert-butyl (2S,5S)-2-((2S,4RS)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate from Step a) (227 mg, 0.34 mmol). The mixture was stirred at rt for 5 h. The mixture was quenched with sat. aq. $NaHCO_3$ (50 mL) and extracted with DCM (50 mL). The organic layer was dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (127 mg, 66%) as a white solid; MS m/z (ES+) $[M+H]^+$=576.3; $^1H$ NMR (400 MHz, DMSO-$d_6$, 22° C.) δ 0.15-0.45 (4H, m), 0.54-0.82 (2H, m), 1.00-1.15 (7H, m), 1.22-1.31 (2H, m), 1.34-1.43 (1H, m), 1.47-1.87 (5H, m), 1.93-2.14 (2H, m), 2.45-2.49 (1H, m), 2.51-2.57 (3H, m), 2.64-2.81 (1H, m), 2.88-3.01 (1H, m), 3.10-3.26 (1H, m), 3.38-3.57 (1H, m), 3.61-3.79 (2H, m), 3.79-3.93 (1H, m), 4.33-4.48 (1H, m), 4.77-4.90 (1H, m), 7.52-7.64 (2H, m), 7.68-7.80 (1H, m), 7.83-7.95 (1H, m), 8.25-8.37 (2H, m).

Example 64: 5-Fluoro-N,N-diisopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide (Mixture of Atropisomers)

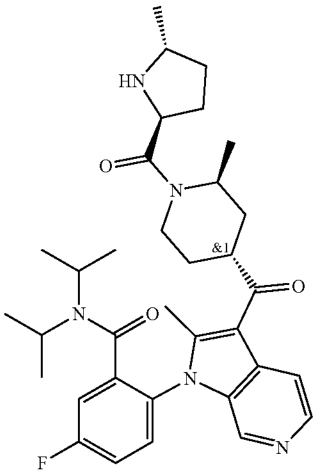 [SMILES: Cc1c(C(=O)[C@@H]2CCN(C(=O)[C@@H]3CC[C@@H](C)N3)[C@@H](C)C2)c2ccncc2n1-c1ccc(F)cc1C(=O)N(C(C)C)C(C)C]

Step a) tert-butyl (2S,5R)-2-((2S,4RS)-4-(1-(2-(diisopropylcarbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate (Mixture of Atropisomers)

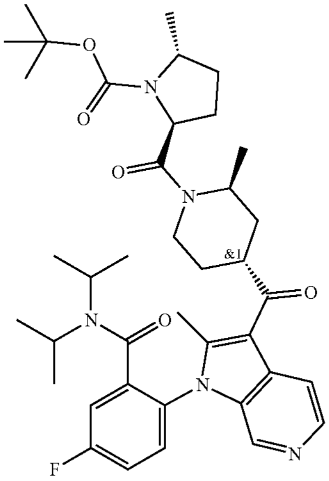 [SMILES: Cc1c(C(=O)[C@@H]2CCN(C(=O)[C@@H]3CC[C@@H](C)N3C(=O)OC(C)(C)C)[C@@H](C)C2)c2ccncc2n1-c1ccc(F)cc1C(=O)N(C(C)C)C(C)C]

Intermediate 134 (280 mg, 0.59 mmol) was added to a solution of (2S,5R)-1-(tert-butoxycarbonyl)-5-methylpyrrolidine-2-carboxylic acid (134 mg, 0.59 mmol), EDC (135 mg, 0.70 mmol), HOBt (108 mg, 0.70 mmol) and DIPEA (204 μL, 1.17 mmol) in DCM (4 mL). The resulting mixture was stirred at rt for 4 h. Additional (2S,5R)-1-(tert-butoxycarbonyl)-5-methylpyrrolidine-2-carboxylic acid (134 mg, 0.59 mmol), EDC (135 mg, 0.70 mmol), HOBt (108 mg, 0.70 mmol) and DIPEA (204 μL, 1.17 mmol) were added and the mixture was stirred at rt for another 2 h. The reaction mixture was diluted with DCM (10 mL) and was stirred vigorously with sat. aq. $NaHCO_3$ (10 mL) for 5 min. The organic layer was passed over a phase separator and concentrated under reduced pressure. The residue was purified by straight phase flash chromatography on silica (gradient: 0-10% MeOH in DCM) to give the title compound (423 mg, 100%) as a light yellow gum; MS m/z (ES+) $[M+H]^+$=690.4.

Step b) 5-fluoro-N,N-diisopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide (Mixture of Atropisomers) (Example 64)

FA (7 mL) was added to a solution of tert-butyl (2S,5R)-2-((2S,4RS)-4-(1-(2-(diisopropylcarbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate from Step a) (423 mg, 0.54 mmol, th.). The mixture was stirred at rt for 5 h. The mixture was quenched with sat. aq. $NaHCO_3$ (50 mL) and extracted with DCM (50 mL). The organic layer was dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (197 mg, 62%) as a white solid; MS m/z (ES+) $[M+H]^+$=590.4; $^1H$ NMR (400 MHz, DMSO-$d_6$, 22° C.) δ 0.42 (3H, dd), 0.55-0.78 (3H, m), 0.96-1.13 (6H, m), 1.20-1.30 (5H, m), 1.35-1.43 (1H, m), 1.43-1.91 (6H, m), 2.03-2.24 (1H, m), 2.51-2.56 (3H, m), 2.69-3.01 (1H, m), 3.13-3.27 (2H, m), 3.35-3.55 (1H, m), 3.61-3.77 (2H, m), 3.81-4.03 (2H, m), 4.35-4.49 (1H, m), 4.74-4.89 (1H, m), 7.48-7.61 (2H, m), 7.65-7.80 (1H, m), 7.84-7.96 (1H, m), 8.26-8.40 (2H, m).

Example 65: N-Ethyl-5-fluoro-N-isopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide (Mixture of Atropisomers)

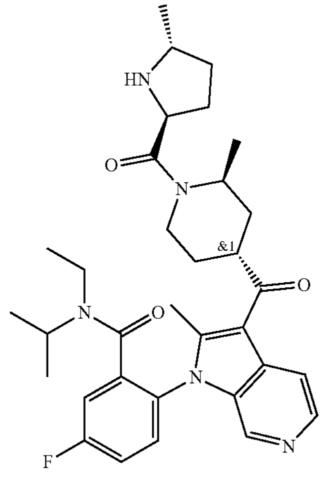 [SMILES: CCN(C(=O)c1cc(F)ccc1-n1c(C)c(C(=O)[C@@H]2CCN(C(=O)[C@@H]3CC[C@@H](C)N3)[C@@H](C)C2)c2ccncc21)C(C)C]

Step a) tert-butyl (2S,5R)-2-((2S,4RS)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate (Mixture of Atropisomers)

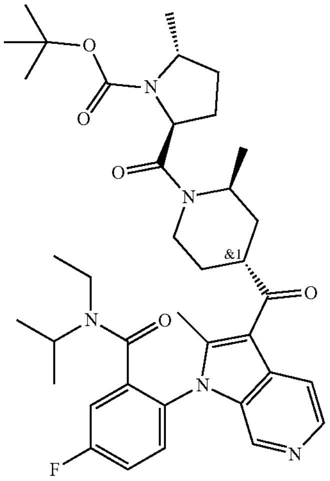 [SMILES: CCN(C(=O)c1cc(F)ccc1-n1c(C)c(C(=O)[C@@H]2CCN(C(=O)[C@@H]3CC[C@@H](C)N3C(=O)OC(C)(C)C)[C@@H](C)C2)c2ccncc21)C(C)C]

Intermediate 138 (160 mg, 0.34 mmol) was added to a solution of (2S,5R)-1-(tert-butoxycarbonyl)-5-methylpyrrolidine-2-carboxylic acid (79.0 mg, 0.34 mmol), EDC (79.0 mg, 0.41 mmol), HOBt (63.3 mg, 0.41 mmol) and DIPEA (120 μL, 0.69 mmol) in DCM (3 mL). The resulting mixture was stirred at rt for 4 h. Additional (2S,5R)-1-(tert-butoxycarbonyl)-5-methylpyrrolidine-2-carboxylic acid (79.0 mg, 0.34 mmol), EDC (79.0 mg, 0.41 mmol), HOBt (63.3 mg, 0.41 mmol) and DIPEA (120 μL, 0.69 mmol) were added and the mixture was stirred at rt for another 2 h. The reaction mixture was diluted with DCM (10 mL) and was stirred vigorously with sat. aq. $NaHCO_3$ (10 mL) for 5 min. The organic layer was passed over a phase separator and concentrated under reduced pressure. The residue was purified by straight phase flash chromatography on silica (gradient: 0-10% MeOH in DCM) to give the title compound (232 mg, 100%) as a light yellow gum; MS m/z (ES+) $[M+H]^+$=676.4.

Step b) N-ethyl-5-fluoro-N-isopropyl-2-(2-methyl-3-((2S,4RS)-2-methyl-1-((2S,5R)-5-methylpyrrolidine-2-carbonyl)piperidine-4-carbonyl)-1H-pyrrolo[2,3-c]pyridin-1-yl)benzamide (Mixture of Atropisomers) (Example 65)

FA (5 mL) was added to a solution of tert-butyl (2S,5R)-2-((2S,4RS)-4-(1-(2-(ethyl(isopropyl)carbamoyl)-4-fluorophenyl)-2-methyl-1H-pyrrolo[2,3-c]pyridine-3-carbonyl)-2-methylpiperidine-1-carbonyl)-5-methylpyrrolidine-1-carboxylate from Step a) (232 mg, 0.34 mmol). The mixture was stirred at rt for 5 h. The mixture was quenched with sat. aq. $NaHCO_3$ (50 mL) and extracted with DCM (50 mL). The organic layer was dried over $Na_2SO_4$, filtered, and concentrated under reduced pressure. The residue was purified by straight phase flash chromatography on silica (gradient: 0-25% 0.7 M $NH_3$ in MeOH in DCM) to give the title compound (134 mg, 68%) as a white solid; MS m/z (ES+) $[M+H]^+$=576.3; $^1H$ NMR (400 MHz, DMSO-$d_6$, 22° C.) δ 0.13-0.47 (4H, m), 0.54-0.79 (2H, m), 0.93-1.10 (6H, m), 1.19-1.32 (3H, m), 1.35-1.87 (7H, m), 2.04-2.24 (1H, m), 2.44-2.49 (1H, m), 2.51-2.56 (3H, m), 2.65-3.00 (2H, m), 3.13-3.28 (2H, m), 3.62-3.76 (2H, m), 3.82-4.01 (1H, m), 4.25-4.52 (1H, m), 4.69-4.91 (1H, m), 7.49-7.64 (2H, m), 7.67-7.82 (1H, m), 7.83-7.97 (1H, m), 8.22-8.40 (2H, m).

D. Biological Data

Example 66: Menin/MLL Fluorescence Polarization (FP) Assay

Compounds were tested in a biochemical binding assay using Menin protein at 2 nM (N6his-tev-Menin_4i80, PB-20-1459) and the substrate cRho110-Ahx-MBM1/MBM2 peptide (UbiQ, UbiQ-Q20201030; cRh110-Ahx-SCRWRFPARPGTTGGGGGGGRRGLGGAPR-QRVPALLLPPG-NH2) at 1 nM.

384 Low volume black plates (Corning #4514) were used. 5 μL/well compound or 3% DMSO was added at 10-fold serial dilutions in DMSO from 10 M. 5 μL/well cRhol 10-Ahx-MBM1/MBM2 peptide or binding buffer (50 mM Tris pH 7.5, 50 mM NaCl, 1 mM TCEP, 0.01% BGG, 0.01% Brij-35) was added to all wells. 5 μL/well Menin protein or binding buffer (50 mM Tris pH 7.5, 50 mM NaCl, 1 mM TCEP, 0.01% BGG, 0.01% Brij-35) was added to all wells. Plates were read on an EnVision plate reader (Perkin Elmer) with excitation at 480 nm and emission at 535 nm P+S, and measured every 5 minutes for 180 minutes.

Data were analyzed in Genedata Screener®. $IC_{50}$ values were determined by plotting % inhibition versus log compound concentration and using a one site dose response model. Raw data signals were normalized using 1% DMSO no Menin as 100% inhibitor control and 1% DMSO with Menin and no inhibitor as 0% inhibitor control. Data are reported in Table 1.

TABLE 1

| EXAMPLE | FP $IC_{50}$ (μM)[1] |
|---|---|
| 1 | 0.029 |
| 2 | 0.047 |
| 3 | 0.025 |
| 4 | 0.054 |
| 5 | 0.018 |
| 6 | 0.042 |
| 7 | 0.024 |
| 8 | 0.027 |
| 9 | 0.051 |
| 10 | 0.004 |
| 11 | 0.004 |
| 12 | 0.006 |
| 13 | 0.004 |
| 14 | 0.139 |
| 15 | 0.017 |
| 16 | 0.021 |
| 17 | 0.021 |
| 18 | 0.037 |
| 19 | 0.016 |
| 20 | 0.022 |
| 21 | 0.016 |
| 22 | 0.025 |
| 23 | 0.007 |
| 24 | 0.019 |
| 25 | 0.027 |
| 26 | 0.043 |
| 27 | 0.025 |
| 28 | 0.017 |
| 29 | 0.020 |
| 30 | 0.017 |
| 31 | 0.010 |
| 32 | 0.036 |
| 33 | 0.037 |
| 34 | 0.029 |
| 35 | 0.097 |
| 36 | 0.024 |
| 37 | 0.009 |
| 38 | 0.013 |
| 39 | 0.007 |
| 40 | 0.018 |
| 41 | 0.010 |
| 42 | 0.009 |
| 43 | 0.020 |
| 44 | 0.058 |
| 45 | 0.036 |
| 46 | 0.034 |
| 47 | 0.015 |
| 48-1 | 1.975 |
| 48-2 | 0.013 |
| 49-1 | 2.137 |
| 49-2 | 0.029 |
| 50-1 | 5.497 |
| 50-2 | 0.029 |
| 51-1 | 0.778 |
| 51-2 | 0.022 |
| 52-1 | 0.016 |
| 52-2 | 0.018 |
| 52-3 | 5.950 |
| 52-4 | 2.468 |
| 53-1 | 8.028 |
| 53-2 | 7.798 |
| 53-3 | 0.014 |
| 53-4 | 0.048 |
| 54 | 0.015 |
| 55-1 | 1.345 |
| 55-2 | 0.009 |
| 56-1 | 2.148 |
| 56-2 | 0.043 |
| 57-1 | 0.033 |
| 57-2 | >10.000 |
| 58-1 | 0.351 |
| 58-2 | 0.030 |
| 59 | 0.102 |
| 60 | 0.105 |
| 61 | 0.115 |
| 62 | 0.076 |
| 63 | 0.059 |
| 64 | 0.084 |
| 65 | 0.079 |

[1] $IC_{50}$ is reported after a single measurement (n = 1) or as an average for multiple measurements (n > 1).

Example 67: Proliferation Assay

The anti-proliferative effect of compounds was tested in human leukaemia cell lines. The cell lines MOLM-3 and MV4;11 each harbor an MLL translocation expressing the MLL fusion proteins MLL-AF9 and MLL-AF4, respectively. Each also express the wildtype protein from the second allele. OCI-AML3 cells carrying the NPM1c gene mutation were also tested. HEL cells which do not carry MLL1 translocation or NPM1c mutations were used as a control cell line to exclude compounds that displayed general cytotoxic effects.

MOLM-13 and HEL cells were cultured in RPMI 1640 (Gibco) supplemented with 10% FBS (Gibco) and 1% Pen/Strep (Gibco). MV4;11 cells were cultured in IMDM (Gibco) supplemented with 10% FBS (Gibco) and 1% Pen/Strep (Gibco). OCI-AML3 cells were cultured in MEMα (Gibco) supplemented with 20% FBS (Gibco) and 1% Pen/Strep (Gibco).

To assess proliferative effects, 125 MOLM-13 cells, 300 MV4;11 cells, 75 OCI-AML3 cells, and 200 HEL cells were seeded in 40 μL media per well in 384-well ViewPlates (Perkin Elmer, 6007480). Cell seeding numbers were chosen based on growth curves to ensure linear growth throughout the experiments. Test compounds were added at 3.16-fold serial dilutions in DMSO from M and DMSO content was normalized to 0.1%. Cells were incubated for 7 days at 37° C. and 5% $CO_2$. A day 0 plate was seeded for each cell line and used as a standard control.

To measure cell viability, CellTiter-Glo 2.0 (Promega, G9242) luminescent growth indicator was used. 10 μL CellTiter-Glo reagent was added per well. Plates were placed on a plate shaker for 2 minutes in the dark and left to incubate off the shaker for another 8 minutes in the dark, for a total of 10 minutes. Plates were read using an EnVision plate reader (Perkin Elmer) using the Luminescence aperture and a measurement time of 0.1 second.

Data were analyzed in Genedata Screener®. $IC_{50}$ values were determined by plotting % inhibition versus log compound concentration and using a one site dose response model. Raw data signals were normalized using 0.1% DMSO media only as background control, 0.1% DMSO with cells no compound as 100% viability (maximum signal), and day 0 0.1% DM with cells no compound as 0% viability (minimum signal). Data are reported in Table 2.

TABLE 2

| EXAMPLE | MOLM-13 $IC_{50}$ (μM)[1] | MV-4-11 $IC_{50}$ (μM)[1] | OCI-AML3 $IC_{50}$ (μM)[1] | HEL $IC_{50}$ (μM)[1] |
|---|---|---|---|---|
| 1 | 0.149 | 0.166 | 0.313 | >10.0 |
| 2 | 0.105 | 0.097 | 0.126 | >10.0 |
| 3 | 0.098 | 0.099 | 0.113 | >10.0 |
| 4 | 0.156 | 0.132 | 0.223 | >10.0 |
| 5 | 0.074 | 0.085 | 0.125 | >10.0 |
| 6 | 0.073 | 0.046 | | >10.0 |
| 7 | 0.063 | 0.072 | 0.115 | >10.0 |
| 8 | 0.142 | 0.100 | 0.193 | >10.0 |
| 9 | 0.121 | 0.100 | 0.225 | >10.0 |
| 10 | 0.023 | 0.024 | 0.024 | >10.0 |
| 11 | 0.050 | 0.031 | 0.051 | >10.0 |
| 12 | 0.102 | | | >10.0 |
| 13 | 0.051 | 0.034 | 0.037 | >10.0 |
| 14 | 0.476 | 0.345 | 0.626 | >10.0 |
| 15 | 0.098 | 0.053 | 0.103 | >10.0 |
| 16 | 0.035 | 0.029 | 0.051 | >10.0 |
| 17 | 0.107 | 0.320 | 0.356 | >10.0 |
| 18 | 0.057 | 0.044 | | >10.0 |
| 19 | 0.034 | 0.025 | | >10.0 |
| 20 | 0.040 | 0.025 | | >10.0 |
| 21 | 0.034 | 0.027 | | >10.0 |
| 22 | 0.030 | 0.017 | | >10.0 |
| 23 | 0.037 | 0.020 | | >10.0 |
| 24 | 0.032 | 0.020 | 0.021 | >10.0 |
| 25 | 0.050 | 0.024 | 0.037 | >10.0 |
| 26 | 0.103 | 0.050 | 0.140 | >10.0 |
| 27 | 0.038 | 0.035 | 0.034 | >10.0 |
| 28 | 0.039 | 0.034 | | >10.0 |
| 29 | 0.058 | 0.057 | | >10.0 |
| 30 | 0.044 | 0.033 | 0.059 | >10.0 |
| 31 | 0.038 | 0.032 | | >10.0 |
| 32 | 0.154 | 0.144 | 0.275 | >10.0 |
| 33 | 0.111 | 0.103 | 0.207 | >10.0 |
| 34 | 0.062 | 0.039 | | >10.0 |
| 35 | 0.297 | 0.146 | 0.412 | >10.0 |
| 36 | 0.060 | 0.043 | | >10.0 |
| 37 | 0.068 | 0.034 | | >10.0 |
| 38 | 0.027 | 0.024 | | >10.0 |
| 39 | 0.065 | 0.031 | 0.047 | 6.9 |
| 40 | 0.061 | 0.037 | | >10.0 |
| 41 | 0.042 | | | >10.0 |
| 42 | 0.040 | 0.043 | 0.076 | >10.0 |
| 43 | 0.064 | 0.044 | | >10.0 |
| 44 | 0.073 | 0.065 | 0.117 | >10.0 |
| 45 | 0.109 | | | >10.0 |
| 46 | 0.052 | 0.037 | | >10.0 |
| 47 | 0.042 | 0.033 | 0.026 | >10.0 |
| 48-1 | 1.246 | | | >10.0 |
| 48-2 | 0.027 | 0.029 | 0.023 | >10.0 |

TABLE 2-continued

| EXAMPLE | MOLM-13 $IC_{50}$ (μM)[1] | MV-4-11 $IC_{50}$ (μM)[1] | OCI-AML3 $IC_{50}$ (μM)[1] | HEL $IC_{50}$ (μM)[1] |
|---|---|---|---|---|
| 49-1 | 2.293 | 2.952 | | >10.0 |
| 49-2 | 0.080 | 0.034 | >0.233 | >10.0 |
| 50-1 | 2.066 | | | >10.0 |
| 50-2 | 0.044 | 0.039 | 0.063 | >10.0 |
| 51-1 | 1.608 | | | >10.0 |
| 51-2 | 0.031 | 0.029 | 0.037 | >10.0 |
| 52-1 | | 0.022 | 0.040 | |
| 52-2 | 0.048 | 0.056 | 0.082 | >10.0 |
| 52-3 | 1.470 | | | >10.0 |
| 52-4 | 1.091 | | | >10.0 |
| 53-1 | 3.270 | | | >10.0 |
| 53-2 | 1.297 | | | >10.0 |
| 53-3 | 0.015 | 0.013 | 0.014 | >10.0 |
| 53-4 | 0.071 | 0.053 | 0.118 | >10.0 |
| 54 | 0.049 | 0.040 | 0.043 | >10.0 |
| 55-1 | 1.258 | 1.725 | | >10.0 |
| 55-2 | 0.025 | 0.031 | 0.029 | >10.0 |
| 56-1 | 1.931 | | | >10.0 |
| 56-2 | 0.040 | 0.035 | 0.047 | >10.0 |
| 57-1 | 0.093 | 0.051 | 0.077 | >10.0 |
| 57-2 | >10.0 | | | >10.0 |
| 58-1 | >10.0 | | | >10.0 |
| 58-2 | 0.037 | 0.035 | 0.035 | >10.0 |
| 59 | 0.094 | | | >10.0 |
| 60 | 0.071 | 0.088 | | >10.0 |
| 61 | 0.092 | 0.114 | | >10.0 |
| 62 | 0.052 | | | >10.0 |
| 63 | 0.047 | | | >10.0 |
| 64 | 0.053 | | 0.313 | >10.0 |
| 65 | 0.056 | | 0.126 | >10.0 |

[1] $IC_{50}$ is reported after a single measurement (n = 1) or as an average for multiple measurements (n > 1).

Example 68: hERG Assays

A. hERG Assay 1 (Standard)

Experiments were performed on the SyncroPatch 384PE (Nanion Technologies) high throughput patch clamp platform at room temperature and used medium resistance chips with 4 patch holes per site. hERG-expressing Chinese hamster ovary K1 (CHO) cell line was used in assay-ready format and kept in liquid nitrogen until use. 2 vials of cells (10×10^6 cells per vial) were thawed and added to 20 ml Hepes-buffered saline solution (HBSS). HBSS comprised 140 mM NaCl, 4 mM KCl, 10 mM HEPES and 5 mM Glucose (pH 7.4). The internal patch clamp solution was KF 120 mM, KCl 20 mM, HEPES 10 mM, EGTA 10 mM, and 25 μM Escin (pH 7.2). After the initial sealing process was complete, a seal enhancer solution comprising HBSS supplemented with 10 mM $CaCl_2$ and 1 mM $MgCl_2$ was applied to cells. The external solution was then exchanged (4 times) for external patch clamp solution comprising NaCl 80 mM, KCl 4 mM, HEPES 10 mM, $CaCl_2$ 2 mM, $MgCl_2$ 1 mM, glucose 5 mM, and NMDG 60 mM (pH7.4). All compounds were dispensed from initial 10 mM DMSO stocks. An industry standard +60/−40 mV voltage protocol was applied every 15 seconds. Compounds were tested in a 6-point cumulative assay (final DMSO concentration 0.33%), with a concentration range of 139 nM to 40 uM. Data were analyzed in Genedata Screener®. $IC_{50}$ values were determined by plotting % inhibition versus log compound concentration and using a one site dose response model. Only wells that passed acceptance criteria for this platform were used in this analysis (30 MegaOhm seal resistance, Z prime>0.4 and current size>0.2 nA). Data are reported in Table 3.

B. hERG Assay 2

Experiments were performed on the QPatch II 48X (Sophion Biosciences) high throughput patch clamp platform at room temperature and used single hole Qplates. hERG DUO cell line (BSys) was used. The internal patch clamp solution was KF 60 mM, KCl 70 mM, HEPES 10 mM, EGTA 10 mM, and 5 mM Mg ATP (pH7.2). After sealing and whole cell access was gained the external solution (NaCl 140 mM, KCl 4 mM, HEPES 10 mM, $CaCl_2$ 2 mM, $MgCl_2$ 1 mM, glucose 5 mM (pH 7.4) was applied twice to establish stable baseline currents. An industry standard +40/−40 mV voltage protocol was applied every 15 seconds. All compounds were tested in a 6-point cumulative assay (final DMSO concentration 0.4-2% depending on stock concentration of compounds). Compounds were dispensed from initial 10 mM or 50 mM DMSO stocks after which DMSO dilutions were undertaken with a top concentration of 200 M tested. Solvent controls were run in all experiments in line with the DMSO % required. Only wells that passed acceptance criteria for this platform were used in this analysis (500 MegaOhm seal resistance and current size>0.2 nA). Analysis was completed in Prism Graphpad to complete a composite $IC_{50}$, by plotting % inhibition versus log compound concentration and using a log(inhibitor) vs. response—Variable slope. Data are reported in Table 3.

C. hERG Assay 3

Experiments were performed on the QPatchII 48X (Sophion Biosciences) high throughput patch clamp platform at 30 degrees Celsius using single holes QChips (Sophion Bioscience). Chinese hamster ovary K1 (CHO) cell lines over-expressing the hERG ion channel were used from live culture. All compounds were dispensed as solid stocks in glass vials. Compounds were solubilised to 10 or 50 mM DMSO stocks on the day of experiments, after which dilutions in DMSO we undertaken. Stamps of DMSO stocks were made into an MTP plate using glass vials, after which extracellular solution was backfilled creating testing concentrations with a highest concentration of 40 and 200 M, respectively. The internal patch clamp solution was KF 60 mM, KCl 70 mM, HEPES 10 mM, EGTA 10 mM, and 5 mM Mg ATP (pH7.2). After sealing and whole cell access was gained the external solution (NaCl 140 mM, KCl 4 mM, HEPES 10 mM, $CaCl_2$ 2 mM, $MgCl_2$ 1 mM, glucose 5 mM (pH7.4) supplemented with 0.4% DMSO was applied twice to establish stable baseline currents. An industry standard +40/−40 mV voltage protocol was applied every 15 seconds. Cells were then applied with a single concentration of compound for a minimum of 15 minutes (a bolus addition every 3 minutes). Analysis was completed in Prism Graphpad to complete a composite $IC_{50}$, by plotting % inhibition versus log compound concentration and using a log(inhibitor) vs. response—Variable slope Only wells that passed previously agreed acceptance criteria for this platform were used in this analysis (500 MegaOhm seal resistance and current size>0.2 nA). Data are reported in Table 3.

TABLE 3

| EXAMPLE | hERG ASSAY 1 (μM)[1] | hERG ASSAY 2 (μM)[1] | hERG ASSAY 3 (μM)[1] |
|---|---|---|---|
| 1 | 9.9 | | |
| 2 | >40.0 | >200.0 | |
| 3 | 38.8 | | |
| 4 | 6.3 | | |
| 5 | >40.0 | >200.0 | |
| 7 | >40.0 | 150.3 | |
| 8 | >40.0 | | |
| 10 | >40.0 | 79.1 | 33.8 |
| 11 | >40.0 | | |
| 12 | >40.0 | | |
| 13 | 35.8 | | |
| 15 | 24.9 | | |
| 16 | >40.0 | 127.7 | |
| 17 | 9.1 | | |
| 18 | >40.0 | | |
| 19 | >40.0 | 128.3 | |
| 20 | >40.0 | >200.0 | |
| 21 | >40.0 | | |
| 22 | >40.0 | | |
| 23 | 30.6 | | |
| 24 | 38.3 | | |
| 25 | >40.0 | | |
| 26 | >40.0 | | |
| 27 | >40.0 | | |
| 28 | >40.0 | >200.0 | |
| 29 | >40.0 | | |
| 30 | >40.0 | | |
| 31 | >40.0 | >200.0 | |
| 33 | >40.0 | | |
| 34 | >40.0 | | |
| 36 | >40.0 | 36.5 | |
| 37 | >40.0 | >200.0 | |
| 38 | >40.0 | 26.0 | |
| 40 | >40.0 | | |
| 41 | >40.0 | | |
| 42 | >40.0 | | |
| 43 | >40.0 | 54.0 | |
| 44 | >40.0 | | |
| 46 | >40.0 | >200.0 | |
| 48-2 | >40.0 | >200.0 | |
| 49-2 | >38.0 | | |
| 47 | >40.0 | 193.7 | |
| 48-1 | >40.0 | | |
| 49-1 | >40.0 | >200.0 | |
| 50-2 | >40.0 | | |
| 51-2 | >40.0 | >200.0 | |
| 52-2 | 14.2 | | |
| 53-3 | 31.4 | | |
| 51-1 | >40.0 | | |
| 55-2 | >40.0 | 82.3 | |
| 54 | 13.1 | | |
| 55-1 | >40.0 | | |
| 56-2 | >40.0 | 138.3 | 42.9 |
| 56-1 | >40.0 | | |
| 57-2 | >40.0 | | |
| 57-1 | >38.5 | | |
| 58-2 | >40.0 | | 111.0 |
| 59 | >40 | | |
| 60 | >40 | | |
| 61 | >40 | | |
| 62 | >40 | | |
| 63 | >40 | | |
| 64 | 32.7 | | |
| 65 | >40 | | |

[1] $IC_{50}$ is reported after a single measurement (n = 1) or as an average for multiple measurements (n > 1).

Example 69: Muscarinic M2 Receptor Assays

A. Muscarinic M2 Receptor Binding Assay (Assay 1)

Cell membrane homogenates (60 μg protein) were incubated for 60 minutes at 22° C. with 2 nM [3H]AF-DX 384 in the absence or presence of the test compound in a buffer containing 50 mM Tris-HCl (pH 7.4), 120 mM NaCl, 5 mM KCl, 5 mM $MgCl_2$, and 1 mM EDTA. Nonspecific binding was determined in the presence of 1 μM atropine. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results were expressed as a percent inhibition of the control radioligand specific binding, from which the $K_i$ was calculated. Data were analyzed using software developed at Cerep (Hill software) and validated by comparison with data generated by the commercial software SigmaPlot®4.0 for Windows® (© 1997 by SPSS Inc.). The inhibition constant, $K_i$, was calculated using the Cheng Prusoff equation:

$$K_i = IC_{50}/(1+L/Kd)$$

where L=concentration of ligand in the assay, and Kd=affinity of the ligand for the receptor. The standard reference compound was methoctramine, which was tested in each experiment at several concentrations to obtain a competition curve from which its $IC_{50}$ was calculated. Data are reported in Table 4.

B. Muscarinic M2 Receptor Functional Assay—Antagonist Effect (Assay 2)

The cells were suspended in HBSS buffer (Invitrogen) complemented with 20 mM HEPES (pH 7.4) and 500 µM IBMX, then distributed in microplates at a density of 104 cells/well and reincubated for 5 minutes at room temperature in the presence of either of the following: HBSS (stimulated control), the reference antagonist methoctramine at 10 µM (basal control), various concentrations of methoctramine ($IC_{50}$ determination), or various concentrations of the test compounds ($IC_{50}$ determination). Thereafter, the reference agonist acetylcholine and the adenylyl cyclase activator NKH 477 were added at respective final concentrations of 1 µM and 5 µM. For basal control measurements, acetylcholine was omitted from the wells containing 10 µM methoctramine. Following 10 minutes incubation at 37° C., the cells were lysed, and the fluorescence acceptor (D2-labeled cAMP) and fluorescence donor (anti-cAMP antibody labelled with europium cryptate) were added. After 60 minutes at room temperature, the fluorescence transfer was measured at λex=337 nm and λem=620 and 665 nm using a microplate reader (Rubystar, BMG). The cAMP concentration was determined by dividing the signal measured at 665 nm by that measured at 620 nm (ratio). The results were expressed as a percent inhibition of the control response to 1 µM acetylcholine. For test compounds and for standard reference antagonist methoctramine, which is tested in each experiment, assays were run in eight-point concentration response mode and $IC_{50}$ values determined following non-linear regression curve analysis. Curve analysis was completed using software developed at Cerep (Hill software) and validated by comparison with data generated by the commercial software SigmaPlot®4.0 for Windows® (© 1997 by SPSS Inc.). Data are reported in Table 4.

TABLE 4

| EXAMPLE | M2 Ki (BINDING) (µM)[1] | M2 FUNCTIONAL ANTAGONIST (µM)[1] |
|---|---|---|
| 1 | 8.1 | |
| 2 | 0.8 | 5.2 |
| 5 | 6.6 | >100.0 |
| 6 | 2.3 | |
| 7 | 14.4 | |

TABLE 4-continued

| EXAMPLE | M2 Ki (BINDING) (µM)[1] | M2 FUNCTIONAL ANTAGONIST (µM)[1] |
|---|---|---|
| 8 | 8.0 | |
| 10 | 10.5 | |
| 11 | 5.0 | |
| 12 | 6.9 | |
| 13 | 9.7 | |
| 15 | 13.6 | |
| 16 | 0.2 | 1.1 |
| 18 | 1.0 | |
| 19 | 1.4 | 21.3 |
| 20 | 0.8 | 5.2 |
| 21 | 0.5 | |
| 22 | 0.7 | |
| 23 | 0.1 | |
| 24 | 1.2 | |
| 25 | 1.9 | |
| 26 | 2.6 | |
| 27 | 1.6 | |
| 28 | 0.4 | |
| 29 | 0.2 | |
| 31 | 0.1 | |
| 33 | 0.3 | |
| 34 | 0.0 | |
| 36 | 1.2 | |
| 37 | 0.3 | |
| 38 | 0.3 | |
| 41 | 0.1 | |
| 42 | 0.5 | |
| 43 | 4.0 | |
| 44 | 2.8 | |
| 46 | 7.1 | |
| 47 | 7.3 | 62.8 |
| 49-2 | 27.4 | |
| 48-1 | 6.7 | |
| 48-2 | 19.0 | |
| 50-2 | 34.3 | |
| 51-2 | 30.7 | |
| 53-3 | 19.8 | |
| 54 | 3.5 | |
| 55-1 | 3.8 | |
| 55-2 | 51.9 | |
| 57-1 | >100.0 | |
| 56-1 | 7.4 | |
| 56-2 | >100.0 | |
| 58-2 | 4.2 | 8.6 |

[1]$IC_{50}$ is reported after a single measurement (n = 1) or as an average for multiple measurements (n > 1).

Example 70: Metabolic Stability Assays

A. Human Liver Microsomes (HLMs) Intrinsic Clearance Assay

Material and Reagents

Human liver microsomes (HLMs) were obtained from Corning (UltraPool 150 donors) at a concentration of 20 mg/mL protein. HLMs were stored at −80° C. until use and prior to use, thawed in a 37° C. water bath and then stored on wet ice. DMSO and NADPH were sourced from Solarbio S&T Co Ltd.

Performing the HLM Intrinsic Clearance Assay

Preparation of Stock Solutions 2 mL of 10 mM DMSO stock solutions of test compound were added to 198 mL acetonitrile to produce 100 mmol/L concentration. 1325 mL of 20 mg/mL HLM were added to 22260 mL of phosphate buffer to produce the HLM mixture. An 8.334 mg/mL solution of NADPH was prepared in 100 mmol/L pH 7.4 phosphate buffer.

HLM Incubation 222.5 mL of the HLM mixture and 25 mL of the 10 mM NADPH were added into the incubation plates (1 mL 96 well deep well plate from Thermo). The mixture was vortexed for 10 seconds at 1000 rpm. The incubation plate was pre-warmed in a water bath at 37° C. for 8 minutes. 2.5 mL of the 100 mM stocks of test compound was added to initiate the reaction. The mix was vortexed for 12 seconds at 1000 rpm and incubated at 37° C. The incubation mixture (250 mL) contained 1 mg/mL HLM, 1 mmol/L NADPH and 1 mM test compound.

The reaction was quenched by transferring 20 mL of the incubation mixture at 0.5, 5, 10, 15, 20 and 30 minutes into the quenching plate containing 100 mL of cold stop solution (acetonitrile containing internal standards). The plate was vortexed at 800 rpm for 2 minutes.

The quenching plates were centrifuged for 20 minutes at 4000 rpm and 4° C. 40 mL of the supernatant was transferred into a 96-well analysis plate containing 160 mL of water. The analysis plate was shaken at 1000 rpm for 2 minutes and the samples analysed by LC-MS/MS.

Calculation of HLM $CL_{int}$

Peak areas were determined from extracted ion chromatograms. Percent parent remaining was calculated from peak area of test compound. The slope value, k, was determined by linear regression of the natural logarithm of percent parent remaining versus incubation time.

The in vitro half-life ($t_{1/2}$) was determined from the slope value by the equation:

$$\text{in vitro } t_{1/2} = -(0.693/k)$$

Conversion of the in vitro half-life (min) into in vitro $CL_{int}$ (mL/min/mg proteins) was completed using the equation:

$$\text{in vitro } CL_{int} = \left(\frac{0.693}{(t_{1/2})}\right) * \left(\frac{\text{volume of incubation } (\mu\text{L})}{\text{amount of proteins (mg)}}\right)$$

Data are reported in Table 5.

B. Human Hepatocyte Intrinsic Clearance Assay

Material and Reagents

Human hepatocytes (LiverPool™ 10-Donor Human hepatocytes (Mixed Gender, PEG-free, Product No. S01205, 5 million cells per vial) were obtained from BioreclamationIVT. DMSO was sourced from Solarbio S&T Co Ltd. Leibovitz's L-15 Medium, Williams' Medium E, GlutaMAX™-1 (100×), HEPES, DPBS (10×) and Human Recombinant Insulin Solution were purchased from Gibco. Isotonic Percoll Solution was purchased from GE Healthcare. Fetal Bovine Serum (FBS) was purchased from Corning.

Performing the Human Hepatocyte Intrinsic Clearance Assay

Preparation of Thawing Medium 10 mM dexamethasone stock solution was prepared by dissolving 3.9 mg dexamethasone in 1 mL of DMSO. An Isotonic Percoll Solution was prepared by dilution of Percoll with DPBS (10×). 15 mL of Isotonic Percoll Solution (90% Percoll/10% DPBS) was added to 31.25 mL William's E medium containing 500 mL of GlutaMAX™-1 (100×), 750 mL of 1M HEPES, 2.5 mL of 5% FBS, 50 mL of 4 mg/mL Human Recombinant Insulin Solution and 5 mL of the 10 mM dexamethasone stock.

Preparation of Stock Solutions 2 mL of 10 mM DMSO stock solutions of test compound were added to 198 mL acetonitrile to produce 100 mmol/L concentration.

Human Hepatocyte Incubation

The human hepatocyte vial was thawed at 37° C. in a waterbath. Once thawed, contents were poured into a 50 mL conical tube and centrifuged at 100 g for 10 minutes. The thawing medium was poured out and 4 mL L-15 medium was added. The tube was gently shaken to resuspend the hepatocytes and cells were counted with an appropriate cell counter. 247.5 mL of the hepatocyte suspension was transferred into each well of the plate and pre-warmed at 600 rpm and 50° C. to enable the temperature to rise to 37° C.

2.5 mL of the 100 mmol/L test compound solution was added to initiate the reaction (final concentration 1 mM) and incubated at 37° C. with shaking at 900 rpm. At 0.5, 5, 15, 30, 45, 60, 80, 100 and 120 minutes, 20 mL was taken into a quenching solution of acetonitrile containing internal standards. The mix was vortexed at 800 rpm for 2 minutes followed by centrifugation for 20 minutes at 4000 rpm at 4° C. 40 mL of supernatant was transferred into a 96 well analysis plate containing 160 mL of water in each well. The analysis plate was shaken at 100 rpm for 2 minutes prior to analysis by LC-MS/MS.

Calculation of Human Hepatocyte $CL_{int}$

Peak areas were determined from extracted ion chromatograms. Percent parent remaining was calculated from peak area of test compound. The slope value, k, was determined by linear regression of the natural logarithm of percent parent remaining versus incubation time.

The in vitro intrinsic clearance (in vitro $CL_{int}$ in mL/min/$10^6$ cells) was determined from the slope value using the following equation:

$$\text{in vitro } CL_{int} = kV/N$$

where V is the incubation volume (0.25 mL) and N is the number of hepatocytes per well ($0.25\times10^6$ cells). Data are reported in Table 5.

TABLE 5

| EXAMPLE | HLM $CL_{int}$ (µl/min/mg)[1] | HH $CL_{int}$ (µl/min/1E6)[1] |
|---|---|---|
| 1 | 178 | 2.6 |
| 2 | 43 | <1.0 |
| 3 | 41 | <1.0 |
| 4 | 171 | 2.3 |
| 5 | 35 | <1.0 |
| 6 | 40 | |
| 7 | 148 | 3.2 |
| 8 | 21 | |
| 9 | 27 | 3.8 |
| 10 | 182 | <2.2 |
| 11 | >294 | <1.0 |
| 12 | 216 | 3.9 |
| 13 | 119 | |
| 14 | 38 | |
| 15 | 132 | 2.9 |
| 16 | 27 | <1.0 |
| 17 | 52 | 1.2 |
| 18 | 172 | 1.6 |
| 19 | 56 | 3.6 |
| 20 | 27 | <1.0 |
| 21 | 197 | 2.0 |
| 22 | 91 | <1.7 |
| 23 | 156 | 3.8 |
| 24 | 145 | 4.1 |
| 25 | 94 | 3.6 |
| 26 | 51 | <1.0 |
| 27 | 46 | <1.0 |
| 28 | 41 | <1.0 |

TABLE 5-continued

| EXAMPLE | HLM $CL_{int}$ (μl/min/mg)[1] | HH $CL_{int}$ (μl/min/1E6)[1] |
|---|---|---|
| 29 | 26 | |
| 30 | 54 | |
| 31 | 23 | <1.0 |
| 32 | 18 | |
| 33 | 50 | |
| 34 | 11 | |
| 35 | 5 | |
| 36 | 58 | <1.0 |
| 37 | 52 | <1.0 |
| 38 | 131 | <1.0 |
| 39 | 259 | |
| 40 | 18 | <1.0 |
| 41 | 180 | 1.7 |
| 42 | 219 | 2.5 |
| 43 | 101 | <1.0 |
| 44 | 17 | |
| 45 | 139 | |
| 46 | 50 | <1.0 |
| 47 | 54 | 2.1 |
| 49-2 | 127 | 6.0 |
| 48-1 | 69 | <1.0 |
| 48-2 | 55 | <1.0 |
| 49-1 | >300 | |
| 50-1 | 183 | |
| 50-2 | 48 | <1.0 |
| 51-1 | 54 | |
| 51-2 | 52 | 1.9 |
| 52-1 | 150 | 4.1 |
| 52-2 | 150 | 3.5 |
| 52-3 | 210 | 5.7 |
| 52-4 | >300 | 7.9 |
| 53-1 | 116 | |
| 53-2 | 77 | |
| 53-3 | 155 | 3.3 |
| 53-4 | 89 | |
| 54 | 73 | 6.4 |
| 55-1 | 125 | 4.4 |
| 55-2 | 194 | 4.2 |
| 57-1 | 84 | 3.2 |
| 56-1 | 133 | 6.9 |
| 56-2 | 91 | 3.4 |
| 57-2 | 95 | |
| 58-1 | 128 | |
| 58-2 | 85 | 1.9 |
| 59 | 59 | |
| 60 | 106 | |
| 61 | 83 | |
| 62 | 12 | |
| 63 | 63 | |
| 64 | 88 | |
| 65 | 55 | |

[1]$IC_{50}$ is reported after a single measurement (n = 1) or as an average for multiple measurements (n > 1).

Example 71: Intrinsic Intestinal Caco-2 Cell Monolayers Cell Permeation Assay in the Presence of Efflux Inhibitors Material and Reagents Caco-2 cells were obtained from American Type Culture Collection (ATCC). HEPES, penicillin, streptomycin, bovine serum albumin (BSA) were obtained from Beijing Xinjingke Biotechnology Co, Ltd. Fetal bovine serum, Hank's balanced salt solution (HBSS) and non-essential amino acids (NEAA) were purchased from Gibco. Dulbecco's Modified Eagle's Medium (DMEM) was purchased from Corning and MES from Sigma. HTS Transwell-24 permeable supports were purchased from Corning. Zosuquidar and Ko-143 were obtained from MedChemExpress and Benzbromarone from Sigma.

Preparation for Cell Seeding

The Caco-2 cell culture medium consisted of DMEM with high glucose and L-glutamine supplemented with 10% FBS, 0.1 mg/mL streptomycin, 100 units of penicillin, 0.6 mg/mL kanamycin sulfate and 1×NEAA. 100 mL culture medium was added to each Transwell insert with 800 mL added to each well of the reservoir. After incubation at 37° C. in 5% $CO_2$ for 1 hour, the plates were ready for seeding.

The cells were cultivated in T-75 flasks at 37° C., 5% $CO_2$, 95% relative humidity. At 80 to 90% confluence, cells were treated with trypsin/EDTA treatment until they became detached. The trypsin/EDTA was inactivated by adding excess serum containing medium. The cell suspension was centrifuged at 120 g for 10 minutes followed by resuspension of the cell pellet in seeding medium at a cell density of $7.92\times10^5$ cells/mL.

Seeding and Feeding of Caco-2 Cells into Transwell Plates 100 mL of the resulting cell suspension was added to each well of the Transwell plate and incubated for 14 to 18 days, with medium replaced every other day. After incubation for 14 to 18 days, the cells should have reached confluence and should be tested for electrical resistance using a Millicel Epithelial Volt-Ohm measuring system (Millipore).

Performing the Drug Transport Assay

The cell monolayers were washed twice with pre-warmed HBSS and incubated at 37° C. for 30 minutes under gentle shaking (480 rpm).

The compound under test was presented as a 10 mM DMSO stock solution. 2 mL of the 10 mM stock was added to 8 mL DMSO to produce a 2 mM stock. 2 mL was added to 398 mL of HBSS containing 10 mM Zosuquidar, 30 mM Benzbromarone and 2 mM KO-143 to make a 10 mM drug stock solution.

210 mL of the test compound solution was added to the apical compartment of the Transwell plate, with a 10 mL sample taken to act as the time 0 sample. The wells of the receiver (basolateral) compartment were filled with 800 mL HBSS (containing the efflux inhibitors). The plates were incubated at 37° C. with shaking at 480 rpm for 120 minutes with sampling at 45 and 120 minutes.

At each sampling time (0, 45 and 120 minutes) 10 mL was removed from the apical compartment and add to 90 mL (HBSS containing the efflux inhibitors). 100 mL was removed from each basolateral compartment. 3 volumes of cold acetonitrile containing internal standard was added to each sample and vortex mixed for 10 minutes at 100 rpm. Samples were then centrifuged at 400 rpm for 20 minutes. 50 mL of the supernatant was taken for LC/MS/MS analysis to determine compound concentration.

Calculation of Apparent Permeability and Recovery

The apparent permeability (Papp), in units of centimetre per second, were calculated for Caco-2 drug transport using the following equation:

$$P_{app} = \frac{C_R^{120}\times 0.8 - C_R^{45}\times 0.7}{(C_D^{45}+C_D^{120})/2\times \text{Area}\times \text{time}}$$

Where $C_R$ is the concentration of compound in the receiver side at the respective time point, $C_D$ is the concentration of compound in the donor side at the respective timepoint. Area is the surface area of the membrane and time is 4500 seconds (75×60 seconds).

The recovery rate (0-120 minutes) was determined using the following equation:

$$\text{Recovery (\%)}(0-120\text{ min}) = \left(\frac{C_R^{120}\times V_R + C_R^{45}\times 0.1 + C_D^{45}\times 0.01 + C_D^{120}\times V_D}{D_0\times V_0}\right)\times 100$$

where $V_R$ is the volume (in mL) in the acceptor well and $V_D$ is the volume (in mL) in the donor well. Data are reported in Table 6.

TABLE 6

| EXAMPLE | Caco-2 A to B $P_{app}$ (1E−6.cm/s)[1] |
|---|---|
| 1 | 2.7 |
| 2 | 0.4 |
| 3 | 0.3 |
| 4 | 2.0 |
| 5 | 1.2 |
| 6 | <0.5 |
| 7 | 2.2 |
| 8 | 0.2 |
| 9 | 0.5 |
| 10 | 2.6 |
| 11 | 0.7 |
| 12 | 1.6 |
| 13 | 1.7 |
| 14 | |
| 15 | 4.2 |
| 16 | 0.6 |
| 17 | 1.8 |
| 18 | 3.1 |
| 19 | 2.6 |
| 20 | 0.8 |
| 21 | 1.7 |
| 22 | 3.0 |
| 23 | 1.5 |
| 24 | 18.2 |
| 25 | 3.0 |
| 26 | 0.8 |
| 27 | 1.9 |
| 28 | 1.1 |
| 29 | |
| 30 | 0.8 |
| 31 | 0.1 |
| 32 | 0.4 |
| 33 | 0.5 |
| 34 | 0.2 |
| 35 | |
| 36 | 0.6 |
| 37 | 1.0 |
| 38 | 1.5 |
| 39 | |
| 40 | 0.3 |
| 41 | 0.5 |
| 42 | 1.3 |
| 43 | 2.2 |
| 44 | 1.0 |
| 45 | |
| 46 | 0.3 |
| 47 | 1.9 |
| 49-2 | 6.3 |
| 48-1 | 1.5 |
| 48-2 | 1.7 |
| 49-1 | 8.0 |
| 50-2 | 1.2 |
| 51-1 | 1.7 |
| 51-2 | 2.2 |
| 52-1 | 10.9 |
| 52-2 | 10.4 |
| 52-3 | 10.5 |
| 52-4 | 9.5 |
| 53-3 | 3.6 |
| 54 | 4.0 |

TABLE 6-continued

| EXAMPLE | Caco-2 A to B $P_{app}$ (1E−6.cm/s)[1] |
|---|---|
| 55-1 | 3.7 |
| 55-2 | 4.4 |
| 57-1 | 4.3 |
| 56-1 | 2.8 |
| 56-2 | 3.5 |
| 57-2 | 13.5 |
| 58-2 | 5.4 |
| 62 | 4.9 |
| 63 | 1.5 |
| 64 | 4.3 |
| 65 | 1.7 |

[1]$IC_{50}$ is reported after a single measurement (n = 1) or as an average for multiple measurements (n > 1).

Example 72: Anti-Tumor Effect in MLLr AML Xenograft Model MV-4-11

A study was conducted to evaluate the in vivo efficacy of monotherapy with a Menin inhibitor in a human MLLr AML xenograft model.

A. Materials

MV-4-11 cells were grown in RPM1 1640 (Gibco, #21875091) supplemented with 10% FBS (Gibco; #10091-148) and 1% Pen/Strep (Gibco; #15140-122). Cells were harvested and resuspended in PBS/Matrigel (Corning; #CLS354234) (50/50). The compound of Example 56-2 was formulated in water at pH 4.5-5 using 1 M MSA as pH-adjusting agent at the concentrations up to 100 mg/mL to achieve a uniform suspension and dosed twice daily by oral gavage 10 mL/kg. For convenience, the compound of Example 56-2 is referred to as "Compound 56-2" in this Example and the other Examples.

B. Procedure 10 million human MV-4-11 AML cells were implanted subcutaneously in the right flank of female CB17 SCID mice. Mice were randomized into groups of 5 when average tumor volume reached approximately 160 $mm^3$. Mice were treated for 14 days with vehicle (water at pH 4.5-5 using 1M MSA) or Compound 56-2 at 30, 100, or 200 mg/kg. Compound 56-2 was dosed orally twice daily 8/16 hours apart. The group administered Compound 56-2 at 30, 100, 200 mg/kg were monitored for regrowth for 6 weeks. Compound 56-2 at 100 mg/kg and 200 mg/kg resulted in no tumor regrowth compared to Compound 56-2 at 30 mg/kg. FIG. 1 illustrates the effect of treatment with Compound 56-2 on tumor volume in this MLLr MV-4-11 human AML cancer xenograft mouse model. Data for Compound 56-2 are reported in Table 7.

TABLE 7

| DOSE (COMPOUND 56-2) | % REGRESSION AT DOSING END | % TUMOR REGROWTH AT STUDY END |
|---|---|---|
| 30 mg/kg | 88% | 100% |
| 100 mg/kg | 97% | 0% |
| 200 mg/kg | 99% | 0% |

Example 73: Anti-Tumor Effect in MLLr AML Xenograft Model MOLM-13

A study was conducted to evaluate the in vivo efficacy of a Menin inhibitor in a human MLLr AML xenograft model.

A. Materials

MOLM-13 cells were grown in RPM1 1640 (Gibco, #21875091) supplemented with 10% FBS (Gibco; #10091-148) and 1% Pen/Strep (Gibco; #15140-122). Cells were harvested and resuspended in PBS/Matrigel (Corning; #CLS354234) (50/50). Compound 56-2 was formulated in water at pH 4.5-5 using 1 M MSA as pH-adjusting agent at the concentrations up to 100 mg/mL to achieve a uniform suspension and dosed twice daily by oral gavage 10 mL/kg.

Figure 2A:
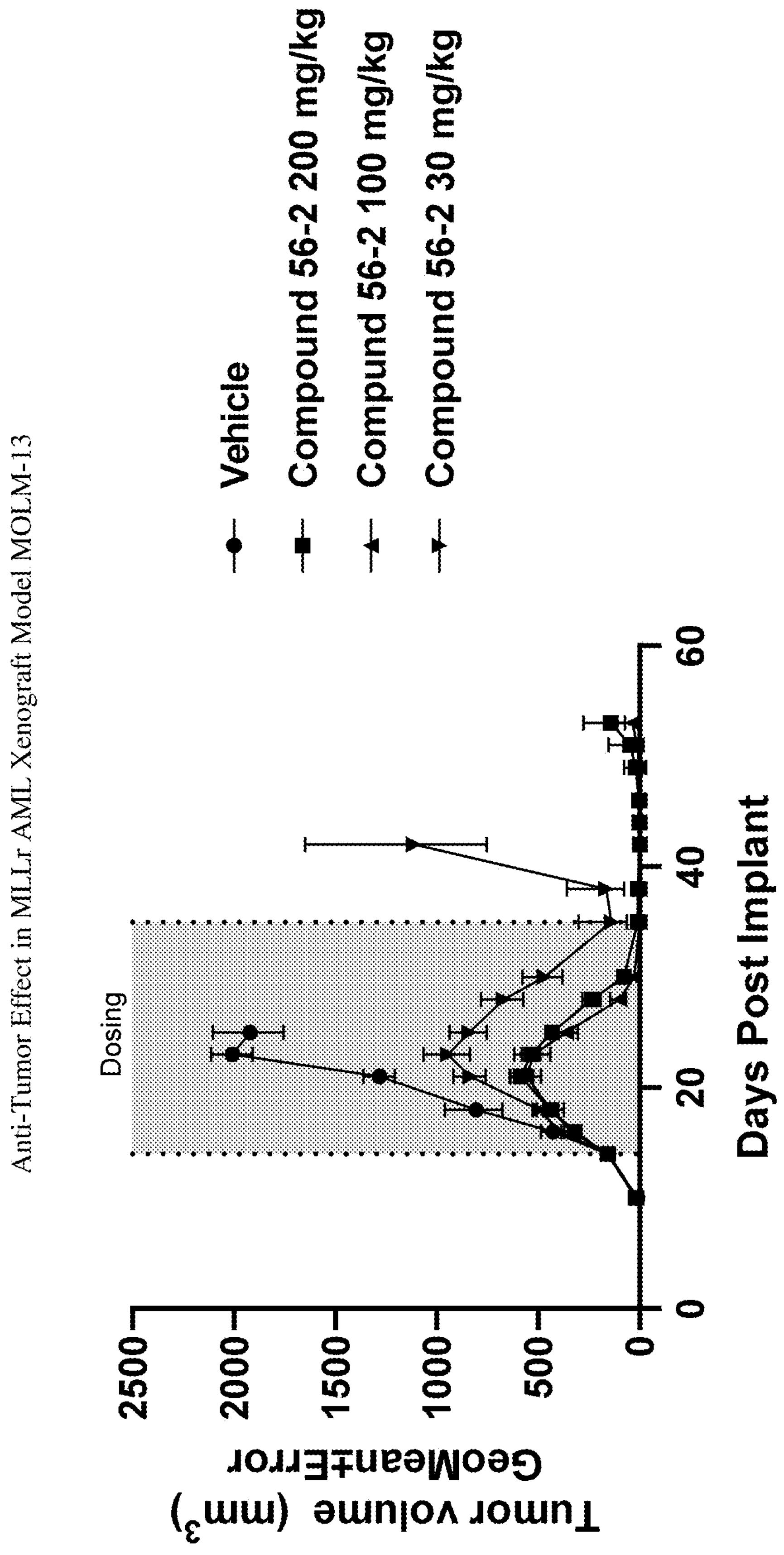
FIGS. 2A and 2B illustrate the effect of treatment with a Menin inhibitor (the compound of Example 56-2) on tumor volume in MLLr AML Xenograft Model MOLM-13.

B. Procedure 1 million human MOLM-13 AML cells were implanted subcutaneously in the right flank of female CB17 SCID mice. Mice were randomized into groups of 5 when average tumor volume reached approximately 160 $mm^3$. Mice were treated for 21 days with vehicle (water at pH 4.5-5 using 1 M MSA) or Compound 56-2 at 30, 100, or 200 mg/kg. Test compound was dosed orally twice daily 8/16 hours apart. The group administered Compound 56-2 at 30, 100, 200 mg/kg were monitored for regrowth for 3 weeks. Compound 56-2 at 100 mg/kg and 200 mg/kg resulted in complete tumor regressions at the end of treatment and tumors regrew 3 weeks after stopping treatment compared to 30 mg/kg which outgrew after treatment end. FIG. 2A illustrates the effect of treatment with Compound 56-2 on tumor volume in this MLLr MOLM-13 human AML cancer xenograft mouse model. Data for Compound 56-2 are reported in Table 8A.

TABLE 8A

| DOSE (COMPOUND 56-2) | % REGRESSION AT END OF TREATMENT | % TUMOR REGROWTH AT STUDY END |
|---|---|---|
| 30 mg/kg | 6.2% | 100% |
| 100 mg/kg | 89.8% | 80% |
| 200 mg/kg | 98.5% | 100% |

Figure 2B:
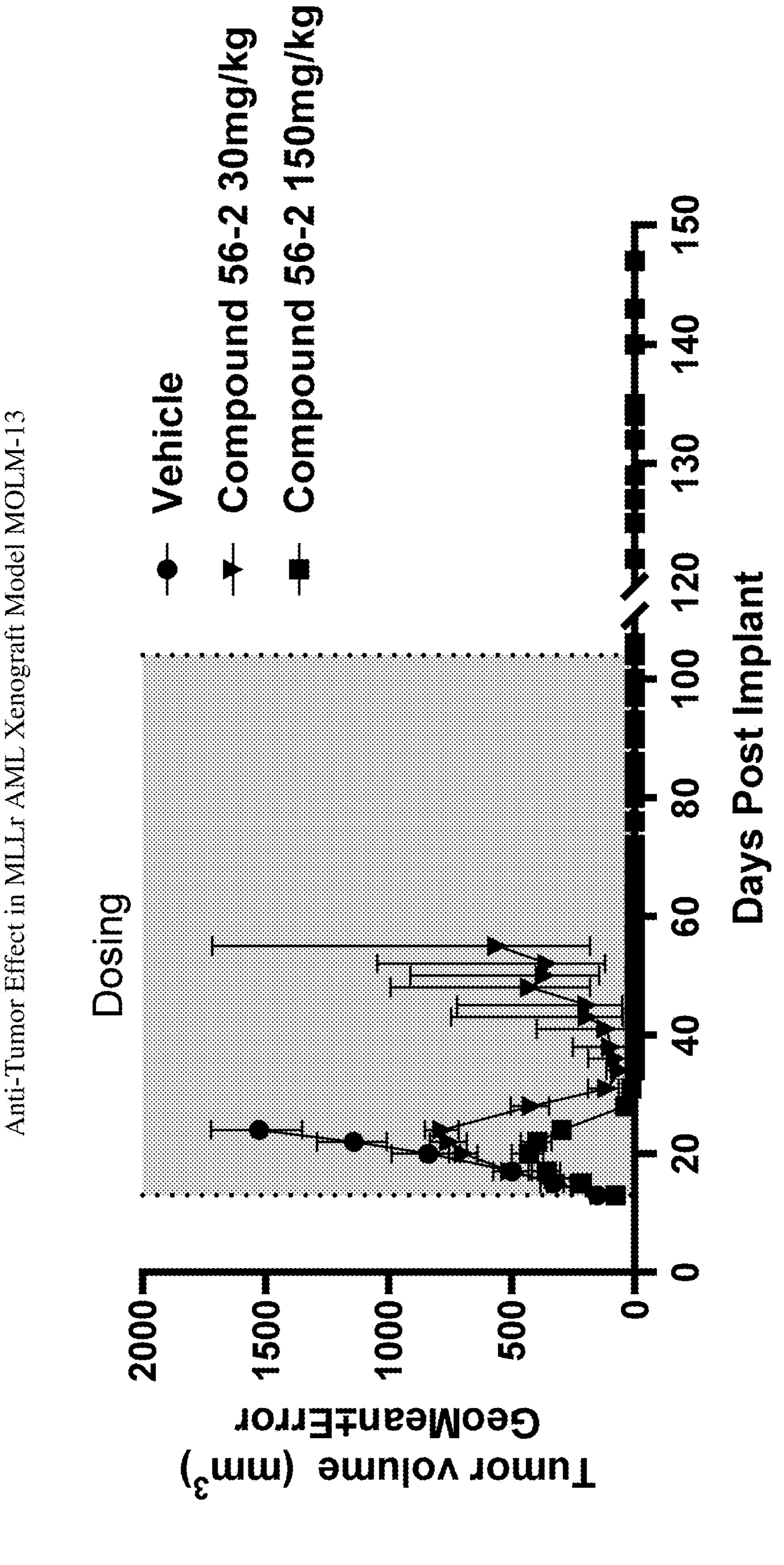

In a second cohort of mice, MOLM-13 AML cells were implanted and randomized as described above. Mice were treated until tumor outgrowth with vehicle (water at pH 4.5-5 using 1 M MSA) or Compound 56-2 at 30 mg/kg or 150 mg/kg. Test compound was dosed orally twice daily 8/16 hours apart. The group administered Compound 56-2 at 30 mg/kg were dosed for a total of 41 days or less and all animals outgrew treatment. The group administered Compound 56-2 at 150 mg/kg were dosed for a total of 90 days and monitored for regrowth for an additional 70 days and resulted in complete tumor regression at the end of treatment. FIG. 2B illustrates the effect of treatment with Compound 56-2 on tumor volume in this MLLr MOLM-13 human AML cancer xenograft mouse model. Data for Compound 56-2 are reported in Table 8B.

TABLE 8B

| DOSE (COMPOUND 56-2) | % REGRESSION AT END OF TREATMENT | % TUMOR REGROWTH AT STUDY END |
|---|---|---|
| 30 mg/kg | 0% | 0% |
| 150 mg/kg | 100% | 100% |

Example 74: Anti-Tumor Effect in MLLr AML Patient Derived Disseminated Xenograft Models CBAM-68552, CBAM-44728, and DFAL-49600

A study was conducted to evaluate the in vivo efficacy of monotherapy with a Menin inhibitor in three human MLLr AML Patient Derived Disseminated Xenograft Models.

A. Materials

Viably frozen A. CBAM-68552, B. CBAM-44728, and C. DFAL-49600 single cell suspensions from spleens of donor mice were prepared into frozen stock. Flow cytometry antibodies for Ter119 (Miltenyi 130-112-914), mouse CD45 (Miltenyi 130-110-665), and human CD45 (Miltenyi 130-110-634) and Fixable Live Dead Stain (ThermoFisher; #L34963) for disease evaluation via flow cytometry on MACSQuant (Miltenyi). Compound 56-2 was formulated in water at pH 4.5-5 using 1M MSA as pH-adjusting agent at concentrations up to 100 mg/mL to achieve a uniform suspension and dosed twice daily by oral gavage 10 mL/kg.

B. Procedure

A. CBAM-68552, B. CBAM-44728, and C. DFAL-49600 cells were thawed and 1 million cells implanted via the tail vein in to female NSG mice. Mice were randomized into groups of 5 when human CD45 levels reached average of A. CBAM-68552 6.5%, B. CBAM-44728 4.8%, and C. DFAL-49600 12.4% in the bone marrow of satellite animals. Mice were treated for 21 days with vehicle (water at pH 4.5-5 using 1 M MSA) or Compound 56-2 at 150 mg/kg. Compound 56-2 was dosed orally twice daily 8/16 hours apart and mice were monitored for overall survival. FIGS. 3-A, 3-B, and 3-C further illustrate the effect of treatment with Compound 56-2 in human MLLr AML Patient Derived Disseminated Xenograft Models A. CBAM-68552, B. CBAM-44728, and C. DFAL-49600, respectively. Data for Compound 56-2 are reported in Table 9.

TABLE 9

| MODEL | VEHICLE LATENCY | COMPOUND 56-2 LATENCY |
|---|---|---|
| CBAM-68552 | 92 days | 188 days |
| CBAM-44728 | 66 days | 106 days |
| DFAL-49600 | 76 days | 161 days |

Example 75: Anti-Tumor Effect in NPM1 Mutant AML Patient Derived Disseminated Xenograft Model DFAM-16835

A study was conducted to evaluate the in vivo efficacy of monotherapy with a Menin inhibitor in human NPM1 mutant AML Patient Derived Disseminated Xenograft Model DFAM-16835.

A. Materials

Viably frozen DFAM-16835 single cell suspensions from spleens of donor mice were prepared into frozen stock. Flow cytometry antibodies for Ter119 (Miltenyi 130-112-914), mouse CD45 (Miltenyi 130-110-665), and human CD45 (Miltenyi 130-110-634) and Fixable Live Dead Stain (ThermoFisher; #L34963) for disease evaluation via flow cytometry on MACSQuant (Miltenyi). Compound 56-2 was formulated in water at pH 4.5-5 using 1 M MSA as pH-adjusting agent at the concentrations up to 100 mg/mL to achieve a uniform suspension and dosed twice daily by oral gavage 10 mL/kg.

B. Procedure

Figure 4:
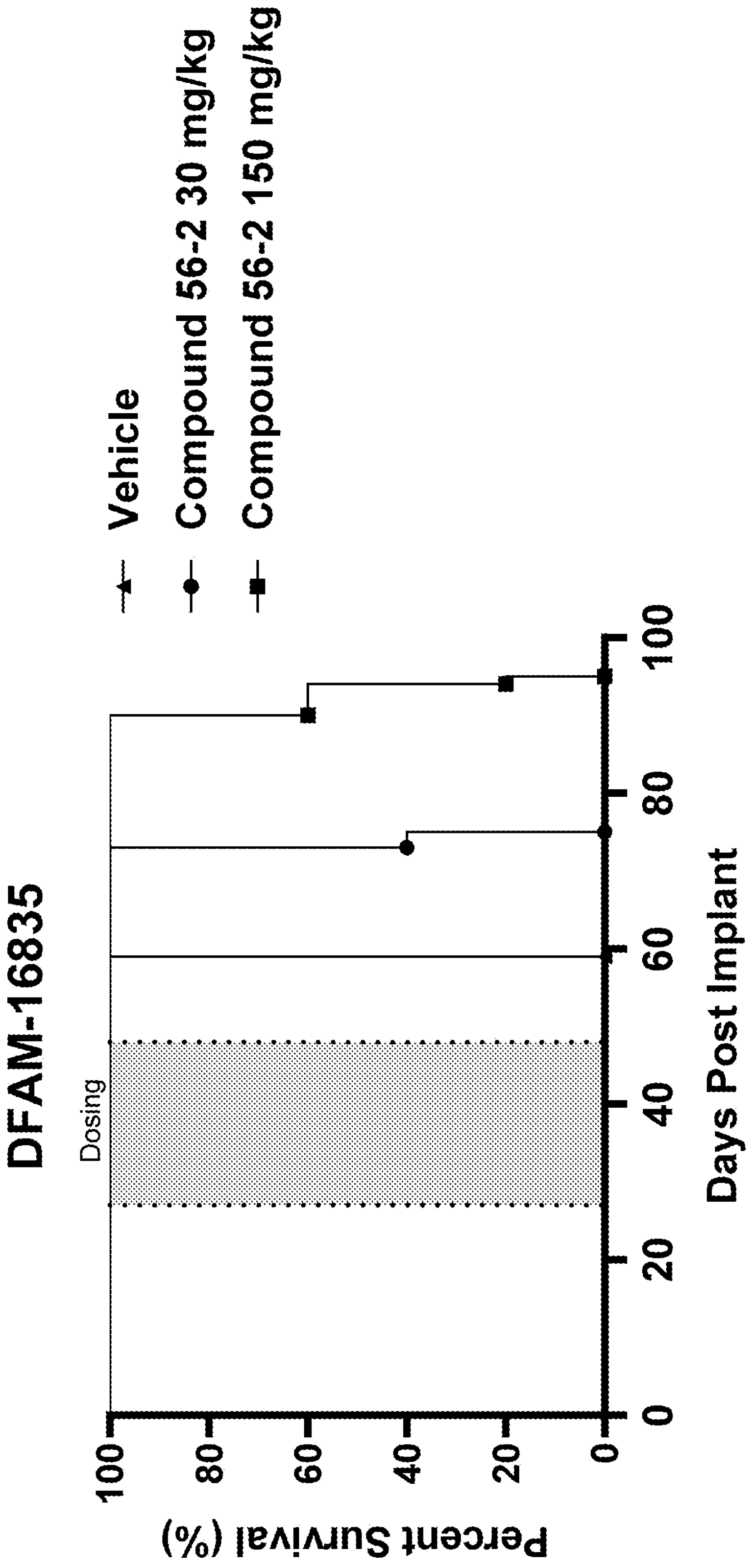
FIG. 4 illustrates the effect of treatment with a Menin inhibitor (the compound of Example 56-2) on survival in NPM1 mutant AML Patient Derived Disseminated Xenograft Model DFAM-16835.

DFAM-16835 cells were thawed and 1 million cells implanted via the tail vein into female NSG mice. Mice were randomized into groups of 10 when human CD45 levels reached average of 22.3% in the bone marrow of satellite animals. Mice were treated for 21 days with vehicle (water at pH4.5-5 using 1M MSA) or Compound 56-2 at 30 and 150 mg/kg. Compound 56-2 was dosed orally twice daily 8/16 hours apart. An increase in overall survival was observed with Compound 56-2 extending latency from 59 days to 73 days (30 mg/kg) and 94 days (150 mg/kg). FIG. 4 further illustrates the effect of treatment with Compound 56-2 in human NPM1 mutant AML Patient Derived Disseminated Xenograft Model DFAM-16835. Data for Compound 56-2 are reported in Table 10.

TABLE 10

| MODEL | VEHICLE LATENCY | COMPOUND 56-2 LATENCY |
|---|---|---|
| DFAM-16835 | 59 days | 73 days |

Example 76: Enhanced Cell Death in MOLM-13 Cell Line with Compound 56-2 and BCL2 Inhibitor (Venetoclax)

Induction of cell death was assessed in a human MOLM-13 AML MLLr cell line treated with Compound 56-2 alone or in combination with a BCL2 inhibitor (venetoclax).

Test compound was dispensed using a Tecan compound dispenser into 384-well plates (Microplate 384-well, polypropylene, F-bottom; Greiner Bio-One, #781201) in a ten-by-ten response matrix to assess the combination effects of Menin inhibition (Compound 56-2) together with BCL-2 inhibition (venetoclax) at the following concentrations after subsequent cell seeding in 40 μL of growth media: 10 μM, 3.16 μM, 1 μM, 0.316 μM, 0.1 μM, 0.0316 μM, 0.01 μM, 0.00316 μM, 0.001 μM, and vehicle (DMSO; Sigma-Aldrich, D2650). Cells were seeded at 1000 cells per well and incubated at 37° C. and 5% $CO_2$. MOLM-13 cells were grown in RPMI 1640 (Gibco, #21875091) supplemented with 10% FBS (Gibco; #10091-148) and 1% Pen/Strep (Gibco; #15140-122). After 4 days of compound treatment, plates were placed at room temperature for 15 minutes. 10 μL CellTiter-Glo reagent (Promega, #G9242) was added to the cells and incubated for 10 minutes in the dark on a plate shaker at room temperature. A backseal (Perkin Elmer; #6005199) was added to the plates and luminescence was measured at 0.1 sec/well in an Envision (Perkin Elmer). Data were normalized for each plate so that the average of control wells (DMSO) was set to 0%, and the maximum observed value across the plate was set as 100%. Data fitting was performed using Graphpad Prism and combination effect was assessed using SynergyFinder.

Figure 5:
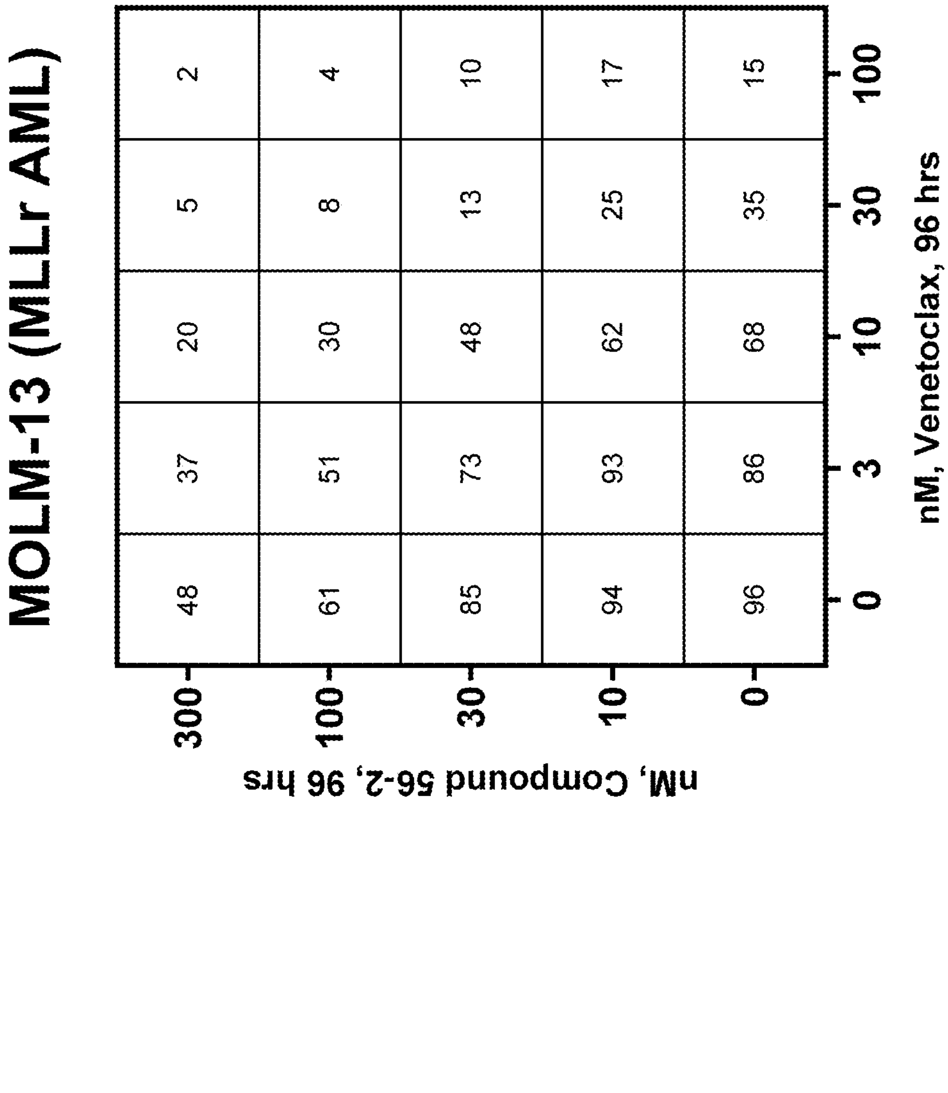
FIG. 5 illustrates a combination signal heatmap (% inhibition of growth signal) for MOLM-13 cells after treatment with a Menin inhibitor (the compound of Example 56-2), a BCL-2 inhibitor (venetoclax), or a combination of a Menin inhibitor (the compound of Example 56-2) and a BCL-2 inhibitor (venetoclax).

In vitro combination benefit was seen in the MOLM-13 cells and cell viability loss was induced with both agents as a monotherapy. FIG. 5 illustrates a combination signal heatmap (% viability) for the MLLr MOLM-13 cells after treatment with Compound 56-2, venetoclax, or Compound 56-2 in combination with venetoclax.

Example 77: Anti-Tumor Effect in NPM1 Mutant AML Patient Derived Disseminated Xenograft Model DFAM-16835 (Compound 56-2 in Combination with Venetoclax)

A study was conducted to evaluate the in vivo efficacy of monotherapy with a Menin inhibitor (Compound 56-2) and combination therapy with a BCL2 inhibitor (venetoclax) and 5-azacytidine in a human NPM1 mutant AML Patient Derived Disseminated Xenograft Model.

A. Materials

Viably frozen DFAM-16835 single cell suspensions from spleens of donor mice were prepared into frozen stock. Flow cytometry antibodies for Ter119 (Miltenyi 130-112-914), mouse CD45 (Miltenyi 130-110-665), and human CD45 (Miltenyi 130-110-634) and Fixable Live Dead Stain (ThermoFisher; #L34963) for disease evaluation via flow cytometry on MACSQuant (Miltenyi). Compound 56-2 was formulated in water at pH 4.5-5 using 1M MSA as pH-adjusting agent at the concentrations up to 100 mg/mL to achieve a uniform suspension and dosed twice daily by oral gavage 10 mL/kg. 5-Azacytidine was formulated in saline at 0.2 mg/mL and dosed twice daily by intraperitoneal injection 5 ml/kg on days 1-5 of treatment. Venetoclax was formulated in 10% ethanol plus 60% Phosal 50 PG (Sigma, MO) plus 30% polyethylene glycol 400 at 5 mg/mL and dosed once daily 2 hrs after Compound 56-2 in the combination group. 5-Azacytidine was formulated in saline at 0.2 mg/mL and dosed twice daily by intraperitoneal injection 5 ml/kg.

Figure 6:
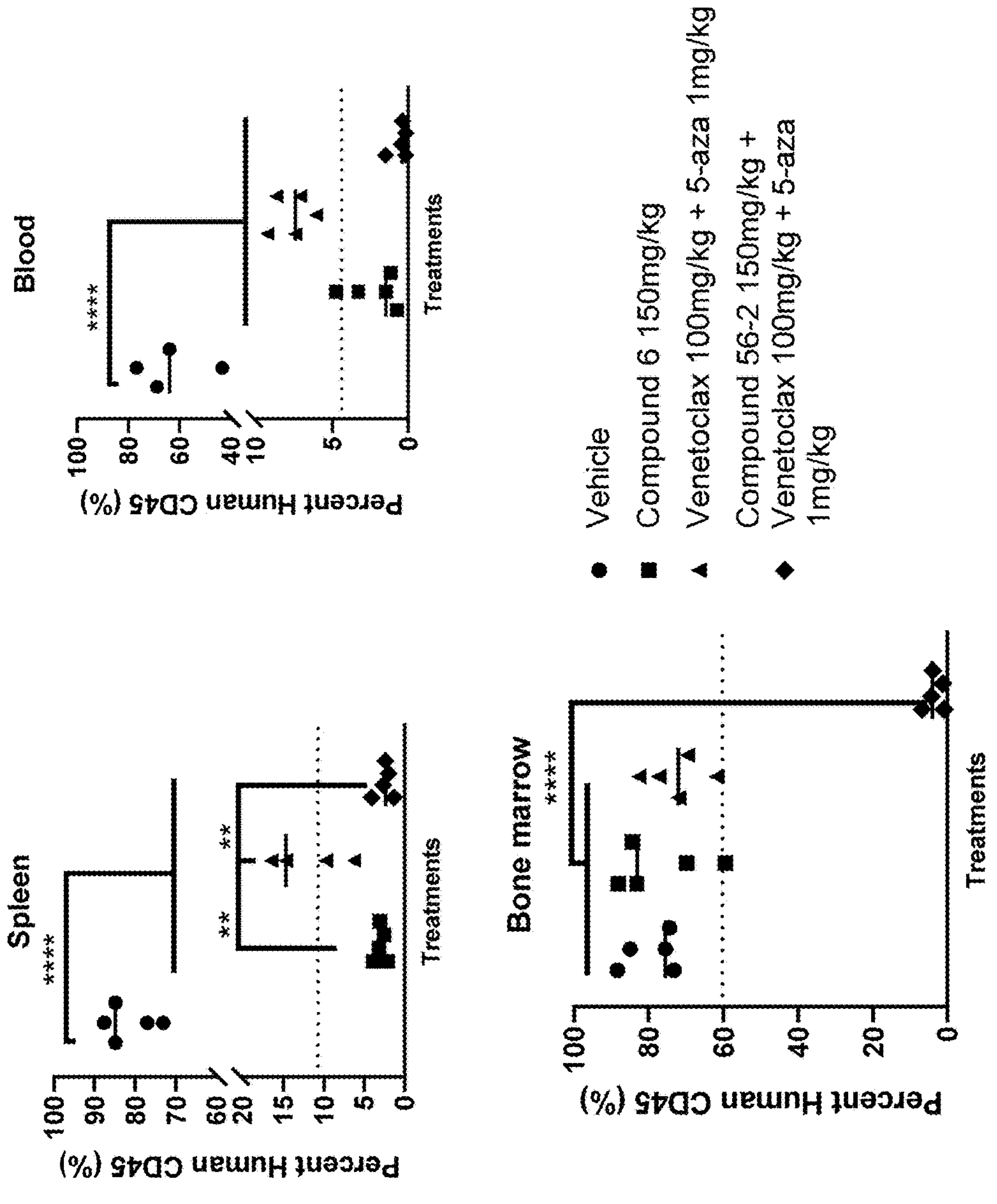
FIG. 6 illustrates the effect of treatment with a combination of a Menin inhibitor (the compound of Example 56-2), a BCL-2 inhibitor (venetoclax), and 5-azacytadine on human CD45 levels in NPM1 mutant AML Patient Derived Disseminated Xenograft Model DFAM-16835.

B. Procedure 1 million DFAM-16835 cells were thawed and 1 million cells implanted via the tail vein. Mice were randomized into groups of 5 when human CD45 levels reached average of 64.2% in the bone marrow of satellite animals. Mice were treated for 21 days with (i) vehicle (water at pH 4.5-5 using 1M MSA), (ii) Compound 56-2 at 150 mg/kg, (iii) venetoclax at 100 mg/kg in combination with 5-azacytidine at 1 mg/kg, or (iv) the combination of Compound 56-2 and venetoclax with 5-azacytidine. Combination group (iv) was dosed as follows: (a) Days 1-5: AM dosing: Compound 56-2 was initially administered, 5-azacytidine was administered 15 minutes later, and venetoclax was administered 2 hours after Compound 56-2; and PM dosing: Compound 56-2 was initially administered and 5-azacytidine was administered 15 minutes later; and (b) Days 6-21: AM dosing: Compound 56-2 was initially administered and venetoclax was administered 2 hours after Compound 56-2; and PM dosing: Compound 56-2 was administered. FIG. 6 further illustrates the effect of treatment with Compound 56-2 and venetoclax and 5-azacytidine in human NPM1 mutant AML Patient Derived Disseminated Xenograft Model DFAM-16835. Data are reported in Table 11.

TABLE 11

| PERCENT HUMAN CD45 | VEHICLE | COMPOUND 56-2 | VENETOCLAX + 5-AZACYTIDINE | COMPOUND 56-2 + VENETOCLAX + 5-AZACYTIDINE |
|---|---|---|---|---|
| Blood | 57.7% | 2.3% | 7.7% | 0.5% |
| Spleen | 81.5% | 3.0% | 14.8% | 2.5% |
| Bone marrow | 79.3% | 77.0% | 72.7% | 3.5% |

Example 78: Protein Degradation Effect in MV-4-11 Cell Line with Compound 56-2

Protein degradation was assessed in human MV-4-11 AML MLLr cell lines treated with Compound 56-2 alone.

A. Materials

An MV-4-11 cell line was passaged at least eight times in SILAC-IMDM (ThermoFisher, #88367), which lacks L-lysine and L-arginine, and supplemented with 10% (v/v) dialyzed FBS (ThermoFisher, #A3382001), [$^{13}C_6$, $^{15}N_2$]-L-lysine, and [$^{13}C_6$, $^{15}N_4$]-L-arginine (Sigma #608041 and #608033) (100 μg/mL each) to achieve "heavy cell" status as determined by LC-MS/MS. Whenever thawed, the "heavy-labelled" cells were passaged at least three times before use in experiments. "Light" medium was prepared by supplementing SILAC-IMDM with 10% (v/v) dialyzed FBS and unlabeled L-arginine and L-lysine (Sigma, #A6969, #L8662). SILAC-IMDM was either supplemented with 300 nM of Compound 56-2 (10 mM solution in DMSO) or the equivalent amounts of DMSO as control. Cells were transferred to "light" media, incubated at 37° C., 5% $CO_2$, and collected at various time points (0 hrs, 1 hrs, 2 hrs, 4.25 hrs, 10.25 hrs, 20.75 hrs, 28.5 hrs, 47 hrs, 72 hrs) by two washes with ice cold PBS and pelleted by centrifugation.

B. Procedure

Cell pellets (approximately $2\times10^5$ cells) were transferred to 96-well plate using cell lysis buffer (4% SDS, 50 mM HEPES pH 7.4, 5 mM TCEP, and 10 mM chloroacetamide) and heated to 95° C. for 10 minutes. Lysed-samples were cleaned up using magnetic bead-assisted-SP3 protocol (Ref.) and the proteome was digested to peptides using LysC (Waco, #12505061) and trypsin enzymes (Promega, #V5111) overnight at 37° C. Peptides were eluted from SP3-beads, desalted (The Nest Group, #HNSS18V) and dried using speed vacuum (Fisher Scientific, #SPD140DDA) before for mass spectrometry analysis. Proteomics data were collected using nano-liquid chromatography and Orbitrap® Exploris480 mass spectrometry system (ThermoFisher Scientific, #VNS10A01 and #BRE725533) coupled to a High-field asymmetric waveform IMS (FAIMS) interface (ThermoFisher Scientific, #OPTON-20068) and by employing parallel reaction monitoring (PRM) data acquisition targeting three unique peptides for Menin ($^{121}$VSDVIWNSLSR$^{131}$, $^{368}$EFFEVAND-VIPNLLK$^{382}$, $^{597}$VSTPSDYTLSFLK$^{609}$). The PRM data were analyzed with Skyline (University of Washington, Seattle, WA., Ref.) using high-selectivity data extraction. Plots were constructed in GraphPad Prism™ using 1st order decay function to yield endogenous degradation and resynthesis.

FIGS. 7-A, 7-B, and 7-C further illustrate the effect of treatment on Menin protein in the human MLLr AML MV-4-11 SILAC cell line. Time is shown horizontally. The heavy and light Menin protein signals are shown vertically for A. DMSO (control) (FIG. 7-A), B. Compound 56-2 (FIG. 7-B), and C. Total Menin protein ("heavy" and "light") signal normalized to DMSO (FIG. 7-C). Data for Compound 56-2 on Menin protein degradation in MLLr AML MV-4-11 SILAC cells is reported in Table 12. The rate at which a "heavy" Menin protein decreases represents its rate of degradation ($k_{deg}$).

TABLE 12

| | DMSO (CONTROL) | COMPOUND 56-2 |
|---|---|---|
| $k_{deg}$ (1/h) | 0.052 | 0.14 |

REFERENCES

Pulse SILAC: Doherty M K, Hammond D E, Clague M J, Gaskell S J, Beynon R J (2009) Turnover of the human proteome: determination of protein intracellular stability by dynamic SILAC. J Proteome Res 8:104-112.

SP3: Hughes, C. S., Moggridge, S., Müller, T. et al. Single-pot, solid-phase-enhanced sample preparation for proteomics experiments. *Nat Protoc* 14, 68-85 (2019).

Skyline: MacLean, B. et al. Skyline: An open-source document editor for creating and analyzing targeted proteomics experiments. *Bioinformatics* 26 (7), 966-968 (2010).

IX. Further Embodiments

Embodiment 1: A compound having the structure of Formula (I):

(I)

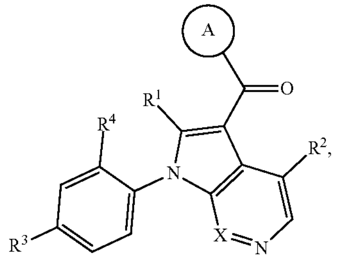

or a pharmaceutically acceptable salt thereof, wherein:

$R^1$ is selected from the group consisting of hydrogen and methyl;

$R^2$ is hydrogen or fluoro;

$R^3$ is hydrogen or fluoro;

$R^4$ is selected from the group consisting of:

(a) —C(O)$NR^5R^6$;

(b) phenyl optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and (c) 5- or 6-membered ring heteroaryl having one, two, or three ring atoms independently selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

$R^5$ and $R^6$ are independently selected from $C_{1-4}$-alkyl and halo-$C_{1-4}$-alkyl; or $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl;

X is —C($R^9$)— or —N—;

$R^9$ is selected from the group consisting of hydrogen, fluorine, and methyl;

A is selected from the group consisting of:

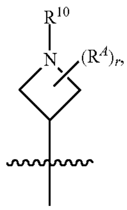 , 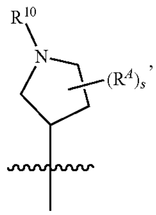 , 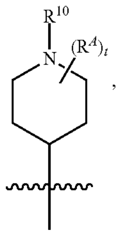 , and

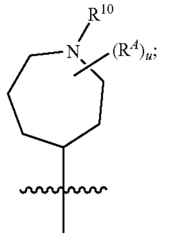 ;

each $R^A$ substituent is optionally and independently selected from the group consisting of fluoro and $C_{1-4}$-alkyl;

r is 0, 1, or 2;

s is 0, 1, 2, or 3;

t is 0, 1, 2, 3, or 4;

u is 0, 1, 2, 3, 4, or 5;

$R^{10}$ is selected from the group consisting of $C_{1-10}$-alkyl, —$CH_2R^{11}$, or —C(O)$R^{12}$; wherein the $C_{1-10}$-alkyl is substituted with one or more —$NR^{13}R^{14}$.

$R^{11}$ is cyclohexyl optionally substituted with one or more substituents independently selected from the group consisting of $C_{1-4}$-alkyl, —$NR^{15}R^{16}$, and —N($R^{17}$)S(O)$_2R^{18}$;

$R^{12}$ is 5- to 10-membered ring heterocyclyl, wherein the heterocyclyl: (i) is a saturated or partially saturated monocyclic ring, bicyclic ring, or spirocyclic ring system, (ii) has one or two nitrogen ring atoms with the remaining ring atoms being carbon, and (iii) is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —N($R^{22}$)S(O)$_2R^{23}$;

$R^{13}$ and $R^{14}$ are independently selected from the group consisting of $C_{1-6}$-alkyl and $C_{1-6}$alkoxy-$C_{1-6}$-alkyl; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

Embodiment 2: The compound of Embodiment 1, or a pharmaceutically acceptable salt thereof, wherein the compound has the structure of Formula (I-A):

(I-A)

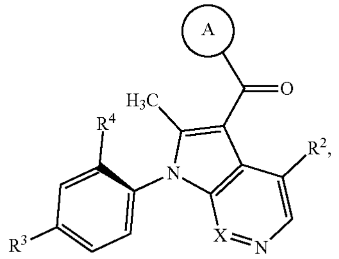

and wherein $R^2$, $R^3$, $R^4$, and A are as defined in Embodiment 1.

Embodiment 3: The compound of Embodiment 1 or Embodiment 2, or a pharmaceutically acceptable salt thereof, wherein $R^3$ is hydrogen.

Embodiment 4: The compound of Embodiment 1 or Embodiment 2, or a pharmaceutically acceptable salt thereof, wherein $R^3$ is fluoro.

Embodiment 5: The compound of any of Embodiments 1 to 4, or a pharmaceutically acceptable salt thereof, wherein X is —C($R^9$)—.

Embodiment 6: The compound of Embodiment 5, or a pharmaceutically acceptable salt thereof, wherein $R^9$ is hydrogen.

Embodiment 7: The compound of Embodiment 5, or a pharmaceutically acceptable salt thereof, wherein $R^9$ is fluoro.

Embodiment 8: The compound of Embodiment 5, or a pharmaceutically acceptable salt thereof, wherein $R^9$ is methyl.

Embodiment 9: The compound of any of Embodiments 1 to 4, or a pharmaceutically acceptable salt thereof, wherein X is —N—.

Embodiment 10: The compound of any of Embodiments 1 to 4, or a pharmaceutically acceptable salt thereof, wherein X is —C($R^9$)— or —N—, and $R^9$ is hydrogen or fluoro.

Embodiment 11: The compound of any of Embodiments 1 to 10, or a pharmaceutically acceptable salt thereof, wherein $R^2$ is hydrogen.

Embodiment 12: The compound of any of Embodiments 1 to 10, or a pharmaceutically acceptable salt thereof, wherein $R^2$ is fluoro.

Embodiment 13: The compound of any of Embodiments 1 to 12, or a pharmaceutically acceptable salt thereof, wherein $R^1$ is hydrogen.

Embodiment 14: The compound of any of Embodiments 1 to 12, or a pharmaceutically acceptable salt thereof, wherein $R^1$ is methyl.

Embodiment 15: The compound of any of Embodiments 1 to 14, or a pharmaceutically acceptable salt thereof, wherein $R^4$ is —C(O)NR$^5$R$^6$.

Embodiment 16: The compound of Embodiment 15, or a pharmaceutically acceptable salt thereof, wherein $R^5$ and $R^6$ are independently selected from $C_{1-4}$-alkyl and halo-$C_{1-4}$-alkyl.

Embodiment 17: The compound of Embodiment 15, or a pharmaceutically acceptable salt thereof, wherein $R^5$ and $R^6$ are independently selected from $C_{1-4}$-alkyl.

Embodiment 18: The compound of Embodiment 17 or a pharmaceutically acceptable salt thereof, wherein at least one of $R^5$ and $R^6$ is methyl.

Embodiment 19: The compound of Embodiment 17, or a pharmaceutically acceptable salt thereof, wherein at least one of $R^5$ and $R^6$ is ethyl.

Embodiment 20: The compound of Embodiment 17, or a pharmaceutically acceptable salt thereof, wherein at least one of $R^5$ and $R^6$ is isopropyl.

Embodiment 21: The compound of Embodiment 17, or a pharmaceutically acceptable salt thereof, wherein $R^5$ and $R^6$ are each ethyl.

Embodiment 22: The compound of Embodiment 17, or a pharmaceutically acceptable salt thereof, wherein one of $R^5$ and $R^6$ is methyl and the other is isopropyl.

Embodiment 23: The compound of Embodiment 17, or a pharmaceutically acceptable salt thereof, wherein one of $R^5$ and $R^6$ is ethyl and the other is isopropyl.

Embodiment 24: The compound of Embodiment 17, or a pharmaceutically acceptable salt thereof, wherein $R^5$ and $R^6$ are each isopropyl.

Embodiment 25: The compound of Embodiment 17, or a pharmaceutically acceptable salt thereof, wherein $R^5$ and $R^6$ are independently selected from ethyl and isopropyl.

Embodiment 26: The compound of Embodiment 15, or a pharmaceutically acceptable salt thereof, wherein one of $R^5$ and $R^6$ is $C_{1-4}$-alkyl and the other is halo-$C_{1-4}$-alkyl.

Embodiment 27: The compound of Embodiment 26, or a pharmaceutically acceptable salt thereof, wherein one of $R^5$ and $R^6$ is methyl.

Embodiment 28: The compound of Embodiment 26, or a pharmaceutically acceptable salt thereof, wherein one of $R^5$ and $R^6$ is ethyl.

Embodiment 29: The compound of Embodiment 26, or a pharmaceutically acceptable salt thereof, wherein one of $R^5$ and $R^6$ is isopropyl.

Embodiment 30: The compound of Embodiment 26, or a pharmaceutically acceptable salt thereof, wherein one of $R^5$ and $R^6$ is trifluoroethyl.

Embodiment 31: The compound of Embodiment 26, or a pharmaceutically acceptable salt thereof, wherein one of $R^5$ and $R^6$ is trifluoroisopropyl.

Embodiment 32: The compound of Embodiment 26, or a pharmaceutically acceptable salt thereof, wherein one of $R^5$ and $R^6$ is ethyl and the other is trifluoroethyl.

Embodiment 33: The compound of Embodiment 26, or a pharmaceutically acceptable salt thereof, wherein one of $R^5$ and $R^6$ is ethyl and the other is trifluoroisopropyl.

Embodiment 34: The compound of Embodiment 26, or a pharmaceutically acceptable salt thereof, wherein one of $R^5$ and $R^6$ is isopropyl and the other is trifluoroethyl.

Embodiment 35: The compound of Embodiment 26, or a pharmaceutically acceptable salt thereof, wherein one of $R^5$ and $R^6$ is isopropyl and the other is trifluoroisopropyl.

Embodiment 36: The compound of Embodiment 26, or a pharmaceutically acceptable salt thereof, wherein $R^5$ is selected from ethyl and isopropyl, and $R^6$ is selected from trifluoroethyl and trifluoroisopropyl.

Embodiment 37: The compound of Embodiment 15, or a pharmaceutically acceptable salt thereof, wherein $R^5$ and $R^6$ are independently selected from halo-$C_{1-4}$-alkyl.

Embodiment 38: The compound of Embodiment 37, or a pharmaceutically acceptable salt thereof, wherein $R^5$ and $R^6$ are trifluoro-$C_{1-4}$-alkyl.

Embodiment 39: The compound of Embodiment 15, or a pharmaceutically acceptable salt thereof, wherein $R^5$ and $R^6$ are independently selected from the group consisting of ethyl, isopropyl, trifluoroethyl, and trifluoroisopropyl.

Embodiment 40: The compound of any of Embodiments 1 to 14, or a pharmaceutically acceptable salt thereof, wherein $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

Embodiment 41: The compound of Embodiment 40, or a pharmaceutically acceptable salt thereof, wherein the 5- to 7-membered ring heterocyclyl is selected from the group consisting of optionally substituted pyrrolidinyl, piperidinyl, and morpholinyl.

Embodiment 42: The compound of Embodiment 40 or 41, or a pharmaceutically acceptable salt thereof, wherein the 5- to 7-membered ring heterocyclyl is optionally substituted with one or two $C_{1-4}$-alkyl.

Embodiment 43: The compound of Embodiment 40 or 41, or a pharmaceutically acceptable salt thereof, wherein the 5- to 7-membered ring heterocyclyl is optionally substituted with one or two methyl.

Embodiment 44: The compound of Embodiment 40 or 41, or a pharmaceutically acceptable salt thereof, wherein the 5- to 7-membered ring heterocyclyl is optionally substituted with one or two halo-$C_{1-4}$-alkyl.

Embodiment 45: The compound of Embodiment 40 or 41, or a pharmaceutically acceptable salt thereof, wherein the 5- to 7-membered ring heterocyclyl is optionally substituted with one or two trifluoromethyl.

Embodiment 46: The compound of any of Embodiments 40 to 45, or a pharmaceutically acceptable salt thereof, wherein the 5- to 7-membered ring heterocyclyl is optionally substituted pyrrolidinyl.

Embodiment 47: The compound of Embodiment 46, or a pharmaceutically acceptable salt thereof, wherein the pyrrolidinyl is substituted with one or two methyl.

Embodiment 48: The compound of any of Embodiments 40 to 45, or a pharmaceutically acceptable salt thereof, wherein the 5- to 7-membered ring heterocyclyl is optionally substituted piperidinyl.

Embodiment 49: The compound of Embodiment 48, or a pharmaceutically acceptable salt thereof, wherein the piperidinyl is substituted with one or two methyl.

Embodiment 50: The compound of any of Embodiments 40 to 45, or a pharmaceutically acceptable salt thereof, wherein the 5- to 7-membered ring heterocyclyl is optionally substituted morpholinyl.

Embodiment 51: The compound of Embodiment 50, or a pharmaceutically acceptable salt thereof, wherein the morpholinyl is substituted with one or two methyl.

Embodiment 52: The compound of any of Embodiments 1 to 14, or a pharmaceutically acceptable salt thereof, wherein $R^4$ is phenyl optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl.

Embodiment 53: The compound of Embodiment 52, or a pharmaceutically acceptable salt thereof, wherein $R^4$ is phenyl optionally substituted with one to three substituents independently selected from fluoro, cyano, $C_{1-4}$-alkyl, and halo-$C_{1-4}$-alkyl.

Embodiment 54: The compound of Embodiment 52, or a pharmaceutically acceptable salt thereof, wherein $R^4$ is phenyl optionally substituted with one to three fluoro.

Embodiment 55: The compound of Embodiment 52, or a pharmaceutically acceptable salt thereof, wherein $R^4$ is phenyl optionally substituted with one to three cyano.

Embodiment 56: The compound of Embodiment 52, or a pharmaceutically acceptable salt thereof, wherein $R^4$ is phenyl optionally substituted with one to three $C_{1-4}$-alkyl.

Embodiment 57: The compound of Embodiment 52, or a pharmaceutically acceptable salt thereof, wherein $R^4$ is phenyl optionally substituted with one to three halo-$C_{1-4}$-alkyl.

Embodiment 58: The compound of Embodiment 52, or a pharmaceutically acceptable salt thereof, wherein $R^4$ is phenyl optionally substituted with one to three $C_{3-4}$-cycloalkyl.

Embodiment 59: The compound of Embodiment 52, or a pharmaceutically acceptable salt thereof, wherein $R^4$ is phenyl optionally substituted with one to three halo-$C_{3-4}$-cycloalkyl.

Embodiment 60: The compound of any of Embodiments 1 to 14, or a pharmaceutically acceptable salt thereof, wherein $R^4$ is 5- or 6-membered ring heteroaryl having one, two, or three ring atoms independently selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl.

Embodiment 61: The compound of Embodiment 60, or a pharmaceutically acceptable salt thereof, wherein $R^4$ is 5-membered ring heteroaryl having one or two ring atoms independently selected from nitrogen, oxygen, and sulfur with the remaining ring atoms being carbon, wherein the heteroaryl is optionally substituted with one to three substituents independently selected from the group consisting of fluoro, $C_{1-4}$-alkyl, halo-$C_{1-4}$-alkyl, $C_{3-4}$-cycloalkyl, and halo-$C_{3-4}$-cycloalkyl.

Embodiment 62: The compound of Embodiment 60 or a pharmaceutically acceptable salt thereof, wherein $R^4$ is 6-membered ring heteroaryl having one or two ring atoms independently selected from nitrogen, oxygen, and sulfur with the remaining ring atoms being carbon, wherein the heteroaryl is optionally substituted with one to three substituents independently selected from the group consisting of fluoro, $C_{1-4}$-alkyl, halo-$C_{1-4}$-alkyl, $C_{3-4}$-cycloalkyl, and halo-$C_{3-4}$-cycloalkyl.

Embodiment 63: The compound of Embodiment 60, or a pharmaceutically acceptable salt thereof, wherein the 5- or 6-membered ring heteroaryl is selected from the group consisting of optionally substituted pyrazolyl, imidazolyl, thiazolyl, isothiazolyl, pyridinyl, pyrimidinyl, pyrazinyl, and pyridazinyl.

Embodiment 64: The compound of Embodiment 60, or a pharmaceutically acceptable salt thereof, wherein the heteroaryl is selected from the group consisting of optionally substituted pyrazolyl, thiazolyl, pyridinyl, and pyrimidinyl.

Embodiment 65: The compound of Embodiment 60, or a pharmaceutically acceptable salt thereof, wherein the heteroaryl is optionally substituted pyrazolyl.

Embodiment 66: The compound of Embodiment 60, or a pharmaceutically acceptable salt thereof, wherein the heteroaryl is optionally substituted thiazolyl.

Embodiment 67: The compound of Embodiment 60, or a pharmaceutically acceptable salt thereof, wherein the heteroaryl is optionally substituted pyridinyl.

Embodiment 68: The compound of Embodiment 60, or a pharmaceutically acceptable salt thereof, wherein the heteroaryl is optionally substituted pyrimidinyl.

Embodiment 69: The compound of any of Embodiments 60 to 68, or a pharmaceutically acceptable salt thereof, wherein the heteroaryl is optionally substituted with one to three substituents independently selected from the group consisting of $C_{1-4}$-alkyl, halo-$C_{1-4}$-alkyl, and $C_{3-4}$-cycloalkyl.

Embodiment 70: The compound of any of Embodiments 60 to 68, or a pharmaceutically acceptable salt thereof, wherein the heteroaryl is optionally substituted with one or two substituents independently selected from the group consisting of $C_{1-4}$-alkyl and halo-$C_{1-4}$-alkyl.

Embodiment 71: The compound of any of Embodiments 60 to 68, or a pharmaceutically acceptable salt thereof, wherein the heteroaryl is substituted with one or two fluoro.

Embodiment 72: The compound of any of Embodiments 60 to 68, or a pharmaceutically acceptable salt thereof, wherein the heteroaryl is substituted with one or two cyano.

Embodiment 73: The compound of any of Embodiments 60 to 68, or a pharmaceutically acceptable salt thereof, wherein the heteroaryl is substituted with one or two $C_{1-4}$-alkyl.

Embodiment 74: The compound of any of Embodiments 60 to 68, or a pharmaceutically acceptable salt thereof, wherein the heteroaryl is substituted with one or two $C_{1-3}$-alkyl.

Embodiment 75: The compound of any of Embodiments 60 to 68, or a pharmaceutically acceptable salt thereof, wherein the heteroaryl is substituted with methyl and isopropyl.

Embodiment 76: The compound of any of Embodiments 60 to 68, or a pharmaceutically acceptable salt thereof, wherein the heteroaryl is substituted with one or two halo-$C_{1-4}$-alkyl.

Embodiment 77: The compound of any of Embodiments 60 to 68, or a pharmaceutically acceptable salt thereof, wherein the heteroaryl is substituted with one or two fluoropropyl.

Embodiment 78: The compound of any of Embodiments 60 to 68, or a pharmaceutically acceptable salt thereof, wherein the heteroaryl is substituted with one or two $C_{3-4}$-cycloalkyl.

Embodiment 79: The compound of any of Embodiments 60 to 68, or a pharmaceutically acceptable salt thereof, wherein the heteroaryl is substituted with one or two cyclopropyl.

Embodiment 80: The compound of any of Embodiments 60 to 68, or a pharmaceutically acceptable salt thereof, wherein the heteroaryl is substituted with one or two halo-$C_{3-4}$-cycloalkyl.

Embodiment 81: The compound of any of Embodiments 1 to 14, or a pharmaceutically acceptable salt thereof, wherein:

$R^4$ is selected from the group consisting of:

(a) —C(O)NR$^5$R$^6$; and (b) 5- or 6-membered ring heteroaryl having one, two, or three ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- to 7-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

Embodiment 82: The compound of any of Embodiments 1 to 14, or a pharmaceutically acceptable salt thereof, wherein:

$R^4$ is selected from the group consisting of:

(a) —C(O)$NR^5R^6$; and (b) 5-membered ring heteroaryl having one or two ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- or 6-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

Embodiment 83: The compound of any of Embodiments 1 to 14, or a pharmaceutically acceptable salt thereof, wherein:

$R^4$ is selected from the group consisting of:

(a) —C(O)$NR^5R^6$; and (b) 6-membered ring heteroaryl having one or two ring atoms selected from nitrogen, oxygen, and sulfur with the remaining ring atoms being carbon, wherein the heteroaryl is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and $R^5$ and $R^6$ are independently selected from $C_{1-4}$-alkyl and halo-$C_{1-4}$-alkyl; or $R^5$ and $R^6$, together with the nitrogen atom to which they are attached, form a 5- or 6-membered ring heterocyclyl, wherein the heterocyclyl: (i) is a saturated monocyclic ring, (ii) has one or two ring atoms independently selected from nitrogen and oxygen with the remaining ring atoms being carbon, and (iii) is optionally substituted with one to three substituents independently selected from the group consisting of $C_{1-4}$-alkyl and halo-$C_{1-4}$-alkyl.

Embodiment 84: The compound of any of Embodiments 1 to 83, or a pharmaceutically acceptable salt thereof, wherein $R^A$ is fluoro.

Embodiment 85: The compound of any of Embodiments 1 to 83, or a pharmaceutically acceptable salt thereof, wherein $R^A$ is $C_{1-4}$-alkyl.

Embodiment 86: The compound of any of Embodiments 1 to 83, or a pharmaceutically acceptable salt thereof, wherein $R^A$ is methyl.

Embodiment 87: The compound of any of Embodiments 1 to 86, or a pharmaceutically acceptable salt thereof, wherein r, s, t, and u are independently 0 or 1.

Embodiment 88: The compound of any of Embodiments 1 to 86, or a pharmaceutically acceptable salt thereof, wherein r, s, t, and u are 1.

Embodiment 89: The compound of any of Embodiments 1 to 86, or a pharmaceutically acceptable salt thereof, wherein r, s, t, and u are 1, and $R^A$ is methyl.

Embodiment 90: The compound of any of Embodiments 1 to 83, or a pharmaceutically acceptable salt thereof, wherein r, s, t, and u are 0.

Embodiment 91: The compound of any of Embodiments 1 to 90, or a pharmaceutically acceptable salt thereof, wherein A is selected from the group consisting of:

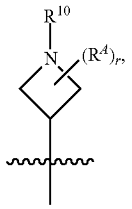
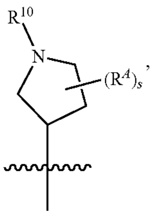
and
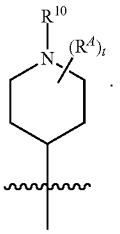

Embodiment 92: The compound of any of Embodiments 1 to 90, or a pharmaceutically acceptable salt thereof, wherein A is selected from the group consisting of:

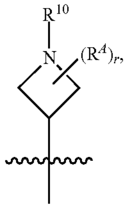
and
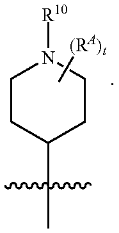

Embodiment 93: The compound of any of Embodiments 1 to 90, or a pharmaceutically acceptable salt thereof, wherein A is selected from the group consisting of:

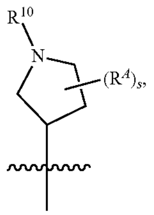
and
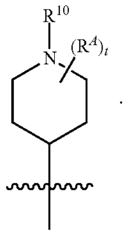

Embodiment 94: The compound of any of Embodiments 1 to 90, or a pharmaceutically acceptable salt thereof, wherein A is:

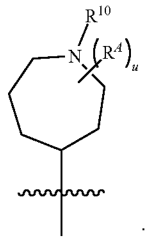

Embodiment 95: The compound of any of Embodiments 1 to 90, or a pharmaceutically acceptable salt thereof, wherein A is:

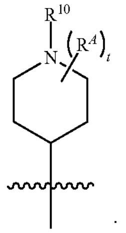

Embodiment 96: The compound of any of Embodiments 1 to 90, or a pharmaceutically acceptable salt thereof, wherein A is:

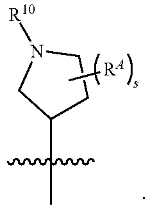

Embodiment 97: The compound of any of Embodiments 1 to 90, or a pharmaceutically acceptable salt thereof, wherein A is:

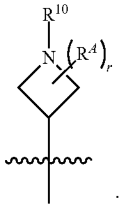

Embodiment 98: The compound of any of Embodiments 1 to 97, or a pharmaceutically acceptable salt thereof, wherein $R^{10}$ is $C_{1-10}$-alkyl substituted with one or more —$NR^{13}R^{14}$; and $R^{13}$ and $R^{14}$ are independently selected from the group consisting of $C_{1-6}$-alkyl and $C_{1-6}$-alkoxy-$C_{1-6}$-alkyl.

Embodiment 99: The compound of Embodiment 98, or a pharmaceutically acceptable salt thereof, wherein $R^{10}$ is $C_{1-10}$-alkyl substituted with —$NR^{13}R^{14}$; and $R^{13}$ and $R^{14}$ are independently selected from the group consisting of $C_{1-6}$-alkyl and $C_{1-6}$-alkoxy-$C_{1-6}$-alkyl.

Embodiment 100: The compound of Embodiment 98, or a pharmaceutically acceptable salt thereof, wherein $R^{10}$ is $C_{1-10}$-alkyl substituted with —$NR^{13}R^{14}$; $R^{13}$ is $C_{1-3}$-alkyl; and $R^{14}$ is $C_{1-3}$-alkoxy-$C_{1-3}$-alkyl.

Embodiment 101: The compound of Embodiment 98, or a pharmaceutically acceptable salt thereof, wherein $R^{10}$ is $C_{1-10}$-alkyl substituted with —$NR^{13}R^{14}$; $R^{13}$ is methyl; and $R^{14}$ is methoxyethyl.

Embodiment 102: The compound of any of Embodiments 1 to 97, or a pharmaceutically acceptable salt thereof, wherein $R^{10}$ is —$CH_2R^{11}$; $R^{11}$ is cyclohexyl optionally substituted with one or more substituents independently selected from the group consisting of $C_{1-4}$-alkyl, —$NR^{15}R^{16}$, and —$N(R^{17})S(O)_2R^{18}$; and $R^{15}$, $R^{16}$, $R^{17}$, and $R^{18}$ are independently selected from the group consisting of hydrogen and $C_{1-4}$-alkyl.

Embodiment 103: The compound of Embodiment 102, or a pharmaceutically acceptable salt thereof, wherein $R^{11}$ is cyclohexyl optionally substituted with one or more $C_{1-4}$-alkyl.

Embodiment 104: The compound of Embodiment 102, or a pharmaceutically acceptable salt thereof, wherein $R^{11}$ is cyclohexyl optionally substituted with one or more methyl.

Embodiment 105: The compound of Embodiment 102, or a pharmaceutically acceptable salt thereof, wherein $R^{11}$ is cyclohexyl optionally substituted with one or more —$NR^{15}R^{16}$; and $R^{15}$ and $R^{16}$ are independently selected from the group consisting of hydrogen and $C_{1-4}$-alkyl.

Embodiment 106: The compound of Embodiment 102, or a pharmaceutically acceptable salt thereof, wherein $R^{11}$ is cyclohexyl optionally substituted with one or more —$NR^{15}R^{16}$; and $R^{15}$ and $R^{16}$ are independently selected from the group consisting of hydrogen and methyl.

Embodiment 107: The compound of Embodiment 102, or a pharmaceutically acceptable salt thereof, wherein $R^{11}$ is cyclohexyl optionally substituted with one or more —$N(R^{17})S(O)_2R^{18}$; and $R^{17}$ and $R^{18}$ are independently selected from the group consisting of hydrogen and $C_{1-4}$-alkyl.

Embodiment 108: The compound of Embodiment 102, or a pharmaceutically acceptable salt thereof, wherein $R^{11}$ is cyclohexyl optionally substituted with one or more —$N(R^{17})S(O)_2R^{18}$; and $R^{17}$ is hydrogen and $R^{18}$ is $C_{1-4}$-alkyl.

Embodiment 109: The compound of Embodiment 102, or a pharmaceutically acceptable salt thereof, wherein $R^{11}$ is cyclohexyl optionally substituted with one or more —$N(R^{17})S(O)_2R^{18}$; and $R^{17}$ is hydrogen and $R^{18}$ is methyl.

Embodiment 110: The compound of any of Embodiments 102 to 109, or a pharmaceutically acceptable salt thereof, wherein the $R^{11}$ cyclohexyl is substituted at the para position.

Embodiment 111: The compound of any of Embodiments 1 to 97, or a pharmaceutically acceptable salt thereof, wherein:

$R^{10}$ is —$C(O)R^{12}$;

$R^{12}$ is 5- to 10-membered ring heterocyclyl, wherein the heterocyclyl: (i) is a saturated or partially saturated monocyclic ring, bicyclic ring, or spirocyclic ring system, (ii) has one or two nitrogen ring atoms with the remaining ring atoms being carbon, and (iii) is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and $R^{19}$, $R^{20}$, $R^{21}$, $R^{22}$, and $R^{23}$ are independently selected from the group consisting of hydrogen and $C_{1-4}$-alkyl.

Embodiment 112: The compound of Embodiment 111, or a pharmaceutically acceptable salt thereof, wherein the $R^{12}$ heterocyclyl comprises a nitrogen ring atom adjacent to a carbon ring atom bonded to the carbonyl of the $R^{10}$ substituent.

Embodiment 113: The compound of Embodiment 111 or 112, or a pharmaceutically acceptable salt thereof, wherein the $R^{12}$ heterocyclyl is an optionally substituted, saturated or partially saturated monocyclic ring.

Embodiment 114: The compound of Embodiment 113, or a pharmaceutically acceptable salt thereof, wherein the $R^{12}$ heterocyclyl is an optionally substituted saturated monocyclic ring.

Embodiment 115: The compound of Embodiment 111 or 112, or a pharmaceutically acceptable salt thereof, wherein the $R^{12}$ heterocyclyl is an optionally substituted, saturated or partially saturated bicyclic ring.

Embodiment 116: The compound of Embodiment 115, or a pharmaceutically acceptable salt thereof, wherein the $R^{12}$ heterocyclyl is an optionally substituted saturated bicyclic ring.

Embodiment 117: The compound of Embodiment 115 or 116, or a pharmaceutically acceptable salt thereof, wherein the bicyclic ring is a fused bicyclic ring.

Embodiment 118: The compound of Embodiment 115 or 116, or a pharmaceutically acceptable salt thereof, wherein the bicyclic ring is a bridged bicyclic ring.

Embodiment 119: The compound of Embodiment 111 or 112, or a pharmaceutically acceptable salt thereof, wherein the $R^{12}$ heterocyclyl is an optionally substituted, saturated or partially saturated spirocyclic ring system.

Embodiment 120: The compound of Embodiment 119, or a pharmaceutically acceptable salt thereof, wherein the $R^{12}$ heterocyclyl is an optionally substituted saturated spirocyclic ring system.

Embodiment 121: The compound of Embodiment 111 or 112, or a pharmaceutically acceptable salt thereof, wherein $R^{12}$ is optionally substituted 5-membered ring heterocyclyl.

Embodiment 122: The compound of Embodiment 111 or 112, or a pharmaceutically acceptable salt thereof, wherein $R^{12}$ is optionally substituted 6-membered ring heterocyclyl.

Embodiment 123: The compound of Embodiment 111 or 112, or a pharmaceutically acceptable salt thereof, wherein $R^{12}$ is optionally substituted 7-membered ring heterocyclyl.

Embodiment 124: The compound of Embodiment 111 or 112, or a pharmaceutically acceptable salt thereof, wherein $R^{12}$ is optionally substituted 8-membered ring heterocyclyl.

Embodiment 125: The compound of Embodiment 111 or 112, or a pharmaceutically acceptable salt thereof, wherein $R^{12}$ is optionally substituted 9-membered ring heterocyclyl.

Embodiment 126: The compound of Embodiment 111 or 112, or a pharmaceutically acceptable salt thereof, wherein $R^{12}$ is optionally substituted 10-membered ring heterocyclyl.

Embodiment 127: The compound of Embodiment 111, or a pharmaceutically acceptable salt thereof:

wherein the $R^{12}$ heterocyclyl is selected from the group consisting of:

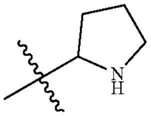 , 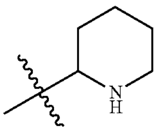 , 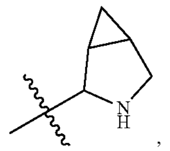 ,

-continued

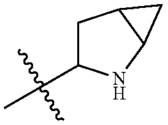 , 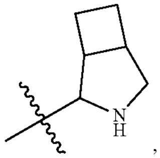 , 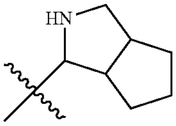 ,

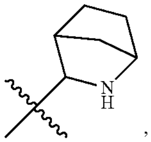 , 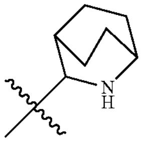 , 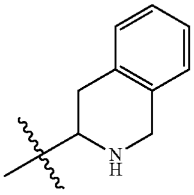 ,

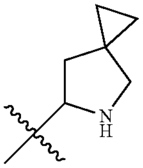 , and 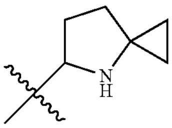 ;

and wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 128: The compound of Embodiment 111, or a pharmaceutically acceptable salt thereof:

wherein the $R^{12}$ heterocyclyl is selected from the group consisting of:

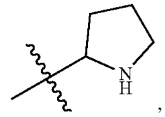 [SMILES: *C1CCCN1] , 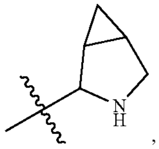 [SMILES: *C1NCC2CC21] , 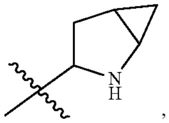 [SMILES: *C1CC2CC2N1] ,

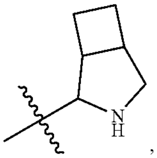 , 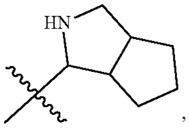 , 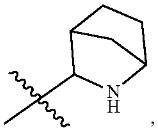 ,

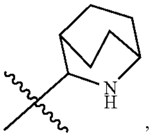 , 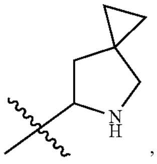 , and 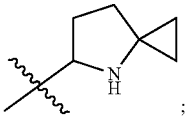 ;

and wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 129: The compound of Embodiment 111, or a pharmaceutically acceptable salt thereof:

wherein the $R^{12}$ heterocyclyl is selected from the group consisting of:

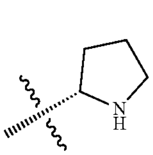
,
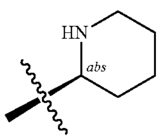
,
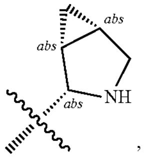
,
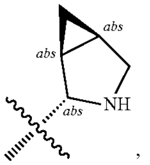
,
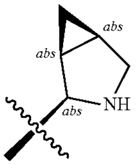
,
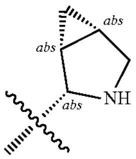
,
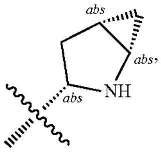
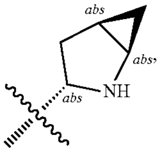
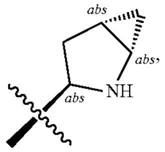
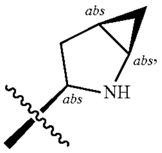
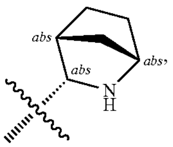
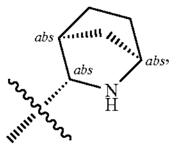
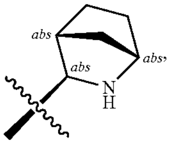
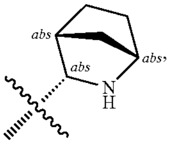
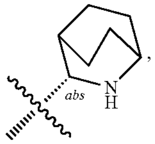
,
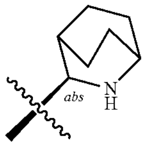
,
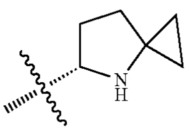
,
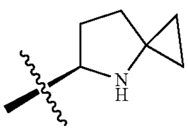
,
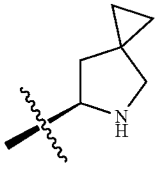
,
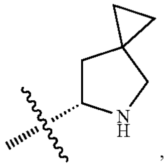
,
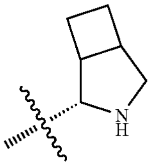
,
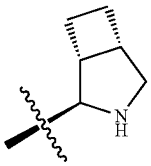
,
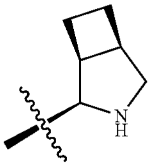
,
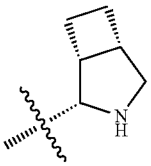
, and
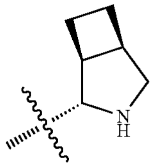
;

and;

wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 130: The compound of any of Embodiments 127 to 129, or a pharmaceutically acceptable salt thereof, wherein the optionally substituted $R^{12}$ heterocyclyl is a monocyclic ring.

Embodiment 131: The compound of any of Embodiments 127 to 129, or a pharmaceutically acceptable salt thereof, wherein the optionally substituted $R^{12}$ heterocyclyl is a fused bicyclic ring.

Embodiment 132: The compound of any of Embodiments 127 to 129, or a pharmaceutically acceptable salt thereof, wherein the optionally substituted $R^{12}$ heterocyclyl is a bridged bicyclic ring.

Embodiment 133: The compound of any of Embodiments 127 to 129, or a pharmaceutically acceptable salt thereof, wherein the optionally substituted $R^{12}$ heterocyclyl is a spirocyclic ring system.

Embodiment 134: The compound of Embodiment 127, or a pharmaceutically acceptable salt thereof, wherein the $R^{12}$ heterocyclyl is:

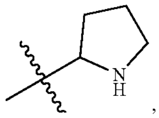
, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 135: The compound of Embodiment 127, or a pharmaceutically acceptable salt thereof, wherein the $R^{12}$ heterocyclyl is:

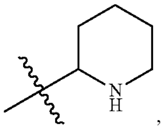
, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 136: The compound of Embodiment 127, or a pharmaceutically acceptable salt thereof, wherein the $R^{12}$ heterocyclyl is:

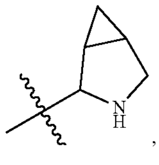
, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 137: The compound of Embodiment 127, or a pharmaceutically acceptable salt thereof, wherein the $R^{12}$ heterocyclyl is:

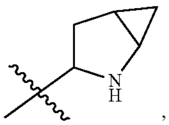

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 138: The compound of Embodiment 127, or a pharmaceutically acceptable salt thereof, wherein the $R^{12}$ heterocyclyl is:

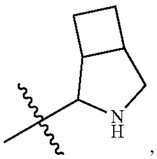 [SMILES: *C1NCC2CCC21]

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 139: The compound of Embodiment 127, or a pharmaceutically acceptable salt thereof, wherein the $R^{12}$ heterocyclyl is:

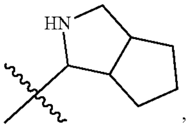 [SMILES: *C1NCC2CCCC21]

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 140: The compound of Embodiment 127, or a pharmaceutically acceptable salt thereof, wherein the $R^{12}$ heterocyclyl is:

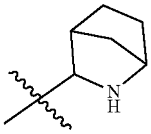

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 141: The compound of Embodiment 127, or a pharmaceutically acceptable salt thereof, wherein the $R^{12}$ heterocyclyl is:

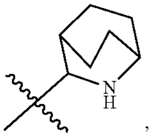 [SMILES: *C1NC2CCC1CC2]

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 142: The compound of Embodiment 127, or a pharmaceutically acceptable salt thereof, wherein the $R^{12}$ heterocyclyl is:

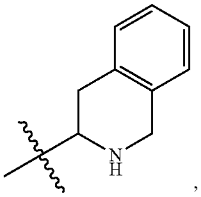 [SMILES: *C1Cc2ccccc2CN1]

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 143: The compound of Embodiment 127, or a pharmaceutically acceptable salt thereof, wherein the $R^{12}$ heterocyclyl is:

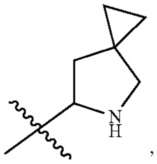 [SMILES: *C1CC2(CC2)CN1]

, and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 144: The compound of Embodiment 127, or a pharmaceutically acceptable salt thereof, wherein the $R^{12}$ heterocyclyl is:

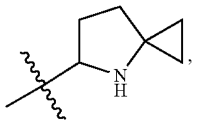 [SMILES: *C1CCC2(CC2)N1]

and is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; wherein $R^{19}$, $R^{20}$, $R^{21}$, $R^{22}$, and $R^{23}$ are independently selected from the group consisting of hydrogen and $C_{1-4}$-alkyl.

Embodiment 145: The compound of any of Embodiments 127 to 144, or a pharmaceutically acceptable salt thereof, wherein the $R^{12}$ heterocyclyl is unsubstituted.

Embodiment 146: The compound of any of Embodiments 127 to 144, or a pharmaceutically acceptable salt thereof, wherein the $R^{12}$ heterocyclyl is optionally substituted with one or more substituents independently selected from the group consisting of fluoro, $C_{1-4}$-alkyl, halo-$C_{1-4}$-alkyl, $C_{1-4}$-alkenyl, and —$OR^{19}$.

Embodiment 147: The compound of any of Embodiments 127 to 144, or a pharmaceutically acceptable salt thereof, wherein the $R^{12}$ heterocyclyl is optionally substituted with one or more substituents independently selected from the group consisting of fluoro, methyl, halomethyl, methylenyl, and methoxy.

Embodiment 148: The compound of any of Embodiments 127 to 144, or a pharmaceutically acceptable salt thereof, wherein the $R^{12}$ heterocyclyl is optionally substituted with one or more substituents independently selected from the group consisting of fluoro, methyl, trifluoromethyl, methylenyl, and methoxy.

Embodiment 149: The compound of any of Embodiments 127 to 144, or a pharmaceutically acceptable salt thereof, wherein the $R^{12}$ heterocyclyl is optionally substituted with one or more substituents independently selected from the group consisting of fluoro, methyl, and methylenyl.

Embodiment 150: The compound of any of Embodiments 127 to 144, or a pharmaceutically acceptable salt thereof, wherein the $R^{12}$ heterocyclyl is optionally substituted with one or more fluoro.

Embodiment 151: The compound of any of Embodiments 127 to 144, or a pharmaceutically acceptable salt thereof, wherein the $R^{12}$ heterocyclyl is optionally substituted with one or more $C_{1-4}$-alkyl.

Embodiment 152: The compound of any of Embodiments 127 to 144, or a pharmaceutically acceptable salt thereof, wherein the $R^{12}$ heterocyclyl is optionally substituted with one or more methyl.

Embodiment 153: The compound of any of Embodiments 127 to 144, or a pharmaceutically acceptable salt thereof, wherein the $R^{12}$ heterocyclyl is optionally substituted with one or more halo-$C_{1-4}$-alkyl.

Embodiment 154: The compound of any of Embodiments 127 to 144, or a pharmaceutically acceptable salt thereof, wherein the $R^{12}$ heterocyclyl is optionally substituted with one or more halomethyl.

Embodiment 155: The compound of any of Embodiments 127 to 144, or a pharmaceutically acceptable salt thereof, wherein the $R^{12}$ heterocyclyl is optionally substituted with one or more trifluoromethyl.

Embodiment 156: The compound of any of Embodiments 127 to 144, or a pharmaceutically acceptable salt thereof, wherein the $R^{12}$ heterocyclyl is optionally substituted with one or more $C_{1-4}$-alkenyl.

Embodiment 157: The compound of any of Embodiments 127 to 144, or a pharmaceutically acceptable salt thereof, wherein the $R^{12}$ heterocyclyl is optionally substituted with one or more methenyl.

Embodiment 158: The compound of any of Embodiments 127 to 144, or a pharmaceutically acceptable salt thereof, wherein the $R^{12}$ heterocyclyl is optionally substituted with one or more —$OR^{19}$; wherein $R^{19}$ is $C_{1-4}$-alkyl.

Embodiment 159: The compound of any of Embodiments 127 to 144, or a pharmaceutically acceptable salt thereof, wherein the $R^{12}$ heterocyclyl is optionally substituted with one or more methoxy.

Embodiment 160: The compound of any of Embodiments 127 to 144, or a pharmaceutically acceptable salt thereof, wherein the $R^{12}$ heterocyclyl is optionally substituted with one or more —$NR^{20}R^{21}$; wherein $R^{20}$ and $R^{21}$ are independently selected from the group consisting of hydrogen and $C_{1-4}$-alkyl.

Embodiment 161: The compound of any of Embodiments 127 to 144, or a pharmaceutically acceptable salt thereof, wherein the $R^{12}$ heterocyclyl is optionally substituted with one or more —$NR^{20}R^{21}$; wherein $R^{20}$ and $R^{21}$ are independently selected from the group consisting of hydrogen and methyl.

Embodiment 162: The compound of any of Embodiments 127 to 144, or a pharmaceutically acceptable salt thereof, wherein the $R^{12}$ heterocyclyl is optionally substituted with one or more —$N(R^{22})S(O)_2R^{23}$; wherein $R^{22}$ and $R^{23}$ are independently selected from the group consisting of hydrogen and $C_{1-4}$-alkyl.

Embodiment 163: The compound of any of Embodiments 127 to 144, or a pharmaceutically acceptable salt thereof, wherein the $R^{12}$ heterocyclyl is optionally substituted with one or more —$N(R^{22})S(O)_2R^{23}$; wherein $R^{22}$ and $R^{23}$ are independently selected from the group consisting of hydrogen and methyl.

Embodiment 164: The compound of Embodiment 127, or a pharmaceutically acceptable salt thereof, wherein the $R^{12}$ heterocyclyl is selected from the group consisting of:

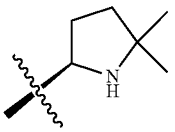

and

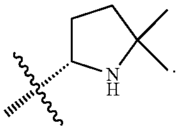

Embodiment 165: The compound of Embodiment 127, or a pharmaceutically acceptable salt thereof, wherein the $R^{12}$ heterocyclyl is selected from the group consisting of:

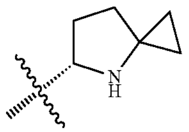

and

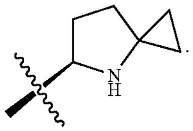

Embodiment 166: The compound of Embodiment 127, or a pharmaceutically acceptable salt thereof, wherein the $R^{12}$ heterocyclyl is:

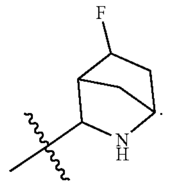 [SMILES: *C1NC2CC(F)C1C2]

Embodiment 167: The compound of Embodiment 127, or a pharmaceutically acceptable salt thereof, wherein the $R^{12}$ heterocyclyl is:

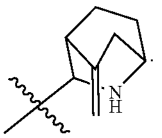

Embodiment 168: The compound of Embodiment 1, or a pharmaceutically acceptable salt thereof, wherein:

the compound of Formula (I) has a structure selected from the group consisting of:

Formula (I-1)

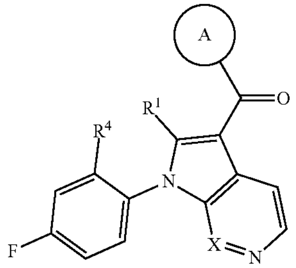

Formula (I-2)

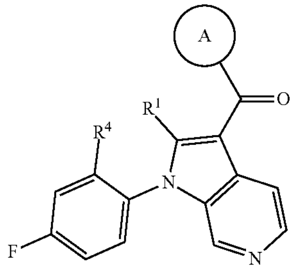

Formula (I-3)

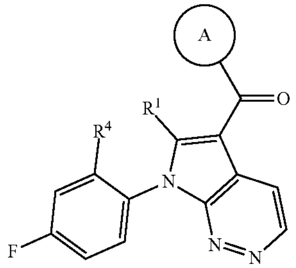

-continued

Formula (I-4)

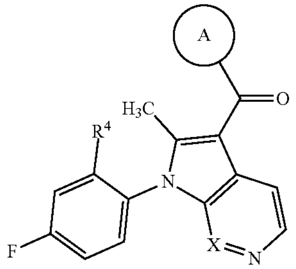

Formula (I-5)

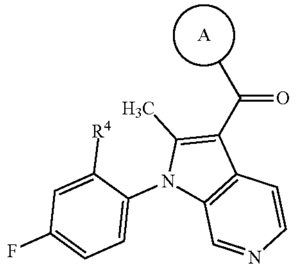

Formula (I-6)

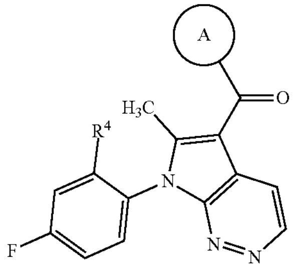

Formula (I-7)

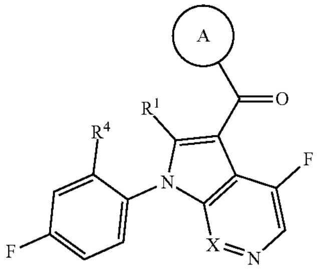

Formula (I-8)

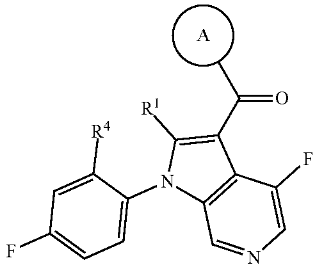

-continued
Formula (I-9)
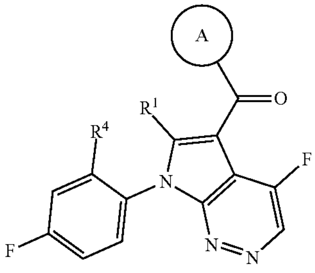
Formula (I-10)
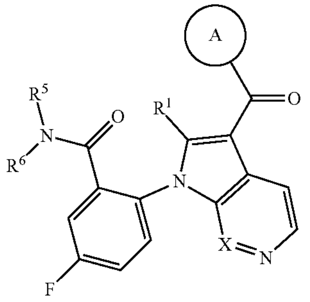
Formula (I-11)
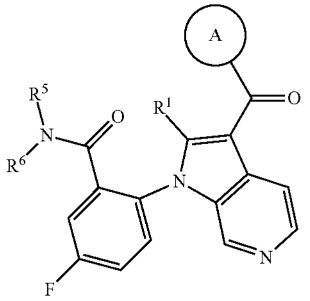
Formula (I-12)
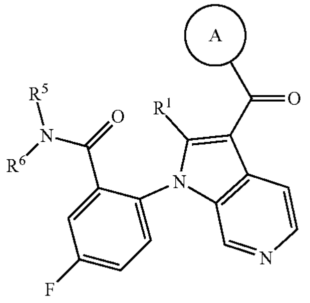
Formula (I-13)
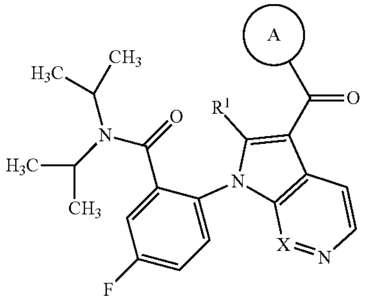
-continued
Formula (I-14)
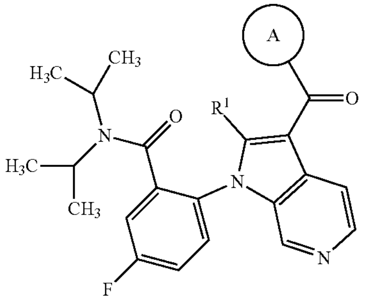
Formula (I-15)
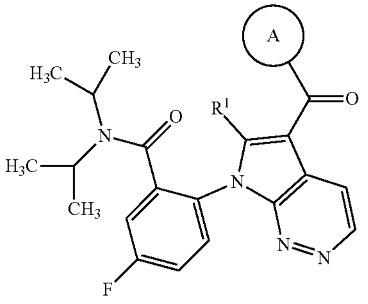
Formula (I-16)
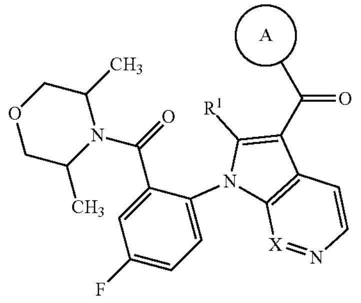
Formula (I-17)
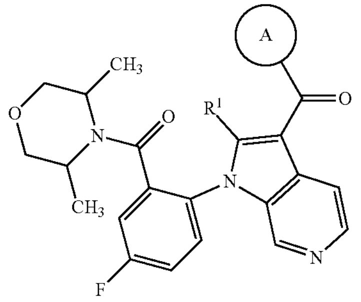
Formula (I-18)
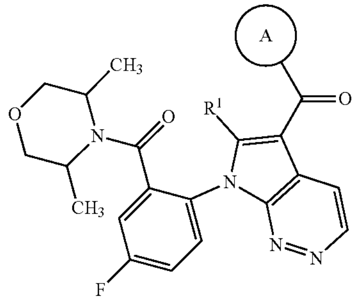

-continued
Formula (I-19)
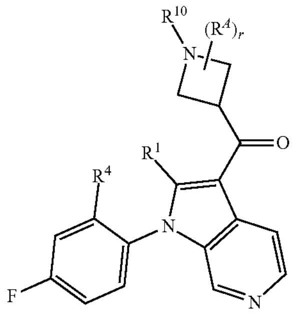
Formula (I-20)
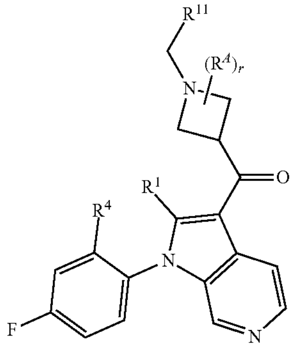
Formula (I-21)
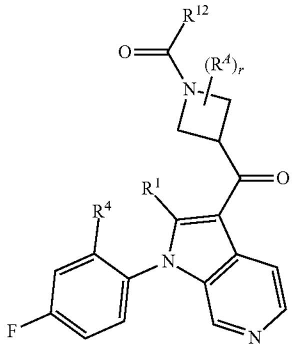
Formula (I-22)
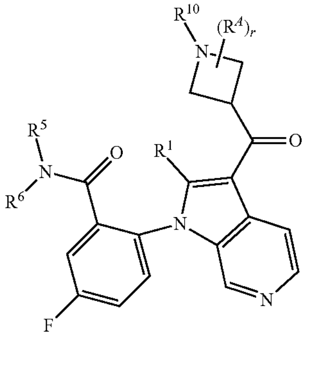
-continued
Formula (I-23)
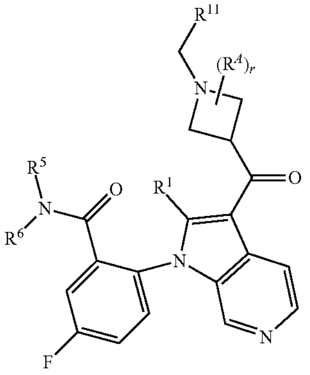
Formula (I-24)
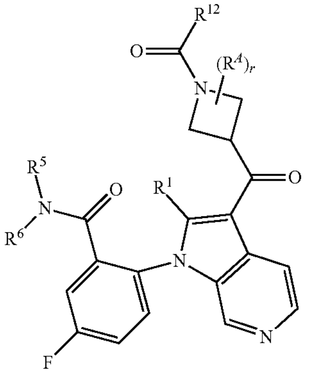
Formula (I-25)
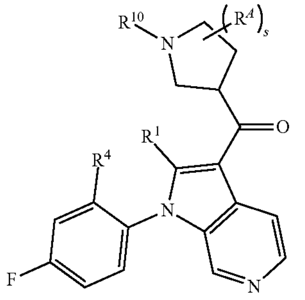
Formula (I-26)
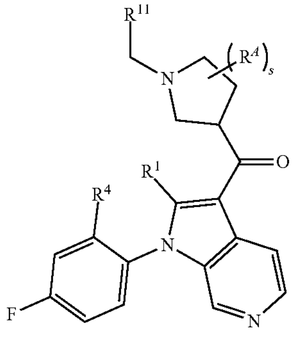

-continued
Formula (I-27)
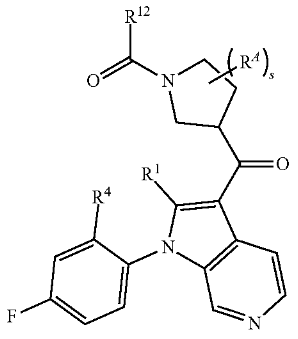
Formula (I-28)
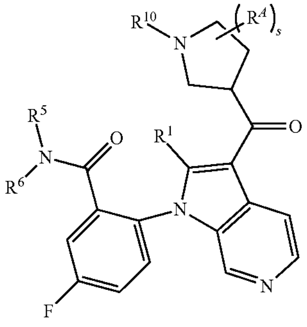
Formula (I-29)
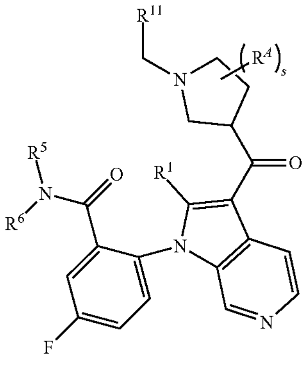
Formula (I-30)
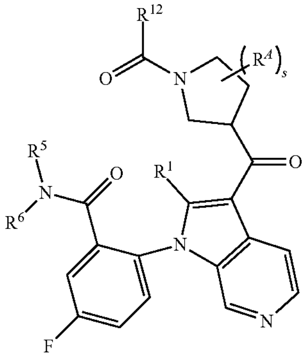
-continued
Formula (I-31)
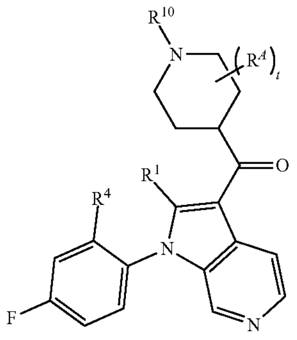
Formula (I-32)
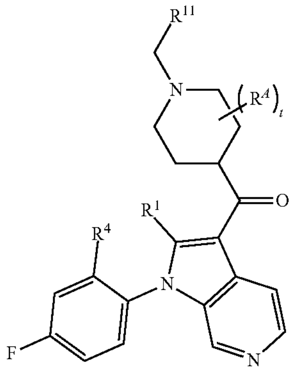
Formula (I-33)
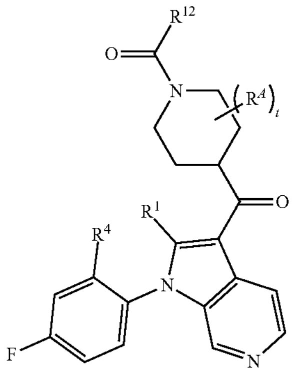
Formula (I-34)
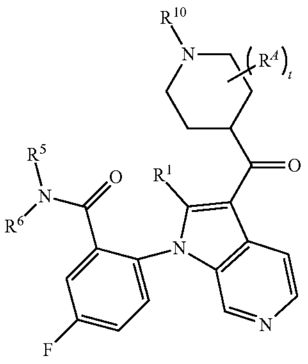

-continued
Formula (I-35)
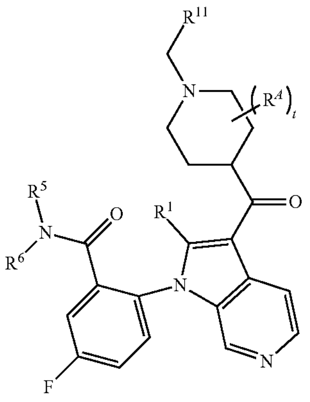
Formula (I-36)
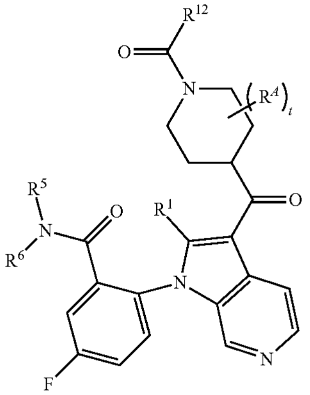
Formula (I-37)
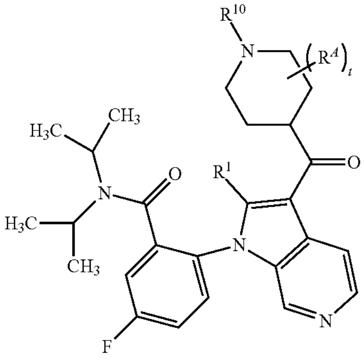
Formula (I-38)
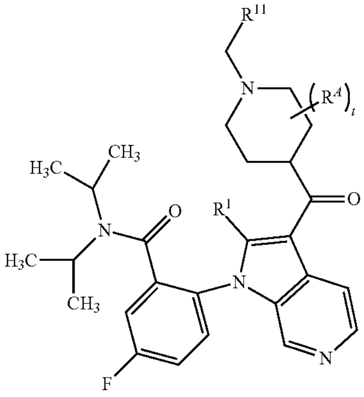
-continued
Formula (I-39)
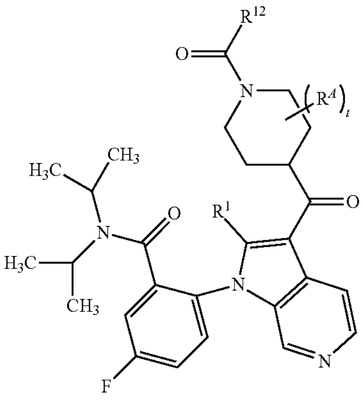
Formula (I-40)
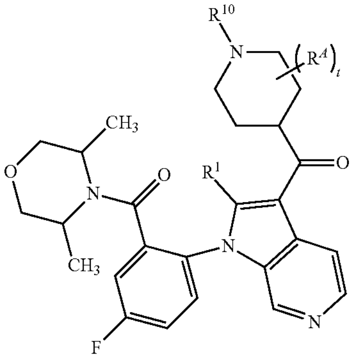
Formula (I-41)
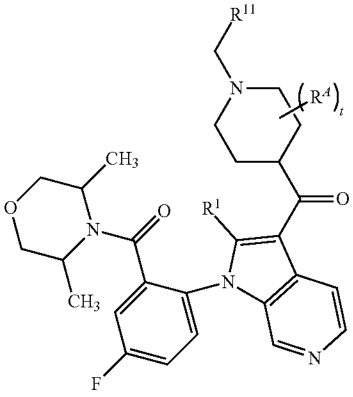
Formula (I-42)
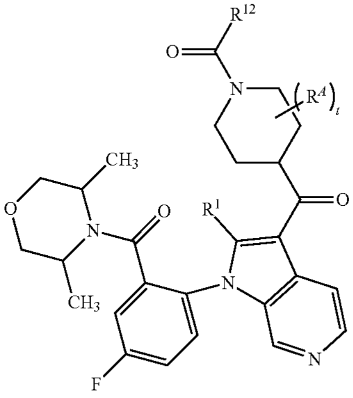

-continued
Formula (I-43)
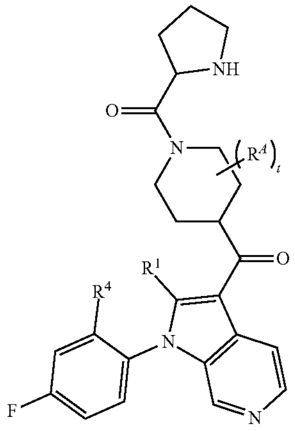
Formula (I-44)
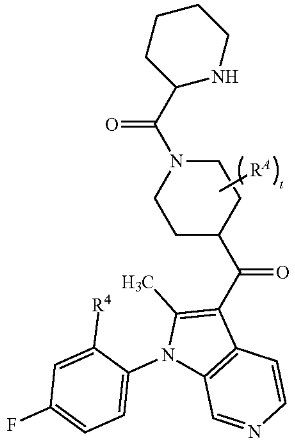
Formula (I-45)
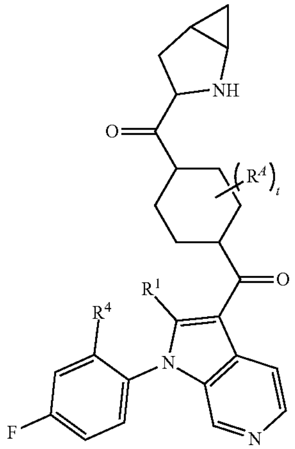
-continued
Formula (I-46)
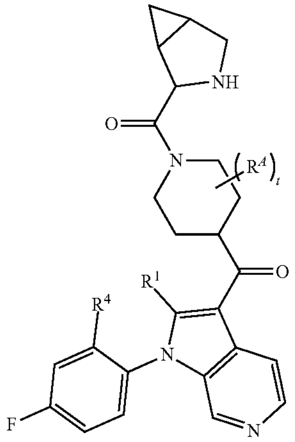
Formula (I-47)
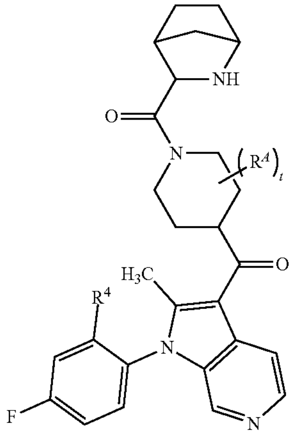
Formula (I-48)
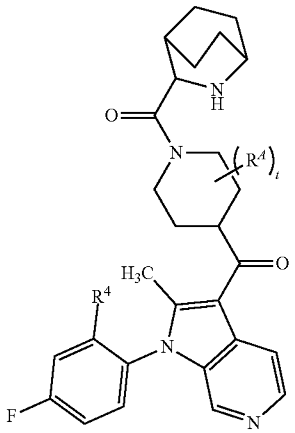

-continued
Formula (I-49)
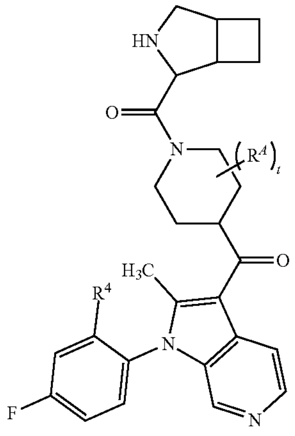
Formula (I-50)
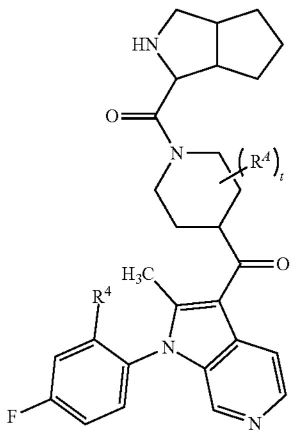
Formula (I-51)
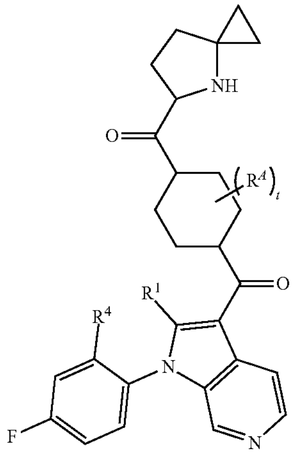
-continued
Formula (I-52)
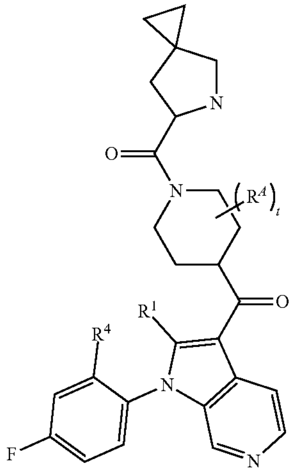
Formula (I-53)
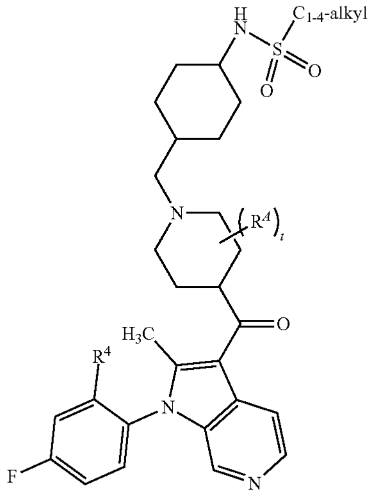
Formula (I-54)
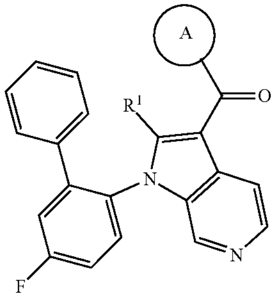
Formula (I-55)
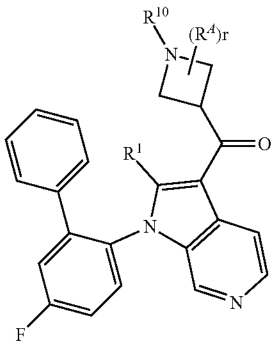

-continued
Formula (I-56)
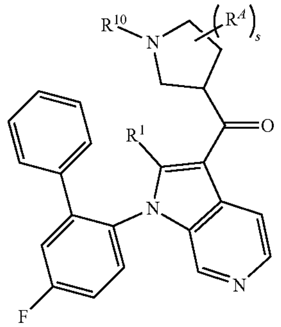
Formula (I-57)
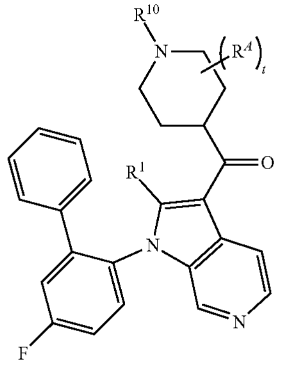
Formula (I-58)
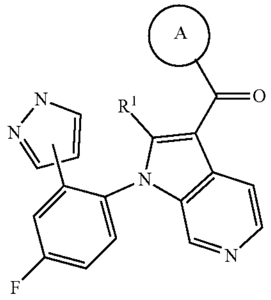
Formula (I-59)
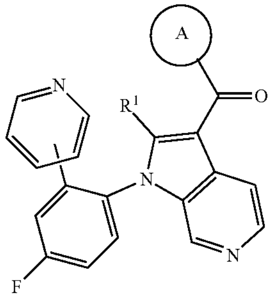
Formula (I-60)
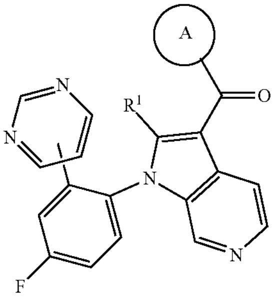
Formula (I-61)
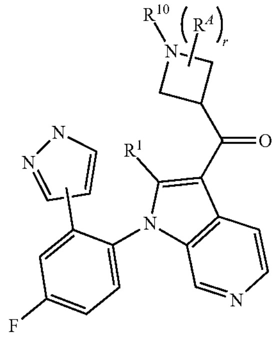
Formula (I-62)
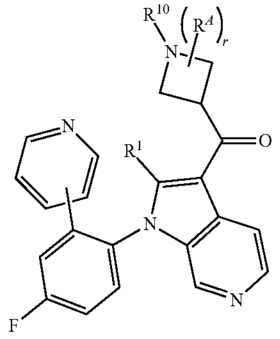
Formula (I-63)
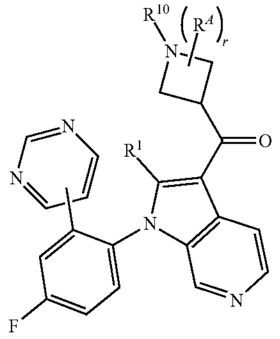
Formula (I-64)
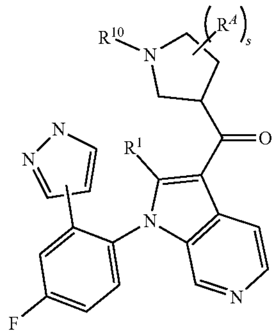

-continued

Formula (I-65)

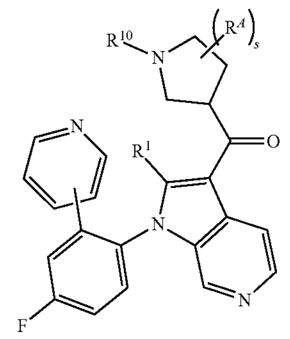

Formula (I-66)

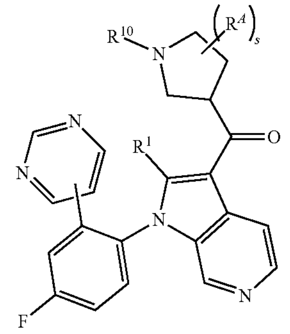

Formula (I-67)

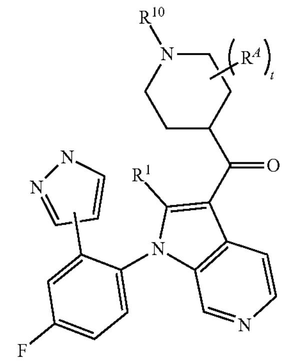

Formula (I-68)

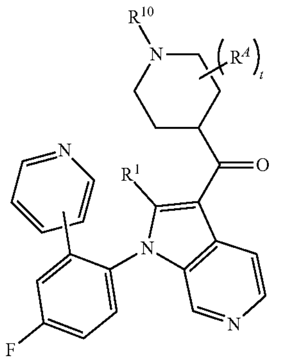

and

-continued

Formula (I-69)

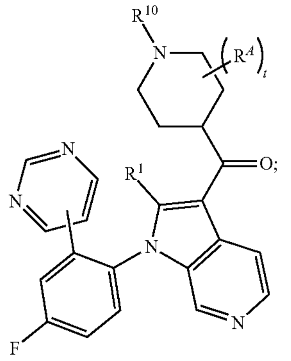

wherein, as applicable:

$R^1$, $R^4$, $R^5$, $R^6$, $R^{10}$, $R^{11}$, $R^{12}$, X, A, $R^A$, r, s, and t are as defined in Embodiment 1;

the $R^4$ phenyl present in the structures of Formula I-54 through Formula I-57 is optionally substituted with one or more substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

the $R^4$ pyrazolyl, pyridinyl, and pyrimidinyl present in the structures of Formula I-58 through Formula I-69 are optionally substituted with one or more substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

the $R^{11}$ cyclohexyl present in the structure of Formula I-53 is optionally substituted with one or more substituents independently selected from the group consisting of $C_{1-4}$-alkyl, —$NR^{15}R^{16}$, and —$N(R^{17})S(O)_2R^{18}$;

the $R^{12}$ heterocyclyl present in the structures of Formula I-43 through Formula I-52 is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

Embodiment 169: The compound of Embodiment 168, or a pharmaceutically acceptable salt thereof, wherein:

the $R^4$ phenyl present in the structures of Formula I-54 through Formula I-57 is optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl; and the $R^4$ pyrazolyl, pyridinyl, and pyrimidinyl present in the structures of Formula I-58 through Formula I-69 are optionally substituted with one to three substituents independently selected from the group consisting of fluoro, cyano, $C_{1-4}$-alkyl, halo-$C_{1-4}$-alkyl, $C_{3-4}$-cycloalkyl, and halo-$C_{3-4}$-cycloalkyl;

X is —$C(R^9)$—;

$R^9$ is hydrogen;

$R^A$ is methyl;

r, s, and t are independently 0 or 1;

the $R^{11}$ cyclohexyl present in the structure of Formula I-53 is optionally substituted with one or more substituents independently selected from the group consisting of $C_{1-4}$-alkyl, —$NR^{15}R^{16}$, and —$N(R^{17})S(O)_2R^{18}$;

the $R^{12}$ heterocyclyl present in the structures of Formula I-43 through Formula I-52 is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen and $C_{1-4}$-alkyl.

Embodiment 170: The compound of Embodiment 169, or a pharmaceutically acceptable salt thereof, wherein:

$R^1$ is methyl;

r, s, and t are each 0;

the structure is selected from Formula I-43 through Formula I-52;

the $R^{12}$ heterocyclyl present in the structure is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and $R^{19}$, $R^{20}$, $R^{21}$, $R^{22}$, and $R^{23}$ are independently selected from the group consisting of hydrogen and $C_{1-4}$-alkyl.

Embodiment 171: The compound of Embodiment 169, or a pharmaceutically acceptable salt thereof, wherein:

$R^1$ is methyl;

r, s, and t are each 0;

the structure is selected from Formula I-43 through Formula I-52; and the $R^{12}$ heterocyclyl present in the structure is optionally substituted with one or more substituents independently selected from the group consisting of fluoro, $C_{1-4}$-alkyl, halo-$C_{1-4}$-alkyl, and $C_{1-4}$-alkenyl.

Embodiment 172: The compound of Embodiment 169, or a pharmaceutically acceptable salt thereof, wherein:

$R^1$ is hydrogen;

r, s, and t are each 0;

the structure is selected from Formula I-43 through Formula I-52;

the $R^{12}$ heterocyclyl present in the structure is optionally substituted with one or more substituents independently selected from the group consisting of fluoro, $C_{1-4}$-alkyl, halo-$C_{1-4}$-alkyl, $C_{1-4}$-alkenyl, —$OR^{19}$, —$NR^{20}R^{21}$, and —$N(R^{22})S(O)_2R^{23}$; and $R^{19}$, $R^{20}$, $R^{21}$, $R^{22}$, and $R^{23}$ are independently selected from the group consisting of hydrogen and $C_{1-4}$-alkyl.

Embodiment 173: The compound of Embodiment 169, or a pharmaceutically acceptable salt thereof, wherein:

$R^1$ is hydrogen;

r, s, and t are each 0;

the structure is selected from Formula I-43 through Formula I-52; and the $R^{12}$ heterocyclyl present in the structure is optionally substituted with one or more substituents independently selected from the group consisting of fluoro, $C_{1-4}$-alkyl, halo-$C_{1-4}$-alkyl, and $C_{1-4}$-alkenyl.

Embodiment 174: The compound of Embodiment 1, or a pharmaceutically acceptable salt thereof, wherein the compound has the structure of Formula I-5A:

(I-5A)

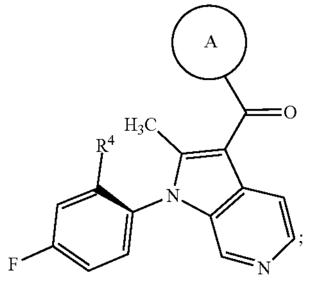

and $R^4$ and A are as defined in Embodiment 1.

Embodiment 175: The compound of Embodiment 1, or a pharmaceutically acceptable salt thereof, wherein the compound has the structure of Formula I-33A:

(I-33A)

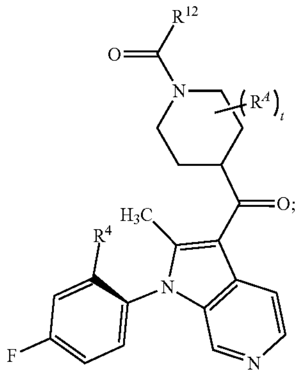

and $R^4$, $R^{12}$, $R^A$, and t are as defined in Embodiment 1.

Embodiment 176: The compound of Embodiment 175, or a pharmaceutically acceptable salt thereof, wherein t is 0.

Embodiment 177: A pharmaceutical composition comprising a compound of any of Embodiments 1 to 176, or a pharmaceutically acceptable salt thereof, and one or more pharmaceutically acceptable excipients.

Embodiment 178: A method of treating or preventing a Menin-mediated condition in a subject suffering from or susceptible to the Menin-mediated condition, the method comprising administering to the subject a therapeutically effective amount of a compound of any of Embodiments 1 to 176, or a pharmaceutically acceptable salt thereof.

Embodiment 179: The method of Embodiment 178, wherein the Menin-mediated condition is a hematological malignancy.

Embodiment 180: The method of Embodiment 179, wherein the hematological malignancy is selected from the group consisting of leukemias, myeloma, and myelodysplastic syndrome.

Embodiment 181: The method of Embodiment 179, wherein the Menin-mediated condition is leukemia.

Embodiment 182: The method of Embodiment 181, wherein the leukemia is selected from the group consisting of acute leukemia, chronic leukemia, myeloid leukemia, myelogeneous leukemia, lymphoblastic leukemia, lymphocytic leukemia, acute myelogeneous leukemia (AML), chronic myelogenous leukemia (CML), acute lymphoblastic leukemia (ALL), chronic lymphocytic leukemia (CLL), T cell prolymphocytic leukemia (T-PLL), large granular lymphocytic leukemia, hairy cell leukemia (HCL), mixed-lineage leukemia (MLL)-rearranged leukemia, mixed lineage leukemia-partial tandem duplication (MLL-PTD) leukemia, MLL-amplified leukemias, MLL-positive leukemias, NPM1-mutant acute myelogeneous leukemia (AML), NUP98-acute myelogeneous leukemia (AML), SETD2/RUNX1 mutant leukemia, and leukemia exhibiting an HOX/MEIS1 gene expression signature.

Embodiment 183: The method of Embodiment 182, wherein the leukemia is mixed-lineage leukemia (MLL)-rearranged leukemia.

Embodiment 184: The method of Embodiment 182, wherein the leukemia is acute myeloid leukemia (AML).

Embodiment 185: The method of Embodiment 182, wherein the leukemia is NPM1-mutant acute myeloid leukemia (AML).

Embodiment 186: The method of Embodiment 178, wherein the Menin-mediated condition is a solid tumor cancer.

Embodiment 187: The method of Embodiment 186, wherein the solid tumor cancer is selected from the group consisting of ovarian cancer, head and neck cancer, prostate cancer, lung cancer, breast cancer, pancreatic cancer, colorectal cancer, liver cancer, melanoma, glioblastoma, and sarcoma cancers.

Embodiment 188: The method of Embodiment 178, wherein the Menin-mediated condition is breast cancer.

Embodiment 189: The method of Embodiment 178, wherein the Menin-mediated condition is prostate cancer.

Embodiment 190: The method of Embodiment 178, wherein the Menin-mediated condition is liver cancer.

Although specific embodiments and examples have been described above, these embodiments and examples are only illustrative and do not limit the scope of the disclosure. Changes and modifications can be made in accordance with ordinary skill in the art without departing from the disclosure in its broader aspects as defined in the following claims. For example, any embodiment described herein can be combined with any other suitable embodiment described herein to provide additional embodiments.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present disclosure. It is also understood that such values inherently contain variability necessarily resulting from the standard deviations found in their respective testing measurements.

One skilled in the art will also readily recognize that where members are grouped together in a common manner, such as in a Markush group, the present disclosure encompasses not only the entire group listed as a whole, but each member of the group individually and all possible subgroups of the main group. Additionally, for all purposes, the present disclosure encompasses not only the main group, but also the main group absent one or more of the group members. The present disclosure also envisages the explicit exclusion or disclaimer of one or more of any of the group members in the claimed disclosure.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_{(1-6)}$, includes the subranges $C_{(2-6)}$, $C_{(3-6)}$, $C_{(3-5)}$, $C_{(4-6)}$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

Reference to a "step" in this disclosure is used for convenience purposes only and does not categorize, define, or limit the disclosure as set forth herein.

What is claimed is:

1. A compound that is(S)-2-(3-(1-(5,5-dimethylpyrrolidine-2-carbonyl) piperidine-4-carbonyl)-2-methyl-1H-pyrrolo[2,3-c]pyridin-1-yl)-5-fluoro-N,N-diisopropylbenzamide having the structure:

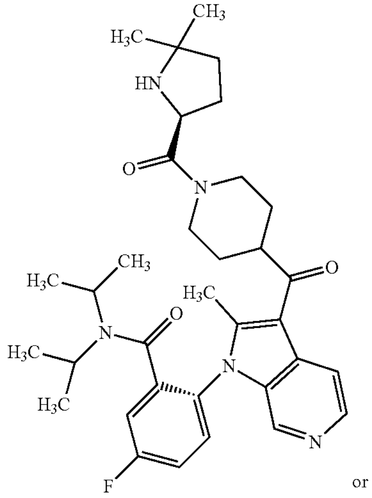

or

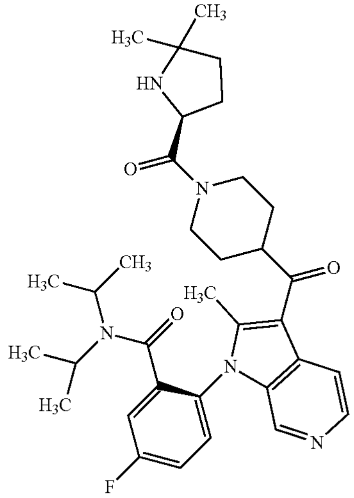

, or a pharmaceutically acceptable salt thereof.

2. A compound that is (S)-2-(3-(1-(5,5-dimethylpyrrolidine-2-carbonyl) piperidine-4-carbonyl)-2-methyl-1H-pyrrolo[2,3-c]pyridin-1-yl)-5-fluoro-N,N-diisopropylbenzamide having the structure:

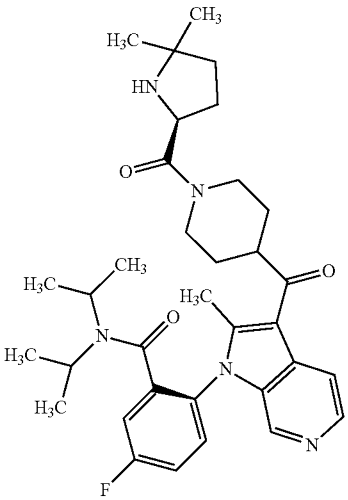

, or a pharmaceutically acceptable salt thereof.

3. The compound of claim 2 that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

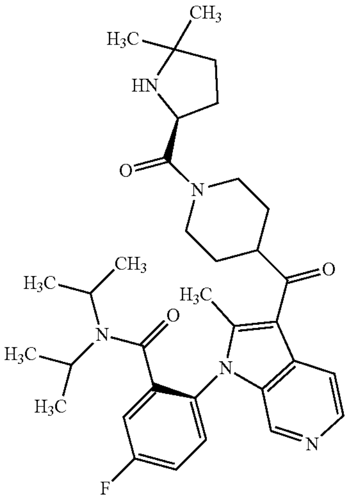

.

4. The salt of claim 2 that is the pharmaceutically acceptable salt of the compound that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

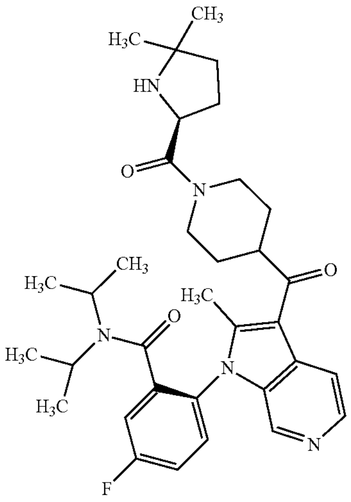

.

5. A pharmaceutical composition comprising a compound that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

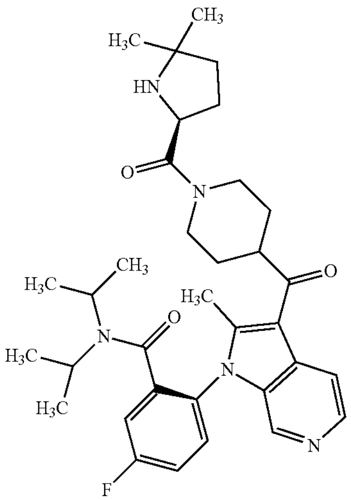

.

or a pharmaceutically acceptable salt thereof; and one or more pharmaceutically acceptable excipients.

6. The pharmaceutical composition of claim 5 comprising the compound that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

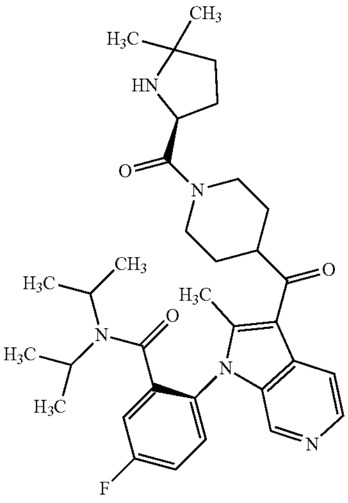

;

and one or more pharmaceutically acceptable excipients.

7. The pharmaceutical composition of claim 5 comprising the pharmaceutically acceptable salt of the compound that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

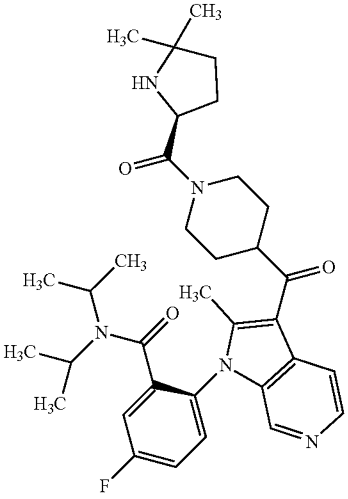

;

and one or more pharmaceutically acceptable excipients.

8. A method of treating leukemia in a subject suffering from or susceptible to the leukemia, wherein the method comprises administering to the subject a therapeutically effective amount of a compound that is (S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

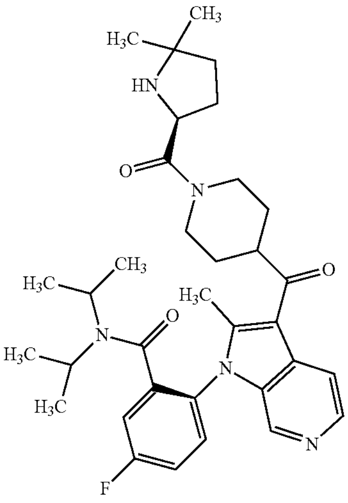

, or a pharmaceutically acceptable salt thereof.

9. The method of claim 8, wherein the method comprises administering to the subject a therapeutically effective amount of a compound that is ((S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

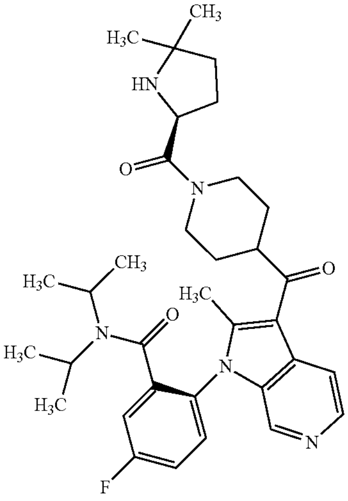

.

10. The method of claim 8, wherein the method comprises administering to the subject a therapeutically effective amount of the pharmaceutically acceptable salt of the compound that is(S)-2-(3-(1-(5,5-dimethylpyrrolidine-2-carbonyl)piperidine-4-carbonyl)-2-methyl-1H-pyrrolo[2,3-c]pyridin-1-yl)-5-fluoro-N,N-diisopropylbenzamide having the structure:

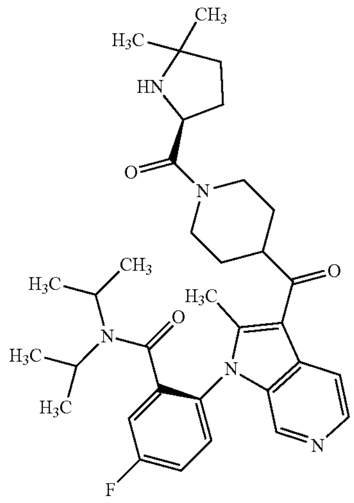

.

11. The method of claim 8, wherein the leukemia is selected from the group consisting of acute myeloid leukemia and acute lymphoid leukemia.

12. The method of claim 8, wherein the leukemia is acute myeloid leukemia.

13. The method of claim 8, wherein the leukemia is selected from the group consisting of mixed-lineage leukemia (MLL)-rearranged leukemia and NPM1-mutant acute myeloid leukemia.

14. The method of claim 9, wherein the leukemia is selected from the group consisting of acute myeloid leukemia and acute lymphoid leukemia.

15. The method of claim 9, wherein the leukemia is acute myeloid leukemia.

16. The method of claim 9, wherein the leukemia is selected from the group consisting of mixed-lineage leukemia (MLL)-rearranged leukemia and NPM1-mutant acute myeloid leukemia.

17. The method of claim 10, wherein the leukemia is selected from the group consisting of acute myeloid leukemia and acute lymphoid leukemia.

18. The method of claim 10, wherein the leukemia is acute myeloid leukemia.

19. The method of claim 10, wherein the leukemia is selected from the group consisting of mixed-lineage leukemia (MLL)-rearranged leukemia and NPM1-mutant acute myeloid leukemia.

* * * * *